US009822416B2

(12) United States Patent
Keller et al.

(10) Patent No.: US 9,822,416 B2
(45) Date of Patent: Nov. 21, 2017

(54) MIRNA IN THE DIAGNOSIS OF OVARIAN CANCER

(75) Inventors: Andreas Keller, Puettlingen (DE); Matthias Scheffler, Hirschberg-Leutershausen (DE); Markus Beier, Weinheim (DE)

(73) Assignee: Hummingbird Diagnostics GmbH, Heidelberg (DE)

(*) Notice: Subject to any disclaimer, the term of this patent is extended or adjusted under 35 U.S.C. 154(b) by 0 days.

(21) Appl. No.: 13/577,335

(22) PCT Filed: Feb. 7, 2011

(86) PCT No.: PCT/EP2011/051734
§ 371 (c)(1),
(2), (4) Date: Aug. 14, 2012

(87) PCT Pub. No.: WO2011/095623
PCT Pub. Date: Aug. 11, 2011

(65) Prior Publication Data
US 2012/0309645 A1 Dec. 6, 2012

(30) Foreign Application Priority Data
Feb. 5, 2010 (EP) .................................... 10152809

(51) Int. Cl.
*C12Q 1/68* (2006.01)

(52) U.S. Cl.
CPC ..... *C12Q 1/6886* (2013.01); *C12Q 2600/156* (2013.01); *C12Q 2600/178* (2013.01)

(58) Field of Classification Search
CPC ............ C12Q 1/6886; C12Q 2600/156; C12Q 2600/178
See application file for complete search history.

(56) References Cited

U.S. PATENT DOCUMENTS

| | | | | |
|---|---|---|---|---|
| 2008/0076674 | A1 | 3/2008 | Litman et al. | |
| 2009/0233297 | A1* | 9/2009 | Mambo ................ | C12Q 1/6886 435/6.14 |
| 2016/0326588 | A1 | 11/2016 | Beier | |

FOREIGN PATENT DOCUMENTS

| | | | | |
|---|---|---|---|---|
| CN | 101622349 | A | | 1/2010 |
| WO | WO 2009/036236 | A1 | | 3/2009 |
| WO | WO 2009/033140 | | * | 9/2009 |
| WO | 2009143379 | A2 | | 11/2009 |
| WO | WO 2010/083312 | A2 | * | 7/2010 |
| WO | WO 2011/029903 | A1 | | 3/2011 |
| WO | WO 2013/036936 | A1 | | 3/2013 |
| WO | WO 2013/124816 | A2 | | 8/2013 |
| WO | WO 2013/150105 | A1 | | 10/2013 |

OTHER PUBLICATIONS

Jaarsveld, M. et al Jan. 2010 International Journal of Biochemistry and Cell Biology 42: 1282-1290.*
Taylor et al 2008 Gynecologic Oncology 110: 13-21.*
Taylor et al 2008 Gynecologic Oncology 110: 13-21, Appendix A.*
Mature sequence hsa-miR-342-3p. Datasheet [online]. miRBase. [retrieved on Dec. 12, 2012]. Retrieved from the Internet: <http://www.mirbase.org/cgi-bin/mature.pl?mature_acc=MIMAT0000753>.*
Chen et al 2008 Cell Research 18: 997-1006.*
Keller (BMC Cancer 2009 9:353).*
Esteller (Nature Reviews Genetic vol. 12 Dec. 2011 pp. 861-874).*
Krell et al. Frontiers in Bioscience (Elite Edition), vol. 5, pp. 204-213, Jan. 2013; e.g., Abstract).*
McShane et al. British Journal of Cancer, vol. 93, pp. 387-391, 2005.*
Ghorai (Frontiers in Genetics Apr. 2014 vol. 5 article 100).*
Griffiths-Jones et al., "miRBase: microRNA sequences, targets and gene nomenclature", Nucleic Acids Research Jan. 1, 2006, vol. 34, No. Database issue, pp. D140-D144.
Database Nucleotide [Online], Aug. 15, 2010, "*Homo sapiens* microRNA 1248 (M1R1248)", XP002600729, retrieved from MCBI, Database accession No. NR_031650 Abstract.
Database MirBase [Online] "*Homo sapiens* miR-1248 stem-loop", XP002600730, Database accession No. M10006383 Abstract.
Database Mirbase [Online] *Homo sapiens* miR-342 stem-loop, XP000002659179, Database accession No. M10000805, the whole document.
Cheng et al., The detection of microRNA associated with Alzheimer's disease in biological fluids using next-generation sequencing technologies. Front Genet. Aug. 8, 2013;4:150. doi:10.3389/fgene.2013.00150. eCollection 2013.
Geekiyanage et al., Blood serum miRNA: non-invasive biomarkers for Alzheimer's disease. Exp Neurol. Jun. 2012;235(2):491-6. doi:10.1016/j.expneurol.2011.11.026. Epub Dec. 1, 2011.
Leidinger et al., A blood based 12-miRNA signature of Alzheimer disease patients. Genome Biol. Jul. 29, 2013;14(7):R78. doi:10.1186/gb-2013-14-7-r78.
Martins et al., Convergence of miRNA expression profiling, α-synuclein interacton and GWAS in Parkinson's disease. PLoS One. 2011;6(10):e25443. doi:10.1371/journal.pone.0025443. Epub Oct. 7, 2011.
Shaffer et al., miRNA profiling from blood—challenges and recommendations. Jan. 1, 2012.
Sheinerman et al., Plasma microRNA biomarkers for detection of mild cognitive impairment. Aging (Albany NY). Sep. 2012;4(9):590-605.
U.S. Appl. No. 15/105,766, filed Jun. 17, 2016, Beier.
PCT/EP2011/051734, Aug. 16, 2012, International Preliminary Report on Patentability.
PCT/EP2011/051734, Sep. 30, 2011, International Search Report and Written Opinion.

* cited by examiner

*Primary Examiner* — Amanda Haney
(74) *Attorney, Agent, or Firm* — Kilpatrick Townsend & Stockton LLP

(57) ABSTRACT

The present invention provides novel methods for diagnosing a state of health based on the determination of specific miRNAs that have altered expression levels in different conditions, e.g. disease states compared to healthy controls.

4 Claims, 157 Drawing Sheets

FIG. 1

Figure 3:
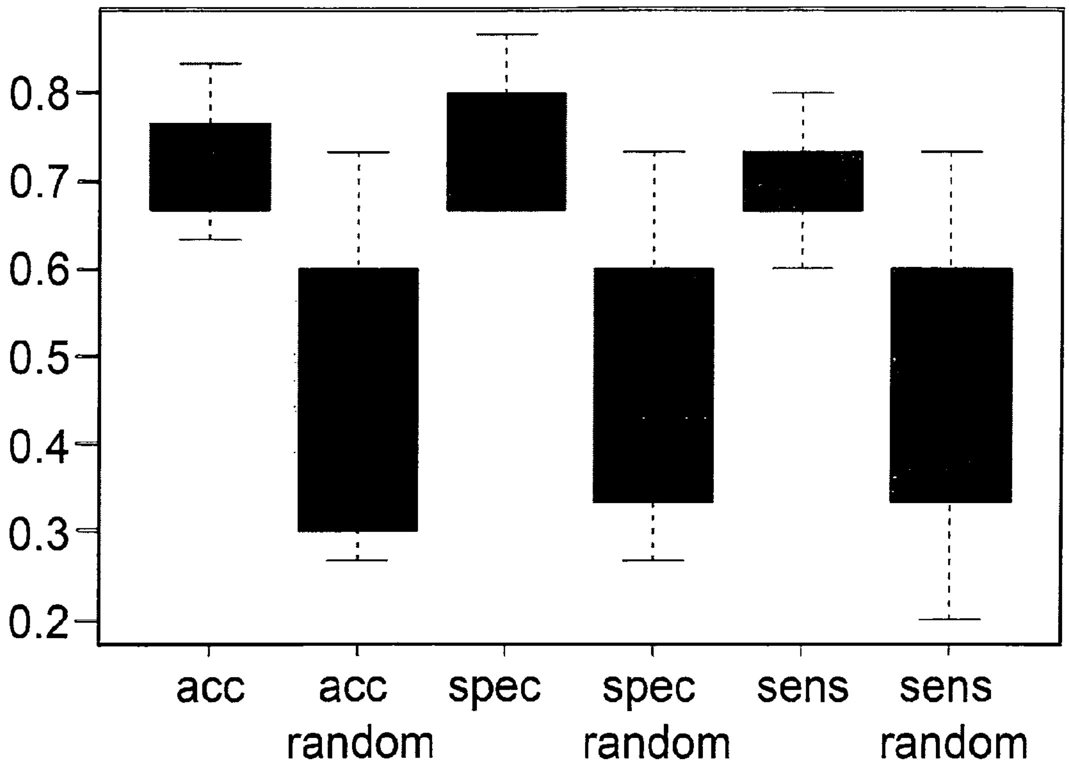
Figure 4:
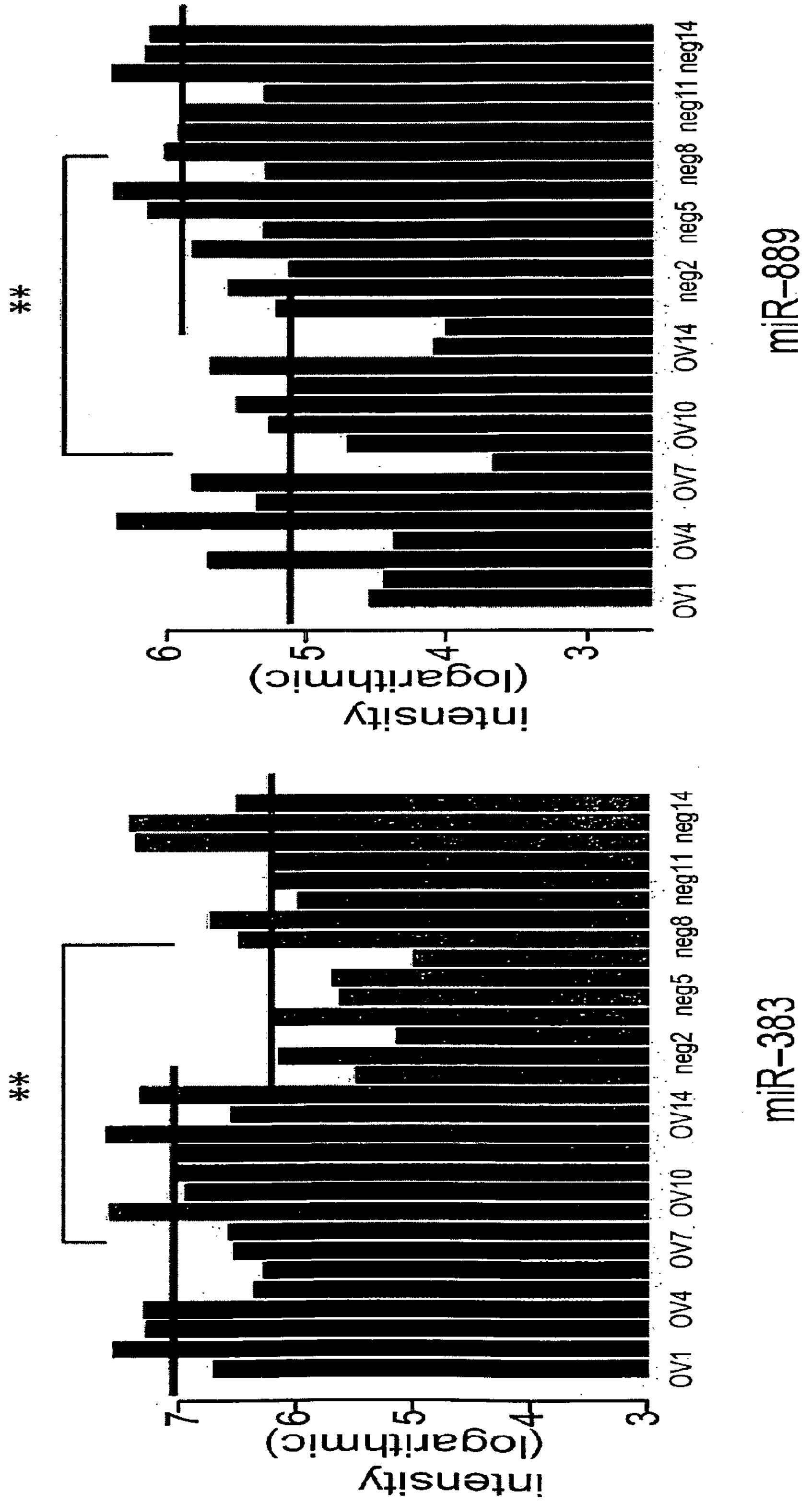
Figure 5:
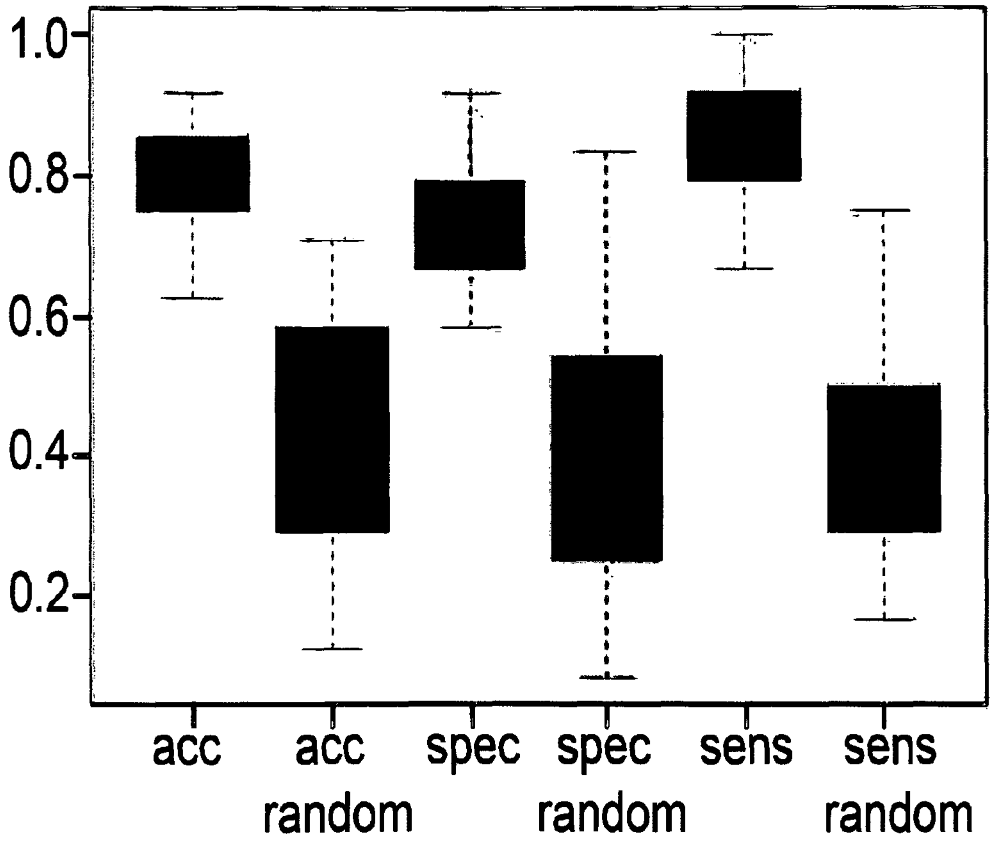

| SEQ ID No. | Name (miRNA, miRNA*) | SEQUENCE | SEQ ID No. | Name (miRNA, miRNA*) | SEQUENCE |
|---|---|---|---|---|---|
| 1 | hsa-miR-99b* | CAAGCUCGUGUCUGUGGGUCCG | 482 | hsa-miR-30c-1* | CUGGGAGAGGGUUGUUUACUCC |
| 2 | hsa-miR-99b | CACCCGUAGAACCGACCUUGCG | 483 | hsa-miR-30c | UGUAAACAUCCUACACUCUCAGC |
| 3 | hsa-miR-99a* | CAAGCUCGCUUCUAUGGGUCUG | 484 | hsa-miR-30b* | CUGGGAGGUGGAUGUUUACUUC |
| 4 | hsa-miR-99a | AACCCGUAGAUCCGAUCUUGUG | 485 | hsa-miR-30b | UGUAAACAUCCUACACUCAGCU |
| 5 | hsa-miR-98 | UGAGGUAGUAAGUUGUAUUGUU | 486 | hsa-miR-30a* | CUUUCAGUCGGAUGUUUGCAGC |
| 6 | hsa-miR-96* | AAUCAUGUGCAGUGCCAAUAUG | 487 | hsa-miR-30a | UGUAAACAUCCUCGACUGGAAG |
| 7 | hsa-miR-96 | UUUGGCACUAGCACAUUUUUGCU | 488 | hsa-miR-302f | UAAUUGCUUCCAUGUUU |
| 8 | hsa-miR-95 | UUCAACGGGUAUUUAUUGAGCA | 489 | hsa-miR-302e | UAAGUGCUUCCAUGCUU |
| 9 | hsa-miR-944 | AAAUUAUUGUACAUCGGAUGAG | 490 | hsa-miR-302d* | ACUUUAACAUGGAGGCACUUGC |
| 10 | hsa-miR-943 | CUGACUGUUGCCGUCCUCCAG | 491 | hsa-miR-302d | UAAGUGCUUCCAUGUUUGAGUGU |
| 11 | hsa-miR-942 | UCUUCUCUGUUUUGGCCAUGUG | 492 | hsa-miR-302c* | UUUAACAUGGGGGUACCUGCUG |
| 12 | hsa-miR-941 | CACCCGGCUGUGUGCACAUGUGC | 493 | hsa-miR-302c | UAAGUGCUUCCAUGUUUCAGUGG |
| 13 | hsa-miR-940 | AAGGCAGGGCCCCCGCUCCCC | 494 | hsa-miR-302b* | ACUUUAACAUGGAAGUGCUUUC |
| 14 | hsa-miR-939 | UGGGGAGCUGAGGCUCUGGGGGUG | 495 | hsa-miR-302b | UAAGUGCUUCCAUGUUUUAGUAG |
| 15 | hsa-miR-938 | UGCCCUUAAAGGUGAACCCAGU | 496 | hsa-miR-302a* | ACUUAAACGUGGAUGUACUUGCU |
| 16 | hsa-miR-937 | AUCCGCGCUCUGACUCUCUGCC | 497 | hsa-miR-302a | UAAGUGCUUCCAUGUUUUGGUGA |
| 17 | hsa-miR-936 | ACAGUAGAGGGAGGAAUCGCAG | 498 | hsa-miR-301b | CAGUGCAAUGAUAUUGUCAAAGC |
| 18 | hsa-miR-935 | CCAGUUACCGCUUCCGCUACCGC | 499 | hsa-miR-301a | CAGUGCAAUAGUAUUGUCAAAGC |
| 19 | hsa-miR-934 | UGUCUACUACUGGAGACACUGG | 500 | hsa-miR-300 | UAUACAAGGGCAGACUCUCUCU |

FIG. 1 (continued)

| SEQ ID | | | SEQ ID | | |
|---|---|---|---|---|---|
| 20 | hsa-miR-933 | UGUGCGCAGGGAGACCUCUCCC | 501 | hsa-miR-29c* | UGACCGAUUUCUCCUGGUGUUC |
| 21 | hsa-miR-93* | ACUGCUGAGCUAGCACUUCCCG | 502 | hsa-miR-29c | UAGCACCAUUUGAAAUCGGUUA |
| 22 | hsa-miR-93 | CAAAGUGCUGUUCGUGCAGGUAG | 503 | hsa-miR-29b-2* | CUGGUUUCACAUGGUGGCUUAG |
| 23 | hsa-miR-92b* | AGGGACGGGACGCGGUGCAGUG | 504 | hsa-miR-29b-1* | GCUGGUUUCAUAUGGUGGUUUAGA |
| 24 | hsa-miR-92b | UAUUGCACUCGUCCCGGCCUCC | 505 | hsa-miR-29b | UAGCACCAUUUGAAAUCAGUGUU |
| 25 | hsa-miR-92a-2* | GGGUGGGGAUUUGUUGCAUUAC | 506 | hsa-miR-29a* | ACUGAUUUCUUUUGGUGUUCAG |
| 26 | hsa-miR-92a-1* | AGGUUGGGAUCGGUUGCAAUGCU | 507 | hsa-miR-29a | UAGCACCAUCUGAAAUCGGUUA |
| 27 | hsa-miR-92a | UAUUGCACUUGUCCCGGCCUGU | 508 | hsa-miR-299-5p | UGGUUUACCGUCCCACAUACAU |
| 28 | hsa-miR-924 | AGAGUCUUGUGAUGUCUUGC | 509 | hsa-miR-299-3p | UAUGUGGGAUGGUAAACCGCUU |
| 29 | hsa-miR-922 | GCAGCAGAGAAUAGGACUACGUC | 510 | hsa-miR-298 | AGCAGAAGCAGGGAGGUUCUCCCA |
| 30 | hsa-miR-921 | CUAGUGAGGGACAGAACCAGGAUUC | 511 | hsa-miR-297 | AUGUAUGUGUGCAUGUGCAUG |
| 31 | hsa-miR-920 | GGGGAGCUGUGGAAGCAGUA | 512 | hsa-miR-296-5p | AGGGCCCCCCCUCAAUCCUGU |
| 32 | hsa-miR-9* | AUAAAGCUAGAUAACCGAAAGU | 513 | hsa-miR-296-3p | GAGGGUUGGGUGGAGGCUCUCC |
| 33 | hsa-miR-9 | UCUUUGGUUAUCUAGCUGUAUGA | 514 | hsa-miR-28-5p | AAGGAGCUCACAGUCUAUUGAG |
| 34 | hsa-miR-892b | CACUGGCUCCUUUCUGGGUAGA | 515 | hsa-miR-28-3p | CACUAGAUUGUGAGCUCCUGGA |
| 35 | hsa-miR-892a | CACUGUGUCCUUUCUGCGUAG | 516 | hsa-miR-27b* | AGAGCUUAGCUGAUUGGUGAAC |
| 36 | hsa-miR-891b | UGCAACUUACCUGAGUCAUUGA | 517 | hsa-miR-27b | UUCACAGUGGCUAAGUUCUGC |
| 37 | hsa-miR-891a | UGCAACGAACCUGAGCCACUGA | 518 | hsa-miR-27a* | AGGGCUUAGCUGCUUGUGAGCA |
| 38 | hsa-miR-890 | UACUUGGAAAGGCAUCAGUUG | 519 | hsa-miR-27a | UUCACAGUGGCUAAGUUCCGC |

FIG. 1 (continued)

| SEQ ID | | | SEQ ID | | |
|---|---|---|---|---|---|
| 39 | hsa-miR-889 | UUAAUAUCGGACAACCAUUGU | 520 | hsa-miR-26b* | CCUGUUCUCCAUUACUUGGCUC |
| 40 | hsa-miR-888* | GACUGACACCUCUUUGGGUGAA | 521 | hsa-miR-26b | UUCAAGUAAUUCAGGAUAGGU |
| 41 | hsa-miR-888 | UACUCAAAAAGCUGUCAGUCA | 522 | hsa-miR-26a-2* | CCUAUUCUUGAUUACUUGUUUC |
| 42 | hsa-miR-887 | GUGAACGGGCGCCAUCCCGAGG | 523 | hsa-miR-26a-1* | CCUAUUCUUGGUUACUUGCACG |
| 43 | hsa-miR-886-5p | CGGGUCGGAGUUAGCUCAAGCGG | 524 | hsa-miR-26a | UUCAAGUAAUCCAGGAUAGGCU |
| 44 | hsa-miR-886-3p | CGCGGGUGCUUACUGACCCUU | 525 | hsa-miR-25* | AGGCGGAGACUUGGGCAAUUG |
| 45 | hsa-miR-885-5p | UCCAUUACACUACCCUGCCUCU | 526 | hsa-miR-25 | CAUUGCACUUGUCUCGGUCUGA |
| 46 | hsa-miR-885-3p | AGGCAGCGGGGUGUAGUGGAUA | 527 | hsa-miR-24-2* | UGCCUACUGAGCUGAAACACAG |
| 47 | hsa-miR-877* | UCCUCUUCUCCCUCCUCCCAG | 528 | hsa-miR-24-1* | UGCCUACUGAGCUGAUAUCAGU |
| 48 | hsa-miR-877 | GUAGAGGAGAUGGCGCAGGG | 529 | hsa-miR-24 | UGGCUCAGUUCAGCAGGAACAG |
| 49 | hsa-miR-876-5p | UGGAUUUCUUUGUGAAUCACCA | 530 | hsa-miR-23b* | UGGGUUCCUGGCAUGCUGAUUU |
| 50 | hsa-miR-876-3p | UGGUGGUUUACAAAGUAAUUCA | 531 | hsa-miR-23b | AUCACAUUGCCAGGGAUUACC |
| 51 | hsa-miR-875-5p | UAUACCUCAGUUUUAUCAGGUG | 532 | hsa-miR-23a* | GGGGUUCCUGGGGAUGGGAUUU |
| 52 | hsa-miR-875-3p | CCUGGAAACACUGAGGUUGUG | 533 | hsa-miR-23a | AUCACAUUGCCAGGGAUUUCC |
| 53 | hsa-miR-874 | CUGCCCUGGCCCGAGGGACCGA | 534 | hsa-miR-2278 | GAGAGCAGUGUGUGUUGCCUGG |
| 54 | hsa-miR-873 | GCAGGAACUUGUGAGUCUCCU | 535 | hsa-miR-2277 | UGACAGCGCCCUGCCUGGCUC |
| 55 | hsa-miR-802 | CAGUAACAAAGAUUCAUCCUUGU | 536 | hsa-miR-2276 | UCUGCAAGUGUCAGAGGCGAGG |
| 56 | hsa-miR-770-5p | UCCAGUACCACGUGUCAGGGCCA | 537 | hsa-miR-224* | AAAAUGGUGCCCUAGUGACUACA |
| 57 | hsa-miR-769-5p | UGAGACCUCUGGGUUCUGAGCU | 538 | hsa-miR-224 | CAAGUCACUAGUGGUUCCGUU |
| 58 | hsa-miR-769-3p | CUGGGAUCUCCGGGGUCUUGGUU | 539 | hsa-miR-223* | CGUGUAUUUGACAAGCUGAGUU |
| 59 | hsa-miR-767-5p | UGCACCAUGGUUGUCUGAGCAUG | 540 | hsa-miR-223 | UGUCAGUUUGUCAAAUACCCCA |

FIG. 1 (continued)

| SEQ ID | | | SEQ ID | | |
|---|---|---|---|---|---|
| 60 | hsa-miR-767-3p | UCUGCUCAUACCCCAUGGUUUCU | 541 | hsa-miR-222* | CUCAGUAGCCAGUGUAGAUCCU |
| 61 | hsa-miR-766 | ACUCCAGCCCCACAGCCUCAGC | 542 | hsa-miR-222 | AGCUACAUCUGGCUACUGGGU |
| 62 | hsa-miR-765 | UGGAGGAGAAGGAAGGUGAUG | 543 | hsa-miR-221* | ACCUGGCAUACAAUGUAGAUUU |
| 63 | hsa-miR-764 | GCAGGUGCUCACUUGUCCUCCU | 544 | hsa-miR-221 | AGCUACAUUGUCUGCUGGGUUUC |
| 64 | hsa-miR-762 | GGGGCUGGGGCCGGGGCCGAGC | 545 | hsa-miR-220c | ACACAGGGCUGUUGUGAAGACU |
| 65 | hsa-miR-761 | GCAGCAGGGUGAAACUGACACA | 546 | hsa-miR-220b | CCACCACCGUGUCUGACACUU |
| 66 | hsa-miR-760 | CGGCUCUGGGUCUGUGGGGA | 547 | hsa-miR-220a | CCACACCGUAUCUGACACUUU |
| 67 | hsa-miR-759 | GCAGAGUGCAAACAAUUUUGAC | 548 | hsa-miR-22* | AGUUCUUCAGUGGCAAGCUUUA |
| 68 | hsa-miR-758 | UUUGUGACCUGGUCCACUAACC | 549 | hsa-miR-22 | AAGCUGCCAGUUGAAGAACUGU |
| 69 | hsa-miR-744* | CUGUUGCCACUAACCUCAACCU | 550 | hsa-miR-219-5p | UGAUUGUCCAAACGCAAUUCU |
| 70 | hsa-miR-744 | UGCGGGGCUAGGGCUAACAGCA | 551 | hsa-miR-219-2-3p | AGAAUUGUGGCUGGACAUCUGU |
| 71 | hsa-miR-720 | UCUCGCUGGGGCCUCCA | 552 | hsa-miR-219-1-3p | AGAGUUGAGUCUGGACGUCCCG |
| 72 | hsa-miR-7-2* | CAACAAAUCCCAGUCUACCUAA | 553 | hsa-miR-218-2* | CAUGGUUCUGUCAAGCACCGCG |
| 73 | hsa-miR-718 | CUUCCGCCCCGCCGGGCGUCG | 554 | hsa-miR-218-1* | AUGGUUCCGUCAAGCACCAUGG |
| 74 | hsa-miR-711 | GGGACCCAGGGAGAGACGUAAG | 555 | hsa-miR-218 | UUGUGCUUGAUCUAACCAUGU |
| 75 | hsa-miR-7-1* | CAACAAAUCACAGUCUGCCAUA | 556 | hsa-miR-217 | UACUGCAUCAGGAACUGAUUGGA |
| 76 | hsa-miR-708* | CAACUAGACUGUGAGCUUCUAG | 557 | hsa-miR-216b | AAAUCUCUGCAGGCAAAUGUGA |
| 77 | hsa-miR-708 | AAGGAGCUUACAAUCUAGCUGGG | 558 | hsa-miR-216a | UAAUCUCAGCUGGCAACUGUGA |
| 78 | hsa-miR-7 | UGGAAGACUAGUGAUUUUGUUGU | 559 | hsa-miR-215 | AUGACCUAUGAAUUGACAGAC |
| 79 | hsa-miR-675* | CUGUAUGCCCUCACCGCUCA | 560 | hsa-miR-214* | UGCCUGUCUACACUUGCUGUGC |

FIG. 1 (continued)

| SEQ ID | | | SEQ ID | | |
|---|---|---|---|---|---|
| 80 | hsa-miR-675 | UGGUGCGGAGAGGGCCCACAGUG | 561 | hsa-miR-214 | ACAGCAGGCACAGACAGGCAGU |
| 81 | hsa-miR-671-5p | AGGAAGCCCUGGAGGGGCUGGAG | 562 | hsa-miR-212 | UAACAGUCUCCAGUCACGGCC |
| 82 | hsa-miR-671-3p | UCCGGUUCUCAGGGCUCCACC | 563 | hsa-miR-2117 | UGUUCUCUUUGCCAAGGACAG |
| 83 | hsa-miR-670 | GUCCCUGAGUGUAUGUGGUG | 564 | hsa-miR-2116* | CCUCCCAUGCCAAGAACUCCC |
| 84 | hsa-miR-668 | UGUCACUCGGCUCGGCCCACUAC | 565 | hsa-miR-2116 | GGUUCUUAGCAUAGGAGGUCU |
| 85 | hsa-miR-665 | ACCAGGAGGCUGAGGCCCCU | 566 | hsa-miR-2115* | CAUCAGAAUUCAUGGAGGCUAG |
| 86 | hsa-miR-664* | ACUGGCUAGGGAAAAUGAUUGGAU | 567 | hsa-miR-2115 | AGCUUCCAUGACUCCUGAUGGA |
| 87 | hsa-miR-664 | UAUUCAUUUAUCCCCAGCCUACA | 568 | hsa-miR-2114* | CGAGCCUCAAGCAAGGGACUU |
| 88 | hsa-miR-663b | GGUGGCCCGGCCGUGCCUGAGG | 569 | hsa-miR-2114 | UAGUCCCUUCCUUGAAGCGGUC |
| 89 | hsa-miR-663 | AGGCGGGGCGCCGCGGGACCGC | 570 | hsa-miR-2113 | AUUUGUGCUUGGCUCUGUCAC |
| 90 | hsa-miR-662 | UCCCACGUUGUGGCCCAGCAG | 571 | hsa-miR-2110 | UUGGGGAAACGGCCGCUGAGUG |
| 91 | hsa-miR-661 | UGCCUGGGUCUCUGGCCUGCGCGU | 572 | hsa-miR-211 | UUCCCUUUGUCAUCCUUCGCCU |
| 92 | hsa-miR-660 | UACCCAUUGCAUAUCGGAGUUG | 573 | hsa-miR-210 | CUGUGCGUGUGACAGCGGCUGA |
| 93 | hsa-miR-659 | CUUGGUUCAGGGAGGGUCCCCA | 574 | hsa-miR-21* | CAACACCAGUCGAUGGGCUGU |
| 94 | hsa-miR-658 | GGCGGAGGGAAGUAGGUCCGUUGGU | 575 | hsa-miR-21 | UAGCUUAUCAGACUGAUGUUGA |
| 95 | hsa-miR-657 | GGCAGGUUCUCACCCUCUCUAGG | 576 | hsa-miR-20b* | ACUGUAGUAUGGGCACUUCCAG |
| 96 | hsa-miR-656 | AAUAUUAUACAGUCAACCUCU | 577 | hsa-miR-20b | CAAAGUGCUCAUAGUGCAGGUAG |
| 97 | hsa-miR-655 | AUAAUACAUGGUUAACCUCUUU | 578 | hsa-miR-20a* | ACUGCAUUAUGAGCACUUAAAG |
| 98 | hsa-miR-654-5p | UGGUGGGCCGCAGAACAUGUGC | 579 | hsa-miR-20a | UAAAGUGCUUAUAGUGCAGGUAG |
| 99 | hsa-miR-654-3p | UAUGUCUGCUGACCAUCACCUU | 580 | hsa-miR-208b | AUAAGACGAACAAAAGGUUUGU |

FIG. 1 (continued)

| SEQ ID | | | SEQ ID | | |
|---|---|---|---|---|---|
| 100 | hsa-miR-653 | GUGUUGAAACAAUCUCUACUG | 581 | hsa-miR-208a | AUAAGACGAGCAAAAAGCUUGU |
| 101 | hsa-miR-652 | AAUGGCGCCACUAGGGUUGUG | 582 | hsa-miR-206 | UGGAAUGUAAGGAAGUGUGUGG |
| 102 | hsa-miR-651 | UUUAGGAUAAGCUUGACUUUUG | 583 | hsa-miR-2054 | CUGUAAUAUAAAUUUAAUUUAUU |
| 103 | hsa-miR-650 | AGGAGGCAGCGCUCUCAGGAC | 584 | hsa-miR-2053 | GUGUUAAUUAAACCUCUAUUUAC |
| 104 | hsa-miR-649 | AAACCUGUGUUGUUCAAGAGUC | 585 | hsa-miR-2052 | UGUUUUGAUAACAGUAAUGU |
| 105 | hsa-miR-648 | AAGUGUGCAGGGCACUGGU | 586 | hsa-miR-205* | GAUUUCAGUGGAGUGAAGUUC |
| 106 | hsa-miR-647 | GUGGCUGCACUCACUUCCUUC | 587 | hsa-miR-205 | UCCUUCAUUCCACCGGAGUCUG |
| 107 | hsa-miR-646 | AAGCAGCUGCCUCUGAGGC | 588 | hsa-miR-204 | UUCCCUUUGUCAUCCUAUGCCU |
| 108 | hsa-miR-645 | UCUAGGCUGGUACUGCUGA | 589 | hsa-miR-203 | GUGAAAUGUUUAGGACCACUAG |
| 109 | hsa-miR-644 | AGUGUGGCUUUCUUAGAGC | 590 | hsa-miR-202* | UUCCUAUGCAUAUACUUCUUUG |
| 110 | hsa-miR-643 | ACUUGUAUGCUAGCUCAGGUAG | 591 | hsa-miR-202 | AGAGGUAUAGGGCAUGGGAA |
| 111 | hsa-miR-642 | GUCCCUCUCCAAAUGUGUCUUG | 592 | hsa-miR-200c* | CGUCUUACCCAGCAGUGUUUGG |
| 112 | hsa-miR-641 | AAAGACAUAGGAUAGAGUCACCUC | 593 | hsa-miR-200c | UAAUACUGCCGGGUAAUGAUGGA |
| 113 | hsa-miR-640 | AUGAUCCAGGAACCUGCCUCU | 594 | hsa-miR-200b* | CAUCUUACUGGGCAGCAUUGGA |
| 114 | hsa-miR-639 | AUCGCUGCGGUUGCGAGCGCUGU | 595 | hsa-miR-200b | UAAUACUGCCUGGUAAUGAUGA |
| 115 | hsa-miR-638 | AGGGAUCGCGGGCGGGUGGCGGCC U | 596 | hsa-miR-200a* | CAUCUUACCGGACAGUGCUGGA |
| 116 | hsa-miR-637 | ACUGGGGGCUUUCGGGCUCUGCGU | 597 | hsa-miR-200a | UAACACUGUCUGGUAACGAUGU |
| 117 | hsa-miR-636 | UGUGCUUGCUCGUCCCGCCCGCA | 598 | hsa-miR-19b-2* | AGUUUUGCAGGUUUGCAUUUCA |
| 118 | hsa-miR-635 | ACUUGGGCACUGAAACAAUGUCC | 599 | hsa-miR-19b-1* | AGUUUUGCAGGUUUGCAUCCAGC |
| 119 | hsa-miR-634 | AACCAGCACCCCAACUUUGGAC | 600 | hsa-miR-19b | UGUGCAAAUCCAUGCAAAACUGA |

FIG. 1 (continued)

| SEQ ID | | | SEQ ID | | |
|---|---|---|---|---|---|
| 120 | hsa-miR-633 | CUAAUAGUAUCUACCACAAUAAA | 601 | hsa-miR-19a* | AGUUUUGCAUAGUUGCACUACA |
| 121 | hsa-miR-632 | GUGUCUGCUUCCUGUGGGA | 602 | hsa-miR-19a | UGUGCAAAUCUAUGCAAAACUGA |
| 122 | hsa-miR-631 | AGACCUGGCCCAGACCUCAGC | 603 | hsa-miR-199b-5p | CCCAGUGUUUAGACUAUCUGUUC |
| 123 | hsa-miR-630 | AGUAUUCUGUACCAGGGAAGGU | 604 | hsa-miR-199b-3p | ACAGUAGUCUGCACAUUGGUUA |
| 124 | hsa-miR-629* | GUUCUCCCAACGUAAGCCCAGC | 605 | hsa-miR-199a-5p | CCCAGUGUUCAGACUACCUGUUC |
| 125 | hsa-miR-629 | UGGGUUUACGUUGGGAGAACU | 606 | hsa-miR-199a-3p | ACAGUAGUCUGCACAUUGGUUA |
| 126 | hsa-miR-628-5p | AUGCUGACAUAUUUACUAGAGG | 607 | hsa-miR-198 | GGUCCAGAGGGGAGAUAGGUUC |
| 127 | hsa-miR-628-3p | UCUAGUAAGAGUGGCAGUCGA | 608 | hsa-miR-1979 | CUCCCACUGCUUCACUUGACUA |
| 128 | hsa-miR-627 | GUGAGUCUCUAAGAAAAGAGGA | 609 | hsa-miR-1978 | GGUUUGGUCCUAGCCUUUCUA |
| 129 | hsa-miR-626 | AGCUGUCUGAAAAUGUCUU | 610 | hsa-miR-1977 | GAUUAGGGUGCUUAGCUGUUAA |
| 130 | hsa-miR-625* | GACUAUAGAACUUUCCCCCUCA | 611 | hsa-miR-1976 | CCUCCUGCCCUCCUUGCUGU |
| 131 | hsa-miR-625 | AGGGGGAAAGUUCUAUAGUCC | 612 | hsa-miR-1975 | CCCCCACAACCGCGCUUGACUAGCU |
| 132 | hsa-miR-624* | UAGUACCAGUACCUUGUGUUCA | 613 | hsa-miR-1974 | UGGUUGUAGUCCGUGCGAGAAUA |
| 133 | hsa-miR-624 | CACAAGGUAUUGGUAUUACCU | 614 | hsa-miR-1973 | ACCGUGCAAAGGUAGCAUA |
| 134 | hsa-miR-623 | AUCCCUUGCAGGGGCUGUUGGGU | 615 | hsa-miR-1972 | UCAGGCCAGGCACAGUGGCUCA |
| 135 | hsa-miR-622 | ACAGUCUGCUGAGGUUGGAGC | 616 | hsa-miR-197 | UUCACCACCUUCUCCACCCAGC |
| 136 | hsa-miR-621 | GGCUAGCAACAGCGCUUACCU | 617 | hsa-miR-196b* | UCGACAGCACGACACUGCCUUC |
| 137 | hsa-miR-620 | AUGGAGAUAGAUAUAGAAAU | 618 | hsa-miR-196b | UAGGUAGUUUCCUGUUGUUGGG |
| 138 | hsa-miR-619 | GACCUGGACAUGUUUGUGCCCAGU | 619 | hsa-miR-196a* | CGGCAACAAGAAACUGCCUGAG |

FIG. 1 (continued)

| SEQ ID | | | SEQ ID | | |
|---|---|---|---|---|---|
| 139 | hsa-miR-618 | AAACUCUACUUGUCCUUCUGAGU | 620 | hsa-miR-196a | UAGGUAGUUUCAUGUUGUUGGG |
| 140 | hsa-miR-617 | AGACUUCCCAUUUGAAGGUGGC | 621 | hsa-miR-195* | CCAAUAUUGGCUGUGCUGCUCC |
| 141 | hsa-miR-616* | ACUCAAAACCCUUCAGUGACUU | 622 | hsa-miR-195 | UAGCAGCACAGAAAUAUUGGC |
| 142 | hsa-miR-616 | AGUCAUUGGAGGGUUUGAGCAG | 623 | hsa-miR-194* | CCAGUGGGGCUGCUGUUAUCUG |
| 143 | hsa-miR-615-5p | GGGGGUCCCCGGUGCUCGGAUC | 624 | hsa-miR-194 | UGUAACAGCAACUCCAUGUGGA |
| 144 | hsa-miR-615-3p | UCCGAGCCUGGGUCUCCCUCUU | 625 | hsa-miR-193b* | CGGGGUUUUGAGGGCGAGAUGA |
| 145 | hsa-miR-614 | GAACGCCUGUUCUUGCCAGGUGG | 626 | hsa-miR-193b | AACUGGCCCUCAAAGUCCCGCU |
| 146 | hsa-miR-613 | AGGAAUGUUCCUUCUUUGCC | 627 | hsa-miR-193a-5p | UGGGUCUUUGCGGGCGAGAUGA |
| 147 | hsa-miR-612 | GCUGGGCAGGGCUUCUGAGCUCCU U | 628 | hsa-miR-193a-3p | AACUGGCCUACAAAGUCCCAGU |
| 148 | hsa-miR-611 | GCGAGGACCCCUCGGGGUCUGAC | 629 | hsa-miR-192* | CUGCCAAUUCCAUAGGUCACAG |
| 149 | hsa-miR-610 | UGAGCUAAAUGUGUGCUGGGA | 630 | hsa-miR-192 | CUGACCUAUGAAUUGACAGCC |
| 150 | hsa-miR-609 | AGGGUGUUUCUCUCAUCUCU | 631 | hsa-miR-1915* | ACCUUGCCUUGCUGCCCGGGCC |
| 151 | hsa-miR-608 | AGGGGUGGUGUUGGGACAGCUCCG U | 632 | hsa-miR-1915 | CCCCAGGGCGACGCGGCGGG |
| 152 | hsa-miR-607 | GUUCAAAUCCAGAUCUAUAAC | 633 | hsa-miR-1914* | GGAGGGGUCCCGCACUGGGAGG |
| 153 | hsa-miR-606 | AAACUACUGAAAAUCAAAGAU | 634 | hsa-miR-1914 | CCCUGUGCCCGGCCCACUUCUG |
| 154 | hsa-miR-605 | UAAAUCCCAUGGUGCCUUCUCCU | 635 | hsa-miR-1913 | UCUGCCCCCUCCGCUGCUGCCA |
| 155 | hsa-miR-604 | AGGCUGCGGAAUUCAGGAC | 636 | hsa-miR-1912 | UACCCAGAGCAUGCAGUGUGAA |
| 156 | hsa-miR-603 | CACACACUGCAAUUACUUUUGC | 637 | hsa-miR-1911* | CACCAGGCAUUGUGGUCUCC |
| 157 | hsa-miR-602 | GACACGGGCGACAGCUGCGGCCC | 638 | hsa-miR-1911 | UGAGUACCGCCAUGUCUGUUGGG |
| 158 | hsa-miR-601 | UGGUCUAGGAUUGUUGGAGGAG | 639 | hsa-miR-1910 | CCAGUCCUGUGCCUGCCGCCU |

FIG. 1 (continued)

| SEQ ID | | | SEQ ID | | |
|---|---|---|---|---|---|
| 159 | hsa-miR-600 | ACUUACAGACAAGAGCCUUGCUC | 640 | hsa-miR-191* | GCUGCGCUUGGAUUUCGUCCCC |
| 160 | hsa-miR-599 | GUUGUGUCAGUUUAUCAAAC | 641 | hsa-miR-191 | CAACGGAAUCCCAAAAGCAGCUG |
| 161 | hsa-miR-598 | UACGUCAUCGUUGUCAUCGUCA | 642 | hsa-miR-190b | UGAUAUGUUUGAUAUUGGGUU |
| 162 | hsa-miR-597 | UGUGUCACUCGAUGACCACUGU | 643 | hsa-miR-1909* | UGAGUGCCGGUGCCUGCCCUG |
| 163 | hsa-miR-596 | AAGCCUGCCCGGCUCCUCGGG | 644 | hsa-miR-1909 | CGCAGGGGCCGGGUGCUCACCG |
| 164 | hsa-miR-595 | GAAGUGUGCCGUGGUGUGUCU | 645 | hsa-miR-1908 | CGGCGGGGACGGCGAUUGGUC |
| 165 | hsa-miR-593* | AGGCACCAGCCAGGCAUUGCUCAGC | 646 | hsa-miR-190 | UGAUAUGUUUGAUAUAUUAGGU |
| 166 | hsa-miR-593 | UGUCUCUGCUGGGGUUUCU | 647 | hsa-miR-18b* | UGCCCUAAAUGCCCCUUCUGGC |
| 167 | hsa-miR-592 | UUGUGUCAAUAUGCGAUGAUGU | 648 | hsa-miR-18b | UAAGGUGCAUCUAGUGCAGUUAG |
| 168 | hsa-miR-591 | AGACCAUGGGUUCUCAUUGU | 649 | hsa-miR-18a* | ACUGCCCUAAGUGCUCCUUCUGG |
| 169 | hsa-miR-590-5p | GAGCUUAUUCAUAAAAGUGCAG | 650 | hsa-miR-18a | UAAGGUGCAUCUAGUGCAGAUAG |
| 170 | hsa-miR-590-3p | UAAUUUUAUGUAUAAGCUAGU | 651 | hsa-miR-188-5p | CAUCCCUUGCAUGGUGGAGGG |
| 171 | hsa-miR-589* | UCAGAACAAAUGCCGGUUCCCAGA | 652 | hsa-miR-188-3p | CUCCCACAUGCAGGGUUUGCA |
| 172 | hsa-miR-589 | UGAGAACCACGUCUGCUCUGAG | 653 | hsa-miR-187* | GGCUACAACACAGGACCCGGGC |
| 173 | hsa-miR-588 | UUGGCCACAAUGGGUUAGAAC | 654 | hsa-miR-187 | UCGUGUCUUGUGUUGCAGCCGG |
| 174 | hsa-miR-587 | UUUCCAUAGGUGAUGAGUCAC | 655 | hsa-miR-186* | GCCCAAAGGUGAAUUUUUUGGG |
| 175 | hsa-miR-586 | UAUGCAUUGUAUUUUUAGGUCC | 656 | hsa-miR-186 | CAAAGAAUUCUCCUUUUGGGCU |
| 176 | hsa-miR-585 | UGGGCGUAUCUGUAUGCUA | 657 | hsa-miR-185* | AGGGGCUGGCUUUCCUCUGGUC |
| 177 | hsa-miR-584 | UUAUGGUUUGCCUGGGACUGAG | 658 | hsa-miR-185 | UGGAGAGAAAGGCAGUUCCUGA |
| 178 | hsa-miR-583 | CAAAGAGGAAGGUCCCAUUAC | 659 | hsa-miR-184 | UGGACGGAGAACUGAUAAGGGU |

FIG. 1 (continued)

| SEQ ID | | | SEQ ID | | |
|---|---|---|---|---|---|
| 179 | hsa-miR-582-5p | UUACAGUUGUUCAACCAGUUACU | 660 | hsa-miR-183* | GUGAAUUACCGAAGGGCCAUAA |
| 180 | hsa-miR-582-3p | UAACUGGUUGAACAACUGAACC | 661 | hsa-miR-183 | UAUGGCACUGGUAGAAUUCACU |
| 181 | hsa-miR-581 | UCUUGUGUUCUCUAGAUCAGU | 662 | hsa-miR-1827 | UGAGGCAGUAGAUUGAAU |
| 182 | hsa-miR-580 | UUGAGAAUGAUGAAUCAUUAGG | 663 | hsa-miR-1826 | AUUGAUCAUCGACACUUCGAACGC AAU |
| 183 | hsa-miR-579 | UUCAUUUGGUAUAAACCGCGAUU | 664 | hsa-miR-1825 | UCCAGUGCCCUCCUCUCC |
| 184 | hsa-miR-578 | CUUCUUGUGCUCUAGGAUUGU | 665 | hsa-miR-182* | UGGUUCUAGACUUGCCAACUA |
| 185 | hsa-miR-577 | UAGAUAAAAUAUUGGUACCUG | 666 | hsa-miR-182 | UUUGGCAAUGGUAGAACUCACACU |
| 186 | hsa-miR-576-5p | AUUCUAAUUUCUCCACGUCUUU | 667 | hsa-miR-181d | AACAUUCAUUGUUGUCGGUGGGU |
| 187 | hsa-miR-576-3p | AAGAUGUGGAAAAAUUGGAAUC | 668 | hsa-miR-181c* | AACCAUCGACCGUUGAGUGGAC |
| 188 | hsa-miR-575 | GAGCCAGUUGGACAGGAGC | 669 | hsa-miR-181c | AACAUUCAACCUGUCGGUGAGU |
| 189 | hsa-miR-574-5p | UGAGUGUGUGUGUGUGAGUGUGU | 670 | hsa-miR-181b | AACAUUCAUUGCUGUCGGUGGGU |
| 190 | hsa-miR-574-3p | CACGCUCAUGCACACACCCACA | 671 | hsa-miR-181a-2* | ACCACUGACCGUUGACUGUACC |
| 191 | hsa-miR-573 | CUGAAGUGAUGUGUAACUGAUCAG | 672 | hsa-miR-181a* | ACCAUCGACCGUUGAUUGUACC |
| 192 | hsa-miR-572 | GUCCGCUCGGCGGUGGCCCA | 673 | hsa-miR-181a | AACAUUCAACGCUGUCGGUGAGU |
| 193 | hsa-miR-571 | UGAGUUGGCCAUCUGAGUGAG | 674 | hsa-miR-17* | ACUGCAGUGAAGGCACUUGUAG |
| 194 | hsa-miR-570 | CGAAAACAGCAAUUACCUUUGC | 675 | hsa-miR-17 | CAAAGUGCUUACAGUGCAGGUAG |
| 195 | hsa-miR-569 | AGUUAAUGAAUCCUGGAAAGU | 676 | hsa-miR-16-2* | CCAAUAUUACUGUGCUGCUUUA |
| 196 | hsa-miR-568 | AUGUAUAAAUGUAUACACAC | 677 | hsa-miR-16-1* | CCAGUAUUAACUGUGCUGCUGA |
| 197 | hsa-miR-567 | AGUAUGUUCUUCCAGGACAGAAC | 678 | hsa-miR-16 | UAGCAGCACGUAAAUAUUGGCG |
| 198 | hsa-miR-566 | GGGCGCCUGUGAUCCCAAC | 679 | hsa-miR-15b* | CGAAUCAUUAUUUGCUGCUCUA |

FIG. 1 (continued)

| SEQ ID | | | SEQ ID | | |
|---|---|---|---|---|---|
| 199 | hsa-miR-564 | AGGCACGGUGUCAGCAGGC | 680 | hsa-miR-15b | UAGCAGCACAUCAUGGUUUACA |
| 200 | hsa-miR-563 | AGGUUGACAUACGUUUCCC | 681 | hsa-miR-15a* | CAGGCCAUAUUGUGCUGCCUCA |
| 201 | hsa-miR-562 | AAAGUAGCUGUACCAUUUGC | 682 | hsa-miR-15a | UAGCAGCACAUAAUGGUUUGUG |
| 202 | hsa-miR-561 | CAAAGUUUAAGAUCCUUGAAGU | 683 | hsa-miR-155* | CUCCUACAUAUUAGCAUUAACA |
| 203 | hsa-miR-559 | UAAAGUAAAUAUGCACCAAAA | 684 | hsa-miR-155 | UUAAUGCUAAUCGUGAUAGGGGU |
| 204 | hsa-miR-558 | UGAGCUGCUGUACCAAAAU | 685 | hsa-miR-154* | AAUCAUACACGGUUGACCUAUU |
| 205 | hsa-miR-557 | GUUUGCACGGGUGGGCCUUGUCU | 686 | hsa-miR-154 | UAGGUUAUCCGUGUUGCCUUCG |
| 206 | hsa-miR-556-5p | GAUGAGCUCAUUGUAAUAUGAG | 687 | hsa-miR-1539 | UCCUGCGCGUCCCAGAUGCCC |
| 207 | hsa-miR-556-3p | AUAUUACCAUUAGCUCAUCUUU | 688 | hsa-miR-1538 | CGGCCCGGGCUGCUGCUGUUCCU |
| 208 | hsa-miR-555 | AGGGUAAGCUGAACCUCUGAU | 689 | hsa-miR-1537 | AAAACCGUCUAGUUACAGUUGU |
| 209 | hsa-miR-554 | GCUAGUCCUGACUCAGCCAGU | 690 | hsa-miR-153 | UUGCAUAGUCACAAAAGUGAUC |
| 210 | hsa-miR-553 | AAAACGGUGAGAUUUUGUUUU | 691 | hsa-miR-152 | UCAGUGCAUGACAGAACUUGG |
| 211 | hsa-miR-552 | AACAGGUGACUGGUUAGACAA | 692 | hsa-miR-151-5p | UCGAGGAGCUCACAGUCUAGU |
| 212 | hsa-miR-551b* | GAAAUCAAGCGUGGGUGAGACC | 693 | hsa-miR-151-3p | CUAGACUGAAGCUCCUUGAGG |
| 213 | hsa-miR-551b | GCGACCCAUACUUGGUUUCAG | 694 | hsa-miR-150* | CUGGUACAGGCCUGGGGGACAG |
| 214 | hsa-miR-551a | GCGACCCACUCUUGGUUUCCA | 695 | hsa-miR-150 | UCUCCCAACCCUUGUACCAGUG |
| 215 | hsa-miR-550* | UGUCUUACUCCCUCAGGCACAU | 696 | hsa-miR-149* | AGGGAGGGACGGGGGCUGUGC |
| 216 | hsa-miR-550 | AGUGCCUGAGGGAGUAAGAGCCC | 697 | hsa-miR-149 | UCUGGCUCCGUGUCUUCACUCCC |
| 217 | hsa-miR-549 | UGACAACUAUGGAUGAGCUCU | 698 | hsa-miR-148b* | AAGUUCUGUUAUACACUCAGGC |
| 218 | hsa-miR-548q | GCUGGUGCAAAAGUAAUGGCGG | 699 | hsa-miR-148b | UCAGUGCAUCACAGAACUUUGU |

FIG. 1 (continued)

| SEQ ID | | | SEQ ID | | |
|---|---|---|---|---|---|
| 219 | hsa-miR-548p | UAGCAAAAACUGCAGUUACUUU | 700 | hsa-miR-148a* | AAAGUUCUGAGACACUCCGACU |
| 220 | hsa-miR-548o | CCAAAACUGCAGUUACUUUUGC | 701 | hsa-miR-148a | UCAGUGCACUACAGAACUUUGU |
| 221 | hsa-miR-548n | CAAAAGUAAUUGUGGAUUUUGU | 702 | hsa-miR-147b | GUGUGCGGAAAUGCUUCUGCUA |
| 222 | hsa-miR-548m | CAAAGGUAUUUGUGGUUUUUG | 703 | hsa-miR-1471 | GCCCGCGUGUGGAGCCAGGUGU |
| 223 | hsa-miR-548l | AAAAGUAUUUGCGGGUUUUGUC | 704 | hsa-miR-1470 | GCCCUCCGCCCGUGCACCCCG |
| 224 | hsa-miR-548k | AAAAGUACUUGCGGAUUUUGCU | 705 | hsa-miR-147 | GUGUGUGGAAAUGCUUCUGC |
| 225 | hsa-miR-548j | AAAAGUAAUUGCGGUCUUUGGU | 706 | hsa-miR-146b-5p | UGAGAACUGAAUUCCAUAGGCU |
| 226 | hsa-miR-548i | AAAAGUAAUUGCGGAUUUUGCC | 707 | hsa-miR-146b-3p | UGCCCUGUGGACUCAGUUCUGG |
| 227 | hsa-miR-548h | AAAAGUAAUCGCGGUUUUUGUC | 708 | hsa-miR-146a* | CCUCUGAAAUUCAGUUCUUCAG |
| 228 | hsa-miR-548g | AAAACUGUAAUUACUUUUGUAC | 709 | hsa-miR-146a | UGAGAACUGAAUUCCAUGGGUU |
| 229 | hsa-miR-548f | AAAAACUGUAAUUACUUUU | 710 | hsa-miR-1469 | CUCGGCGCGGGGCGCGGGCUCC |
| 230 | hsa-miR-548e | AAAAACUGAGACUACUUUUGCA | 711 | hsa-miR-1468 | CUCCGUUUGCCUGUUUCGCUG |
| 231 | hsa-miR-548d-5p | AAAAGUAAUUGUGGUUUUUGCC | 712 | hsa-miR-145* | GGAUUCCUGGAAAUACUGUUCU |
| 232 | hsa-miR-548d-3p | CAAAAACCACAGUUUCUUUUGC | 713 | hsa-miR-145 | GUCCAGUUUUCCCAGGAAUCCCU |
| 233 | hsa-miR-548c-5p | AAAAGUAAUUGCGGUUUUUGCC | 714 | hsa-miR-144* | GGAUAUCAUCAUAUACUGUAAG |
| 234 | hsa-miR-548c-3p | CAAAAAUCUCAAUUACUUUUGC | 715 | hsa-miR-144 | UACAGUAUAGAUGAUGUACU |
| 235 | hsa-miR-548b-5p | AAAAGUAAUUGUGGUUUUGGCC | 716 | hsa-miR-143* | GGUGCAGUGCUGCAUCUCUGGU |
| 236 | hsa-miR-548b-3p | CAAGAACCUCAGUUGCUUUUGU | 717 | hsa-miR-143 | UGAGAUGAAGCACUGUAGCUC |
| 237 | hsa-miR-548a-5p | AAAAGUAAUUGCGAGUUUUACC | 718 | hsa-miR-142-5p | CAUAAAGUAGAAAGCACUACU |
| 238 | hsa-miR-548a-3p | CAAAACUGGCAAUUACUUUUGC | 719 | hsa-miR-142- | UGUAGUGUUUCCUACUUUAUGGA |

FIG. 1 (continued)

| SEQ ID | | | SEQ ID | | |
|---|---|---|---|---|---|
| | | | | 3p | |
| 239 | hsa-miR-545* | UCAGUAAAUGUUUAUUAGAUGA | 720 | hsa-miR-141* | CAUCUUCCAGUACAGUGUUGGA |
| 240 | hsa-miR-545 | UCAGCAAACAUUUAUUGUGUGC | 721 | hsa-miR-141 | UAACACUGUCUGGUAAAGAUGG |
| 241 | hsa-miR-544 | AUUCUGCAUUUUUAGCAAGUUC | 722 | hsa-miR-140-5p | CAGUGGUUUUACCCUAUGGUAG |
| 242 | hsa-miR-543 | AAACAUUCGCGGUGCACUUCUU | 723 | hsa-miR-140-3p | UACCACAGGGUAGAACCACGG |
| 243 | hsa-miR-542-5p | UCGGGGAUCAUCAUGUCACGAGA | 724 | hsa-miR-139-5p | UCUACAGUGCACGUGUCUCCAG |
| 244 | hsa-miR-542-3p | UGUGACAGAUUGAUAACUGAAA | 725 | hsa-miR-139-3p | GGAGACGCGGCCCUGUUGGAGU |
| 245 | hsa-miR-541* | AAAGGAUUCUGCUGUCGGUCCCACU | 726 | hsa-miR-138-2* | GCUAUUUCACGACACCAGGGUU |
| 246 | hsa-miR-541 | UGGUGGGCACAGAAUCUGGACU | 727 | hsa-miR-138-1* | GCUACUUCACAACACCAGGGCC |
| 247 | hsa-miR-539 | GGAGAAAUUAUCCUUGGUGUGU | 728 | hsa-miR-138 | AGCUGGUGUUGUGAAUCAGGCCG |
| 248 | hsa-miR-532-5p | CAUGCCUUGAGUGUAGGACCGU | 729 | hsa-miR-137 | UUAUUGCUUAAGAAUACGCGUAG |
| 249 | hsa-miR-532-3p | CCUCCCACACCCAAGGCUUGCA | 730 | hsa-miR-136* | CAUCAUCGUCUCAAAUGAGUCU |
| 250 | hsa-miR-527 | CUGCAAAGGGAAGCCCUUUC | 731 | hsa-miR-136 | ACUCCAUUUGUUUUGAUGAUGGA |
| 251 | hsa-miR-526b* | GAAAGUGCUUCCUUUUAGAGGC | 732 | hsa-miR-135b* | AUGUAGGGCUAAAAGCCAUGGG |
| 252 | hsa-miR-526b | CUCUUGAGGGAAGCACUUUCUGU | 733 | hsa-miR-135b | UAUGGCUUUUCAUUCCUAUGUGA |
| 253 | hsa-miR-526a | CUCUAGAGGGAAGCACUUUCUG | 734 | hsa-miR-135a* | UAUAGGGAUUGGAGCCGUGGCG |
| 254 | hsa-miR-525-5p | CUCCAGAGGGAUGCACUUUCU | 735 | hsa-miR-135a | UAUGGCUUUUUAUUCCUAUGUGA |
| 255 | hsa-miR-525-3p | GAAGGCGCUUCCCUUUAGAGCG | 736 | hsa-miR-134 | UGUGACUGGUUGACCAGAGGGG |
| 256 | hsa-miR-524-5p | CUACAAAGGGAAGCACUUUCUC | 737 | hsa-miR-133b | UUUGGUCCCCUUCAACCAGCUA |

FIG. 1 (continued)

| SEQ ID | | | SEQ ID | | |
|---|---|---|---|---|---|
| 257 | hsa-miR-524-3p | GAAGGCGCUUCCCUUUGGAGU | 738 | hsa-miR-133a | UUUGGUCCCCUUCAACCAGCUG |
| 258 | hsa-miR-523* | CUCUAGAGGGAAGCGCUUUCUG | 739 | hsa-miR-1324 | CCAGACAGAAUUCUAUGCACUUUC |
| 259 | hsa-miR-523 | GAACGCGCUUCCCUAUAGAGGGU | 740 | hsa-miR-1323 | UCAAAACUGAGGGGCAUUUUCU |
| 260 | hsa-miR-522* | CUCUAGAGGGAAGCGCUUUCUG | 741 | hsa-miR-1322 | GAUGAUGCUGCUGAUGCUG |
| 261 | hsa-miR-522 | AAAAUGGUUCCCUUUAGAGUGU | 742 | hsa-miR-1321 | CAGGGAGGUGAAUGUGAU |
| 262 | hsa-miR-521 | AACGCACUUCCCUUUAGAGUGU | 743 | hsa-miR-132* | ACCGUGGCUUUCGAUUGUUACU |
| 263 | hsa-miR-520h | ACAAAGUGCUUCCCUUUAGAGU | 744 | hsa-miR-132 | UAACAGUCUACAGCCAUGGUCG |
| 264 | hsa-miR-520g | ACAAAGUGCUUCCCUUUAGAGUGU | 745 | hsa-miR-130b* | ACUCUUUCCCUGUUGCACUAC |
| 265 | hsa-miR-520f | AAGUGCUUCCUUUUAGAGGGUU | 746 | hsa-miR-130b | CAGUGCAAUGAUGAAAGGGCAU |
| 266 | hsa-miR-520e | AAAGUGCUUCCUUUUUGAGGG | 747 | hsa-miR-130a* | UUCACAUUGUGCUACUGUCUGC |
| 267 | hsa-miR-520d-5p | CUACAAAGGGAAGCCCUUUC | 748 | hsa-miR-130a | CAGUGCAAUGUUAAAAGGGCAU |
| 268 | hsa-miR-520d-3p | AAAGUGCUUCUCUUUGGUGGGU | 749 | hsa-miR-1308 | GCAUGGGUGGUUCAGUGG |
| 269 | hsa-miR-520c-5p | CUCUAGAGGGAAGCACUUUCUG | 750 | hsa-miR-1307 | ACUCGGCGUGGCGUCGGUCGUG |
| 270 | hsa-miR-520c-3p | AAAGUGCUUCCUUUUAGAGGGU | 751 | hsa-miR-1306 | ACGUUGGCUCUGGUGGUG |
| 271 | hsa-miR-520b | AAAGUGCUUCCUUUUAGAGGG | 752 | hsa-miR-1305 | UUUUCAACUCUAAUGGGAGAGA |
| 272 | hsa-miR-520a-5p | CUCCAGAGGGAAGUACUUUCU | 753 | hsa-miR-1304 | UUUGAGGCUACAGUGAGAUGUG |
| 273 | hsa-miR-520a-3p | AAAGUGCUUCCCUUUGGACUGU | 754 | hsa-miR-1303 | UUUAGAGACGGGGUCUUGCUCU |
| 274 | hsa-miR-519e* | UUCUCCAAAAGGGAGCACUUUC | 755 | hsa-miR-1302 | UUGGGACAUACUUAUGCUAAA |
| 275 | hsa-miR-519e | AAGUGCCUCCUUUUAGAGUGUU | 756 | hsa-miR-1301 | UUGCAGCUGCCUGGGAGUGACUU C |
| 276 | hsa-miR-519d | CAAAGUGCCUCCCUUUAGAGUG | 757 | hsa-miR-1299 | UUCUGGAAUUCUGUGUGAGGGA |

FIG. 1 (continued)

| SEQ ID | | | SEQ ID | | |
|---|---|---|---|---|---|
| 277 | hsa-miR-519c-5p | CUCUAGAGGGAAGCGCUUUCUG | 758 | hsa-miR-1298 | UUCAUUCGGCUGUCCAGAUGUA |
| 278 | hsa-miR-519c-3p | AAAGUGCAUCUUUUUAGAGGAU | 759 | hsa-miR-1297 | UUCAAGUAAUUCAGGUG |
| 279 | hsa-miR-519b-5p | CUCUAGAGGGAAGCGCUUUCUG | 760 | hsa-miR-1296 | UUAGGGCCCUGGCUCCAUCUCC |
| 280 | hsa-miR-519b-3p | AAAGUGCAUCCUUUUAGAGGUU | 761 | hsa-miR-129-5p | CUUUUUGCGGUCUGGGCUUGC |
| 281 | hsa-miR-519a* | CUCUAGAGGGAAGCGCUUUCUG | 762 | hsa-miR-1295 | UUAGGCCGCAGAUCUGGGUGA |
| 282 | hsa-miR-519a | AAAGUGCAUCCUUUUAGAGUGU | 763 | hsa-miR-1294 | UGUGAGGUUGGCAUUGUUGUCU |
| 283 | hsa-miR-518f* | CUCUAGAGGGAAGCACUUUCUC | 764 | hsa-miR-129-3p | AAGCCCUUACCCCAAAAAGCAU |
| 284 | hsa-miR-518f | GAAAGCGCUUCUCUUUAGAGG | 765 | hsa-miR-1293 | UGGGUGGUCUGGAGAUUUGUGC |
| 285 | hsa-miR-518e* | CUCUAGAGGGAAGCGCUUUCUG | 766 | hsa-miR-1292 | UGGGAACGGGUUCCGGCAGACGCUG |
| 286 | hsa-miR-518e | AAAGCGCUUCCCUUCAGAGUG | 767 | hsa-miR-1291 | UGGCCCUGACUGAAGACCAGCAGU |
| 287 | hsa-miR-518d-5p | CUCUAGAGGGAAGCACUUUCUG | 768 | hsa-miR-1290 | UGGAUUUUUGGAUCAGGGA |
| 288 | hsa-miR-518d-3p | CAAAGCGCUUCCCUUUGGAGC | 769 | hsa-miR-129* | AAGCCCUUACCCCAAAAAGUAU |
| 289 | hsa-miR-518c* | UCUCUGGAGGGAAGCACUUUCUG | 770 | hsa-miR-1289 | UGGAGUCCAGGAAUCUGCAUUUU |
| 290 | hsa-miR-518c | CAAAGCGCUUCUCUUUAGAGUGU | 771 | hsa-miR-1288 | UGGACUGCCCUGAUCUGGAGA |
| 291 | hsa-miR-518b | CAAAGCGCUCCCCUUUAGAGGU | 772 | hsa-miR-1287 | UGCUGGAUCAGUGGUUCGAGUC |
| 292 | hsa-miR-518a-5p | CUGCAAAGGGAAGCCCUUUC | 773 | hsa-miR-1286 | UGCAGGACCAAGAUGAGCCCU |
| 293 | hsa-miR-518a-3p | GAAAGCGCUUCCCUUUGCUGGA | 774 | hsa-miR-1285 | UCUGGGCAACAAAGUGAGACCU |
| 294 | hsa-miR-517c | AUCGUGCAUCCUUUUAGAGUGU | 775 | hsa-miR-1284 | UCUAUACAGACCCUGGCUUUUC |
| 295 | hsa-miR-517b | UCGUGCAUCCCUUUAGAGUGUU | 776 | hsa-miR-1283 | UCUACAAAGGAAAGCGCUUUCU |
| 296 | hsa-miR-517a | AUCGUGCAUCCCUUUAGAGUGU | 777 | hsa-miR-1282 | UCGUUUGCCUUUUUCUGCUU |

FIG. 1 (continued)

| SEQ ID | | | SEQ ID | | |
|---|---|---|---|---|---|
| 297 | hsa-miR-517* | CCUCUAGAUGGAAGCACUGUCU | 778 | hsa-miR-1281 | UCGCCUCCUCCUCUCCC |
| 298 | hsa-miR-516b* | UGCUUCCUUUCAGAGGGU | 779 | hsa-miR-1280 | UCCCACCGCUGCCACCC |
| 299 | hsa-miR-516b | AUCUGGAGGUAAGAAGCACUUU | 780 | hsa-miR-128 | UCACAGUGAACCGGUCUCUUU |
| 300 | hsa-miR-516a-5p | UUCUCGAGGAAAGAAGCACUUUC | 781 | hsa-miR-1279 | UCAUAUUGCUUCUUUCU |
| 301 | hsa-miR-516a-3p | UGCUUCCUUUCAGAGGGU | 782 | hsa-miR-1278 | UAGUACUGUGCAUAUCAUCUAU |
| 302 | hsa-miR-515-5p | UUCUCCAAAAGAAAGCACUUUCUG | 783 | hsa-miR-1277 | UACGUAGAUAUAUAUGUAUUUU |
| 303 | hsa-miR-515-3p | GAGUGCCUUCUUUUGGAGCGUU | 784 | hsa-miR-1276 | UAAAGAGCCCUGUGGAGACA |
| 304 | hsa-miR-514 | AUUGACACUUCUGUGAGUAGA | 785 | hsa-miR-127-5p | CUGAAGCUCAGAGGGCUCUGAU |
| 305 | hsa-miR-513c | UUCUCAAGGAGGUGUCGUUUAU | 786 | hsa-miR-1275 | GUGGGGGAGAGGCUGUC |
| 306 | hsa-miR-513b | UUCACAAGGAGGUGUCAUUUAU | 787 | hsa-miR-1274b | UCCCUGUUCGGGCGCCA |
| 307 | hsa-miR-513a-5p | UUCACAGGGAGGUGUCAU | 788 | hsa-miR-1274a | GUCCCUGUUCAGGCGCCA |
| 308 | hsa-miR-513a-3p | UAAAUUUCACCUUUCUGAGAAGG | 789 | hsa-miR-127-3p | UCGGAUCCGUCUGAGCUUGGCU |
| 309 | hsa-miR-512-5p | CACUCAGCCUUGAGGGCACUUUC | 790 | hsa-miR-1273 | GGGCGACAAAGCAAGACUCUUUCUU |
| 310 | hsa-miR-512-3p | AAGUGCUGUCAUAGCUGAGGUC | 791 | hsa-miR-1272 | GAUGAUGAUGGCAGCAAAUUCUGAAA |
| 311 | hsa-miR-511 | GUGUCUUUUGCUCUGCAGUCA | 792 | hsa-miR-1271 | CUUGGCACCUAGCAAGCACUCA |
| 312 | hsa-miR-510 | UACUCAGGAGAGUGGCAAUCAC | 793 | hsa-miR-1270 | CUGGAGAUAUGGAAGAGCUGUGU |
| 313 | hsa-miR-509-5p | UACUGCAGACAGUGGCAAUCA | 794 | hsa-miR-1269 | CUGGACUGAGCCGUGCUACUGG |
| 314 | hsa-miR-509-3p | UGAUUGGUACGUCUGUGGGUAG | 795 | hsa-miR-1268 | CGGGCGUGGUGGUGGGG |
| 315 | hsa-miR-509-3-5p | UACUGCAGACGUGGCAAUCAUG | 796 | hsa-miR-1267 | CCUGUUGAAGUGUAAUCCCCA |

FIG. 1 (continued)

| SEQ ID | | | SEQ ID | | |
|---|---|---|---|---|---|
| 316 | hsa-miR-508-5p | UACUCCAGAGGGCGUCACUCAUG | 797 | hsa-miR-1266 | CCUCAGGGCUGUAGAACAGGGCU |
| 317 | hsa-miR-508-3p | UGAUUGUAGCCUUUUGGAGUAGA | 798 | hsa-miR-1265 | CAGGAUGUGGUCAAGUGUUGUU |
| 318 | hsa-miR-507 | UUUUGCACCUUUUGGAGUGAA | 799 | hsa-miR-1264 | CAAGUCUUAUUUGAGCACCUGUU |
| 319 | hsa-miR-506 | UAAGGCACCCUUCUGAGUAGA | 800 | hsa-miR-1263 | AUGGUACCCUGGCAUACUGAGU |
| 320 | hsa-miR-505* | GGGAGCCAGGAAGUAUUGAUGU | 801 | hsa-miR-1262 | AUGGGUGAAUUUGUAGAAGGAU |
| 321 | hsa-miR-505 | CGUCAACACUUGCUGGUUUCCU | 802 | hsa-miR-1261 | AUGGAUAAGGCUUUGGCUU |
| 322 | hsa-miR-504 | AGACCCUGGUCUGCACUCUAUC | 803 | hsa-miR-1260 | AUCCCACCUCUGCCACCA |
| 323 | hsa-miR-503 | UAGCAGCGGGAACAGUUCUGCAG | 804 | hsa-miR-126* | CAUUAUUACUUUUGGUACGCG |
| 324 | hsa-miR-502-5p | AUCCUUGCUAUCUGGGUGCUA | 805 | hsa-miR-126 | UCGUACCGUGAGUAAUAAUGCG |
| 325 | hsa-miR-502-3p | AAUGCACCUGGGCAAGGAUUCA | 806 | hsa-miR-125b-2* | UCACAAGUCAGGCUCUUGGGAC |
| 326 | hsa-miR-501-5p | AAUCCUUUGUCCCUGGGUGAGA | 807 | hsa-miR-125b-1* | ACGGGUUAGGCUCUUGGGAGCU |
| 327 | hsa-miR-501-3p | AAUGCACCCGGGCAAGGAUUCU | 808 | hsa-miR-125b | UCCCUGAGACCCUAACUUGUGA |
| 328 | hsa-miR-500* | AUGCACCUGGGCAAGGAUUCUG | 809 | hsa-miR-125a-5p | UCCCUGAGACCCUUUAACCUGUGA |
| 329 | hsa-miR-500 | UAAUCCUUGCUACCUGGGUGAGA | 810 | hsa-miR-125a-3p | ACAGGUGAGGUUCUUGGGAGCC |
| 330 | hsa-miR-499-5p | UUAAGACUUGCAGUGAUGUUU | 811 | hsa-miR-1259 | AUAUAUGAUGACUUAGCUUUU |
| 331 | hsa-miR-499-3p | AACAUCACAGCAAGUCUGUGCU | 812 | hsa-miR-1258 | AGUUAGGAUUAGGUCGUGGAA |
| 332 | hsa-miR-498 | UUUCAAGCCAGGGGGCGUUUUUC | 813 | hsa-miR-1257 | AGUGAAUGAUGGGUUCUGACC |
| 333 | hsa-miR-497* | CAAACCACACUGUGGUGUUAGA | 814 | hsa-miR-1256 | AGGCAUUGACUUCUCACUAGCU |
| 334 | hsa-miR-497 | CAGCAGCACACUGUGGUUUGU | 815 | hsa-miR-1255b | CGGAUGAGCAAAGAAAGUGGUU |

FIG. 1 (continued)

| SEQ ID | | | SEQ ID | | |
|---|---|---|---|---|---|
| 335 | hsa-miR-496 | UGAGUAUUACAUGGCCAAUCUC | 816 | hsa-miR-1255a | AGGAUGAGCAAAGAAAGUAGAUU |
| 336 | hsa-miR-495 | AAACAAACAUGGUGCACUUCUU | 817 | hsa-miR-1254 | AGCCUGGAAGCUGGAGCCUGCAG U |
| 337 | hsa-miR-494 | UGAAACAUACACGGGAAACCUC | 818 | hsa-miR-1253 | AGAGAAGAAGAUCAGCCUGCA |
| 338 | hsa-miR-493* | UUGUACAUGGUAGGCUUUCAUU | 819 | hsa-miR-1252 | AGAAGGAAAUUGAAUUCAUUUA |
| 339 | hsa-miR-493 | UGAAGGUCUACUGUGUGCCAGG | 820 | hsa-miR-1251 | ACUCUAGCUGCCAAAGGCGCU |
| 340 | hsa-miR-492 | AGGACCUGCGGGACAAGAUUCUU | 821 | hsa-miR-1250 | ACGGUGCUGGAUGUGGCCUUU |
| 341 | hsa-miR-491-5p | AGUGGGGAACCCUUCCAUGAGG | 822 | hsa-miR-1249 | ACGCCCUUCCCCCCCUUCUUCA |
| 342 | hsa-miR-491-3p | CUUAUGCAAGAUUCCCUUCUAC | 823 | hsa-miR-1248 | ACCUUCUUGUAUAAGCACUGUGCU AAA |
| 343 | hsa-miR-490-5p | CCAUGGAUCUCCAGGUGGGU | 824 | hsa-miR-1247 | ACCCGUCCCGUUCGUCCCCGGA |
| 344 | hsa-miR-490-3p | CAACCUGGAGGACUCCAUGCUG | 825 | hsa-miR-1246 | AAUGGAUUUUUGGAGCAGG |
| 345 | hsa-miR-489 | GUGACAUCACAUAUACGGCAGC | 826 | hsa-miR-1245 | AAGUGAUCUAAAGGCCUACAU |
| 346 | hsa-miR-488* | CCCAGAUAAUGGCACUCUCAA | 827 | hsa-miR-1244 | AAGUAGUUGGUUUGUAUGAGAUG GUU |
| 347 | hsa-miR-488 | UUGAAAGGCUAUUUCUUGGUC | 828 | hsa-miR-1243 | AACUGGAUCAAUUAUAGGAGUG |
| 348 | hsa-miR-487b | AAUCGUACAGGGUCAUCCACUU | 829 | hsa-miR-124* | CGUGUUCACAGCGGACCUUGAU |
| 349 | hsa-miR-487a | AAUCAUACAGGGACAUCCAGUU | 830 | hsa-miR-124 | UAAGGCACGCGGUGAAUGCC |
| 350 | hsa-miR-486-5p | UCCUGUACUGAGCUGCCCCGAG | 831 | hsa-miR-1238 | CUUCCUCGUCUGUCUGCCCC |
| 351 | hsa-miR-486-3p | CGGGGCAGCUCAGUACAGGAU | 832 | hsa-miR-1237 | UCCUUCUGCUCCGUCCCCCAG |
| 352 | hsa-miR-485-5p | AGAGGCUGGCCGUGAUGAAUUC | 833 | hsa-miR-1236 | CCUCUUCCCCUUGUCUCUCCAG |
| 353 | hsa-miR-485-3p | GUCAUACACGGCUCUCCUCUCU | 834 | hsa-miR-1234 | UCGGCCUGACCACCCACCCCAC |
| 354 | hsa-miR-484 | UCAGGCUCAGUCCCCUCCCGAU | 835 | hsa-miR-1233 | UGAGCCCUGUCCUCCCGCAG |

FIG. 1 (continued)

| SEQ ID | | | SEQ ID | | |
|---|---|---|---|---|---|
| 355 | hsa-miR-483-5p | AAGACGGGAGGAAAGAAGGGAG | 836 | hsa-miR-1231 | GUGUCUGGGCGGACAGCUGC |
| 356 | hsa-miR-483-3p | UCACUCCUCUCCUCCCGUCUU | 837 | hsa-miR-1229 | CUCUCACCACUGCCCUCCCACAG |
| 357 | hsa-miR-455-5p | UAUGUGCCUUUGGACUACAUCG | 838 | hsa-miR-1228* | GUGGGCGGGGGCAGGUGUGUG |
| 358 | hsa-miR-455-3p | GCAGUCCAUGGGCAUAUACAC | 839 | hsa-miR-1228 | UCACACCUGCCUCGCCCCCC |
| 359 | hsa-miR-454* | ACCCUAUCAAUAUUGUCUCUGC | 840 | hsa-miR-1227 | CGUGCCACCCUUUUCCCCAG |
| 360 | hsa-miR-454 | UAGUGCAAUAUUGCUUAUAGGGU | 841 | hsa-miR-1226* | GUGAGGGCAUGCAGGCCUGGAUG GGG |
| 361 | hsa-miR-453 | AGGUUGUCCGUGGUGAGUUCGCA | 842 | hsa-miR-1226 | UCACCAGCCCUGUGUUCCCUAG |
| 362 | hsa-miR-452* | CUCAUCUGCAAAGAAGUAAGUG | 843 | hsa-miR-1225-5p | GUGGGUACGGCCCAGUGGGGGG |
| 363 | hsa-miR-452 | AACUGUUUGCAGAGGAAACUGA | 844 | hsa-miR-1225-3p | UGAGCCCCUGUGCCGCCCCCAG |
| 364 | hsa-miR-451 | AAACCGUUACCAUUACUGAGUU | 845 | hsa-miR-1224-5p | GUGAGGACUCGGGAGGUGG |
| 365 | hsa-miR-450b-5p | UUUUGCAAUAUGUUCCUGAAUA | 846 | hsa-miR-1224-3p | CCCCACCUCCUCUCUCCUCAG |
| 366 | hsa-miR-450b-3p | UUGGGAUCAUUUUGCAUCCAUA | 847 | hsa-miR-122* | AACGCCAUUAUCACACUAAAUA |
| 367 | hsa-miR-450a | UUUUGCGAUGUGUUCCUAAUAU | 848 | hsa-miR-122 | UGGAGUGUGACAAUGGUGUUUG |
| 368 | hsa-miR-449c* | UUGCUAGUUGCACUCCUCUCUGU | 849 | hsa-miR-1208 | UCACUGUUCAGACAGGCGGA |
| 369 | hsa-miR-449c | UAGGCAGUGUAUUGCUAGCGGCUG U | 850 | hsa-miR-1207-5p | UGGCAGGGAGGCUGGGAGGGG |
| 370 | hsa-miR-449b* | CAGCCACAACUACCCUGCCACU | 851 | hsa-miR-1207-3p | UCAGCUGGCCCUCAUUUC |
| 371 | hsa-miR-449b | AGGCAGUGUAUUGUUAGCUGGC | 852 | hsa-miR-1206 | UGUUCAUGUAGAUGUUUAAGC |
| 372 | hsa-miR-449a | UGGCAGUGUAUUGUUAGCUGGU | 853 | hsa-miR-1205 | UCUGCAGGGUUUGCUUUGAG |

FIG. 1 (continued)

| SEQ ID | | | SEQ ID | | |
|---|---|---|---|---|---|
| 373 | hsa-miR-448 | UUGCAUAUGUAGGAUGUCCCAU | 854 | hsa-miR-1204 | UCGUGGCCUGGUCUCCAUUAU |
| 374 | hsa-miR-433 | AUCAUGAUGGGCUCCUCGGUGU | 855 | hsa-miR-1203 | CCCGGAGCCAGGAUGCAGCUC |
| 375 | hsa-miR-432* | CUGGAUGGCUCCUCCAUGUCU | 856 | hsa-miR-1202 | GUGCCAGCUGCAGUGGGGGAG |
| 376 | hsa-miR-432 | UCUUGGAGUAGGUCAUUGGGUGG | 857 | hsa-miR-1201 | AGCCUGAUUAAACACAUGCUCUGA |
| 377 | hsa-miR-431* | CAGGUCGUCUUGCAGGGCUUCU | 858 | hsa-miR-1200 | CUCCUGAGCCAUUCUGAGCCUC |
| 378 | hsa-miR-431 | UGUCUUGCAGGCCGUCAUGCA | 859 | hsa-miR-1197 | UAGGACACAUGGUCUACUUCU |
| 379 | hsa-miR-429 | UAAUACUGUCUGGUAAAACCGU | 860 | hsa-miR-1185 | AGAGGAUACCCUUUGUAUGUU |
| 380 | hsa-miR-425* | AUCGGGAAUGUCGUGUCCGCCC | 861 | hsa-miR-1184 | CCUGCAGCGACUUGAUGGCUUCC |
| 381 | hsa-miR-425 | AAUGACACGAUCACUCCCGUUGA | 862 | hsa-miR-1183 | CACUGUAGGUGAUGGUGAGAGUG GGCA |
| 382 | hsa-miR-424* | CAAAACGUGAGGCGCUGCUAU | 863 | hsa-miR-1182 | GAGGGUCUUGGGAGGGAUGUGAC |
| 383 | hsa-miR-424 | CAGCAGCAAUUCAUGUUUUGAA | 864 | hsa-miR-1181 | CCGUCGCCGCCACCCGAGCCG |
| 384 | hsa-miR-423-5p | UGAGGGGCAGAGAGCGAGACUUU | 865 | hsa-miR-1180 | UUUCCGGCUCGCGUGGGUGUGU |
| 385 | hsa-miR-423-3p | AGCUCGGUCUGAGGCCCCUCAGU | 866 | hsa-miR-1179 | AAGCAUUCUUUCAUUGGUUGG |
| 386 | hsa-miR-422a | ACUGGACUUAGGGUCAGAAGGC | 867 | hsa-miR-1178 | UUGCUCACUGUUCUUCCCUAG |
| 387 | hsa-miR-421 | AUCAACAGACAUUAAUUGGGCGC | 868 | hsa-miR-10b* | ACAGAUUCGAUUCUAGGGGAAU |
| 388 | hsa-miR-412 | ACUUCACCUGGUCCACUAGCCGU | 869 | hsa-miR-10b | UACCCUGUAGAACCGAAUUUGUG |
| 389 | hsa-miR-411* | UAUGUAACACGGUCCACUAACC | 870 | hsa-miR-10a* | CAAAUUCGUAUCUAGGGGAAUA |
| 390 | hsa-miR-411 | UAGUAGACCGUAUAGCGUACG | 871 | hsa-miR-10a | UACCCUGUAGAUCCGAAUUUGUG |
| 391 | hsa-miR-410 | AAUAUAACACAGAUGGCCUGU | 872 | hsa-miR-107 | AGCAGCAUUGUACAGGGCUAUCA |
| 392 | hsa-miR-409-5p | AGGUUACCCGAGCAACUUUGCAU | 873 | hsa-miR-106b* | CCGCACUGUGGGUACUUGCUGC |

FIG. 1 (continued)

| SEQ ID | | | SEQ ID | | |
|---|---|---|---|---|---|
| 393 | hsa-miR-409-3p | GAAUGUUGCUCGGUGAACCCCU | 874 | hsa-miR-106b | UAAAGUGCUGACAGUGCAGAU |
| 394 | hsa-miR-384 | AUUCCUAGAAAUUGUUCAUA | 875 | hsa-miR-106a* | CUGCAAUGUAAGCACUUCUUAC |
| 395 | hsa-miR-383 | AGAUCAGAAGGUGAUUGUGGCU | 876 | hsa-miR-106a | AAAAGUGCUUACAGUGCAGGUAG |
| 396 | hsa-miR-382 | GAAGUUGUUCGUGGUGGAUUCG | 877 | hsa-miR-105* | ACGGAUGUUUGAGCAUGUGCUA |
| 397 | hsa-miR-381 | UAUACAAGGGCAAGCUCUCUGU | 878 | hsa-miR-105 | UCAAAUGCUCAGACUCCUGUGGU |
| 398 | hsa-miR-380* | UGGUUGACCAUAGAACAUGCGC | 879 | hsa-miR-103-as | UCAUAGCCCUGUACAAUGCUGCU |
| 399 | hsa-miR-380 | UAUGUAAUAUGGUCCACAUCUU | 880 | hsa-miR-103-2* | AGCUUCUUUACAGUGCUGCCUUG |
| 400 | hsa-miR-379* | UAUGUAACAUGGUCCACUAACU | 881 | hsa-miR-103 | AGCAGCAUUGUACAGGGCUAUGA |
| 401 | hsa-miR-379 | UGGUAGACUAUGGAACGUAGG | 882 | hsa-miR-101* | CAGUUAUCACAGUGCUGAUGCU |
| 402 | hsa-miR-378* | CUCCUGACUCCAGGUCCUGUGU | 883 | hsa-miR-101 | UACAGUACUGUGAUAACUGAA |
| 403 | hsa-miR-378 | ACUGGACUUGGAGUCAGAAGG | 884 | hsa-miR-100* | CAAGCUUGUAUCUAUAGGUAUG |
| 404 | hsa-miR-377* | AGAGGUUGCCCUUGGUGAAUUC | 885 | hsa-miR-100 | AACCCGUAGAUCCGAACUUGUG |
| 405 | hsa-miR-377 | AUCACACAAAGGCAACUUUUGU | 886 | hsa-miR-1 | UGGAAUGUAAAGAAGUAUGUAU |
| 406 | hsa-miR-376c | AACAUAGAGGAAAUUCCACGU | 887 | hsa-let-7i* | CUGCGCAAGCUACUGCCUUGCU |
| 407 | hsa-miR-376b | AUCAUAGAGGAAAAUCCAUGUU | 888 | hsa-let-7i | UGAGGUAGUAGUUUGUGCUGUU |
| 408 | hsa-miR-376a* | GUAGAUUCUCCUUCUAUGAGUA | 889 | hsa-let-7g* | CUGUACAGGCCACUGCCUUGC |
| 409 | hsa-miR-376a | AUCAUAGAGGAAAAUCCACGU | 890 | hsa-let-7g | UGAGGUAGUAGUUUGUACAGUU |
| 410 | hsa-miR-375 | UUUGUUCGUUCGGCUCGCGUGA | 891 | hsa-let-7f-2* | CUAUACAGUCUACUGUCUUUCC |
| 411 | hsa-miR-374b* | CUUAGCAGGUUGUAUUAUCAUU | 892 | hsa-let-7f-1* | CUAUACAAUCUAUUGCCUUCCC |
| 412 | hsa-miR-374b | AUAUAAUACAACCUGCUAAGUG | 893 | hsa-let-7f | UGAGGUAGUAGAUUGUAUAGUU |

FIG. 1 (continued)

| SEQ ID | | | SEQ ID | | |
|---|---|---|---|---|---|
| 413 | hsa-miR-374a* | CUUAUCAGAUUGUAUUGUAAUU | 894 | hsa-let-7e* | CUAUACGGCCUCCUAGCUUUCC |
| 414 | hsa-miR-374a | UUAUAAUACAACCUGAUAAGUG | 895 | hsa-let-7e | UGAGGUAGGAGGUUGUAUAGUU |
| 415 | hsa-miR-373* | ACUCAAAAUGGGGGCGCUUUCC | 896 | hsa-let-7d* | CUAUACGACCUGCUGCCUUUCU |
| 416 | hsa-miR-373 | GAAGUGCUUCGAUUUUGGGGUGU | 897 | hsa-let-7d | AGAGGUAGUAGGUUGCAUAGUU |
| 417 | hsa-miR-372 | AAAGUGCUGCGACAUUUGAGCGU | 898 | hsa-let-7c* | UAGAGUUACACCCUGGGAGUUA |
| 418 | hsa-miR-371-5p | ACUCAAACUGUGGGGGCACU | 899 | hsa-let-7c | UGAGGUAGUAGGUUGUAUGGUU |
| 419 | hsa-miR-371-3p | AAGUGCCGCCAUCUUUUGAGUGU | 900 | hsa-let-7b* | CUAUACAACCUACUGCCUUCCC |
| 420 | hsa-miR-370 | GCCUGCUGGGGUGGAACCUGGU | 901 | hsa-let-7b | UGAGGUAGUAGGUUGUGUGGUU |
| 421 | hsa-miR-369-5p | AGAUCGACCGUGUUAUAUUCGC | 902 | hsa-let-7a-2* | CUGUACAGCCUCCUAGCUUUCC |
| 422 | hsa-miR-369-3p | AAUAAUACAUGGUUGAUCUUU | 903 | hsa-let-7a* | CUAUACAAUCUACUGUCUUUC |
| 423 | hsa-miR-367* | ACUGUUGCUAAUAUGCAACUCU | 904 | hsa-let-7a | UGAGGUAGUAGGUUGUAUAGUU |
| 424 | hsa-miR-367 | AAUUGCACUUUAGCAAUGGUGA | 905 | hsa-plus-1 | UAAUACUGCCUGGUAAUGAUGA |
| 425 | hsa-miR-365* | AGGGACUUUCAGGGGCAGCUGU | 906 | hsa-plus-2 | CUCUCCUCUCCUAACCUCGCU |
| 426 | hsa-miR-365 | UAAUGCCCCUAAAAAUCCUUAU | 907 | hsa-plus-2-AS | AGUCGAGAGUGGGAGAAGAGCGG |
| 427 | hsa-miR-363* | CGGGUGGAUCACGAUGCAAUUU | 908 | hsa-plus-3 | AAAACCGUCUAGUUACAGU |
| 428 | hsa-miR-363 | AAUUGCACGGUAUCCAUCUGUA | 909 | hsa-plus-4 | CUCAGUGAUGAAAACUUUGUCCA |
| 429 | hsa-miR-362-5p | AAUCCUUGGAACCUAGGUGUGAGU | 910 | hsa-plus-6-5p | GUUGCCUUUUUGUUCCCAUGC |
| 430 | hsa-miR-362-3p | AACACACCUAUUCAAGGAUUCA | 911 | hsa-plus-6-3p | UAGGCACCAAAAAGCAACAAC |
| 431 | hsa-miR-361-5p | UUAUCAGAAUCUCCAGGGGUAC | 912 | hsa-plus-7-AS | GCUGCACCGGAGACUGGGUAA |
| 432 | hsa-miR-361-3p | UCCCCCAGGUGUGAUUCUGAUUU | 913 | hsa-plus-7 | UACCCAGUCUCCGGUGCAGCC |
| 433 | hsa-miR-34c-5p | AGGCAGUGUAGUUAGCUGAUUGC | 914 | hsa-plus-9 | UUCCUCUGAUGACUUCCUGUUAGU |

FIG. 1 (continued)

| SEQ ID | | | SEQ ID | | |
|---|---|---|---|---|---|
| 434 | hsa-miR-34c-3p | AAUCACUAACCACACGGCCAGG | 915 | hsa-plus-9-AS | UGGAACUGAGGAUCUGAGGAA |
| 435 | hsa-miR-34b* | UAGGCAGUGUCAUUAGCUGAUUG | 916 | hsa-plus-11 | AGUGGCAAAGUCUUUCCAUAU |
| 436 | hsa-miR-34b | CAAUCACUAACUCCACUGCCAU | 917 | hsa-plus-12-5p | UUAGCUCAGCGGUUACUUCGAC |
| 437 | hsa-miR-34a* | CAAUCAGCAAGUAUACUGCCCU | 918 | hsa-plus-12-3p | CAAGCAACCUGUCUGGGUUGU |
| 438 | hsa-miR-34a | UGGCAGUGUCUUAGCUGGUUGU | 919 | hsa-plus-13-3p | UAACGCAUAAUAUGGACAU |
| 439 | hsa-miR-346 | UGUCUGCCCGCAUGCCUGCCUCU | 920 | hsa-plus-13-5p | AUGUCCAUAUUAUGGGUUAGU |
| 440 | hsa-miR-345 | GCUGACUCCUAGUCCAGGGCUC | 921 | hsa-plus-14-3p | CAGUUGCUAGUUGCACUCCUC |
| 441 | hsa-miR-342-5p | AGGGGUGCUAUCUGUGAUUGA | 922 | hsa-plus-14-5p | AGGCAGUGUAUUGCUAGCGGC |
| 442 | hsa-miR-342-3p | UCUCACACAGAAAUCGCACCCGU | 923 | hsa-plus-17 | AGUUCUUGCCUGGUUUCUCUA |
| 443 | hsa-miR-340* | UCCGUCUCAGUUACUUUAUAGC | 924 | hsa-plus-21 | UCUGCAUUGCCAGGGAUU |
| 444 | hsa-miR-340 | UUAUAAAGCAAUGAGACUGAUU | 925 | hsa-plus-22 | UAGCUUUAGAGACUGAGAG |
| 445 | hsa-miR-33b* | CAGUGCCUCGGCAGUGCAGCCC | 926 | hsa-plus-26-3p | UGAGACAGGCUUAUGCUGCUAUC |
| 446 | hsa-miR-33b | GUGCAUUGCUGUUGCAUUGC | 927 | hsa-plus-26-5p | AGCAGCAUGAACCUGUCUCAC |
| 447 | hsa-miR-33a* | CAAUGUUUCCACAGUGCAUCAC | 928 | hsa-plus-27 | CCGGCGGCAGGGGUGGCACCG |
| 448 | hsa-miR-33a | GUGCAUUGUAGUUGCAUUGCA | 929 | hsa-plus-31-5p | GCCUUAGGAGAAAGUUUCUG |
| 449 | hsa-miR-339-5p | UCCCUGUCCUCCAGGAGCUCACG | 930 | hsa-plus-31-3p | UCCUAAGGCAGUCCCUGGA |
| 450 | hsa-miR-339-3p | UGAGCGCCUCGACGACAGAGCCG | 931 | hsa-plus-33-AS | AAGGUCGCCCUCAAGGUGACC |
| 451 | hsa-miR-338-5p | AACAAUAUCCUGGUGCUGAGUG | 932 | hsa-plus-33 | AUGCCUGGGAGUUGCGAUCUG |
| 452 | hsa-miR-338-3p | UCCAGCAUCAGUGAUUUUGUUG | 933 | hsa-plus-36-3p | UGGAGUUAAAGACUUUUUCUC |
| 453 | hsa-miR-337-5p | GAACGGCUUCAUACAGGAGUU | 934 | hsa-plus-36-5p | CAGAGAAUAGUUUAAAUUAGAAUC |
| 454 | hsa-miR-337-3p | CUCCUAUAUGAUGCCUUUCUUC | 935 | hsa-plus-37-3p | UGCAACUUACUGAGGGCUUUGAA |

FIG. 1 (continued)

| SEQ ID | | | SEQ ID | | |
|---|---|---|---|---|---|
| 455 | hsa-miR-335* | UUUUUCAUUAUUGCUCCUGACC | 936 | hsa-plus-37-5p | UGGGGUUUUGCAGUCCUUAGC |
| 456 | hsa-miR-335 | UCAAGAGCAAUAACGAAAAAUGU | 937 | hsa-plus-5-5p | AGACACUAUACGAGUCAUAUA |
| 457 | hsa-miR-331-5p | CUAGGUAUGGUCCCAGGGAUCC | 938 | hsa-plus-5-3p | AUAGGACUCAUAUAGUGCCAG |
| 458 | hsa-miR-331-3p | GCCCCUGGGCCUAUCCUAGAA | 939 | hsa-plus-8 | AUCCCCAGAUACAAUGGACAAU |
| 459 | hsa-miR-330-5p | UCUCUGGGCCUGUGUCUUAGGC | 940 | hsa-plus-10 | UUCACCUGUUAGCCUGUCCAGAG |
| 460 | hsa-miR-330-3p | GCAAAGCACACGGCCUGCAGAGA | 941 | hsa-plus-15-3p | UGACAGCGCCCUGCCUGGCUCGG |
| 461 | hsa-miR-329 | AACACACCUGGUUAACCUCUUU | 942 | hsa-plus-15-5p | AGCGCGGGCUGAGCGCUGCCAGU |
| 462 | hsa-miR-328 | CUGGCCCUCUCUGCCCUUCCGU | 943 | hsa-plus-16-5p | UAUACUACAUAUAAUAUAUGUA |
| 463 | hsa-miR-326 | CCUCUGGGCCCUUCCUCCAG | 944 | hsa-plus-16-3p | UAUACUACAUAUAAUAUAUGUA |
| 464 | hsa-miR-325 | CCUAGUAGGUGUCCAGUAAGUGU | 945 | hsa-plus-18 | UAGCACCAUCUGAAAUCGGUUAU |
| 465 | hsa-miR-324-5p | CGCAUCCCCUAGGGCAUUGGUGU | 946 | hsa-plus-19-5p | GUGCAAAAGUCAUCACGGUUUU |
| 466 | hsa-miR-324-3p | ACUGCCCCAGGUGCUGCUGG | 947 | hsa-plus-19-3p | ACCGCGAUGACUUUUGCAUCA |
| 467 | hsa-miR-323-5p | AGGUGGUCCGUGGCGCGUUCGC | 948 | hsa-plus-20-3p | UCACCGCGGUCUUUUCCUCCCAC |
| 468 | hsa-miR-323-3p | CACAUUACACGGUCGACCUCU | 949 | hsa-plus-20-5p | UUGGGGAAACGGCCGCUGAGU |
| 469 | hsa-miR-320d | AAAAGCUGGGUUGAGAGGA | 950 | hsa-plus-23-3p | UCCUCCCAUGCCAAGAACUCC |
| 470 | hsa-miR-320c | AAAAGCUGGGUUGAGAGGGU | 951 | hsa-plus-23-5p | GGUUCUUAGCAUAGGAGGUCU |
| 471 | hsa-miR-320b | AAAAGCUGGGUUGAGAGGGCAA | 952 | hsa-plus-24 | CUGCGUGUCCCUAGGUGAGGGG |
| 472 | hsa-miR-320a | AAAAGCUGGGUUGAGAGGGCGA | 953 | hsa-plus-25 | GGCACAGGGCGAGUGGAAAGAA |
| 473 | hsa-miR-32* | CAAUUUAGUGUGUGUGAUAUUU | 954 | hsa-plus-28-3p | UCACUACCUGACAAUACAGUAU |
| 474 | hsa-miR-32 | UAUUGCACAUUACUAAGUUGCA | 955 | hsa-plus-28-5p | UGCUGUAUUGUCAGGUAGUGAU |
| 475 | hsa-miR-31* | UGCUAUGCCAACAUAUUGCCAU | 956 | hsa-plus-29 | UGGAGGUGAUGAACUGUCUGAGC |

FIG. 1 (continued)

| SEQ ID | | | SEQ ID | | |
|---|---|---|---|---|---|
| | | | | | C |
| 476 | hsa-miR-31 | AGGCAAGAUGCUGGCAUAGCU | 957 | hsa-plus-30 | UGCGUGUCCCGCCUGUUCCCU |
| 477 | hsa-miR-30e* | CUUUCAGUCGGAUGUUUACAGC | 958 | hsa-plus-32-AS | UGUGCUGAUUGUCACGUUCUGAU U |
| 478 | hsa-miR-30e | UGUAAACAUCCUUGACUGGAAG | 959 | hsa-plus-32 | ACAGAUGAUGAACUUAUUGACGGG |
| 479 | hsa-miR-30d* | CUUUCAGUCAGAUGUUUGCUGC | 960 | hsa-plus-34-3p | ACCUUCCUCUCCAUGGGUCUUUC |
| 480 | hsa-miR-30d | UGUAAACAUCCCCGACUGGAAG | 961 | hsa-plus-34-5p | AGACCCAUUGAGGAGAAGGUUC |
| 481 | hsa-miR-30c-2* | CUGGGAGAAGGCUGUUUACUCU | 962 | hsa-plus-35 | UUCUCAAGAGGGAGGCAAUCA |

FIG 2

| No. | miRNA, miRNA* | median g1 | median g2 | qmedian | Logq median | Ttest_ rawp | Ttest_ adjp | Limma_ rawp | Limma_ adjp |
|---|---|---|---|---|---|---|---|---|---|
| 1 | hsa-miR-1248 | 2.177E+01 | 1.000E-00 | 2.177E+01 | 3.081E-00 | 7.597E-09 | 3.278E-06 | 7.689E-05 | 1.659E-02 |
| 2 | hsa-miR-342-3p | 4.401E+03 | 2.357E+03 | 1.867E-00 | 6.244E-01 | 6.662E-09 | 3.278E-06 | 9.012E-06 | 7.777E-03 |
| 3 | hsa-miR-133b | 1.680E+01 | 1.000E-00 | 1.680E+01 | 2.821E-00 | 1.523E-07 | 4.382E-05 | 5.484E-04 | 5.258E-02 |
| 4 | hsa-miR-605 | 1.336E+01 | 1.000E-00 | 1.336E+01 | 2.592E-00 | 4.035E-07 | 8.706E-05 | 1.849E-03 | 7.297E-02 |
| 5 | hsa-miR-450b-3p | 3.376E+01 | 8.612E-00 | 3.920E-00 | 1.366E-00 | 1.473E-06 | 1.867E-04 | 4.976E-04 | 5.258E-02 |
| 6 | hsa-miR-520a-3p | 1.000E-00 | 1.000E-00 | 1.000E-00 | 0.000E+01 | 1.514E-06 | 1.867E-04 | 1.771E-03 | 7.297E-02 |
| 7 | hsa-miR-23b* | 2.851E+01 | 1.000E-00 | 2.851E+01 | 3.350E-00 | 1.090E-06 | 1.867E-04 | 7.434E-05 | 1.659E-02 |
| 8 | hsa-miR-423-5p | 2.877E+03 | 1.962E+03 | 1.466E-00 | 3.827E-01 | 1.855E-06 | 2.002E-04 | 5.752E-03 | 1.418E-01 |
| 9 | hsa-miR-219-1-3p | 1.586E+01 | 1.000E-00 | 1.586E+01 | 2.764E-00 | 3.193E-06 | 2.755E-04 | 4.285E-03 | 1.176E-01 |
| 10 | hsa-miR-454* | 1.252E+01 | 1.000E-00 | 1.252E+01 | 2.527E-00 | 3.157E-06 | 2.755E-04 | 7.623E-03 | 1.481E-01 |
| 11 | hsa-miR-26b* | 1.997E-00 | 1.000E-00 | 1.997E-00 | 6.915E-01 | 5.271E-06 | 4.135E-04 | 1.467E-03 | 7.297E-02 |
| 12 | hsa-miR-1259 | 2.515E+01 | 1.000E-00 | 2.515E+01 | 3.225E-00 | 1.176E-05 | 8.459E-04 | 2.060E-03 | 7.408E-02 |
| 13 | hsa-miR-655 | 2.765E+01 | 1.000E-00 | 2.765E+01 | 3.320E-00 | 1.847E-05 | 1.226E-03 | 6.249E-03 | 1.431E-01 |
| 14 | hsa-miR-302c | 7.413E-00 | 1.000E-00 | 7.413E-00 | 2.003E-00 | 2.664E-05 | 1.642E-03 | 1.060E-03 | 7.297E-02 |
| 10 | hsa-miR-383 | 5.068E+01 | 9.810E+01 | 5.166E-01 | -6.605E-01 | 3.246E-05 | 1.868E-03 | 1.907E-03 | 7.297E-02 |
| 16 | hsa-miR-150 | 1.620E+03 | 6.288E+02 | 2.576E-00 | 9.462E-01 | 3.632E-05 | 1.959E-03 | 3.894E-05 | 1.659E-02 |
| 17 | hsa-miR-412 | 5.144E+01 | 3.238E+01 | 1.589E-00 | 4.630E-01 | 5.672E-05 | 2.880E-03 | 1.945E-03 | 7.297E-02 |
| 18 | hsa-miR-548i | 4.779E-00 | 1.000E-00 | 4.779E-00 | 1.564E-00 | 6.469E-05 | 3.101E-03 | 7.647E-03 | 1.481E-01 |
| 19 | hsa-let-7e* | 1.139E+01 | 1.000E-00 | 1.139E+01 | 2.433E-00 | 8.264E-05 | 3.448E-03 | 1.440E-02 | 2.301E-01 |
| 20 | hsa-miR-324-3p | 8.192E+02 | 5.331E+02 | 1.537E-00 | 4.296E-01 | 8.309E-05 | 3.448E-03 | 3.891E-03 | 1.158E-01 |

FIG 2 (continued)

| | | | | | | | | | |
|---|---|---|---|---|---|---|---|---|---|
| 21 | hsa-miR-335* | 1.000E-00 | 1.000E-00 | 1.000E-00 | 0.000E+01 | 8.390E-05 | 3.448E-03 | 1.636E-02 | 2.393E-01 |
| 22 | hsa-miR-320a | 1.763E+04 | 9.808E+03 | 1.798E-00 | 5.867E-01 | 1.173E-04 | 4.600E-03 | 1.248E-04 | 2.154E-02 |
| 23 | hsa-miR-320d | 8.946E+02 | 5.129E+02 | 1.744E-00 | 5.562E-01 | 1.576E-04 | 5.915E-03 | 8.577E-02 | 4.158E-01 |
| 24 | hsa-miR-409-3p | 3.526E+01 | 1.000E-00 | 3.526E+01 | 3.563E-00 | 2.236E-04 | 8.040E-03 | 4.622E-03 | 1.209E-01 |
| 25 | hsa-miR-590-3p | 4.779E-00 | 1.000E-00 | 4.779E-00 | 1.564E-00 | 2.761E-04 | 8.947E-03 | 4.150E-03 | 1.176E-01 |
| 26 | hsa-miR-545* | 2.384E+01 | 5.671E-00 | 4.203E-00 | 1.436E-00 | 2.777E-04 | 8.947E-03 | 6.709E-03 | 1.443E-01 |
| 27 | hsa-miR-889 | 2.904E+01 | 5.416E-00 | 5.362E-00 | 1.679E-00 | 2.799E-04 | 8.947E-03 | 1.003E-03 | 7.297E-02 |
| 28 | hsa-miR-1224-3p | 9.372E+01 | 5.332E+01 | 1.758E-00 | 5.640E-01 | 2.993E-04 | 9.226E-03 | 2.603E-04 | 3.744E-02 |
| 29 | hsa-miR-148a* | 2.355E+01 | 4.674E-00 | 5.038E-00 | 1.617E-00 | 3.256E-04 | 9.690E-03 | 8.259E-02 | 4.158E-01 |
| 30 | hsa-miR-9 | 1.000E-00 | 1.000E-00 | 1.000E-00 | 0.000E+01 | 3.462E-04 | 9.958E-03 | 4.018E-02 | 3.373E-01 |
| 31 | hsa-miR-518f | 5.239E+01 | 7.637E+01 | 6.860E-01 | -3.769E-01 | 4.282E-04 | 1.185E-02 | 1.575E-02 | 2.379E-01 |
| 32 | hsa-miR-488 | 1.000E-00 | 1.000E-00 | 1.000E-00 | 0.000E+01 | 4.393E-04 | 1.185E-02 | 1.392E-01 | 4.686E-01 |
| 33 | hsa-miR-182 | 4.196E+03 | 7.310E+03 | 5.739E-01 | -5.553E-01 | 4.808E-04 | 1.257E-02 | 1.110E-03 | 7.297E-02 |
| 34 | hsa-miR-10a* | 3.879E+01 | 1.502E+01 | 2.582E-00 | 9.486E-01 | 5.253E-04 | 1.333E-02 | 5.307E-02 | 3.652E-01 |
| 35 | hsa-miR-19b | 1.041E+04 | 1.298E+04 | 8.018E-01 | -2.209E-01 | 5.887E-04 | 1.452E-02 | 8.427E-02 | 4.158E-01 |
| 36 | hsa-miR-15a | 2.877E+03 | 5.379E+03 | 5.349E-01 | -6.257E-01 | 6.373E-04 | 1.487E-02 | 8.735E-03 | 1.538E-01 |
| 37 | hsa-miR-1289 | 9.249E+01 | 1.244E+02 | 7.435E-01 | -2.964E-01 | 6.278E-04 | 1.487E-02 | 3.237E-02 | 3.139E-01 |
| 38 | hsa-miR-500 | 2.119E+02 | 1.141E+02 | 1.857E-00 | 6.188E-01 | 7.321E-04 | 1.620E-02 | 4.125E-02 | 3.373E-01 |
| 39 | hsa-miR-1281 | 6.814E+01 | 1.756E+01 | 3.880E-00 | 1.356E-00 | 7.178E-04 | 1.620E-02 | 1.776E-03 | 7.297E-02 |
| 40 | hsa-miR-942 | 1.575E+01 | 1.000E-00 | 1.575E+01 | 2.757E-00 | 8.446E-04 | 1.822E-02 | 1.263E-02 | 2.096E-01 |
| 41 | hsa-miR-877* | 7.382E+01 | 1.734E+01 | 4.256E-00 | 1.448E-00 | 8.971E-04 | 1.888E-02 | 9.014E-02 | 4.174E-01 |
| 42 | hsa-let-7f-1* | 3.466E+01 | 1.555E+01 | 2.229E-00 | 8.017E-01 | 9.460E-04 | 1.944E-02 | 7.439E-02 | 4.115E-01 |
| 43 | hsa-miR-651 | 1.359E-00 | 1.000E-00 | 1.359E-00 | 3.070E-01 | 1.086E-03 | 2.037E-02 | 4.143E-02 | 3.373E-01 |
| 44 | hsa-miR-610 | 4.835E+01 | 1.137E+02 | 4.253E-01 | -8.550E-01 | 1.078E-03 | 2.037E-02 | 7.004E-03 | 1.443E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 45 | hsa-miR-664 | 2.530E+02 | 1.385E+02 | 1.826E-00 | 6.021E-01 | 1.077E-03 | 2.037E-02 | 8.152E-03 | 1.497E-01 |
| 46 | hsa-miR-613 | 2.449E-00 | 1.000E-00 | 2.449E-00 | 8.959E-01 | 1.081E-03 | 2.037E-02 | 3.134E-02 | 3.110E-01 |
| 47 | hsa-miR-483-3p | 1.898E+01 | 1.000E-00 | 1.898E+01 | 2.943E-00 | 1.302E-03 | 2.391E-02 | 5.193E-02 | 3.644E-01 |
| 48 | hsa-miR-320c | 7.734E+02 | 4.231E+02 | 1.828E-00 | 6.032E-01 | 1.338E-03 | 2.405E-02 | 7.911E-02 | 4.158E-01 |
| 49 | hsa-miR-720 | 4.196E+03 | 2.998E+03 | 1.399E-00 | 3.360E-01 | 1.407E-03 | 2.478E-02 | 6.483E-02 | 4.025E-01 |
| 50 | hsa-miR-299-5p | 2.066E+01 | 1.000E-00 | 2.066E+01 | 3.028E-00 | 1.510E-03 | 2.607E-02 | 1.842E-03 | 7.297E-02 |
| 51 | hsa-miR-579 | 3.200E+01 | 2.329E+01 | 1.374E-00 | 3.176E-01 | 1.964E-03 | 3.020E-02 | 2.834E-02 | 3.110E-01 |
| 52 | hsa-miR-636 | 1.575E+02 | 1.131E+02 | 1.392E-00 | 3.310E-01 | 1.972E-03 | 3.020E-02 | 1.397E-01 | 4.686E-01 |
| 53 | hsa-miR-197 | 6.478E+02 | 4.526E+02 | 1.431E-00 | 3.586E-01 | 1.915E-03 | 3.020E-02 | 1.391E-01 | 4.686E-01 |
| 54 | hsa-miR-668 | 3.705E+01 | 1.125E+01 | 3.294E-00 | 1.192E-00 | 2.022E-03 | 3.020E-02 | 2.528E-03 | 8.431E-02 |
| 55 | hsa-miR-494 | 5.553E+01 | 3.701E+01 | 1.500E-00 | 4.058E-01 | 1.970E-03 | 3.020E-02 | 7.556E-02 | 4.133E-01 |
| 56 | hsa-miR-1262 | 1.000E-00 | 1.000E-00 | 1.000E-00 | 0.000E+01 | 1.837E-03 | 3.020E-02 | 7.977E-02 | 4.158E-01 |
| 57 | hsa-miR-578 | 1.000E-00 | 1.000E-00 | 1.000E-00 | 0.000E+01 | 1.842E-03 | 3.020E-02 | 3.172E-02 | 3.110E-01 |
| 58 | hsa-miR-708* | 5.144E+01 | 8.373E+01 | 6.144E-01 | -4.871E-01 | 2.030E-03 | 3.020E-02 | 2.033E-02 | 2.699E-01 |
| 59 | hsa-miR-369-3p | 1.680E+01 | 6.601E-00 | 2.545E-00 | 9.341E-01 | 2.214E-03 | 3.239E-02 | 8.434E-02 | 4.158E-01 |
| 60 | hsa-miR-329 | 5.447E+01 | 4.534E+01 | 1.201E-00 | 1.834E-01 | 2.535E-03 | 3.445E-02 | 1.915E-01 | 5.248E-01 |
| 61 | hsa-miR-941 | 1.027E+02 | 1.264E+02 | 8.123E-01 | -2.079E-01 | 2.460E-03 | 3.445E-02 | 2.318E-02 | 2.817E-01 |
| 62 | hsa-miR-155 | 8.508E+01 | 4.958E+01 | 1.716E-00 | 5.400E-01 | 2.609E-03 | 3.445E-02 | 4.720E-02 | 3.580E-01 |
| 63 | hsa-miR-26a-1* | 1.031E+01 | 1.000E-00 | 1.031E+01 | 2.333E-00 | 2.634E-03 | 3.445E-02 | 3.964E-02 | 3.373E-01 |
| 64 | hsa-miR-1246 | 1.000E-00 | 1.000E-00 | 1.000E-00 | 0.000E+01 | 2.629E-03 | 3.445E-02 | 3.650E-01 | 6.763E-01 |
| 65 | hsa-miR-892b | 2.729E+01 | 1.252E+01 | 2.180E-00 | 7.794E-01 | 2.580E-03 | 3.445E-02 | 5.343E-02 | 3.652E-01 |
| 66 | hsa-miR-146a | 1.886E+02 | 1.218E+02 | 1.549E-00 | 4.376E-01 | 2.504E-03 | 3.445E-02 | 1.731E-01 | 5.030E-01 |
| 67 | hsa-miR-337-3p | 8.436E-00 | 1.000E-00 | 8.436E-00 | 2.133E-00 | 2.816E-03 | 3.627E-02 | 1.715E-03 | 7.297E-02 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 68 | hsa-miR-130a* | 5.317E+01 | 3.526E+01 | 1.508E-00 | 4.106E-01 | 2.927E-03 | 3.715E-02 | 3.526E-01 | 6.760E-01 |
| 69 | hsa-let-7b | 9.066E+02 | 6.222E+02 | 1.457E-00 | 3.764E-01 | 3.110E-03 | 3.890E-02 | 1.199E-01 | 4.510E-01 |
| 70 | hsa-miR-744* | 3.994E+01 | 9.746E-00 | 4.098E-00 | 1.410E-00 | 3.456E-03 | 4.261E-02 | 5.313E-04 | 5.258E-02 |
| 71 | hsa-miR-140-3p | 2.473E+04 | 3.058E+04 | 8.085E-01 | -2.126E-01 | 3.613E-03 | 4.391E-02 | 6.848E-02 | 4.115E-01 |
| 72 | hsa-miR-573 | 5.144E+01 | 7.302E+01 | 7.045E-01 | -3.503E-01 | 3.772E-03 | 4.402E-02 | 2.212E-02 | 2.756E-01 |
| 73 | hsa-miR-378 | 2.555E+02 | 1.645E+02 | 1.553E-00 | 4.402E-01 | 3.775E-03 | 4.402E-02 | 6.382E-01 | 8.540E-01 |
| 74 | hsa-miR-1237 | 7.937E+01 | 6.762E+01 | 1.174E-00 | 1.603E-01 | 3.718E-03 | 4.402E-02 | 1.801E-01 | 5.097E-01 |
| 75 | hsa-miR-363* | 6.193E+01 | 9.794E+01 | 6.323E-01 | -4.583E-01 | 3.969E-03 | 4.567E-02 | 4.736E-02 | 3.580E-01 |
| 76 | hsa-miR-888 | 4.958E+01 | 1.060E+01 | 4.676E-00 | 1.543E-00 | 4.855E-03 | 5.200E-02 | 1.930E-01 | 5.254E-01 |
| 77 | hsa-miR-607 | 8.159E+01 | 6.327E+01 | 1.290E-00 | 2.543E-01 | 4.880E-03 | 5.200E-02 | 4.643E-01 | 7.529E-01 |
| 78 | hsa-miR-1236 | 2.177E+01 | 1.000E-00 | 2.177E+01 | 3.081E-00 | 4.822E-03 | 5.200E-02 | 3.683E-02 | 3.311E-01 |
| 79 | hsa-miR-34b | 4.111E+01 | 1.784E+01 | 2.304E-00 | 8.346E-01 | 4.600E-03 | 5.200E-02 | 3.631E-02 | 3.299E-01 |
| 80 | hsa-miR-532-3p | 4.401E+03 | 3.623E+03 | 1.215E-00 | 1.946E-01 | 4.684E-03 | 5.200E-02 | 1.002E-01 | 4.218E-01 |
| 81 | hsa-miR-1229 | 1.841E+02 | 1.173E+02 | 1.570E-00 | 4.511E-01 | 4.869E-03 | 5.200E-02 | 5.329E-01 | 7.996E-01 |
| 82 | hsa-miR-520g | 4.835E+01 | 2.566E+01 | 1.884E-00 | 6.336E-01 | 5.042E-03 | 5.295E-02 | 1.362E-01 | 4.686E-01 |
| 83 | hsa-miR-581 | 8.436E-00 | 1.000E-00 | 8.436E-00 | 2.133E-00 | 5.092E-03 | 5.295E-02 | 4.551E-02 | 3.570E-01 |
| 84 | hsa-miR-323-3p | 3.376E+01 | 8.612E-00 | 3.920E-00 | 1.366E-00 | 5.278E-03 | 5.422E-02 | 1.054E-01 | 4.251E-01 |
| 85 | hsa-miR-155* | 5.900E+01 | 4.958E+01 | 1.190E-00 | 1.739E-01 | 5.375E-03 | 5.458E-02 | 5.366E-01 | 7.996E-01 |
| 86 | hsa-miR-15b | 1.415E+04 | 1.763E+04 | 8.024E-01 | -2.201E-01 | 5.635E-03 | 5.592E-02 | 2.837E-02 | 3.110E-01 |
| 87 | hsa-miR-548d-3p | 4.508E+01 | 3.289E+01 | 1.371E-00 | 3.154E-01 | 5.702E-03 | 5.592E-02 | 7.075E-01 | 8.834E-01 |
| 88 | hsa-miR-302d* | 4.723E+01 | 3.029E+01 | 1.559E-00 | 4.440E-01 | 5.700E-03 | 5.592E-02 | 7.414E-02 | 4.115E-01 |
| 89 | hsa-miR-496 | 6.894E+01 | 4.697E+01 | 1.468E-00 | 3.836E-01 | 5.900E-03 | 5.721E-02 | 1.980E-01 | 5.254E-01 |
| 90 | hsa-miR-186* | 1.016E+02 | 1.325E+02 | 7.664E-01 | -2.661E-01 | 6.042E-03 | 5.794E-02 | 4.939E-02 | 3.580E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 91 | hsa-miR-599 | 3.010E+01 | 1.694E+01 | 1.777E-00 | 5.748E-01 | 6.315E-03 | 5.988E-02 | 6.814E-01 | 8.698E-01 |
| 92 | hsa-miR-589 | 7.844E+01 | 1.003E+02 | 7.817E-01 | -2.462E-01 | 7.001E-03 | 6.567E-02 | 7.262E-02 | 4.115E-01 |
| 93 | hsa-miR-519c-5p | 1.283E+02 | 2.042E+02 | 6.282E-01 | -4.648E-01 | 7.199E-03 | 6.610E-02 | 2.487E-02 | 2.925E-01 |
| 94 | hsa-miR-1249 | 6.645E+01 | 4.048E+01 | 1.642E-00 | 4.956E-01 | 7.125E-03 | 6.610E-02 | 8.486E-02 | 4.158E-01 |
| 95 | hsa-miR-22 | 7.714E+03 | 9.808E+03 | 7.865E-01 | -2.401E-01 | 7.502E-03 | 6.815E-02 | 1.599E-02 | 2.379E-01 |
| 96 | hsa-miR-614 | 3.507E+01 | 1.995E+01 | 1.758E-00 | 5.640E-01 | 7.830E-03 | 6.907E-02 | 4.757E-01 | 7.581E-01 |
| 97 | hsa-miR-634 | 1.008E+02 | 7.302E+01 | 1.380E-00 | 3.220E-01 | 7.843E-03 | 6.907E-02 | 8.165E-01 | 9.284E-01 |
| 98 | hsa-miR-486-5p | 4.147E+04 | 4.147E+04 | 1.000E-00 | 0.000E+01 | 7.837E-03 | 6.907E-02 | 5.488E-01 | 8.015E-01 |
| 99 | hsa-miR-548h | 1.000E-00 | 1.000E-00 | 1.000E-00 | 0.000E+01 | 8.428E-03 | 7.347E-02 | 3.117E-02 | 3.110E-01 |
| 100 | hsa-miR-19a | 2.412E+03 | 2.998E+03 | 8.044E-01 | -2.176E-01 | 9.090E-03 | 7.845E-02 | 5.061E-02 | 3.580E-01 |
| 101 | hsa-miR-32* | 2.821E+01 | 6.702E+01 | 4.209E-01 | -8.653E-01 | 9.596E-03 | 8.200E-02 | 5.502E-03 | 1.397E-01 |
| 102 | hsa-miR-367* | 5.144E+01 | 3.289E+01 | 1.564E-00 | 4.474E-01 | 1.021E-02 | 8.636E-02 | 7.338E-02 | 4.115E-01 |
| 103 | hsa-miR-218-1* | 6.686E+01 | 4.995E+01 | 1.338E-00 | 2.915E-01 | 1.080E-02 | 9.048E-02 | 7.790E-01 | 9.019E-01 |
| 104 | hsa-let-7a* | 1.000E-00 | 1.000E-00 | 1.000E-00 | 0.000E+01 | 1.101E-02 | 9.051E-02 | 1.528E-01 | 4.795E-01 |
| 105 | hsa-miR-328 | 5.447E+01 | 2.530E+01 | 2.153E-00 | 7.667E-01 | 1.098E-02 | 9.051E-02 | 2.760E-01 | 6.190E-01 |
| 106 | hsa-miR-571 | 4.419E+01 | 5.868E+01 | 7.532E-01 | -2.834E-01 | 1.120E-02 | 9.059E-02 | 3.026E-02 | 3.110E-01 |
| 107 | hsa-miR-424* | 1.110E+02 | 9.232E+01 | 1.202E-00 | 1.838E-01 | 1.123E-02 | 9.059E-02 | 6.421E-01 | 8.565E-01 |
| 108 | hsa-miR-374b* | 2.384E+01 | 1.596E+01 | 1.493E-00 | 4.010E-01 | 1.143E-02 | 9.130E-02 | 4.299E-01 | 7.218E-01 |
| 109 | hsa-let-7d | 2.008E+03 | 1.687E+03 | 1.190E-00 | 1.742E-01 | 1.155E-02 | 9.145E-02 | 8.924E-01 | 9.651E-01 |
| 110 | hsa-miR-16 | 1.574E+04 | 1.763E+04 | 8.927E-01 | -1.135E-01 | 1.219E-02 | 9.566E-02 | 2.224E-02 | 2.756E-01 |
| 111 | hsa-miR-490-3p | 8.739E+01 | 1.283E+02 | 6.812E-01 | -3.839E-01 | 1.256E-02 | 9.767E-02 | 3.434E-02 | 3.208E-01 |
| 112 | hsa-miR-1914* | 1.374E+02 | 1.249E+02 | 1.100E-00 | 9.557E-02 | 1.294E-02 | 9.974E-02 | 3.608E-01 | 6.763E-01 |
| 113 | hsa-miR-543 | 3.800E+01 | 1.756E+01 | 2.163E-00 | 7.716E-01 | 1.329E-02 | 1.006E-01 | 1.478E-02 | 2.319E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 114 | hsa-miR-526a | 1.385E+02 | 2.306E+02 | 6.008E-01 | -5.095E-01 | 1.318E-02 | 1.006E-01 | 6.692E-03 | 1.443E-01 |
| 115 | hsa-miR-875-5p | 2.660E+01 | 9.746E-00 | 2.729E-00 | 1.004E-00 | 1.365E-02 | 1.024E-01 | 1.388E-01 | 4.686E-01 |
| 116 | hsa-miR-1252 | 7.413E-00 | 1.000E-00 | 7.413E-00 | 2.003E-00 | 1.391E-02 | 1.035E-01 | 1.548E-02 | 2.379E-01 |
| 117 | hsa-miR-495 | 6.746E+01 | 4.785E+01 | 1.410E-00 | 3.435E-01 | 1.416E-02 | 1.044E-01 | 1.279E-01 | 4.625E-01 |
| 118 | hsa-miR-210 | 7.902E+02 | 4.768E+02 | 1.657E-00 | 5.053E-01 | 1.447E-02 | 1.049E-01 | 2.986E-01 | 6.348E-01 |
| 119 | hsa-miR-514 | 3.902E+01 | 2.660E+01 | 1.467E-00 | 3.834E-01 | 1.435E-02 | 1.049E-01 | 3.967E-01 | 7.046E-01 |
| 120 | hsa-miR-572 | 5.810E+01 | 4.111E+01 | 1.413E-00 | 3.460E-01 | 1.499E-02 | 1.078E-01 | 3.877E-01 | 6.985E-01 |
| 121 | hsa-miR-1228 | 2.272E+02 | 1.820E+02 | 1.248E-00 | 2.215E-01 | 1.592E-02 | 1.126E-01 | 1.721E-01 | 5.030E-01 |
| 122 | hsa-miR-589* | 8.323E+01 | 1.043E+02 | 7.983E-01 | -2.253E-01 | 1.589E-02 | 1.126E-01 | 7.347E-02 | 4.115E-01 |
| 123 | hsa-miR-1538 | 7.057E+01 | 9.539E+01 | 7.397E-01 | -3.015E-01 | 1.628E-02 | 1.133E-01 | 5.683E-02 | 3.715E-01 |
| 124 | hsa-miR-300 | 4.865E+01 | 1.964E+01 | 2.478E-00 | 9.074E-01 | 1.616E-02 | 1.133E-01 | 6.989E-02 | 4.115E-01 |
| 125 | hsa-miR-320b | 2.998E+03 | 2.110E+03 | 1.421E-00 | 3.515E-01 | 1.741E-02 | 1.193E-01 | 3.781E-02 | 3.364E-01 |
| 126 | hsa-miR-190b | 1.000E-00 | 1.000E-00 | 1.000E-00 | 0.000E+01 | 1.740E-02 | 1.193E-01 | 8.434E-02 | 4.158E-01 |
| 127 | hsa-miR-330-5p | 1.307E+01 | 9.198E-00 | 1.421E-00 | 3.514E-01 | 1.773E-02 | 1.205E-01 | 2.056E-01 | 5.254E-01 |
| 128 | hsa-miR-506 | 3.800E+01 | 1.479E+01 | 2.569E-00 | 9.437E-01 | 1.848E-02 | 1.246E-01 | 9.682E-02 | 4.199E-01 |
| 129 | hsa-miR-1295 | 1.110E+02 | 1.493E+02 | 7.429E-01 | -2.972E-01 | 1.989E-02 | 1.331E-01 | 7.017E-02 | 4.115E-01 |
| 130 | hsa-miR-485-3p | 5.144E+01 | 3.733E+01 | 1.378E-00 | 3.206E-01 | 2.043E-02 | 1.357E-01 | 4.205E-01 | 7.157E-01 |
| 131 | hsa-miR-629* | 9.088E+01 | 8.596E+01 | 1.057E-00 | 5.567E-02 | 2.116E-02 | 1.373E-01 | 9.908E-01 | 9.975E-01 |
| 132 | hsa-miR-130b* | 1.000E-00 | 1.000E-00 | 1.000E-00 | 0.000E+01 | 2.113E-02 | 1.373E-01 | 1.785E-01 | 5.097E-01 |
| 133 | hsa-miR-297 | 4.958E+01 | 1.076E+02 | 4.608E-01 | -7.749E-01 | 2.092E-02 | 1.373E-01 | 1.160E-03 | 7.297E-02 |
| 134 | hsa-miR-1915* | 2.765E+01 | 8.814E-00 | 3.138E-00 | 1.143E-00 | 2.141E-02 | 1.379E-01 | 2.672E-01 | 6.068E-01 |
| 135 | hsa-miR-623 | 5.068E+01 | 6.936E+01 | 7.306E-01 | -3.139E-01 | 2.235E-02 | 1.418E-01 | 1.376E-01 | 4.686E-01 |
| 136 | hsa-miR-133a | 4.958E+01 | 2.704E+01 | 1.834E-00 | 6.063E-01 | 2.224E-02 | 1.418E-01 | 3.966E-02 | 3.373E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 137 | hsa-miR-433 | 6.273E+01 | 1.218E+02 | 5.150E-01 | -6.635E-01 | 2.305E-02 | 1.452E-01 | 1.944E-02 | 2.663E-01 |
| 138 | hsa-miR-148b* | 3.217E+01 | 1.995E+01 | 1.612E-00 | 4.775E-01 | 2.351E-02 | 1.457E-01 | 3.674E-01 | 6.763E-01 |
| 139 | hsa-miR-372 | 3.315E+01 | 2.035E+01 | 1.629E-00 | 4.881E-01 | 2.356E-02 | 1.457E-01 | 1.380E-01 | 4.686E-01 |
| 140 | hsa-miR-1288 | 5.447E+01 | 3.753E+01 | 1.451E-00 | 3.726E-01 | 2.364E-02 | 1.457E-01 | 4.782E-01 | 7.581E-01 |
| 141 | hsa-miR-520e | 1.000E-00 | 1.000E-00 | 1.000E-00 | 0.000E+01 | 2.449E-02 | 1.497E-01 | 1.405E-01 | 4.686E-01 |
| 142 | hsa-miR-429 | 3.037E+01 | 1.071E+01 | 2.835E-00 | 1.042E-00 | 2.480E-02 | 1.497E-01 | 4.020E-01 | 7.080E-01 |
| 143 | hsa-miR-30a | 3.229E+02 | 2.185E+02 | 1.478E-00 | 3.909E-01 | 2.463E-02 | 1.497E-01 | 1.519E-01 | 4.795E-01 |
| 144 | hsa-miR-556-3p | 1.000E-00 | 1.000E-00 | 1.000E-00 | 0.000E+01 | 2.518E-02 | 1.500E-01 | 9.830E-02 | 4.199E-01 |
| 145 | hsa-miR-576-3p | 1.000E-00 | 1.000E-00 | 1.000E-00 | 0.000E+01 | 2.520E-02 | 1.500E-01 | 1.216E-02 | 2.058E-01 |
| 146 | hsa-miR-200a* | 6.273E+01 | 4.471E+01 | 1.403E-00 | 3.385E-01 | 2.620E-02 | 1.538E-01 | 3.072E-01 | 6.412E-01 |
| 147 | hsa-miR-450b-5p | 6.084E+01 | 4.315E+01 | 1.410E-00 | 3.434E-01 | 2.609E-02 | 1.538E-01 | 1.937E-01 | 5.254E-01 |
| 148 | hsa-miR-219-2-3p | 1.000E-00 | 1.000E-00 | 1.000E-00 | 0.000E+01 | 2.727E-02 | 1.580E-01 | 1.115E-01 | 4.396E-01 |
| 149 | hsa-miR-633 | 7.302E+01 | 6.006E+01 | 1.216E-00 | 1.954E-01 | 2.712E-02 | 1.580E-01 | 7.653E-01 | 8.949E-01 |
| 150 | hsa-miR-182* | 4.708E+01 | 3.114E+01 | 1.512E-00 | 4.134E-01 | 2.779E-02 | 1.588E-01 | 2.511E-01 | 5.856E-01 |
| 151 | hsa-miR-582-5p | 1.898E+01 | 1.000E-00 | 1.898E+01 | 2.943E-00 | 2.775E-02 | 1.588E-01 | 4.272E-02 | 3.414E-01 |
| 152 | hsa-miR-520c-5p | 1.212E+02 | 1.881E+02 | 6.442E-01 | -4.398E-01 | 2.823E-02 | 1.603E-01 | 3.170E-02 | 3.110E-01 |
| 153 | hsa-miR-934 | 8.572E+01 | 6.702E+01 | 1.279E-00 | 2.460E-01 | 2.970E-02 | 1.663E-01 | 4.700E-02 | 3.580E-01 |
| 154 | hsa-miR-526b* | 1.336E+01 | 1.745E+01 | 7.655E-01 | -2.673E-01 | 3.006E-02 | 1.663E-01 | 6.560E-01 | 8.645E-01 |
| 155 | hsa-miR-770-5p | 5.447E+01 | 9.611E+01 | 5.667E-01 | -5.679E-01 | 3.026E-02 | 1.663E-01 | 7.309E-02 | 4.115E-01 |
| 156 | hsa-miR-660 | 4.413E+02 | 3.840E+02 | 1.149E-00 | 1.392E-01 | 3.017E-02 | 1.663E-01 | 6.066E-01 | 8.369E-01 |
| 157 | hsa-miR-411* | 5.046E+01 | 3.581E+01 | 1.409E-00 | 3.432E-01 | 3.064E-02 | 1.663E-01 | 2.508E-02 | 2.925E-01 |
| 158 | hsa-miR-576-5p | 1.000E-00 | 1.000E-00 | 1.000E-00 | 0.000E+01 | 3.044E-02 | 1.663E-01 | 1.937E-02 | 2.663E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 159 | hsa-miR-606 | 6.273E+01 | 5.092E+01 | 1.232E-00 | 2.086E-01 | 3.063E-02 | 1.663E-01 | 6.948E-01 | 8.769E-01 |
| 160 | hsa-miR-205 | 4.708E+01 | 2.904E+01 | 1.621E-00 | 4.830E-01 | 3.141E-02 | 1.694E-01 | 4.697E-01 | 7.556E-01 |
| 161 | hsa-miR-1302 | 3.119E+01 | 1.953E+01 | 1.597E-00 | 4.680E-01 | 3.211E-02 | 1.711E-01 | 1.837E-01 | 5.104E-01 |
| 162 | hsa-miR-301b | 1.857E+02 | 2.627E+02 | 7.069E-01 | -3.468E-01 | 3.204E-02 | 1.711E-01 | 7.725E-03 | 1.481E-01 |
| 163 | hsa-miR-891a | 1.082E+02 | 1.857E+02 | 5.824E-01 | -5.405E-01 | 3.412E-02 | 1.795E-01 | 8.556E-03 | 1.538E-01 |
| 164 | hsa-miR-516b* | 2.024E+01 | 2.234E-00 | 9.060E-00 | 2.204E-00 | 3.401E-02 | 1.795E-01 | 1.039E-01 | 4.251E-01 |
| 165 | hsa-miR-376a* | 1.000E-00 | 1.000E-00 | 1.000E-00 | 0.000E+01 | 3.481E-02 | 1.810E-01 | 2.138E-01 | 5.318E-01 |
| 166 | hsa-miR-936 | 6.298E+01 | 8.307E+01 | 7.581E-01 | -2.769E-01 | 3.482E-02 | 1.810E-01 | 4.805E-02 | 3.580E-01 |
| 167 | hsa-miR-26a-2* | 1.000E-00 | 1.000E-00 | 1.000E-00 | 0.000E+01 | 3.527E-02 | 1.818E-01 | 6.729E-02 | 4.115E-01 |
| 168 | hsa-miR-544 | 3.683E+01 | 2.530E+01 | 1.456E-00 | 3.755E-01 | 3.539E-02 | 1.818E-01 | 1.377E-01 | 4.686E-01 |
| 169 | hsa-miR-134 | 5.693E+01 | 4.088E+01 | 1.393E-00 | 3.311E-01 | 3.637E-02 | 1.857E-01 | 5.933E-01 | 8.254E-01 |
| 170 | hsa-miR-542-3p | 7.419E+01 | 9.334E+01 | 7.949E-01 | -2.295E-01 | 3.657E-02 | 1.857E-01 | 4.143E-02 | 3.373E-01 |
| 171 | hsa-miR-518d-5p | 1.569E+02 | 2.542E+02 | 6.170E-01 | -4.828E-01 | 3.791E-02 | 1.901E-01 | 7.024E-03 | 1.443E-01 |
| 172 | hsa-miR-513a-3p | 3.315E+01 | 1.964E+01 | 1.688E-00 | 5.238E-01 | 3.811E-02 | 1.901E-01 | 3.578E-01 | 6.760E-01 |
| 173 | hsa-miR-548a-3p | 7.070E+01 | 6.366E+01 | 1.110E-00 | 1.048E-01 | 3.779E-02 | 1.901E-01 | 7.208E-01 | 8.841E-01 |
| 174 | hsa-miR-559 | 4.850E+01 | 3.289E+01 | 1.475E-00 | 3.885E-01 | 3.873E-02 | 1.921E-01 | 1.819E-03 | 7.297E-02 |
| 175 | hsa-miR-1308 | 4.419E+01 | 7.310E+01 | 6.046E-01 | -5.032E-01 | 3.986E-02 | 1.966E-01 | 4.591E-02 | 3.570E-01 |
| 176 | hsa-miR-1825 | 4.629E+01 | 3.136E+01 | 1.476E-00 | 3.895E-01 | 4.048E-02 | 1.985E-01 | 7.134E-01 | 8.840E-01 |
| 177 | hsa-miR-585 | 1.336E+01 | 1.000E-00 | 1.336E+01 | 2.592E-00 | 4.100E-02 | 1.988E-01 | 5.375E-02 | 3.652E-01 |
| 178 | hsa-miR-181a | 6.353E+02 | 2.272E+02 | 2.797E-00 | 1.028E-00 | 4.094E-02 | 1.988E-01 | 6.299E-03 | 1.431E-01 |
| 179 | hsa-miR-1470 | 1.590E+02 | 1.203E+02 | 1.322E-00 | 2.789E-01 | 4.252E-02 | 1.994E-01 | 3.190E-01 | 6.508E-01 |
| 180 | hsa-miR-513c | 2.133E-00 | 2.660E+01 | 8.020E-02 | -2.523E-00 | 4.164E-02 | 1.994E-01 | 2.679E-03 | 8.564E-02 |
| 181 | hsa-miR-885-3p | 1.738E+02 | 2.568E+02 | 6.769E-01 | -3.902E-01 | 4.197E-02 | 1.994E-01 | 3.137E-03 | 9.669E-02 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 182 | hsa-miR-1205 | 7.070E+01 | 1.309E+02 | 5.402E-01 | -6.158E-01 | 4.162E-02 | 1.994E-01 | 3.457E-02 | 3.208E-01 |
| 183 | hsa-miR-518f* | 1.220E+02 | 1.684E+02 | 7.247E-01 | -3.219E-01 | 4.251E-02 | 1.994E-01 | 2.236E-02 | 2.756E-01 |
| 184 | hsa-miR-1305 | 9.061E+01 | 7.452E+01 | 1.216E-00 | 1.954E-01 | 4.234E-02 | 1.994E-01 | 4.078E-01 | 7.106E-01 |
| 185 | hsa-miR-190 | 1.000E-00 | 1.000E-00 | 1.000E-00 | 0.000E+01 | 4.291E-02 | 2.002E-01 | 7.885E-02 | 4.158E-01 |
| 186 | hsa-miR-363 | 3.450E+03 | 3.998E+03 | 8.629E-01 | -1.475E-01 | 4.421E-02 | 2.034E-01 | 7.128E-02 | 4.115E-01 |
| 187 | hsa-miR-519d | 5.762E+01 | 5.046E+01 | 1.142E-00 | 1.325E-01 | 4.390E-02 | 2.034E-01 | 1.614E-01 | 4.883E-01 |
| 188 | hsa-miR-181a-2* | 8.635E+01 | 7.727E+01 | 1.117E-00 | 1.111E-01 | 4.430E-02 | 2.034E-01 | 5.383E-01 | 7.996E-01 |
| 189 | hsa-miR-220b | 4.639E+01 | 6.233E+01 | 7.442E-01 | -2.954E-01 | 4.557E-02 | 2.081E-01 | 2.383E-02 | 2.856E-01 |
| 190 | hsa-miR-29c* | 1.359E-00 | 1.000E-00 | 1.359E-00 | 3.070E-01 | 4.646E-02 | 2.110E-01 | 1.129E-01 | 4.396E-01 |
| 191 | hsa-miR-1265 | 1.359E-00 | 4.629E+01 | 2.936E-02 | -3.528E-00 | 4.779E-02 | 2.133E-01 | 7.927E-03 | 1.487E-01 |
| 192 | hsa-miR-1468 | 1.000E-00 | 1.000E-00 | 1.000E-00 | 0.000E+01 | 4.754E-02 | 2.133E-01 | 4.797E-01 | 7.581E-01 |
| 193 | hsa-miR-96* | 1.152E+02 | 1.141E+02 | 1.009E-00 | 9.048E-03 | 4.739E-02 | 2.133E-01 | 7.321E-01 | 8.857E-01 |
| 194 | hsa-miR-562 | 2.904E+01 | 1.502E+01 | 1.933E-00 | 6.593E-01 | 4.819E-02 | 2.133E-01 | 5.514E-01 | 8.015E-01 |
| 195 | hsa-miR-580 | 4.327E+01 | 2.566E+01 | 1.686E-00 | 5.226E-01 | 4.809E-02 | 2.133E-01 | 2.110E-02 | 2.725E-01 |
| 196 | hsa-miR-92b | 3.182E+02 | 2.627E+02 | 1.212E-00 | 1.919E-01 | 4.889E-02 | 2.153E-01 | 3.699E-01 | 6.792E-01 |
| 197 | hsa-miR-523* | 1.152E+02 | 1.417E+02 | 8.125E-01 | -2.076E-01 | 4.970E-02 | 2.177E-01 | 7.615E-02 | 4.133E-01 |
| 198 | hsa-miR-548c-3p | 3.674E+01 | 2.643E+01 | 1.390E-00 | 3.293E-01 | 4.998E-02 | 2.178E-01 | 4.174E-01 | 7.134E-01 |
| 199 | hsa-miR-618 | 1.534E+01 | 1.000E-00 | 1.534E+01 | 2.730E-00 | 5.044E-02 | 2.188E-01 | 2.540E-03 | 8.431E-02 |
| 200 | hsa-miR-662 | 5.200E+01 | 4.639E+01 | 1.121E-00 | 1.142E-01 | 5.083E-02 | 2.193E-01 | 4.777E-01 | 7.581E-01 |
| 201 | hsa-miR-539 | 1.000E-00 | 1.000E-00 | 1.000E-00 | 0.000E+01 | 5.112E-02 | 2.195E-01 | 7.836E-02 | 4.158E-01 |
| 202 | hsa-miR-548n | 2.896E+01 | 1.479E+01 | 1.958E-00 | 6.721E-01 | 5.154E-02 | 2.202E-01 | 6.621E-01 | 8.657E-01 |
| 203 | hsa-miR-203 | 8.436E-00 | 1.000E-00 | 8.436E-00 | 2.133E-00 | 5.360E-02 | 2.279E-01 | 8.337E-02 | 4.158E-01 |
| 204 | hsa-miR-152 | 2.154E+02 | 3.279E+02 | 6.569E-01 | -4.202E-01 | 5.501E-02 | 2.303E-01 | 1.717E-02 | 2.469E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 205 | hsa-miR-1279 | 1.000E-00 | 1.000E-00 | 1.000E-00 | 0.000E+01 | 5.472E-02 | 2.303E-01 | 5.518E-02 | 3.692E-01 |
| 206 | hsa-miR-640 | 9.955E+01 | 9.140E+01 | 1.089E-00 | 8.550E-02 | 5.525E-02 | 2.303E-01 | 4.958E-01 | 7.737E-01 |
| 207 | hsa-miR-520a-5p | 1.003E+02 | 1.502E+02 | 6.681E-01 | -4.033E-01 | 5.461E-02 | 2.303E-01 | 2.028E-02 | 2.699E-01 |
| 208 | hsa-miR-23b | 3.143E+03 | 3.790E+03 | 8.294E-01 | -1.870E-01 | 5.719E-02 | 2.324E-01 | 9.788E-02 | 4.199E-01 |
| 209 | hsa-miR-431 | 1.758E+02 | 2.001E+02 | 8.786E-01 | -1.294E-01 | 5.762E-02 | 2.324E-01 | 8.349E-02 | 4.158E-01 |
| 210 | hsa-miR-376b | 6.046E+01 | 9.322E+01 | 6.486E-01 | -4.329E-01 | 5.603E-02 | 2.324E-01 | 2.922E-02 | 3.110E-01 |
| 211 | hsa-miR-92a | 1.198E+04 | 1.198E+04 | 1.000E-00 | 0.000E+01 | 5.753E-02 | 2.324E-01 | 4.503E-01 | 7.402E-01 |
| 212 | hsa-miR-548k | 1.139E+01 | 1.000E-00 | 1.139E+01 | 2.433E-00 | 5.758E-02 | 2.324E-01 | 3.104E-02 | 3.110E-01 |
| 213 | hsa-miR-380 | 2.076E+01 | 1.680E+01 | 1.236E-00 | 2.119E-01 | 5.689E-02 | 2.324E-01 | 1.256E-01 | 4.594E-01 |
| 214 | hsa-miR-202 | 2.177E+01 | 6.601E-00 | 3.298E-00 | 1.193E-00 | 5.676E-02 | 2.324E-01 | 4.165E-01 | 7.132E-01 |
| 215 | hsa-miR-19b-2* | 1.000E-00 | 1.000E-00 | 1.000E-00 | 0.000E+01 | 5.800E-02 | 2.328E-01 | 3.646E-01 | 6.763E-01 |
| 216 | hsa-miR-128 | 6.222E+02 | 9.066E+02 | 6.863E-01 | -3.764E-01 | 5.900E-02 | 2.332E-01 | 5.430E-02 | 3.661E-01 |
| 217 | hsa-miR-520d-3p | 1.000E-00 | 1.000E-00 | 1.000E-00 | 0.000E+01 | 5.945E-02 | 2.332E-01 | 5.693E-01 | 8.120E-01 |
| 218 | hsa-miR-1282 | 1.000E-00 | 1.000E-00 | 1.000E-00 | 0.000E+01 | 5.945E-02 | 2.332E-01 | 1.045E-01 | 4.251E-01 |
| 219 | hsa-miR-564 | 1.565E+02 | 2.008E+02 | 7.793E-01 | -2.494E-01 | 5.879E-02 | 2.332E-01 | 4.232E-02 | 3.413E-01 |
| 220 | hsa-miR-1226 | 4.944E+01 | 3.581E+01 | 1.381E-00 | 3.226E-01 | 5.844E-02 | 2.332E-01 | 9.508E-01 | 9.850E-01 |
| 221 | hsa-miR-224 | 4.774E+01 | 5.917E+01 | 8.069E-01 | -2.146E-01 | 6.034E-02 | 2.339E-01 | 2.945E-02 | 3.110E-01 |
| 222 | hsa-miR-574-5p | 8.284E+02 | 1.242E+03 | 6.671E-01 | -4.048E-01 | 6.044E-02 | 2.339E-01 | 1.020E-02 | 1.760E-01 |
| 223 | hsa-miR-548b-5p | 1.000E-00 | 1.000E-00 | 1.000E-00 | 0.000E+01 | 6.037E-02 | 2.339E-01 | 7.569E-02 | 4.133E-01 |
| 224 | hsa-miR-512-3p | 3.587E+01 | 2.530E+01 | 1.418E-00 | 3.489E-01 | 6.095E-02 | 2.348E-01 | 7.806E-01 | 9.019E-01 |
| 225 | hsa-miR-296-5p | 2.352E+02 | 1.906E+02 | 1.234E-00 | 2.103E-01 | 6.316E-02 | 2.423E-01 | 2.610E-01 | 5.971E-01 |
| 226 | hsa-miR-302a | 1.000E-00 | 1.000E-00 | 1.000E-00 | 0.000E+01 | 6.570E-02 | 2.502E-01 | 1.890E-01 | 5.194E-01 |
| 227 | hsa-miR-501-5p | 3.808E+01 | 1.555E+01 | 2.449E-00 | 8.957E-01 | 6.611E-02 | 2.502E-01 | 9.431E-02 | 4.174E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 228 | hsa-miR-382 | 1.439E+01 | 5.529E+01 | 2.603E-01 | -1.346E-00 | 6.588E-02 | 2.502E-01 | 5.841E-02 | 3.768E-01 |
| 229 | hsa-miR-18b* | 7.232E+01 | 9.249E+01 | 7.819E-01 | -2.461E-01 | 6.672E-02 | 2.503E-01 | 1.131E-01 | 4.396E-01 |
| 230 | hsa-miR-24-2* | 1.506E+02 | 1.462E+02 | 1.030E-00 | 2.924E-02 | 6.658E-02 | 2.503E-01 | 7.583E-01 | 8.928E-01 |
| 231 | hsa-miR-944 | 1.439E+01 | 1.000E-00 | 1.439E+01 | 2.667E-00 | 6.707E-02 | 2.506E-01 | 2.036E-01 | 5.254E-01 |
| 232 | hsa-miR-520f | 1.000E-00 | 1.000E-00 | 1.000E-00 | 0.000E+01 | 6.750E-02 | 2.511E-01 | 3.353E-01 | 6.638E-01 |
| 233 | hsa-miR-1290 | 1.000E-00 | 1.000E-00 | 1.000E-00 | 0.000E+01 | 6.882E-02 | 2.549E-01 | 1.617E-01 | 4.883E-01 |
| 234 | hsa-miR-595 | 1.025E+02 | 1.325E+02 | 7.733E-01 | -2.570E-01 | 6.960E-02 | 2.567E-01 | 1.643E-01 | 4.908E-01 |
| 235 | hsa-miR-144* | 6.543E+02 | 3.352E+02 | 1.952E-00 | 6.688E-01 | 7.001E-02 | 2.569E-01 | 6.307E-01 | 8.496E-01 |
| 236 | hsa-miR-644 | 2.530E+01 | 1.840E+01 | 1.375E-00 | 3.188E-01 | 7.024E-02 | 2.569E-01 | 7.561E-01 | 8.927E-01 |
| 237 | hsa-miR-650 | 1.236E+02 | 1.300E+02 | 9.509E-01 | -5.033E-02 | 7.318E-02 | 2.665E-01 | 9.347E-02 | 4.174E-01 |
| 238 | hsa-miR-518a-5p | 1.649E+02 | 3.160E+02 | 5.218E-01 | -6.505E-01 | 7.517E-02 | 2.702E-01 | 1.785E-02 | 2.526E-01 |
| 239 | hsa-miR-129* | 4.433E+01 | 3.081E+01 | 1.439E-00 | 3.638E-01 | 7.521E-02 | 2.702E-01 | 9.255E-01 | 9.719E-01 |
| 240 | hsa-miR-1238 | 2.851E+01 | 1.745E+01 | 1.634E-00 | 4.907E-01 | 7.545E-02 | 2.702E-01 | 3.372E-01 | 6.638E-01 |
| 241 | hsa-miR-154 | 1.000E-00 | 1.000E-00 | 1.000E-00 | 0.000E+01 | 7.483E-02 | 2.702E-01 | 2.927E-01 | 6.299E-01 |
| 242 | hsa-miR-106b | 1.041E+04 | 1.041E+04 | 1.000E-00 | 0.000E+01 | 7.601E-02 | 2.711E-01 | 7.807E-01 | 9.019E-01 |
| 243 | hsa-miR-431* | 2.729E+01 | 1.953E+01 | 1.397E-00 | 3.344E-01 | 7.737E-02 | 2.725E-01 | 1.024E-01 | 4.251E-01 |
| 244 | hsa-miR-1202 | 2.102E+02 | 3.279E+02 | 6.411E-01 | -4.446E-01 | 7.700E-02 | 2.725E-01 | 5.561E-02 | 3.692E-01 |
| 245 | hsa-miR-587 | 3.902E+01 | 2.566E+01 | 1.521E-00 | 4.192E-01 | 7.731E-02 | 2.725E-01 | 5.048E-01 | 7.779E-01 |
| 246 | hsa-miR-708 | 3.648E+01 | 2.680E+01 | 1.361E-00 | 3.084E-01 | 7.788E-02 | 2.732E-01 | 6.271E-01 | 8.496E-01 |
| 247 | hsa-miR-451 | 1.585E+03 | 1.096E+03 | 1.446E-00 | 3.687E-01 | 7.914E-02 | 2.754E-01 | 1.397E-01 | 4.686E-01 |
| 248 | hsa-miR-519a* | 1.458E+02 | 1.852E+02 | 7.874E-01 | -2.391E-01 | 7.892E-02 | 2.754E-01 | 5.044E-02 | 3.580E-01 |
| 249 | hsa-miR-105* | 8.304E-00 | 7.252E-00 | 1.145E-00 | 1.356E-01 | 8.011E-02 | 2.777E-01 | 5.436E-01 | 8.015E-01 |
| 250 | hsa-miR-625* | 2.318E+02 | 1.788E+02 | 1.296E-00 | 2.596E-01 | 8.246E-02 | 2.847E-01 | 1.643E-01 | 4.908E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 251 | hsa-miR-127-3p | 5.339E+01 | 7.302E+01 | 7.311E-01 | -3.131E-01 | 8.319E-02 | 2.860E-01 | 1.388E-01 | 4.686E-01 |
| 252 | hsa-miR-1911 | 2.319E+01 | 1.734E+01 | 1.337E-00 | 2.905E-01 | 8.368E-02 | 2.866E-01 | 7.787E-01 | 9.019E-01 |
| 253 | hsa-let-7c | 4.231E+02 | 1.649E+02 | 2.566E-00 | 9.424E-01 | 8.475E-02 | 2.891E-01 | 1.267E-01 | 4.614E-01 |
| 254 | hsa-miR-1269 | 4.656E+01 | 5.868E+01 | 7.935E-01 | -2.313E-01 | 8.548E-02 | 2.904E-01 | 2.012E-01 | 5.254E-01 |
| 255 | hsa-miR-370 | 4.835E+01 | 7.104E+01 | 6.806E-01 | -3.848E-01 | 8.674E-02 | 2.936E-01 | 2.322E-01 | 5.594E-01 |
| 256 | hsa-miR-298 | 1.192E+02 | 1.678E+02 | 7.104E-01 | -3.419E-01 | 8.763E-02 | 2.943E-01 | 3.994E-02 | 3.373E-01 |
| 257 | hsa-miR-1 | 1.322E+01 | 1.000E-00 | 1.322E+01 | 2.581E-00 | 8.742E-02 | 2.943E-01 | 1.229E-01 | 4.534E-01 |
| 258 | hsa-miR-28-3p | 1.809E+02 | 1.689E+02 | 1.071E-00 | 6.829E-02 | 8.810E-02 | 2.945E-01 | 9.110E-01 | 9.682E-01 |
| 259 | hsa-miR-635 | 1.008E+02 | 1.268E+02 | 7.944E-01 | -2.302E-01 | 8.839E-02 | 2.945E-01 | 5.623E-02 | 3.705E-01 |
| 260 | hsa-miR-26a | 6.572E+03 | 7.310E+03 | 8.991E-01 | -1.064E-01 | 8.943E-02 | 2.960E-01 | 1.449E-01 | 4.686E-01 |
| 261 | hsa-miR-1261 | 1.000E-00 | 1.000E-00 | 1.000E-00 | 0.000E+01 | 8.952E-02 | 2.960E-01 | 2.583E-02 | 2.973E-01 |
| 262 | hsa-miR-211 | 1.000E-00 | 1.000E-00 | 1.000E-00 | 0.000E+01 | 9.213E-02 | 3.025E-01 | 8.318E-02 | 4.158E-01 |
| 263 | hsa-miR-99b* | 4.995E+01 | 5.959E+01 | 8.382E-01 | -1.765E-01 | 9.242E-02 | 3.025E-01 | 5.851E-02 | 3.768E-01 |
| 264 | hsa-miR-183 | 3.304E+02 | 4.953E+02 | 6.670E-01 | -4.049E-01 | 9.252E-02 | 3.025E-01 | 4.902E-02 | 3.580E-01 |
| 265 | hsa-miR-1184 | 1.769E+02 | 1.862E+02 | 9.502E-01 | -5.110E-02 | 9.401E-02 | 3.062E-01 | 3.136E-02 | 3.110E-01 |
| 266 | hsa-let-7g* | 1.107E+02 | 1.624E+02 | 6.814E-01 | -3.837E-01 | 9.489E-02 | 3.079E-01 | 1.735E-01 | 5.030E-01 |
| 267 | hsa-miR-519e | 1.000E-00 | 1.000E-00 | 1.000E-00 | 0.000E+01 | 9.526E-02 | 3.079E-01 | 6.003E-01 | 8.318E-01 |
| 268 | hsa-miR-453 | 2.056E+01 | 4.534E+01 | 4.535E-01 | -7.909E-01 | 9.612E-02 | 3.084E-01 | 3.120E-01 | 6.426E-01 |
| 269 | hsa-miR-30a* | 3.985E+01 | 1.745E+01 | 2.283E-00 | 8.254E-01 | 9.586E-02 | 3.084E-01 | 6.428E-02 | 4.020E-01 |
| 270 | hsa-miR-1324 | 1.254E+02 | 1.498E+02 | 8.373E-01 | -1.775E-01 | 9.882E-02 | 3.135E-01 | 9.042E-02 | 4.174E-01 |
| 271 | hsa-miR-611 | 9.955E+01 | 1.325E+02 | 7.512E-01 | -2.861E-01 | 9.854E-02 | 3.135E-01 | 2.557E-01 | 5.917E-01 |
| 272 | hsa-miR-1322 | 7.419E+01 | 1.322E+02 | 5.610E-01 | -5.780E-01 | 9.824E-02 | 3.135E-01 | 2.116E-02 | 2.725E-01 |
| 273 | hsa-miR-1250 | 3.683E+01 | 7.661E+01 | 4.807E-01 | -7.324E-01 | 9.994E-02 | 3.159E-01 | 3.452E-01 | 6.710E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 274 | hsa-miR-574-3p | 2.110E+03 | 1.492E+03 | 1.414E-00 | 3.466E-01 | 1.027E-01 | 3.194E-01 | 9.801E-02 | 4.199E-01 |
| 275 | hsa-miR-518e | 5.959E+01 | 8.991E+01 | 6.628E-01 | -4.113E-01 | 1.021E-01 | 3.194E-01 | 1.682E-01 | 4.987E-01 |
| 276 | hsa-miR-410 | 7.244E+01 | 6.163E+01 | 1.175E-00 | 1.616E-01 | 1.027E-01 | 3.194E-01 | 7.127E-01 | 8.840E-01 |
| 277 | hsa-miR-125b-2* | 3.249E+01 | 6.762E+01 | 4.805E-01 | -7.330E-01 | 1.016E-01 | 3.194E-01 | 3.530E-02 | 3.241E-01 |
| 278 | hsa-miR-146b-3p | 5.447E+01 | 8.415E+01 | 6.473E-01 | -4.349E-01 | 1.029E-01 | 3.194E-01 | 6.910E-02 | 4.115E-01 |
| 279 | hsa-miR-1537 | 2.729E+01 | 1.756E+01 | 1.554E-00 | 4.406E-01 | 1.037E-01 | 3.207E-01 | 2.334E-01 | 5.594E-01 |
| 280 | hsa-miR-34c-3p | 8.188E+01 | 7.773E+01 | 1.053E-00 | 5.201E-02 | 1.084E-01 | 3.240E-01 | 3.569E-01 | 6.760E-01 |
| 281 | hsa-miR-1264 | 2.013E+01 | 1.624E+01 | 1.239E-00 | 2.145E-01 | 1.082E-01 | 3.240E-01 | 9.025E-01 | 9.671E-01 |
| 282 | hsa-miR-302d | 1.000E-00 | 1.000E-00 | 1.000E-00 | 0.000E+01 | 1.074E-01 | 3.240E-01 | 1.489E-01 | 4.742E-01 |
| 283 | hsa-miR-221* | 1.034E+02 | 1.268E+02 | 8.156E-01 | -2.038E-01 | 1.068E-01 | 3.240E-01 | 1.612E-01 | 4.883E-01 |
| 284 | hsa-miR-1471 | 1.112E+02 | 1.543E+02 | 7.210E-01 | -3.271E-01 | 1.085E-01 | 3.240E-01 | 7.293E-02 | 4.115E-01 |
| 285 | hsa-miR-1183 | 8.815E+01 | 1.649E+02 | 5.346E-01 | -6.262E-01 | 1.072E-01 | 3.240E-01 | 1.465E-03 | 7.297E-02 |
| 286 | hsa-miR-338-3p | 1.273E+02 | 1.743E+02 | 7.302E-01 | -3.144E-01 | 1.065E-01 | 3.240E-01 | 1.415E-01 | 4.686E-01 |
| 287 | hsa-miR-519e* | 6.006E+01 | 8.761E+01 | 6.855E-01 | -3.776E-01 | 1.075E-01 | 3.240E-01 | 1.336E-01 | 4.686E-01 |
| 288 | hsa-miR-1298 | 4.315E+01 | 1.596E+01 | 2.704E-00 | 9.946E-01 | 1.053E-01 | 3.240E-01 | 6.941E-02 | 4.115E-01 |
| 289 | hsa-miR-376a | 8.836E+01 | 1.218E+02 | 7.255E-01 | -3.209E-01 | 1.062E-01 | 3.240E-01 | 8.382E-02 | 4.158E-01 |
| 290 | hsa-miR-517c | 8.713E-00 | 6.601E-00 | 1.320E-00 | 2.776E-01 | 1.094E-01 | 3.256E-01 | 9.605E-01 | 9.865E-01 |
| 291 | hsa-miR-1286 | 1.200E+02 | 1.620E+02 | 7.410E-01 | -2.998E-01 | 1.101E-01 | 3.265E-01 | 1.226E-01 | 4.534E-01 |
| 292 | hsa-miR-30b* | 1.711E+01 | 3.701E+01 | 4.622E-01 | -7.717E-01 | 1.114E-01 | 3.269E-01 | 1.054E-01 | 4.251E-01 |
| 293 | hsa-miR-361-5p | 4.159E+02 | 3.138E+02 | 1.325E-00 | 2.817E-01 | 1.111E-01 | 3.269E-01 | 3.446E-01 | 6.710E-01 |
| 294 | hsa-miR-509-3-5p | 2.136E+02 | 3.721E+02 | 5.739E-01 | -5.554E-01 | 1.108E-01 | 3.269E-01 | 5.056E-02 | 3.580E-01 |
| 295 | hsa-miR-194 | 6.572E+03 | 6.927E+03 | 9.488E-01 | -5.259E-02 | 1.124E-01 | 3.276E-01 | 2.093E-01 | 5.292E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 296 | hsa-miR-135b | 1.000E-00 | 1.000E-00 | 1.000E-00 | 0.000E+01 | 1.122E-01 | 3.276E-01 | 6.027E-03 | 1.431E-01 |
| 297 | hsa-miR-153 | 1.027E+02 | 1.473E+02 | 6.968E-01 | -3.613E-01 | 1.141E-01 | 3.284E-01 | 5.034E-02 | 3.580E-01 |
| 298 | hsa-miR-522* | 1.325E+02 | 2.063E+02 | 6.423E-01 | -4.427E-01 | 1.132E-01 | 3.284E-01 | 9.343E-02 | 4.174E-01 |
| 299 | hsa-miR-1301 | 2.019E+02 | 2.627E+02 | 7.686E-01 | -2.632E-01 | 1.140E-01 | 3.284E-01 | 8.120E-02 | 4.158E-01 |
| 300 | hsa-miR-147b | 3.190E+01 | 2.485E+01 | 1.284E-00 | 2.498E-01 | 1.144E-01 | 3.284E-01 | 2.024E-01 | 5.254E-01 |
| 301 | hsa-miR-548d-5p | 1.000E-00 | 1.000E-00 | 1.000E-00 | 0.000E+01 | 1.145E-01 | 3.284E-01 | 1.798E-01 | 5.097E-01 |
| 302 | hsa-miR-29a | 6.967E+02 | 9.970E+02 | 6.988E-01 | -3.585E-01 | 1.157E-01 | 3.305E-01 | 1.425E-01 | 4.686E-01 |
| 303 | hsa-miR-943 | 3.902E+01 | 3.029E+01 | 1.288E-00 | 2.533E-01 | 1.162E-01 | 3.308E-01 | 2.304E-01 | 5.594E-01 |
| 304 | hsa-miR-1306 | 2.496E+01 | 3.701E+01 | 6.744E-01 | -3.939E-01 | 1.170E-01 | 3.310E-01 | 3.563E-01 | 6.760E-01 |
| 305 | hsa-miR-521 | 4.708E+01 | 4.271E+01 | 1.102E-00 | 9.725E-02 | 1.170E-01 | 3.310E-01 | 3.976E-01 | 7.046E-01 |
| 306 | hsa-miR-124 | 1.045E+02 | 1.218E+02 | 8.579E-01 | -1.532E-01 | 1.207E-01 | 3.405E-01 | 1.117E-01 | 4.396E-01 |
| 307 | hsa-miR-485-5p | 4.708E+01 | 6.563E+01 | 7.173E-01 | -3.322E-01 | 1.219E-01 | 3.421E-01 | 9.428E-02 | 4.174E-01 |
| 308 | hsa-miR-212 | 5.653E+01 | 5.577E+01 | 1.014E-00 | 1.350E-02 | 1.229E-01 | 3.421E-01 | 8.363E-01 | 9.407E-01 |
| 309 | hsa-miR-886-3p | 1.000E-00 | 1.125E+01 | 8.889E-02 | -2.420E-00 | 1.223E-01 | 3.421E-01 | 4.886E-01 | 7.667E-01 |
| 310 | hsa-miR-652 | 1.096E+03 | 1.127E+03 | 9.723E-01 | -2.811E-02 | 1.229E-01 | 3.421E-01 | 4.656E-01 | 7.529E-01 |
| 311 | hsa-miR-135a | 1.000E-00 | 1.000E-00 | 1.000E-00 | 0.000E+01 | 1.233E-01 | 3.423E-01 | 1.953E-01 | 5.254E-01 |
| 312 | hsa-miR-608 | 5.339E+01 | 6.084E+01 | 8.775E-01 | -1.306E-01 | 1.260E-01 | 3.470E-01 | 7.806E-01 | 9.019E-01 |
| 313 | hsa-miR-887 | 1.027E+02 | 9.810E+01 | 1.047E-00 | 4.554E-02 | 1.271E-01 | 3.470E-01 | 9.738E-01 | 9.887E-01 |
| 314 | hsa-miR-106b* | 1.769E+02 | 2.027E+02 | 8.728E-01 | -1.361E-01 | 1.268E-01 | 3.470E-01 | 9.322E-02 | 4.174E-01 |
| 315 | hsa-miR-34b* | 4.482E+01 | 6.574E+01 | 6.817E-01 | -3.831E-01 | 1.260E-01 | 3.470E-01 | 6.365E-02 | 4.020E-01 |
| 316 | hsa-miR-1257 | 3.777E-00 | 1.000E-00 | 3.777E-00 | 1.329E-00 | 1.270E-01 | 3.470E-01 | 1.835E-01 | 5.104E-01 |
| 317 | hsa-miR-1263 | 5.339E+01 | 4.785E+01 | 1.116E-00 | 1.095E-01 | 1.276E-01 | 3.474E-01 | 4.418E-01 | 7.304E-01 |
| 318 | hsa-miR-588 | 1.197E+02 | 1.543E+02 | 7.762E-01 | -2.534E-01 | 1.306E-01 | 3.527E-01 | 1.325E-01 | 4.686E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 319 | hsa-miR-30d* | 5.068E+01 | 3.753E+01 | 1.350E-00 | 3.003E-01 | 1.304E-01 | 3.527E-01 | 9.086E-01 | 9.671E-01 |
| 320 | hsa-miR-423-3p | 1.096E+03 | 1.376E+03 | 7.968E-01 | -2.271E-01 | 1.308E-01 | 3.527E-01 | 1.395E-01 | 4.686E-01 |
| 321 | hsa-miR-766 | 4.858E+02 | 2.644E+02 | 1.837E-00 | 6.083E-01 | 1.315E-01 | 3.535E-01 | 2.934E-01 | 6.299E-01 |
| 322 | hsa-miR-122 | 2.066E+01 | 2.530E+01 | 8.166E-01 | -2.026E-01 | 1.328E-01 | 3.559E-01 | 5.360E-01 | 7.996E-01 |
| 323 | hsa-miR-29a* | 1.000E-00 | 1.000E-00 | 1.000E-00 | 0.000E+01 | 1.332E-01 | 3.560E-01 | 2.110E-01 | 5.294E-01 |
| 324 | hsa-miR-107 | 1.326E+03 | 1.687E+03 | 7.864E-01 | -2.403E-01 | 1.343E-01 | 3.565E-01 | 8.529E-02 | 4.158E-01 |
| 325 | hsa-miR-493 | 2.474E+01 | 2.423E+01 | 1.021E-00 | 2.083E-02 | 1.341E-01 | 3.565E-01 | 9.154E-01 | 9.693E-01 |
| 326 | hsa-miR-1323 | 4.032E+01 | 1.756E+01 | 2.296E-00 | 8.310E-01 | 1.347E-01 | 3.565E-01 | 1.041E-01 | 4.251E-01 |
| 327 | hsa-miR-486-3p | 2.194E+02 | 1.862E+02 | 1.179E-00 | 1.645E-01 | 1.364E-01 | 3.577E-01 | 6.806E-01 | 8.698E-01 |
| 328 | hsa-miR-583 | 4.708E+01 | 3.289E+01 | 1.431E-00 | 3.587E-01 | 1.356E-01 | 3.577E-01 | 1.194E-01 | 4.510E-01 |
| 329 | hsa-miR-19a* | 4.471E+01 | 3.081E+01 | 1.451E-00 | 3.723E-01 | 1.361E-01 | 3.577E-01 | 8.844E-01 | 9.618E-01 |
| 330 | hsa-miR-497 | 1.672E+02 | 2.251E+02 | 7.427E-01 | -2.974E-01 | 1.386E-01 | 3.582E-01 | 5.288E-02 | 3.652E-01 |
| 331 | hsa-miR-504 | 3.406E+01 | 3.172E+01 | 1.074E-00 | 7.121E-02 | 1.379E-01 | 3.582E-01 | 4.789E-01 | 7.581E-01 |
| 332 | hsa-miR-508-3p | 1.000E-00 | 1.000E-00 | 1.000E-00 | 0.000E+01 | 1.385E-01 | 3.582E-01 | 2.044E-01 | 5.254E-01 |
| 333 | hsa-miR-93* | 1.326E+03 | 1.242E+03 | 1.068E-00 | 6.581E-02 | 1.372E-01 | 3.582E-01 | 5.235E-01 | 7.967E-01 |
| 334 | hsa-miR-659 | 6.387E+01 | 6.629E+01 | 9.635E-01 | -3.716E-02 | 1.379E-01 | 3.582E-01 | 7.797E-01 | 9.019E-01 |
| 335 | hsa-miR-524-3p | 2.066E+01 | 3.753E+01 | 5.506E-01 | -5.968E-01 | 1.422E-01 | 3.592E-01 | 1.185E-01 | 4.505E-01 |
| 336 | hsa-miR-503 | 2.595E+02 | 3.543E+02 | 7.325E-01 | -3.113E-01 | 1.428E-01 | 3.592E-01 | 1.205E-01 | 4.510E-01 |
| 337 | hsa-miR-517b | 1.680E+01 | 1.252E+01 | 1.342E-00 | 2.944E-01 | 1.427E-01 | 3.592E-01 | 7.551E-01 | 8.926E-01 |
| 338 | hsa-miR-617 | 1.868E+01 | 5.416E-00 | 3.449E-00 | 1.238E-00 | 1.412E-01 | 3.592E-01 | 2.765E-01 | 6.190E-01 |
| 339 | hsa-miR-590-5p | 1.539E+02 | 1.565E+02 | 9.831E-01 | -1.705E-02 | 1.427E-01 | 3.592E-01 | 1.143E-01 | 4.408E-01 |
| 340 | hsa-miR-138-1* | 9.249E+01 | 9.249E+01 | 1.000E-00 | 0.000E+01 | 1.418E-01 | 3.592E-01 | 9.088E-01 | 9.671E-01 |
| 341 | hsa-miR-135a* | 1.000E-00 | 1.000E-00 | 1.000E-00 | 0.000E+01 | 1.420E-01 | 3.592E-01 | 2.830E-01 | 6.220E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 342 | hsa-miR-577 | 1.868E+01 | 1.596E+01 | 1.170E-00 | 1.574E-01 | 1.397E-01 | 3.592E-01 | 6.797E-01 | 8.698E-01 |
| 343 | hsa-miR-549 | 5.144E+01 | 3.733E+01 | 1.378E-00 | 3.206E-01 | 1.428E-01 | 3.592E-01 | 1.720E-01 | 5.030E-01 |
| 344 | hsa-miR-194* | 4.339E+01 | 6.327E+01 | 6.858E-01 | -3.771E-01 | 1.439E-01 | 3.600E-01 | 1.218E-01 | 4.531E-01 |
| 345 | hsa-miR-199b-3p | 9.372E+01 | 7.937E+01 | 1.181E-00 | 1.662E-01 | 1.436E-01 | 3.600E-01 | 3.580E-01 | 6.760E-01 |
| 346 | hsa-miR-541* | 1.000E-00 | 1.000E-00 | 1.000E-00 | 0.000E+01 | 1.463E-01 | 3.643E-01 | 1.567E-01 | 4.881E-01 |
| 347 | hsa-miR-1299 | 3.618E+01 | 5.447E+01 | 6.643E-01 | -4.091E-01 | 1.465E-01 | 3.643E-01 | 1.326E-02 | 2.158E-01 |
| 348 | hsa-miR-374a* | 3.249E+01 | 2.660E+01 | 1.221E-00 | 2.000E-01 | 1.472E-01 | 3.650E-01 | 8.692E-01 | 9.543E-01 |
| 349 | hsa-miR-7-2* | 2.715E+01 | 2.485E+01 | 1.092E-00 | 8.840E-02 | 1.501E-01 | 3.694E-01 | 3.375E-01 | 6.638E-01 |
| 350 | hsa-miR-621 | 3.404E+02 | 4.720E+02 | 7.212E-01 | -3.268E-01 | 1.502E-01 | 3.694E-01 | 1.126E-01 | 4.396E-01 |
| 351 | hsa-miR-1203 | 2.001E+02 | 2.352E+02 | 8.509E-01 | -1.614E-01 | 1.502E-01 | 3.694E-01 | 8.915E-02 | 4.174E-01 |
| 352 | hsa-miR-27a* | 3.406E+01 | 3.289E+01 | 1.036E-00 | 3.494E-02 | 1.510E-01 | 3.703E-01 | 8.560E-01 | 9.508E-01 |
| 353 | hsa-miR-548f | 4.835E+01 | 4.315E+01 | 1.120E-00 | 1.137E-01 | 1.515E-01 | 3.704E-01 | 8.738E-01 | 9.545E-01 |
| 354 | hsa-miR-151-3p | 6.222E+02 | 6.967E+02 | 8.931E-01 | -1.130E-01 | 1.519E-01 | 3.704E-01 | 9.692E-01 | 9.875E-01 |
| 355 | hsa-miR-409-5p | 7.844E+01 | 6.163E+01 | 1.273E-00 | 2.412E-01 | 1.524E-01 | 3.705E-01 | 2.810E-01 | 6.204E-01 |
| 356 | hsa-miR-129-3p | 7.541E+01 | 8.653E+01 | 8.715E-01 | -1.375E-01 | 1.530E-01 | 3.708E-01 | 3.311E-01 | 6.638E-01 |
| 357 | hsa-miR-922 | 1.266E+02 | 2.119E+02 | 5.976E-01 | -5.148E-01 | 1.536E-01 | 3.713E-01 | 4.032E-02 | 3.373E-01 |
| 358 | hsa-miR-890 | 3.674E+01 | 4.629E+01 | 7.937E-01 | -2.310E-01 | 1.558E-01 | 3.749E-01 | 2.080E-01 | 5.280E-01 |
| 359 | hsa-miR-7-1* | 2.947E+02 | 2.306E+02 | 1.278E-00 | 2.452E-01 | 1.560E-01 | 3.749E-01 | 4.590E-01 | 7.498E-01 |
| 360 | hsa-miR-548j | 1.000E-00 | 1.000E-00 | 1.000E-00 | 0.000E+01 | 1.566E-01 | 3.754E-01 | 3.579E-01 | 6.760E-01 |
| 361 | hsa-miR-498 | 2.787E+01 | 2.397E+01 | 1.163E-00 | 1.508E-01 | 1.575E-01 | 3.755E-01 | 7.439E-01 | 8.883E-01 |
| 362 | hsa-miR-195* | 6.733E+01 | 9.249E+01 | 7.279E-01 | -3.176E-01 | 1.571E-01 | 3.755E-01 | 8.927E-02 | 4.174E-01 |
| 363 | hsa-miR-507 | 1.745E+01 | 1.720E-00 | 1.015E+01 | 2.317E-00 | 1.588E-01 | 3.755E-01 | 1.945E-01 | 5.254E-01 |
| 364 | hsa-miR-593* | 2.965E+02 | 4.673E+02 | 6.346E-01 | -4.547E-01 | 1.583E-01 | 3.755E-01 | 9.745E-02 | 4.199E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 365 | hsa-miR-501-3p | 3.753E+02 | 3.840E+02 | 9.773E-01 | -2.294E-02 | 1.586E-01 | 3.755E-01 | 1.426E-01 | 4.686E-01 |
| 366 | hsa-miR-302e | 2.335E-00 | 1.000E-00 | 2.335E-00 | 8.481E-01 | 1.614E-01 | 3.806E-01 | 1.584E-01 | 4.883E-01 |
| 367 | hsa-miR-204 | 1.000E-00 | 1.000E-00 | 1.000E-00 | 0.000E+01 | 1.619E-01 | 3.807E-01 | 4.080E-02 | 3.373E-01 |
| 368 | hsa-miR-767-3p | 4.433E+01 | 4.315E+01 | 1.027E-00 | 2.696E-02 | 1.629E-01 | 3.819E-01 | 3.089E-01 | 6.412E-01 |
| 369 | hsa-miR-483-5p | 1.792E+02 | 1.649E+02 | 1.087E-00 | 8.339E-02 | 1.651E-01 | 3.847E-01 | 5.884E-01 | 8.254E-01 |
| 370 | hsa-miR-193a-5p | 5.447E+01 | 5.868E+01 | 9.283E-01 | -7.437E-02 | 1.654E-01 | 3.847E-01 | 6.575E-01 | 8.645E-01 |
| 371 | hsa-miR-1270 | 2.066E+01 | 4.674E-00 | 4.421E-00 | 1.486E-00 | 1.648E-01 | 3.847E-01 | 2.321E-01 | 5.594E-01 |
| 372 | hsa-miR-658 | 4.881E+01 | 6.006E+01 | 8.126E-01 | -2.075E-01 | 1.666E-01 | 3.864E-01 | 6.335E-02 | 4.020E-01 |
| 373 | hsa-miR-656 | 2.821E+01 | 1.964E+01 | 1.437E-00 | 3.624E-01 | 1.671E-01 | 3.865E-01 | 9.563E-01 | 9.865E-01 |
| 374 | hsa-miR-1197 | 3.710E+01 | 2.530E+01 | 1.466E-00 | 3.826E-01 | 1.684E-01 | 3.885E-01 | 3.891E-01 | 6.996E-01 |
| 375 | hsa-miR-342-5p | 8.373E+01 | 7.844E+01 | 1.068E-00 | 6.533E-02 | 1.706E-01 | 3.926E-01 | 4.368E-02 | 3.458E-01 |
| 376 | hsa-miR-612 | 6.841E+01 | 8.174E+01 | 8.369E-01 | -1.780E-01 | 1.719E-01 | 3.939E-01 | 1.471E-01 | 4.728E-01 |
| 377 | hsa-miR-876-5p | 3.674E+01 | 3.114E+01 | 1.180E-00 | 1.656E-01 | 1.725E-01 | 3.939E-01 | 1.814E-01 | 5.104E-01 |
| 378 | hsa-miR-136 | 2.904E+01 | 2.146E+01 | 1.353E-00 | 3.024E-01 | 1.722E-01 | 3.939E-01 | 1.778E-01 | 5.097E-01 |
| 379 | hsa-miR-1253 | 6.936E+01 | 8.531E+01 | 8.131E-01 | -2.070E-01 | 1.795E-01 | 4.065E-01 | 1.523E-01 | 4.795E-01 |
| 380 | hsa-miR-641 | 5.762E+01 | 8.991E+01 | 6.408E-01 | -4.450E-01 | 1.791E-01 | 4.065E-01 | 4.738E-01 | 7.572E-01 |
| 381 | hsa-miR-671-3p | 3.637E+01 | 3.149E+01 | 1.155E-00 | 1.442E-01 | 1.799E-01 | 4.065E-01 | 9.146E-01 | 9.693E-01 |
| 382 | hsa-miR-548g | 2.615E+01 | 1.876E+01 | 1.394E-00 | 3.323E-01 | 1.799E-01 | 4.065E-01 | 6.166E-01 | 8.420E-01 |
| 383 | hsa-miR-548c-5p | 5.192E-00 | 1.071E+01 | 4.847E-01 | -7.243E-01 | 1.822E-01 | 4.105E-01 | 9.043E-01 | 9.671E-01 |
| 384 | hsa-miR-603 | 1.152E+02 | 1.218E+02 | 9.456E-01 | -5.589E-02 | 1.831E-01 | 4.105E-01 | 9.548E-01 | 9.865E-01 |
| 385 | hsa-miR-520b | 1.450E+01 | 2.234E-00 | 6.488E-00 | 1.870E-00 | 1.828E-01 | 4.105E-01 | 2.215E-01 | 5.476E-01 |
| 386 | hsa-miR-1283 | 1.098E+02 | 8.126E+01 | 1.351E-00 | 3.009E-01 | 1.854E-01 | 4.145E-01 | 4.831E-01 | 7.617E-01 |
| 387 | hsa-miR-1255a | 4.835E+01 | 7.714E+01 | 6.268E-01 | -4.672E-01 | 1.882E-01 | 4.154E-01 | 6.406E-02 | 4.020E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 388 | hsa-miR-296-3p | 5.144E+01 | 4.958E+01 | 1.038E-00 | 3.686E-02 | 1.874E-01 | 4.154E-01 | 9.167E-01 | 9.695E-01 |
| 389 | hsa-miR-202* | 5.447E+01 | 6.563E+01 | 8.300E-01 | -1.863E-01 | 1.871E-01 | 4.154E-01 | 7.703E-01 | 8.986E-01 |
| 390 | hsa-miR-1200 | 7.370E+01 | 9.487E+01 | 7.769E-01 | -2.525E-01 | 1.881E-01 | 4.154E-01 | 2.049E-01 | 5.254E-01 |
| 391 | hsa-miR-630 | 3.081E+01 | 2.485E+01 | 1.240E-00 | 2.151E-01 | 1.882E-01 | 4.154E-01 | 6.601E-01 | 8.656E-01 |
| 392 | hsa-miR-609 | 1.000E-00 | 1.000E-00 | 1.000E-00 | 0.000E+01 | 1.899E-01 | 4.178E-01 | 4.605E-01 | 7.498E-01 |
| 393 | hsa-miR-149 | 2.100E+01 | 1.995E+01 | 1.053E-00 | 5.121E-02 | 1.902E-01 | 4.178E-01 | 8.707E-01 | 9.545E-01 |
| 394 | hsa-miR-767-5p | 1.590E+02 | 1.862E+02 | 8.543E-01 | -1.575E-01 | 1.936E-01 | 4.220E-01 | 7.753E-02 | 4.158E-01 |
| 395 | hsa-miR-548m | 1.000E-00 | 1.000E-00 | 1.000E-00 | 0.000E+01 | 1.930E-01 | 4.220E-01 | 3.102E-01 | 6.412E-01 |
| 396 | hsa-miR-381 | 8.739E+01 | 9.232E+01 | 9.466E-01 | -5.489E-02 | 1.936E-01 | 4.220E-01 | 1.716E-01 | 5.030E-01 |
| 397 | hsa-miR-200c* | 4.835E+01 | 3.172E+01 | 1.525E-00 | 4.217E-01 | 1.961E-01 | 4.262E-01 | 4.706E-01 | 7.556E-01 |
| 398 | hsa-miR-425* | 6.788E+01 | 7.937E+01 | 8.552E-01 | -1.564E-01 | 1.968E-01 | 4.268E-01 | 1.237E-01 | 4.543E-01 |
| 399 | hsa-miR-30c | 2.158E+03 | 2.630E+03 | 8.203E-01 | -1.981E-01 | 1.984E-01 | 4.290E-01 | 1.174E-01 | 4.483E-01 |
| 400 | hsa-miR-1201 | 5.959E+01 | 5.518E+01 | 1.080E-00 | 7.687E-02 | 1.988E-01 | 4.290E-01 | 8.289E-01 | 9.363E-01 |
| 401 | hsa-miR-548a-5p | 1.000E-00 | 1.000E-00 | 1.000E-00 | 0.000E+01 | 2.001E-01 | 4.300E-01 | 2.964E-01 | 6.325E-01 |
| 402 | hsa-miR-33a* | 6.151E+01 | 6.327E+01 | 9.721E-01 | -2.826E-02 | 2.003E-01 | 4.300E-01 | 5.121E-01 | 7.822E-01 |
| 403 | hsa-miR-450a | 1.000E-00 | 6.601E-00 | 1.515E-01 | -1.887E-00 | 2.012E-01 | 4.309E-01 | 8.096E-01 | 9.242E-01 |
| 404 | hsa-miR-331-3p | 9.557E+02 | 7.902E+02 | 1.209E-00 | 1.901E-01 | 2.017E-01 | 4.309E-01 | 3.073E-01 | 6.412E-01 |
| 405 | hsa-miR-32 | 1.417E+02 | 1.411E+02 | 1.005E-00 | 4.663E-03 | 2.032E-01 | 4.330E-01 | 7.156E-01 | 8.841E-01 |
| 406 | hsa-miR-223* | 2.888E+01 | 2.566E+01 | 1.125E-00 | 1.181E-01 | 2.049E-01 | 4.355E-01 | 4.710E-01 | 7.556E-01 |
| 407 | hsa-miR-200b | 4.865E+01 | 4.376E+01 | 1.112E-00 | 1.060E-01 | 2.064E-01 | 4.377E-01 | 9.893E-01 | 9.974E-01 |
| 408 | hsa-miR-509-3p | 1.000E-00 | 1.860E-00 | 5.375E-01 | -6.208E-01 | 2.089E-01 | 4.418E-01 | 8.653E-01 | 9.528E-01 |
| 409 | hsa-miR-129-5p | 3.315E+01 | 1.252E+01 | 2.649E-00 | 9.742E-01 | 2.105E-01 | 4.420E-01 | 3.748E-01 | 6.823E-01 |
| 410 | hsa-miR-10b* | 5.144E+01 | 5.046E+01 | 1.019E-00 | 1.919E-02 | 2.095E-01 | 4.420E-01 | 4.142E-01 | 7.106E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 411 | hsa-miR-195 | 6.222E+02 | 7.305E+02 | 8.518E-01 | -1.605E-01 | 2.105E-01 | 4.420E-01 | 1.566E-01 | 4.881E-01 |
| 412 | hsa-miR-92a-2* | 1.000E-00 | 1.000E-00 | 1.000E-00 | 0.000E+01 | 2.113E-01 | 4.425E-01 | 7.189E-01 | 8.841E-01 |
| 413 | hsa-miR-548l | 1.000E-00 | 1.000E-00 | 1.000E-00 | 0.000E+01 | 2.124E-01 | 4.430E-01 | 9.939E-01 | 9.982E-01 |
| 414 | hsa-miR-345 | 1.066E+02 | 1.120E+02 | 9.513E-01 | -4.996E-02 | 2.125E-01 | 4.430E-01 | 1.789E-01 | 5.097E-01 |
| 415 | hsa-miR-377* | 1.000E-00 | 1.000E-00 | 1.000E-00 | 0.000E+01 | 2.139E-01 | 4.448E-01 | 6.770E-01 | 8.698E-01 |
| 416 | hsa-miR-181c | 1.259E+02 | 8.783E+01 | 1.434E-00 | 3.603E-01 | 2.154E-01 | 4.469E-01 | 3.816E-01 | 6.917E-01 |
| 417 | hsa-miR-33b* | 1.358E+02 | 1.488E+02 | 9.131E-01 | -9.094E-02 | 2.161E-01 | 4.469E-01 | 1.420E-01 | 4.686E-01 |
| 418 | hsa-miR-455-5p | 1.322E+01 | 6.768E-00 | 1.953E-00 | 6.692E-01 | 2.165E-01 | 4.469E-01 | 3.595E-01 | 6.763E-01 |
| 419 | hsa-miR-181c* | 6.030E+01 | 6.127E+01 | 9.841E-01 | -1.605E-02 | 2.171E-01 | 4.471E-01 | 5.557E-01 | 8.023E-01 |
| 420 | hsa-miR-616 | 1.711E+01 | 2.485E+01 | 6.884E-01 | -3.734E-01 | 2.206E-01 | 4.498E-01 | 9.876E-01 | 9.974E-01 |
| 421 | hsa-miR-208b | 6.046E+01 | 6.281E+01 | 9.626E-01 | -3.812E-02 | 2.220E-01 | 4.498E-01 | 8.384E-01 | 9.407E-01 |
| 422 | hsa-miR-891b | 9.652E+01 | 8.761E+01 | 1.102E-00 | 9.681E-02 | 2.221E-01 | 4.498E-01 | 7.642E-01 | 8.948E-01 |
| 423 | hsa-miR-138 | 3.376E+01 | 5.092E+01 | 6.630E-01 | -4.110E-01 | 2.190E-01 | 4.498E-01 | 2.811E-01 | 6.204E-01 |
| 424 | hsa-miR-135b* | 5.332E+01 | 6.983E+01 | 7.636E-01 | -2.697E-01 | 2.217E-01 | 4.498E-01 | 1.328E-01 | 4.686E-01 |
| 425 | hsa-miR-1266 | 1.129E+02 | 1.264E+02 | 8.929E-01 | -1.133E-01 | 2.217E-01 | 4.498E-01 | 1.526E-01 | 4.795E-01 |
| 426 | hsa-let-7i* | 2.293E+02 | 2.676E+02 | 8.570E-01 | -1.543E-01 | 2.197E-01 | 4.498E-01 | 1.044E-01 | 4.251E-01 |
| 427 | hsa-miR-877 | 5.900E+01 | 4.737E+01 | 1.245E-00 | 2.194E-01 | 2.239E-01 | 4.504E-01 | 5.729E-01 | 8.132E-01 |
| 428 | hsa-miR-132* | 1.000E-00 | 1.000E-00 | 1.000E-00 | 0.000E+01 | 2.229E-01 | 4.504E-01 | 4.667E-01 | 7.529E-01 |
| 429 | hsa-miR-192 | 5.646E+03 | 6.228E+03 | 9.067E-01 | -9.800E-02 | 2.239E-01 | 4.504E-01 | 2.942E-01 | 6.299E-01 |
| 430 | hsa-miR-940 | 1.565E+02 | 1.594E+02 | 9.819E-01 | -1.831E-02 | 2.254E-01 | 4.524E-01 | 9.692E-01 | 9.875E-01 |
| 431 | hsa-miR-24-1* | 8.704E+01 | 8.687E+01 | 1.002E-00 | 1.921E-03 | 2.274E-01 | 4.554E-01 | 7.955E-01 | 9.130E-01 |
| 432 | hsa-miR-302b* | 6.685E-00 | 1.000E-00 | 6.685E-00 | 1.900E-00 | 2.292E-01 | 4.558E-01 | 3.247E-01 | 6.562E-01 |
| 433 | hsa-miR-602 | 1.072E+02 | 1.350E+02 | 7.941E-01 | -2.305E-01 | 2.291E-01 | 4.558E-01 | 2.901E-01 | 6.289E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 434 | hsa-miR-33b | 1.728E+02 | 1.784E+02 | 9.684E-01 | -3.214E-02 | 2.292E-01 | 4.558E-01 | 6.912E-01 | 8.767E-01 |
| 435 | hsa-miR-323-5p | 4.708E+01 | 5.868E+01 | 8.023E-01 | -2.203E-01 | 2.301E-01 | 4.566E-01 | 4.908E-02 | 3.580E-01 |
| 436 | hsa-miR-1908 | 1.028E+03 | 1.326E+03 | 7.755E-01 | -2.543E-01 | 2.308E-01 | 4.568E-01 | 8.966E-02 | 4.174E-01 |
| 437 | hsa-miR-339-5p | 6.883E+02 | 4.526E+02 | 1.521E-00 | 4.192E-01 | 2.313E-01 | 4.568E-01 | 1.429E-01 | 4.686E-01 |
| 438 | hsa-miR-657 | 5.943E+01 | 5.015E+01 | 1.185E-00 | 1.697E-01 | 2.360E-01 | 4.618E-01 | 7.406E-01 | 8.878E-01 |
| 439 | hsa-miR-553 | 3.329E-00 | 9.746E-00 | 3.416E-01 | -1.074E-00 | 2.357E-01 | 4.618E-01 | 5.569E-01 | 8.023E-01 |
| 440 | hsa-miR-183* | 8.383E+01 | 9.955E+01 | 8.421E-01 | -1.719E-01 | 2.347E-01 | 4.618E-01 | 2.071E-01 | 5.273E-01 |
| 441 | hsa-miR-516a-3p | 6.768E-00 | 9.746E-00 | 6.944E-01 | -3.646E-01 | 2.352E-01 | 4.618E-01 | 8.422E-01 | 9.427E-01 |
| 442 | hsa-miR-125b | 5.429E+02 | 4.231E+02 | 1.283E-00 | 2.493E-01 | 2.372E-01 | 4.621E-01 | 8.608E-01 | 9.528E-01 |
| 443 | hsa-miR-1909* | 4.482E+01 | 4.629E+01 | 9.682E-01 | -3.233E-02 | 2.370E-01 | 4.621E-01 | 5.411E-01 | 8.006E-01 |
| 444 | hsa-miR-505 | 1.898E+01 | 1.502E+01 | 1.263E-00 | 2.338E-01 | 2.389E-01 | 4.634E-01 | 8.664E-01 | 9.528E-01 |
| 445 | hsa-miR-616* | 5.447E+01 | 5.380E+01 | 1.012E-00 | 1.236E-02 | 2.384E-01 | 4.634E-01 | 4.974E-01 | 7.748E-01 |
| 446 | hsa-miR-875-3p | 5.239E+01 | 8.174E+01 | 6.409E-01 | -4.449E-01 | 2.409E-01 | 4.661E-01 | 8.770E-02 | 4.174E-01 |
| 447 | hsa-miR-527 | 1.562E+02 | 1.938E+02 | 8.060E-01 | -2.157E-01 | 2.430E-01 | 4.692E-01 | 1.078E-01 | 4.325E-01 |
| 448 | hsa-miR-365 | 6.366E+01 | 3.753E+01 | 1.696E-00 | 5.285E-01 | 2.443E-01 | 4.707E-01 | 3.085E-02 | 3.110E-01 |
| 449 | hsa-miR-147 | 2.925E+01 | 3.489E+01 | 8.382E-01 | -1.765E-01 | 2.467E-01 | 4.741E-01 | 9.116E-02 | 4.174E-01 |
| 450 | hsa-miR-516a-5p | 1.900E+02 | 2.854E+02 | 6.656E-01 | -4.070E-01 | 2.472E-01 | 4.741E-01 | 9.183E-02 | 4.174E-01 |
| 451 | hsa-miR-493* | 3.395E+01 | 2.397E+01 | 1.416E-00 | 3.480E-01 | 2.487E-01 | 4.757E-01 | 8.594E-01 | 9.528E-01 |
| 452 | hsa-miR-933 | 1.763E+02 | 2.530E+02 | 6.970E-01 | -3.610E-01 | 2.491E-01 | 4.757E-01 | 7.820E-02 | 4.158E-01 |
| 453 | hsa-miR-20a* | 1.407E+02 | 1.738E+02 | 8.095E-01 | -2.114E-01 | 2.529E-01 | 4.819E-01 | 1.618E-01 | 4.883E-01 |
| 454 | hsa-miR-671-5p | 6.193E+01 | 6.905E+01 | 8.970E-01 | -1.087E-01 | 2.539E-01 | 4.827E-01 | 1.846E-01 | 5.107E-01 |
| 455 | hsa-miR-490-5p | 1.306E+02 | 1.430E+02 | 9.132E-01 | -9.080E-02 | 2.560E-01 | 4.855E-01 | 2.058E-01 | 5.254E-01 |
| 456 | hsa-miR-302c* | 2.496E+01 | 2.566E+01 | 9.727E-01 | -2.766E-02 | 2.565E-01 | 4.855E-01 | 9.313E-01 | 9.739E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 457 | hsa-let-7c* | 1.816E+01 | 1.000E-00 | 1.816E+01 | 2.899E-00 | 2.572E-01 | 4.856E-01 | 1.609E-01 | 4.883E-01 |
| 458 | hsa-miR-484 | 7.714E+03 | 6.927E+03 | 1.114E-00 | 1.075E-01 | 2.622E-01 | 4.929E-01 | 6.563E-01 | 8.645E-01 |
| 459 | hsa-miR-187 | 1.406E+01 | 3.289E+01 | 4.277E-01 | -8.494E-01 | 2.619E-01 | 4.929E-01 | 4.275E-01 | 7.192E-01 |
| 460 | hsa-miR-1251 | 1.300E+02 | 1.414E+02 | 9.192E-01 | -8.426E-02 | 2.634E-01 | 4.941E-01 | 1.474E-01 | 4.728E-01 |
| 461 | hsa-miR-1307 | 5.601E+01 | 7.255E+01 | 7.719E-01 | -2.589E-01 | 2.668E-01 | 4.995E-01 | 1.609E-01 | 4.883E-01 |
| 462 | hsa-miR-17* | 5.591E+02 | 8.284E+02 | 6.749E-01 | -3.932E-01 | 2.697E-01 | 5.005E-01 | 1.443E-01 | 4.686E-01 |
| 463 | hsa-miR-648 | 4.708E+01 | 4.367E+01 | 1.078E-00 | 7.512E-02 | 2.699E-01 | 5.005E-01 | 9.571E-01 | 9.865E-01 |
| 464 | hsa-miR-1274b | 7.558E+02 | 5.531E+02 | 1.366E-00 | 3.122E-01 | 2.689E-01 | 5.005E-01 | 5.496E-01 | 8.015E-01 |
| 465 | hsa-miR-96 | 1.569E+02 | 1.543E+02 | 1.017E-00 | 1.661E-02 | 2.702E-01 | 5.005E-01 | 2.655E-01 | 6.045E-01 |
| 466 | hsa-miR-302f | 1.000E-00 | 1.000E-00 | 1.000E-00 | 0.000E+01 | 2.689E-01 | 5.005E-01 | 3.445E-01 | 6.710E-01 |
| 467 | hsa-miR-331-5p | 3.260E+01 | 6.601E-00 | 4.938E-00 | 1.597E-00 | 2.715E-01 | 5.007E-01 | 2.138E-01 | 5.318E-01 |
| 468 | hsa-miR-149* | 7.135E+02 | 1.127E+03 | 6.329E-01 | -4.575E-01 | 2.710E-01 | 5.007E-01 | 1.153E-01 | 4.422E-01 |
| 469 | hsa-miR-99a | 1.021E+02 | 9.862E+01 | 1.036E-00 | 3.511E-02 | 2.737E-01 | 5.010E-01 | 4.401E-01 | 7.290E-01 |
| 470 | hsa-miR-1228* | 1.351E+03 | 1.760E+03 | 7.675E-01 | -2.646E-01 | 2.735E-01 | 5.010E-01 | 8.307E-02 | 4.158E-01 |
| 471 | hsa-miR-30d | 7.714E+03 | 5.922E+03 | 1.303E-00 | 2.643E-01 | 2.740E-01 | 5.010E-01 | 8.086E-01 | 9.242E-01 |
| 472 | hsa-miR-21* | 1.016E+02 | 1.288E+02 | 7.885E-01 | -2.377E-01 | 2.735E-01 | 5.010E-01 | 1.837E-01 | 5.104E-01 |
| 473 | hsa-miR-545 | 1.152E+02 | 1.358E+02 | 8.478E-01 | -1.651E-01 | 2.751E-01 | 5.019E-01 | 1.840E-01 | 5.104E-01 |
| 474 | hsa-miR-600 | 7.396E+01 | 5.653E+01 | 1.308E-00 | 2.688E-01 | 2.761E-01 | 5.025E-01 | 3.366E-02 | 3.208E-01 |
| 475 | hsa-miR-424 | 2.194E+02 | 3.051E+02 | 7.192E-01 | -3.295E-01 | 2.766E-01 | 5.025E-01 | 1.281E-01 | 4.625E-01 |
| 476 | hsa-miR-21 | 8.391E+02 | 9.187E+02 | 9.133E-01 | -9.066E-02 | 2.772E-01 | 5.026E-01 | 1.669E-01 | 4.966E-01 |
| 477 | hsa-miR-18b | 1.672E+02 | 1.257E+02 | 1.330E-00 | 2.853E-01 | 2.791E-01 | 5.039E-01 | 3.055E-01 | 6.412E-01 |
| 478 | hsa-miR-448 | 8.557E+01 | 1.030E+02 | 8.306E-01 | -1.856E-01 | 2.788E-01 | 5.039E-01 | 4.667E-01 | 7.529E-01 |
| 479 | hsa-miR-126* | 2.133E-00 | 1.720E-00 | 1.240E-00 | 2.153E-01 | 2.802E-01 | 5.049E-01 | 7.231E-01 | 8.841E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 480 | hsa-miR-98 | 4.937E-00 | 1.000E-00 | 4.937E-00 | 1.597E-00 | 2.850E-01 | 5.124E-01 | 6.811E-02 | 4.115E-01 |
| 481 | hsa-miR-148a | 9.557E+02 | 1.431E+03 | 6.677E-01 | -4.040E-01 | 2.861E-01 | 5.132E-01 | 1.691E-01 | 4.998E-01 |
| 482 | hsa-miR-1280 | 4.196E+03 | 4.640E+03 | 9.042E-01 | -1.008E-01 | 2.866E-01 | 5.132E-01 | 6.790E-01 | 8.698E-01 |
| 483 | hsa-miR-380* | 7.294E+01 | 7.160E+01 | 1.019E-00 | 1.851E-02 | 2.874E-01 | 5.135E-01 | 1.988E-01 | 5.254E-01 |
| 484 | hsa-miR-136* | 5.092E+01 | 3.692E+01 | 1.379E-00 | 3.214E-01 | 2.889E-01 | 5.140E-01 | 9.332E-01 | 9.739E-01 |
| 485 | hsa-miR-411 | 5.092E+01 | 4.785E+01 | 1.064E-00 | 6.215E-02 | 2.883E-01 | 5.140E-01 | 2.905E-01 | 6.289E-01 |
| 486 | hsa-miR-523 | 8.399E+01 | 8.023E+01 | 1.047E-00 | 4.578E-02 | 2.911E-01 | 5.170E-01 | 5.830E-01 | 8.222E-01 |
| 487 | hsa-miR-187* | 1.251E+02 | 2.154E+02 | 5.807E-01 | -5.436E-01 | 2.934E-01 | 5.184E-01 | 6.680E-01 | 8.661E-01 |
| 488 | hsa-miR-196b | 1.000E-00 | 1.000E-00 | 1.000E-00 | 0.000E+01 | 2.929E-01 | 5.184E-01 | 3.213E-01 | 6.524E-01 |
| 489 | hsa-miR-34c-5p | 5.068E+01 | 4.088E+01 | 1.240E-00 | 2.147E-01 | 2.944E-01 | 5.184E-01 | 6.551E-01 | 8.645E-01 |
| 490 | hsa-miR-627 | 1.535E+02 | 1.565E+02 | 9.806E-01 | -1.957E-02 | 2.940E-01 | 5.184E-01 | 8.385E-01 | 9.407E-01 |
| 491 | hsa-miR-1296 | 4.723E+01 | 4.629E+01 | 1.020E-00 | 1.993E-02 | 2.981E-01 | 5.240E-01 | 2.779E-01 | 6.190E-01 |
| 492 | hsa-miR-637 | 9.439E-00 | 1.479E+01 | 6.383E-01 | -4.490E-01 | 2.988E-01 | 5.241E-01 | 9.062E-01 | 9.671E-01 |
| 493 | hsa-miR-1268 | 3.635E+02 | 5.176E+02 | 7.022E-01 | -3.536E-01 | 2.998E-01 | 5.241E-01 | 9.293E-02 | 4.174E-01 |
| 494 | hsa-miR-379 | 8.436E-00 | 6.601E-00 | 1.278E-00 | 2.453E-01 | 3.011E-01 | 5.241E-01 | 6.679E-01 | 8.661E-01 |
| 495 | hsa-miR-362-5p | 1.259E+02 | 1.096E+02 | 1.149E-00 | 1.390E-01 | 3.008E-01 | 5.241E-01 | 1.054E-01 | 4.251E-01 |
| 496 | hsa-miR-557 | 2.715E+01 | 3.753E+01 | 7.233E-01 | -3.239E-01 | 3.012E-01 | 5.241E-01 | 2.441E-01 | 5.739E-01 |
| 497 | hsa-miR-326 | 8.606E+01 | 9.955E+01 | 8.644E-01 | -1.457E-01 | 3.020E-01 | 5.244E-01 | 2.409E-01 | 5.711E-01 |
| 498 | hsa-miR-34a* | 9.061E+01 | 8.761E+01 | 1.034E-00 | 3.359E-02 | 3.026E-01 | 5.244E-01 | 9.687E-01 | 9.875E-01 |
| 499 | hsa-miR-548p | 1.145E+02 | 1.371E+02 | 8.356E-01 | -1.796E-01 | 3.036E-01 | 5.251E-01 | 6.994E-01 | 8.798E-01 |
| 500 | hsa-miR-1271 | 1.509E+02 | 1.543E+02 | 9.784E-01 | -2.183E-02 | 3.043E-01 | 5.252E-01 | 9.557E-01 | 9.865E-01 |
| 501 | hsa-miR-876-3p | 1.015E+01 | 1.418E+01 | 7.155E-01 | -3.348E-01 | 3.080E-01 | 5.257E-01 | 9.349E-01 | 9.744E-01 |
| 502 | hsa-miR-30c-1* | 3.915E+01 | 4.598E+01 | 8.514E-01 | -1.608E-01 | 3.080E-01 | 5.257E-01 | 9.942E-02 | 4.218E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 503 | hsa-miR-489 | 1.562E+02 | 2.293E+02 | 6.810E-01 | -3.842E-01 | 3.058E-01 | 5.257E-01 | 1.770E-01 | 5.097E-01 |
| 504 | hsa-miR-500* | 2.513E+02 | 3.254E+02 | 7.722E-01 | -2.585E-01 | 3.082E-01 | 5.257E-01 | 1.316E-01 | 4.686E-01 |
| 505 | hsa-miR-100* | 6.193E+01 | 6.233E+01 | 9.937E-01 | -6.367E-03 | 3.076E-01 | 5.257E-01 | 5.492E-01 | 8.015E-01 |
| 506 | hsa-miR-892a | 2.646E-00 | 1.125E+01 | 2.352E-01 | -1.447E-00 | 3.074E-01 | 5.257E-01 | 2.054E-01 | 5.254E-01 |
| 507 | hsa-miR-556-5p | 1.181E+02 | 9.232E+01 | 1.279E-00 | 2.463E-01 | 3.108E-01 | 5.259E-01 | 2.889E-01 | 6.289E-01 |
| 508 | hsa-miR-140-5p | 2.904E+01 | 4.088E+01 | 7.104E-01 | -3.419E-01 | 3.106E-01 | 5.259E-01 | 9.106E-02 | 4.174E-01 |
| 509 | hsa-miR-20b* | 6.151E+01 | 7.294E+01 | 8.432E-01 | -1.705E-01 | 3.099E-01 | 5.259E-01 | 9.141E-01 | 9.693E-01 |
| 510 | hsa-miR-760 | 4.181E+01 | 5.621E+01 | 7.438E-01 | -2.959E-01 | 3.104E-01 | 5.259E-01 | 6.673E-02 | 4.113E-01 |
| 511 | hsa-miR-101* | 6.894E+01 | 6.905E+01 | 9.985E-01 | -1.529E-03 | 3.144E-01 | 5.309E-01 | 6.881E-01 | 8.759E-01 |
| 512 | hsa-miR-1224-5p | 2.888E+01 | 3.289E+01 | 8.780E-01 | -1.301E-01 | 3.181E-01 | 5.351E-01 | 1.998E-01 | 5.254E-01 |
| 513 | hsa-miR-19b-1* | 4.944E+01 | 4.471E+01 | 1.106E-00 | 1.005E-01 | 3.178E-01 | 5.351E-01 | 7.359E-01 | 8.857E-01 |
| 514 | hsa-miR-92a-1* | 1.406E+01 | 9.746E-00 | 1.443E-00 | 3.668E-01 | 3.202E-01 | 5.376E-01 | 8.884E-01 | 9.632E-01 |
| 515 | hsa-miR-16-2* | 8.373E+01 | 8.653E+01 | 9.677E-01 | -3.286E-02 | 3.241E-01 | 5.432E-01 | 5.535E-01 | 8.015E-01 |
| 516 | hsa-miR-373* | 2.990E+01 | 1.840E+01 | 1.625E-00 | 4.856E-01 | 3.272E-01 | 5.468E-01 | 4.274E-01 | 7.192E-01 |
| 517 | hsa-let-7i | 5.480E+02 | 4.452E+02 | 1.231E-00 | 2.078E-01 | 3.276E-01 | 5.468E-01 | 7.232E-01 | 8.841E-01 |
| 518 | hsa-miR-555 | 2.975E+01 | 1.734E+01 | 1.715E-00 | 5.395E-01 | 3.301E-01 | 5.499E-01 | 1.391E-01 | 4.686E-01 |
| 519 | hsa-miR-218 | 3.305E+01 | 3.289E+01 | 1.005E-00 | 5.066E-03 | 3.323E-01 | 5.515E-01 | 6.383E-01 | 8.540E-01 |
| 520 | hsa-miR-25* | 5.802E+01 | 6.958E+01 | 8.339E-01 | -1.817E-01 | 3.317E-01 | 5.515E-01 | 1.801E-01 | 5.097E-01 |
| 521 | hsa-miR-449a | 1.000E-00 | 8.612E-00 | 1.161E-01 | -2.153E-00 | 3.336E-01 | 5.526E-01 | 7.849E-01 | 9.043E-01 |
| 522 | hsa-miR-582-3p | 6.018E+01 | 6.327E+01 | 9.512E-01 | -5.001E-02 | 3.351E-01 | 5.540E-01 | 5.068E-01 | 7.781E-01 |
| 523 | hsa-miR-502-5p | 1.015E+01 | 1.000E-00 | 1.015E+01 | 2.317E-00 | 3.366E-01 | 5.555E-01 | 2.097E-01 | 5.292E-01 |
| 524 | hsa-miR-515-3p | 1.000E-00 | 1.000E-00 | 1.000E-00 | 0.000E+01 | 3.394E-01 | 5.590E-01 | 7.841E-01 | 9.043E-01 |
| 525 | hsa-miR-654-5p | 1.820E+02 | 2.042E+02 | 8.914E-01 | -1.149E-01 | 3.412E-01 | 5.598E-01 | 1.737E-01 | 5.030E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 526 | hsa-miR-214* | 5.794E+01 | 6.177E+01 | 9.380E-01 | -6.406E-02 | 3.410E-01 | 5.598E-01 | 3.105E-01 | 6.412E-01 |
| 527 | hsa-miR-455-3p | 1.706E+02 | 1.689E+02 | 1.010E-00 | 9.945E-03 | 3.428E-01 | 5.613E-01 | 2.907E-01 | 6.289E-01 |
| 528 | hsa-miR-199b-5p | 3.443E-00 | 9.198E-00 | 3.743E-01 | -9.827E-01 | 3.450E-01 | 5.628E-01 | 9.866E-01 | 9.974E-01 |
| 529 | hsa-miR-509-5p | 2.165E+02 | 2.818E+02 | 7.681E-01 | -2.638E-01 | 3.450E-01 | 5.628E-01 | 9.649E-02 | 4.199E-01 |
| 530 | hsa-miR-421 | 8.761E+01 | 8.307E+01 | 1.055E-00 | 5.328E-02 | 3.464E-01 | 5.640E-01 | 6.282E-01 | 8.496E-01 |
| 531 | hsa-miR-1909 | 1.012E+02 | 1.361E+02 | 7.435E-01 | -2.964E-01 | 3.477E-01 | 5.650E-01 | 1.044E-01 | 4.251E-01 |
| 532 | hsa-miR-425 | 1.198E+04 | 1.198E+04 | 1.000E-00 | 0.000E+01 | 3.515E-01 | 5.702E-01 | 9.688E-01 | 9.875E-01 |
| 533 | hsa-miR-1273 | 9.825E+01 | 1.037E+02 | 9.478E-01 | -5.359E-02 | 3.529E-01 | 5.703E-01 | 9.381E-01 | 9.756E-01 |
| 534 | hsa-miR-1293 | 1.711E+01 | 1.876E+01 | 9.120E-01 | -9.211E-02 | 3.529E-01 | 5.703E-01 | 6.724E-01 | 8.686E-01 |
| 535 | hsa-miR-566 | 8.653E+01 | 1.096E+02 | 7.896E-01 | -2.363E-01 | 3.553E-01 | 5.731E-01 | 2.927E-01 | 6.299E-01 |
| 536 | hsa-miR-7 | 3.010E+01 | 8.612E-00 | 3.495E-00 | 1.251E-00 | 3.566E-01 | 5.742E-01 | 2.147E-01 | 5.325E-01 |
| 537 | hsa-miR-638 | 3.607E+02 | 4.025E+02 | 8.962E-01 | -1.096E-01 | 3.589E-01 | 5.768E-01 | 7.351E-01 | 8.857E-01 |
| 538 | hsa-miR-1284 | 1.784E+01 | 2.942E+01 | 6.064E-01 | -5.002E-01 | 3.608E-01 | 5.787E-01 | 3.739E-01 | 6.822E-01 |
| 539 | hsa-miR-1913 | 3.543E+02 | 3.006E+02 | 1.179E-00 | 1.644E-01 | 3.614E-01 | 5.787E-01 | 5.928E-01 | 8.254E-01 |
| 540 | hsa-miR-1178 | 1.624E+01 | 1.000E-00 | 1.624E+01 | 2.788E-00 | 3.640E-01 | 5.794E-01 | 1.001E-01 | 4.218E-01 |
| 541 | hsa-miR-1304 | 4.944E+01 | 3.733E+01 | 1.324E-00 | 2.808E-01 | 3.646E-01 | 5.794E-01 | 2.755E-01 | 6.190E-01 |
| 542 | hsa-miR-1911* | 8.704E+01 | 1.076E+02 | 8.089E-01 | -2.121E-01 | 3.645E-01 | 5.794E-01 | 2.586E-01 | 5.968E-01 |
| 543 | hsa-miR-518a-3p | 5.339E+01 | 5.255E+01 | 1.016E-00 | 1.577E-02 | 3.632E-01 | 5.794E-01 | 1.877E-01 | 5.175E-01 |
| 544 | hsa-miR-330-3p | 3.784E+02 | 5.591E+02 | 6.768E-01 | -3.903E-01 | 3.671E-01 | 5.803E-01 | 3.667E-01 | 6.763E-01 |
| 545 | hsa-miR-518c* | 5.332E+01 | 4.958E+01 | 1.075E-00 | 7.273E-02 | 3.671E-01 | 5.803E-01 | 8.308E-01 | 9.373E-01 |
| 546 | hsa-miR-491-3p | 7.786E+01 | 7.844E+01 | 9.927E-01 | -7.326E-03 | 3.666E-01 | 5.803E-01 | 1.449E-01 | 4.686E-01 |
| 547 | hsa-miR-649 | 1.031E+01 | 1.000E-00 | 1.031E+01 | 2.333E-00 | 3.696E-01 | 5.832E-01 | 7.232E-02 | 4.115E-01 |
| 548 | hsa-miR-558 | 6.894E+01 | 9.249E+01 | 7.454E-01 | -2.939E-01 | 3.716E-01 | 5.849E-01 | 5.706E-01 | 8.125E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 549 | hsa-miR-10b | 5.068E+01 | 5.868E+01 | 8.637E-01 | -1.466E-01 | 3.721E-01 | 5.849E-01 | 6.776E-01 | 8.698E-01 |
| 550 | hsa-miR-335 | 4.413E+02 | 3.931E+02 | 1.123E-00 | 1.156E-01 | 3.732E-01 | 5.857E-01 | 8.849E-01 | 9.618E-01 |
| 551 | hsa-miR-103-as | 1.264E+02 | 1.502E+02 | 8.416E-01 | -1.725E-01 | 3.777E-01 | 5.895E-01 | 2.899E-01 | 6.289E-01 |
| 552 | hsa-miR-106a* | 1.318E+02 | 1.911E+02 | 6.894E-01 | -3.719E-01 | 3.772E-01 | 5.895E-01 | 1.089E-01 | 4.352E-01 |
| 553 | hsa-miR-27b | 2.035E+02 | 2.008E+02 | 1.013E-00 | 1.292E-02 | 3.777E-01 | 5.895E-01 | 2.032E-01 | 5.254E-01 |
| 554 | hsa-miR-1278 | 5.447E+01 | 5.332E+01 | 1.022E-00 | 2.131E-02 | 3.786E-01 | 5.897E-01 | 4.053E-01 | 7.094E-01 |
| 555 | hsa-miR-505* | 1.609E+02 | 1.417E+02 | 1.135E-00 | 1.269E-01 | 3.824E-01 | 5.946E-01 | 7.211E-01 | 8.841E-01 |
| 556 | hsa-miR-628-3p | 1.539E+02 | 1.312E+02 | 1.173E-00 | 1.596E-01 | 3.856E-01 | 5.959E-01 | 7.171E-01 | 8.841E-01 |
| 557 | hsa-miR-542-5p | 8.383E+01 | 7.786E+01 | 1.077E-00 | 7.387E-02 | 3.855E-01 | 5.959E-01 | 9.917E-01 | 9.975E-01 |
| 558 | hsa-miR-1233 | 8.159E+01 | 8.307E+01 | 9.822E-01 | -1.794E-02 | 3.858E-01 | 5.959E-01 | 7.339E-01 | 8.857E-01 |
| 559 | hsa-miR-185 | 2.473E+04 | 2.473E+04 | 1.000E-00 | 0.000E+01 | 3.860E-01 | 5.959E-01 | 9.877E-01 | 9.974E-01 |
| 560 | hsa-miR-132 | 1.105E+02 | 1.120E+02 | 9.861E-01 | -1.400E-02 | 3.875E-01 | 5.961E-01 | 6.531E-01 | 8.645E-01 |
| 561 | hsa-miR-139-3p | 7.874E+01 | 8.307E+01 | 9.479E-01 | -5.356E-02 | 3.874E-01 | 5.961E-01 | 8.524E-01 | 9.488E-01 |
| 562 | hsa-miR-1226* | 1.900E+02 | 2.627E+02 | 7.233E-01 | -3.240E-01 | 3.908E-01 | 5.991E-01 | 1.637E-01 | 4.908E-01 |
| 563 | hsa-miR-1272 | 1.312E+02 | 1.506E+02 | 8.712E-01 | -1.379E-01 | 3.903E-01 | 5.991E-01 | 3.099E-01 | 6.412E-01 |
| 564 | hsa-miR-512-5p | 5.361E+01 | 5.332E+01 | 1.005E-00 | 5.344E-03 | 3.918E-01 | 5.995E-01 | 5.099E-01 | 7.802E-01 |
| 565 | hsa-miR-299-3p | 1.450E+01 | 1.000E-00 | 1.450E+01 | 2.674E-00 | 3.939E-01 | 6.016E-01 | 1.207E-01 | 4.510E-01 |
| 566 | hsa-miR-937 | 3.940E+01 | 3.753E+01 | 1.050E-00 | 4.858E-02 | 3.956E-01 | 6.032E-01 | 8.218E-01 | 9.320E-01 |
| 567 | hsa-miR-499-3p | 5.601E+01 | 7.727E+01 | 7.248E-01 | -3.218E-01 | 3.990E-01 | 6.073E-01 | 3.291E-01 | 6.621E-01 |
| 568 | hsa-miR-216b | 1.184E+02 | 1.371E+02 | 8.635E-01 | -1.467E-01 | 4.031E-01 | 6.124E-01 | 6.165E-01 | 8.420E-01 |
| 569 | hsa-miR-568 | 7.147E+01 | 7.844E+01 | 9.112E-01 | -9.304E-02 | 4.056E-01 | 6.152E-01 | 1.999E-01 | 5.254E-01 |
| 570 | hsa-miR-596 | 7.255E+01 | 8.991E+01 | 8.070E-01 | -2.144E-01 | 4.065E-01 | 6.155E-01 | 4.203E-01 | 7.157E-01 |
| 571 | hsa-miR-619 | 5.397E+01 | 5.255E+01 | 1.027E-00 | 2.658E-02 | 4.125E-01 | 6.175E-01 | 5.903E-01 | 8.254E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 572 | hsa-miR-1225-5p | 5.975E+01 | 5.577E+01 | 1.071E-00 | 6.899E-02 | 4.132E-01 | 6.175E-01 | 3.650E-01 | 6.763E-01 |
| 573 | hsa-miR-1181 | 1.710E+02 | 1.798E+02 | 9.510E-01 | -5.024E-02 | 4.119E-01 | 6.175E-01 | 7.352E-01 | 8.857E-01 |
| 574 | hsa-miR-188-5p | 1.120E+02 | 1.072E+02 | 1.045E-00 | 4.386E-02 | 4.136E-01 | 6.175E-01 | 8.990E-01 | 9.671E-01 |
| 575 | hsa-let-7d* | 5.728E+01 | 6.719E+01 | 8.525E-01 | -1.595E-01 | 4.119E-01 | 6.175E-01 | 3.470E-01 | 6.715E-01 |
| 576 | hsa-miR-218-2* | 5.144E+01 | 4.190E+01 | 1.228E-00 | 2.052E-01 | 4.135E-01 | 6.175E-01 | 9.327E-01 | 9.739E-01 |
| 577 | hsa-miR-647 | 6.884E+01 | 8.586E+01 | 8.018E-01 | -2.209E-01 | 4.131E-01 | 6.175E-01 | 3.973E-01 | 7.046E-01 |
| 578 | hsa-miR-139-5p | 1.249E+02 | 1.266E+02 | 9.863E-01 | -1.384E-02 | 4.102E-01 | 6.175E-01 | 7.112E-01 | 8.840E-01 |
| 579 | hsa-miR-654-3p | 3.087E+01 | 1.745E+01 | 1.769E-00 | 5.703E-01 | 4.174E-01 | 6.204E-01 | 2.783E-01 | 6.190E-01 |
| 580 | hsa-miR-138-2* | 5.447E+01 | 5.845E+01 | 9.319E-01 | -7.054E-02 | 4.176E-01 | 6.204E-01 | 3.625E-01 | 6.763E-01 |
| 581 | hsa-miR-675 | 1.354E+02 | 1.195E+02 | 1.133E-00 | 1.248E-01 | 4.177E-01 | 6.204E-01 | 7.549E-01 | 8.926E-01 |
| 582 | hsa-miR-377 | 1.135E+02 | 1.179E+02 | 9.627E-01 | -3.799E-02 | 4.203E-01 | 6.232E-01 | 7.344E-01 | 8.857E-01 |
| 583 | hsa-miR-374a | 2.496E+02 | 2.119E+02 | 1.178E-00 | 1.639E-01 | 4.265E-01 | 6.313E-01 | 9.884E-01 | 9.974E-01 |
| 584 | hsa-miR-215 | 3.753E+02 | 4.413E+02 | 8.503E-01 | -1.621E-01 | 4.275E-01 | 6.318E-01 | 2.535E-01 | 5.897E-01 |
| 585 | hsa-miR-15a* | 1.107E+02 | 1.208E+02 | 9.164E-01 | -8.735E-02 | 4.289E-01 | 6.328E-01 | 3.331E-01 | 6.638E-01 |
| 586 | hsa-miR-769-5p | 1.000E-00 | 6.768E-00 | 1.478E-01 | -1.912E-00 | 4.308E-01 | 6.345E-01 | 9.257E-01 | 9.719E-01 |
| 587 | hsa-miR-362-3p | 2.019E+02 | 1.788E+02 | 1.129E-00 | 1.213E-01 | 4.339E-01 | 6.379E-01 | 6.311E-01 | 8.496E-01 |
| 588 | hsa-miR-192* | 1.141E+02 | 1.405E+02 | 8.124E-01 | -2.077E-01 | 4.354E-01 | 6.391E-01 | 3.968E-01 | 7.046E-01 |
| 589 | hsa-miR-125a-5p | 1.506E+02 | 1.122E+02 | 1.342E-00 | 2.939E-01 | 4.371E-01 | 6.394E-01 | 8.748E-01 | 9.545E-01 |
| 590 | hsa-miR-491-5p | 8.739E+01 | 8.415E+01 | 1.039E-00 | 3.784E-02 | 4.371E-01 | 6.394E-01 | 7.037E-01 | 8.807E-01 |
| 591 | hsa-miR-802 | 5.975E+01 | 5.728E+01 | 1.043E-00 | 4.222E-02 | 4.384E-01 | 6.401E-01 | 3.797E-01 | 6.898E-01 |
| 592 | hsa-miR-33a | 1.027E+02 | 9.862E+01 | 1.041E-00 | 4.022E-02 | 4.395E-01 | 6.406E-01 | 2.388E-01 | 5.709E-01 |
| 593 | hsa-miR-142-5p | 7.475E+02 | 7.051E+02 | 1.060E-00 | 5.842E-02 | 4.453E-01 | 6.481E-01 | 4.439E-01 | 7.313E-01 |
| 594 | hsa-miR-663b | 6.353E+01 | 6.006E+01 | 1.058E-00 | 5.621E-02 | 4.473E-01 | 6.498E-01 | 7.084E-01 | 8.834E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 595 | hsa-miR-1539 | 8.086E+01 | 9.844E+01 | 8.214E-01 | -1.967E-01 | 4.512E-01 | 6.525E-01 | 2.105E-01 | 5.294E-01 |
| 596 | hsa-miR-95 | 1.635E+01 | 2.660E+01 | 6.147E-01 | -4.866E-01 | 4.505E-01 | 6.525E-01 | 1.096E-01 | 4.361E-01 |
| 597 | hsa-miR-1275 | 6.006E+01 | 6.629E+01 | 9.061E-01 | -9.861E-02 | 4.514E-01 | 6.525E-01 | 8.444E-01 | 9.427E-01 |
| 598 | hsa-miR-191* | 4.967E+01 | 5.959E+01 | 8.335E-01 | -1.821E-01 | 4.525E-01 | 6.531E-01 | 7.628E-01 | 8.948E-01 |
| 599 | hsa-miR-502-3p | 6.676E+02 | 6.967E+02 | 9.583E-01 | -4.260E-02 | 4.586E-01 | 6.573E-01 | 4.126E-01 | 7.106E-01 |
| 600 | hsa-miR-563 | 2.234E-00 | 1.000E-00 | 2.234E-00 | 8.038E-01 | 4.575E-01 | 6.573E-01 | 2.432E-01 | 5.735E-01 |
| 601 | hsa-miR-1321 | 1.000E-00 | 6.601E-00 | 1.515E-01 | -1.887E-00 | 4.586E-01 | 6.573E-01 | 4.883E-01 | 7.667E-01 |
| 602 | hsa-miR-1914 | 5.144E+01 | 5.116E+01 | 1.005E-00 | 5.484E-03 | 4.593E-01 | 6.573E-01 | 2.296E-01 | 5.594E-01 |
| 603 | hsa-miR-185* | 1.565E+01 | 2.530E+01 | 6.185E-01 | -4.805E-01 | 4.590E-01 | 6.573E-01 | 3.055E-01 | 6.412E-01 |
| 604 | hsa-miR-639 | 6.105E+01 | 5.529E+01 | 1.104E-00 | 9.907E-02 | 4.606E-01 | 6.581E-01 | 7.448E-01 | 8.883E-01 |
| 605 | hsa-miR-122* | 4.881E+01 | 4.785E+01 | 1.020E-00 | 1.985E-02 | 4.639E-01 | 6.617E-01 | 9.089E-01 | 9.671E-01 |
| 606 | hsa-miR-643 | 4.016E+01 | 3.315E+01 | 1.211E-00 | 1.916E-01 | 4.662E-01 | 6.630E-01 | 5.337E-01 | 7.996E-01 |
| 607 | hsa-miR-1469 | 1.609E+02 | 1.986E+02 | 8.101E-01 | -2.106E-01 | 4.663E-01 | 6.630E-01 | 9.641E-02 | 4.199E-01 |
| 608 | hsa-miR-1234 | 6.745E+02 | 7.475E+02 | 9.024E-01 | -1.027E-01 | 4.708E-01 | 6.682E-01 | 7.022E-01 | 8.807E-01 |
| 609 | hsa-miR-622 | 6.387E+01 | 8.174E+01 | 7.814E-01 | -2.467E-01 | 4.752E-01 | 6.722E-01 | 5.417E-01 | 8.006E-01 |
| 610 | hsa-miR-222* | 6.170E+01 | 8.687E+01 | 7.102E-01 | -3.422E-01 | 4.750E-01 | 6.722E-01 | 3.508E-01 | 6.758E-01 |
| 611 | hsa-miR-499-5p | 2.056E+01 | 1.995E+01 | 1.031E-00 | 3.006E-02 | 4.781E-01 | 6.753E-01 | 8.748E-01 | 9.545E-01 |
| 612 | hsa-miR-1260 | 2.412E+03 | 2.756E+03 | 8.750E-01 | -1.336E-01 | 4.804E-01 | 6.765E-01 | 7.634E-01 | 8.948E-01 |
| 613 | hsa-miR-517a | 2.821E+01 | 1.876E+01 | 1.504E-00 | 4.082E-01 | 4.805E-01 | 6.765E-01 | 6.303E-01 | 8.496E-01 |
| 614 | hsa-miR-34a | 2.191E+01 | 2.485E+01 | 8.817E-01 | -1.259E-01 | 4.824E-01 | 6.781E-01 | 6.487E-01 | 8.639E-01 |
| 615 | hsa-miR-624* | 2.076E+01 | 1.995E+01 | 1.041E-00 | 3.984E-02 | 4.835E-01 | 6.785E-01 | 8.532E-01 | 9.488E-01 |
| 616 | hsa-miR-28-5p | 3.635E+02 | 2.609E+02 | 1.393E-00 | 3.314E-01 | 4.851E-01 | 6.796E-01 | 6.137E-01 | 8.407E-01 |
| 617 | hsa-miR-100 | 1.224E+02 | 1.257E+02 | 9.734E-01 | -2.697E-02 | 4.873E-01 | 6.816E-01 | 4.364E-01 | 7.256E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 618 | hsa-miR-625 | 5.728E+01 | 6.177E+01 | 9.273E-01 | -7.550E-02 | 4.911E-01 | 6.858E-01 | 9.601E-01 | 9.865E-01 |
| 619 | hsa-miR-148b | 5.277E+02 | 5.757E+02 | 9.166E-01 | -8.705E-02 | 4.942E-01 | 6.879E-01 | 2.331E-01 | 5.594E-01 |
| 620 | hsa-miR-584 | 8.363E+01 | 1.195E+02 | 7.000E-01 | -3.567E-01 | 4.936E-01 | 6.879E-01 | 4.231E-01 | 7.159E-01 |
| 621 | hsa-miR-769-3p | 2.879E-00 | 1.624E+01 | 1.773E-01 | -1.730E-00 | 4.961E-01 | 6.881E-01 | 9.312E-02 | 4.174E-01 |
| 622 | hsa-miR-1182 | 2.729E+01 | 1.479E+01 | 1.845E-00 | 6.126E-01 | 4.965E-01 | 6.881E-01 | 9.295E-01 | 9.735E-01 |
| 623 | hsa-miR-198 | 4.708E+01 | 6.177E+01 | 7.621E-01 | -2.717E-01 | 4.967E-01 | 6.881E-01 | 5.265E-01 | 7.972E-01 |
| 624 | hsa-miR-18a* | 1.900E+02 | 2.165E+02 | 8.777E-01 | -1.305E-01 | 4.977E-01 | 6.883E-01 | 4.077E-01 | 7.106E-01 |
| 625 | hsa-miR-206 | 1.000E-00 | 4.315E+01 | 2.317E-02 | -3.765E-00 | 4.998E-01 | 6.901E-01 | 4.359E-03 | 1.176E-01 |
| 626 | hsa-miR-645 | 5.339E+01 | 3.289E+01 | 1.623E-00 | 4.845E-01 | 5.014E-01 | 6.912E-01 | 5.029E-01 | 7.779E-01 |
| 627 | hsa-miR-508-5p | 1.139E+02 | 1.139E+02 | 1.000E-00 | 0.000E+01 | 5.058E-01 | 6.954E-01 | 8.524E-01 | 9.488E-01 |
| 628 | hsa-miR-518b | 9.590E+01 | 9.810E+01 | 9.776E-01 | -2.262E-02 | 5.069E-01 | 6.954E-01 | 8.799E-01 | 9.587E-01 |
| 629 | hsa-miR-873 | 6.387E+01 | 8.373E+01 | 7.628E-01 | -2.708E-01 | 5.064E-01 | 6.954E-01 | 3.134E-01 | 6.438E-01 |
| 630 | hsa-miR-371-5p | 4.348E+01 | 5.518E+01 | 7.880E-01 | -2.382E-01 | 5.105E-01 | 6.993E-01 | 3.529E-01 | 6.760E-01 |
| 631 | hsa-miR-1910 | 3.902E+01 | 3.081E+01 | 1.266E-00 | 2.362E-01 | 5.120E-01 | 7.001E-01 | 7.487E-01 | 8.913E-01 |
| 632 | hsa-miR-646 | 2.063E+02 | 2.396E+02 | 8.611E-01 | -1.495E-01 | 5.127E-01 | 7.001E-01 | 2.052E-01 | 5.254E-01 |
| 633 | hsa-miR-452 | 5.025E+01 | 4.190E+01 | 1.199E-00 | 1.818E-01 | 5.203E-01 | 7.029E-01 | 2.492E-01 | 5.831E-01 |
| 634 | hsa-miR-106a | 5.922E+03 | 6.228E+03 | 9.510E-01 | -5.028E-02 | 5.213E-01 | 7.029E-01 | 4.089E-01 | 7.106E-01 |
| 635 | hsa-miR-1287 | 5.424E+01 | 5.860E+01 | 9.256E-01 | -7.732E-02 | 5.206E-01 | 7.029E-01 | 6.929E-01 | 8.767E-01 |
| 636 | hsa-miR-217 | 1.417E+02 | 1.788E+02 | 7.926E-01 | -2.324E-01 | 5.208E-01 | 7.029E-01 | 6.533E-01 | 8.645E-01 |
| 637 | hsa-miR-1258 | 1.000E-00 | 1.000E-00 | 1.000E-00 | 0.000E+01 | 5.179E-01 | 7.029E-01 | 1.377E-01 | 4.686E-01 |
| 638 | hsa-miR-620 | 1.354E+01 | 1.479E+01 | 9.154E-01 | -8.844E-02 | 5.175E-01 | 7.029E-01 | 7.125E-01 | 8.840E-01 |
| 639 | hsa-miR-511 | 2.821E+01 | 1.479E+01 | 1.908E-00 | 6.459E-01 | 5.170E-01 | 7.029E-01 | 1.982E-01 | 5.254E-01 |
| 640 | hsa-miR-301a | 2.694E+02 | 2.836E+02 | 9.498E-01 | -5.148E-02 | 5.209E-01 | 7.029E-01 | 2.037E-01 | 5.254E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 641 | hsa-miR-1247 | 5.339E+01 | 6.084E+01 | 8.775E-01 | -1.306E-01 | 5.249E-01 | 7.056E-01 | 1.819E-01 | 5.104E-01 |
| 642 | hsa-miR-325 | 5.144E+01 | 5.529E+01 | 9.304E-01 | -7.214E-02 | 5.247E-01 | 7.056E-01 | 5.076E-01 | 7.781E-01 |
| 643 | hsa-miR-552 | 2.024E+01 | 1.964E+01 | 1.031E-00 | 3.029E-02 | 5.260E-01 | 7.060E-01 | 6.923E-01 | 8.767E-01 |
| 644 | hsa-miR-642 | 2.704E+01 | 2.530E+01 | 1.069E-00 | 6.643E-02 | 5.288E-01 | 7.069E-01 | 8.177E-01 | 9.285E-01 |
| 645 | hsa-miR-92b* | 1.283E+02 | 1.405E+02 | 9.132E-01 | -9.077E-02 | 5.288E-01 | 7.069E-01 | 2.724E-01 | 6.155E-01 |
| 646 | hsa-miR-193b* | 3.479E+01 | 1.105E+01 | 3.148E-00 | 1.147E-00 | 5.292E-01 | 7.069E-01 | 2.799E-01 | 6.204E-01 |
| 647 | hsa-miR-340 | 1.411E+02 | 1.624E+02 | 8.686E-01 | -1.409E-01 | 5.329E-01 | 7.109E-01 | 3.721E-01 | 6.804E-01 |
| 648 | hsa-miR-520h | 3.648E+01 | 2.660E+01 | 1.372E-00 | 3.160E-01 | 5.346E-01 | 7.120E-01 | 9.588E-01 | 9.865E-01 |
| 649 | hsa-miR-9* | 8.586E+01 | 8.307E+01 | 1.034E-00 | 3.313E-02 | 5.388E-01 | 7.165E-01 | 1.144E-01 | 4.408E-01 |
| 650 | hsa-miR-758 | 9.746E-00 | 1.000E-00 | 9.746E-00 | 2.277E-00 | 5.397E-01 | 7.166E-01 | 3.434E-02 | 3.208E-01 |
| 651 | hsa-miR-101 | 5.865E+02 | 4.561E+02 | 1.286E-00 | 2.515E-01 | 5.415E-01 | 7.179E-01 | 7.806E-01 | 9.019E-01 |
| 652 | hsa-miR-591 | 5.361E+01 | 6.177E+01 | 8.678E-01 | -1.418E-01 | 5.475E-01 | 7.224E-01 | 7.517E-01 | 8.926E-01 |
| 653 | hsa-miR-1297 | 4.433E+01 | 5.046E+01 | 8.785E-01 | -1.295E-01 | 5.468E-01 | 7.224E-01 | 8.646E-01 | 9.528E-01 |
| 654 | hsa-miR-548e | 3.789E+01 | 3.733E+01 | 1.015E-00 | 1.465E-02 | 5.470E-01 | 7.224E-01 | 3.720E-01 | 6.804E-01 |
| 655 | hsa-miR-524-5p | 4.865E+01 | 4.471E+01 | 1.088E-00 | 8.451E-02 | 5.491E-01 | 7.235E-01 | 6.276E-01 | 8.496E-01 |
| 656 | hsa-miR-935 | 2.904E+01 | 2.680E+01 | 1.084E-00 | 8.041E-02 | 5.512E-01 | 7.251E-01 | 7.941E-01 | 9.130E-01 |
| 657 | hsa-miR-575 | 1.273E+02 | 1.414E+02 | 8.998E-01 | -1.056E-01 | 5.572E-01 | 7.319E-01 | 4.332E-01 | 7.246E-01 |
| 658 | hsa-miR-145* | 6.006E+01 | 5.635E+01 | 1.066E-00 | 6.385E-02 | 5.596E-01 | 7.340E-01 | 7.139E-01 | 8.840E-01 |
| 659 | hsa-miR-29b-1* | 1.000E-00 | 4.674E-00 | 2.140E-01 | -1.542E-00 | 5.624E-01 | 7.365E-01 | 4.992E-01 | 7.749E-01 |
| 660 | hsa-miR-27a | 2.728E+02 | 2.854E+02 | 9.558E-01 | -4.520E-02 | 5.634E-01 | 7.367E-01 | 4.049E-01 | 7.094E-01 |
| 661 | hsa-miR-615-3p | 2.896E+01 | 3.029E+01 | 9.560E-01 | -4.500E-02 | 5.644E-01 | 7.368E-01 | 6.202E-01 | 8.442E-01 |
| 662 | hsa-miR-1243 | 5.046E+01 | 4.958E+01 | 1.018E-00 | 1.766E-02 | 5.652E-01 | 7.368E-01 | 8.735E-01 | 9.545E-01 |
| 663 | hsa-miR-525-3p | 5.802E+01 | 6.127E+01 | 9.469E-01 | -5.455E-02 | 5.690E-01 | 7.374E-01 | 6.364E-01 | 8.540E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 664 | hsa-miR-551b* | 3.800E+01 | 4.271E+01 | 8.896E-01 | -1.170E-01 | 5.694E-01 | 7.374E-01 | 2.428E-01 | 5.735E-01 |
| 665 | hsa-miR-1292 | 5.959E+01 | 7.070E+01 | 8.429E-01 | -1.709E-01 | 5.700E-01 | 7.374E-01 | 2.968E-01 | 6.325E-01 |
| 666 | hsa-miR-302a* | 4.327E+01 | 3.733E+01 | 1.159E-00 | 1.476E-01 | 5.675E-01 | 7.374E-01 | 2.898E-01 | 6.289E-01 |
| 667 | hsa-miR-30e | 2.331E+02 | 1.454E+02 | 1.602E-00 | 4.716E-01 | 5.688E-01 | 7.374E-01 | 3.461E-01 | 6.711E-01 |
| 668 | hsa-miR-541 | 1.051E+02 | 1.030E+02 | 1.020E-00 | 1.960E-02 | 5.748E-01 | 7.414E-01 | 2.239E-01 | 5.508E-01 |
| 669 | hsa-miR-124* | 9.436E+01 | 1.056E+02 | 8.934E-01 | -1.127E-01 | 5.748E-01 | 7.414E-01 | 4.557E-01 | 7.477E-01 |
| 670 | hsa-miR-196a* | 1.400E+02 | 1.632E+02 | 8.576E-01 | -1.536E-01 | 5.784E-01 | 7.445E-01 | 9.225E-01 | 9.719E-01 |
| 671 | hsa-miR-222 | 4.489E+02 | 4.061E+02 | 1.105E-00 | 1.001E-01 | 5.789E-01 | 7.445E-01 | 9.082E-01 | 9.671E-01 |
| 672 | hsa-miR-519c-3p | 3.879E+01 | 1.964E+01 | 1.975E-00 | 6.807E-01 | 5.833E-01 | 7.491E-01 | 3.106E-01 | 6.412E-01 |
| 673 | hsa-miR-146a* | 6.841E+01 | 1.003E+02 | 6.818E-01 | -3.830E-01 | 5.874E-01 | 7.532E-01 | 3.336E-01 | 6.638E-01 |
| 674 | hsa-miR-432 | 1.000E-00 | 6.601E-00 | 1.515E-01 | -1.887E-00 | 5.890E-01 | 7.540E-01 | 3.410E-01 | 6.674E-01 |
| 675 | hsa-miR-601 | 1.000E-00 | 5.416E-00 | 1.846E-01 | -1.689E-00 | 5.897E-01 | 7.540E-01 | 5.918E-01 | 8.254E-01 |
| 676 | hsa-miR-663 | 3.460E+02 | 3.662E+02 | 9.447E-01 | -5.690E-02 | 5.914E-01 | 7.551E-01 | 2.250E-01 | 5.513E-01 |
| 677 | hsa-let-7b* | 4.252E-00 | 1.252E+01 | 3.397E-01 | -1.080E-00 | 5.975E-01 | 7.616E-01 | 9.383E-01 | 9.756E-01 |
| 678 | hsa-miR-452* | 2.947E+02 | 3.229E+02 | 9.125E-01 | -9.161E-02 | 6.013E-01 | 7.654E-01 | 4.595E-01 | 7.498E-01 |
| 679 | hsa-miR-220c | 1.037E+02 | 1.137E+02 | 9.118E-01 | -9.234E-02 | 6.061E-01 | 7.703E-01 | 7.635E-01 | 8.948E-01 |
| 680 | hsa-miR-519b-3p | 2.666E+01 | 3.581E+01 | 7.447E-01 | -2.948E-01 | 6.089E-01 | 7.719E-01 | 5.863E-01 | 8.253E-01 |
| 681 | hsa-miR-1227 | 6.327E+01 | 6.193E+01 | 1.022E-00 | 2.136E-02 | 6.091E-01 | 7.719E-01 | 5.592E-01 | 8.031E-01 |
| 682 | hsa-miR-200b* | 6.788E+01 | 7.104E+01 | 9.556E-01 | -4.544E-02 | 6.177E-01 | 7.792E-01 | 3.244E-01 | 6.562E-01 |
| 683 | hsa-miR-143 | 1.701E+02 | 1.763E+02 | 9.645E-01 | -3.617E-02 | 6.182E-01 | 7.792E-01 | 4.665E-01 | 7.529E-01 |
| 684 | hsa-miR-1274a | 1.417E+02 | 1.066E+02 | 1.330E-00 | 2.851E-01 | 6.194E-01 | 7.792E-01 | 8.270E-01 | 9.354E-01 |
| 685 | hsa-miR-25 | 6.228E+03 | 6.228E+03 | 1.000E-00 | 0.000E+01 | 6.158E-01 | 7.792E-01 | 5.720E-01 | 8.132E-01 |
| 686 | hsa-miR-938 | 8.635E+01 | 9.232E+01 | 9.353E-01 | -6.692E-02 | 6.190E-01 | 7.792E-01 | 5.037E-01 | 7.779E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 687 | hsa-miR-519b-5p | 1.280E+02 | 1.493E+02 | 8.570E-01 | -1.543E-01 | 6.213E-01 | 7.796E-01 | 2.255E-01 | 5.513E-01 |
| 688 | hsa-miR-924 | 1.816E+01 | 2.530E+01 | 7.176E-01 | -3.318E-01 | 6.215E-01 | 7.796E-01 | 9.061E-01 | 9.671E-01 |
| 689 | hsa-miR-127-5p | 1.264E+02 | 1.385E+02 | 9.123E-01 | -9.184E-02 | 6.254E-01 | 7.834E-01 | 1.482E-01 | 4.738E-01 |
| 690 | hsa-miR-920 | 2.729E+01 | 3.587E+01 | 7.608E-01 | -2.734E-01 | 6.316E-01 | 7.882E-01 | 1.376E-01 | 4.686E-01 |
| 691 | hsa-miR-525-5p | 8.126E+01 | 8.761E+01 | 9.275E-01 | -7.521E-02 | 6.330E-01 | 7.882E-01 | 4.213E-01 | 7.157E-01 |
| 692 | hsa-miR-17 | 6.228E+03 | 5.922E+03 | 1.052E-00 | 5.028E-02 | 6.321E-01 | 7.882E-01 | 5.171E-01 | 7.884E-01 |
| 693 | hsa-miR-324-5p | 3.304E+02 | 3.515E+02 | 9.399E-01 | -6.203E-02 | 6.303E-01 | 7.882E-01 | 3.958E-01 | 7.046E-01 |
| 694 | hsa-miR-188-3p | 1.312E+02 | 1.551E+02 | 8.459E-01 | -1.673E-01 | 6.339E-01 | 7.883E-01 | 3.384E-01 | 6.638E-01 |
| 695 | hsa-miR-31 | 1.293E+02 | 1.165E+02 | 1.110E-00 | 1.042E-01 | 6.376E-01 | 7.906E-01 | 3.206E-01 | 6.524E-01 |
| 696 | hsa-miR-661 | 4.419E+01 | 2.530E+01 | 1.747E-00 | 5.577E-01 | 6.369E-01 | 7.906E-01 | 2.616E-01 | 5.971E-01 |
| 697 | hsa-miR-379* | 5.397E+01 | 6.563E+01 | 8.224E-01 | -1.956E-01 | 6.415E-01 | 7.943E-01 | 2.778E-01 | 6.190E-01 |
| 698 | hsa-miR-1245 | 4.459E+01 | 3.427E+01 | 1.301E-00 | 2.634E-01 | 6.537E-01 | 8.082E-01 | 3.963E-01 | 7.046E-01 |
| 699 | hsa-miR-142-3p | 1.784E+01 | 1.000E-00 | 1.784E+01 | 2.882E-00 | 6.547E-01 | 8.083E-01 | 8.938E-02 | 4.174E-01 |
| 700 | hsa-miR-513a-5p | 4.797E+01 | 4.048E+01 | 1.185E-00 | 1.697E-01 | 6.565E-01 | 8.083E-01 | 1.934E-01 | 5.254E-01 |
| 701 | hsa-let-7f-2* | 4.779E-00 | 1.000E-00 | 4.779E-00 | 1.564E-00 | 6.565E-01 | 8.083E-01 | 6.081E-01 | 8.369E-01 |
| 702 | hsa-miR-150* | 7.626E+01 | 9.436E+01 | 8.081E-01 | -2.130E-01 | 6.577E-01 | 8.086E-01 | 2.240E-01 | 5.508E-01 |
| 703 | hsa-miR-367 | 8.557E+01 | 8.687E+01 | 9.850E-01 | -1.506E-02 | 6.598E-01 | 8.100E-01 | 5.922E-01 | 8.254E-01 |
| 704 | hsa-miR-548b-3p | 4.708E+01 | 4.923E+01 | 9.562E-01 | -4.474E-02 | 6.618E-01 | 8.113E-01 | 9.024E-01 | 9.671E-01 |
| 705 | hsa-miR-518c | 6.298E+01 | 6.563E+01 | 9.596E-01 | -4.120E-02 | 6.780E-01 | 8.299E-01 | 6.075E-01 | 8.369E-01 |
| 706 | hsa-miR-99b | 1.664E+02 | 1.775E+02 | 9.378E-01 | -6.420E-02 | 6.814E-01 | 8.329E-01 | 5.930E-01 | 8.254E-01 |
| 707 | hsa-miR-27b* | 6.105E+01 | 6.281E+01 | 9.719E-01 | -2.850E-02 | 6.841E-01 | 8.351E-01 | 6.777E-01 | 8.698E-01 |
| 708 | hsa-miR-214 | 3.006E+02 | 3.871E+02 | 7.766E-01 | -2.528E-01 | 6.858E-01 | 8.360E-01 | 2.407E-01 | 5.711E-01 |
| 709 | hsa-miR-145 | 1.264E+02 | 1.397E+02 | 9.050E-01 | -9.987E-02 | 6.878E-01 | 8.362E-01 | 6.119E-01 | 8.406E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 710 | hsa-miR-653 | 2.384E+01 | 1.756E+01 | 1.357E-00 | 3.054E-01 | 6.880E-01 | 8.362E-01 | 5.939E-01 | 8.254E-01 |
| 711 | hsa-miR-765 | 4.881E+01 | 4.938E+01 | 9.884E-01 | -1.164E-02 | 6.916E-01 | 8.394E-01 | 6.950E-01 | 8.769E-01 |
| 712 | hsa-miR-570 | 7.701E+01 | 8.472E+01 | 9.090E-01 | -9.537E-02 | 6.953E-01 | 8.427E-01 | 6.894E-01 | 8.762E-01 |
| 713 | hsa-miR-604 | 8.976E+01 | 1.082E+02 | 8.300E-01 | -1.864E-01 | 6.968E-01 | 8.434E-01 | 7.543E-01 | 8.926E-01 |
| 714 | hsa-miR-93 | 3.450E+03 | 3.374E+03 | 1.023E-00 | 2.227E-02 | 7.010E-01 | 8.459E-01 | 5.611E-01 | 8.044E-01 |
| 715 | hsa-miR-146b-5p | 1.016E+02 | 1.005E+02 | 1.011E-00 | 1.071E-02 | 7.009E-01 | 8.459E-01 | 2.712E-01 | 6.143E-01 |
| 716 | hsa-miR-29b | 4.061E+02 | 3.902E+02 | 1.041E-00 | 3.997E-02 | 7.018E-01 | 8.459E-01 | 6.547E-01 | 8.645E-01 |
| 717 | hsa-miR-181a* | 7.344E+01 | 7.937E+01 | 9.252E-01 | -7.773E-02 | 7.029E-01 | 8.460E-01 | 5.380E-01 | 7.996E-01 |
| 718 | hsa-miR-422a | 1.385E+02 | 1.769E+02 | 7.833E-01 | -2.443E-01 | 7.040E-01 | 8.462E-01 | 3.380E-01 | 6.638E-01 |
| 719 | hsa-miR-1206 | 6.041E+01 | 5.653E+01 | 1.069E-00 | 6.646E-02 | 7.078E-01 | 8.484E-01 | 3.619E-01 | 6.763E-01 |
| 720 | hsa-miR-23a | 4.401E+03 | 3.998E+03 | 1.101E-00 | 9.621E-02 | 7.073E-01 | 8.484E-01 | 6.610E-01 | 8.656E-01 |
| 721 | hsa-miR-487b | 5.424E+01 | 5.917E+01 | 9.167E-01 | -8.703E-02 | 7.090E-01 | 8.487E-01 | 7.344E-01 | 8.857E-01 |
| 722 | hsa-miR-339-3p | 2.728E+02 | 2.542E+02 | 1.073E-00 | 7.055E-02 | 7.123E-01 | 8.506E-01 | 5.362E-01 | 7.996E-01 |
| 723 | hsa-miR-191 | 1.198E+04 | 1.109E+04 | 1.080E-00 | 7.663E-02 | 7.127E-01 | 8.506E-01 | 6.670E-01 | 8.661E-01 |
| 724 | hsa-miR-340* | 1.586E+01 | 6.601E-00 | 2.402E-00 | 8.763E-01 | 7.292E-01 | 8.675E-01 | 3.831E-01 | 6.917E-01 |
| 725 | hsa-miR-1291 | 9.487E+01 | 1.096E+02 | 8.657E-01 | -1.442E-01 | 7.286E-01 | 8.675E-01 | 3.316E-01 | 6.638E-01 |
| 726 | hsa-miR-208a | 5.959E+01 | 6.629E+01 | 8.990E-01 | -1.065E-01 | 7.298E-01 | 8.675E-01 | 7.042E-01 | 8.807E-01 |
| 727 | hsa-miR-23a* | 4.779E-00 | 1.000E-00 | 4.779E-00 | 1.564E-00 | 7.398E-01 | 8.757E-01 | 9.270E-01 | 9.720E-01 |
| 728 | hsa-miR-1826 | 1.952E+02 | 2.078E+02 | 9.395E-01 | -6.241E-02 | 7.385E-01 | 8.757E-01 | 4.047E-01 | 7.094E-01 |
| 729 | hsa-miR-1208 | 9.372E+01 | 1.179E+02 | 7.951E-01 | -2.293E-01 | 7.393E-01 | 8.757E-01 | 4.381E-01 | 7.271E-01 |
| 730 | hsa-miR-1207-5p | 4.673E+02 | 6.478E+02 | 7.213E-01 | -3.267E-01 | 7.413E-01 | 8.764E-01 | 2.493E-01 | 5.831E-01 |
| 731 | hsa-miR-31* | 1.722E+02 | 1.718E+02 | 1.002E-00 | 2.479E-03 | 7.427E-01 | 8.768E-01 | 4.137E-01 | 7.106E-01 |
| 732 | hsa-miR-143* | 1.110E+02 | 1.203E+02 | 9.221E-01 | -8.109E-02 | 7.447E-01 | 8.780E-01 | 4.735E-01 | 7.572E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 733 | hsa-let-7f | 4.159E+02 | 2.433E+02 | 1.709E-00 | 5.359E-01 | 7.540E-01 | 8.865E-01 | 4.227E-01 | 7.159E-01 |
| 734 | hsa-miR-105 | 4.881E+01 | 4.327E+01 | 1.128E-00 | 1.203E-01 | 7.537E-01 | 8.865E-01 | 4.986E-01 | 7.749E-01 |
| 735 | hsa-miR-569 | 1.139E+01 | 1.995E+01 | 5.709E-01 | -5.606E-01 | 7.553E-01 | 8.868E-01 | 4.951E-01 | 7.737E-01 |
| 736 | hsa-miR-30c-2* | 2.222E+01 | 5.416E-00 | 4.103E-00 | 1.412E-00 | 7.610E-01 | 8.887E-01 | 4.264E-01 | 7.192E-01 |
| 737 | hsa-miR-921 | 5.900E+01 | 5.868E+01 | 1.005E-00 | 5.454E-03 | 7.584E-01 | 8.887E-01 | 9.237E-01 | 9.719E-01 |
| 738 | hsa-miR-628-5p | 7.874E+01 | 9.775E+01 | 8.054E-01 | -2.164E-01 | 7.592E-01 | 8.887E-01 | 4.094E-01 | 7.106E-01 |
| 739 | hsa-miR-1225-3p | 1.371E+02 | 1.713E+02 | 8.000E-01 | -2.232E-01 | 7.607E-01 | 8.887E-01 | 6.703E-01 | 8.673E-01 |
| 740 | hsa-miR-597 | 6.298E+01 | 6.814E+01 | 9.242E-01 | -7.886E-02 | 7.630E-01 | 8.898E-01 | 5.076E-01 | 7.781E-01 |
| 741 | hsa-miR-10a | 4.697E+01 | 4.785E+01 | 9.817E-01 | -1.843E-02 | 7.641E-01 | 8.899E-01 | 8.438E-01 | 9.427E-01 |
| 742 | hsa-miR-302b | 1.000E-00 | 1.000E-00 | 1.000E-00 | 0.000E+01 | 7.664E-01 | 8.912E-01 | 5.490E-01 | 8.015E-01 |
| 743 | hsa-miR-1277 | 5.339E+01 | 5.868E+01 | 9.099E-01 | -9.444E-02 | 7.672E-01 | 8.912E-01 | 6.517E-01 | 8.645E-01 |
| 744 | hsa-miR-1207-3p | 3.466E+01 | 4.697E+01 | 7.379E-01 | -3.040E-01 | 7.697E-01 | 8.929E-01 | 7.213E-01 | 8.841E-01 |
| 745 | hsa-miR-186 | 3.227E+01 | 4.168E+01 | 7.743E-01 | -2.558E-01 | 7.713E-01 | 8.935E-01 | 2.832E-01 | 6.220E-01 |
| 746 | hsa-miR-626 | 3.440E+01 | 4.271E+01 | 8.053E-01 | -2.165E-01 | 7.730E-01 | 8.942E-01 | 4.597E-01 | 7.498E-01 |
| 747 | hsa-miR-554 | 8.815E+01 | 8.761E+01 | 1.006E-00 | 6.096E-03 | 7.742E-01 | 8.944E-01 | 6.739E-01 | 8.693E-01 |
| 748 | hsa-miR-99a* | 3.526E+01 | 3.927E+01 | 8.980E-01 | -1.076E-01 | 7.771E-01 | 8.965E-01 | 2.400E-01 | 5.711E-01 |
| 749 | hsa-miR-497* | 1.027E+02 | 1.032E+02 | 9.949E-01 | -5.156E-03 | 7.789E-01 | 8.965E-01 | 6.268E-01 | 8.496E-01 |
| 750 | hsa-miR-487a | 6.487E+01 | 8.023E+01 | 8.085E-01 | -2.126E-01 | 7.791E-01 | 8.965E-01 | 6.127E-01 | 8.406E-01 |
| 751 | hsa-miR-199a-5p | 2.352E+02 | 2.056E+02 | 1.144E-00 | 1.342E-01 | 7.802E-01 | 8.966E-01 | 6.964E-01 | 8.773E-01 |
| 752 | hsa-miR-454 | 1.154E+02 | 8.415E+01 | 1.371E-00 | 3.154E-01 | 7.832E-01 | 8.976E-01 | 6.326E-01 | 8.504E-01 |
| 753 | hsa-miR-492 | 7.192E+01 | 5.959E+01 | 1.207E-00 | 1.881E-01 | 7.831E-01 | 8.976E-01 | 3.575E-01 | 6.760E-01 |
| 754 | hsa-miR-338-5p | 3.200E+01 | 3.587E+01 | 8.922E-01 | -1.141E-01 | 7.843E-01 | 8.977E-01 | 9.989E-01 | 9.999E-01 |
| 755 | hsa-miR-125a-3p | 1.523E+01 | 3.315E+01 | 4.593E-01 | -7.781E-01 | 7.860E-01 | 8.983E-01 | 5.766E-01 | 8.170E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 756 | hsa-miR-20a | 3.623E+03 | 3.143E+03 | 1.153E-00 | 1.420E-01 | 7.869E-01 | 8.983E-01 | 4.118E-01 | 7.106E-01 |
| 757 | hsa-miR-518d-3p | 7.874E+01 | 8.399E+01 | 9.374E-01 | -6.461E-02 | 7.943E-01 | 9.055E-01 | 7.452E-01 | 8.883E-01 |
| 758 | hsa-miR-664* | 5.424E+01 | 4.949E+01 | 1.096E-00 | 9.159E-02 | 8.005E-01 | 9.072E-01 | 5.569E-01 | 8.023E-01 |
| 759 | hsa-miR-520c-3p | 1.000E-00 | 1.000E-00 | 1.000E-00 | 0.000E+01 | 7.979E-01 | 9.072E-01 | 7.261E-01 | 8.851E-01 |
| 760 | hsa-miR-1303 | 3.010E+01 | 2.743E+01 | 1.097E-00 | 9.294E-02 | 7.991E-01 | 9.072E-01 | 1.572E-01 | 4.881E-01 |
| 761 | hsa-miR-26b | 3.229E+02 | 1.911E+02 | 1.690E-00 | 5.244E-01 | 8.009E-01 | 9.072E-01 | 8.868E-01 | 9.626E-01 |
| 762 | hsa-miR-1256 | 6.665E+01 | 7.584E+01 | 8.788E-01 | -1.292E-01 | 8.010E-01 | 9.072E-01 | 9.247E-01 | 9.719E-01 |
| 763 | hsa-miR-361-3p | 1.886E+02 | 1.986E+02 | 9.497E-01 | -5.162E-02 | 8.035E-01 | 9.077E-01 | 6.684E-01 | 8.661E-01 |
| 764 | hsa-miR-22* | 4.639E+01 | 5.046E+01 | 9.192E-01 | -8.429E-02 | 8.056E-01 | 9.077E-01 | 9.722E-01 | 9.882E-01 |
| 765 | hsa-miR-103 | 6.927E+03 | 6.228E+03 | 1.112E-00 | 1.065E-01 | 8.056E-01 | 9.077E-01 | 5.652E-01 | 8.076E-01 |
| 766 | hsa-miR-888* | 4.708E+01 | 5.116E+01 | 9.201E-01 | -8.323E-02 | 8.053E-01 | 9.077E-01 | 2.038E-01 | 5.254E-01 |
| 767 | hsa-miR-1180 | 6.116E+01 | 5.529E+01 | 1.106E-00 | 1.009E-01 | 8.085E-01 | 9.097E-01 | 3.020E-01 | 6.403E-01 |
| 768 | hsa-miR-432* | 4.471E+01 | 5.092E+01 | 8.781E-01 | -1.300E-01 | 8.096E-01 | 9.098E-01 | 5.261E-01 | 7.972E-01 |
| 769 | hsa-miR-126 | 1.620E+03 | 1.262E+03 | 1.284E-00 | 2.498E-01 | 8.129E-01 | 9.098E-01 | 7.705E-01 | 8.986E-01 |
| 770 | hsa-miR-200a | 9.031E+01 | 9.775E+01 | 9.239E-01 | -7.920E-02 | 8.125E-01 | 9.098E-01 | 6.402E-01 | 8.553E-01 |
| 771 | hsa-miR-1285 | 2.644E+02 | 3.515E+02 | 7.522E-01 | -2.848E-01 | 8.121E-01 | 9.098E-01 | 1.450E-01 | 4.686E-01 |
| 772 | hsa-miR-154* | 4.482E+01 | 4.315E+01 | 1.039E-00 | 3.788E-02 | 8.202E-01 | 9.168E-01 | 3.951E-01 | 7.046E-01 |
| 773 | hsa-miR-371-3p | 3.466E+01 | 2.530E+01 | 1.370E-00 | 3.147E-01 | 8.233E-01 | 9.175E-01 | 1.970E-01 | 5.254E-01 |
| 774 | hsa-miR-193a-3p | 1.234E+02 | 1.385E+02 | 8.910E-01 | -1.154E-01 | 8.229E-01 | 9.175E-01 | 3.141E-01 | 6.438E-01 |
| 775 | hsa-miR-1244 | 1.000E-00 | 1.000E-00 | 1.000E-00 | 0.000E+01 | 8.239E-01 | 9.175E-01 | 1.579E-01 | 4.883E-01 |
| 776 | hsa-miR-200c | 9.283E+01 | 8.531E+01 | 1.088E-00 | 8.443E-02 | 8.254E-01 | 9.180E-01 | 6.185E-01 | 8.432E-01 |
| 777 | hsa-miR-125b-1* | 7.413E-00 | 1.000E-00 | 7.413E-00 | 2.003E-00 | 8.299E-01 | 9.182E-01 | 5.355E-01 | 7.996E-01 |
| 778 | hsa-miR-517* | 1.661E+02 | 1.664E+02 | 9.979E-01 | -2.082E-03 | 8.281E-01 | 9.182E-01 | 3.675E-01 | 6.763E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 779 | hsa-miR-216a | 1.420E+02 | 1.364E+02 | 1.042E-00 | 4.069E-02 | 8.288E-01 | 9.182E-01 | 3.487E-01 | 6.732E-01 |
| 780 | hsa-miR-586 | 3.200E+01 | 3.087E+01 | 1.036E-00 | 3.580E-02 | 8.276E-01 | 9.182E-01 | 7.288E-01 | 8.857E-01 |
| 781 | hsa-miR-375 | 8.713E-00 | 1.000E-00 | 8.713E-00 | 2.165E-00 | 8.418E-01 | 9.301E-01 | 5.046E-01 | 7.779E-01 |
| 782 | hsa-let-7a | 9.830E+02 | 1.096E+03 | 8.968E-01 | -1.089E-01 | 8.494E-01 | 9.360E-01 | 5.455E-01 | 8.015E-01 |
| 783 | hsa-miR-1827 | 3.648E+01 | 3.753E+01 | 9.721E-01 | -2.833E-02 | 8.499E-01 | 9.360E-01 | 5.476E-01 | 8.015E-01 |
| 784 | hsa-miR-518e* | 1.407E+02 | 1.300E+02 | 1.082E-00 | 7.909E-02 | 8.503E-01 | 9.360E-01 | 3.992E-01 | 7.060E-01 |
| 785 | hsa-miR-513b | 4.708E+01 | 5.380E+01 | 8.750E-01 | -1.335E-01 | 8.539E-01 | 9.378E-01 | 8.062E-01 | 9.228E-01 |
| 786 | hsa-miR-196a | 1.000E-00 | 1.000E-00 | 1.000E-00 | 0.000E+01 | 8.541E-01 | 9.378E-01 | 7.953E-01 | 9.130E-01 |
| 787 | hsa-miR-1915 | 6.883E+02 | 8.284E+02 | 8.309E-01 | -1.852E-01 | 8.571E-01 | 9.399E-01 | 4.008E-01 | 7.073E-01 |
| 788 | hsa-miR-1204 | 1.935E+01 | 1.756E+01 | 1.101E-00 | 9.666E-02 | 8.592E-01 | 9.410E-01 | 9.456E-01 | 9.820E-01 |
| 789 | hsa-miR-15b* | 6.281E+01 | 7.320E+01 | 8.582E-01 | -1.530E-01 | 8.619E-01 | 9.428E-01 | 4.899E-01 | 7.673E-01 |
| 790 | hsa-miR-516b | 3.581E+01 | 4.111E+01 | 8.710E-01 | -1.381E-01 | 8.634E-01 | 9.432E-01 | 4.326E-01 | 7.246E-01 |
| 791 | hsa-miR-1912 | 1.539E+02 | 1.862E+02 | 8.265E-01 | -1.905E-01 | 8.661E-01 | 9.450E-01 | 6.582E-01 | 8.645E-01 |
| 792 | hsa-miR-550* | 6.883E+02 | 6.607E+02 | 1.042E-00 | 4.090E-02 | 8.693E-01 | 9.472E-01 | 8.667E-01 | 9.528E-01 |
| 793 | hsa-miR-632 | 2.066E+01 | 2.485E+01 | 8.315E-01 | -1.845E-01 | 8.706E-01 | 9.474E-01 | 7.407E-01 | 8.878E-01 |
| 794 | hsa-miR-24 | 1.760E+03 | 1.830E+03 | 9.619E-01 | -3.882E-02 | 8.745E-01 | 9.505E-01 | 3.536E-01 | 6.760E-01 |
| 795 | hsa-miR-561 | 3.994E+01 | 3.753E+01 | 1.064E-00 | 6.221E-02 | 8.776E-01 | 9.512E-01 | 9.713E-01 | 9.882E-01 |
| 796 | hsa-miR-219-5p | 5.025E+01 | 5.092E+01 | 9.870E-01 | -1.310E-02 | 8.784E-01 | 9.512E-01 | 5.623E-01 | 8.047E-01 |
| 797 | hsa-miR-20b | 2.877E+03 | 2.515E+03 | 1.144E-00 | 1.345E-01 | 8.764E-01 | 9.512E-01 | 5.531E-01 | 8.015E-01 |
| 798 | hsa-miR-220a | 6.127E+01 | 6.719E+01 | 9.119E-01 | -9.218E-02 | 8.799E-01 | 9.515E-01 | 2.613E-01 | 5.971E-01 |
| 799 | hsa-miR-199a-3p | 9.671E+01 | 9.048E+01 | 1.069E-00 | 6.663E-02 | 8.849E-01 | 9.558E-01 | 8.111E-01 | 9.246E-01 |
| 800 | hsa-miR-665 | 9.565E+01 | 1.008E+02 | 9.493E-01 | -5.201E-02 | 8.891E-01 | 9.579E-01 | 2.557E-01 | 5.917E-01 |
| 801 | hsa-miR-519a | 3.200E+01 | 1.953E+01 | 1.638E-00 | 4.937E-01 | 8.885E-01 | 9.579E-01 | 7.015E-01 | 8.807E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 802 | hsa-miR-488* | 7.382E+01 | 7.714E+01 | 9.570E-01 | -4.400E-02 | 8.916E-01 | 9.594E-01 | 7.307E-01 | 8.857E-01 |
| 803 | hsa-miR-449b | 3.406E+01 | 3.289E+01 | 1.036E-00 | 3.494E-02 | 9.055E-01 | 9.636E-01 | 4.837E-01 | 7.617E-01 |
| 804 | hsa-miR-151-5p | 4.401E+03 | 4.640E+03 | 9.485E-01 | -5.288E-02 | 8.976E-01 | 9.636E-01 | 7.524E-01 | 8.926E-01 |
| 805 | hsa-miR-567 | 5.339E+01 | 3.315E+01 | 1.610E-00 | 4.764E-01 | 9.045E-01 | 9.636E-01 | 4.137E-01 | 7.106E-01 |
| 806 | hsa-miR-522 | 1.000E-00 | 1.000E-00 | 1.000E-00 | 0.000E+01 | 9.009E-01 | 9.636E-01 | 2.780E-02 | 3.110E-01 |
| 807 | hsa-miR-1267 | 4.271E+01 | 3.029E+01 | 1.410E-00 | 3.436E-01 | 9.038E-01 | 9.636E-01 | 9.981E-01 | 9.999E-01 |
| 808 | hsa-miR-874 | 1.547E+02 | 1.454E+02 | 1.064E-00 | 6.165E-02 | 9.038E-01 | 9.636E-01 | 5.404E-01 | 8.006E-01 |
| 809 | hsa-miR-376c | 6.788E+01 | 5.868E+01 | 1.157E-00 | 1.458E-01 | 9.021E-01 | 9.636E-01 | 9.999E-01 | 9.999E-01 |
| 810 | hsa-miR-510 | 6.030E+01 | 7.037E+01 | 8.568E-01 | -1.545E-01 | 8.986E-01 | 9.636E-01 | 9.625E-01 | 9.865E-01 |
| 811 | hsa-miR-374b | 4.953E+02 | 4.905E+02 | 1.010E-00 | 9.630E-03 | 9.055E-01 | 9.636E-01 | 6.005E-01 | 8.318E-01 |
| 812 | hsa-miR-29c | 5.591E+02 | 5.224E+02 | 1.070E-00 | 6.791E-02 | 9.070E-01 | 9.640E-01 | 8.393E-01 | 9.407E-01 |
| 813 | hsa-miR-137 | 7.689E+01 | 7.773E+01 | 9.891E-01 | -1.092E-02 | 9.084E-01 | 9.642E-01 | 4.343E-01 | 7.249E-01 |
| 814 | hsa-miR-337-5p | 4.433E+01 | 4.697E+01 | 9.438E-01 | -5.786E-02 | 9.165E-01 | 9.647E-01 | 8.969E-01 | 9.671E-01 |
| 815 | hsa-miR-1254 | 1.129E+02 | 1.264E+02 | 8.929E-01 | -1.133E-01 | 9.143E-01 | 9.647E-01 | 4.113E-01 | 7.106E-01 |
| 816 | hsa-miR-193b | 5.703E+01 | 6.327E+01 | 9.014E-01 | -1.038E-01 | 9.106E-01 | 9.647E-01 | 7.983E-01 | 9.149E-01 |
| 817 | hsa-miR-520d-5p | 5.975E+01 | 5.752E+01 | 1.039E-00 | 3.801E-02 | 9.149E-01 | 9.647E-01 | 5.284E-01 | 7.986E-01 |
| 818 | hsa-miR-1179 | 2.715E+01 | 2.530E+01 | 1.073E-00 | 7.032E-02 | 9.143E-01 | 9.647E-01 | 3.385E-01 | 6.638E-01 |
| 819 | hsa-miR-181b | 4.708E+01 | 4.534E+01 | 1.038E-00 | 3.748E-02 | 9.167E-01 | 9.647E-01 | 3.174E-01 | 6.490E-01 |
| 820 | hsa-miR-30b | 7.310E+03 | 8.166E+03 | 8.952E-01 | -1.107E-01 | 9.147E-01 | 9.647E-01 | 5.527E-01 | 8.015E-01 |
| 821 | hsa-miR-532-5p | 2.127E+02 | 1.678E+02 | 1.268E-00 | 2.371E-01 | 9.203E-01 | 9.674E-01 | 6.873E-01 | 8.759E-01 |
| 822 | hsa-miR-369-5p | 3.037E+01 | 3.753E+01 | 8.093E-01 | -2.116E-01 | 9.295E-01 | 9.735E-01 | 7.401E-01 | 8.878E-01 |
| 823 | hsa-miR-631 | 1.300E+02 | 1.259E+02 | 1.032E-00 | 3.190E-02 | 9.290E-01 | 9.735E-01 | 7.187E-01 | 8.841E-01 |
| 824 | hsa-miR-130b | 1.492E+03 | 1.326E+03 | 1.125E-00 | 1.176E-01 | 9.285E-01 | 9.735E-01 | 5.593E-01 | 8.031E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 825 | hsa-miR-551a | 5.092E+01 | 6.084E+01 | 8.369E-01 | -1.780E-01 | 9.324E-01 | 9.754E-01 | 5.795E-01 | 8.185E-01 |
| 826 | hsa-miR-551b | 7.370E+01 | 9.048E+01 | 8.146E-01 | -2.051E-01 | 9.355E-01 | 9.774E-01 | 4.440E-01 | 7.313E-01 |
| 827 | hsa-miR-593 | 1.071E+01 | 5.416E-00 | 1.978E-00 | 6.820E-01 | 9.372E-01 | 9.780E-01 | 8.624E-01 | 9.528E-01 |
| 828 | hsa-miR-886-5p | 7.170E+01 | 6.177E+01 | 1.161E-00 | 1.489E-01 | 9.387E-01 | 9.783E-01 | 7.576E-01 | 8.928E-01 |
| 829 | hsa-miR-184 | 1.322E+01 | 1.995E+01 | 6.623E-01 | -4.120E-01 | 9.443E-01 | 9.819E-01 | 3.369E-01 | 6.638E-01 |
| 830 | hsa-miR-624 | 5.144E+01 | 5.015E+01 | 1.026E-00 | 2.540E-02 | 9.442E-01 | 9.819E-01 | 7.245E-01 | 8.844E-01 |
| 831 | hsa-miR-548o | 9.997E+01 | 9.810E+01 | 1.019E-00 | 1.889E-02 | 9.494E-01 | 9.824E-01 | 3.060E-01 | 6.412E-01 |
| 832 | hsa-miR-223 | 2.206E+03 | 2.254E+03 | 9.784E-01 | -2.184E-02 | 9.461E-01 | 9.824E-01 | 9.624E-01 | 9.865E-01 |
| 833 | hsa-miR-1231 | 8.373E+01 | 1.072E+02 | 7.809E-01 | -2.473E-01 | 9.494E-01 | 9.824E-01 | 3.031E-01 | 6.411E-01 |
| 834 | hsa-miR-1276 | 3.985E+01 | 3.499E+01 | 1.139E-00 | 1.300E-01 | 9.486E-01 | 9.824E-01 | 7.444E-01 | 8.883E-01 |
| 835 | hsa-miR-29b-2* | 3.526E+01 | 2.942E+01 | 1.199E-00 | 1.812E-01 | 9.565E-01 | 9.850E-01 | 9.826E-01 | 9.964E-01 |
| 836 | hsa-miR-346 | 5.397E+01 | 5.778E+01 | 9.340E-01 | -6.823E-02 | 9.541E-01 | 9.850E-01 | 9.083E-01 | 9.671E-01 |
| 837 | hsa-miR-141* | 8.857E+01 | 9.334E+01 | 9.489E-01 | -5.240E-02 | 9.552E-01 | 9.850E-01 | 8.245E-01 | 9.338E-01 |
| 838 | hsa-miR-181d | 3.010E+01 | 2.530E+01 | 1.190E-00 | 1.736E-01 | 9.559E-01 | 9.850E-01 | 8.659E-01 | 9.528E-01 |
| 839 | hsa-miR-615-5p | 4.835E+01 | 5.015E+01 | 9.641E-01 | -3.660E-02 | 9.671E-01 | 9.864E-01 | 5.527E-01 | 8.015E-01 |
| 840 | hsa-miR-1185 | 1.187E+01 | 1.502E+01 | 7.905E-01 | -2.351E-01 | 9.637E-01 | 9.864E-01 | 9.506E-01 | 9.850E-01 |
| 841 | hsa-miR-141 | 3.902E+01 | 3.701E+01 | 1.054E-00 | 5.303E-02 | 9.654E-01 | 9.864E-01 | 8.330E-01 | 9.385E-01 |
| 842 | hsa-miR-885-5p | 2.515E+01 | 3.581E+01 | 7.024E-01 | -3.533E-01 | 9.656E-01 | 9.864E-01 | 2.318E-01 | 5.594E-01 |
| 843 | hsa-miR-18a | 1.203E+03 | 1.281E+03 | 9.392E-01 | -6.276E-02 | 9.637E-01 | 9.864E-01 | 4.764E-01 | 7.581E-01 |
| 844 | hsa-let-7g | 2.694E+02 | 1.649E+02 | 1.634E-00 | 4.909E-01 | 9.668E-01 | 9.864E-01 | 5.350E-01 | 7.996E-01 |
| 845 | hsa-miR-130a | 1.431E+03 | 1.326E+03 | 1.079E-00 | 7.624E-02 | 9.648E-01 | 9.864E-01 | 5.794E-01 | 8.185E-01 |
| 846 | hsa-miR-744 | 6.104E+02 | 6.222E+02 | 9.810E-01 | -1.914E-02 | 9.681E-01 | 9.864E-01 | 6.656E-01 | 8.661E-01 |
| 847 | hsa-miR-221 | 8.143E+01 | 8.490E+01 | 9.591E-01 | -4.177E-02 | 9.644E-01 | 9.864E-01 | 8.900E-01 | 9.637E-01 |

FIG 2 (continued)

| No. | miRNA, miRNA* | median g1 | median g2 | qmedian | logqmedian | ttest_rawp | ttest_adjp | limma_rawp | limma_adjp |
|---|---|---|---|---|---|---|---|---|---|
| 848 | hsa-miR-1255b | 7.515E+01 | 6.116E+01 | 1.229E-00 | 2.061E-01 | 9.704E-01 | 9.876E-01 | 8.939E-01 | 9.655E-01 |
| 849 | hsa-miR-378* | 5.106E+01 | 5.860E+01 | 8.712E-01 | -1.378E-01 | 9.758E-01 | 9.893E-01 | 2.120E-01 | 5.302E-01 |
| 850 | hsa-miR-629 | 5.447E+01 | 2.462E+01 | 2.212E-00 | 7.941E-01 | 9.766E-01 | 9.893E-01 | 3.614E-01 | 6.763E-01 |
| 851 | hsa-miR-526b | 4.271E+01 | 4.271E+01 | 1.000E-00 | 0.000E+01 | 9.764E-01 | 9.893E-01 | 6.638E-01 | 8.661E-01 |
| 852 | hsa-miR-373 | 1.000E-00 | 6.601E-00 | 1.515E-01 | -1.887E-00 | 9.755E-01 | 9.893E-01 | 2.604E-01 | 5.971E-01 |
| 853 | hsa-miR-515-5p | 1.609E+02 | 1.784E+02 | 9.019E-01 | -1.033E-01 | 9.779E-01 | 9.893E-01 | 4.356E-01 | 7.256E-01 |
| 854 | hsa-miR-592 | 4.546E+01 | 4.339E+01 | 1.048E-00 | 4.651E-02 | 9.822E-01 | 9.926E-01 | 3.829E-01 | 6.917E-01 |
| 855 | hsa-miR-16-1* | 7.396E+01 | 7.160E+01 | 1.033E-00 | 3.234E-02 | 9.885E-01 | 9.959E-01 | 5.249E-01 | 7.972E-01 |
| 856 | hsa-miR-30e* | 3.940E+01 | 3.499E+01 | 1.126E-00 | 1.187E-01 | 9.890E-01 | 9.959E-01 | 9.186E-01 | 9.703E-01 |
| 857 | hsa-let-7e | 1.385E+02 | 8.174E+01 | 1.695E-00 | 5.277E-01 | 9.881E-01 | 9.959E-01 | 3.657E-01 | 6.763E-01 |
| 858 | hsa-miR-550 | 1.137E+02 | 1.103E+02 | 1.031E-00 | 3.040E-02 | 9.937E-01 | 9.984E-01 | 5.304E-01 | 7.996E-01 |
| 859 | hsa-miR-1294 | 9.057E-00 | 1.000E-00 | 9.057E-00 | 2.204E-00 | 9.927E-01 | 9.984E-01 | 6.027E-01 | 8.336E-01 |
| 860 | hsa-miR-144 | 1.687E+03 | 2.008E+03 | 8.401E-01 | -1.742E-01 | 9.952E-01 | 9.987E-01 | 3.254E-01 | 6.562E-01 |
| 861 | hsa-miR-939 | 4.938E+01 | 5.200E+01 | 9.496E-01 | -5.169E-02 | 9.996E-01 | 9.998E-01 | 9.947E-01 | 9.982E-01 |
| 862 | hsa-miR-384 | 5.900E+01 | 6.629E+01 | 8.900E-01 | -1.165E-01 | 9.977E-01 | 9.998E-01 | 9.650E-01 | 9.875E-01 |
| 863 | hsa-miR-598 | 5.144E+01 | 3.927E+01 | 1.310E-00 | 2.700E-01 | 9.998E-01 | 9.998E-01 | 8.154E-01 | 9.283E-01 |

FIG 6

| Number | year of birth | histology | current therapy | pre-therapies | tumor load |
|---|---|---|---|---|---|
| 1 | 1980 | serous | pegylated liposomal Doxorubicin | Paclitaxel/Carboplatin; | ++ |
| 2 | 1938 | serous | Topotecan | Paclitaxel/Carboplatin; Carboplatin mono; | ++ |
| 3 | 1951 | serous | Gemcitabine | Paclitaxel/Carboplatin; pegylated liposomal Doxorubicin; Topotecan, Treosulfan | ++ |
| 4 | 1931 | serous | Topotecan | Carboplatin mono | + |
| 5 | 1937 | serous OvCA or uterine carcinoma | Treosulfan | Paclitaxel/Carboplatin; Epirubicin; Carboplatin mono; | + |
| 6 | 1937 | solid | Topotecan | Cyclophosphamid/Carboplatin; Carboplatin mono; Paclitaxel/Carboplatin; | + |

FIG 6 (continued)

| | | | | | |
|---|---|---|---|---|---|
| **7** | 1947 | serous | Topotecan | Paclitaxel/Carboplatin; | ++ |
| **8** | 1939 | serous | Topotecan | Paclitaxel/Carboplatin; | +++ |
| **9** | 1955 | serous | pegylated liposomal Doxorubicin | Paclitaxel/Carboplatin; Topotecan; | + |
| **10** | 1931 | serous | Paclitaxel | Carboplatin mono; Topotecan; pegylated liposomal Doxorubicin; Treosulfan; | + |
| **11** | 1954 | serous | Treosulfan | Paclitaxel/Carboplatin; Topotecan; Carboplatin mono; pegylated liposomal Doxorubicin; | +++ |
| **12** | 1954 | serous | Topotecan | Paclitaxel/Carboplatin; pegylated liposomal Doxorubicin; HIPEC with Mitomycin; | ++ |
| **13** | 1943 | serous | Gemcitabine | Paclitaxel/Carboplatin; peg.-lip. Doxorubicin; Topotecan; Vinorelbin; Treosulfan; Carboplatin mono; Paclitaxel; | ++ |

FIG 6 (continued)

| | | | | | |
|---|---|---|---|---|---|
| **14** | 1960 | serous | Carboplatin mono | Paclitaxel/Carboplatin; Topotecan; | + |
| **15** | 1929 | endmetrioid | Carboplatin mono | Carboplatin mono; Topotecan; pegylated liposomal Doxorubicin; Treosulfan; | + |

FIG 7

| No. | miRNA | median g1 | median g2 | qmedian | Logq median | ttest_rawp | ttest_adjp | Limma_ rawp | Limma_ adjp |
|---|---|---|---|---|---|---|---|---|---|
| 1 | hsa-miR-1224-3p | 1.834E+02 | 5.332E+01 | 3.439E-00 | 1.235E-00 | 1.369E-06 | 2.418E-04 | 9.054E-07 | 3.907E-04 |
| 2 | hsa-miR-610 | 3.285E+01 | 1.137E+02 | 2.890E-01 | -1.241E-00 | 1.401E-06 | 2.418E-04 | 1.338E-04 | 6.592E-03 |
| 3 | hsa-miR-668 | 5.874E+01 | 1.125E+01 | 5.221E-00 | 1.653E-00 | 1.339E-06 | 2.418E-04 | 7.246E-08 | 6.253E-05 |
| 4 | hsa-miR-328 | 1.231E+02 | 2.530E+01 | 4.865E-00 | 1.582E-00 | 7.944E-07 | 2.418E-04 | 1.607E-04 | 7.300E-03 |
| 5 | hsa-miR-942 | 7.305E+01 | 1.000E-00 | 7.305E+01 | 4.291E-00 | 1.167E-06 | 2.418E-04 | 5.287E-05 | 4.002E-03 |
| 6 | hsa-miR-500 | 4.451E+02 | 1.141E+02 | 3.900E-00 | 1.361E-00 | 2.262E-06 | 2.913E-04 | 1.307E-05 | 2.553E-03 |
| 7 | hsa-miR-423-5p | 4.132E+03 | 1.962E+03 | 2.106E-00 | 7.446E-01 | 2.363E-06 | 2.913E-04 | 3.278E-05 | 2.888E-03 |
| 8 | hsa-miR-1248 | 2.331E+01 | 1.000E-00 | 2.331E+01 | 3.149E-00 | 4.071E-06 | 4.391E-04 | 2.418E-05 | 2.888E-03 |
| 9 | hsa-miR-324-3p | 1.056E+03 | 5.331E+02 | 1.980E-00 | 6.833E-01 | 6.926E-06 | 6.642E-04 | 2.352E-05 | 2.888E-03 |
| 10 | hsa-miR-1281 | 1.491E+02 | 1.756E+01 | 8.491E-00 | 2.139E-00 | 1.020E-05 | 8.003E-04 | 5.131E-06 | 1.476E-03 |
| 11 | hsa-miR-193a-5p | 1.251E+02 | 5.868E+01 | 2.133E-00 | 7.573E-01 | 9.625E-06 | 8.003E-04 | 4.210E-04 | 1.397E-02 |
| 12 | hsa-miR-1825 | 9.320E+01 | 3.136E+01 | 2.972E-00 | 1.089E-00 | 1.511E-05 | 1.086E-03 | 1.542E-02 | 8.933E-02 |
| 13 | hsa-miR-605 | 1.780E+01 | 1.000E-00 | 1.780E+01 | 2.879E-00 | 2.247E-05 | 1.492E-03 | 4.474E-04 | 1.430E-02 |
| 14 | hsa-miR-383 | 4.355E+01 | 9.810E+01 | 4.439E-01 | -8.121E-01 | 2.616E-05 | 1.613E-03 | 1.917E-03 | 2.954E-02 |
| 15 | hsa-miR-485-3p | 1.028E+02 | 3.733E+01 | 2.754E-00 | 1.013E-00 | 2.955E-05 | 1.700E-03 | 3.859E-04 | 1.350E-02 |
| 16 | hsa-miR-148a* | 4.038E+01 | 4.674E-00 | 8.640E-00 | 2.156E-00 | 4.232E-05 | 2.283E-03 | 2.533E-04 | 1.041E-02 |
| 17 | hsa-miR-877* | 1.188E+02 | 1.734E+01 | 6.852E-00 | 1.925E-00 | 4.626E-05 | 2.348E-03 | 4.871E-04 | 1.446E-02 |
| 18 | hsa-miR-130a* | 7.695E+01 | 3.526E+01 | 2.182E-00 | 7.802E-01 | 5.468E-05 | 2.442E-03 | 1.827E-03 | 2.954E-02 |
| 19 | hsa-let-7d* | 1.661E+02 | 6.719E+01 | 2.472E-00 | 9.051E-01 | 5.943E-05 | 2.442E-03 | 1.608E-02 | 9.025E-02 |

FIG 7 (continued)

| | | | | | | | | | |
|---|---|---|---|---|---|---|---|---|---|
| 20 | hsa-miR-337-3p | 1.739E+01 | 1.000E-00 | 1.739E+01 | 2.856E-00 | 5.155E-05 | 2.442E-03 | 1.479E-05 | 2.553E-03 |
| 21 | hsa-miR-1226 | 8.481E+01 | 3.581E+01 | 2.369E-00 | 8.623E-01 | 5.892E-05 | 2.442E-03 | 5.492E-02 | 1.810E-01 |
| 22 | hsa-miR-148a | 6.814E+02 | 1.431E+03 | 4.761E-01 | -7.422E-01 | 8.042E-05 | 3.155E-03 | 1.295E-04 | 6.592E-03 |
| 23 | hsa-miR-219-1-3p | 2.026E+01 | 1.000E-00 | 2.026E+01 | 3.009E-00 | 8.581E-05 | 3.220E-03 | 3.347E-05 | 2.888E-03 |
| 24 | hsa-miR-29c* | 2.456E+01 | 1.000E-00 | 2.456E+01 | 3.201E-00 | 1.113E-04 | 4.002E-03 | 8.181E-03 | 6.139E-02 |
| 25 | hsa-miR-483-3p | 5.069E+01 | 1.000E-00 | 5.069E+01 | 3.926E-00 | 1.476E-04 | 5.095E-03 | 1.077E-03 | 2.324E-02 |
| 26 | hsa-miR-133a | 8.744E+01 | 2.704E+01 | 3.234E-00 | 1.174E-00 | 1.556E-04 | 5.165E-03 | 6.857E-03 | 5.476E-02 |
| 27 | hsa-miR-323-3p | 5.378E+01 | 8.612E-00 | 6.245E-00 | 1.832E-00 | 1.671E-04 | 5.300E-03 | 4.320E-03 | 4.608E-02 |
| 28 | hsa-miR-125a-5p | 4.177E+02 | 1.122E+02 | 3.722E-00 | 1.314E-00 | 1.781E-04 | 5.300E-03 | 6.980E-03 | 5.476E-02 |
| 29 | hsa-miR-130b* | 2.031E+01 | 1.000E-00 | 2.031E+01 | 3.011E-00 | 1.761E-04 | 5.300E-03 | 1.895E-03 | 2.954E-02 |
| 30 | hsa-miR-133b | 1.760E+01 | 1.000E-00 | 1.760E+01 | 2.868E-00 | 1.997E-04 | 5.696E-03 | 7.368E-04 | 1.829E-02 |
| 31 | hsa-miR-186* | 7.367E+01 | 1.325E+02 | 5.559E-01 | -5.871E-01 | 2.142E-04 | 5.696E-03 | 4.622E-03 | 4.652E-02 |
| 32 | hsa-miR-576-3p | 9.768E-00 | 1.000E-00 | 9.768E-00 | 2.279E-00 | 2.104E-04 | 5.696E-03 | 1.348E-04 | 6.592E-03 |
| 33 | hsa-miR-150 | 1.919E+03 | 6.288E+02 | 3.051E-00 | 1.116E-00 | 2.178E-04 | 5.696E-03 | 3.136E-04 | 1.184E-02 |
| 34 | hsa-miR-26b* | 1.118E+01 | 1.000E-00 | 1.118E+01 | 2.414E-00 | 2.356E-04 | 5.981E-03 | 2.208E-04 | 9.528E-03 |
| 35 | hsa-miR-302c | 1.095E+01 | 1.000E-00 | 1.095E+01 | 2.394E-00 | 2.438E-04 | 6.011E-03 | 1.375E-04 | 6.592E-03 |
| 36 | hsa-miR-299-5p | 2.402E+01 | 1.000E-00 | 2.402E+01 | 3.179E-00 | 2.616E-04 | 6.042E-03 | 3.171E-03 | 3.966E-02 |
| 37 | hsa-miR-361-5p | 6.290E+02 | 3.138E+02 | 2.005E-00 | 6.954E-01 | 2.624E-04 | 6.042E-03 | 8.445E-04 | 2.025E-02 |
| 38 | hsa-miR-770-5p | 4.400E+01 | 9.611E+01 | 4.578E-01 | -7.813E-01 | 2.661E-04 | 6.042E-03 | 6.917E-03 | 5.476E-02 |
| 39 | hsa-miR-1303 | 5.650E+01 | 2.743E+01 | 2.060E-00 | 7.227E-01 | 3.004E-04 | 6.482E-03 | 1.636E-01 | 3.511E-01 |
| 40 | hsa-miR-576-5p | 1.189E+01 | 1.000E-00 | 1.189E+01 | 2.476E-00 | 2.938E-04 | 6.482E-03 | 4.733E-04 | 1.446E-02 |
| 41 | hsa-miR-636 | 1.733E+02 | 1.131E+02 | 1.533E-00 | 4.270E-01 | 3.286E-04 | 6.501E-03 | 1.369E-01 | 3.150E-01 |

FIG 7 (continued)

| | | | | | | | | | |
|---|---|---|---|---|---|---|---|---|---|
| 42 | hsa-miR-1237 | 1.164E+02 | 6.762E+01 | 1.721E-00 | 5.428E-01 | 3.242E-04 | 6.501E-03 | 4.741E-02 | 1.635E-01 |
| 43 | hsa-miR-15a | 3.143E+03 | 5.379E+03 | 5.844E-01 | -5.372E-01 | 3.390E-04 | 6.501E-03 | 7.419E-04 | 1.829E-02 |
| 44 | hsa-miR-15b | 1.198E+04 | 1.763E+04 | 6.792E-01 | -3.868E-01 | 3.314E-04 | 6.501E-03 | 2.475E-03 | 3.288E-02 |
| 45 | hsa-miR-720 | 5.784E+03 | 2.998E+03 | 1.929E-00 | 6.571E-01 | 3.386E-04 | 6.501E-03 | 2.346E-03 | 3.265E-02 |
| 46 | hsa-miR-409-3p | 4.765E+01 | 1.000E-00 | 4.765E+01 | 3.864E-00 | 3.578E-04 | 6.713E-03 | 6.098E-03 | 5.316E-02 |
| 47 | hsa-miR-659 | 1.096E+02 | 6.629E+01 | 1.654E-00 | 5.030E-01 | 4.080E-04 | 7.335E-03 | 6.850E-02 | 2.089E-01 |
| 48 | hsa-miR-664 | 4.128E+02 | 1.385E+02 | 2.980E-00 | 1.092E-00 | 4.015E-04 | 7.335E-03 | 1.906E-03 | 2.954E-02 |
| 49 | hsa-miR-21* | 7.883E+01 | 1.288E+02 | 6.120E-01 | -4.911E-01 | 4.238E-04 | 7.465E-03 | 4.756E-03 | 4.652E-02 |
| 50 | hsa-miR-199a-5p | 5.730E+02 | 2.056E+02 | 2.786E-00 | 1.025E-00 | 4.413E-04 | 7.617E-03 | 3.155E-04 | 1.184E-02 |
| 51 | hsa-miR-518f* | 8.323E+01 | 1.684E+02 | 4.943E-01 | -7.046E-01 | 4.590E-04 | 7.617E-03 | 9.386E-04 | 2.132E-02 |
| 52 | hsa-miR-146b-3p | 3.417E+01 | 8.415E+01 | 4.061E-01 | -9.012E-01 | 4.549E-04 | 7.617E-03 | 1.731E-03 | 2.929E-02 |
| 53 | hsa-miR-23b* | 1.880E+01 | 1.000E-00 | 1.880E+01 | 2.934E-00 | 4.857E-04 | 7.835E-03 | 5.565E-05 | 4.002E-03 |
| 54 | hsa-miR-331-3p | 1.620E+03 | 7.902E+02 | 2.050E-00 | 7.176E-01 | 4.949E-04 | 7.835E-03 | 1.408E-03 | 2.683E-02 |
| 55 | hsa-miR-708* | 4.430E+01 | 8.373E+01 | 5.291E-01 | -6.366E-01 | 4.993E-04 | 7.835E-03 | 2.039E-03 | 2.956E-02 |
| 56 | hsa-miR-329 | 8.301E+01 | 4.534E+01 | 1.831E-00 | 6.047E-01 | 5.354E-04 | 7.994E-03 | 9.177E-02 | 2.545E-01 |
| 57 | hsa-miR-564 | 1.260E+02 | 2.008E+02 | 6.274E-01 | -4.661E-01 | 5.373E-04 | 7.994E-03 | 8.707E-03 | 6.315E-02 |
| 58 | hsa-miR-744* | 4.643E+01 | 9.746E-00 | 4.764E-00 | 1.561E-00 | 5.252E-04 | 7.994E-03 | 2.681E-05 | 2.888E-03 |
| 59 | hsa-miR-1282 | 1.000E-00 | 1.000E-00 | 1.000E-00 | 0.000E+01 | 5.647E-04 | 8.260E-03 | 3.985E-03 | 4.585E-02 |
| 60 | hsa-miR-454* | 1.323E+01 | 1.000E-00 | 1.323E+01 | 2.583E-00 | 5.978E-04 | 8.599E-03 | 4.811E-03 | 4.652E-02 |
| 61 | hsa-miR-302d* | 6.675E+01 | 3.029E+01 | 2.203E-00 | 7.900E-01 | 6.107E-04 | 8.640E-03 | 1.544E-01 | 3.402E-01 |
| 62 | hsa-miR-197 | 8.391E+02 | 4.526E+02 | 1.854E-00 | 6.173E-01 | 7.366E-04 | 1.025E-02 | 1.284E-03 | 2.577E-02 |
| 63 | hsa-miR-1538 | 6.564E+01 | 9.539E+01 | 6.881E-01 | -3.739E-01 | 8.092E-04 | 1.091E-02 | 6.257E-03 | 5.400E-02 |

FIG 7 (continued)

| | | | | | | | | | |
|---|---|---|---|---|---|---|---|---|---|
| 64 | hsa-miR-877 | 1.021E+02 | 4.737E+01 | 2.155E-00 | 7.679E-01 | 8.063E-04 | 1.091E-02 | 2.921E-03 | 3.707E-02 |
| 65 | hsa-miR-652 | 1.462E+03 | 1.127E+03 | 1.296E-00 | 2.597E-01 | 8.520E-04 | 1.131E-02 | 1.258E-02 | 7.754E-02 |
| 66 | hsa-miR-573 | 4.304E+01 | 7.302E+01 | 5.894E-01 | -5.286E-01 | 9.046E-04 | 1.148E-02 | 4.328E-03 | 4.608E-02 |
| 67 | hsa-miR-18b* | 5.817E+01 | 9.249E+01 | 6.289E-01 | -4.637E-01 | 9.037E-04 | 1.148E-02 | 9.006E-03 | 6.363E-02 |
| 68 | hsa-miR-494 | 7.704E+01 | 3.701E+01 | 2.082E-00 | 7.332E-01 | 9.012E-04 | 1.148E-02 | 2.940E-02 | 1.233E-01 |
| 69 | hsa-miR-220b | 2.544E+01 | 6.233E+01 | 4.082E-01 | -8.959E-01 | 9.936E-04 | 1.225E-02 | 1.430E-03 | 2.683E-02 |
| 70 | hsa-miR-1274a | 2.748E+02 | 1.066E+02 | 2.579E-00 | 9.473E-01 | 9.930E-04 | 1.225E-02 | 3.494E-02 | 1.371E-01 |

FIG 8

| No. | miRNA | median g1 | median g2 | qmedian | Logq median | ttest_rawp | ttest_adjp | Limma_ rawp | Limma_ adjp |
|---|---|---|---|---|---|---|---|---|---|
| 1 | hsa-miR-328 | 1.804E+02 | 2.530E+01 | 7.128E-00 | 1.964E-00 | 1.202E-12 | 1.037E-09 | 2.677E-09 | 2.566E-07 |
| 2 | hsa-miR-500 | 4.595E+02 | 1.141E+02 | 4.026E-00 | 1.393E-00 | 4.802E-12 | 1.382E-09 | 2.103E-09 | 2.269E-07 |
| 3 | hsa-miR-424* | 2.078E+02 | 9.232E+01 | 2.250E-00 | 8.111E-01 | 3.656E-12 | 1.382E-09 | 2.895E-10 | 4.997E-08 |
| 4 | hsa-miR-1281 | 1.876E+02 | 1.756E+01 | 1.068E+01 | 2.369E-00 | 5.858E-11 | 1.011E-08 | 6.398E-11 | 2.761E-08 |
| 5 | hsa-miR-186 | 2.094E+02 | 4.168E+01 | 5.024E-00 | 1.614E-00 | 4.876E-11 | 1.011E-08 | 3.656E-09 | 2.868E-07 |
| 6 | hsa-miR-1224-3p | 1.952E+02 | 5.332E+01 | 3.661E-00 | 1.298E-00 | 9.155E-11 | 1.317E-08 | 9.177E-10 | 1.320E-07 |
| 7 | hsa-miR-1248 | 5.728E+01 | 1.000E-00 | 5.728E+01 | 4.048E-00 | 1.359E-10 | 1.676E-08 | 3.592E-11 | 2.761E-08 |
| 8 | hsa-miR-483-3p | 8.635E+01 | 1.000E-00 | 8.635E+01 | 4.458E-00 | 4.171E-10 | 4.475E-08 | 1.345E-10 | 3.870E-08 |
| 9 | hsa-miR-1295 | 5.507E+01 | 1.493E+02 | 3.687E-01 | -9.977E-01 | 4.667E-10 | 4.475E-08 | 4.123E-04 | 2.427E-03 |
| 10 | hsa-miR-130a* | 1.064E+02 | 3.526E+01 | 3.016E-00 | 1.104E-00 | 1.944E-09 | 1.620E-07 | 9.344E-07 | 1.875E-05 |
| 11 | hsa-miR-409-3p | 1.189E+02 | 1.000E-00 | 1.189E+02 | 4.779E-00 | 2.201E-09 | 1.620E-07 | 8.651E-08 | 3.246E-06 |
| 12 | hsa-miR-664 | 5.176E+02 | 1.385E+02 | 3.736E-00 | 1.318E-00 | 2.252E-09 | 1.620E-07 | 1.325E-07 | 4.500E-06 |
| 13 | hsa-miR-146a | 3.160E+02 | 1.218E+02 | 2.595E-00 | 9.535E-01 | 2.483E-09 | 1.648E-07 | 2.629E-10 | 4.997E-08 |
| 14 | hsa-miR-155 | 1.695E+02 | 4.958E+01 | 3.418E-00 | 1.229E-00 | 5.959E-09 | 3.673E-07 | 1.899E-03 | 7.880E-03 |
| 15 | hsa-miR-1249 | 1.502E+02 | 4.048E+01 | 3.710E-00 | 1.311E-00 | 6.399E-09 | 3.681E-07 | 4.414E-07 | 1.120E-05 |
| 16 | hsa-miR-629* | 1.604E+02 | 8.596E+01 | 1.865E-00 | 6.235E-01 | 7.716E-09 | 4.162E-07 | 3.272E-06 | 4.706E-05 |
| 17 | hsa-miR-148a* | 5.845E+01 | 4.674E-00 | 1.251E+01 | 2.526E-00 | 1.326E-08 | 6.581E-07 | 8.909E-07 | 1.836E-05 |
| 18 | hsa-miR-193a-5p | 1.378E+02 | 5.868E+01 | 2.348E-00 | 8.535E-01 | 1.373E-08 | 6.581E-07 | 2.541E-06 | 4.081E-05 |
| 19 | hsa-miR-1226 | 1.025E+02 | 3.581E+01 | 2.862E-00 | 1.052E-00 | 4.538E-08 | 2.061E-06 | 1.038E-05 | 1.208E-04 |

FIG 8 (continued)

| | | | | | | | | | |
|---|---|---|---|---|---|---|---|---|---|
| 20 | hsa-miR-29c* | 6.063E+01 | 1.000E-00 | 6.063E+01 | 4.105E-00 | 5.141E-08 | 2.218E-06 | 4.196E-06 | 5.658E-05 |
| 21 | hsa-let-7d* | 1.834E+02 | 6.719E+01 | 2.729E-00 | 1.004E-00 | 6.194E-08 | 2.545E-06 | 1.088E-06 | 2.069E-05 |
| 22 | hsa-miR-99a | 2.194E+02 | 9.862E+01 | 2.225E-00 | 7.998E-01 | 6.556E-08 | 2.572E-06 | 8.175E-06 | 1.008E-04 |
| 23 | hsa-miR-1237 | 1.306E+02 | 6.762E+01 | 1.931E-00 | 6.580E-01 | 8.388E-08 | 3.147E-06 | 7.175E-08 | 2.949E-06 |
| 24 | hsa-miR-361-5p | 7.558E+02 | 3.138E+02 | 2.409E-00 | 8.791E-01 | 8.936E-08 | 3.152E-06 | 1.117E-08 | 7.415E-07 |
| 25 | hsa-miR-30a | 6.353E+02 | 2.185E+02 | 2.908E-00 | 1.068E-00 | 9.130E-08 | 3.152E-06 | 1.223E-09 | 1.507E-07 |
| 26 | hsa-miR-634 | 1.393E+02 | 7.302E+01 | 1.907E-00 | 6.458E-01 | 1.389E-07 | 4.610E-06 | 9.823E-04 | 4.840E-03 |
| 27 | hsa-miR-877* | 1.212E+02 | 1.734E+01 | 6.987E-00 | 1.944E-00 | 1.663E-07 | 5.316E-06 | 1.050E-05 | 1.208E-04 |
| 28 | hsa-miR-133a | 9.452E+01 | 2.704E+01 | 3.496E-00 | 1.252E-00 | 1.784E-07 | 5.498E-06 | 3.875E-07 | 1.079E-05 |
| 29 | hsa-miR-454* | 4.367E+01 | 1.000E-00 | 4.367E+01 | 3.777E-00 | 1.851E-07 | 5.508E-06 | 1.114E-05 | 1.265E-04 |
| 30 | hsa-miR-133b | 5.200E+01 | 1.000E-00 | 5.200E+01 | 3.951E-00 | 2.253E-07 | 6.482E-06 | 2.915E-06 | 4.414E-05 |
| 31 | hsa-miR-30e* | 1.053E+02 | 3.499E+01 | 3.009E-00 | 1.102E-00 | 3.038E-07 | 7.945E-06 | 1.748E-06 | 3.079E-05 |
| 32 | hsa-miR-501-5p | 1.107E+02 | 1.555E+01 | 7.118E-00 | 1.963E-00 | 3.034E-07 | 7.945E-06 | 4.363E-07 | 1.120E-05 |
| 33 | hsa-miR-150 | 2.303E+03 | 6.288E+02 | 3.663E-00 | 1.298E-00 | 3.015E-07 | 7.945E-06 | 6.094E-06 | 7.968E-05 |
| 34 | hsa-miR-181a-2* | 1.604E+02 | 7.727E+01 | 2.075E-00 | 7.301E-01 | 3.156E-07 | 8.010E-06 | 1.248E-04 | 9.532E-04 |
| 35 | hsa-miR-1825 | 1.020E+02 | 3.136E+01 | 3.252E-00 | 1.179E-00 | 3.371E-07 | 8.312E-06 | 3.225E-04 | 2.031E-03 |
| 36 | hsa-miR-135b | 3.547E+01 | 1.000E-00 | 3.547E+01 | 3.569E-00 | 3.574E-07 | 8.567E-06 | 6.831E-07 | 1.512E-05 |
| 37 | hsa-miR-337-3p | 3.427E+01 | 1.000E-00 | 3.427E+01 | 3.534E-00 | 3.738E-07 | 8.719E-06 | 1.304E-06 | 2.344E-05 |
| 38 | hsa-miR-383 | 3.200E+01 | 9.810E+01 | 3.262E-01 | -1.120E-00 | 3.960E-07 | 8.763E-06 | 4.802E-05 | 4.456E-04 |
| 39 | hsa-miR-26b* | 4.546E+01 | 1.000E-00 | 4.546E+01 | 3.817E-00 | 3.928E-07 | 8.763E-06 | 1.338E-07 | 4.500E-06 |
| 40 | hsa-miR-365 | 1.657E+02 | 3.753E+01 | 4.416E-00 | 1.485E-00 | 4.478E-07 | 9.425E-06 | 5.193E-08 | 2.359E-06 |
| 41 | hsa-miR-942 | 5.025E+01 | 1.000E-00 | 5.025E+01 | 3.917E-00 | 4.409E-07 | 9.425E-06 | 7.553E-07 | 1.630E-05 |

FIG 8 (continued)

| | | | | | | | | | |
|---|---|---|---|---|---|---|---|---|---|
| 42 | hsa-miR-342-5p | 2.001E+02 | 7.844E+01 | 2.551E-00 | 9.366E-01 | 4.684E-07 | 9.624E-06 | 3.101E-06 | 4.536E-05 |
| 43 | hsa-miR-146b-3p | 1.457E+01 | 8.415E+01 | 1.732E-01 | -1.753E-00 | 5.651E-07 | 1.134E-05 | 3.939E-06 | 5.422E-05 |
| 44 | hsa-miR-363* | 4.664E+01 | 9.794E+01 | 4.762E-01 | -7.420E-01 | 8.580E-07 | 1.683E-05 | 2.332E-03 | 9.317E-03 |
| 45 | hsa-miR-636 | 1.979E+02 | 1.131E+02 | 1.750E-00 | 5.594E-01 | 1.083E-06 | 2.077E-05 | 1.012E-05 | 1.208E-04 |
| 46 | hsa-miR-605 | 3.000E+01 | 1.000E-00 | 3.000E+01 | 3.401E-00 | 1.127E-06 | 2.115E-05 | 2.554E-06 | 4.081E-05 |
| 47 | hsa-miR-610 | 4.299E+01 | 1.137E+02 | 3.781E-01 | -9.726E-01 | 1.250E-06 | 2.286E-05 | 2.045E-04 | 1.368E-03 |
| 48 | hsa-miR-1289 | 7.358E+01 | 1.244E+02 | 5.915E-01 | -5.251E-01 | 1.271E-06 | 2.286E-05 | 4.636E-05 | 4.349E-04 |
| 49 | hsa-miR-519c-5p | 6.884E+01 | 2.042E+02 | 3.371E-01 | -1.087E-00 | 1.831E-06 | 3.226E-05 | 2.490E-04 | 1.616E-03 |
| 50 | hsa-miR-220a | 1.512E+01 | 6.719E+01 | 2.250E-01 | -1.492E-00 | 2.007E-06 | 3.465E-05 | 1.854E-04 | 1.270E-03 |
| 51 | hsa-miR-1324 | 8.102E+01 | 1.498E+02 | 5.410E-01 | -6.144E-01 | 2.272E-06 | 3.844E-05 | 1.883E-03 | 7.848E-03 |
| 52 | hsa-miR-125a-5p | 3.543E+02 | 1.122E+02 | 3.157E-00 | 1.150E-00 | 2.657E-06 | 4.409E-05 | 1.338E-08 | 8.247E-07 |
| 53 | hsa-miR-1274a | 2.581E+02 | 1.066E+02 | 2.422E-00 | 8.846E-01 | 3.274E-06 | 5.332E-05 | 1.356E-07 | 4.500E-06 |
| 54 | hsa-miR-1259 | 3.081E+01 | 1.000E-00 | 3.081E+01 | 3.428E-00 | 3.780E-06 | 6.042E-05 | 5.059E-05 | 4.636E-04 |
| 55 | hsa-miR-378 | 3.607E+02 | 1.645E+02 | 2.193E-00 | 7.852E-01 | 4.394E-06 | 6.894E-05 | 2.439E-07 | 7.259E-06 |
| 56 | hsa-let-7d | 2.998E+03 | 1.687E+03 | 1.778E-00 | 5.753E-01 | 4.590E-06 | 7.074E-05 | 6.175E-05 | 5.225E-04 |
| 57 | hsa-miR-421 | 1.931E+02 | 8.307E+01 | 2.324E-00 | 8.433E-01 | 5.253E-06 | 7.953E-05 | 6.400E-06 | 8.123E-05 |
| 58 | hsa-miR-148a | 5.224E+02 | 1.431E+03 | 3.649E-01 | -1.008E-00 | 5.532E-06 | 8.232E-05 | 5.213E-09 | 3.749E-07 |
| 59 | hsa-miR-224 | 2.335E-00 | 5.917E+01 | 3.946E-02 | -3.232E-00 | 5.977E-06 | 8.742E-05 | 1.478E-05 | 1.615E-04 |
| 60 | hsa-miR-541 | 5.116E+01 | 1.030E+02 | 4.966E-01 | -7.000E-01 | 6.169E-06 | 8.873E-05 | 8.338E-04 | 4.258E-03 |
| 61 | hsa-miR-15b | 1.198E+04 | 1.763E+04 | 6.792E-01 | -3.868E-01 | 6.784E-06 | 9.598E-05 | 1.810E-06 | 3.124E-05 |
| 62 | hsa-miR-490-3p | 5.820E+01 | 1.283E+02 | 4.537E-01 | -7.904E-01 | 7.629E-06 | 1.045E-04 | 1.080E-03 | 5.178E-03 |
| 63 | hsa-miR-485-3p | 8.606E+01 | 3.733E+01 | 2.305E-00 | 8.351E-01 | 7.546E-06 | 1.045E-04 | 2.944E-03 | 1.115E-02 |

FIG 8 (continued)

| | | | | | | | | |
|---|---|---|---|---|---|---|---|---|
| 64 | hsa-miR-299-5p | 4.708E+01 | 1.000E-00 | 4.708E+01 | 3.852E-00 | 1.012E-05 | 1.365E-04 | 1.696E-03 | 7.284E-03 |
| 65 | hsa-miR-1288 | 8.704E+01 | 3.753E+01 | 2.319E-00 | 8.413E-01 | 1.398E-05 | 1.857E-04 | 1.544E-04 | 1.110E-03 |
| 66 | hsa-miR-494 | 9.088E+01 | 3.701E+01 | 2.456E-00 | 8.984E-01 | 1.427E-05 | 1.866E-04 | 1.364E-02 | 3.656E-02 |
| 67 | hsa-miR-1228 | 2.986E+02 | 1.820E+02 | 1.640E-00 | 4.948E-01 | 1.507E-05 | 1.941E-04 | 1.279E-05 | 1.415E-04 |
| 68 | hsa-miR-744* | 7.037E+01 | 9.746E-00 | 7.221E-00 | 1.977E-00 | 1.605E-05 | 2.036E-04 | 5.799E-05 | 5.005E-04 |
| 69 | hsa-miR-668 | 5.495E+01 | 1.125E+01 | 4.885E-00 | 1.586E-00 | 1.740E-05 | 2.145E-04 | 2.354E-04 | 1.539E-03 |
| 70 | hsa-miR-92a | 1.574E+04 | 1.198E+04 | 1.314E-00 | 2.733E-01 | 1.728E-05 | 2.145E-04 | 1.364E-03 | 6.326E-03 |

FIG 9

| No. | miRNA | median g1 | median g2 | qmedian | Logq median | ttest_rawp | ttest_adjp | Limma_ rawp | Limma_ adjp |
|---|---|---|---|---|---|---|---|---|---|
| 1 | hsa-let-7d | 1.687E+03 | 3.220E+03 | 5.237E-01 | -6.468E-01 | 3.535E-06 | 1.758E-03 | 1.467E-04 | 8.443E-03 |
| 2 | hsa-miR-146b-3p | 8.415E+01 | 1.868E+01 | 4.504E-00 | 1.505E-00 | 4.074E-06 | 1.758E-03 | 4.169E-05 | 3.998E-03 |
| 3 | hsa-miR-150 | 6.288E+02 | 2.206E+03 | 2.851E-01 | -1.255E-00 | 6.918E-06 | 1.990E-03 | 1.820E-04 | 9.027E-03 |
| 4 | hsa-miR-454* | 1.000E-00 | 4.217E+01 | 2.371E-02 | -3.742E-00 | 2.952E-05 | 6.370E-03 | 3.718E-06 | 5.348E-04 |
| 5 | hsa-miR-1248 | 1.000E-00 | 2.888E+01 | 3.463E-02 | -3.363E-00 | 6.025E-05 | 6.500E-03 | 9.000E-07 | 2.589E-04 |
| 6 | hsa-miR-133b | 1.000E-00 | 2.821E+01 | 3.545E-02 | -3.340E-00 | 4.399E-05 | 6.500E-03 | 1.052E-04 | 6.982E-03 |
| 7 | hsa-miR-610 | 1.137E+02 | 4.843E+01 | 2.348E-00 | 8.534E-01 | 4.578E-05 | 6.500E-03 | 1.607E-03 | 2.877E-02 |
| 8 | hsa-miR-148a | 1.431E+03 | 6.967E+02 | 2.054E-00 | 7.200E-01 | 5.770E-05 | 6.500E-03 | 4.069E-04 | 1.350E-02 |
| 9 | hsa-miR-888 | 1.060E+01 | 6.012E+01 | 1.764E-01 | -1.735E-00 | 7.858E-05 | 6.781E-03 | 1.566E-04 | 8.445E-03 |
| 10 | hsa-miR-519e* | 8.761E+01 | 1.354E+01 | 6.472E-00 | 1.868E-00 | 7.826E-05 | 6.781E-03 | 7.104E-05 | 5.109E-03 |
| 11 | hsa-miR-1288 | 3.753E+01 | 9.917E+01 | 3.784E-01 | -9.718E-01 | 8.788E-05 | 6.895E-03 | 2.053E-04 | 9.027E-03 |
| 12 | hsa-miR-655 | 1.000E-00 | 4.493E+01 | 2.226E-02 | -3.805E-00 | 1.338E-04 | 8.566E-03 | 1.086E-03 | 2.351E-02 |
| 13 | hsa-miR-302d* | 3.029E+01 | 8.086E+01 | 3.746E-01 | -9.818E-01 | 1.221E-04 | 8.566E-03 | 3.965E-03 | 4.819E-02 |
| 14 | hsa-miR-942 | 1.000E-00 | 4.447E+01 | 2.249E-02 | -3.795E-00 | 1.390E-04 | 8.566E-03 | 8.544E-06 | 1.053E-03 |
| 15 | hsa-miR-374b* | 1.596E+01 | 5.005E+01 | 3.189E-01 | -1.143E-00 | 1.612E-04 | 9.273E-03 | 4.713E-04 | 1.453E-02 |
| 16 | hsa-miR-605 | 1.000E-00 | 3.692E+01 | 2.709E-02 | -3.609E-00 | 1.743E-04 | 9.401E-03 | 2.501E-06 | 4.319E-04 |
| 17 | hsa-miR-10a* | 1.502E+01 | 5.222E+01 | 2.877E-01 | -1.246E-00 | 2.020E-04 | 1.026E-02 | 1.438E-02 | 9.399E-02 |
| 18 | hsa-miR-182 | 7.310E+03 | 3.790E+03 | 1.929E-00 | 6.570E-01 | 2.268E-04 | 1.088E-02 | 2.197E-04 | 9.027E-03 |
| 19 | hsa-miR-148a* | 4.674E-00 | 3.499E+01 | 1.336E-01 | -2.013E-00 | 2.836E-04 | 1.224E-02 | 9.424E-04 | 2.140E-02 |

FIG 9 (continued)

| | | | | | | | | | |
|---|---|---|---|---|---|---|---|---|---|
| 20 | hsa-miR-656 | 1.964E+01 | 6.702E+01 | 2.930E-01 | -1.228E-00 | 2.791E-04 | 1.224E-02 | 2.632E-03 | 3.850E-02 |
| 21 | hsa-miR-374a | 2.119E+02 | 6.288E+02 | 3.370E-01 | -1.088E-00 | 3.358E-04 | 1.380E-02 | 8.373E-02 | 2.503E-01 |
| 22 | hsa-miR-744* | 9.746E-00 | 6.719E+01 | 1.451E-01 | -1.931E-00 | 3.538E-04 | 1.388E-02 | 1.908E-03 | 3.107E-02 |
| 23 | hsa-miR-429 | 1.071E+01 | 5.350E+01 | 2.003E-01 | -1.608E-00 | 4.250E-04 | 1.431E-02 | 2.494E-04 | 9.785E-03 |
| 24 | hsa-miR-144* | 3.352E+02 | 9.970E+02 | 3.362E-01 | -1.090E-00 | 4.479E-04 | 1.431E-02 | 1.297E-02 | 9.330E-02 |
| 25 | hsa-miR-144 | 2.008E+03 | 3.623E+03 | 5.541E-01 | -5.904E-01 | 3.828E-04 | 1.431E-02 | 7.290E-03 | 6.707E-02 |
| 26 | hsa-miR-668 | 1.125E+01 | 6.074E+01 | 1.852E-01 | -1.686E-00 | 4.046E-04 | 1.431E-02 | 8.764E-03 | 7.504E-02 |
| 27 | hsa-miR-888* | 5.116E+01 | 1.336E+01 | 3.829E-00 | 1.343E-00 | 4.424E-04 | 1.431E-02 | 4.315E-04 | 1.379E-02 |
| 28 | hsa-miR-1259 | 1.000E-00 | 3.927E+01 | 2.547E-02 | -3.670E-00 | 5.824E-04 | 1.620E-02 | 1.276E-03 | 2.623E-02 |
| 29 | hsa-miR-29a | 9.970E+02 | 6.222E+02 | 1.602E-00 | 4.715E-01 | 6.005E-04 | 1.620E-02 | 5.468E-03 | 5.826E-02 |
| 30 | hsa-miR-194 | 6.927E+03 | 4.640E+03 | 1.493E-00 | 4.007E-01 | 5.684E-04 | 1.620E-02 | 6.637E-04 | 1.831E-02 |
| 31 | hsa-miR-1205 | 1.309E+02 | 6.629E+01 | 1.974E-00 | 6.802E-01 | 5.376E-04 | 1.620E-02 | 3.218E-03 | 4.230E-02 |
| 32 | hsa-miR-149* | 1.127E+03 | 3.543E+02 | 3.182E-00 | 1.157E-00 | 5.663E-04 | 1.620E-02 | 1.436E-03 | 2.754E-02 |
| 33 | hsa-miR-221* | 1.268E+02 | 7.329E+01 | 1.730E-00 | 5.484E-01 | 6.609E-04 | 1.728E-02 | 1.004E-02 | 8.098E-02 |
| 34 | hsa-miR-302d | 1.000E-00 | 1.429E+01 | 6.996E-02 | -2.660E-00 | 7.042E-04 | 1.787E-02 | 7.906E-04 | 1.949E-02 |
| 35 | hsa-miR-299-5p | 1.000E-00 | 3.208E+01 | 3.117E-02 | -3.468E-00 | 8.960E-04 | 1.837E-02 | 7.468E-04 | 1.895E-02 |
| 36 | hsa-miR-1908 | 1.326E+03 | 6.745E+02 | 1.966E-00 | 6.761E-01 | 9.343E-04 | 1.837E-02 | 8.863E-04 | 2.067E-02 |
| 37 | hsa-miR-573 | 7.302E+01 | 4.555E+01 | 1.603E-00 | 4.718E-01 | 7.994E-04 | 1.837E-02 | 1.199E-02 | 8.997E-02 |
| 38 | hsa-miR-877 | 4.737E+01 | 1.100E+02 | 4.305E-01 | -8.428E-01 | 9.158E-04 | 1.837E-02 | 4.395E-03 | 5.266E-02 |
| 39 | hsa-miR-212 | 5.577E+01 | 1.680E+01 | 3.320E-00 | 1.200E-00 | 9.364E-04 | 1.837E-02 | 6.341E-04 | 1.824E-02 |
| 40 | hsa-miR-130a* | 3.526E+01 | 1.074E+02 | 3.282E-01 | -1.114E-00 | 9.059E-04 | 1.837E-02 | 2.108E-04 | 9.027E-03 |
| 41 | hsa-miR-551a | 6.084E+01 | 3.215E-00 | 1.892E+01 | 2.940E-00 | 8.983E-04 | 1.837E-02 | 3.529E-04 | 1.218E-02 |

FIG 9 (continued)

| | | | | | | | | | |
|---|---|---|---|---|---|---|---|---|---|
| 42 | hsa-miR-936 | 8.307E+01 | 4.199E+01 | 1.978E-00 | 6.822E-01 | 7.493E-04 | 1.837E-02 | 3.025E-03 | 4.158E-02 |
| 43 | hsa-miR-1226 | 3.581E+01 | 9.452E+01 | 3.788E-01 | -9.707E-01 | 8.793E-04 | 1.837E-02 | 1.426E-01 | 3.487E-01 |
| 44 | hsa-miR-892b | 1.252E+01 | 4.199E+01 | 2.980E-01 | -1.211E-00 | 9.209E-04 | 1.837E-02 | 3.050E-04 | 1.144E-02 |
| 45 | hsa-miR-200a* | 4.471E+01 | 8.257E+01 | 5.415E-01 | -6.135E-01 | 9.955E-04 | 1.868E-02 | 3.240E-03 | 4.230E-02 |
| 46 | hsa-miR-519a* | 1.852E+02 | 1.032E+02 | 1.795E-00 | 5.849E-01 | 9.766E-04 | 1.868E-02 | 6.402E-03 | 6.424E-02 |
| 47 | hsa-miR-891a | 1.857E+02 | 6.864E+01 | 2.705E-00 | 9.953E-01 | 1.024E-03 | 1.880E-02 | 1.361E-03 | 2.670E-02 |
| 48 | hsa-miR-1287 | 5.860E+01 | 8.268E+01 | 7.087E-01 | -3.443E-01 | 1.250E-03 | 2.074E-02 | 9.029E-03 | 7.565E-02 |
| 49 | hsa-miR-770-5p | 9.611E+01 | 4.032E+01 | 2.384E-00 | 8.687E-01 | 1.249E-03 | 2.074E-02 | 3.333E-03 | 4.230E-02 |
| 50 | hsa-miR-363* | 9.794E+01 | 5.887E+01 | 1.664E-00 | 5.090E-01 | 1.230E-03 | 2.074E-02 | 1.923E-02 | 1.129E-01 |
| 51 | hsa-miR-302c | 1.000E-00 | 1.125E+01 | 8.889E-02 | -2.420E-00 | 1.208E-03 | 2.074E-02 | 2.196E-05 | 2.369E-03 |
| 52 | hsa-miR-218-1* | 4.995E+01 | 8.937E+01 | 5.589E-01 | -5.817E-01 | 1.196E-03 | 2.074E-02 | 2.017E-01 | 4.278E-01 |
| 53 | hsa-miR-541 | 1.030E+02 | 6.340E+01 | 1.625E-00 | 4.855E-01 | 1.357E-03 | 2.209E-02 | 1.482E-02 | 9.471E-02 |
| 54 | hsa-miR-500* | 3.254E+02 | 2.014E+02 | 1.616E-00 | 4.801E-01 | 1.497E-03 | 2.343E-02 | 2.648E-02 | 1.302E-01 |
| 55 | hsa-miR-485-3p | 3.733E+01 | 7.409E+01 | 5.039E-01 | -6.854E-01 | 1.521E-03 | 2.343E-02 | 8.068E-03 | 7.105E-02 |
| 56 | hsa-miR-21* | 1.288E+02 | 7.727E+01 | 1.667E-00 | 5.111E-01 | 1.520E-03 | 2.343E-02 | 1.064E-02 | 8.422E-02 |
| 57 | hsa-miR-662 | 4.639E+01 | 7.469E+01 | 6.210E-01 | -4.764E-01 | 1.582E-03 | 2.395E-02 | 3.655E-02 | 1.550E-01 |
| 58 | hsa-miR-506 | 1.479E+01 | 5.162E+01 | 2.865E-01 | -1.250E-00 | 1.663E-03 | 2.444E-02 | 5.210E-03 | 5.620E-02 |
| 59 | hsa-miR-1200 | 9.487E+01 | 5.350E+01 | 1.773E-00 | 5.729E-01 | 1.671E-03 | 2.444E-02 | 1.449E-02 | 9.399E-02 |
| 60 | hsa-miR-22 | 9.808E+03 | 6.927E+03 | 1.416E-00 | 3.477E-01 | 1.735E-03 | 2.496E-02 | 1.589E-02 | 9.857E-02 |
| 61 | hsa-miR-101 | 4.561E+02 | 8.001E+02 | 5.700E-01 | -5.621E-01 | 1.774E-03 | 2.510E-02 | 3.233E-03 | 4.230E-02 |
| 62 | hsa-miR-129* | 3.081E+01 | 5.162E+01 | 5.969E-01 | -5.160E-01 | 1.855E-03 | 2.550E-02 | 1.175E-02 | 8.892E-02 |
| 63 | hsa-miR-224 | 5.917E+01 | 6.685E-00 | 8.852E-00 | 2.181E-00 | 1.862E-03 | 2.550E-02 | 6.293E-05 | 4.937E-03 |

FIG 9 (continued)

| | | | | | | | | | |
|---|---|---|---|---|---|---|---|---|---|
| 64 | hsa-miR-371-5p | 5.518E+01 | 2.251E+01 | 2.452E-00 | 8.968E-01 | 2.064E-03 | 2.783E-02 | 1.377E-02 | 9.342E-02 |
| 65 | hsa-miR-106a | 6.228E+03 | 9.808E+03 | 6.350E-01 | -4.542E-01 | 2.203E-03 | 2.908E-02 | 7.360E-03 | 6.707E-02 |
| 66 | hsa-miR-647 | 8.586E+01 | 2.162E+01 | 3.972E-00 | 1.379E-00 | 2.224E-03 | 2.908E-02 | 1.647E-03 | 2.877E-02 |
| 67 | hsa-miR-219-1-3p | 1.000E-00 | 2.329E+01 | 4.293E-02 | -3.148E-00 | 2.279E-03 | 2.935E-02 | 6.971E-04 | 1.831E-02 |
| 68 | hsa-miR-519c-5p | 2.042E+02 | 9.468E+01 | 2.157E-00 | 7.686E-01 | 2.449E-03 | 2.935E-02 | 1.355E-02 | 9.342E-02 |
| 69 | hsa-miR-330-5p | 9.198E-00 | 2.868E+01 | 3.207E-01 | -1.137E-00 | 2.389E-03 | 2.935E-02 | 1.640E-02 | 9.909E-02 |
| 70 | hsa-miR-450a | 6.601E-00 | 3.339E+01 | 1.977E-01 | -1.621E-00 | 2.437E-03 | 2.935E-02 | 1.703E-03 | 2.881E-02 |

FIG 10

| No. | miRNA | median g1 | median g2 | qmedian | Logq median | Ttest_ rawp | ttest_adjp | Limma_ rawp | Limma_ adjp |
|---|---|---|---|---|---|---|---|---|---|
| 1 | hsa-miR-500 | 1.14E+02 | 4.99E+02 | 2.29E-01 | -1.48E-00 | 2.72E-08 | 9.08E-06 | 3.30E-06 | 2.38E-04 |
| 2 | hsa-miR-342-3p | 2.36E+03 | 5.13E+03 | 4.60E-01 | -7.77E-01 | 3.16E-08 | 9.08E-06 | 9.21E-07 | 1.06E-04 |
| 3 | hsa-miR-744* | 9.75E-00 | 1.12E+02 | 8.70E-02 | -2.44E-00 | 1.72E-08 | 9.08E-06 | 1.47E-07 | 3.17E-05 |
| 4 | hsa-miR-363* | 9.79E+01 | 3.69E+01 | 2.65E-00 | 9.76E-01 | 9.97E-08 | 2.15E-05 | 1.23E-04 | 2.58E-03 |
| 5 | hsa-miR-1295 | 1.49E+02 | 6.85E+01 | 2.18E-00 | 7.79E-01 | 2.26E-07 | 3.90E-05 | 7.64E-04 | 7.09E-03 |
| 6 | hsa-miR-361-5p | 3.14E+02 | 7.31E+02 | 4.30E-01 | -8.45E-01 | 3.15E-07 | 4.53E-05 | 9.86E-07 | 1.06E-04 |
| 7 | hsa-miR-519b-5p | 1.49E+02 | 1.45E+01 | 1.03E+01 | 2.33E-00 | 4.89E-07 | 6.03E-05 | 5.93E-06 | 3.41E-04 |
| 8 | hsa-miR-1324 | 1.50E+02 | 7.16E+01 | 2.09E-00 | 7.38E-01 | 5.89E-07 | 6.35E-05 | 7.78E-04 | 7.14E-03 |
| 9 | hsa-miR-519c-5p | 2.04E+02 | 4.55E+01 | 4.49E-00 | 1.50E-00 | 6.93E-07 | 6.65E-05 | 4.42E-05 | 1.47E-03 |
| 10 | hsa-miR-942 | 1.00E-00 | 6.17E+01 | 1.62E-02 | -4.12E-00 | 9.06E-07 | 7.82E-05 | 1.52E-08 | 4.38E-06 |
| 11 | hsa-miR-15b | 1.76E+04 | 1.04E+04 | 1.69E-00 | 5.27E-01 | 2.00E-06 | 1.23E-04 | 8.18E-05 | 2.01E-03 |
| 12 | hsa-miR-148a | 1.43E+03 | 4.60E+02 | 3.11E-00 | 1.14E-00 | 1.73E-06 | 1.23E-04 | 5.78E-07 | 9.97E-05 |
| 13 | hsa-miR-335* | 1.00E-00 | 4.30E+01 | 2.33E-02 | -3.76E-00 | 1.90E-06 | 1.23E-04 | 6.97E-09 | 3.01E-06 |
| 14 | hsa-miR-20a* | 1.74E+02 | 6.40E+01 | 2.72E-00 | 9.99E-01 | 1.85E-06 | 1.23E-04 | 3.82E-04 | 4.52E-03 |
| 15 | hsa-miR-1289 | 1.24E+02 | 7.24E+01 | 1.72E-00 | 5.41E-01 | 2.35E-06 | 1.35E-04 | 3.19E-04 | 3.99E-03 |
| 16 | hsa-miR-133b | 1.00E-00 | 5.58E+01 | 1.79E-02 | -4.02E-00 | 4.08E-06 | 2.20E-04 | 2.62E-12 | 2.27E-09 |
| 17 | hsa-miR-423-5p | 1.96E+03 | 4.40E+03 | 4.46E-01 | -8.08E-01 | 4.65E-06 | 2.36E-04 | 2.29E-06 | 1.98E-04 |
| 18 | hsa-miR-708* | 8.37E+01 | 1.72E+01 | 4.86E-00 | 1.58E-00 | 5.80E-06 | 2.78E-04 | 1.62E-04 | 2.85E-03 |
| 19 | hsa-miR-490-3p | 1.28E+02 | 5.40E+01 | 2.38E-00 | 8.66E-01 | 9.97E-06 | 4.29E-04 | 2.27E-03 | 1.49E-02 |

FIG 10 (continued)

| | | | | | | | | | |
|---|---|---|---|---|---|---|---|---|---|
| 20 | hsa-miR-383 | 9.81E+01 | 1.24E+01 | 7.94E-00 | 2.07E-00 | 1.00E-05 | 4.29E-04 | 4.02E-05 | 1.39E-03 |
| 21 | hsa-miR-877* | 1.73E+01 | 1.83E+02 | 9.49E-02 | -2.35E-00 | 1.09E-05 | 4.29E-04 | 3.11E-04 | 3.95E-03 |
| 22 | hsa-miR-1226 | 3.58E+01 | 1.06E+02 | 3.38E-01 | -1.08E-00 | 1.06E-05 | 4.29E-04 | 6.02E-05 | 1.68E-03 |
| 23 | hsa-miR-629* | 8.60E+01 | 2.21E+02 | 3.88E-01 | -9.46E-01 | 1.29E-05 | 4.47E-04 | 1.40E-01 | 2.63E-01 |
| 24 | hsa-miR-1281 | 1.76E+01 | 2.09E+02 | 8.42E-02 | -2.47E-00 | 1.28E-05 | 4.47E-04 | 1.06E-05 | 5.38E-04 |
| 25 | hsa-miR-664 | 1.39E+02 | 4.31E+02 | 3.22E-01 | -1.13E-00 | 1.29E-05 | 4.47E-04 | 7.20E-05 | 1.87E-03 |
| 26 | hsa-miR-338-3p | 1.74E+02 | 4.97E+01 | 3.51E-00 | 1.26E-00 | 1.44E-05 | 4.77E-04 | 2.60E-04 | 3.68E-03 |
| 27 | hsa-miR-378 | 1.64E+02 | 3.51E+02 | 4.68E-01 | -7.59E-01 | 1.66E-05 | 5.23E-04 | 8.61E-05 | 2.01E-03 |
| 28 | hsa-miR-137 | 7.77E+01 | 3.00E+01 | 2.59E-00 | 9.52E-01 | 1.76E-05 | 5.23E-04 | 6.42E-04 | 6.09E-03 |
| 29 | hsa-miR-328 | 2.53E+01 | 1.62E+02 | 1.56E-01 | -1.86E-00 | 1.75E-05 | 5.23E-04 | 7.35E-05 | 1.87E-03 |
| 30 | hsa-miR-1225-5p | 5.58E+01 | 1.36E+02 | 4.11E-01 | -8.88E-01 | 1.96E-05 | 5.39E-04 | 1.78E-03 | 1.26E-02 |
| 31 | hsa-miR-668 | 1.12E+01 | 8.22E+01 | 1.37E-01 | -1.99E-00 | 1.92E-05 | 5.39E-04 | 1.71E-04 | 2.90E-03 |
| 32 | hsa-miR-320a | 9.81E+03 | 2.05E+04 | 4.79E-01 | -7.36E-01 | 2.00E-05 | 5.39E-04 | 1.53E-04 | 2.82E-03 |
| 33 | hsa-miR-27a* | 3.29E+01 | 7.04E+01 | 4.67E-01 | -7.61E-01 | 2.08E-05 | 5.44E-04 | 5.33E-03 | 2.72E-02 |
| 34 | hsa-miR-135a* | 1.00E-00 | 6.86E+01 | 1.46E-02 | -4.23E-00 | 2.35E-05 | 5.96E-04 | 1.53E-05 | 6.76E-04 |
| 35 | hsa-miR-1825 | 3.14E+01 | 1.36E+02 | 2.31E-01 | -1.47E-00 | 2.59E-05 | 6.04E-04 | 9.72E-04 | 8.30E-03 |
| 36 | hsa-miR-483-3p | 1.00E-00 | 8.47E+01 | 1.18E-02 | -4.44E-00 | 2.46E-05 | 6.04E-04 | 2.61E-05 | 1.02E-03 |
| 37 | hsa-miR-522* | 2.06E+02 | 4.55E+01 | 4.54E-00 | 1.51E-00 | 2.55E-05 | 6.04E-04 | 5.79E-05 | 1.68E-03 |
| 38 | hsa-miR-15a | 5.38E+03 | 2.76E+03 | 1.95E-00 | 6.69E-01 | 2.68E-05 | 6.08E-04 | 3.39E-04 | 4.12E-03 |
| 39 | hsa-miR-193a-5p | 5.87E+01 | 1.22E+02 | 4.81E-01 | -7.32E-01 | 2.83E-05 | 6.14E-04 | 8.05E-02 | 1.75E-01 |
| 40 | hsa-miR-424* | 9.23E+01 | 1.81E+02 | 5.10E-01 | -6.72E-01 | 2.85E-05 | 6.14E-04 | 1.69E-01 | 2.99E-01 |
| 41 | hsa-miR-21* | 1.29E+02 | 4.06E+01 | 3.17E-00 | 1.15E-00 | 2.94E-05 | 6.19E-04 | 2.08E-04 | 3.30E-03 |

FIG 10 (continued)

| | | | | | | | | | |
|---|---|---|---|---|---|---|---|---|---|
| 42 | hsa-miR-494 | 3.70E+01 | 9.32E+01 | 3.97E-01 | -9.24E-01 | 3.20E-05 | 6.57E-04 | 3.28E-04 | 4.04E-03 |
| 43 | hsa-miR-1237 | 6.76E+01 | 1.53E+02 | 4.41E-01 | -8.20E-01 | 3.89E-05 | 7.81E-04 | 3.70E-02 | 1.01E-01 |
| 44 | hsa-miR-578 | 1.00E-00 | 3.83E+01 | 2.61E-02 | -3.64E-00 | 4.03E-05 | 7.91E-04 | 7.15E-05 | 1.87E-03 |
| 45 | hsa-miR-635 | 1.27E+02 | 5.54E+01 | 2.29E-00 | 8.28E-01 | 4.92E-05 | 9.43E-04 | 1.09E-04 | 2.34E-03 |
| 46 | hsa-miR-33b | 1.78E+02 | 1.02E+02 | 1.75E-00 | 5.58E-01 | 5.19E-05 | 9.74E-04 | 2.84E-03 | 1.74E-02 |
| 47 | hsa-miR-541 | 1.03E+02 | 4.87E+01 | 2.12E-00 | 7.50E-01 | 5.87E-05 | 1.05E-03 | 2.10E-04 | 3.30E-03 |
| 48 | hsa-miR-526a | 2.31E+02 | 1.69E+01 | 1.36E+01 | 2.61E-00 | 5.96E-05 | 1.05E-03 | 1.71E-06 | 1.64E-04 |
| 49 | hsa-miR-519a* | 1.85E+02 | 4.91E+01 | 3.77E-00 | 1.33E-00 | 5.76E-05 | 1.05E-03 | 4.39E-06 | 2.92E-04 |
| 50 | hsa-miR-573 | 7.30E+01 | 2.32E+01 | 3.15E-00 | 1.15E-00 | 6.36E-05 | 1.10E-03 | 8.41E-05 | 2.01E-03 |
| 51 | hsa-miR-888 | 1.06E+01 | 7.33E+01 | 1.45E-01 | -1.93E-00 | 6.70E-05 | 1.13E-03 | 4.23E-04 | 4.84E-03 |
| 52 | hsa-miR-33a | 9.86E+01 | 4.64E+01 | 2.13E-00 | 7.54E-01 | 6.82E-05 | 1.13E-03 | 1.03E-03 | 8.73E-03 |
| 53 | hsa-miR-1229 | 1.17E+02 | 4.34E+02 | 2.70E-01 | -1.31E-00 | 7.36E-05 | 1.20E-03 | 9.04E-02 | 1.92E-01 |
| 54 | hsa-miR-103-as | 1.50E+02 | 9.27E+01 | 1.62E-00 | 4.83E-01 | 8.03E-05 | 1.22E-03 | 9.79E-03 | 3.99E-02 |
| 55 | hsa-miR-197 | 4.53E+02 | 1.03E+03 | 4.40E-01 | -8.21E-01 | 8.09E-05 | 1.22E-03 | 1.55E-05 | 6.76E-04 |
| 56 | hsa-miR-324-3p | 5.33E+02 | 8.95E+02 | 5.96E-01 | -5.18E-01 | 7.74E-05 | 1.22E-03 | 4.06E-04 | 4.73E-03 |
| 57 | hsa-miR-433 | 1.22E+02 | 3.90E+01 | 3.12E-00 | 1.14E-00 | 8.16E-05 | 1.22E-03 | 2.37E-04 | 3.50E-03 |
| 58 | hsa-miR-671-3p | 3.15E+01 | 7.19E+01 | 4.38E-01 | -8.26E-01 | 8.21E-05 | 1.22E-03 | 6.25E-03 | 3.05E-02 |
| 59 | hsa-miR-211 | 1.00E-00 | 4.91E+01 | 2.04E-02 | -3.89E-00 | 8.84E-05 | 1.29E-03 | 5.63E-06 | 3.41E-04 |
| 60 | hsa-miR-150 | 6.29E+02 | 2.01E+03 | 3.13E-01 | -1.16E-00 | 9.19E-05 | 1.32E-03 | 5.35E-04 | 5.43E-03 |
| 61 | hsa-miR-885-5p | 3.58E+01 | 7.17E+01 | 4.99E-01 | -6.94E-01 | 9.41E-05 | 1.33E-03 | 6.70E-03 | 3.21E-02 |
| 62 | hsa-miR-34b | 1.78E+01 | 7.13E+01 | 2.50E-01 | -1.39E-00 | 1.00E-04 | 1.35E-03 | 3.74E-04 | 4.48E-03 |
| 63 | hsa-miR-551b* | 4.27E+01 | 1.22E+02 | 3.51E-01 | -1.05E-00 | 9.89E-05 | 1.35E-03 | 6.34E-03 | 3.07E-02 |

FIG 10 (continued)

| | | | | | | | | | |
|---|---|---|---|---|---|---|---|---|---|
| 64 | hsa-miR-362-5p | 1.10E+02 | 2.27E+02 | 4.82E-01 | -7.29E-01 | 9.89E-05 | 1.35E-03 | 1.53E-03 | 1.11E-02 |
| 65 | hsa-miR-409-3p | 1.00E-00 | 7.79E+01 | 1.28E-02 | -4.35E-00 | 1.09E-04 | 1.44E-03 | 2.65E-06 | 2.08E-04 |
| 66 | hsa-miR-186* | 1.33E+02 | 5.28E+01 | 2.51E-00 | 9.20E-01 | 1.23E-04 | 1.56E-03 | 8.41E-04 | 7.48E-03 |
| 67 | hsa-miR-216a | 1.36E+02 | 6.93E+01 | 1.97E-00 | 6.78E-01 | 1.22E-04 | 1.56E-03 | 1.20E-03 | 9.28E-03 |
| 68 | hsa-miR-516b* | 2.23E-00 | 5.63E+01 | 3.97E-02 | -3.23E-00 | 1.21E-04 | 1.56E-03 | 1.32E-04 | 2.61E-03 |
| 69 | hsa-miR-1205 | 1.31E+02 | 4.09E+01 | 3.20E-00 | 1.16E-00 | 1.29E-04 | 1.62E-03 | 1.93E-04 | 3.14E-03 |
| 70 | hsa-miR-1224-3p | 5.33E+01 | 2.24E+02 | 2.38E-01 | -1.44E-00 | 1.31E-04 | 1.62E-03 | 1.67E-04 | 2.88E-03 |

FIG 11

| No. | miRNA | median g1 | median g2 | qmedian | Logq median | ttest_rawp | ttest_adjp | Limma_ rawp | Limma_ adjp |
|---|---|---|---|---|---|---|---|---|---|
| 1 | hsa-miR-363 | 3.998E+03 | 1.620E+03 | 2.468E-00 | 9.035E-01 | 1.141E-05 | 9.847E-03 | 4.456E-05 | 1.227E-02 |
| 2 | hsa-miR-144 | 2.008E+03 | 3.090E+02 | 6.498E-00 | 1.871E-00 | 2.866E-05 | 1.018E-02 | 5.689E-05 | 1.227E-02 |
| 3 | hsa-miR-139-5p | 1.266E+02 | 1.986E+02 | 6.375E-01 | -4.502E-01 | 3.539E-05 | 1.018E-02 | 3.059E-02 | 3.734E-01 |
| 4 | hsa-miR-639 | 5.529E+01 | 1.056E+02 | 5.235E-01 | -6.473E-01 | 5.323E-05 | 1.148E-02 | 6.196E-03 | 2.235E-01 |
| 5 | hsa-miR-662 | 4.639E+01 | 8.399E+01 | 5.523E-01 | -5.937E-01 | 4.082E-04 | 7.045E-02 | 6.721E-02 | 4.285E-01 |
| 6 | hsa-miR-886-3p | 1.125E+01 | 3.765E+01 | 2.988E-01 | -1.208E-00 | 8.131E-04 | 7.797E-02 | 7.250E-03 | 2.235E-01 |
| 7 | hsa-miR-342-3p | 2.357E+03 | 8.166E+03 | 2.887E-01 | -1.242E-00 | 5.485E-04 | 7.797E-02 | 1.235E-05 | 5.328E-03 |
| 8 | hsa-miR-218 | 3.289E+01 | 1.099E+01 | 2.991E-00 | 1.096E-00 | 6.606E-04 | 7.797E-02 | 4.817E-02 | 3.922E-01 |
| 9 | hsa-miR-22 | 9.808E+03 | 5.922E+03 | 1.656E-00 | 5.045E-01 | 8.126E-04 | 7.797E-02 | 1.470E-02 | 3.300E-01 |
| 10 | hsa-miR-140-5p | 4.088E+01 | 8.181E-00 | 4.997E-00 | 1.609E-00 | 1.222E-03 | 9.025E-02 | 4.710E-03 | 1.944E-01 |
| 11 | hsa-miR-590-5p | 1.565E+02 | 1.139E+02 | 1.374E-00 | 3.179E-01 | 1.062E-03 | 9.025E-02 | 6.754E-03 | 2.235E-01 |
| 12 | hsa-miR-20b | 2.515E+03 | 1.162E+03 | 2.164E-00 | 7.718E-01 | 1.255E-03 | 9.025E-02 | 7.189E-03 | 2.235E-01 |
| 13 | hsa-miR-206 | 4.315E+01 | 1.000E-00 | 4.315E+01 | 3.765E-00 | 1.432E-03 | 9.510E-02 | 9.914E-05 | 1.711E-02 |
| 14 | hsa-miR-614 | 1.995E+01 | 3.857E+01 | 5.172E-01 | -6.592E-01 | 2.121E-03 | 1.307E-01 | 5.181E-02 | 3.981E-01 |
| 15 | hsa-miR-103 | 6.228E+03 | 3.623E+03 | 1.719E-00 | 5.417E-01 | 3.286E-03 | 1.772E-01 | 9.801E-03 | 2.728E-01 |
| 16 | hsa-miR-720 | 2.998E+03 | 1.574E+04 | 1.905E-01 | -1.658E-00 | 3.191E-03 | 1.772E-01 | 7.625E-06 | 5.328E-03 |
| 17 | hsa-miR-181d | 2.530E+01 | 4.937E-00 | 5.125E-00 | 1.634E-00 | 3.607E-03 | 1.831E-01 | 3.786E-02 | 3.813E-01 |
| 18 | hsa-miR-17 | 5.922E+03 | 3.143E+03 | 1.884E-00 | 6.334E-01 | 4.254E-03 | 2.040E-01 | 1.230E-02 | 3.036E-01 |
| 19 | hsa-miR-20a | 3.143E+03 | 1.550E+03 | 2.028E-00 | 7.070E-01 | 4.534E-03 | 2.060E-01 | 4.846E-03 | 1.944E-01 |

FIG 11 (continued)

| | | | | | | | | | |
|---|---|---|---|---|---|---|---|---|---|
| 20 | hsa-miR-580 | 2.566E+01 | 7.452E+01 | 3.443E-01 | -1.066E-00 | 5.848E-03 | 2.403E-01 | 3.619E-02 | 3.809E-01 |
| 21 | hsa-miR-96 | 1.543E+02 | 9.975E+01 | 1.547E-00 | 4.361E-01 | 5.832E-03 | 2.403E-01 | 7.110E-02 | 4.352E-01 |
| 22 | hsa-miR-425 | 1.198E+04 | 7.714E+03 | 1.553E-00 | 4.400E-01 | 6.447E-03 | 2.419E-01 | 2.354E-02 | 3.471E-01 |
| 23 | hsa-miR-144* | 3.352E+02 | 1.788E+02 | 1.874E-00 | 6.283E-01 | 6.261E-03 | 2.419E-01 | 3.112E-02 | 3.734E-01 |
| 24 | hsa-miR-875-5p | 9.746E-00 | 1.000E-00 | 9.746E-00 | 2.277E-00 | 6.732E-03 | 2.421E-01 | 2.788E-02 | 3.701E-01 |
| 25 | hsa-miR-92a-1* | 9.746E-00 | 1.000E-00 | 9.746E-00 | 2.277E-00 | 8.131E-03 | 2.599E-01 | 4.310E-02 | 3.883E-01 |
| 26 | hsa-miR-15a | 5.379E+03 | 2.303E+03 | 2.336E-00 | 8.483E-01 | 7.737E-03 | 2.599E-01 | 4.079E-03 | 1.944E-01 |
| 27 | hsa-miR-16 | 1.763E+04 | 1.415E+04 | 1.246E-00 | 2.201E-01 | 8.073E-03 | 2.599E-01 | 5.446E-02 | 4.069E-01 |
| 28 | hsa-miR-21 | 9.187E+02 | 4.595E+02 | 1.999E-00 | 6.928E-01 | 8.500E-03 | 2.620E-01 | 2.313E-02 | 3.471E-01 |
| 29 | hsa-miR-323-5p | 5.868E+01 | 3.123E+01 | 1.879E-00 | 6.305E-01 | 9.314E-03 | 2.741E-01 | 2.057E-02 | 3.439E-01 |
| 30 | hsa-miR-105* | 7.252E-00 | 1.000E-00 | 7.252E-00 | 1.981E-00 | 9.530E-03 | 2.741E-01 | 5.841E-02 | 4.132E-01 |
| 31 | hsa-miR-30b* | 3.701E+01 | 1.000E-00 | 3.701E+01 | 3.611E-00 | 1.004E-02 | 2.794E-01 | 2.016E-02 | 3.439E-01 |
| 32 | hsa-miR-324-3p | 5.331E+02 | 1.376E+03 | 3.875E-01 | -9.480E-01 | 1.062E-02 | 2.795E-01 | 4.062E-03 | 1.944E-01 |
| 33 | hsa-miR-665 | 1.008E+02 | 1.340E+02 | 7.522E-01 | -2.848E-01 | 1.069E-02 | 2.795E-01 | 5.004E-02 | 3.955E-01 |
| 34 | hsa-miR-384 | 6.629E+01 | 2.624E+01 | 2.526E-00 | 9.265E-01 | 1.254E-02 | 3.093E-01 | 2.094E-01 | 6.502E-01 |
| 35 | hsa-miR-1276 | 3.499E+01 | 5.693E+01 | 6.146E-01 | -4.868E-01 | 1.248E-02 | 3.093E-01 | 1.137E-01 | 5.273E-01 |
| 36 | hsa-miR-19a | 2.998E+03 | 2.515E+03 | 1.192E-00 | 1.758E-01 | 1.309E-02 | 3.138E-01 | 7.681E-02 | 4.416E-01 |
| 37 | hsa-miR-106a | 6.228E+03 | 3.998E+03 | 1.558E-00 | 4.433E-01 | 1.485E-02 | 3.287E-01 | 1.566E-02 | 3.300E-01 |
| 38 | hsa-miR-182 | 7.310E+03 | 3.790E+03 | 1.929E-00 | 6.570E-01 | 1.459E-02 | 3.287E-01 | 2.754E-02 | 3.701E-01 |
| 39 | hsa-miR-632 | 2.485E+01 | 8.181E-00 | 3.037E-00 | 1.111E-00 | 1.432E-02 | 3.287E-01 | 5.206E-01 | 8.510E-01 |
| 40 | hsa-miR-141* | 9.334E+01 | 5.693E+01 | 1.639E-00 | 4.944E-01 | 1.550E-02 | 3.344E-01 | 5.609E-02 | 4.069E-01 |
| 41 | hsa-miR-1288 | 3.753E+01 | 1.234E+02 | 3.040E-01 | -1.191E-00 | 1.607E-02 | 3.382E-01 | 4.375E-02 | 3.883E-01 |

FIG 11 (continued)

| | | | | | | | | | |
|---|---|---|---|---|---|---|---|---|---|
| 42 | hsa-miR-16-1* | 7.160E+01 | 4.835E+01 | 1.481E-00 | 3.927E-01 | 1.671E-02 | 3.433E-01 | 1.025E-02 | 2.763E-01 |
| 43 | hsa-miR-1268 | 5.176E+02 | 2.909E+02 | 1.780E-00 | 5.764E-01 | 1.894E-02 | 3.470E-01 | 9.759E-02 | 4.996E-01 |
| 44 | hsa-miR-550 | 1.103E+02 | 1.788E+02 | 6.167E-01 | -4.833E-01 | 2.075E-02 | 3.470E-01 | 5.572E-02 | 4.069E-01 |
| 45 | hsa-miR-517b | 1.252E+01 | 3.857E+01 | 3.244E-01 | -1.126E-00 | 2.155E-02 | 3.470E-01 | 3.235E-02 | 3.770E-01 |
| 46 | hsa-miR-545 | 1.358E+02 | 9.775E+01 | 1.390E-00 | 3.290E-01 | 2.030E-02 | 3.470E-01 | 2.947E-02 | 3.734E-01 |
| 47 | hsa-miR-668 | 1.125E+01 | 5.464E+01 | 2.059E-01 | -1.580E-00 | 2.121E-02 | 3.470E-01 | 2.291E-02 | 3.471E-01 |
| 48 | hsa-miR-374b | 4.905E+02 | 1.792E+02 | 2.737E-00 | 1.007E-00 | 2.165E-02 | 3.470E-01 | 5.611E-02 | 4.069E-01 |
| 49 | hsa-miR-10b* | 5.046E+01 | 8.159E+01 | 6.185E-01 | -4.804E-01 | 2.172E-02 | 3.470E-01 | 1.494E-01 | 5.838E-01 |
| 50 | hsa-miR-320a | 9.808E+03 | 2.473E+04 | 3.966E-01 | -9.247E-01 | 1.903E-02 | 3.470E-01 | 6.272E-03 | 2.235E-01 |
| 51 | hsa-miR-30b | 8.166E+03 | 3.998E+03 | 2.043E-00 | 7.143E-01 | 1.905E-02 | 3.470E-01 | 4.090E-02 | 3.813E-01 |
| 52 | hsa-miR-526b | 4.271E+01 | 5.959E+01 | 7.168E-01 | -3.330E-01 | 2.137E-02 | 3.470E-01 | 1.253E-01 | 5.605E-01 |
| 53 | hsa-miR-302d* | 3.029E+01 | 4.697E+01 | 6.449E-01 | -4.387E-01 | 2.142E-02 | 3.470E-01 | 6.637E-02 | 4.284E-01 |
| 54 | hsa-miR-187 | 3.289E+01 | 1.000E-00 | 3.289E+01 | 3.493E-00 | 2.211E-02 | 3.470E-01 | 1.224E-01 | 5.556E-01 |
| 55 | hsa-miR-382 | 5.529E+01 | 1.000E-00 | 5.529E+01 | 4.013E-00 | 1.734E-02 | 3.470E-01 | 6.530E-02 | 4.284E-01 |
| 56 | hsa-miR-453 | 4.534E+01 | 1.000E-00 | 4.534E+01 | 3.814E-00 | 2.264E-02 | 3.489E-01 | 6.341E-02 | 4.275E-01 |
| 57 | hsa-miR-1250 | 7.661E+01 | 2.624E+01 | 2.919E-00 | 1.071E-00 | 2.448E-02 | 3.706E-01 | 4.795E-01 | 8.360E-01 |
| 58 | hsa-miR-30c | 2.630E+03 | 1.917E+03 | 1.372E-00 | 3.164E-01 | 2.618E-02 | 3.895E-01 | 1.646E-02 | 3.300E-01 |
| 59 | hsa-miR-943 | 3.029E+01 | 6.041E+01 | 5.014E-01 | -6.903E-01 | 2.691E-02 | 3.936E-01 | 3.451E-02 | 3.770E-01 |
| 60 | hsa-miR-636 | 1.131E+02 | 2.071E+02 | 5.462E-01 | -6.047E-01 | 2.763E-02 | 3.974E-01 | 1.528E-02 | 3.300E-01 |
| 61 | hsa-miR-107 | 1.687E+03 | 9.187E+02 | 1.836E-00 | 6.075E-01 | 2.875E-02 | 4.002E-01 | 3.077E-02 | 3.734E-01 |
| 62 | hsa-miR-744* | 9.746E-00 | 4.697E+01 | 2.075E-01 | -1.573E-00 | 2.839E-02 | 4.002E-01 | 2.152E-02 | 3.439E-01 |
| 63 | hsa-miR-1294 | 1.000E-00 | 1.000E-00 | 1.000E-00 | 0.000E+01 | 2.983E-02 | 4.086E-01 | 1.866E-01 | 6.405E-01 |

FIG 11 (continued)

| | | | | | | | | | |
|---|---|---|---|---|---|---|---|---|---|
| 64 | hsa-miR-802 | 5.728E+01 | 3.618E+01 | 1.583E-00 | 4.594E-01 | 3.090E-02 | 4.103E-01 | 3.006E-03 | 1.944E-01 |
| 65 | hsa-miR-181a-2* | 7.727E+01 | 1.343E+02 | 5.752E-01 | -5.530E-01 | 3.060E-02 | 4.103E-01 | 1.273E-01 | 5.605E-01 |
| 66 | hsa-miR-572 | 4.111E+01 | 6.746E+01 | 6.093E-01 | -4.954E-01 | 3.275E-02 | 4.283E-01 | 3.704E-02 | 3.813E-01 |
| 67 | hsa-miR-93 | 3.374E+03 | 2.206E+03 | 1.530E-00 | 4.250E-01 | 3.418E-02 | 4.398E-01 | 2.742E-02 | 3.701E-01 |
| 68 | hsa-miR-595 | 1.325E+02 | 5.679E+01 | 2.334E-00 | 8.474E-01 | 3.469E-02 | 4.398E-01 | 2.689E-01 | 6.843E-01 |
| 69 | hsa-miR-195* | 9.249E+01 | 4.697E+01 | 1.969E-00 | 6.775E-01 | 3.517E-02 | 4.398E-01 | 4.955E-02 | 3.955E-01 |
| 70 | hsa-miR-126 | 1.262E+03 | 3.692E+02 | 3.417E-00 | 1.229E-00 | 3.826E-02 | 4.650E-01 | 1.037E-01 | 5.112E-01 |

FIG 12

| No. | miRNA | median g1 | median g2 | qmedian | logqmedian | ttest_rawp | ttest_adjp | Limma_rawp | Limma_adjp |
|---|---|---|---|---|---|---|---|---|---|
| 1 | hsa-miR-1248 | 3.93E+01 | 1.00E-00 | 3.93E+01 | 3.67E-00 | 6.39E-08 | 2.76E-05 | 8.98E-06 | 8.61E-04 |
| 2 | hsa-miR-1295 | 6.68E+01 | 1.49E+02 | 4.47E-01 | -8.05E-01 | 4.55E-08 | 2.76E-05 | 2.38E-03 | 3.16E-02 |
| 3 | hsa-miR-454* | 3.71E+01 | 1.00E-00 | 3.71E+01 | 3.61E-00 | 1.43E-07 | 4.10E-05 | 1.54E-09 | 1.33E-06 |
| 4 | hsa-miR-942 | 4.35E+01 | 1.00E-00 | 4.35E+01 | 3.77E-00 | 3.11E-07 | 6.70E-05 | 2.54E-06 | 3.13E-04 |
| 5 | hsa-miR-1228 | 5.06E+02 | 1.82E+02 | 2.78E-00 | 1.02E-00 | 5.96E-07 | 7.35E-05 | 4.31E-02 | 1.64E-01 |
| 6 | hsa-miR-337-3p | 2.80E+01 | 1.00E-00 | 2.80E+01 | 3.33E-00 | 5.61E-07 | 7.35E-05 | 2.14E-08 | 5.94E-06 |
| 7 | hsa-miR-605 | 2.35E+01 | 1.00E-00 | 2.35E+01 | 3.16E-00 | 5.44E-07 | 7.35E-05 | 1.78E-05 | 1.47E-03 |
| 8 | hsa-miR-363* | 4.00E+01 | 9.79E+01 | 4.08E-01 | -8.96E-01 | 9.05E-07 | 8.68E-05 | 1.05E-03 | 1.80E-02 |
| 9 | hsa-let-7d | 3.00E+03 | 1.69E+03 | 1.78E-00 | 5.75E-01 | 8.23E-07 | 8.68E-05 | 4.64E-02 | 1.68E-01 |
| 10 | hsa-miR-135b | 2.07E+01 | 1.00E-00 | 2.07E+01 | 3.03E-00 | 1.09E-06 | 9.41E-05 | 3.42E-06 | 3.69E-04 |
| 11 | hsa-miR-133b | 3.52E+01 | 1.00E-00 | 3.52E+01 | 3.56E-00 | 1.60E-06 | 1.26E-04 | 7.02E-05 | 3.35E-03 |
| 12 | hsa-miR-130a* | 8.83E+01 | 3.53E+01 | 2.50E-00 | 9.18E-01 | 3.06E-06 | 2.03E-04 | 2.86E-03 | 3.57E-02 |
| 13 | hsa-miR-589 | 5.25E+01 | 1.00E+02 | 5.24E-01 | -6.47E-01 | 2.91E-06 | 2.03E-04 | 3.10E-03 | 3.77E-02 |
| 14 | hsa-miR-610 | 2.77E+01 | 1.14E+02 | 2.43E-01 | -1.41E-00 | 3.68E-06 | 2.27E-04 | 1.17E-04 | 4.41E-03 |
| 15 | hsa-miR-150 | 2.23E+03 | 6.29E+02 | 3.55E-00 | 1.27E-00 | 4.21E-06 | 2.42E-04 | 2.00E-05 | 1.47E-03 |
| 16 | hsa-miR-655 | 3.97E+01 | 1.00E-00 | 3.97E+01 | 3.68E-00 | 6.89E-06 | 3.72E-04 | 2.32E-04 | 6.67E-03 |
| 17 | hsa-miR-409-3p | 6.02E+01 | 1.00E-00 | 6.02E+01 | 4.10E-00 | 7.51E-06 | 3.81E-04 | 1.84E-04 | 5.76E-03 |
| 18 | hsa-miR-1259 | 2.76E+01 | 1.00E-00 | 2.76E+01 | 3.32E-00 | 8.33E-06 | 4.00E-04 | 5.99E-04 | 1.20E-02 |
| 19 | hsa-miR-573 | 3.34E+01 | 7.30E+01 | 4.57E-01 | -7.83E-01 | 1.14E-05 | 4.83E-04 | 8.71E-04 | 1.57E-02 |

FIG 12 (continued)

| | | | | | | | | | |
|---|---|---|---|---|---|---|---|---|---|
| 20 | hsa-miR-539 | 1.81E+01 | 1.00E-00 | 1.81E+01 | 2.90E-00 | 1.10E-05 | 4.83E-04 | 4.05E-04 | 9.21E-03 |
| 21 | hsa-miR-578 | 2.09E+01 | 1.00E-00 | 2.09E+01 | 3.04E-00 | 1.18E-05 | 4.83E-04 | 6.80E-04 | 1.30E-02 |
| 22 | hsa-miR-668 | 5.19E+01 | 1.12E+01 | 4.61E-00 | 1.53E-00 | 1.27E-05 | 4.99E-04 | 6.15E-08 | 1.06E-05 |
| 23 | hsa-miR-576-5p | 1.92E+01 | 1.00E-00 | 1.92E+01 | 2.95E-00 | 1.56E-05 | 5.87E-04 | 2.78E-05 | 1.85E-03 |
| 24 | hsa-miR-651 | 1.87E+01 | 1.00E-00 | 1.87E+01 | 2.93E-00 | 1.77E-05 | 6.36E-04 | 5.70E-04 | 1.17E-02 |
| 25 | hsa-miR-335* | 1.65E+01 | 1.00E-00 | 1.65E+01 | 2.80E-00 | 2.13E-05 | 7.36E-04 | 3.68E-05 | 2.02E-03 |
| 26 | hsa-miR-744* | 5.28E+01 | 9.75E-00 | 5.42E-00 | 1.69E-00 | 2.29E-05 | 7.61E-04 | 3.21E-05 | 1.98E-03 |
| 27 | hsa-miR-148a | 6.42E+02 | 1.43E+03 | 4.48E-01 | -8.02E-01 | 2.59E-05 | 7.99E-04 | 1.09E-04 | 4.29E-03 |
| 28 | hsa-miR-516b* | 4.35E+01 | 2.23E-00 | 1.95E+01 | 2.97E-00 | 2.55E-05 | 7.99E-04 | 3.75E-05 | 2.02E-03 |
| 29 | hsa-miR-302c | 1.58E+01 | 1.00E-00 | 1.58E+01 | 2.76E-00 | 2.90E-05 | 8.62E-04 | 1.81E-04 | 5.76E-03 |
| 30 | hsa-miR-892b | 4.16E+01 | 1.25E+01 | 3.32E-00 | 1.20E-00 | 3.04E-05 | 8.75E-04 | 1.67E-03 | 2.54E-02 |
| 31 | hsa-miR-26b* | 1.94E+01 | 1.00E-00 | 1.94E+01 | 2.96E-00 | 3.68E-05 | 1.01E-03 | 2.04E-05 | 1.47E-03 |
| 32 | hsa-miR-520a-3p | 9.77E-00 | 1.00E-00 | 9.77E-00 | 2.28E-00 | 3.76E-05 | 1.01E-03 | 7.08E-05 | 3.35E-03 |
| 33 | hsa-miR-146b-3p | 2.11E+01 | 8.41E+01 | 2.51E-01 | -1.38E-00 | 4.21E-05 | 1.10E-03 | 2.70E-04 | 7.51E-03 |
| 34 | hsa-miR-877* | 1.01E+02 | 1.73E+01 | 5.81E-00 | 1.76E-00 | 4.75E-05 | 1.17E-03 | 1.85E-04 | 5.76E-03 |
| 35 | hsa-miR-522* | 5.63E+01 | 2.06E+02 | 2.73E-01 | -1.30E-00 | 4.67E-05 | 1.17E-03 | 2.79E-04 | 7.52E-03 |
| 36 | hsa-miR-582-5p | 4.11E+01 | 1.00E-00 | 4.11E+01 | 3.72E-00 | 5.15E-05 | 1.23E-03 | 2.05E-04 | 6.10E-03 |
| 37 | hsa-miR-9 | 2.50E+01 | 1.00E-00 | 2.50E+01 | 3.22E-00 | 5.36E-05 | 1.25E-03 | 7.19E-04 | 1.35E-02 |
| 38 | hsa-miR-133a | 7.67E+01 | 2.70E+01 | 2.84E-00 | 1.04E-00 | 6.09E-05 | 1.38E-03 | 9.26E-05 | 3.81E-03 |
| 39 | hsa-miR-599 | 4.43E+01 | 1.69E+01 | 2.62E-00 | 9.62E-01 | 6.47E-05 | 1.43E-03 | 1.10E-01 | 2.73E-01 |
| 40 | hsa-miR-299-5p | 2.18E+01 | 1.00E-00 | 2.18E+01 | 3.08E-00 | 7.03E-05 | 1.52E-03 | 9.88E-03 | 6.93E-02 |

FIG 12 (continued)

| | | | | | | | | | |
|---|---|---|---|---|---|---|---|---|---|
| 41 | hsa-miR-302d | 6.61E-00 | 1.00E-00 | 6.61E-00 | 1.89E-00 | 7.29E-05 | 1.53E-03 | 1.33E-03 | 2.12E-02 |
| 42 | hsa-miR-374a | 5.62E+02 | 2.12E+02 | 2.65E-00 | 9.75E-01 | 9.58E-05 | 1.97E-03 | 5.47E-02 | 1.84E-01 |
| 43 | hsa-miR-576-3p | 7.38E-00 | 1.00E-00 | 7.38E-00 | 2.00E-00 | 1.08E-04 | 2.16E-03 | 4.77E-04 | 1.04E-02 |
| 44 | hsa-miR-383 | 4.98E+01 | 9.81E+01 | 5.08E-01 | -6.77E-01 | 1.17E-04 | 2.30E-03 | 1.99E-03 | 2.82E-02 |
| 45 | hsa-miR-374b* | 4.87E+01 | 1.60E+01 | 3.05E-00 | 1.11E-00 | 1.25E-04 | 2.40E-03 | 4.84E-03 | 4.75E-02 |
| 46 | hsa-miR-1911 | 4.30E+01 | 1.73E+01 | 2.48E-00 | 9.08E-01 | 1.37E-04 | 2.47E-03 | 3.46E-03 | 3.94E-02 |
| 47 | hsa-miR-182 | 3.62E+03 | 7.31E+03 | 4.96E-01 | -7.02E-01 | 1.40E-04 | 2.47E-03 | 1.87E-04 | 5.76E-03 |
| 48 | hsa-miR-564 | 1.06E+02 | 2.01E+02 | 5.27E-01 | -6.41E-01 | 1.39E-04 | 2.47E-03 | 4.39E-03 | 4.68E-02 |
| 49 | hsa-miR-223* | 5.21E+01 | 2.57E+01 | 2.03E-00 | 7.08E-01 | 1.39E-04 | 2.47E-03 | 1.35E-01 | 3.06E-01 |
| 50 | hsa-miR-1226 | 7.62E+01 | 3.58E+01 | 2.13E-00 | 7.55E-01 | 1.50E-04 | 2.59E-03 | 9.82E-02 | 2.54E-01 |
| 51 | hsa-miR-302d* | 5.91E+01 | 3.03E+01 | 1.95E-00 | 6.68E-01 | 1.55E-04 | 2.62E-03 | 6.67E-03 | 5.75E-02 |
| 52 | hsa-miR-92a | 1.57E+04 | 1.20E+04 | 1.31E-00 | 2.73E-01 | 1.69E-04 | 2.74E-03 | 4.61E-02 | 1.67E-01 |
| 53 | hsa-miR-548b-5p | 1.57E-00 | 1.00E-00 | 1.57E-00 | 4.49E-01 | 1.66E-04 | 2.74E-03 | 4.72E-03 | 4.75E-02 |
| 54 | hsa-miR-551a | 1.42E+01 | 6.08E+01 | 2.33E-01 | -1.46E-00 | 2.10E-04 | 3.32E-03 | 3.52E-04 | 8.62E-03 |
| 55 | hsa-miR-205 | 6.34E+01 | 2.90E+01 | 2.18E-00 | 7.80E-01 | 2.11E-04 | 3.32E-03 | 6.26E-02 | 1.96E-01 |
| 56 | hsa-miR-1249 | 1.05E+02 | 4.05E+01 | 2.59E-00 | 9.51E-01 | 2.42E-04 | 3.73E-03 | 2.00E-03 | 2.82E-02 |
| 57 | hsa-miR-496 | 8.75E+01 | 4.70E+01 | 1.86E-00 | 6.22E-01 | 2.76E-04 | 4.17E-03 | 1.66E-02 | 9.20E-02 |
| 58 | hsa-miR-130b* | 1.10E+01 | 1.00E-00 | 1.10E+01 | 2.40E-00 | 2.89E-04 | 4.29E-03 | 1.12E-02 | 7.74E-02 |
| 59 | hsa-miR-618 | 1.76E+01 | 1.00E-00 | 1.76E+01 | 2.87E-00 | 2.98E-04 | 4.35E-03 | 8.07E-05 | 3.48E-03 |
| 60 | hsa-miR-23b* | 2.86E+01 | 1.00E-00 | 2.86E+01 | 3.35E-00 | 3.06E-04 | 4.40E-03 | 5.35E-04 | 1.13E-02 |
| 61 | hsa-miR-211 | 1.57E-00 | 1.00E-00 | 1.57E-00 | 4.49E-01 | 3.18E-04 | 4.50E-03 | 3.98E-03 | 4.40E-02 |
| 62 | hsa-miR-500* | 1.85E+02 | 3.25E+02 | 5.67E-01 | -5.67E-01 | 3.32E-04 | 4.62E-03 | 8.61E-03 | 6.54E-02 |

FIG 12 (continued)

| | | | | | | | | | |
|---|---|---|---|---|---|---|---|---|---|
| 63 | hsa-miR-204 | 3.95E-00 | 1.00E-00 | 3.95E-00 | 1.37E-00 | 3.83E-04 | 5.25E-03 | 4.84E-04 | 1.04E-02 |
| 64 | hsa-miR-1288 | 7.59E+01 | 3.75E+01 | 2.02E-00 | 7.04E-01 | 3.95E-04 | 5.32E-03 | 4.38E-02 | 1.66E-01 |
| 65 | hsa-miR-19b-1* | 7.89E+01 | 4.47E+01 | 1.76E-00 | 5.68E-01 | 4.12E-04 | 5.47E-03 | 1.44E-01 | 3.22E-01 |
| 66 | hsa-miR-126* | 2.83E+01 | 1.72E-00 | 1.65E+01 | 2.80E-00 | 4.23E-04 | 5.54E-03 | 1.02E-02 | 7.10E-02 |
| 67 | hsa-miR-888 | 5.02E+01 | 1.06E+01 | 4.73E-00 | 1.55E-00 | 4.44E-04 | 5.59E-03 | 3.59E-04 | 8.62E-03 |
| 68 | hsa-miR-526a | 8.24E+01 | 2.31E+02 | 3.57E-01 | -1.03E-00 | 4.46E-04 | 5.59E-03 | 3.11E-04 | 8.14E-03 |
| 69 | hsa-miR-26a-1* | 1.96E+01 | 1.00E-00 | 1.96E+01 | 2.97E-00 | 4.47E-04 | 5.59E-03 | 5.68E-03 | 5.33E-02 |
| 70 | hsa-miR-26a-2* | 1.00E-00 | 1.00E-00 | 1.00E-00 | 0.00E+01 | 4.74E-04 | 5.84E-03 | 1.52E-03 | 2.38E-02 |

FIG 13

| No. | miRNA | median g1 | median g2 | qmedian | logqmedian | ttest_rawp | ttest_adjp | Limma_rawp | Limma_adjp |
|---|---|---|---|---|---|---|---|---|---|
| 1 | hsa-let-7d | 1.69E+03 | 3.22E+03 | 5.24E-01 | -6.47E-01 | 3.54E-06 | 1.76E-03 | 1.47E-04 | 8.44E-03 |
| 2 | hsa-miR-146b-3p | 8.41E+01 | 1.87E+01 | 4.50E-00 | 1.51E-00 | 4.07E-06 | 1.76E-03 | 4.17E-05 | 4.00E-03 |
| 3 | hsa-miR-150 | 6.29E+02 | 2.21E+03 | 2.85E-01 | -1.25E-00 | 6.92E-06 | 1.99E-03 | 1.82E-04 | 9.03E-03 |
| 4 | hsa-miR-454* | 1.00E-00 | 4.22E+01 | 2.37E-02 | -3.74E-00 | 2.95E-05 | 6.37E-03 | 3.72E-06 | 5.35E-04 |
| 5 | hsa-miR-1248 | 1.00E-00 | 2.89E+01 | 3.46E-02 | -3.36E-00 | 6.03E-05 | 6.50E-03 | 9.00E-07 | 2.59E-04 |
| 6 | hsa-miR-133b | 1.00E-00 | 2.82E+01 | 3.54E-02 | -3.34E-00 | 4.40E-05 | 6.50E-03 | 1.05E-04 | 6.98E-03 |
| 7 | hsa-miR-610 | 1.14E+02 | 4.84E+01 | 2.35E-00 | 8.53E-01 | 4.58E-05 | 6.50E-03 | 1.61E-03 | 2.88E-02 |
| 8 | hsa-miR-148a | 1.43E+03 | 6.97E+02 | 2.05E-00 | 7.20E-01 | 5.77E-05 | 6.50E-03 | 4.07E-04 | 1.35E-02 |
| 9 | hsa-miR-888 | 1.06E+01 | 6.01E+01 | 1.76E-01 | -1.74E-00 | 7.86E-05 | 6.78E-03 | 1.57E-04 | 8.45E-03 |
| 10 | hsa-miR-519e* | 8.76E+01 | 1.35E+01 | 6.47E-00 | 1.87E-00 | 7.83E-05 | 6.78E-03 | 7.10E-05 | 5.11E-03 |
| 11 | hsa-miR-1288 | 3.75E+01 | 9.92E+01 | 3.78E-01 | -9.72E-01 | 8.79E-05 | 6.89E-03 | 2.05E-04 | 9.03E-03 |
| 12 | hsa-miR-655 | 1.00E-00 | 4.49E+01 | 2.23E-02 | -3.81E-00 | 1.34E-04 | 8.57E-03 | 1.09E-03 | 2.35E-02 |
| 13 | hsa-miR-302d* | 3.03E+01 | 8.09E+01 | 3.75E-01 | -9.82E-01 | 1.22E-04 | 8.57E-03 | 3.96E-03 | 4.82E-02 |
| 14 | hsa-miR-942 | 1.00E-00 | 4.45E+01 | 2.25E-02 | -3.79E-00 | 1.39E-04 | 8.57E-03 | 8.54E-06 | 1.05E-03 |
| 15 | hsa-miR-374b* | 1.60E+01 | 5.01E+01 | 3.19E-01 | -1.14E-00 | 1.61E-04 | 9.27E-03 | 4.71E-04 | 1.45E-02 |
| 16 | hsa-miR-605 | 1.00E-00 | 3.69E+01 | 2.71E-02 | -3.61E-00 | 1.74E-04 | 9.40E-03 | 2.50E-06 | 4.32E-04 |
| 17 | hsa-miR-10a* | 1.50E+01 | 5.22E+01 | 2.88E-01 | -1.25E-00 | 2.02E-04 | 1.03E-02 | 1.44E-02 | 9.40E-02 |
| 18 | hsa-miR-182 | 7.31E+03 | 3.79E+03 | 1.93E-00 | 6.57E-01 | 2.27E-04 | 1.09E-02 | 2.20E-04 | 9.03E-03 |

FIG 13 (continued)

| | | | | | | | | | |
|---|---|---|---|---|---|---|---|---|---|
| 19 | hsa-miR-148a* | 4.67E-00 | 3.50E+01 | 1.34E-01 | -2.01E-00 | 2.84E-04 | 1.22E-02 | 9.42E-04 | 2.14E-02 |
| 20 | hsa-miR-656 | 1.96E+01 | 6.70E+01 | 2.93E-01 | -1.23E-00 | 2.79E-04 | 1.22E-02 | 2.63E-03 | 3.85E-02 |
| 21 | hsa-miR-374a | 2.12E+02 | 6.29E+02 | 3.37E-01 | -1.09E-00 | 3.36E-04 | 1.38E-02 | 8.37E-02 | 2.50E-01 |
| 22 | hsa-miR-744* | 9.75E-00 | 6.72E+01 | 1.45E-01 | -1.93E-00 | 3.54E-04 | 1.39E-02 | 1.91E-03 | 3.11E-02 |
| 23 | hsa-miR-429 | 1.07E+01 | 5.35E+01 | 2.00E-01 | -1.61E-00 | 4.25E-04 | 1.43E-02 | 2.49E-04 | 9.78E-03 |
| 24 | hsa-miR-144* | 3.35E+02 | 9.97E+02 | 3.36E-01 | -1.09E-00 | 4.48E-04 | 1.43E-02 | 1.30E-02 | 9.33E-02 |
| 25 | hsa-miR-144 | 2.01E+03 | 3.62E+03 | 5.54E-01 | -5.90E-01 | 3.83E-04 | 1.43E-02 | 7.29E-03 | 6.71E-02 |
| 26 | hsa-miR-668 | 1.12E+01 | 6.07E+01 | 1.85E-01 | -1.69E-00 | 4.05E-04 | 1.43E-02 | 8.76E-03 | 7.50E-02 |
| 27 | hsa-miR-888* | 5.12E+01 | 1.34E+01 | 3.83E-00 | 1.34E-00 | 4.42E-04 | 1.43E-02 | 4.32E-04 | 1.38E-02 |
| 28 | hsa-miR-1259 | 1.00E-00 | 3.93E+01 | 2.55E-02 | -3.67E-00 | 5.82E-04 | 1.62E-02 | 1.28E-03 | 2.62E-02 |
| 29 | hsa-miR-29a | 9.97E+02 | 6.22E+02 | 1.60E-00 | 4.71E-01 | 6.01E-04 | 1.62E-02 | 5.47E-03 | 5.83E-02 |
| 30 | hsa-miR-194 | 6.93E+03 | 4.64E+03 | 1.49E-00 | 4.01E-01 | 5.68E-04 | 1.62E-02 | 6.64E-04 | 1.83E-02 |
| 31 | hsa-miR-1205 | 1.31E+02 | 6.63E+01 | 1.97E-00 | 6.80E-01 | 5.38E-04 | 1.62E-02 | 3.22E-03 | 4.23E-02 |
| 32 | hsa-miR-149* | 1.13E+03 | 3.54E+02 | 3.18E-00 | 1.16E-00 | 5.66E-04 | 1.62E-02 | 1.44E-03 | 2.75E-02 |
| 33 | hsa-miR-221* | 1.27E+02 | 7.33E+01 | 1.73E-00 | 5.48E-01 | 6.61E-04 | 1.73E-02 | 1.00E-02 | 8.10E-02 |
| 34 | hsa-miR-302d | 1.00E-00 | 1.43E+01 | 7.00E-02 | -2.66E-00 | 7.04E-04 | 1.79E-02 | 7.91E-04 | 1.95E-02 |
| 35 | hsa-miR-299-5p | 1.00E-00 | 3.21E+01 | 3.12E-02 | -3.47E-00 | 8.96E-04 | 1.84E-02 | 7.47E-04 | 1.90E-02 |
| 36 | hsa-miR-1908 | 1.33E+03 | 6.75E+02 | 1.97E-00 | 6.76E-01 | 9.34E-04 | 1.84E-02 | 8.86E-04 | 2.07E-02 |
| 37 | hsa-miR-573 | 7.30E+01 | 4.56E+01 | 1.60E-00 | 4.72E-01 | 7.99E-04 | 1.84E-02 | 1.20E-02 | 9.00E-02 |
| 38 | hsa-miR-877 | 4.74E+01 | 1.10E+02 | 4.31E-01 | -8.43E-01 | 9.16E-04 | 1.84E-02 | 4.40E-03 | 5.27E-02 |
| 39 | hsa-miR-212 | 5.58E+01 | 1.68E+01 | 3.32E-00 | 1.20E-00 | 9.36E-04 | 1.84E-02 | 6.34E-04 | 1.82E-02 |
| 40 | hsa-miR-130a* | 3.53E+01 | 1.07E+02 | 3.28E-01 | -1.11E-00 | 9.06E-04 | 1.84E-02 | 2.11E-04 | 9.03E-03 |

FIG 13 (continued)

| | | | | | | | | | |
|---|---|---|---|---|---|---|---|---|---|
| 41 | hsa-miR-551a | 6.08E+01 | 3.22E-00 | 1.89E+01 | 2.94E-00 | 8.98E-04 | 1.84E-02 | 3.53E-04 | 1.22E-02 |
| 42 | hsa-miR-936 | 8.31E+01 | 4.20E+01 | 1.98E-00 | 6.82E-01 | 7.49E-04 | 1.84E-02 | 3.02E-03 | 4.16E-02 |
| 43 | hsa-miR-1226 | 3.58E+01 | 9.45E+01 | 3.79E-01 | -9.71E-01 | 8.79E-04 | 1.84E-02 | 1.43E-01 | 3.49E-01 |
| 44 | hsa-miR-892b | 1.25E+01 | 4.20E+01 | 2.98E-01 | -1.21E-00 | 9.21E-04 | 1.84E-02 | 3.05E-04 | 1.14E-02 |
| 45 | hsa-miR-200a* | 4.47E+01 | 8.26E+01 | 5.41E-01 | -6.13E-01 | 9.95E-04 | 1.87E-02 | 3.24E-03 | 4.23E-02 |
| 46 | hsa-miR-519a* | 1.85E+02 | 1.03E+02 | 1.79E-00 | 5.85E-01 | 9.77E-04 | 1.87E-02 | 6.40E-03 | 6.42E-02 |
| 47 | hsa-miR-891a | 1.86E+02 | 6.86E+01 | 2.71E-00 | 9.95E-01 | 1.02E-03 | 1.88E-02 | 1.36E-03 | 2.67E-02 |
| 48 | hsa-miR-1287 | 5.86E+01 | 8.27E+01 | 7.09E-01 | -3.44E-01 | 1.25E-03 | 2.07E-02 | 9.03E-03 | 7.57E-02 |
| 49 | hsa-miR-770-5p | 9.61E+01 | 4.03E+01 | 2.38E-00 | 8.69E-01 | 1.25E-03 | 2.07E-02 | 3.33E-03 | 4.23E-02 |
| 50 | hsa-miR-363* | 9.79E+01 | 5.89E+01 | 1.66E-00 | 5.09E-01 | 1.23E-03 | 2.07E-02 | 1.92E-02 | 1.13E-01 |
| 51 | hsa-miR-302c | 1.00E-00 | 1.12E+01 | 8.89E-02 | -2.42E-00 | 1.21E-03 | 2.07E-02 | 2.20E-05 | 2.37E-03 |
| 52 | hsa-miR-218-1* | 5.00E+01 | 8.94E+01 | 5.59E-01 | -5.82E-01 | 1.20E-03 | 2.07E-02 | 2.02E-01 | 4.28E-01 |
| 53 | hsa-miR-541 | 1.03E+02 | 6.34E+01 | 1.62E-00 | 4.85E-01 | 1.36E-03 | 2.21E-02 | 1.48E-02 | 9.47E-02 |
| 54 | hsa-miR-500* | 3.25E+02 | 2.01E+02 | 1.62E-00 | 4.80E-01 | 1.50E-03 | 2.34E-02 | 2.65E-02 | 1.30E-01 |
| 55 | hsa-miR-485-3p | 3.73E+01 | 7.41E+01 | 5.04E-01 | -6.85E-01 | 1.52E-03 | 2.34E-02 | 8.07E-03 | 7.10E-02 |
| 56 | hsa-miR-21* | 1.29E+02 | 7.73E+01 | 1.67E-00 | 5.11E-01 | 1.52E-03 | 2.34E-02 | 1.06E-02 | 8.42E-02 |
| 57 | hsa-miR-662 | 4.64E+01 | 7.47E+01 | 6.21E-01 | -4.76E-01 | 1.58E-03 | 2.40E-02 | 3.65E-02 | 1.55E-01 |
| 58 | hsa-miR-506 | 1.48E+01 | 5.16E+01 | 2.86E-01 | -1.25E-00 | 1.66E-03 | 2.44E-02 | 5.21E-03 | 5.62E-02 |
| 59 | hsa-miR-1200 | 9.49E+01 | 5.35E+01 | 1.77E-00 | 5.73E-01 | 1.67E-03 | 2.44E-02 | 1.45E-02 | 9.40E-02 |
| 60 | hsa-miR-22 | 9.81E+03 | 6.93E+03 | 1.42E-00 | 3.48E-01 | 1.74E-03 | 2.50E-02 | 1.59E-02 | 9.86E-02 |

FIG 13 (continued)

| | | | | | | | | | |
|---|---|---|---|---|---|---|---|---|---|
| 61 | hsa-miR-101 | 4.56E+02 | 8.00E+02 | 5.70E-01 | -5.62E-01 | 1.77E-03 | 2.51E-02 | 3.23E-03 | 4.23E-02 |
| 62 | hsa-miR-129* | 3.08E+01 | 5.16E+01 | 5.97E-01 | -5.16E-01 | 1.86E-03 | 2.55E-02 | 1.17E-02 | 8.89E-02 |
| 63 | hsa-miR-224 | 5.92E+01 | 6.68E-00 | 8.85E-00 | 2.18E-00 | 1.86E-03 | 2.55E-02 | 6.29E-05 | 4.94E-03 |
| 64 | hsa-miR-371-5p | 5.52E+01 | 2.25E+01 | 2.45E-00 | 8.97E-01 | 2.06E-03 | 2.78E-02 | 1.38E-02 | 9.34E-02 |
| 65 | hsa-miR-106a | 6.23E+03 | 9.81E+03 | 6.35E-01 | -4.54E-01 | 2.20E-03 | 2.91E-02 | 7.36E-03 | 6.71E-02 |
| 66 | hsa-miR-647 | 8.59E+01 | 2.16E+01 | 3.97E-00 | 1.38E-00 | 2.22E-03 | 2.91E-02 | 1.65E-03 | 2.88E-02 |
| 67 | hsa-miR-219-1-3p | 1.00E-00 | 2.33E+01 | 4.29E-02 | -3.15E-00 | 2.28E-03 | 2.94E-02 | 6.97E-04 | 1.83E-02 |
| 68 | hsa-miR-519c-5p | 2.04E+02 | 9.47E+01 | 2.16E-00 | 7.69E-01 | 2.45E-03 | 2.94E-02 | 1.35E-02 | 9.34E-02 |
| 69 | hsa-miR-330-5p | 9.20E-00 | 2.87E+01 | 3.21E-01 | -1.14E-00 | 2.39E-03 | 2.94E-02 | 1.64E-02 | 9.91E-02 |
| 70 | hsa-miR-450a | 6.60E-00 | 3.34E+01 | 1.98E-01 | -1.62E-00 | 2.44E-03 | 2.94E-02 | 1.70E-03 | 2.88E-02 |

FIG 14

| SEQ ID NO | miRNA | median g1 | median g2 | qmedian | logqmedian | Wmw_rawp | Wmw_adjp | Ttest_rawp | Ttest_adjp | AUC |
|---|---|---|---|---|---|---|---|---|---|---|
| SEQ ID NO: 714 | hsa-miR-144* | 784 | 236 | 3.32 | 1.20 | 6.98E-07 | 3.08E-04 | 1.53E-08 | 1.30E-05 | 0.84 |
| SEQ ID NO: 709 | hsa-miR-146a | 189 | 83 | 2.28 | 0.82 | 1.76E-06 | 4.86E-04 | 4.12E-08 | 1.75E-05 | 0.83 |
| SEQ ID NO: 684 | hsa-miR-155 | 85 | 45 | 1.89 | 0.64 | 2.70E-05 | 1.64E-03 | 2.44E-07 | 6.89E-05 | 0.79 |
| SEQ ID NO: 530 | hsa-miR-23b* | 18 | 1 | 18.17 | 2.90 | 1.23E-04 | 3.51E-03 | 3.30E-07 | 7.00E-05 | 0.75 |
| SEQ ID NO: 442 | hsa-miR-342-3p | 3920 | 2168 | 1.81 | 0.59 | 3.46E-05 | 1.87E-03 | 1.57E-06 | 2.21E-04 | 0.78 |
| SEQ ID NO: 92 | hsa-miR-660 | 457 | 181 | 2.53 | 0.93 | 3.61E-05 | 1.87E-03 | 1.57E-06 | 2.21E-04 | 0.78 |
| SEQ ID NO: 874 | hsa-miR-106b | 11866 | 6240 | 1.90 | 0.64 | 2.00E-05 | 1.64E-03 | 1.83E-06 | 2.21E-04 | 0.79 |
| SEQ ID NO: 403 | hsa-miR-378 | 235 | 129 | 1.82 | 0.60 | 1.60E-04 | 3.98E-03 | 2.62E-06 | 2.77E-04 | 0.76 |
| SEQ ID NO: 127 | hsa-miR-628-3p | 173 | 111 | 1.56 | 0.45 | 2.61E-04 | 5.82E-03 | 3.65E-06 | 3.42E-04 | 0.75 |
| SEQ ID NO: 897 | hsa-let-7d | 2332 | 1410 | 1.65 | 0.50 | 1.04E-04 | 3.28E-03 | 4.04E-06 | 3.42E-04 | 0.76 |
| SEQ ID NO: 395 | hsa-miR-383 | 56 | 90 | 0.63 | -0.47 | 6.71E-06 | 1.14E-03 | 5.34E-06 | 4.12E-04 | 0.19 |
| SEQ ID NO: 573 | hsa-miR-210 | 751 | 390 | 1.92 | 0.65 | 5.15E-05 | 2.19E-03 | 9.50E-06 | 6.71E-04 | 0.78 |
| SEQ ID NO: 393 | hsa-miR-409-3p | 28 | 1 | 28.29 | 3.34 | 2.12E-04 | 5.14E-03 | 1.04E-05 | 6.78E-04 | 0.75 |

FIG 14 (continued)

| | | | | | | | | | | |
|---|---|---|---|---|---|---|---|---|---|---|
| SEQ ID NO: 441 | hsa-miR-342-5p | 123 | 31 | 3.98 | 1.38 | 2.16E-05 | 1.64E-03 | 1.44E-05 | 8.15E-04 | 0.79 |
| SEQ ID NO: 382 | hsa-miR-424* | 127 | 87 | 1.47 | 0.38 | 1.84E-03 | 2.21E-02 | 1.44E-05 | 8.15E-04 | 0.71 |
| SEQ ID NO: 520 | hsa-miR-26b* | 3 | 1 | 2.85 | 1.05 | 6.37E-04 | 1.15E-02 | 1.84E-05 | 9.74E-04 | 0.71 |
| SEQ ID NO: 97 | hsa-miR-655 | 22 | 3 | 6.96 | 1.94 | 8.28E-03 | 5.05E-02 | 2.96E-05 | 1.48E-03 | 0.68 |
| SEQ ID NO: 542 | hsa-miR-222 | 489 | 261 | 1.87 | 0.63 | 3.74E-05 | 1.87E-03 | 3.63E-05 | 1.71E-03 | 0.78 |
| SEQ ID NO: 11 | hsa-miR-942 | 7 | 1 | 6.65 | 1.89 | 1.10E-02 | 6.08E-02 | 4.54E-05 | 2.03E-03 | 0.66 |
| SEQ ID NO: 87 | hsa-miR-664 | 262 | 118 | 2.22 | 0.80 | 1.27E-03 | 1.74E-02 | 6.13E-05 | 2.60E-03 | 0.72 |
| SEQ ID NO: 883 | hsa-miR-101 | 666 | 359 | 1.86 | 0.62 | 1.28E-05 | 1.47E-03 | 6.47E-05 | 2.61E-03 | 0.80 |
| SEQ ID NO: 892 | hsa-let-7f-1* | 28 | 12 | 2.33 | 0.85 | 3.44E-03 | 3.02E-02 | 8.41E-05 | 2.89E-03 | 0.70 |
| SEQ ID NO: 350 | hsa-miR-486-5p | 38028 | 38028 | 1.00 | 0.00 | 1.38E-02 | 6.89E-02 | 8.37E-05 | 2.89E-03 | 0.39 |
| SEQ ID NO: 154 | hsa-miR-605 | 14 | 1 | 14.45 | 2.67 | 1.20E-03 | 1.69E-02 | 7.62E-05 | 2.89E-03 | 0.71 |
| SEQ ID NO: 671 | hsa-miR-181a-2* | 96 | 66 | 1.46 | 0.38 | 3.06E-03 | 2.85E-02 | 8.53E-05 | 2.89E-03 | 0.70 |
| SEQ ID NO: 658 | hsa-miR-185 | 28729 | 19766 | 1.45 | 0.37 | 7.39E-04 | 1.21E-02 | 1.09E-04 | 3.31E-03 | 0.73 |

FIG 14 (continued)

| | | | | | | | | | | |
|---|---|---|---|---|---|---|---|---|---|---|
| SEQ ID NO: 284 | hsa-miR-518f | 58 | 73 | 0.79 | -0.24 | 7.23E-04 | 1.21E-02 | 1.06E-04 | 3.31E-03 | 0.27 |
| SEQ ID NO: 466 | hsa-miR-324-3p | 682 | 482 | 1.42 | 0.35 | 1.29E-03 | 1.74E-02 | 1.09E-04 | 3.31E-03 | 0.72 |
| SEQ ID NO: 455 | hsa-miR-335* | 1 | 1 | 1.00 | 0.00 | 2.54E-03 | 2.56E-02 | 1.68E-04 | 4.90E-03 | 0.67 |
| SEQ ID NO: 706 | hsa-miR-146b-5p | 115 | 77 | 1.50 | 0.40 | 1.35E-03 | 1.79E-02 | 2.28E-04 | 6.44E-03 | 0.72 |
| SEQ ID NO: 762 | hsa-miR-1295 | 104 | 145 | 0.72 | -0.33 | 6.05E-05 | 2.33E-03 | 2.53E-04 | 6.92E-03 | 0.23 |
| SEQ ID NO: 436 | hsa-miR-34b | 36 | 21 | 1.72 | 0.54 | 6.11E-03 | 4.18E-02 | 2.62E-04 | 6.95E-03 | 0.69 |
| SEQ ID NO: 170 | hsa-miR-590-3p | 5 | 1 | 4.61 | 1.53 | 1.87E-03 | 2.21E-02 | 2.72E-04 | 6.99E-03 | 0.70 |
| SEQ ID NO: 336 | hsa-miR-495 | 72 | 47 | 1.53 | 0.43 | 1.92E-03 | 2.21E-02 | 3.28E-04 | 7.94E-03 | 0.71 |
| SEQ ID NO: 378 | hsa-miR-431 | 151 | 213 | 0.71 | -0.34 | 7.32E-05 | 2.59E-03 | 3.29E-04 | 7.94E-03 | 0.23 |
| SEQ ID NO: 366 | hsa-miR-450b-3p | 28 | 10 | 2.68 | 0.99 | 4.71E-03 | 3.57E-02 | 3.37E-04 | 7.94E-03 | 0.69 |
| SEQ ID NO: 187 | hsa-miR-576-3p | 1 | 1 | 1.00 | 0.00 | 2.53E-02 | 1.01E-01 | 4.08E-04 | 9.36E-03 | 0.63 |
| SEQ ID NO: 234 | hsa-miR-548c-3p | 35 | 20 | 1.75 | 0.56 | 4.96E-03 | 3.63E-02 | 4.85E-04 | 9.44E-03 | 0.69 |
| SEQ ID NO: 838 | hsa-miR-1228* | 1082 | 2148 | 0.50 | -0.69 | 7.27E-07 | 3.08E-04 | 4.56E-04 | 9.44E-03 | 0.16 |

FIG 14 (continued)

| | | | | | | | | | | |
|---|---|---|---|---|---|---|---|---|---|---|
| SEQ ID NO: 199 | hsa-miR-564 | 146 | 212 | 0.69 | -0.37 | 1.39E-05 | 1.47E-03 | 4.77E-04 | 9.44E-03 | 0.20 |
| SEQ ID NO: 431 | hsa-miR-361-5p | 400 | 273 | 1.46 | 0.38 | 3.31E-03 | 2.99E-02 | 4.71E-04 | 9.44E-03 | 0.70 |
| SEQ ID NO: 456 | hsa-miR-335 | 419 | 291 | 1.44 | 0.36 | 4.89E-04 | 1.01E-02 | 4.90E-04 | 9.44E-03 | 0.74 |
| SEQ ID NO: 646 | hsa-miR-190 | 1 | 1 | 1.00 | 0.00 | 5.04E-03 | 3.66E-02 | 4.38E-04 | 9.44E-03 | 0.66 |
| SEQ ID NO: 715 | hsa-miR-144 | 2387 | 1304 | 1.83 | 0.60 | 1.97E-03 | 2.21E-02 | 4.61E-04 | 9.44E-03 | 0.71 |
| SEQ ID NO: 544 | hsa-miR-221 | 96 | 64 | 1.51 | 0.42 | 7.96E-04 | 1.25E-02 | 5.04E-04 | 9.50E-03 | 0.73 |
| SEQ ID NO: 277 | hsa-miR-519c-5p | 115 | 176 | 0.65 | -0.43 | 8.57E-04 | 1.30E-02 | 5.37E-04 | 9.90E-03 | 0.27 |
| SEQ ID NO: 75 | hsa-miR-7-1* | 293 | 158 | 1.86 | 0.62 | 6.65E-04 | 1.17E-02 | 5.56E-04 | 1.00E-02 | 0.73 |
| SEQ ID NO: 353 | hsa-miR-485-3p | 62 | 40 | 1.55 | 0.44 | 1.40E-02 | 6.89E-02 | 6.08E-04 | 1.07E-02 | 0.67 |
| SEQ ID NO: 802 | hsa-miR-1261 | 1 | 1 | 1.00 | 0.00 | 1.33E-01 | 3.06E-01 | 7.14E-04 | 1.24E-02 | 0.59 |
| SEQ ID NO: 444 | hsa-miR-340 | 164 | 107 | 1.53 | 0.42 | 3.83E-03 | 3.22E-02 | 7.63E-04 | 1.25E-02 | 0.70 |
| SEQ ID NO: 645 | hsa-miR-1908 | 867 | 1640 | 0.53 | -0.64 | 2.46E-05 | 1.64E-03 | 7.60E-04 | 1.25E-02 | 0.21 |
| SEQ ID NO: 89 | hsa-miR-663 | 272 | 491 | 0.55 | -0.59 | 9.80E-05 | 3.20E-03 | 7.66E-04 | 1.25E-02 | 0.23 |

FIG 14 (continued)

| | | | | | | | | | | |
|---|---|---|---|---|---|---|---|---|---|---|
| SEQ ID NO: 253 | hsa-miR-526a | 140 | 206 | 0.68 | -0.39 | 8.70E-05 | 2.95E-03 | 8.17E-04 | 1.28E-02 | 0.23 |
| SEQ ID NO: 76 | hsa-miR-708* | 65 | 81 | 0.81 | -0.22 | 3.27E-03 | 2.98E-02 | 8.12E-04 | 1.28E-02 | 0.30 |
| SEQ ID NO: 669 | hsa-miR-181c | 127 | 69 | 1.85 | 0.61 | 1.24E-04 | 3.51E-03 | 8.74E-04 | 1.35E-02 | 0.76 |
| SEQ ID NO: 733 | hsa-miR-135b | 1 | 1 | 1.00 | 0.00 | 8.26E-03 | 5.05E-02 | 9.28E-04 | 1.41E-02 | 0.63 |
| SEQ ID NO: 698 | hsa-miR-148b* | 28 | 15 | 1.88 | 0.63 | 2.12E-02 | 8.97E-02 | 9.93E-04 | 1.48E-02 | 0.66 |
| SEQ ID NO: 770 | hsa-miR-1289 | 92 | 124 | 0.74 | -0.31 | 4.40E-05 | 1.96E-03 | 1.10E-03 | 1.61E-02 | 0.22 |
| SEQ ID NO: 673 | hsa-miR-181a | 516 | 151 | 3.43 | 1.23 | 2.29E-06 | 4.86E-04 | 1.21E-03 | 1.63E-02 | 0.82 |
| SEQ ID NO: 264 | hsa-miR-520g | 42 | 21 | 2.02 | 0.71 | 4.93E-03 | 3.63E-02 | 1.15E-03 | 1.63E-02 | 0.69 |
| SEQ ID NO: 33 | hsa-miR-9 | 1 | 1 | 1.00 | 0.00 | 1.08E-01 | 2.69E-01 | 1.13E-03 | 1.63E-02 | 0.60 |
| SEQ ID NO: 773 | hsa-miR-1286 | 118 | 200 | 0.59 | -0.53 | 4.53E-04 | 9.85E-03 | 1.20E-03 | 1.63E-02 | 0.26 |
| SEQ ID NO: 779 | hsa-miR-1280 | 3117 | 6387 | 0.49 | -0.72 | 1.82E-05 | 1.64E-03 | 1.21E-03 | 1.63E-02 | 0.21 |
| SEQ ID NO: 226 | hsa-miR-548i | 1 | 1 | 1.00 | 0.00 | 2.17E-02 | 9.07E-02 | 1.41E-03 | 1.87E-02 | 0.63 |
| SEQ ID NO: 641 | hsa-miR-191 | 10739 | 15660 | 0.69 | -0.38 | 7.63E-04 | 1.22E-02 | 1.52E-03 | 1.92E-02 | 0.27 |

FIG 14 (continued)

| | | | | | | | | | | |
|---|---|---|---|---|---|---|---|---|---|---|
| SEQ ID NO: 186 | hsa-miR-576-5p | 1 | 1 | 1.00 | 0.00 | 4.58E-02 | 1.54E-01 | 1.50E-03 | 1.92E-02 | 0.59 |
| SEQ ID NO: 632 | hsa-miR-1915 | 560 | 957 | 0.59 | -0.54 | 4.39E-05 | 1.96E-03 | 1.50E-03 | 1.92E-02 | 0.22 |
| SEQ ID NO: 17 | hsa-miR-936 | 66 | 90 | 0.73 | -0.31 | 2.36E-03 | 2.47E-02 | 1.69E-03 | 2.10E-02 | 0.29 |
| SEQ ID NO: 184 | hsa-miR-578 | 1 | 1 | 1.00 | 0.00 | 2.25E-02 | 9.26E-02 | 1.71E-03 | 2.10E-02 | 0.64 |
| SEQ ID NO: 388 | hsa-miR-412 | 40 | 30 | 1.30 | 0.26 | 4.13E-02 | 1.42E-01 | 1.80E-03 | 2.13E-02 | 0.64 |
| SEQ ID NO: 678 | hsa-miR-16 | 17346 | 19766 | 0.88 | -0.13 | 2.66E-03 | 2.59E-02 | 1.84E-03 | 2.13E-02 | 0.30 |
| SEQ ID NO: 189 | hsa-miR-574-5p | 682 | 2137 | 0.32 | -1.14 | 8.79E-06 | 1.24E-03 | 1.82E-03 | 2.13E-02 | 0.20 |
| SEQ ID NO: 281 | hsa-miR-519a* | 131 | 171 | 0.77 | -0.27 | 8.57E-04 | 1.30E-02 | 1.83E-03 | 2.13E-02 | 0.27 |
| SEQ ID NO: 22 | hsa-miR-93 | 3723 | 2693 | 1.38 | 0.32 | 2.02E-03 | 2.21E-02 | 1.86E-03 | 2.13E-02 | 0.71 |
| SEQ ID NO: 422 | hsa-miR-369-3p | 12 | 1 | 12.18 | 2.50 | 2.43E-03 | 2.48E-02 | 1.95E-03 | 2.15E-02 | 0.70 |
| SEQ ID NO: 572 | hsa-miR-211 | 1 | 1 | 1.00 | 0.00 | 1.91E-02 | 8.35E-02 | 1.91E-03 | 2.15E-02 | 0.61 |
| SEQ ID NO: 134 | hsa-miR-623 | 48 | 73 | 0.66 | -0.42 | 1.02E-03 | 1.47E-02 | 1.92E-03 | 2.15E-02 | 0.28 |
| SEQ ID NO: 232 | hsa-miR-548d-3p | 45 | 33 | 1.38 | 0.32 | 4.72E-02 | 1.57E-01 | 2.00E-03 | 2.18E-02 | 0.64 |
| SEQ ID NO: 846 | hsa-miR-1224-3p | 94 | 55 | 1.71 | 0.54 | 3.62E-03 | 3.07E-02 | 2.09E-03 | 2.22E-02 | 0.70 |

FIG 14 (continued)

| | | | | | | | | | | |
|---|---|---|---|---|---|---|---|---|---|---|
| SEQ ID NO: 148 | hsa-miR-611 | 100 | 126 | 0.79 | -0.24 | 1.41E-03 | 1.81E-02 | 2.09E-03 | 2.22E-02 | 0.28 |
| SEQ ID NO: 273 | hsa-miR-520a-3p | 1 | 1 | 1.00 | 0.00 | 1.42E-02 | 6.89E-02 | 2.24E-03 | 2.35E-02 | 0.64 |
| SEQ ID NO: 514 | hsa-miR-28-5p | 362 | 219 | 1.65 | 0.50 | 5.05E-04 | 1.02E-02 | 2.28E-03 | 2.36E-02 | 0.74 |
| SEQ ID NO: 527 | hsa-miR-24-2* | 147 | 117 | 1.25 | 0.23 | 5.85E-02 | 1.78E-01 | 2.33E-03 | 2.39E-02 | 0.63 |
| SEQ ID NO: 34 | hsa-miR-892b | 27 | 14 | 1.87 | 0.63 | 3.15E-02 | 1.18E-01 | 2.60E-03 | 2.43E-02 | 0.65 |
| SEQ ID NO: 793 | hsa-miR-1270 | 27 | 5 | 4.84 | 1.58 | 2.06E-02 | 8.76E-02 | 2.60E-03 | 2.43E-02 | 0.66 |
| SEQ ID NO: 515 | hsa-miR-28-3p | 164 | 111 | 1.48 | 0.39 | 6.57E-03 | 4.35E-02 | 2.52E-03 | 2.43E-02 | 0.69 |
| SEQ ID NO: 710 | hsa-miR-1469 | 145 | 215 | 0.68 | -0.39 | 2.66E-05 | 1.64E-03 | 2.53E-03 | 2.43E-02 | 0.21 |
| SEQ ID NO: 805 | hsa-miR-126 | 1983 | 652 | 3.04 | 1.11 | 1.39E-04 | 3.59E-03 | 2.59E-03 | 2.43E-02 | 0.76 |
| SEQ ID NO: 81 | hsa-miR-671-5p | 57 | 68 | 0.85 | -0.17 | 1.55E-02 | 7.34E-02 | 2.60E-03 | 2.43E-02 | 0.33 |
| SEQ ID NO: 700 | hsa-miR-148a* | 22 | 10 | 2.16 | 0.77 | 2.38E-02 | 9.53E-02 | 2.55E-03 | 2.43E-02 | 0.65 |
| SEQ ID NO: 267 | hsa-miR-520d-5p | 46 | 64 | 0.72 | -0.33 | 7.70E-03 | 4.84E-02 | 2.50E-03 | 2.43E-02 | 0.32 |
| SEQ ID NO: 561 | hsa-miR-214 | 264 | 498 | 0.53 | -0.64 | 2.22E-04 | 5.22E-03 | 2.75E-03 | 2.53E-02 | 0.25 |
| SEQ ID NO: 803 | hsa-miR-1260 | 2277 | 3544 | 0.64 | -0.44 | 4.79E-04 | 1.01E-02 | 2.83E-03 | 2.58E-02 | 0.26 |

FIG 14 (continued)

| | | | | | | | | | | |
|---|---|---|---|---|---|---|---|---|---|---|
| SEQ ID NO: 901 | hsa-let-7b | 861 | 600 | 1.43 | 0.36 | 2.28E-02 | 9.26E-02 | 2.88E-03 | 2.60E-02 | 0.66 |
| SEQ ID NO: 647 | hsa-miR-18b* | 72 | 93 | 0.77 | -0.26 | 1.69E-03 | 2.14E-02 | 2.91E-03 | 2.60E-02 | 0.29 |
| SEQ ID NO: 157 | hsa-miR-602 | 100 | 145 | 0.69 | -0.37 | 1.29E-03 | 1.74E-02 | 2.99E-03 | 2.62E-02 | 0.28 |
| SEQ ID NO: 888 | hsa-let-7i | 578 | 221 | 2.62 | 0.96 | 2.60E-03 | 2.56E-02 | 2.99E-03 | 2.62E-02 | 0.71 |
| SEQ ID NO: 56 | hsa-miR-770-5p | 51 | 72 | 0.71 | -0.34 | 4.72E-03 | 3.57E-02 | 3.30E-03 | 2.83E-02 | 0.31 |
| SEQ ID NO: 227 | hsa-miR-548h | 2 | 1 | 1.65 | 0.50 | 3.73E-02 | 1.35E-01 | 3.30E-03 | 2.83E-02 | 0.63 |
| SEQ ID NO: 841 | hsa-miR-1226* | 162 | 260 | 0.62 | -0.48 | 1.40E-04 | 3.59E-03 | 3.48E-03 | 2.95E-02 | 0.24 |
| SEQ ID NO: 598 | hsa-miR-19b-2* | 1 | 1 | 1.00 | 0.00 | 1.15E-01 | 2.81E-01 | 3.53E-03 | 2.96E-02 | 0.60 |
| SEQ ID NO: 347 | hsa-miR-488 | 1 | 1 | 1.00 | 0.00 | 3.87E-01 | 5.69E-01 | 3.72E-03 | 3.07E-02 | 0.55 |
| SEQ ID NO: 816 | hsa-miR-1255a | 45 | 77 | 0.59 | -0.53 | 3.46E-03 | 3.02E-02 | 3.73E-03 | 3.07E-02 | 0.30 |
| SEQ ID NO: 231 | hsa-miR-548d-5p | 1 | 1 | 1.00 | 0.00 | 4.02E-02 | 1.40E-01 | 3.79E-03 | 3.09E-02 | 0.61 |
| SEQ ID NO: 352 | hsa-miR-485-5p | 39 | 65 | 0.60 | -0.51 | 2.14E-03 | 2.27E-02 | 3.83E-03 | 3.09E-02 | 0.29 |
| SEQ ID NO: 498 | hsa-miR-301b | 180 | 261 | 0.69 | -0.37 | 2.40E-04 | 5.51E-03 | 3.90E-03 | 3.12E-02 | 0.25 |

FIG 14 (continued)

| | | | | | | | | | | |
|---|---|---|---|---|---|---|---|---|---|---|
| SEQ ID NO: 69 | hsa-miR-744* | 33 | 18 | 1.83 | 0.60 | 1.63E-02 | 7.49E-02 | 3.93E-03 | 3.12E-02 | 0.66 |
| SEQ ID NO: 461 | hsa-miR-329 | 59 | 39 | 1.51 | 0.41 | 7.62E-03 | 4.82E-02 | 4.13E-03 | 3.25E-02 | 0.68 |
| SEQ ID NO: 696 | hsa-miR-149* | 526 | 1178 | 0.45 | -0.81 | 5.88E-04 | 1.11E-02 | 4.25E-03 | 3.30E-02 | 0.27 |
| SEQ ID NO: 39 | hsa-miR-889 | 30 | 23 | 1.27 | 0.24 | 4.86E-02 | 1.60E-01 | 4.32E-03 | 3.33E-02 | 0.63 |
| SEQ ID NO: 152 | hsa-miR-607 | 73 | 64 | 1.15 | 0.14 | 2.89E-02 | 1.11E-01 | 4.53E-03 | 3.46E-02 | 0.65 |
| SEQ ID NO: 648 | hsa-miR-18b | 195 | 117 | 1.66 | 0.51 | 4.43E-03 | 3.46E-02 | 4.75E-03 | 3.59E-02 | 0.69 |
| SEQ ID NO: 683 | hsa-miR-155* | 50 | 39 | 1.29 | 0.25 | 7.77E-02 | 2.19E-01 | 4.78E-03 | 3.59E-02 | 0.62 |
| SEQ ID NO: 315 | hsa-miR-509-3-5p | 211 | 424 | 0.50 | -0.70 | 6.95E-04 | 1.20E-02 | 4.83E-03 | 3.60E-02 | 0.27 |
| SEQ ID NO: 642 | hsa-miR-190b | 1 | 1 | 1.00 | 0.00 | 2.56E-02 | 1.01E-01 | 4.96E-03 | 3.66E-02 | 0.63 |
| SEQ ID NO: 397 | hsa-miR-381 | 82 | 101 | 0.81 | -0.21 | 6.17E-03 | 4.18E-02 | 5.16E-03 | 3.77E-02 | 0.31 |
| SEQ ID NO: 487 | hsa-miR-30a | 298 | 162 | 1.84 | 0.61 | 8.71E-03 | 5.10E-02 | 5.31E-03 | 3.85E-02 | 0.68 |
| SEQ ID NO: 703 | hsa-miR-1471 | 110 | 133 | 0.82 | -0.20 | 2.39E-03 | 2.48E-02 | 5.44E-03 | 3.91E-02 | 0.29 |
| SEQ ID NO: 414 | hsa-miR-374a | 262 | 119 | 2.21 | 0.79 | 5.37E-04 | 1.05E-02 | 5.50E-03 | 3.92E-02 | 0.74 |

FIG 14 (continued)

| | | | | | | | | | | |
|---|---|---|---|---|---|---|---|---|---|---|
| SEQ ID NO: 483 | hsa-miR-30c | 1807 | 2824 | 0.64 | -0.45 | 9.59E-04 | 1.40E-02 | 5.57E-03 | 3.94E-02 | 0.27 |
| SEQ ID NO: 529 | hsa-miR-24 | 1807 | 1177 | 1.54 | 0.43 | 7.14E-03 | 4.55E-02 | 5.83E-03 | 4.09E-02 | 0.68 |
| SEQ ID NO: 864 | hsa-miR-1181 | 169 | 205 | 0.82 | -0.19 | 2.16E-02 | 9.07E-02 | 6.28E-03 | 4.37E-02 | 0.34 |
| SEQ ID NO: 183 | hsa-miR-579 | 25 | 12 | 2.05 | 0.72 | 1.80E-02 | 8.06E-02 | 6.35E-03 | 4.37E-02 | 0.66 |
| SEQ ID NO: 4 | hsa-miR-99a | 108 | 76 | 1.42 | 0.35 | 1.94E-02 | 8.35E-02 | 6.56E-03 | 4.48E-02 | 0.66 |
| SEQ ID NO: 850 | hsa-miR-1207-5p | 377 | 764 | 0.49 | -0.71 | 6.25E-04 | 1.15E-02 | 7.05E-03 | 4.60E-02 | 0.27 |
| SEQ ID NO: 740 | hsa-miR-1323 | 33 | 10 | 3.45 | 1.24 | 6.16E-03 | 4.18E-02 | 6.81E-03 | 4.60E-02 | 0.69 |
| SEQ ID NO: 146 | hsa-miR-613 | 1 | 1 | 1.00 | 0.00 | 1.90E-01 | 3.75E-01 | 7.05E-03 | 4.60E-02 | 0.58 |
| SEQ ID NO: 588 | hsa-miR-204 | 1 | 1 | 1.00 | 0.00 | 5.58E-02 | 1.75E-01 | 7.05E-03 | 4.60E-02 | 0.58 |
| SEQ ID NO: 523 | hsa-miR-26a-1* | 4 | 1 | 4.10 | 1.41 | 9.09E-02 | 2.41E-01 | 7.05E-03 | 4.60E-02 | 0.61 |
| SEQ ID NO: 246 | hsa-miR-541 | 96 | 121 | 0.79 | -0.23 | 1.12E-02 | 6.13E-02 | 7.03E-03 | 4.60E-02 | 0.33 |
| SEQ ID NO: 478 | hsa-miR-30e | 242 | 62 | 3.90 | 1.36 | 5.83E-05 | 2.33E-03 | 7.37E-03 | 4.77E-02 | 0.77 |
| SEQ ID NO: 165 | hsa-miR-593* | 259 | 451 | 0.58 | -0.55 | 1.33E-04 | 3.59E-03 | 7.84E-03 | 4.93E-02 | 0.24 |
| SEQ ID NO: 699 | hsa-miR-148b | 596 | 451 | 1.32 | 0.28 | 1.66E-02 | 7.55E-02 | 7.83E-03 | 4.93E-02 | 0.66 |

FIG 14 (continued)

| | | | | | | | | | | |
|---|---|---|---|---|---|---|---|---|---|---|
| SEQ ID NO: 41 | hsa-miR-888 | 46 | 17 | 2.75 | 1.01 | 1.05E-01 | 2.66E-01 | 7.84E-03 | 4.93E-02 | 0.61 |
| SEQ ID NO: 430 | hsa-miR-362-3p | 197 | 113 | 1.75 | 0.56 | 2.00E-03 | 2.21E-02 | 7.82E-03 | 4.93E-02 | 0.71 |
| SEQ ID NO: 861 | hsa-miR-1184 | 209 | 432 | 0.48 | -0.73 | 3.88E-03 | 3.23E-02 | 7.91E-03 | 4.93E-02 | 0.30 |

FIG 15

| Signature | SEQ-ID NOs | miRNA -identifiers | Acc | Spec | Sens |
|---|---|---|---|---|---|
| SNO-1 | SEQ ID NO: 714, SEQ ID NO: 709 | hsa-miR-144*, hsa-miR-146a | 78.8% | 79.3% | 78.3% |
| SNO-2 | SEQ ID NO: 709, SEQ ID NO: 684 | hsa-miR-146a, hsa-miR-155 | 63.8% | 61.3% | 66.2% |
| SNO-3 | SEQ ID NO: 684, SEQ ID NO: 530 | hsa-miR-155, hsa-miR-23b* | 73.5% | 69.2% | 77.8% |
| SNO-4 | SEQ ID NO: 530, SEQ ID NO: 442 | hsa-miR-23b*, hsa-miR-342-3p | 74.2% | 65.2% | 83.2% |
| SNO-5 | SEQ ID NO: 442, SEQ ID NO: 92 | hsa-miR-342-3p, hsa-miR-660 | 76.5% | 71.2% | 81.8% |
| SNO-6 | SEQ ID NO: 92, SEQ ID NO: 874 | hsa-miR-660, hsa-miR-106b | 62.8% | 66.5% | 59.2% |
| SNO-7 | SEQ ID NO: 874, SEQ ID NO: 403 | hsa-miR-106b, hsa-miR-378 | 65.2% | 64.8% | 65.5% |
| SNO-8 | SEQ ID NO: 403, SEQ ID NO: 127 | hsa-miR-378, hsa-miR-628-3p | 68.2% | 54.2% | 82.2% |
| SNO-9 | SEQ ID NO: 127, SEQ ID NO: 897 | hsa-miR-628-3p, hsa-let-7d | 73.0% | 63.5% | 82.5% |
| SNO-10 | SEQ ID NO: 897, SEQ ID NO: 395 | hsa-let-7d, hsa-miR-383 | 75.3% | 76.2% | 74.5% |
| SNO-11 | SEQ ID NO: 395, SEQ ID NO: 573 | hsa-miR-383, hsa-miR-210 | 74.6% | 72.7% | 76.5% |
| SNO-12 | SEQ ID NO: 573, SEQ ID NO: 393 | hsa-miR-210, hsa-miR-409-3p | 70.5% | 62.7% | 78.3% |
| SNO-13 | SEQ ID NO: 393, SEQ ID NO: 441 | hsa-miR-409-3p, hsa-miR-342-5p | 65.9% | 62.8% | 69.0% |
| SNO-14 | SEQ ID NO: 441, SEQ ID NO: 382 | hsa-miR-342-5p, hsa-miR-424* | 66.0% | 57.5% | 74.5% |
| SNO-15 | SEQ ID NO: 382, SEQ ID NO: 520 | hsa-miR-424*, hsa-miR-26b* | 68.6% | 54.0% | 83.2% |
| SNO-16 | SEQ ID NO: 520, SEQ ID NO: 97 | hsa-miR-26b*, hsa-miR-655 | 73.7% | 56.3% | 91.0% |
| SNO-17 | SEQ ID NO: 97, SEQ ID NO: 542 | hsa-miR-655, hsa-miR-222 | 74.0% | 64.2% | 83.8% |
| SNO-18 | SEQ ID NO: 542, SEQ ID NO: 11 | hsa-miR-222, hsa-miR-942 | 69.6% | 71.2% | 68.0% |
| SNO-19 | SEQ ID NO: 11, SEQ ID NO: 87 | hsa-miR-942, hsa-miR-664 | 65.8% | 46.5% | 85.0% |
| SNO-20 | SEQ ID NO: 87, SEQ ID NO: 883 | hsa-miR-664, hsa-miR-101 | 77.7% | 74.7% | 80.7% |
| SNO-21 | SEQ ID NO: 883, SEQ ID NO: 892 | hsa-miR-101, hsa-let-7f-1* | 70.0% | 66.0% | 74.0% |
| SNO-22 | SEQ ID NO: 892, SEQ ID NO: 350 | hsa-let-7f-1*, hsa-miR-486-5p | 75.4% | 60.0% | 90.8% |
| SNO-23 | SEQ ID NO: 350, SEQ ID NO: 154 | hsa-miR-486-5p, hsa-miR-605 | 73.9% | 57.2% | 90.7% |
| SNO-24 | SEQ ID NO: 154, SEQ ID NO: 671 | hsa-miR-605, hsa-miR-181a-2* | 71.0% | 61.3% | 80.7% |

Figure 15:
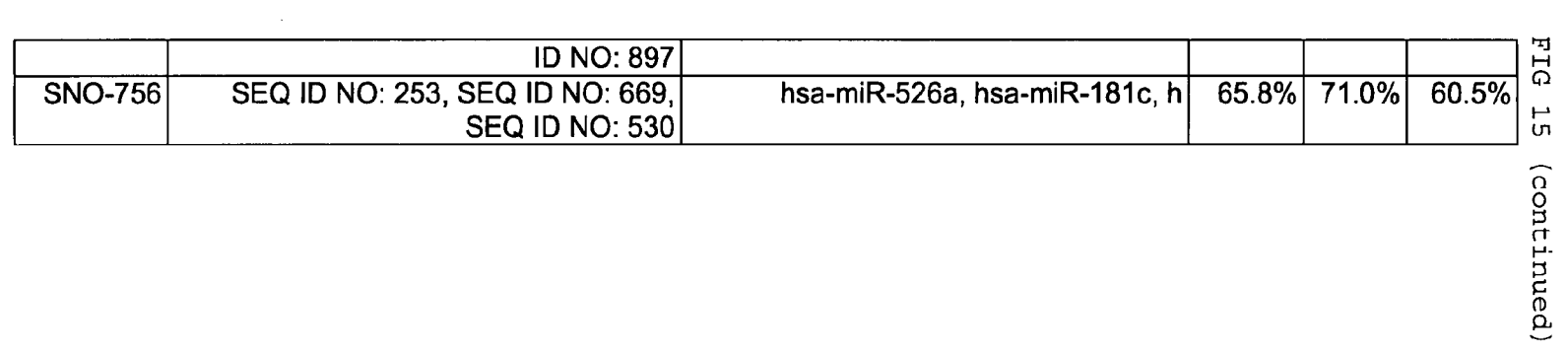

FIG 15 (continued)

| | | | | | |
|---|---|---|---|---|---|
| SNO-25 | SEQ ID NO: 671, SEQ ID NO: 658 | hsa-miR-181a-2*, hsa-miR-185 | 68.3% | 56.0% | 80.7% |
| SNO-26 | SEQ ID NO: 658, SEQ ID NO: 284 | hsa-miR-185, hsa-miR-518f | 70.4% | 55.0% | 85.8% |
| SNO-27 | SEQ ID NO: 284, SEQ ID NO: 466 | hsa-miR-518f, hsa-miR-324-3p | 71.2% | 59.8% | 82.5% |
| SNO-28 | SEQ ID NO: 714, SEQ ID NO: 684 | hsa-miR-144*, hsa-miR-155 | 75.7% | 79.7% | 71.7% |
| SNO-29 | SEQ ID NO: 709, SEQ ID NO: 530 | hsa-miR-146a, hsa-miR-23b* | 72.8% | 64.5% | 81.2% |
| SNO-30 | SEQ ID NO: 684, SEQ ID NO: 442 | hsa-miR-155, hsa-miR-342-3p | 77.1% | 71.3% | 82.8% |
| SNO-31 | SEQ ID NO: 530, SEQ ID NO: 92 | hsa-miR-23b*, hsa-miR-660 | 68.0% | 59.5% | 76.5% |
| SNO-32 | SEQ ID NO: 442, SEQ ID NO: 874 | hsa-miR-342-3p, hsa-miR-106b | 71.3% | 64.8% | 77.7% |
| SNO-33 | SEQ ID NO: 92, SEQ ID NO: 403 | hsa-miR-660, hsa-miR-378 | 69.4% | 61.8% | 77.0% |
| SNO-34 | SEQ ID NO: 874, SEQ ID NO: 127 | hsa-miR-106b, hsa-miR-628-3p | 69.8% | 64.8% | 74.8% |
| SNO-35 | SEQ ID NO: 403, SEQ ID NO: 897 | hsa-miR-378, hsa-let-7d | 73.3% | 66.7% | 80.0% |
| SNO-36 | SEQ ID NO: 127, SEQ ID NO: 395 | hsa-miR-628-3p, hsa-miR-383 | 75.0% | 68.7% | 81.3% |
| SNO-37 | SEQ ID NO: 897, SEQ ID NO: 573 | hsa-let-7d, hsa-miR-210 | 70.2% | 61.8% | 78.5% |
| SNO-38 | SEQ ID NO: 395, SEQ ID NO: 393 | hsa-miR-383, hsa-miR-409-3p | 73.8% | 73.0% | 74.5% |
| SNO-39 | SEQ ID NO: 573, SEQ ID NO: 441 | hsa-miR-210, hsa-miR-342-5p | 65.4% | 63.7% | 67.2% |
| SNO-40 | SEQ ID NO: 393, SEQ ID NO: 382 | hsa-miR-409-3p, hsa-miR-424* | 70.0% | 58.0% | 82.0% |
| SNO-41 | SEQ ID NO: 441, SEQ ID NO: 520 | hsa-miR-342-5p, hsa-miR-26b* | 64.6% | 58.5% | 70.7% |
| SNO-42 | SEQ ID NO: 382, SEQ ID NO: 97 | hsa-miR-424*, hsa-miR-655 | 68.9% | 54.3% | 83.5% |
| SNO-43 | SEQ ID NO: 520, SEQ ID NO: 542 | hsa-miR-26b*, hsa-miR-222 | 63.8% | 62.5% | 65.0% |
| SNO-44 | SEQ ID NO: 97, SEQ ID NO: 11 | hsa-miR-655, hsa-miR-942 | 72.4% | 57.8% | 87.0% |
| SNO-45 | SEQ ID NO: 542, SEQ ID NO: 87 | hsa-miR-222, hsa-miR-664 | 66.0% | 62.2% | 69.8% |
| SNO-46 | SEQ ID NO: 11, SEQ ID NO: 883 | hsa-miR-942, hsa-miR-101 | 73.9% | 67.3% | 80.5% |
| SNO-47 | SEQ ID NO: 87, SEQ ID NO: 892 | hsa-miR-664, hsa-let-7f-1* | 68.9% | 56.0% | 81.8% |
| SNO-48 | SEQ ID NO: 883, SEQ ID NO: 350 | hsa-miR-101, hsa-miR-486-5p | 69.8% | 59.2% | 80.3% |
| SNO-49 | SEQ ID NO: 892, SEQ ID NO: 154 | hsa-let-7f-1*, hsa-miR-605 | 71.0% | 60.0% | 82.0% |

FIG 15 (continued)

| | | | | | |
|---|---|---|---|---|---|
| SNO-50 | SEQ ID NO: 350, SEQ ID NO: 671 | hsa-miR-486-5p, hsa-miR-181a-2* | 70.2% | 48.3% | 92.0% |
| SNO-51 | SEQ ID NO: 154, SEQ ID NO: 658 | hsa-miR-605, hsa-miR-185 | 72.5% | 61.0% | 84.0% |
| SNO-52 | SEQ ID NO: 671, SEQ ID NO: 284 | hsa-miR-181a-2*, hsa-miR-518f | 69.8% | 59.8% | 79.8% |
| SNO-53 | SEQ ID NO: 658, SEQ ID NO: 466 | hsa-miR-185, hsa-miR-324-3p | 74.8% | 67.5% | 82.0% |
| SNO-54 | SEQ ID NO: 714, SEQ ID NO: 530 | hsa-miR-144*, hsa-miR-23b* | 74.3% | 74.0% | 74.7% |
| SNO-55 | SEQ ID NO: 709, SEQ ID NO: 442 | hsa-miR-146a, hsa-miR-342-3p | 75.7% | 71.0% | 80.3% |
| SNO-56 | SEQ ID NO: 684, SEQ ID NO: 92 | hsa-miR-155, hsa-miR-660 | 65.9% | 56.8% | 75.0% |
| SNO-57 | SEQ ID NO: 530, SEQ ID NO: 874 | hsa-miR-23b*, hsa-miR-106b | 70.4% | 63.8% | 77.0% |
| SNO-58 | SEQ ID NO: 442, SEQ ID NO: 403 | hsa-miR-342-3p, hsa-miR-378 | 76.3% | 70.2% | 82.3% |
| SNO-59 | SEQ ID NO: 92, SEQ ID NO: 127 | hsa-miR-660, hsa-miR-628-3p | 68.0% | 54.5% | 81.5% |
| SNO-60 | SEQ ID NO: 874, SEQ ID NO: 897 | hsa-miR-106b, hsa-let-7d | 66.1% | 59.2% | 73.0% |
| SNO-61 | SEQ ID NO: 403, SEQ ID NO: 395 | hsa-miR-378, hsa-miR-383 | 72.7% | 68.5% | 76.8% |
| SNO-62 | SEQ ID NO: 127, SEQ ID NO: 573 | hsa-miR-628-3p, hsa-miR-210 | 71.8% | 63.3% | 80.3% |
| SNO-63 | SEQ ID NO: 897, SEQ ID NO: 393 | hsa-let-7d, hsa-miR-409-3p | 76.9% | 73.7% | 80.2% |
| SNO-64 | SEQ ID NO: 395, SEQ ID NO: 441 | hsa-miR-383, hsa-miR-342-5p | 73.8% | 68.5% | 79.0% |
| SNO-65 | SEQ ID NO: 573, SEQ ID NO: 382 | hsa-miR-210, hsa-miR-424* | 72.0% | 60.7% | 83.3% |
| SNO-66 | SEQ ID NO: 393, SEQ ID NO: 520 | hsa-miR-409-3p, hsa-miR-26b* | 70.4% | 56.8% | 84.0% |
| SNO-67 | SEQ ID NO: 441, SEQ ID NO: 97 | hsa-miR-342-5p, hsa-miR-655 | 72.6% | 64.0% | 81.2% |
| SNO-68 | SEQ ID NO: 382, SEQ ID NO: 542 | hsa-miR-424*, hsa-miR-222 | 63.8% | 56.2% | 71.3% |
| SNO-69 | SEQ ID NO: 520, SEQ ID NO: 11 | hsa-miR-26b*, hsa-miR-942 | 68.7% | 47.5% | 89.8% |
| SNO-70 | SEQ ID NO: 97, SEQ ID NO: 87 | hsa-miR-655, hsa-miR-664 | 71.1% | 58.0% | 84.2% |
| SNO-71 | SEQ ID NO: 542, SEQ ID NO: 883 | hsa-miR-222, hsa-miR-101 | 70.5% | 77.0% | 64.0% |
| SNO-72 | SEQ ID NO: 11, SEQ ID NO: 892 | hsa-miR-942, hsa-let-7f-1* | 64.5% | 44.5% | 84.5% |
| SNO-73 | SEQ ID NO: 87, SEQ ID NO: 350 | hsa-miR-664, hsa-miR-486-5p | 68.9% | 51.7% | 86.2% |
| SNO-74 | SEQ ID NO: 883, SEQ ID NO: 154 | hsa-miR-101, hsa-miR-605 | 70.1% | 68.8% | 71.3% |

FIG 15 (continued)

| | | | | | |
|---|---|---|---|---|---|
| SNO-75 | SEQ ID NO: 892, SEQ ID NO: 671 | hsa-let-7f-1*, hsa-miR-181a-2* | 68.3% | 58.5% | 78.2% |
| SNO-76 | SEQ ID NO: 350, SEQ ID NO: 658 | hsa-miR-486-5p, hsa-miR-185 | 72.8% | 53.8% | 91.8% |
| SNO-77 | SEQ ID NO: 154, SEQ ID NO: 284 | hsa-miR-605, hsa-miR-518f | 69.8% | 55.2% | 84.5% |
| SNO-78 | SEQ ID NO: 671, SEQ ID NO: 466 | hsa-miR-181a-2*, hsa-miR-324-3p | 72.7% | 64.3% | 81.0% |
| SNO-79 | SEQ ID NO: 714, SEQ ID NO: 709, SEQ ID NO: 684 | hsa-miR-144*, hsa-miR-146a, hsa-miR-155 | 76.7% | 78.3% | 75.0% |
| SNO-80 | SEQ ID NO: 709, SEQ ID NO: 684, SEQ ID NO: 530 | hsa-miR-146a, hsa-miR-155, hsa-miR-23b* | 73.7% | 68.2% | 79.2% |
| SNO-81 | SEQ ID NO: 684, SEQ ID NO: 530, SEQ ID NO: 442 | hsa-miR-155, hsa-miR-23b*, hsa-miR-342-3p | 80.3% | 79.2% | 81.3% |
| SNO-82 | SEQ ID NO: 530, SEQ ID NO: 442, SEQ ID NO: 92 | hsa-miR-23b*, hsa-miR-342-3p, hsa-miR-660 | 73.5% | 71.5% | 75.5% |
| SNO-83 | SEQ ID NO: 442, SEQ ID NO: 92, SEQ ID NO: 874 | hsa-miR-342-3p, hsa-miR-660, hsa-miR-106b | 75.9% | 73.0% | 78.8% |
| SNO-84 | SEQ ID NO: 92, SEQ ID NO: 874, SEQ ID NO: 403 | hsa-miR-660, hsa-miR-106b, hsa-miR-378 | 67.8% | 67.2% | 68.3% |
| SNO-85 | SEQ ID NO: 874, SEQ ID NO: 403, SEQ ID NO: 127 | hsa-miR-106b, hsa-miR-378, hsa-miR-628-3p | 72.3% | 70.7% | 74.0% |
| SNO-86 | SEQ ID NO: 403, SEQ ID NO: 127, SEQ ID NO: 897 | hsa-miR-378, hsa-miR-628-3p, hsa-let-7d | 72.3% | 65.7% | 78.8% |
| SNO-87 | SEQ ID NO: 127, SEQ ID NO: 897, SEQ ID NO: 395 | hsa-miR-628-3p, hsa-let-7d, hsa-miR-383 | 79.5% | 79.2% | 79.8% |
| SNO-88 | SEQ ID NO: 897, SEQ ID NO: 395, SEQ ID NO: 573 | hsa-let-7d, hsa-miR-383, hsa-miR-210 | 76.7% | 77.0% | 76.3% |
| SNO-89 | SEQ ID NO: 395, SEQ ID NO: 573, SEQ ID NO: 393 | hsa-miR-383, hsa-miR-210, hsa-miR-409-3p | 75.9% | 76.8% | 75.0% |
| SNO-90 | SEQ ID NO: 573, SEQ ID NO: 393, | hsa-miR-210, hsa-miR-409-3p, hsa- | 71.6% | 68.7% | 74.5% |

FIG 15 (continued)

| | | | | | |
|---|---|---|---|---|---|
| | SEQ ID NO: 441 | miR-342-5p | | | |
| SNO-91 | SEQ ID NO: 393, SEQ ID NO: 441, SEQ ID NO: 382 | hsa-miR-409-3p, hsa-miR-342-5p, hsa-miR-424* | 69.7% | 63.2% | 76.2% |
| SNO-92 | SEQ ID NO: 441, SEQ ID NO: 382, SEQ ID NO: 520 | hsa-miR-342-5p, hsa-miR-424*, hsa-miR-26b* | 66.3% | 58.3% | 74.3% |
| SNO-93 | SEQ ID NO: 382, SEQ ID NO: 520, SEQ ID NO: 97 | hsa-miR-424*, hsa-miR-26b*, hsa-miR-655 | 75.3% | 63.8% | 86.7% |
| SNO-94 | SEQ ID NO: 520, SEQ ID NO: 97, SEQ ID NO: 542 | hsa-miR-26b*, hsa-miR-655, hsa-miR-222 | 79.6% | 68.8% | 90.3% |
| SNO-95 | SEQ ID NO: 97, SEQ ID NO: 542, SEQ ID NO: 11 | hsa-miR-655, hsa-miR-222, hsa-miR-942 | 79.0% | 73.0% | 85.0% |
| SNO-96 | SEQ ID NO: 542, SEQ ID NO: 11, SEQ ID NO: 87 | hsa-miR-222, hsa-miR-942, hsa-miR-664 | 71.2% | 67.5% | 74.8% |
| SNO-97 | SEQ ID NO: 11, SEQ ID NO: 87, SEQ ID NO: 883 | hsa-miR-942, hsa-miR-664, hsa-miR-101 | 78.2% | 75.8% | 80.5% |
| SNO-98 | SEQ ID NO: 87, SEQ ID NO: 883, SEQ ID NO: 892 | hsa-miR-664, hsa-miR-101, hsa-let-7f-1* | 78.3% | 77.0% | 79.5% |
| SNO-99 | SEQ ID NO: 883, SEQ ID NO: 892, SEQ ID NO: 350 | hsa-miR-101, hsa-let-7f-1*, hsa-miR-486-5p | 76.2% | 71.7% | 80.7% |
| SNO-100 | SEQ ID NO: 892, SEQ ID NO: 350, SEQ ID NO: 154 | hsa-let-7f-1*, hsa-miR-486-5p, hsa-miR-605 | 76.2% | 67.0% | 85.3% |
| SNO-101 | SEQ ID NO: 350, SEQ ID NO: 154, SEQ ID NO: 671 | hsa-miR-486-5p, hsa-miR-605, hsa-miR-181a-2* | 79.2% | 68.5% | 89.8% |
| SNO-102 | SEQ ID NO: 154, SEQ ID NO: 671, SEQ ID NO: 658 | hsa-miR-605, hsa-miR-181a-2*, hsa-miR-185 | 76.2% | 69.2% | 83.2% |
| SNO-103 | SEQ ID NO: 671, SEQ ID NO: 658, SEQ ID NO: 284 | hsa-miR-181a-2*, hsa-miR-185, hsa-miR-518f | 73.9% | 61.7% | 86.2% |

FIG 15 (continued)

| | | | | | |
|---|---|---|---|---|---|
| SNO-104 | SEQ ID NO: 658, SEQ ID NO: 284, SEQ ID NO: 466 | hsa-miR-185, hsa-miR-518f, hsa-miR-324-3p | 79.3% | 69.7% | 88.8% |
| SNO-105 | SEQ ID NO: 714, SEQ ID NO: 709, SEQ ID NO: 530 | hsa-miR-144*, hsa-miR-146a, hsa-miR-23b* | 75.7% | 72.5% | 78.8% |
| SNO-106 | SEQ ID NO: 709, SEQ ID NO: 684, SEQ ID NO: 442 | hsa-miR-146a, hsa-miR-155, hsa-miR-342-3p | 74.8% | 70.8% | 78.7% |
| SNO-107 | SEQ ID NO: 684, SEQ ID NO: 530, SEQ ID NO: 92 | hsa-miR-155, hsa-miR-23b*, hsa-miR-660 | 72.9% | 67.0% | 78.8% |
| SNO-108 | SEQ ID NO: 530, SEQ ID NO: 442, SEQ ID NO: 874 | hsa-miR-23b*, hsa-miR-342-3p, hsa-miR-106b | 76.5% | 69.5% | 83.5% |
| SNO-109 | SEQ ID NO: 442, SEQ ID NO: 92, SEQ ID NO: 403 | hsa-miR-342-3p, hsa-miR-660, hsa-miR-378 | 78.8% | 75.5% | 82.2% |
| SNO-110 | SEQ ID NO: 92, SEQ ID NO: 874, SEQ ID NO: 127 | hsa-miR-660, hsa-miR-106b, hsa-miR-628-3p | 72.3% | 67.7% | 76.8% |
| SNO-111 | SEQ ID NO: 874, SEQ ID NO: 403, SEQ ID NO: 897 | hsa-miR-106b, hsa-miR-378, hsa-let-7d | 69.1% | 67.0% | 71.2% |
| SNO-112 | SEQ ID NO: 403, SEQ ID NO: 127, SEQ ID NO: 395 | hsa-miR-378, hsa-miR-628-3p, hsa-miR-383 | 75.8% | 69.2% | 82.5% |
| SNO-113 | SEQ ID NO: 127, SEQ ID NO: 897, SEQ ID NO: 573 | hsa-miR-628-3p, hsa-let-7d, hsa-miR-210 | 72.8% | 64.8% | 80.7% |
| SNO-114 | SEQ ID NO: 897, SEQ ID NO: 395, SEQ ID NO: 393 | hsa-let-7d, hsa-miR-383, hsa-miR-409-3p | 76.2% | 80.8% | 71.5% |
| SNO-115 | SEQ ID NO: 395, SEQ ID NO: 573, SEQ ID NO: 441 | hsa-miR-383, hsa-miR-210, hsa-miR-342-5p | 75.7% | 74.3% | 77.0% |
| SNO-116 | SEQ ID NO: 573, SEQ ID NO: 393, SEQ ID NO: 382 | hsa-miR-210, hsa-miR-409-3p, hsa-miR-424* | 76.3% | 67.3% | 85.2% |
| SNO-117 | SEQ ID NO: 393, SEQ ID NO: 441, | hsa-miR-409-3p, hsa-miR-342-5p, hsa- | 68.3% | 57.3% | 79.2% |

FIG 15 (continued)

| | | | | | |
|---|---|---|---|---|---|
| | SEQ ID NO: 520 | miR-26b* | | | |
| SNO-118 | SEQ ID NO: 441, SEQ ID NO: 382, SEQ ID NO: 97 | hsa-miR-342-5p, hsa-miR-424*, hsa-miR-655 | 75.5% | 65.0% | 86.0% |
| SNO-119 | SEQ ID NO: 382, SEQ ID NO: 520, SEQ ID NO: 542 | hsa-miR-424*, hsa-miR-26b*, hsa-miR-222 | 69.3% | 59.2% | 79.5% |
| SNO-120 | SEQ ID NO: 520, SEQ ID NO: 97, SEQ ID NO: 11 | hsa-miR-26b*, hsa-miR-655, hsa-miR-942 | 77.1% | 64.3% | 89.8% |
| SNO-121 | SEQ ID NO: 97, SEQ ID NO: 542, SEQ ID NO: 87 | hsa-miR-655, hsa-miR-222, hsa-miR-664 | 76.1% | 66.7% | 85.5% |
| SNO-122 | SEQ ID NO: 542, SEQ ID NO: 11, SEQ ID NO: 883 | hsa-miR-222, hsa-miR-942, hsa-miR-101 | 73.9% | 75.8% | 72.0% |
| SNO-123 | SEQ ID NO: 11, SEQ ID NO: 87, SEQ ID NO: 892 | hsa-miR-942, hsa-miR-664, hsa-let-7f-1* | 66.4% | 51.0% | 81.8% |
| SNO-124 | SEQ ID NO: 87, SEQ ID NO: 883, SEQ ID NO: 350 | hsa-miR-664, hsa-miR-101, hsa-miR-486-5p | 80.7% | 77.2% | 84.2% |
| SNO-125 | SEQ ID NO: 883, SEQ ID NO: 892, SEQ ID NO: 154 | hsa-miR-101, hsa-let-7f-1*, hsa-miR-605 | 71.8% | 69.5% | 74.0% |
| SNO-126 | SEQ ID NO: 892, SEQ ID NO: 350, SEQ ID NO: 671 | hsa-let-7f-1*, hsa-miR-486-5p, hsa-miR-181a-2* | 76.1% | 63.7% | 88.5% |
| SNO-127 | SEQ ID NO: 350, SEQ ID NO: 154, SEQ ID NO: 658 | hsa-miR-486-5p, hsa-miR-605, hsa-miR-185 | 75.6% | 64.7% | 86.5% |
| SNO-128 | SEQ ID NO: 154, SEQ ID NO: 671, SEQ ID NO: 284 | hsa-miR-605, hsa-miR-181a-2*, hsa-miR-518f | 72.6% | 62.0% | 83.2% |
| SNO-129 | SEQ ID NO: 671, SEQ ID NO: 658, SEQ ID NO: 466 | hsa-miR-181a-2*, hsa-miR-185, hsa-miR-324-3p | 75.5% | 69.5% | 81.5% |
| SNO-130 | SEQ ID NO: 714, SEQ ID NO: 684, SEQ ID NO: 530 | hsa-miR-144*, hsa-miR-155, hsa-miR-23b* | 73.1% | 74.5% | 71.7% |

FIG 15 (continued)

| | | | | | |
|---|---|---|---|---|---|
| SNO-131 | SEQ ID NO: 709, SEQ ID NO: 530, SEQ ID NO: 442 | hsa-miR-146a, hsa-miR-23b*, hsa-miR-342-3p | 76.8% | 72.3% | 81.2% |
| SNO-132 | SEQ ID NO: 684, SEQ ID NO: 442, SEQ ID NO: 92 | hsa-miR-155, hsa-miR-342-3p, hsa-miR-660 | 75.6% | 72.3% | 78.8% |
| SNO-133 | SEQ ID NO: 530, SEQ ID NO: 92, SEQ ID NO: 874 | hsa-miR-23b*, hsa-miR-660, hsa-miR-106b | 69.8% | 66.2% | 73.5% |
| SNO-134 | SEQ ID NO: 442, SEQ ID NO: 874, SEQ ID NO: 403 | hsa-miR-342-3p, hsa-miR-106b, hsa-miR-378 | 75.3% | 69.3% | 81.2% |
| SNO-135 | SEQ ID NO: 92, SEQ ID NO: 403, SEQ ID NO: 127 | hsa-miR-660, hsa-miR-378, hsa-miR-628-3p | 71.3% | 61.7% | 80.8% |
| SNO-136 | SEQ ID NO: 874, SEQ ID NO: 127, SEQ ID NO: 897 | hsa-miR-106b, hsa-miR-628-3p, hsa-let-7d | 73.3% | 69.0% | 77.7% |
| SNO-137 | SEQ ID NO: 403, SEQ ID NO: 897, SEQ ID NO: 395 | hsa-miR-378, hsa-let-7d, hsa-miR-383 | 75.1% | 74.0% | 76.2% |
| SNO-138 | SEQ ID NO: 127, SEQ ID NO: 395, SEQ ID NO: 573 | hsa-miR-628-3p, hsa-miR-383, hsa-miR-210 | 76.3% | 72.3% | 80.2% |
| SNO-139 | SEQ ID NO: 897, SEQ ID NO: 573, SEQ ID NO: 393 | hsa-let-7d, hsa-miR-210, hsa-miR-409-3p | 72.3% | 66.7% | 78.0% |
| SNO-140 | SEQ ID NO: 395, SEQ ID NO: 393, SEQ ID NO: 441 | hsa-miR-383, hsa-miR-409-3p, hsa-miR-342-5p | 76.3% | 73.0% | 79.7% |
| SNO-141 | SEQ ID NO: 573, SEQ ID NO: 441, SEQ ID NO: 382 | hsa-miR-210, hsa-miR-342-5p, hsa-miR-424* | 70.3% | 61.5% | 79.2% |
| SNO-142 | SEQ ID NO: 393, SEQ ID NO: 382, SEQ ID NO: 520 | hsa-miR-409-3p, hsa-miR-424*, hsa-miR-26b* | 72.1% | 62.2% | 82.0% |
| SNO-143 | SEQ ID NO: 441, SEQ ID NO: 520, SEQ ID NO: 97 | hsa-miR-342-5p, hsa-miR-26b*, hsa-miR-655 | 77.9% | 67.3% | 88.5% |
| SNO-144 | SEQ ID NO: 382, SEQ ID NO: 97, SEQ | hsa-miR-424*, hsa-miR-655, hsa-miR- | 75.3% | 67.2% | 83.3% |

FIG 15 (continued)

| | | | | | |
|---|---|---|---|---|---|
| | ID NO: 542 | 222 | | | |
| SNO-145 | SEQ ID NO: 520, SEQ ID NO: 542, SEQ ID NO: 11 | hsa-miR-26b*, hsa-miR-222, hsa-miR-942 | 71.3% | 67.0% | 75.7% |
| SNO-146 | SEQ ID NO: 97, SEQ ID NO: 11, SEQ ID NO: 87 | hsa-miR-655, hsa-miR-942, hsa-miR-664 | 78.3% | 68.2% | 88.5% |
| SNO-147 | SEQ ID NO: 542, SEQ ID NO: 87, SEQ ID NO: 883 | hsa-miR-222, hsa-miR-664, hsa-miR-101 | 76.9% | 76.3% | 77.5% |
| SNO-148 | SEQ ID NO: 11, SEQ ID NO: 883, SEQ ID NO: 892 | hsa-miR-942, hsa-miR-101, hsa-let-7f-1* | 74.3% | 71.3% | 77.2% |
| SNO-149 | SEQ ID NO: 87, SEQ ID NO: 892, SEQ ID NO: 350 | hsa-miR-664, hsa-let-7f-1*, hsa-miR-486-5p | 75.9% | 61.5% | 90.3% |
| SNO-150 | SEQ ID NO: 883, SEQ ID NO: 350, SEQ ID NO: 154 | hsa-miR-101, hsa-miR-486-5p, hsa-miR-605 | 73.8% | 66.3% | 81.3% |
| SNO-151 | SEQ ID NO: 892, SEQ ID NO: 154, SEQ ID NO: 671 | hsa-let-7f-1*, hsa-miR-605, hsa-miR-181a-2* | 74.4% | 68.7% | 80.2% |
| SNO-152 | SEQ ID NO: 350, SEQ ID NO: 671, SEQ ID NO: 658 | hsa-miR-486-5p, hsa-miR-181a-2*, hsa-miR-185 | 71.5% | 58.3% | 84.7% |
| SNO-153 | SEQ ID NO: 154, SEQ ID NO: 658, SEQ ID NO: 284 | hsa-miR-605, hsa-miR-185, hsa-miR-518f | 73.9% | 62.3% | 85.5% |
| SNO-154 | SEQ ID NO: 671, SEQ ID NO: 284, SEQ ID NO: 466 | hsa-miR-181a-2*, hsa-miR-518f, hsa-miR-324-3p | 76.1% | 68.0% | 84.2% |
| SNO-155 | SEQ ID NO: 714, SEQ ID NO: 684, SEQ ID NO: 442 | hsa-miR-144*, hsa-miR-155, hsa-miR-342-3p | 74.0% | 74.5% | 73.5% |
| SNO-156 | SEQ ID NO: 709, SEQ ID NO: 530, SEQ ID NO: 92 | hsa-miR-146a, hsa-miR-23b*, hsa-miR-660 | 71.4% | 61.2% | 81.7% |
| SNO-157 | SEQ ID NO: 684, SEQ ID NO: 442, SEQ ID NO: 874 | hsa-miR-155, hsa-miR-342-3p, hsa-miR-106b | 77.2% | 71.3% | 83.0% |

FIG 15 (continued)

| | | | | | |
|---|---|---|---|---|---|
| SNO-158 | SEQ ID NO: 530, SEQ ID NO: 92, SEQ ID NO: 403 | hsa-miR-23b*, hsa-miR-660, hsa-miR-378 | 72.7% | 66.7% | 78.7% |
| SNO-159 | SEQ ID NO: 442, SEQ ID NO: 874, SEQ ID NO: 127 | hsa-miR-342-3p, hsa-miR-106b, hsa-miR-628-3p | 80.2% | 72.3% | 88.0% |
| SNO-160 | SEQ ID NO: 92, SEQ ID NO: 403, SEQ ID NO: 897 | hsa-miR-660, hsa-miR-378, hsa-let-7d | 73.2% | 65.3% | 81.0% |
| SNO-161 | SEQ ID NO: 874, SEQ ID NO: 127, SEQ ID NO: 395 | hsa-miR-106b, hsa-miR-628-3p, hsa-miR-383 | 78.3% | 80.2% | 76.3% |
| SNO-162 | SEQ ID NO: 403, SEQ ID NO: 897, SEQ ID NO: 573 | hsa-miR-378, hsa-let-7d, hsa-miR-210 | 74.2% | 65.8% | 82.5% |
| SNO-163 | SEQ ID NO: 127, SEQ ID NO: 395, SEQ ID NO: 393 | hsa-miR-628-3p, hsa-miR-383, hsa-miR-409-3p | 73.8% | 69.5% | 78.2% |
| SNO-164 | SEQ ID NO: 897, SEQ ID NO: 573, SEQ ID NO: 441 | hsa-let-7d, hsa-miR-210, hsa-miR-342-5p | 73.8% | 74.0% | 73.7% |
| SNO-165 | SEQ ID NO: 395, SEQ ID NO: 393, SEQ ID NO: 382 | hsa-miR-383, hsa-miR-409-3p, hsa-miR-424* | 73.8% | 68.8% | 78.8% |
| SNO-166 | SEQ ID NO: 573, SEQ ID NO: 441, SEQ ID NO: 520 | hsa-miR-210, hsa-miR-342-5p, hsa-miR-26b* | 69.5% | 66.5% | 72.5% |
| SNO-167 | SEQ ID NO: 393, SEQ ID NO: 382, SEQ ID NO: 97 | hsa-miR-409-3p, hsa-miR-424*, hsa-miR-655 | 74.5% | 67.5% | 81.5% |
| SNO-168 | SEQ ID NO: 441, SEQ ID NO: 520, SEQ ID NO: 542 | hsa-miR-342-5p, hsa-miR-26b*, hsa-miR-222 | 62.1% | 61.3% | 62.8% |
| SNO-169 | SEQ ID NO: 382, SEQ ID NO: 97, SEQ ID NO: 11 | hsa-miR-424*, hsa-miR-655, hsa-miR-942 | 75.8% | 64.3% | 87.2% |
| SNO-170 | SEQ ID NO: 520, SEQ ID NO: 542, SEQ ID NO: 87 | hsa-miR-26b*, hsa-miR-222, hsa-miR-664 | 70.0% | 62.3% | 77.7% |
| SNO-171 | SEQ ID NO: 97, SEQ ID NO: 11, SEQ | hsa-miR-655, hsa-miR-942, hsa-miR- | 78.3% | 68.5% | 88.2% |

FIG 15 (continued)

| | | | | | |
|---|---|---|---|---|---|
| | ID NO: 883 | 101 | | | |
| SNO-172 | SEQ ID NO: 542, SEQ ID NO: 87, SEQ ID NO: 892 | hsa-miR-222, hsa-miR-664, hsa-let-7f-1* | 67.2% | 61.7% | 72.7% |
| SNO-173 | SEQ ID NO: 11, SEQ ID NO: 883, SEQ ID NO: 350 | hsa-miR-942, hsa-miR-101, hsa-miR-486-5p | 77.1% | 70.0% | 84.2% |
| SNO-174 | SEQ ID NO: 87, SEQ ID NO: 892, SEQ ID NO: 154 | hsa-miR-664, hsa-let-7f-1*, hsa-miR-605 | 71.1% | 60.5% | 81.7% |
| SNO-175 | SEQ ID NO: 883, SEQ ID NO: 350, SEQ ID NO: 671 | hsa-miR-101, hsa-miR-486-5p, hsa-miR-181a-2* | 76.2% | 71.3% | 81.0% |
| SNO-176 | SEQ ID NO: 892, SEQ ID NO: 154, SEQ ID NO: 658 | hsa-let-7f-1*, hsa-miR-605, hsa-miR-185 | 74.8% | 65.2% | 84.3% |
| SNO-177 | SEQ ID NO: 350, SEQ ID NO: 671, SEQ ID NO: 284 | hsa-miR-486-5p, hsa-miR-181a-2*, hsa-miR-518f | 78.9% | 66.5% | 91.3% |
| SNO-178 | SEQ ID NO: 154, SEQ ID NO: 658, SEQ ID NO: 466 | hsa-miR-605, hsa-miR-185, hsa-miR-324-3p | 75.7% | 69.3% | 82.0% |
| SNO-179 | SEQ ID NO: 714, SEQ ID NO: 709, SEQ ID NO: 442 | hsa-miR-144*, hsa-miR-146a, hsa-miR-342-3p | 77.4% | 78.2% | 76.7% |
| SNO-180 | SEQ ID NO: 709, SEQ ID NO: 684, SEQ ID NO: 92 | hsa-miR-146a, hsa-miR-155, hsa-miR-660 | 69.8% | 63.0% | 76.5% |
| SNO-181 | SEQ ID NO: 684, SEQ ID NO: 530, SEQ ID NO: 874 | hsa-miR-155, hsa-miR-23b*, hsa-miR-106b | 77.5% | 76.3% | 78.7% |
| SNO-182 | SEQ ID NO: 530, SEQ ID NO: 442, SEQ ID NO: 403 | hsa-miR-23b*, hsa-miR-342-3p, hsa-miR-378 | 76.4% | 74.5% | 78.3% |
| SNO-183 | SEQ ID NO: 442, SEQ ID NO: 92, SEQ ID NO: 127 | hsa-miR-342-3p, hsa-miR-660, hsa-miR-628-3p | 76.8% | 68.7% | 84.8% |
| SNO-184 | SEQ ID NO: 92, SEQ ID NO: 874, SEQ ID NO: 897 | hsa-miR-660, hsa-miR-106b, hsa-let-7d | 70.8% | 67.3% | 74.3% |

FIG 15 (continued)

| | | | | | |
|---|---|---|---|---|---|
| SNO-185 | SEQ ID NO: 874, SEQ ID NO: 403, SEQ ID NO: 395 | hsa-miR-106b, hsa-miR-378, hsa-miR-383 | 74.4% | 76.0% | 72.8% |
| SNO-186 | SEQ ID NO: 403, SEQ ID NO: 127, SEQ ID NO: 573 | hsa-miR-378, hsa-miR-628-3p, hsa-miR-210 | 69.9% | 59.5% | 80.3% |
| SNO-187 | SEQ ID NO: 127, SEQ ID NO: 897, SEQ ID NO: 393 | hsa-miR-628-3p, hsa-let-7d, hsa-miR-409-3p | 74.0% | 67.3% | 80.7% |
| SNO-188 | SEQ ID NO: 897, SEQ ID NO: 395, SEQ ID NO: 441 | hsa-let-7d, hsa-miR-383, hsa-miR-342-5p | 78.7% | 78.3% | 79.0% |
| SNO-189 | SEQ ID NO: 395, SEQ ID NO: 573, SEQ ID NO: 382 | hsa-miR-383, hsa-miR-210, hsa-miR-424* | 77.8% | 72.2% | 83.5% |
| SNO-190 | SEQ ID NO: 573, SEQ ID NO: 393, SEQ ID NO: 520 | hsa-miR-210, hsa-miR-409-3p, hsa-miR-26b* | 71.9% | 63.7% | 80.2% |
| SNO-191 | SEQ ID NO: 393, SEQ ID NO: 441, SEQ ID NO: 97 | hsa-miR-409-3p, hsa-miR-342-5p, hsa-miR-655 | 74.7% | 66.0% | 83.3% |
| SNO-192 | SEQ ID NO: 441, SEQ ID NO: 382, SEQ ID NO: 542 | hsa-miR-342-5p, hsa-miR-424*, hsa-miR-222 | 65.3% | 66.3% | 64.2% |
| SNO-193 | SEQ ID NO: 382, SEQ ID NO: 520, SEQ ID NO: 11 | hsa-miR-424*, hsa-miR-26b*, hsa-miR-942 | 71.3% | 56.0% | 86.5% |
| SNO-194 | SEQ ID NO: 520, SEQ ID NO: 97, SEQ ID NO: 87 | hsa-miR-26b*, hsa-miR-655, hsa-miR-664 | 75.4% | 61.0% | 89.8% |
| SNO-195 | SEQ ID NO: 97, SEQ ID NO: 542, SEQ ID NO: 883 | hsa-miR-655, hsa-miR-222, hsa-miR-101 | 71.4% | 69.3% | 73.5% |
| SNO-196 | SEQ ID NO: 542, SEQ ID NO: 11, SEQ ID NO: 892 | hsa-miR-222, hsa-miR-942, hsa-let-7f-1* | 69.8% | 67.0% | 72.5% |
| SNO-197 | SEQ ID NO: 11, SEQ ID NO: 87, SEQ ID NO: 350 | hsa-miR-942, hsa-miR-664, hsa-miR-486-5p | 73.2% | 53.3% | 93.0% |
| SNO-198 | SEQ ID NO: 87, SEQ ID NO: 883, SEQ | hsa-miR-664, hsa-miR-101, hsa-miR- | 76.4% | 74.7% | 78.2% |

FIG 15 (continued)

| | | | | | |
|---|---|---|---|---|---|
| | ID NO: 154 | 605 | | | |
| SNO-199 | SEQ ID NO: 883, SEQ ID NO: 892, SEQ ID NO: 671 | hsa-miR-101, hsa-let-7f-1*, hsa-miR-181a-2* | 72.8% | 70.5% | 75.2% |
| SNO-200 | SEQ ID NO: 892, SEQ ID NO: 350, SEQ ID NO: 658 | hsa-let-7f-1*, hsa-miR-486-5p, hsa-miR-185 | 74.2% | 62.8% | 85.5% |
| SNO-201 | SEQ ID NO: 350, SEQ ID NO: 154, SEQ ID NO: 284 | hsa-miR-486-5p, hsa-miR-605, hsa-miR-518f | 79.4% | 66.8% | 92.0% |
| SNO-202 | SEQ ID NO: 154, SEQ ID NO: 671, SEQ ID NO: 466 | hsa-miR-605, hsa-miR-181a-2*, hsa-miR-324-3p | 75.7% | 70.5% | 80.8% |
| SNO-203 | SEQ ID NO: 714, SEQ ID NO: 530, SEQ ID NO: 442 | hsa-miR-144*, hsa-miR-23b*, hsa-miR-342-3p | 76.1% | 75.5% | 76.7% |
| SNO-204 | SEQ ID NO: 709, SEQ ID NO: 442, SEQ ID NO: 92 | hsa-miR-146a, hsa-miR-342-3p, hsa-miR-660 | 78.3% | 73.2% | 83.5% |
| SNO-205 | SEQ ID NO: 684, SEQ ID NO: 92, SEQ ID NO: 874 | hsa-miR-155, hsa-miR-660, hsa-miR-106b | 74.6% | 72.2% | 77.0% |
| SNO-206 | SEQ ID NO: 530, SEQ ID NO: 874, SEQ ID NO: 403 | hsa-miR-23b*, hsa-miR-106b, hsa-miR-378 | 72.2% | 66.7% | 77.7% |
| SNO-207 | SEQ ID NO: 442, SEQ ID NO: 403, SEQ ID NO: 127 | hsa-miR-342-3p, hsa-miR-378, hsa-miR-628-3p | 75.7% | 67.8% | 83.5% |
| SNO-208 | SEQ ID NO: 92, SEQ ID NO: 127, SEQ ID NO: 897 | hsa-miR-660, hsa-miR-628-3p, hsa-let-7d | 74.1% | 67.0% | 81.2% |
| SNO-209 | SEQ ID NO: 874, SEQ ID NO: 897, SEQ ID NO: 395 | hsa-miR-106b, hsa-let-7d, hsa-miR-383 | 75.7% | 77.8% | 73.5% |
| SNO-210 | SEQ ID NO: 403, SEQ ID NO: 395, SEQ ID NO: 573 | hsa-miR-378, hsa-miR-383, hsa-miR-210 | 74.6% | 73.3% | 75.8% |
| SNO-211 | SEQ ID NO: 127, SEQ ID NO: 573, SEQ ID NO: 393 | hsa-miR-628-3p, hsa-miR-210, hsa-miR-409-3p | 70.0% | 62.3% | 77.7% |

FIG 15 (continued)

| | | | | | |
|---|---|---|---|---|---|
| SNO-212 | SEQ ID NO: 897, SEQ ID NO: 393, SEQ ID NO: 441 | hsa-let-7d, hsa-miR-409-3p, hsa-miR-342-5p | 74.4% | 72.8% | 76.0% |
| SNO-213 | SEQ ID NO: 395, SEQ ID NO: 441, SEQ ID NO: 382 | hsa-miR-383, hsa-miR-342-5p, hsa-miR-424* | 76.6% | 72.2% | 81.0% |
| SNO-214 | SEQ ID NO: 573, SEQ ID NO: 382, SEQ ID NO: 520 | hsa-miR-210, hsa-miR-424*, hsa-miR-26b* | 73.7% | 63.0% | 84.3% |
| SNO-215 | SEQ ID NO: 393, SEQ ID NO: 520, SEQ ID NO: 97 | hsa-miR-409-3p, hsa-miR-26b*, hsa-miR-655 | 73.8% | 65.2% | 82.5% |
| SNO-216 | SEQ ID NO: 441, SEQ ID NO: 97, SEQ ID NO: 542 | hsa-miR-342-5p, hsa-miR-655, hsa-miR-222 | 74.2% | 68.3% | 80.0% |
| SNO-217 | SEQ ID NO: 382, SEQ ID NO: 542, SEQ ID NO: 11 | hsa-miR-424*, hsa-miR-222, hsa-miR-942 | 68.9% | 62.7% | 75.2% |
| SNO-218 | SEQ ID NO: 520, SEQ ID NO: 11, SEQ ID NO: 87 | hsa-miR-26b*, hsa-miR-942, hsa-miR-664 | 70.2% | 51.2% | 89.2% |
| SNO-219 | SEQ ID NO: 97, SEQ ID NO: 87, SEQ ID NO: 883 | hsa-miR-655, hsa-miR-664, hsa-miR-101 | 80.0% | 74.8% | 85.2% |
| SNO-220 | SEQ ID NO: 542, SEQ ID NO: 883, SEQ ID NO: 892 | hsa-miR-222, hsa-miR-101, hsa-let-7f-1* | 71.7% | 72.8% | 70.5% |
| SNO-221 | SEQ ID NO: 11, SEQ ID NO: 892, SEQ ID NO: 350 | hsa-miR-942, hsa-let-7f-1*, hsa-miR-486-5p | 75.2% | 60.5% | 89.8% |
| SNO-222 | SEQ ID NO: 87, SEQ ID NO: 350, SEQ ID NO: 154 | hsa-miR-664, hsa-miR-486-5p, hsa-miR-605 | 74.9% | 62.7% | 87.2% |
| SNO-223 | SEQ ID NO: 883, SEQ ID NO: 154, SEQ ID NO: 671 | hsa-miR-101, hsa-miR-605, hsa-miR-181a-2* | 72.7% | 70.7% | 74.7% |
| SNO-224 | SEQ ID NO: 892, SEQ ID NO: 671, SEQ ID NO: 658 | hsa-let-7f-1*, hsa-miR-181a-2*, hsa-miR-185 | 72.7% | 65.3% | 80.0% |
| SNO-225 | SEQ ID NO: 350, SEQ ID NO: 658, | hsa-miR-486-5p, hsa-miR-185, hsa- | 74.8% | 59.0% | 90.7% |

FIG 15 (continued)

| | | | | | |
|---|---|---|---|---|---|
| | SEQ ID NO: 284 | miR-518f | | | |
| SNO-226 | SEQ ID NO: 154, SEQ ID NO: 284, SEQ ID NO: 466 | hsa-miR-605, hsa-miR-518f, hsa-miR-324-3p | 74.0% | 63.0% | 85.0% |
| SNO-227 | SEQ ID NO: 714, SEQ ID NO: 673 | hsa-miR-144*, hsa-miR-181a | 76.7% | 76.3% | 77.0% |
| SNO-228 | SEQ ID NO: 673, SEQ ID NO: 189 | hsa-miR-181a, hsa-miR-574-5p | 73.7% | 67.0% | 80.3% |
| SNO-229 | SEQ ID NO: 189, SEQ ID NO: 779 | hsa-miR-574-5p, hsa-miR-1280 | 70.5% | 76.5% | 64.5% |
| SNO-230 | SEQ ID NO: 779, SEQ ID NO: 92 | hsa-miR-1280, hsa-miR-660 | 71.5% | 78.7% | 64.3% |
| SNO-231 | SEQ ID NO: 92, SEQ ID NO: 805 | hsa-miR-660, hsa-miR-126 | 64.2% | 63.3% | 65.0% |
| SNO-232 | SEQ ID NO: 805, SEQ ID NO: 414 | hsa-miR-126, hsa-miR-374a | 66.0% | 64.8% | 67.2% |
| SNO-233 | SEQ ID NO: 414, SEQ ID NO: 696 | hsa-miR-374a, hsa-miR-149* | 65.3% | 59.5% | 71.0% |
| SNO-234 | SEQ ID NO: 696, SEQ ID NO: 850 | hsa-miR-149*, hsa-miR-1207-5p | 64.2% | 74.3% | 54.0% |
| SNO-235 | SEQ ID NO: 850, SEQ ID NO: 315 | hsa-miR-1207-5p, hsa-miR-509-3-5p | 70.3% | 71.5% | 69.2% |
| SNO-236 | SEQ ID NO: 315, SEQ ID NO: 87 | hsa-miR-509-3-5p, hsa-miR-664 | 55.8% | 64.5% | 47.0% |
| SNO-237 | SEQ ID NO: 87, SEQ ID NO: 888 | hsa-miR-664, hsa-let-7i | 60.3% | 49.5% | 71.2% |
| SNO-238 | SEQ ID NO: 888, SEQ ID NO: 861 | hsa-let-7i, hsa-miR-1184 | 62.6% | 79.5% | 45.7% |
| SNO-239 | SEQ ID NO: 861, SEQ ID NO: 838 | hsa-miR-1184, hsa-miR-1228* | 72.7% | 81.0% | 64.3% |
| SNO-240 | SEQ ID NO: 838, SEQ ID NO: 883 | hsa-miR-1228*, hsa-miR-101 | 67.3% | 64.5% | 70.2% |
| SNO-241 | SEQ ID NO: 883, SEQ ID NO: 199 | hsa-miR-101, hsa-miR-564 | 74.3% | 72.3% | 76.2% |
| SNO-242 | SEQ ID NO: 199, SEQ ID NO: 874 | hsa-miR-564, hsa-miR-106b | 68.0% | 70.3% | 65.7% |
| SNO-243 | SEQ ID NO: 874, SEQ ID NO: 645 | hsa-miR-106b, hsa-miR-1908 | 62.1% | 75.8% | 48.3% |
| SNO-244 | SEQ ID NO: 645, SEQ ID NO: 710 | hsa-miR-1908, hsa-miR-1469 | 61.5% | 70.2% | 52.8% |
| SNO-245 | SEQ ID NO: 710, SEQ ID NO: 442 | hsa-miR-1469, hsa-miR-342-3p | 69.5% | 58.8% | 80.2% |
| SNO-246 | SEQ ID NO: 442, SEQ ID NO: 542 | hsa-miR-342-3p, hsa-miR-222 | 74.1% | 70.8% | 77.3% |
| SNO-247 | SEQ ID NO: 542, SEQ ID NO: 632 | hsa-miR-222, hsa-miR-1915 | 65.3% | 75.2% | 55.3% |
| SNO-248 | SEQ ID NO: 632, SEQ ID NO: 573 | hsa-miR-1915, hsa-miR-210 | 71.1% | 69.8% | 72.3% |
| SNO-249 | SEQ ID NO: 573, SEQ ID NO: 762 | hsa-miR-210, hsa-miR-1295 | 74.8% | 70.5% | 79.0% |

FIG 15 (continued)

| | | | | | |
|---|---|---|---|---|---|
| SNO-250 | SEQ ID NO: 762, SEQ ID NO: 378 | hsa-miR-1295, hsa-miR-431 | 65.3% | 66.2% | 64.5% |
| SNO-251 | SEQ ID NO: 378, SEQ ID NO: 253 | hsa-miR-431, hsa-miR-526a | 64.4% | 77.0% | 51.8% |
| SNO-252 | SEQ ID NO: 253, SEQ ID NO: 89 | hsa-miR-526a, hsa-miR-663 | 68.8% | 81.0% | 56.7% |
| SNO-253 | SEQ ID NO: 89, SEQ ID NO: 897 | hsa-miR-663, hsa-let-7d | 70.3% | 69.0% | 71.5% |
| SNO-254 | SEQ ID NO: 714, SEQ ID NO: 189 | hsa-miR-144*, hsa-miR-574-5p | 72.8% | 73.7% | 72.0% |
| SNO-255 | SEQ ID NO: 673, SEQ ID NO: 779 | hsa-miR-181a, hsa-miR-1280 | 78.6% | 80.8% | 76.3% |
| SNO-256 | SEQ ID NO: 189, SEQ ID NO: 92 | hsa-miR-574-5p, hsa-miR-660 | 61.5% | 71.5% | 51.5% |
| SNO-257 | SEQ ID NO: 779, SEQ ID NO: 805 | hsa-miR-1280, hsa-miR-126 | 69.2% | 76.3% | 62.0% |
| SNO-258 | SEQ ID NO: 92, SEQ ID NO: 414 | hsa-miR-660, hsa-miR-374a | 63.9% | 57.5% | 70.3% |
| SNO-259 | SEQ ID NO: 805, SEQ ID NO: 696 | hsa-miR-126, hsa-miR-149* | 65.3% | 69.8% | 60.7% |
| SNO-260 | SEQ ID NO: 414, SEQ ID NO: 850 | hsa-miR-374a, hsa-miR-1207-5p | 63.7% | 57.5% | 69.8% |
| SNO-261 | SEQ ID NO: 696, SEQ ID NO: 315 | hsa-miR-149*, hsa-miR-509-3-5p | 72.0% | 71.7% | 72.3% |
| SNO-262 | SEQ ID NO: 850, SEQ ID NO: 87 | hsa-miR-1207-5p, hsa-miR-664 | 61.3% | 68.3% | 54.2% |
| SNO-263 | SEQ ID NO: 315, SEQ ID NO: 888 | hsa-miR-509-3-5p, hsa-let-7i | 64.4% | 77.2% | 51.7% |
| SNO-264 | SEQ ID NO: 87, SEQ ID NO: 861 | hsa-miR-664, hsa-miR-1184 | 57.8% | 64.5% | 51.2% |
| SNO-265 | SEQ ID NO: 888, SEQ ID NO: 838 | hsa-let-7i, hsa-miR-1228* | 69.9% | 74.3% | 65.5% |
| SNO-266 | SEQ ID NO: 861, SEQ ID NO: 883 | hsa-miR-1184, hsa-miR-101 | 63.3% | 66.2% | 60.3% |
| SNO-267 | SEQ ID NO: 838, SEQ ID NO: 199 | hsa-miR-1228*, hsa-miR-564 | 70.3% | 72.2% | 68.5% |
| SNO-268 | SEQ ID NO: 883, SEQ ID NO: 874 | hsa-miR-101, hsa-miR-106b | 70.1% | 73.3% | 66.8% |
| SNO-269 | SEQ ID NO: 199, SEQ ID NO: 645 | hsa-miR-564, hsa-miR-1908 | 60.2% | 68.0% | 52.3% |
| SNO-270 | SEQ ID NO: 874, SEQ ID NO: 710 | hsa-miR-106b, hsa-miR-1469 | 63.5% | 67.2% | 59.8% |
| SNO-271 | SEQ ID NO: 645, SEQ ID NO: 442 | hsa-miR-1908, hsa-miR-342-3p | 64.3% | 56.5% | 72.0% |
| SNO-272 | SEQ ID NO: 710, SEQ ID NO: 542 | hsa-miR-1469, hsa-miR-222 | 66.2% | 73.3% | 59.0% |
| SNO-273 | SEQ ID NO: 442, SEQ ID NO: 632 | hsa-miR-342-3p, hsa-miR-1915 | 68.4% | 58.3% | 78.5% |
| SNO-274 | SEQ ID NO: 542, SEQ ID NO: 573 | hsa-miR-222, hsa-miR-210 | 72.1% | 67.8% | 76.3% |

FIG 15 (continued)

| | | | | | |
|---|---|---|---|---|---|
| SNO-275 | SEQ ID NO: 632, SEQ ID NO: 762 | hsa-miR-1915, hsa-miR-1295 | 67.0% | 61.2% | 72.8% |
| SNO-276 | SEQ ID NO: 573, SEQ ID NO: 378 | hsa-miR-210, hsa-miR-431 | 67.4% | 73.2% | 61.7% |
| SNO-277 | SEQ ID NO: 762, SEQ ID NO: 253 | hsa-miR-1295, hsa-miR-526a | 63.8% | 61.3% | 66.2% |
| SNO-278 | SEQ ID NO: 378, SEQ ID NO: 89 | hsa-miR-431, hsa-miR-663 | 61.3% | 70.8% | 51.8% |
| SNO-279 | SEQ ID NO: 253, SEQ ID NO: 897 | hsa-miR-526a, hsa-let-7d | 72.2% | 72.0% | 72.3% |
| SNO-280 | SEQ ID NO: 714, SEQ ID NO: 779 | hsa-miR-144*, hsa-miR-1280 | 73.3% | 71.0% | 75.5% |
| SNO-281 | SEQ ID NO: 673, SEQ ID NO: 92 | hsa-miR-181a, hsa-miR-660 | 71.1% | 65.8% | 76.3% |
| SNO-282 | SEQ ID NO: 189, SEQ ID NO: 805 | hsa-miR-574-5p, hsa-miR-126 | 65.3% | 70.0% | 60.7% |
| SNO-283 | SEQ ID NO: 779, SEQ ID NO: 414 | hsa-miR-1280, hsa-miR-374a | 75.3% | 75.2% | 75.3% |
| SNO-284 | SEQ ID NO: 92, SEQ ID NO: 696 | hsa-miR-660, hsa-miR-149* | 62.4% | 66.0% | 58.8% |
| SNO-285 | SEQ ID NO; 805, SEQ ID NO: 850 | hsa-miR-126, hsa-miR-1207-5p | 66.3% | 65.7% | 66.8% |
| SNO-286 | SEQ ID NO: 414, SEQ ID NO: 315 | hsa-miR-374a, hsa-miR-509-3-5p | 65.7% | 76.8% | 54.5% |
| SNO-287 | SEQ ID NO: 696, SEQ ID NO: 87 | hsa-miR-149*, hsa-miR-664 | 63.8% | 66.0% | 61.7% |
| SNO-288 | SEQ ID NO: 850, SEQ ID NO: 888 | hsa-miR-1207-5p, hsa-let-7i | 60.3% | 66.2% | 54.5% |
| SNO-289 | SEQ ID NO: 315, SEQ ID NO: 861 | hsa-miR-509-3-5p, hsa-miR-1184 | 62.3% | 80.7% | 43.8% |
| SNO-290 | SEQ ID NO: 87, SEQ ID NO: 838 | hsa-miR-664, hsa-miR-1228* | 72.7% | 72.8% | 72.5% |
| SNO-291 | SEQ ID NO: 888, SEQ ID NO: 883 | hsa-let-7i, hsa-miR-101 | 69.3% | 63.0% | 75.7% |
| SNO-292 | SEQ ID NO: 861, SEQ ID NO: 199 | hsa-miR-1184, hsa-miR-564 | 62.8% | 69.5% | 56.0% |
| SNO-293 | SEQ ID NO: 838, SEQ ID NO: 874 | hsa-miR-1228*, hsa-miR-106b | 71.3% | 76.5% | 66.0% |
| SNO-294 | SEQ ID NO: 883, SEQ ID NO: 645 | hsa-miR-101, hsa-miR-1908 | 62.5% | 62.3% | 62.7% |
| SNO-295 | SEQ ID NO: 199, SEQ ID NO: 710 | hsa-miR-564, hsa-miR-1469 | 60.7% | 63.5% | 57.8% |
| SNO-296 | SEQ ID NO: 874, SEQ ID NO: 442 | hsa-miR-106b, hsa-miR-342-3p | 69.2% | 63.2% | 75.2% |
| SNO-297 | SEQ ID NO: 645, SEQ ID NO: 542 | hsa-miR-1908, hsa-miR-222 | 63.3% | 82.7% | 43.8% |
| SNO-298 | SEQ ID NO: 710, SEQ ID NO: 632 | hsa-miR-1469, hsa-miR-1915 | 64.0% | 65.2% | 62.8% |
| SNO-299 | SEQ ID NO: 442, SEQ ID NO: 573 | hsa-miR-342-3p, hsa-miR-210 | 78.1% | 79.0% | 77.2% |

FIG 15 (continued)

| | | | | | |
|---|---|---|---|---|---|
| SNO-300 | SEQ ID NO: 542, SEQ ID NO: 762 | hsa-miR-222, hsa-miR-1295 | 70.7% | 68.2% | 73.2% |
| SNO-301 | SEQ ID NO: 632, SEQ ID NO: 378 | hsa-miR-1915, hsa-miR-431 | 62.8% | 70.8% | 54.8% |
| SNO-302 | SEQ ID NO: 573, SEQ ID NO: 253 | hsa-miR-210, hsa-miR-526a | 61.1% | 66.7% | 55.5% |
| SNO-303 | SEQ ID NO: 762, SEQ ID NO: 89 | hsa-miR-1295, hsa-miR-663 | 63.9% | 65.0% | 62.8% |
| SNO-304 | SEQ ID NO: 378, SEQ ID NO: 897 | hsa-miR-431, hsa-let-7d | 63.8% | 59.8% | 67.8% |
| SNO-305 | SEQ ID NO: 714, SEQ ID NO: 673, SEQ ID NO: 189 | hsa-miR-144*, hsa-miR-181a, hsa-miR-574-5p | 75.5% | 75.8% | 75.2% |
| SNO-306 | SEQ ID NO: 673, SEQ ID NO: 189, SEQ ID NO: 779 | hsa-miR-181a, hsa-miR-574-5p, hsa-miR-1280 | 76.9% | 78.7% | 75.2% |
| SNO-307 | SEQ ID NO: 189, SEQ ID NO: 779, SEQ ID NO: 92 | hsa-miR-574-5p, hsa-miR-1280, hsa-miR-660 | 70.9% | 80.3% | 61.5% |
| SNO-308 | SEQ ID NO: 779, SEQ ID NO: 92, SEQ ID NO: 805 | hsa-miR-1280, hsa-miR-660, hsa-miR-126 | 72.3% | 81.5% | 63.0% |
| SNO-309 | SEQ ID NO: 92, SEQ ID NO: 805, SEQ ID NO: 414 | hsa-miR-660, hsa-miR-126, hsa-miR-374a | 66.3% | 62.7% | 69.8% |
| SNO-310 | SEQ ID NO: 805, SEQ ID NO: 414, SEQ ID NO: 696 | hsa-miR-126, hsa-miR-374a, hsa-miR-149* | 69.3% | 67.8% | 70.8% |
| SNO-311 | SEQ ID NO: 414, SEQ ID NO: 696, SEQ ID NO: 850 | hsa-miR-374a, hsa-miR-149*, hsa-miR-1207-5p | 66.3% | 62.0% | 70.5% |
| SNO-312 | SEQ ID NO: 696, SEQ ID NO: 850, SEQ ID NO: 315 | hsa-miR-149*, hsa-miR-1207-5p, hsa-miR-509-3-5p | 71.5% | 72.7% | 70.3% |
| SNO-313 | SEQ ID NO: 850, SEQ ID NO: 315, SEQ ID NO: 87 | hsa-miR-1207-5p, hsa-miR-509-3-5p, hsa-miR-664 | 68.1% | 71.0% | 65.2% |
| SNO-314 | SEQ ID NO: 315, SEQ ID NO: 87, SEQ ID NO: 888 | hsa-miR-509-3-5p, hsa-miR-664, hsa-let-7i | 56.6% | 55.7% | 57.5% |
| SNO-315 | SEQ ID NO: 87, SEQ ID NO: 888, SEQ ID NO: 861 | hsa-miR-664, hsa-let-7i, hsa-miR-1184 | 55.7% | 58.5% | 52.8% |

FIG 15 (continued)

| | | | | | |
|---|---|---|---|---|---|
| SNO-316 | SEQ ID NO: 888, SEQ ID NO: 861, SEQ ID NO: 838 | hsa-let-7i, hsa-miR-1184, hsa-miR-1228* | 71.3% | 76.7% | 66.0% |
| SNO-317 | SEQ ID NO: 861, SEQ ID NO: 838, SEQ ID NO: 883 | hsa-miR-1184, hsa-miR-1228*, hsa-miR-101 | 69.0% | 75.7% | 62.3% |
| SNO-318 | SEQ ID NO: 838, SEQ ID NO: 883, SEQ ID NO: 199 | hsa-miR-1228*, hsa-miR-101, hsa-miR-564 | 71.5% | 71.2% | 71.8% |
| SNO-319 | SEQ ID NO: 883, SEQ ID NO: 199, SEQ ID NO: 874 | hsa-miR-101, hsa-miR-564, hsa-miR-106b | 74.8% | 79.3% | 70.2% |
| SNO-320 | SEQ ID NO: 199, SEQ ID NO: 874, SEQ ID NO: 645 | hsa-miR-564, hsa-miR-106b, hsa-miR-1908 | 69.4% | 74.2% | 64.7% |
| SNO-321 | SEQ ID NO: 874, SEQ ID NO: 645, SEQ ID NO: 710 | hsa-miR-106b, hsa-miR-1908, hsa-miR-1469 | 63.0% | 70.0% | 56.0% |
| SNO-322 | SEQ ID NO: 645, SEQ ID NO: 710, SEQ ID NO: 442 | hsa-miR-1908, hsa-miR-1469, hsa-miR-342-3p | 68.0% | 59.2% | 76.8% |
| SNO-323 | SEQ ID NO: 710, SEQ ID NO: 442, SEQ ID NO: 542 | hsa-miR-1469, hsa-miR-342-3p, hsa-miR-222 | 76.3% | 72.5% | 80.0% |
| SNO-324 | SEQ ID NO: 442, SEQ ID NO: 542, SEQ ID NO: 632 | hsa-miR-342-3p, hsa-miR-222, hsa-miR-1915 | 76.1% | 70.3% | 81.8% |
| SNO-325 | SEQ ID NO: 542, SEQ ID NO: 632, SEQ ID NO: 573 | hsa-miR-222, hsa-miR-1915, hsa-miR-210 | 68.9% | 70.8% | 67.0% |
| SNO-326 | SEQ ID NO: 632, SEQ ID NO: 573, SEQ ID NO: 762 | hsa-miR-1915, hsa-miR-210, hsa-miR-1295 | 74.4% | 71.8% | 77.0% |
| SNO-327 | SEQ ID NO: 573, SEQ ID NO: 762, SEQ ID NO: 378 | hsa-miR-210, hsa-miR-1295, hsa-miR-431 | 72.3% | 71.0% | 73.5% |
| SNO-328 | SEQ ID NO: 762, SEQ ID NO: 378, SEQ ID NO: 253 | hsa-miR-1295, hsa-miR-431, hsa-miR-526a | 64.1% | 70.5% | 57.7% |
| SNO-329 | SEQ ID NO: 378, SEQ ID NO: 253, | hsa-miR-431, hsa-miR-526a, hsa-miR- | 63.7% | 73.5% | 53.8% |

FIG 15 (continued)

| | | | | | |
|---|---|---|---|---|---|
| | SEQ ID NO: 89 | 663 | | | |
| SNO-330 | SEQ ID NO: 253, SEQ ID NO: 89, SEQ ID NO: 897 | hsa-miR-526a, hsa-miR-663, hsa-let-7d | 69.6% | 73.3% | 65.8% |
| SNO-331 | SEQ ID NO: 714, SEQ ID NO: 673, SEQ ID NO: 779 | hsa-miR-144*, hsa-miR-181a, hsa-miR-1280 | 79.3% | 83.5% | 75.2% |
| SNO-332 | SEQ ID NO: 673, SEQ ID NO: 189, SEQ ID NO: 92 | hsa-miR-181a, hsa-miR-574-5p, hsa-miR-660 | 70.2% | 68.5% | 71.8% |
| SNO-333 | SEQ ID NO: 189, SEQ ID NO: 779, SEQ ID NO: 805 | hsa-miR-574-5p, hsa-miR-1280, hsa-miR-126 | 70.3% | 79.8% | 60.7% |
| SNO-334 | SEQ ID NO: 779, SEQ ID NO: 92, SEQ ID NO: 414 | hsa-miR-1280, hsa-miR-660, hsa-miR-374a | 74.7% | 79.5% | 69.8% |
| SNO-335 | SEQ ID NO: 92, SEQ ID NO: 805, SEQ ID NO: 696 | hsa-miR-660, hsa-miR-126, hsa-miR-149* | 63.2% | 66.3% | 60.0% |
| SNO-336 | SEQ ID NO: 805, SEQ ID NO: 414, SEQ ID NO: 850 | hsa-miR-126, hsa-miR-374a, hsa-miR-1207-5p | 70.3% | 66.0% | 74.5% |
| SNO-337 | SEQ ID NO: 414, SEQ ID NO: 696, SEQ ID NO: 315 | hsa-miR-374a, hsa-miR-149*, hsa-miR-509-3-5p | 72.2% | 68.5% | 75.8% |
| SNO-338 | SEQ ID NO: 696, SEQ ID NO: 850, SEQ ID NO: 87 | hsa-miR-149*, hsa-miR-1207-5p, hsa-miR-664 | 61.0% | 63.2% | 58.8% |
| SNO-339 | SEQ ID NO: 850, SEQ ID NO: 315, SEQ ID NO: 888 | hsa-miR-1207-5p, hsa-miR-509-3-5p, hsa-let-7i | 72.2% | 73.3% | 71.0% |
| SNO-340 | SEQ ID NO: 315, SEQ ID NO: 87, SEQ ID NO: 861 | hsa-miR-509-3-5p, hsa-miR-664, hsa-miR-1184 | 56.9% | 63.0% | 50.8% |
| SNO-341 | SEQ ID NO: 87, SEQ ID NO: 888, SEQ ID NO: 838 | hsa-miR-664, hsa-let-7i, hsa-miR-1228* | 68.3% | 71.3% | 65.3% |
| SNO-342 | SEQ ID NO: 888, SEQ ID NO: 861, SEQ ID NO: 883 | hsa-let-7i, hsa-miR-1184, hsa-miR-101 | 65.1% | 62.2% | 68.0% |

FIG 15 (continued)

| | | | | | |
|---|---|---|---|---|---|
| SNO-343 | SEQ ID NO: 861, SEQ ID NO: 838, SEQ ID NO: 199 | hsa-miR-1184, hsa-miR-1228*, hsa-miR-564 | 69.8% | 76.5% | 63.0% |
| SNO-344 | SEQ ID NO: 838, SEQ ID NO: 883, SEQ ID NO: 874 | hsa-miR-1228*, hsa-miR-101, hsa-miR-106b | 67.5% | 73.0% | 62.0% |
| SNO-345 | SEQ ID NO: 883, SEQ ID NO: 199, SEQ ID NO: 645 | hsa-miR-101, hsa-miR-564, hsa-miR-1908 | 68.4% | 71.2% | 65.7% |
| SNO-346 | SEQ ID NO: 199, SEQ ID NO: 874, SEQ ID NO: 710 | hsa-miR-564, hsa-miR-106b, hsa-miR-1469 | 68.4% | 73.7% | 63.2% |
| SNO-347 | SEQ ID NO: 874, SEQ ID NO: 645, SEQ ID NO: 442 | hsa-miR-106b, hsa-miR-1908, hsa-miR-342-3p | 72.8% | 67.5% | 78.0% |
| SNO-348 | SEQ ID NO: 645, SEQ ID NO: 710, SEQ ID NO: 542 | hsa-miR-1908, hsa-miR-1469, hsa-miR-222 | 62.1% | 74.5% | 49.7% |
| SNO-349 | SEQ ID NO: 710, SEQ ID NO: 442, SEQ ID NO: 632 | hsa-miR-1469, hsa-miR-342-3p, hsa-miR-1915 | 70.2% | 60.0% | 80.3% |
| SNO-350 | SEQ ID NO: 442, SEQ ID NO: 542, SEQ ID NO: 573 | hsa-miR-342-3p, hsa-miR-222, hsa-miR-210 | 82.9% | 84.0% | 81.8% |
| SNO-351 | SEQ ID NO: 542, SEQ ID NO: 632, SEQ ID NO: 762 | hsa-miR-222, hsa-miR-1915, hsa-miR-1295 | 69.1% | 67.2% | 71.0% |
| SNO-352 | SEQ ID NO: 632, SEQ ID NO: 573, SEQ ID NO: 378 | hsa-miR-1915, hsa-miR-210, hsa-miR-431 | 69.8% | 75.2% | 64.3% |
| SNO-353 | SEQ ID NO: 573, SEQ ID NO: 762, SEQ ID NO: 253 | hsa-miR-210, hsa-miR-1295, hsa-miR-526a | 68.7% | 64.0% | 73.3% |
| SNO-354 | SEQ ID NO: 762, SEQ ID NO: 378, SEQ ID NO: 89 | hsa-miR-1295, hsa-miR-431, hsa-miR-663 | 64.7% | 69.8% | 59.5% |
| SNO-355 | SEQ ID NO: 378, SEQ ID NO: 253, SEQ ID NO: 897 | hsa-miR-431, hsa-miR-526a, hsa-let-7d | 69.7% | 71.7% | 67.7% |
| SNO-356 | SEQ ID NO: 714, SEQ ID NO: 189, | hsa-miR-144*, hsa-miR-574-5p, hsa- | 72.0% | 71.2% | 72.8% |

FIG 15 (continued)

| | | | | | |
|---|---|---|---|---|---|
| | SEQ ID NO: 779 | miR-1280 | | | |
| SNO-357 | SEQ ID NO: 673, SEQ ID NO: 779, SEQ ID NO: 92 | hsa-miR-181a, hsa-miR-1280, hsa-miR-660 | 78.1% | 83.0% | 73.2% |
| SNO-358 | SEQ ID NO: 189, SEQ ID NO: 92, SEQ ID NO: 805 | hsa-miR-574-5p, hsa-miR-660, hsa-miR-126 | 62.7% | 67.5% | 57.8% |
| SNO-359 | SEQ ID NO: 779, SEQ ID NO: 805, SEQ ID NO: 414 | hsa-miR-1280, hsa-miR-126, hsa-miR-374a | 70.3% | 74.8% | 65.7% |
| SNO-360 | SEQ ID NO: 92, SEQ ID NO: 414, SEQ ID NO: 696 | hsa-miR-660, hsa-miR-374a, hsa-miR-149* | 63.1% | 60.7% | 65.5% |
| SNO-361 | SEQ ID NO: 805, SEQ ID NO: 696, SEQ ID NO: 850 | hsa-miR-126, hsa-miR-149*, hsa-miR-1207-5p | 64.3% | 65.8% | 62.7% |
| SNO-362 | SEQ ID NO: 414, SEQ ID NO: 850, SEQ ID NO: 315 | hsa-miR-374a, hsa-miR-1207-5p, hsa-miR-509-3-5p | 71.3% | 74.3% | 68.3% |
| SNO-363 | SEQ ID NO: 696, SEQ ID NO: 315, SEQ ID NO: 87 | hsa-miR-149*, hsa-miR-509-3-5p, hsa-miR-664 | 70.8% | 70.3% | 71.3% |
| SNO-364 | SEQ ID NO: 850, SEQ ID NO: 87, SEQ ID NO: 888 | hsa-miR-1207-5p, hsa-miR-664, hsa-let-7i | 64.7% | 65.8% | 63.5% |
| SNO-365 | SEQ ID NO: 315, SEQ ID NO: 888, SEQ ID NO: 861 | hsa-miR-509-3-5p, hsa-let-7i, hsa-miR-1184 | 61.0% | 76.2% | 45.8% |
| SNO-366 | SEQ ID NO: 87, SEQ ID NO: 861, SEQ ID NO: 838 | hsa-miR-664, hsa-miR-1184, hsa-miR-1228* | 71.5% | 76.8% | 66.2% |
| SNO-367 | SEQ ID NO: 888, SEQ ID NO: 838, SEQ ID NO: 883 | hsa-let-7i, hsa-miR-1228*, hsa-miR-101 | 68.3% | 68.7% | 67.8% |
| SNO-368 | SEQ ID NO: 861, SEQ ID NO: 883, SEQ ID NO: 199 | hsa-miR-1184, hsa-miR-101, hsa-miR-564 | 68.5% | 68.5% | 68.5% |
| SNO-369 | SEQ ID NO: 838, SEQ ID NO: 199, SEQ ID NO: 874 | hsa-miR-1228*, hsa-miR-564, hsa-miR-106b | 73.6% | 78.5% | 68.7% |

FIG 15 (continued)

| | | | | | |
|---|---|---|---|---|---|
| SNO-370 | SEQ ID NO: 883, SEQ ID NO: 874, SEQ ID NO: 645 | hsa-miR-101, hsa-miR-106b, hsa-miR-1908 | 64.9% | 75.2% | 54.7% |
| SNO-371 | SEQ ID NO: 199, SEQ ID NO: 645, SEQ ID NO: 710 | hsa-miR-564, hsa-miR-1908, hsa-miR-1469 | 62.1% | 67.7% | 56.5% |
| SNO-372 | SEQ ID NO: 874, SEQ ID NO: 710, SEQ ID NO: 442 | hsa-miR-106b, hsa-miR-1469, hsa-miR-342-3p | 74.3% | 66.8% | 81.7% |
| SNO-373 | SEQ ID NO: 645, SEQ ID NO: 442, SEQ ID NO: 542 | hsa-miR-1908, hsa-miR-342-3p, hsa-miR-222 | 73.7% | 69.8% | 77.5% |
| SNO-374 | SEQ ID NO: 710, SEQ ID NO: 542, SEQ ID NO: 632 | hsa-miR-1469, hsa-miR-222, hsa-miR-1915 | 63.0% | 68.3% | 57.7% |
| SNO-375 | SEQ ID NO: 442, SEQ ID NO: 632, SEQ ID NO: 573 | hsa-miR-342-3p, hsa-miR-1915, hsa-miR-210 | 79.4% | 77.3% | 81.5% |
| SNO-376 | SEQ ID NO: 542, SEQ ID NO: 573, SEQ ID NO: 762 | hsa-miR-222, hsa-miR-210, hsa-miR-1295 | 75.7% | 75.7% | 75.7% |
| SNO-377 | SEQ ID NO: 632, SEQ ID NO: 762, SEQ ID NO: 378 | hsa-miR-1915, hsa-miR-1295, hsa-miR-431 | 65.3% | 67.0% | 63.7% |
| SNO-378 | SEQ ID NO: 573, SEQ ID NO: 378, SEQ ID NO: 253 | hsa-miR-210, hsa-miR-431, hsa-miR-526a | 67.3% | 73.5% | 61.0% |
| SNO-379 | SEQ ID NO: 762, SEQ ID NO: 253, SEQ ID NO: 89 | hsa-miR-1295, hsa-miR-526a, hsa-miR-663 | 63.3% | 67.8% | 58.8% |
| SNO-380 | SEQ ID NO: 378, SEQ ID NO: 89, SEQ ID NO: 897 | hsa-miR-431, hsa-miR-663, hsa-let-7d | 68.2% | 69.2% | 67.2% |
| SNO-381 | SEQ ID NO: 714, SEQ ID NO: 189, SEQ ID NO: 92 | hsa-miR-144*, hsa-miR-574-5p, hsa-miR-660 | 73.0% | 72.7% | 73.3% |
| SNO-382 | SEQ ID NO: 673, SEQ ID NO: 779, SEQ ID NO: 805 | hsa-miR-181a, hsa-miR-1280, hsa-miR-126 | 76.5% | 83.0% | 70.0% |
| SNO-383 | SEQ ID NO: 189, SEQ ID NO: 92, SEQ | hsa-miR-574-5p, hsa-miR-660, hsa- | 65.4% | 67.5% | 63.3% |

FIG 15 (continued)

| | | | | | |
|---|---|---|---|---|---|
| | ID NO: 414 | miR-374a | | | |
| SNO-384 | SEQ ID NO: 779, SEQ ID NO: 805, SEQ ID NO: 696 | hsa-miR-1280, hsa-miR-126, hsa-miR-149* | 68.6% | 75.7% | 61.5% |
| SNO-385 | SEQ ID NO: 92, SEQ ID NO: 414, SEQ ID NO: 850 | hsa-miR-660, hsa-miR-374a, hsa-miR-1207-5p | 63.3% | 58.3% | 68.3% |
| SNO-386 | SEQ ID NO: 805, SEQ ID NO: 696, SEQ ID NO: 315 | hsa-miR-126, hsa-miR-149*, hsa-miR-509-3-5p | 71.0% | 73.5% | 68.5% |
| SNO-387 | SEQ ID NO: 414, SEQ ID NO: 850, SEQ ID NO: 87 | hsa-miR-374a, hsa-miR-1207-5p, hsa-miR-664 | 69.9% | 66.2% | 73.7% |
| SNO-388 | SEQ ID NO: 696, SEQ ID NO: 315, SEQ ID NO: 888 | hsa-miR-149*, hsa-miR-509-3-5p, hsa-let-7i | 70.2% | 66.8% | 73.5% |
| SNO-389 | SEQ ID NO: 850, SEQ ID NO: 87, SEQ ID NO: 861 | hsa-miR-1207-5p, hsa-miR-664, hsa-miR-1184 | 68.5% | 72.5% | 64.5% |
| SNO-390 | SEQ ID NO: 315, SEQ ID NO: 888, SEQ ID NO: 838 | hsa-miR-509-3-5p, hsa-let-7i, hsa-miR-1228* | 74.2% | 77.5% | 70.8% |
| SNO-391 | SEQ ID NO: 87, SEQ ID NO: 861, SEQ ID NO: 883 | hsa-miR-664, hsa-miR-1184, hsa-miR-101 | 74.6% | 71.8% | 77.3% |
| SNO-392 | SEQ ID NO: 888, SEQ ID NO: 838, SEQ ID NO: 199 | hsa-let-7i, hsa-miR-1228*, hsa-miR-564 | 69.0% | 71.2% | 66.8% |
| SNO-393 | SEQ ID NO: 861, SEQ ID NO: 883, SEQ ID NO: 874 | hsa-miR-1184, hsa-miR-101, hsa-miR-106b | 69.6% | 77.3% | 61.8% |
| SNO-394 | SEQ ID NO: 838, SEQ ID NO: 199, SEQ ID NO: 645 | hsa-miR-1228*, hsa-miR-564, hsa-miR-1908 | 68.2% | 71.8% | 64.5% |
| SNO-395 | SEQ ID NO: 883, SEQ ID NO: 874, SEQ ID NO: 710 | hsa-miR-101, hsa-miR-106b, hsa-miR-1469 | 69.7% | 70.5% | 68.8% |
| SNO-396 | SEQ ID NO: 199, SEQ ID NO: 645, SEQ ID NO: 442 | hsa-miR-564, hsa-miR-1908, hsa-miR-342-3p | 72.8% | 68.2% | 77.5% |

FIG 15 (continued)

| | | | | | |
|---|---|---|---|---|---|
| SNO-397 | SEQ ID NO: 874, SEQ ID NO: 710, SEQ ID NO: 542 | hsa-miR-106b, hsa-miR-1469, hsa-miR-222 | 63.5% | 70.2% | 56.8% |
| SNO-398 | SEQ ID NO: 645, SEQ ID NO: 442, SEQ ID NO: 632 | hsa-miR-1908, hsa-miR-342-3p, hsa-miR-1915 | 66.3% | 58.3% | 74.2% |
| SNO-399 | SEQ ID NO: 710, SEQ ID NO: 542, SEQ ID NO: 573 | hsa-miR-1469, hsa-miR-222, hsa-miR-210 | 71.0% | 70.3% | 71.7% |
| SNO-400 | SEQ ID NO: 442, SEQ ID NO: 632, SEQ ID NO: 762 | hsa-miR-342-3p, hsa-miR-1915, hsa-miR-1295 | 73.4% | 61.2% | 85.7% |
| SNO-401 | SEQ ID NO: 542, SEQ ID NO: 573, SEQ ID NO: 378 | hsa-miR-222, hsa-miR-210, hsa-miR-431 | 71.2% | 72.3% | 70.0% |
| SNO-402 | SEQ ID NO: 632, SEQ ID NO: 762, SEQ ID NO: 253 | hsa-miR-1915, hsa-miR-1295, hsa-miR-526a | 68.1% | 68.7% | 67.5% |
| SNO-403 | SEQ ID NO: 573, SEQ ID NO: 378, SEQ ID NO: 89 | hsa-miR-210, hsa-miR-431, hsa-miR-663 | 69.3% | 77.7% | 60.8% |
| SNO-404 | SEQ ID NO: 762, SEQ ID NO: 253, SEQ ID NO: 897 | hsa-miR-1295, hsa-miR-526a, hsa-let-7d | 69.9% | 66.3% | 73.5% |
| SNO-405 | SEQ ID NO: 714, SEQ ID NO: 673, SEQ ID NO: 92 | hsa-miR-144*, hsa-miR-181a, hsa-miR-660 | 74.8% | 77.0% | 72.7% |
| SNO-406 | SEQ ID NO: 673, SEQ ID NO: 189, SEQ ID NO: 805 | hsa-miR-181a, hsa-miR-574-5p, hsa-miR-126 | 70.1% | 67.7% | 72.5% |
| SNO-407 | SEQ ID NO: 189, SEQ ID NO: 779, SEQ ID NO: 414 | hsa-miR-574-5p, hsa-miR-1280, hsa-miR-374a | 68.9% | 69.0% | 68.8% |
| SNO-408 | SEQ ID NO: 779, SEQ ID NO: 92, SEQ ID NO: 696 | hsa-miR-1280, hsa-miR-660, hsa-miR-149* | 72.8% | 75.5% | 70.0% |
| SNO-409 | SEQ ID NO: 92, SEQ ID NO: 805, SEQ ID NO: 850 | hsa-miR-660, hsa-miR-126, hsa-miR-1207-5p | 62.8% | 60.5% | 65.2% |
| SNO-410 | SEQ ID NO: 805, SEQ ID NO: 414, | hsa-miR-126, hsa-miR-374a, hsa-miR- | 66.5% | 72.5% | 60.5% |

FIG 15 (continued)

| | | | | | |
|---|---|---|---|---|---|
| | SEQ ID NO: 315 | 509-3-5p | | | |
| SNO-411 | SEQ ID NO: 414, SEQ ID NO: 696, SEQ ID NO: 87 | hsa-miR-374a, hsa-miR-149*, hsa-miR-664 | 72.8% | 64.0% | 81.7% |
| SNO-412 | SEQ ID NO: 696, SEQ ID NO: 850, SEQ ID NO: 888 | hsa-miR-149*, hsa-miR-1207-5p, hsa-let-7i | 62.7% | 65.0% | 60.3% |
| SNO-413 | SEQ ID NO: 850, SEQ ID NO: 315, SEQ ID NO: 861 | hsa-miR-1207-5p, hsa-miR-509-3-5p, hsa-miR-1184 | 70.7% | 72.8% | 68.5% |
| SNO-414 | SEQ ID NO: 315, SEQ ID NO: 87, SEQ ID NO: 838 | hsa-miR-509-3-5p, hsa-miR-664, hsa-miR-1228* | 74.2% | 77.2% | 71.2% |
| SNO-415 | SEQ ID NO: 87, SEQ ID NO: 888, SEQ ID NO: 883 | hsa-miR-664, hsa-let-7i, hsa-miR-101 | 77.1% | 71.3% | 82.8% |
| SNO-416 | SEQ ID NO: 888, SEQ ID NO: 861, SEQ ID NO: 199 | hsa-let-7i, hsa-miR-1184, hsa-miR-564 | 58.9% | 62.5% | 55.3% |
| SNO-417 | SEQ ID NO: 861, SEQ ID NO: 838, SEQ ID NO: 874 | hsa-miR-1184, hsa-miR-1228*, hsa-miR-106b | 72.3% | 85.0% | 59.7% |
| SNO-418 | SEQ ID NO: 838, SEQ ID NO: 883, SEQ ID NO: 645 | hsa-miR-1228*, hsa-miR-101, hsa-miR-1908 | 64.9% | 63.7% | 66.2% |
| SNO-419 | SEQ ID NO: 883, SEQ ID NO: 199, SEQ ID NO: 710 | hsa-miR-101, hsa-miR-564, hsa-miR-1469 | 72.6% | 70.7% | 74.5% |
| SNO-420 | SEQ ID NO: 199, SEQ ID NO: 874, SEQ ID NO: 442 | hsa-miR-564, hsa-miR-106b, hsa-miR-342-3p | 81.3% | 72.8% | 89.8% |
| SNO-421 | SEQ ID NO: 874, SEQ ID NO: 645, SEQ ID NO: 542 | hsa-miR-106b, hsa-miR-1908, hsa-miR-222 | 65.7% | 78.5% | 52.8% |
| SNO-422 | SEQ ID NO: 645, SEQ ID NO: 710, SEQ ID NO: 632 | hsa-miR-1908, hsa-miR-1469, hsa-miR-1915 | 59.7% | 65.7% | 53.7% |
| SNO-423 | SEQ ID NO: 710, SEQ ID NO: 442, SEQ ID NO: 573 | hsa-miR-1469, hsa-miR-342-3p, hsa-miR-210 | 75.8% | 76.2% | 75.5% |

FIG 15 (continued)

| | | | | | |
|---|---|---|---|---|---|
| SNO-424 | SEQ ID NO: 442, SEQ ID NO: 542, SEQ ID NO: 762 | hsa-miR-342-3p, hsa-miR-222, hsa-miR-1295 | 77.3% | 72.3% | 82.3% |
| SNO-425 | SEQ ID NO: 542, SEQ ID NO: 632, SEQ ID NO: 378 | hsa-miR-222, hsa-miR-1915, hsa-miR-431 | 62.3% | 71.5% | 53.2% |
| SNO-426 | SEQ ID NO: 632, SEQ ID NO: 573, SEQ ID NO: 253 | hsa-miR-1915, hsa-miR-210, hsa-miR-526a | 69.5% | 75.3% | 63.7% |
| SNO-427 | SEQ ID NO: 573, SEQ ID NO: 762, SEQ ID NO: 89 | hsa-miR-210, hsa-miR-1295, hsa-miR-663 | 72.3% | 70.3% | 74.2% |
| SNO-428 | SEQ ID NO: 762, SEQ ID NO: 378, SEQ ID NO: 897 | hsa-miR-1295, hsa-miR-431, hsa-let-7d | 69.4% | 67.3% | 71.5% |
| SNO-429 | SEQ ID NO: 714, SEQ ID NO: 779, SEQ ID NO: 92 | hsa-miR-144*, hsa-miR-1280, hsa-miR-660 | 75.1% | 79.7% | 70.5% |
| SNO-430 | SEQ ID NO: 673, SEQ ID NO: 92, SEQ ID NO: 805 | hsa-miR-181a, hsa-miR-660, hsa-miR-126 | 73.2% | 74.3% | 72.0% |
| SNO-431 | SEQ ID NO: 189, SEQ ID NO: 805, SEQ ID NO: 414 | hsa-miR-574-5p, hsa-miR-126, hsa-miR-374a | 63.5% | 64.8% | 62.2% |
| SNO-432 | SEQ ID NO: 779, SEQ ID NO: 414, SEQ ID NO: 696 | hsa-miR-1280, hsa-miR-374a, hsa-miR-149* | 71.9% | 70.8% | 73.0% |
| SNO-433 | SEQ ID NO: 92, SEQ ID NO: 696, SEQ ID NO: 850 | hsa-miR-660, hsa-miR-149*, hsa-miR-1207-5p | 58.3% | 57.8% | 58.7% |
| SNO-434 | SEQ ID NO: 805, SEQ ID NO: 850, SEQ ID NO: 315 | hsa-miR-126, hsa-miR-1207-5p, hsa-miR-509-3-5p | 69.3% | 71.3% | 67.3% |
| SNO-435 | SEQ ID NO: 414, SEQ ID NO: 315, SEQ ID NO: 87 | hsa-miR-374a, hsa-miR-509-3-5p, hsa-miR-664 | 65.3% | 70.7% | 60.0% |
| SNO-436 | SEQ ID NO: 696, SEQ ID NO: 87, SEQ ID NO: 888 | hsa-miR-149*, hsa-miR-664, hsa-let-7i | 69.3% | 63.5% | 75.0% |
| SNO-437 | SEQ ID NO: 850, SEQ ID NO: 888, | hsa-miR-1207-5p, hsa-let-7i, hsa-miR- | 68.8% | 70.5% | 67.2% |

FIG 15 (continued)

| | | | | | |
|---|---|---|---|---|---|
| | SEQ ID NO: 861 | 1184 | | | |
| SNO-438 | SEQ ID NO: 315, SEQ ID NO: 861, SEQ ID NO: 838 | hsa-miR-509-3-5p, hsa-miR-1184, hsa-miR-1228* | 74.2% | 80.8% | 67.5% |
| SNO-439 | SEQ ID NO: 87, SEQ ID NO: 838, SEQ ID NO: 883 | hsa-miR-664, hsa-miR-1228*, hsa-miR-101 | 77.9% | 76.0% | 79.8% |
| SNO-440 | SEQ ID NO: 888, SEQ ID NO: 883, SEQ ID NO: 199 | hsa-let-7i, hsa-miR-101, hsa-miR-564 | 72.2% | 69.7% | 74.7% |
| SNO-441 | SEQ ID NO: 861, SEQ ID NO: 199, SEQ ID NO: 874 | hsa-miR-1184, hsa-miR-564, hsa-miR-106b | 69.4% | 71.3% | 67.5% |
| SNO-442 | SEQ ID NO: 838, SEQ ID NO: 874, SEQ ID NO: 645 | hsa-miR-1228*, hsa-miR-106b, hsa-miR-1908 | 72.2% | 79.5% | 64.8% |
| SNO-443 | SEQ ID NO: 883, SEQ ID NO: 645, SEQ ID NO: 710 | hsa-miR-101, hsa-miR-1908, hsa-miR-1469 | 63.0% | 60.2% | 65.8% |
| SNO-444 | SEQ ID NO: 199, SEQ ID NO: 710, SEQ ID NO: 442 | hsa-miR-564, hsa-miR-1469, hsa-miR-342-3p | 73.9% | 63.2% | 84.7% |
| SNO-445 | SEQ ID NO: 874, SEQ ID NO: 442, SEQ ID NO: 542 | hsa-miR-106b, hsa-miR-342-3p, hsa-miR-222 | 75.8% | 69.7% | 81.8% |
| SNO-446 | SEQ ID NO: 645, SEQ ID NO: 542, SEQ ID NO: 632 | hsa-miR-1908, hsa-miR-222, hsa-miR-1915 | 61.7% | 75.0% | 48.3% |
| SNO-447 | SEQ ID NO: 710, SEQ ID NO: 632, SEQ ID NO: 573 | hsa-miR-1469, hsa-miR-1915, hsa-miR-210 | 70.8% | 67.3% | 74.2% |
| SNO-448 | SEQ ID NO: 442, SEQ ID NO: 573, SEQ ID NO: 762 | hsa-miR-342-3p, hsa-miR-210, hsa-miR-1295 | 76.3% | 78.0% | 74.7% |
| SNO-449 | SEQ ID NO: 542, SEQ ID NO: 762, SEQ ID NO: 378 | hsa-miR-222, hsa-miR-1295, hsa-miR-431 | 69.9% | 69.8% | 70.0% |
| SNO-450 | SEQ ID NO: 632, SEQ ID NO: 378, SEQ ID NO: 253 | hsa-miR-1915, hsa-miR-431, hsa-miR-526a | 69.5% | 79.2% | 59.8% |

FIG 15 (continued)

| | | | | | |
|---|---|---|---|---|---|
| SNO-451 | SEQ ID NO: 573, SEQ ID NO: 253, SEQ ID NO: 89 | hsa-miR-210, hsa-miR-526a, hsa-miR-663 | 68.8% | 77.2% | 60.3% |
| SNO-452 | SEQ ID NO: 762, SEQ ID NO: 89, SEQ ID NO: 897 | hsa-miR-1295, hsa-miR-663, hsa-let-7d | 70.3% | 66.7% | 74.0% |
| SNO-453 | SEQ ID NO: 709, SEQ ID NO: 673 | hsa-miR-146a, hsa-miR-181a | 69.8% | 64.2% | 75.3% |
| SNO-454 | SEQ ID NO: 92, SEQ ID NO: 478 | hsa-miR-660, hsa-miR-30e | 63.5% | 62.2% | 64.8% |
| SNO-455 | SEQ ID NO: 478, SEQ ID NO: 805 | hsa-miR-30e, hsa-miR-126 | 65.4% | 71.5% | 59.3% |
| SNO-456 | SEQ ID NO: 838, SEQ ID NO: 395 | hsa-miR-1228*, hsa-miR-383 | 74.5% | 80.0% | 69.0% |
| SNO-457 | SEQ ID NO: 395, SEQ ID NO: 883 | hsa-miR-383, hsa-miR-101 | 77.1% | 81.2% | 73.0% |
| SNO-458 | SEQ ID NO: 542, SEQ ID NO: 770 | hsa-miR-222, hsa-miR-1289 | 66.6% | 68.7% | 64.5% |
| SNO-459 | SEQ ID NO: 770, SEQ ID NO: 632 | hsa-miR-1289, hsa-miR-1915 | 65.8% | 61.8% | 69.8% |
| SNO-460 | SEQ ID NO: 709, SEQ ID NO: 189 | hsa-miR-146a, hsa-miR-574-5p | 61.8% | 60.8% | 62.7% |
| SNO-461 | SEQ ID NO: 779, SEQ ID NO: 478 | hsa-miR-1280, hsa-miR-30e | 73.5% | 79.8% | 67.2% |
| SNO-462 | SEQ ID NO: 478, SEQ ID NO: 414 | hsa-miR-30e, hsa-miR-374a | 68.3% | 68.2% | 68.5% |
| SNO-463 | SEQ ID NO: 861, SEQ ID NO: 395 | hsa-miR-1184, hsa-miR-383 | 73.6% | 76.8% | 70.3% |
| SNO-464 | SEQ ID NO: 395, SEQ ID NO: 199 | hsa-miR-383, hsa-miR-564 | 73.3% | 73.7% | 72.8% |
| SNO-465 | SEQ ID NO: 442, SEQ ID NO: 770 | hsa-miR-342-3p, hsa-miR-1289 | 70.8% | 59.7% | 82.0% |
| SNO-466 | SEQ ID NO: 770, SEQ ID NO: 573 | hsa-miR-1289, hsa-miR-210 | 70.8% | 67.7% | 74.0% |
| SNO-467 | SEQ ID NO: 709, SEQ ID NO: 779 | hsa-miR-146a, hsa-miR-1280 | 80.1% | 81.7% | 78.5% |
| SNO-468 | SEQ ID NO: 189, SEQ ID NO: 478 | hsa-miR-574-5p, hsa-miR-30e | 68.9% | 67.7% | 70.2% |
| SNO-469 | SEQ ID NO: 478, SEQ ID NO: 696 | hsa-miR-30e, hsa-miR-149* | 65.2% | 64.8% | 65.5% |
| SNO-470 | SEQ ID NO: 888, SEQ ID NO: 395 | hsa-let-7i, hsa-miR-383 | 68.0% | 67.5% | 68.5% |
| SNO-471 | SEQ ID NO: 395, SEQ ID NO: 874 | hsa-miR-383, hsa-miR-106b | 73.2% | 76.2% | 70.2% |
| SNO-472 | SEQ ID NO: 710, SEQ ID NO: 770 | hsa-miR-1469, hsa-miR-1289 | 62.8% | 55.3% | 70.2% |
| SNO-473 | SEQ ID NO: 770, SEQ ID NO: 762 | hsa-miR-1289, hsa-miR-1295 | 64.8% | 57.3% | 72.2% |
| SNO-474 | SEQ ID NO: 714, SEQ ID NO: 709, | hsa-miR-144*, hsa-miR-146a, hsa- | 76.8% | 76.2% | 77.3% |

FIG 15 (continued)

| | | | | | |
|---|---|---|---|---|---|
| | SEQ ID NO: 673 | miR-181a | | | |
| SNO-475 | SEQ ID NO: 709, SEQ ID NO: 673, SEQ ID NO: 189 | hsa-miR-146a, hsa-miR-181a, hsa-miR-574-5p | 73.0% | 67.7% | 78.3% |
| SNO-476 | SEQ ID NO: 779, SEQ ID NO: 92, SEQ ID NO: 478 | hsa-miR-1280, hsa-miR-660, hsa-miR-30e | 75.0% | 85.0% | 65.0% |
| SNO-477 | SEQ ID NO: 92, SEQ ID NO: 478, SEQ ID NO: 805 | hsa-miR-660, hsa-miR-30e, hsa-miR-126 | 65.5% | 67.2% | 63.8% |
| SNO-478 | SEQ ID NO: 478, SEQ ID NO: 805, SEQ ID NO: 414 | hsa-miR-30e, hsa-miR-126, hsa-miR-374a | 68.8% | 70.3% | 67.2% |
| SNO-479 | SEQ ID NO: 861, SEQ ID NO: 838, SEQ ID NO: 395 | hsa-miR-1184, hsa-miR-1228*, hsa-miR-383 | 73.2% | 76.7% | 69.7% |
| SNO-480 | SEQ ID NO: 838, SEQ ID NO: 395, SEQ ID NO: 883 | hsa-miR-1228*, hsa-miR-383, hsa-miR-101 | 78.0% | 86.5% | 69.5% |
| SNO-481 | SEQ ID NO: 395, SEQ ID NO: 883, SEQ ID NO: 199 | hsa-miR-383, hsa-miR-101, hsa-miR-564 | 77.4% | 82.5% | 72.3% |
| SNO-482 | SEQ ID NO: 442, SEQ ID NO: 542, SEQ ID NO: 770 | hsa-miR-342-3p, hsa-miR-222, hsa-miR-1289 | 73.9% | 69.3% | 78.5% |
| SNO-483 | SEQ ID NO: 542, SEQ ID NO: 770, SEQ ID NO: 632 | hsa-miR-222, hsa-miR-1289, hsa-miR-1915 | 67.4% | 72.8% | 62.0% |
| SNO-484 | SEQ ID NO: 770, SEQ ID NO: 632, SEQ ID NO: 573 | hsa-miR-1289, hsa-miR-1915, hsa-miR-210 | 71.3% | 67.5% | 75.2% |
| SNO-485 | SEQ ID NO: 714, SEQ ID NO: 709, SEQ ID NO: 189 | hsa-miR-144*, hsa-miR-146a, hsa-miR-574-5p | 77.2% | 75.5% | 78.8% |
| SNO-486 | SEQ ID NO: 709, SEQ ID NO: 673, SEQ ID NO: 779 | hsa-miR-146a, hsa-miR-181a, hsa-miR-1280 | 81.3% | 85.0% | 77.7% |
| SNO-487 | SEQ ID NO: 189, SEQ ID NO: 779, SEQ ID NO: 478 | hsa-miR-574-5p, hsa-miR-1280, hsa-miR-30e | 74.4% | 81.8% | 67.0% |

FIG 15 (continued)

| | | | | | |
|---|---|---|---|---|---|
| SNO-488 | SEQ ID NO: 92, SEQ ID NO: 478, SEQ ID NO: 414 | hsa-miR-660, hsa-miR-30e, hsa-miR-374a | 65.6% | 65.2% | 66.0% |
| SNO-489 | SEQ ID NO: 478, SEQ ID NO: 805, SEQ ID NO: 696 | hsa-miR-30e, hsa-miR-126, hsa-miR-149* | 68.1% | 69.3% | 66.8% |
| SNO-490 | SEQ ID NO: 888, SEQ ID NO: 861, SEQ ID NO: 395 | hsa-let-7i, hsa-miR-1184, hsa-miR-383 | 70.4% | 76.8% | 64.0% |
| SNO-491 | SEQ ID NO: 838, SEQ ID NO: 395, SEQ ID NO: 199 | hsa-miR-1228*, hsa-miR-383, hsa-miR-564 | 74.7% | 77.0% | 72.3% |
| SNO-492 | SEQ ID NO: 395, SEQ ID NO: 883, SEQ ID NO: 874 | hsa-miR-383, hsa-miR-101, hsa-miR-106b | 79.0% | 86.0% | 72.0% |
| SNO-493 | SEQ ID NO: 710, SEQ ID NO: 442, SEQ ID NO: 770 | hsa-miR-1469, hsa-miR-342-3p, hsa-miR-1289 | 71.2% | 61.2% | 81.2% |
| SNO-494 | SEQ ID NO: 542, SEQ ID NO: 770, SEQ ID NO: 573 | hsa-miR-222, hsa-miR-1289, hsa-miR-210 | 75.4% | 75.7% | 75.2% |
| SNO-495 | SEQ ID NO: 770, SEQ ID NO: 632, SEQ ID NO: 762 | hsa-miR-1289, hsa-miR-1915, hsa-miR-1295 | 65.1% | 57.7% | 72.5% |
| SNO-496 | SEQ ID NO: 709, SEQ ID NO: 189, SEQ ID NO: 779 | hsa-miR-146a, hsa-miR-574-5p, hsa-miR-1280 | 80.4% | 83.7% | 77.2% |
| SNO-497 | SEQ ID NO: 189, SEQ ID NO: 92, SEQ ID NO: 478 | hsa-miR-574-5p, hsa-miR-660, hsa-miR-30e | 66.9% | 67.3% | 66.5% |
| SNO-498 | SEQ ID NO: 779, SEQ ID NO: 478, SEQ ID NO: 805 | hsa-miR-1280, hsa-miR-30e, hsa-miR-126 | 73.8% | 82.3% | 65.2% |
| SNO-499 | SEQ ID NO: 478, SEQ ID NO: 414, SEQ ID NO: 696 | hsa-miR-30e, hsa-miR-374a, hsa-miR-149* | 69.1% | 63.8% | 74.3% |
| SNO-500 | SEQ ID NO: 888, SEQ ID NO: 838, SEQ ID NO: 395 | hsa-let-7i, hsa-miR-1228*, hsa-miR-383 | 72.7% | 78.0% | 67.3% |
| SNO-501 | SEQ ID NO: 861, SEQ ID NO: 395, | hsa-miR-1184, hsa-miR-383, hsa-miR- | 75.4% | 81.0% | 69.8% |

FIG 15 (continued)

| | | | | | |
|---|---|---|---|---|---|
| | SEQ ID NO: 883 | 101 | | | |
| SNO-502 | SEQ ID NO: 395, SEQ ID NO: 199, SEQ ID NO: 874 | hsa-miR-383, hsa-miR-564, hsa-miR-106b | 77.7% | 81.3% | 74.0% |
| SNO-503 | SEQ ID NO: 710, SEQ ID NO: 542, SEQ ID NO: 770 | hsa-miR-1469, hsa-miR-222, hsa-miR-1289 | 67.2% | 71.7% | 62.7% |
| SNO-504 | SEQ ID NO: 442, SEQ ID NO: 770, SEQ ID NO: 632 | hsa-miR-342-3p, hsa-miR-1289, hsa-miR-1915 | 71.5% | 62.7% | 80.3% |
| SNO-505 | SEQ ID NO: 770, SEQ ID NO: 573, SEQ ID NO: 762 | hsa-miR-1289, hsa-miR-210, hsa-miR-1295 | 73.8% | 71.8% | 75.8% |
| SNO-506 | SEQ ID NO: 709, SEQ ID NO: 189, SEQ ID NO: 92 | hsa-miR-146a, hsa-miR-574-5p, hsa-miR-660 | 66.2% | 62.3% | 70.0% |
| SNO-507 | SEQ ID NO: 673, SEQ ID NO: 779, SEQ ID NO: 478 | hsa-miR-181a, hsa-miR-1280, hsa-miR-30e | 80.1% | 87.2% | 73.0% |
| SNO-508 | SEQ ID NO: 779, SEQ ID NO: 478, SEQ ID NO: 414 | hsa-miR-1280, hsa-miR-30e, hsa-miR-374a | 74.3% | 79.0% | 69.7% |
| SNO-509 | SEQ ID NO: 478, SEQ ID NO: 414, SEQ ID NO: 850 | hsa-miR-30e, hsa-miR-374a, hsa-miR-1207-5p | 62.3% | 58.5% | 66.0% |
| SNO-510 | SEQ ID NO: 87, SEQ ID NO: 861, SEQ ID NO: 395 | hsa-miR-664, hsa-miR-1184, hsa-miR-383 | 71.4% | 73.7% | 69.2% |
| SNO-511 | SEQ ID NO: 861, SEQ ID NO: 395, SEQ ID NO: 199 | hsa-miR-1184, hsa-miR-383, hsa-miR-564 | 72.8% | 71.3% | 74.2% |
| SNO-512 | SEQ ID NO: 395, SEQ ID NO: 199, SEQ ID NO: 645 | hsa-miR-383, hsa-miR-564, hsa-miR-1908 | 72.8% | 73.8% | 71.8% |
| SNO-513 | SEQ ID NO: 645, SEQ ID NO: 442, SEQ ID NO: 770 | hsa-miR-1908, hsa-miR-342-3p, hsa-miR-1289 | 68.3% | 60.0% | 76.5% |
| SNO-514 | SEQ ID NO: 442, SEQ ID NO: 770, SEQ ID NO: 573 | hsa-miR-342-3p, hsa-miR-1289, hsa-miR-210 | 76.0% | 73.7% | 78.3% |

FIG. 15 (continued)

| | | | | | |
|---|---|---|---|---|---|
| SNO-515 | SEQ ID NO: 714, SEQ ID NO: 709, SEQ ID NO: 779 | hsa-miR-144*, hsa-miR-146a, hsa-miR-1280 | 79.8% | 81.3% | 78.2% |
| SNO-516 | SEQ ID NO: 709, SEQ ID NO: 673, SEQ ID NO: 92 | hsa-miR-146a, hsa-miR-181a, hsa-miR-660 | 71.7% | 69.0% | 74.3% |
| SNO-517 | SEQ ID NO: 673, SEQ ID NO: 189, SEQ ID NO: 478 | hsa-miR-181a, hsa-miR-574-5p, hsa-miR-30e | 71.9% | 65.2% | 78.7% |
| SNO-518 | SEQ ID NO: 92, SEQ ID NO: 478, SEQ ID NO: 696 | hsa-miR-660, hsa-miR-30e, hsa-miR-149* | 64.3% | 65.8% | 62.8% |
| SNO-519 | SEQ ID NO: 478, SEQ ID NO: 805, SEQ ID NO: 850 | hsa-miR-30e, hsa-miR-126, hsa-miR-1207-5p | 66.7% | 67.8% | 65.5% |
| SNO-520 | SEQ ID NO: 87, SEQ ID NO: 888, SEQ ID NO: 395 | hsa-miR-664, hsa-let-7i, hsa-miR-383 | 69.2% | 64.2% | 74.2% |
| SNO-521 | SEQ ID NO: 838, SEQ ID NO: 395, SEQ ID NO: 874 | hsa-miR-1228*, hsa-miR-383, hsa-miR-106b | 76.9% | 84.8% | 69.0% |
| SNO-522 | SEQ ID NO: 395, SEQ ID NO: 883, SEQ ID NO: 645 | hsa-miR-383, hsa-miR-101, hsa-miR-1908 | 77.8% | 83.5% | 72.2% |
| SNO-523 | SEQ ID NO: 645, SEQ ID NO: 710, SEQ ID NO: 770 | hsa-miR-1908, hsa-miR-1469, hsa-miR-1289 | 57.2% | 63.5% | 50.8% |
| SNO-524 | SEQ ID NO: 542, SEQ ID NO: 770, SEQ ID NO: 762 | hsa-miR-222, hsa-miR-1289, hsa-miR-1295 | 70.9% | 69.5% | 72.3% |
| SNO-525 | SEQ ID NO: 709, SEQ ID NO: 779, SEQ ID NO: 92 | hsa-miR-146a, hsa-miR-1280, hsa-miR-660 | 79.7% | 84.2% | 75.2% |
| SNO-526 | SEQ ID NO: 673, SEQ ID NO: 92, SEQ ID NO: 478 | hsa-miR-181a, hsa-miR-660, hsa-miR-30e | 70.8% | 69.3% | 72.3% |
| SNO-527 | SEQ ID NO: 189, SEQ ID NO: 478, SEQ ID NO: 805 | hsa-miR-574-5p, hsa-miR-30e, hsa-miR-126 | 68.8% | 70.8% | 66.7% |
| SNO-528 | SEQ ID NO: 478, SEQ ID NO: 696, | hsa-miR-30e, hsa-miR-149*, hsa-miR- | 64.5% | 66.0% | 63.0% |

FIG 15 (continued)

| | | | | | |
|---|---|---|---|---|---|
| | SEQ ID NO: 850 | 1207-5p | | | |
| SNO-529 | SEQ ID NO: 87, SEQ ID NO: 838, SEQ ID NO: 395 | hsa-miR-664, hsa-miR-1228*, hsa-miR-383 | 72.8% | 76.2% | 69.5% |
| SNO-530 | SEQ ID NO: 888, SEQ ID NO: 395, SEQ ID NO: 883 | hsa-let-7i, hsa-miR-383, hsa-miR-101 | 74.4% | 76.0% | 72.8% |
| SNO-531 | SEQ ID NO: 395, SEQ ID NO: 874, SEQ ID NO: 645 | hsa-miR-383, hsa-miR-106b, hsa-miR-1908 | 76.8% | 85.0% | 68.7% |
| SNO-532 | SEQ ID NO: 645, SEQ ID NO: 542, SEQ ID NO: 770 | hsa-miR-1908, hsa-miR-222, hsa-miR-1289 | 62.3% | 70.8% | 53.7% |
| SNO-533 | SEQ ID NO: 710, SEQ ID NO: 770, SEQ ID NO: 632 | hsa-miR-1469, hsa-miR-1289, hsa-miR-1915 | 61.9% | 55.5% | 68.3% |
| SNO-534 | SEQ ID NO: 714, SEQ ID NO: 838 | hsa-miR-144*, hsa-miR-1228* | 73.5% | 75.7% | 71.3% |
| SNO-535 | SEQ ID NO: 838, SEQ ID NO: 709 | hsa-miR-1228*, hsa-miR-146a | 75.5% | 76.8% | 74.2% |
| SNO-536 | SEQ ID NO: 673, SEQ ID NO: 395 | hsa-miR-181a, hsa-miR-383 | 74.4% | 68.0% | 80.8% |
| SNO-537 | SEQ ID NO: 395, SEQ ID NO: 189 | hsa-miR-383, hsa-miR-574-5p | 73.5% | 72.0% | 75.0% |
| SNO-538 | SEQ ID NO: 189, SEQ ID NO: 883 | hsa-miR-574-5p, hsa-miR-101 | 64.8% | 63.5% | 66.2% |
| SNO-539 | SEQ ID NO: 199, SEQ ID NO: 779 | hsa-miR-564, hsa-miR-1280 | 74.6% | 78.3% | 70.8% |
| SNO-540 | SEQ ID NO: 779, SEQ ID NO: 874 | hsa-miR-1280, hsa-miR-106b | 73.1% | 73.8% | 72.3% |
| SNO-541 | SEQ ID NO: 874, SEQ ID NO: 441 | hsa-miR-106b, hsa-miR-342-5p | 65.0% | 72.2% | 57.8% |
| SNO-542 | SEQ ID NO: 441, SEQ ID NO: 645 | hsa-miR-342-5p, hsa-miR-1908 | 63.8% | 79.3% | 48.2% |
| SNO-543 | SEQ ID NO: 710, SEQ ID NO: 684 | hsa-miR-1469, hsa-miR-155 | 64.4% | 57.3% | 71.5% |
| SNO-544 | SEQ ID NO: 92, SEQ ID NO: 542 | hsa-miR-660, hsa-miR-222 | 62.7% | 64.0% | 61.3% |
| SNO-545 | SEQ ID NO: 573, SEQ ID NO: 478 | hsa-miR-210, hsa-miR-30e | 69.8% | 67.5% | 72.0% |
| SNO-546 | SEQ ID NO: 478, SEQ ID NO: 762 | hsa-miR-30e, hsa-miR-1295 | 63.6% | 61.8% | 65.3% |
| SNO-547 | SEQ ID NO: 897, SEQ ID NO: 669 | hsa-let-7d, hsa-miR-181c | 75.1% | 73.0% | 77.2% |
| SNO-548 | SEQ ID NO: 669, SEQ ID NO: 165 | hsa-miR-181c, hsa-miR-593* | 65.8% | 64.2% | 67.3% |

FIG 15 (continued)

| | | | | | |
|---|---|---|---|---|---|
| SNO-549 | SEQ ID NO: 838, SEQ ID NO: 673 | hsa-miR-1228*, hsa-miR-181a | 76.3% | 80.8% | 71.8% |
| SNO-550 | SEQ ID NO: 709, SEQ ID NO: 395 | hsa-miR-146a, hsa-miR-383 | 72.6% | 71.8% | 73.3% |
| SNO-551 | SEQ ID NO: 189, SEQ ID NO: 199 | hsa-miR-574-5p, hsa-miR-564 | 69.3% | 71.5% | 67.0% |
| SNO-552 | SEQ ID NO: 883, SEQ ID NO: 779 | hsa-miR-101, hsa-miR-1280 | 73.8% | 75.8% | 71.8% |
| SNO-553 | SEQ ID NO: 779, SEQ ID NO: 441 | hsa-miR-1280, hsa-miR-342-5p | 72.3% | 80.7% | 63.8% |
| SNO-554 | SEQ ID NO: 441, SEQ ID NO: 710 | hsa-miR-342-5p, hsa-miR-1469 | 63.1% | 63.8% | 62.3% |
| SNO-555 | SEQ ID NO: 645, SEQ ID NO: 684 | hsa-miR-1908, hsa-miR-155 | 65.5% | 60.0% | 71.0% |
| SNO-556 | SEQ ID NO: 92, SEQ ID NO: 770 | hsa-miR-660, hsa-miR-1289 | 65.5% | 56.2% | 74.8% |
| SNO-557 | SEQ ID NO: 632, SEQ ID NO: 478 | hsa-miR-1915, hsa-miR-30e | 63.0% | 68.7% | 57.3% |
| SNO-558 | SEQ ID NO: 478, SEQ ID NO: 378 | hsa-miR-30e, hsa-miR-431 | 66.2% | 67.3% | 65.0% |
| SNO-559 | SEQ ID NO: 89, SEQ ID NO: 669 | hsa-miR-663, hsa-miR-181c | 65.5% | 67.3% | 63.7% |
| SNO-560 | SEQ ID NO: 897, SEQ ID NO: 165 | hsa-let-7d, hsa-miR-593* | 64.4% | 67.0% | 61.8% |
| SNO-561 | SEQ ID NO: 673, SEQ ID NO: 883 | hsa-miR-181a, hsa-miR-101 | 74.3% | 70.3% | 78.2% |
| SNO-562 | SEQ ID NO: 199, SEQ ID NO: 441 | hsa-miR-564, hsa-miR-342-5p | 61.0% | 62.8% | 59.2% |
| SNO-563 | SEQ ID NO: 779, SEQ ID NO: 645 | hsa-miR-1280, hsa-miR-1908 | 73.0% | 73.8% | 72.2% |
| SNO-564 | SEQ ID NO: 441, SEQ ID NO: 684 | hsa-miR-342-5p, hsa-miR-155 | 63.4% | 64.7% | 62.2% |
| SNO-565 | SEQ ID NO: 710, SEQ ID NO: 92 | hsa-miR-1469, hsa-miR-660 | 59.8% | 55.8% | 63.7% |
| SNO-566 | SEQ ID NO: 684, SEQ ID NO: 542 | hsa-miR-155, hsa-miR-222 | 65.3% | 63.8% | 66.8% |
| SNO-567 | SEQ ID NO: 92, SEQ ID NO: 632 | hsa-miR-660, hsa-miR-1915 | 62.3% | 55.5% | 69.2% |
| SNO-568 | SEQ ID NO: 770, SEQ ID NO: 478 | hsa-miR-1289, hsa-miR-30e | 62.1% | 54.5% | 69.7% |
| SNO-569 | SEQ ID NO: 478, SEQ ID NO: 253 | hsa-miR-30e, hsa-miR-526a | 69.7% | 71.8% | 67.5% |
| SNO-570 | SEQ ID NO: 253, SEQ ID NO: 669 | hsa-miR-526a, hsa-miR-181c | 67.4% | 74.2% | 60.7% |
| SNO-571 | SEQ ID NO: 89, SEQ ID NO: 165 | hsa-miR-663, hsa-miR-593* | 62.8% | 68.3% | 57.3% |
| SNO-572 | SEQ ID NO: 714, SEQ ID NO: 838, SEQ ID NO: 709 | hsa-miR-144*, hsa-miR-1228*, hsa-miR-146a | 76.3% | 76.8% | 75.8% |
| SNO-573 | SEQ ID NO: 838, SEQ ID NO: 709, | hsa-miR-1228*, hsa-miR-146a, hsa- | 74.2% | 76.5% | 71.8% |

FIG 15 (continued)

| | | | | | |
|---|---|---|---|---|---|
| | SEQ ID NO: 673 | miR-181a | | | |
| SNO-574 | SEQ ID NO: 709, SEQ ID NO: 673, SEQ ID NO: 395 | hsa-miR-146a, hsa-miR-181a, hsa-miR-383 | 76.5% | 75.2% | 77.8% |
| SNO-575 | SEQ ID NO: 673, SEQ ID NO: 395, SEQ ID NO: 189 | hsa-miR-181a, hsa-miR-383, hsa-miR-574-5p | 76.7% | 70.8% | 82.5% |
| SNO-576 | SEQ ID NO: 395, SEQ ID NO: 189, SEQ ID NO: 883 | hsa-miR-383, hsa-miR-574-5p, hsa-miR-101 | 79.6% | 82.8% | 76.3% |
| SNO-577 | SEQ ID NO: 189, SEQ ID NO: 883, SEQ ID NO: 199 | hsa-miR-574-5p, hsa-miR-101, hsa-miR-564 | 74.9% | 73.2% | 76.7% |
| SNO-578 | SEQ ID NO: 883, SEQ ID NO: 199, SEQ ID NO: 779 | hsa-miR-101, hsa-miR-564, hsa-miR-1280 | 71.3% | 75.5% | 67.0% |
| SNO-579 | SEQ ID NO: 199, SEQ ID NO: 779, SEQ ID NO: 874 | hsa-miR-564, hsa-miR-1280, hsa-miR-106b | 78.0% | 78.7% | 77.3% |
| SNO-580 | SEQ ID NO: 779, SEQ ID NO: 874, SEQ ID NO: 441 | hsa-miR-1280, hsa-miR-106b, hsa-miR-342-5p | 71.3% | 75.8% | 66.8% |
| SNO-581 | SEQ ID NO: 874, SEQ ID NO: 441, SEQ ID NO: 645 | hsa-miR-106b, hsa-miR-342-5p, hsa-miR-1908 | 63.1% | 74.3% | 51.8% |
| SNO-582 | SEQ ID NO: 441, SEQ ID NO: 645, SEQ ID NO: 710 | hsa-miR-342-5p, hsa-miR-1908, hsa-miR-1469 | 65.3% | 76.2% | 54.5% |
| SNO-583 | SEQ ID NO: 645, SEQ ID NO: 710, SEQ ID NO: 684 | hsa-miR-1908, hsa-miR-1469, hsa-miR-155 | 68.3% | 63.5% | 73.2% |
| SNO-584 | SEQ ID NO: 710, SEQ ID NO: 684, SEQ ID NO: 442 | hsa-miR-1469, hsa-miR-155, hsa-miR-342-3p | 76.6% | 69.2% | 84.0% |
| SNO-585 | SEQ ID NO: 442, SEQ ID NO: 92, SEQ ID NO: 542 | hsa-miR-342-3p, hsa-miR-660, hsa-miR-222 | 77.3% | 74.8% | 79.8% |
| SNO-586 | SEQ ID NO: 92, SEQ ID NO: 542, SEQ ID NO: 770 | hsa-miR-660, hsa-miR-222, hsa-miR-1289 | 66.3% | 65.2% | 67.5% |

FIG 15 (continued)

| | | | | | |
|---|---|---|---|---|---|
| SNO-587 | SEQ ID NO: 632, SEQ ID NO: 573, SEQ ID NO: 478 | hsa-miR-1915, hsa-miR-210, hsa-miR-30e | 70.8% | 74.5% | 67.2% |
| SNO-588 | SEQ ID NO: 573, SEQ ID NO: 478, SEQ ID NO: 762 | hsa-miR-210, hsa-miR-30e, hsa-miR-1295 | 68.9% | 68.7% | 69.2% |
| SNO-589 | SEQ ID NO: 478, SEQ ID NO: 762, SEQ ID NO: 378 | hsa-miR-30e, hsa-miR-1295, hsa-miR-431 | 65.3% | 67.8% | 62.7% |
| SNO-590 | SEQ ID NO: 89, SEQ ID NO: 897, SEQ ID NO: 669 | hsa-miR-663, hsa-let-7d, hsa-miR-181c | 75.0% | 74.7% | 75.3% |
| SNO-591 | SEQ ID NO: 897, SEQ ID NO: 669, SEQ ID NO: 165 | hsa-let-7d, hsa-miR-181c, hsa-miR-593* | 71.3% | 69.8% | 72.7% |
| SNO-592 | SEQ ID NO: 714, SEQ ID NO: 838, SEQ ID NO: 673 | hsa-miR-144*, hsa-miR-1228*, hsa-miR-181a | 74.4% | 76.7% | 72.2% |
| SNO-593 | SEQ ID NO: 838, SEQ ID NO: 709, SEQ ID NO: 395 | hsa-miR-1228*, hsa-miR-146a, hsa-miR-383 | 74.7% | 78.5% | 70.8% |
| SNO-594 | SEQ ID NO: 673, SEQ ID NO: 395, SEQ ID NO: 883 | hsa-miR-181a, hsa-miR-383, hsa-miR-101 | 75.8% | 75.7% | 76.0% |
| SNO-595 | SEQ ID NO: 395, SEQ ID NO: 189, SEQ ID NO: 199 | hsa-miR-383, hsa-miR-574-5p, hsa-miR-564 | 75.8% | 77.5% | 74.2% |
| SNO-596 | SEQ ID NO: 189, SEQ ID NO: 883, SEQ ID NO: 779 | hsa-miR-574-5p, hsa-miR-101, hsa-miR-1280 | 68.3% | 72.8% | 63.8% |
| SNO-597 | SEQ ID NO: 199, SEQ ID NO: 779, SEQ ID NO: 441 | hsa-miR-564, hsa-miR-1280, hsa-miR-342-5p | 72.2% | 82.8% | 61.5% |
| SNO-598 | SEQ ID NO: 779, SEQ ID NO: 874, SEQ ID NO: 645 | hsa-miR-1280, hsa-miR-106b, hsa-miR-1908 | 74.3% | 77.2% | 71.3% |
| SNO-599 | SEQ ID NO: 874, SEQ ID NO: 441, SEQ ID NO: 710 | hsa-miR-106b, hsa-miR-342-5p, hsa-miR-1469 | 68.5% | 72.2% | 64.8% |
| SNO-600 | SEQ ID NO: 441, SEQ ID NO: 645, | hsa-miR-342-5p, hsa-miR-1908, hsa- | 64.6% | 70.0% | 59.2% |

FIG 15 (continued)

| | | | | | |
|---|---|---|---|---|---|
| | SEQ ID NO: 684 | miR-155 | | | |
| SNO-601 | SEQ ID NO: 710, SEQ ID NO: 684, SEQ ID NO: 92 | hsa-miR-1469, hsa-miR-155, hsa-miR-660 | 63.8% | 58.7% | 68.8% |
| SNO-602 | SEQ ID NO: 684, SEQ ID NO: 442, SEQ ID NO: 542 | hsa-miR-155, hsa-miR-342-3p, hsa-miR-222 | 75.2% | 76.0% | 74.3% |
| SNO-603 | SEQ ID NO: 442, SEQ ID NO: 92, SEQ ID NO: 770 | hsa-miR-342-3p, hsa-miR-660, hsa-miR-1289 | 77.7% | 73.3% | 82.0% |
| SNO-604 | SEQ ID NO: 92, SEQ ID NO: 542, SEQ ID NO: 632 | hsa-miR-660, hsa-miR-222, hsa-miR-1915 | 64.6% | 66.5% | 62.7% |
| SNO-605 | SEQ ID NO: 770, SEQ ID NO: 632, SEQ ID NO: 478 | hsa-miR-1289, hsa-miR-1915, hsa-miR-30e | 63.7% | 62.5% | 64.8% |
| SNO-606 | SEQ ID NO: 573, SEQ ID NO: 478, SEQ ID NO: 378 | hsa-miR-210, hsa-miR-30e, hsa-miR-431 | 70.8% | 72.5% | 69.2% |
| SNO-607 | SEQ ID NO: 478, SEQ ID NO: 762, SEQ ID NO: 253 | hsa-miR-30e, hsa-miR-1295, hsa-miR-526a | 63.3% | 65.0% | 61.7% |
| SNO-608 | SEQ ID NO: 253, SEQ ID NO: 89, SEQ ID NO: 669 | hsa-miR-526a, hsa-miR-663, hsa-miR-181c | 69.9% | 76.8% | 63.0% |
| SNO-609 | SEQ ID NO: 89, SEQ ID NO: 897, SEQ ID NO: 165 | hsa-miR-663, hsa-let-7d, hsa-miR-593* | 66.5% | 72.5% | 60.5% |
| SNO-610 | SEQ ID NO: 838, SEQ ID NO: 673, SEQ ID NO: 395 | hsa-miR-1228*, hsa-miR-181a, hsa-miR-383 | 75.4% | 80.2% | 70.7% |
| SNO-611 | SEQ ID NO: 709, SEQ ID NO: 395, SEQ ID NO: 189 | hsa-miR-146a, hsa-miR-383, hsa-miR-574-5p | 74.8% | 74.8% | 74.7% |
| SNO-612 | SEQ ID NO: 673, SEQ ID NO: 189, SEQ ID NO: 883 | hsa-miR-181a, hsa-miR-574-5p, hsa-miR-101 | 70.7% | 66.7% | 74.7% |
| SNO-613 | SEQ ID NO: 189, SEQ ID NO: 199, SEQ ID NO: 779 | hsa-miR-574-5p, hsa-miR-564, hsa-miR-1280 | 76.7% | 81.7% | 71.7% |

FIG 15 (continued)

| | | | | | |
|---|---|---|---|---|---|
| SNO-614 | SEQ ID NO: 883, SEQ ID NO: 779, SEQ ID NO: 874 | hsa-miR-101, hsa-miR-1280, hsa-miR-106b | 71.3% | 73.8% | 68.7% |
| SNO-615 | SEQ ID NO: 199, SEQ ID NO: 874, SEQ ID NO: 441 | hsa-miR-564, hsa-miR-106b, hsa-miR-342-5p | 70.1% | 71.7% | 68.5% |
| SNO-616 | SEQ ID NO: 779, SEQ ID NO: 441, SEQ ID NO: 645 | hsa-miR-1280, hsa-miR-342-5p, hsa-miR-1908 | 70.0% | 77.8% | 62.2% |
| SNO-617 | SEQ ID NO: 441, SEQ ID NO: 710, SEQ ID NO: 684 | hsa-miR-342-5p, hsa-miR-1469, hsa-miR-155 | 66.0% | 68.5% | 63.5% |
| SNO-618 | SEQ ID NO: 645, SEQ ID NO: 684, SEQ ID NO: 442 | hsa-miR-1908, hsa-miR-155, hsa-miR-342-3p | 73.2% | 66.5% | 79.8% |
| SNO-619 | SEQ ID NO: 710, SEQ ID NO: 442, SEQ ID NO: 92 | hsa-miR-1469, hsa-miR-342-3p, hsa-miR-660 | 73.8% | 68.5% | 79.0% |
| SNO-620 | SEQ ID NO: 684, SEQ ID NO: 92, SEQ ID NO: 542 | hsa-miR-155, hsa-miR-660, hsa-miR-222 | 68.8% | 66.7% | 71.0% |
| SNO-621 | SEQ ID NO: 92, SEQ ID NO: 770, SEQ ID NO: 632 | hsa-miR-660, hsa-miR-1289, hsa-miR-1915 | 63.7% | 60.3% | 67.0% |
| SNO-622 | SEQ ID NO: 770, SEQ ID NO: 573, SEQ ID NO: 478 | hsa-miR-1289, hsa-miR-210, hsa-miR-30e | 71.2% | 69.0% | 73.3% |
| SNO-623 | SEQ ID NO: 632, SEQ ID NO: 478, SEQ ID NO: 762 | hsa-miR-1915, hsa-miR-30e, hsa-miR-1295 | 66.9% | 65.7% | 68.2% |
| SNO-624 | SEQ ID NO: 478, SEQ ID NO: 378, SEQ ID NO: 253 | hsa-miR-30e, hsa-miR-431, hsa-miR-526a | 71.0% | 76.7% | 65.3% |
| SNO-625 | SEQ ID NO: 253, SEQ ID NO: 897, SEQ ID NO: 669 | hsa-miR-526a, hsa-let-7d, hsa-miR-181c | 73.6% | 73.8% | 73.3% |
| SNO-626 | SEQ ID NO: 89, SEQ ID NO: 669, SEQ ID NO: 165 | hsa-miR-663, hsa-miR-181c, hsa-miR-593* | 64.0% | 64.7% | 63.3% |
| SNO-627 | SEQ ID NO: 714, SEQ ID NO: 709, | hsa-miR-144*, hsa-miR-146a, hsa- | 78.3% | 78.3% | 78.2% |

FIG 15 (continued)

| | | | | | |
|---|---|---|---|---|---|
| | SEQ ID NO: 395 | miR-383 | | | |
| SNO-628 | SEQ ID NO: 838, SEQ ID NO: 673, SEQ ID NO: 189 | hsa-miR-1228*, hsa-miR-181a, hsa-miR-574-5p | 73.6% | 77.0% | 70.2% |
| SNO-629 | SEQ ID NO: 709, SEQ ID NO: 395, SEQ ID NO: 883 | hsa-miR-146a, hsa-miR-383, hsa-miR-101 | 77.0% | 79.5% | 74.5% |
| SNO-630 | SEQ ID NO: 673, SEQ ID NO: 189, SEQ ID NO: 199 | hsa-miR-181a, hsa-miR-574-5p, hsa-miR-564 | 74.9% | 69.2% | 80.7% |
| SNO-631 | SEQ ID NO: 395, SEQ ID NO: 883, SEQ ID NO: 779 | hsa-miR-383, hsa-miR-101, hsa-miR-1280 | 81.2% | 88.2% | 74.2% |
| SNO-632 | SEQ ID NO: 189, SEQ ID NO: 199, SEQ ID NO: 874 | hsa-miR-574-5p, hsa-miR-564, hsa-miR-106b | 77.2% | 78.7% | 75.7% |
| SNO-633 | SEQ ID NO: 883, SEQ ID NO: 779, SEQ ID NO: 441 | hsa-miR-101, hsa-miR-1280, hsa-miR-342-5p | 70.3% | 78.8% | 61.8% |
| SNO-634 | SEQ ID NO: 779, SEQ ID NO: 441, SEQ ID NO: 710 | hsa-miR-1280, hsa-miR-342-5p, hsa-miR-1469 | 73.8% | 81.7% | 65.8% |
| SNO-635 | SEQ ID NO: 874, SEQ ID NO: 645, SEQ ID NO: 684 | hsa-miR-106b, hsa-miR-1908, hsa-miR-155 | 71.6% | 71.3% | 71.8% |
| SNO-636 | SEQ ID NO: 441, SEQ ID NO: 710, SEQ ID NO: 442 | hsa-miR-342-5p, hsa-miR-1469, hsa-miR-342-3p | 69.6% | 63.7% | 75.5% |
| SNO-637 | SEQ ID NO: 645, SEQ ID NO: 684, SEQ ID NO: 92 | hsa-miR-1908, hsa-miR-155, hsa-miR-660 | 68.4% | 64.8% | 72.0% |
| SNO-638 | SEQ ID NO: 684, SEQ ID NO: 92, SEQ ID NO: 770 | hsa-miR-155, hsa-miR-660, hsa-miR-1289 | 72.0% | 66.5% | 77.5% |
| SNO-639 | SEQ ID NO: 92, SEQ ID NO: 770, SEQ ID NO: 573 | hsa-miR-660, hsa-miR-1289, hsa-miR-210 | 70.8% | 68.3% | 73.3% |
| SNO-640 | SEQ ID NO: 542, SEQ ID NO: 632, SEQ ID NO: 478 | hsa-miR-222, hsa-miR-1915, hsa-miR-30e | 61.7% | 67.2% | 56.2% |

FIG 15 (continued)

| | | | | | |
|---|---|---|---|---|---|
| SNO-641 | SEQ ID NO: 632, SEQ ID NO: 478, SEQ ID NO: 378 | hsa-miR-1915, hsa-miR-30e, hsa-miR-431 | 62.6% | 70.2% | 55.0% |
| SNO-642 | SEQ ID NO: 478, SEQ ID NO: 378, SEQ ID NO: 89 | hsa-miR-30e, hsa-miR-431, hsa-miR-663 | 64.9% | 68.8% | 61.0% |
| SNO-643 | SEQ ID NO: 378, SEQ ID NO: 89, SEQ ID NO: 669 | hsa-miR-431, hsa-miR-663, hsa-miR-181c | 65.4% | 71.5% | 59.3% |
| SNO-644 | SEQ ID NO: 253, SEQ ID NO: 897, SEQ ID NO: 165 | hsa-miR-526a, hsa-let-7d, hsa-miR-593* | 66.1% | 72.8% | 59.3% |
| SNO-645 | SEQ ID NO: 714, SEQ ID NO: 838, SEQ ID NO: 395 | hsa-miR-144*, hsa-miR-1228*, hsa-miR-383 | 74.3% | 80.2% | 68.3% |
| SNO-646 | SEQ ID NO: 838, SEQ ID NO: 709, SEQ ID NO: 189 | hsa-miR-1228*, hsa-miR-146a, hsa-miR-574-5p | 72.7% | 74.2% | 71.2% |
| SNO-647 | SEQ ID NO: 709, SEQ ID NO: 673, SEQ ID NO: 883 | hsa-miR-146a, hsa-miR-181a, hsa-miR-101 | 74.3% | 72.0% | 76.5% |
| SNO-648 | SEQ ID NO: 673, SEQ ID NO: 395, SEQ ID NO: 199 | hsa-miR-181a, hsa-miR-383, hsa-miR-564 | 74.8% | 70.0% | 79.5% |
| SNO-649 | SEQ ID NO: 395, SEQ ID NO: 189, SEQ ID NO: 779 | hsa-miR-383, hsa-miR-574-5p, hsa-miR-1280 | 83.6% | 86.8% | 80.3% |
| SNO-650 | SEQ ID NO: 189, SEQ ID NO: 883, SEQ ID NO: 874 | hsa-miR-574-5p, hsa-miR-101, hsa-miR-106b | 68.9% | 75.0% | 62.8% |
| SNO-651 | SEQ ID NO: 883, SEQ ID NO: 199, SEQ ID NO: 441 | hsa-miR-101, hsa-miR-564, hsa-miR-342-5p | 70.8% | 72.2% | 69.3% |
| SNO-652 | SEQ ID NO: 199, SEQ ID NO: 779, SEQ ID NO: 645 | hsa-miR-564, hsa-miR-1280, hsa-miR-1908 | 72.6% | 78.8% | 66.3% |
| SNO-653 | SEQ ID NO: 779, SEQ ID NO: 874, SEQ ID NO: 710 | hsa-miR-1280, hsa-miR-106b, hsa-miR-1469 | 76.6% | 75.2% | 78.0% |
| SNO-654 | SEQ ID NO: 874, SEQ ID NO: 441, | hsa-miR-106b, hsa-miR-342-5p, hsa- | 70.9% | 72.8% | 69.0% |

FIG 15 (continued)

| | | | | | |
|---|---|---|---|---|---|
| | SEQ ID NO: 684 | miR-155 | | | |
| SNO-655 | SEQ ID NO: 441, SEQ ID NO: 645, SEQ ID NO: 442 | hsa-miR-342-5p, hsa-miR-1908, hsa-miR-342-3p | 73.2% | 67.5% | 78.8% |
| SNO-656 | SEQ ID NO: 645, SEQ ID NO: 710, SEQ ID NO: 92 | hsa-miR-1908, hsa-miR-1469, hsa-miR-660 | 57.1% | 58.8% | 55.3% |
| SNO-657 | SEQ ID NO: 710, SEQ ID NO: 684, SEQ ID NO: 542 | hsa-miR-1469, hsa-miR-155, hsa-miR-222 | 68.1% | 65.8% | 70.3% |
| SNO-658 | SEQ ID NO: 684, SEQ ID NO: 442, SEQ ID NO: 770 | hsa-miR-155, hsa-miR-342-3p, hsa-miR-1289 | 77.8% | 73.0% | 82.5% |
| SNO-659 | SEQ ID NO: 442, SEQ ID NO: 92, SEQ ID NO: 632 | hsa-miR-342-3p, hsa-miR-660, hsa-miR-1915 | 77.3% | 68.8% | 85.7% |
| SNO-660 | SEQ ID NO: 92, SEQ ID NO: 542, SEQ ID NO: 573 | hsa-miR-660, hsa-miR-222, hsa-miR-210 | 71.9% | 71.5% | 72.3% |
| SNO-661 | SEQ ID NO: 542, SEQ ID NO: 770, SEQ ID NO: 478 | hsa-miR-222, hsa-miR-1289, hsa-miR-30e | 65.8% | 64.2% | 67.5% |
| SNO-662 | SEQ ID NO: 573, SEQ ID NO: 478, SEQ ID NO: 253 | hsa-miR-210, hsa-miR-30e, hsa-miR-526a | 68.6% | 72.2% | 65.0% |
| SNO-663 | SEQ ID NO: 478, SEQ ID NO: 762, SEQ ID NO: 89 | hsa-miR-30e, hsa-miR-1295, hsa-miR-663 | 67.4% | 72.5% | 62.3% |
| SNO-664 | SEQ ID NO: 378, SEQ ID NO: 253, SEQ ID NO: 669 | hsa-miR-431, hsa-miR-526a, hsa-miR-181c | 68.0% | 74.5% | 61.5% |
| SNO-665 | SEQ ID NO: 253, SEQ ID NO: 89, SEQ ID NO: 165 | hsa-miR-526a, hsa-miR-663, hsa-miR-593* | 66.6% | 77.7% | 55.5% |
| SNO-666 | SEQ ID NO: 714, SEQ ID NO: 673, SEQ ID NO: 395 | hsa-miR-144*, hsa-miR-181a, hsa-miR-383 | 81.3% | 84.5% | 78.2% |
| SNO-667 | SEQ ID NO: 838, SEQ ID NO: 395, SEQ ID NO: 189 | hsa-miR-1228*, hsa-miR-383, hsa-miR-574-5p | 75.6% | 79.8% | 71.3% |

FIG 15 (continued)

| | | | | | |
|---|---|---|---|---|---|
| SNO-668 | SEQ ID NO: 709, SEQ ID NO: 189, SEQ ID NO: 883 | hsa-miR-146a, hsa-miR-574-5p, hsa-miR-101 | 73.6% | 69.0% | 78.2% |
| SNO-669 | SEQ ID NO: 673, SEQ ID NO: 883, SEQ ID NO: 199 | hsa-miR-181a, hsa-miR-101, hsa-miR-564 | 74.6% | 73.3% | 75.8% |
| SNO-670 | SEQ ID NO: 395, SEQ ID NO: 199, SEQ ID NO: 779 | hsa-miR-383, hsa-miR-564, hsa-miR-1280 | 82.6% | 86.8% | 78.3% |
| SNO-671 | SEQ ID NO: 189, SEQ ID NO: 779, SEQ ID NO: 874 | hsa-miR-574-5p, hsa-miR-1280, hsa-miR-106b | 72.5% | 79.5% | 65.5% |
| SNO-672 | SEQ ID NO: 883, SEQ ID NO: 874, SEQ ID NO: 441 | hsa-miR-101, hsa-miR-106b, hsa-miR-342-5p | 73.3% | 80.3% | 66.2% |
| SNO-673 | SEQ ID NO: 199, SEQ ID NO: 441, SEQ ID NO: 645 | hsa-miR-564, hsa-miR-342-5p, hsa-miR-1908 | 61.2% | 71.2% | 51.2% |
| SNO-674 | SEQ ID NO: 779, SEQ ID NO: 645, SEQ ID NO: 710 | hsa-miR-1280, hsa-miR-1908, hsa-miR-1469 | 76.3% | 78.0% | 74.7% |
| SNO-675 | SEQ ID NO: 874, SEQ ID NO: 710, SEQ ID NO: 684 | hsa-miR-106b, hsa-miR-1469, hsa-miR-155 | 71.7% | 70.2% | 73.2% |
| SNO-676 | SEQ ID NO: 441, SEQ ID NO: 684, SEQ ID NO: 442 | hsa-miR-342-5p, hsa-miR-155, hsa-miR-342-3p | 78.2% | 75.7% | 80.7% |
| SNO-677 | SEQ ID NO: 645, SEQ ID NO: 442, SEQ ID NO: 92 | hsa-miR-1908, hsa-miR-342-3p, hsa-miR-660 | 73.2% | 68.0% | 78.3% |
| SNO-678 | SEQ ID NO: 710, SEQ ID NO: 92, SEQ ID NO: 542 | hsa-miR-1469, hsa-miR-660, hsa-miR-222 | 62.3% | 65.5% | 59.2% |
| SNO-679 | SEQ ID NO: 684, SEQ ID NO: 542, SEQ ID NO: 770 | hsa-miR-155, hsa-miR-222, hsa-miR-1289 | 70.3% | 67.2% | 73.3% |
| SNO-680 | SEQ ID NO: 92, SEQ ID NO: 632, SEQ ID NO: 573 | hsa-miR-660, hsa-miR-1915, hsa-miR-210 | 68.6% | 67.2% | 70.0% |
| SNO-681 | SEQ ID NO: 542, SEQ ID NO: 573, | hsa-miR-222, hsa-miR-210, hsa-miR- | 72.5% | 71.0% | 74.0% |

FIG 15 (continued)

| | | | | | |
|---|---|---|---|---|---|
| | SEQ ID NO: 478 | 30e | | | |
| SNO-682 | SEQ ID NO: 770, SEQ ID NO: 478, SEQ ID NO: 762 | hsa-miR-1289, hsa-miR-30e, hsa-miR-1295 | 65.9% | 60.7% | 71.2% |
| SNO-683 | SEQ ID NO: 478, SEQ ID NO: 253, SEQ ID NO: 89 | hsa-miR-30e, hsa-miR-526a, hsa-miR-663 | 71.1% | 76.5% | 65.7% |
| SNO-684 | SEQ ID NO: 378, SEQ ID NO: 897, SEQ ID NO: 669 | hsa-miR-431, hsa-let-7d, hsa-miR-181c | 73.8% | 70.8% | 76.7% |
| SNO-685 | SEQ ID NO: 253, SEQ ID NO: 669, SEQ ID NO: 165 | hsa-miR-526a, hsa-miR-181c, hsa-miR-593* | 67.8% | 78.2% | 57.5% |
| SNO-686 | SEQ ID NO: 673, SEQ ID NO: 709 | hsa-miR-181a, hsa-miR-146a | 68.7% | 63.3% | 74.0% |
| SNO-687 | SEQ ID NO: 710, SEQ ID NO: 441 | hsa-miR-1469, hsa-miR-342-5p | 64.0% | 66.5% | 61.5% |
| SNO-688 | SEQ ID NO: 92, SEQ ID NO: 442 | hsa-miR-660, hsa-miR-342-3p | 75.3% | 68.8% | 81.8% |
| SNO-689 | SEQ ID NO: 632, SEQ ID NO: 770 | hsa-miR-1915, hsa-miR-1289 | 66.4% | 62.7% | 70.2% |
| SNO-690 | SEQ ID NO: 762, SEQ ID NO: 478 | hsa-miR-1295, hsa-miR-30e | 67.1% | 64.7% | 69.5% |
| SNO-691 | SEQ ID NO: 669, SEQ ID NO: 530 | hsa-miR-181c, hsa-miR-23b* | 72.8% | 67.5% | 78.0% |
| SNO-692 | SEQ ID NO: 645, SEQ ID NO: 441 | hsa-miR-1908, hsa-miR-342-5p | 65.2% | 83.2% | 47.2% |
| SNO-693 | SEQ ID NO: 441, SEQ ID NO: 92 | hsa-miR-342-5p, hsa-miR-660 | 65.4% | 67.2% | 63.7% |
| SNO-694 | SEQ ID NO: 897, SEQ ID NO: 530 | hsa-let-7d, hsa-miR-23b* | 75.2% | 64.7% | 85.7% |
| SNO-695 | SEQ ID NO: 709, SEQ ID NO: 883 | hsa-miR-146a, hsa-miR-101 | 72.6% | 67.2% | 78.0% |
| SNO-696 | SEQ ID NO: 779, SEQ ID NO: 710 | hsa-miR-1280, hsa-miR-1469 | 78.5% | 78.5% | 78.5% |
| SNO-697 | SEQ ID NO: 441, SEQ ID NO: 442 | hsa-miR-342-5p, hsa-miR-342-3p | 73.7% | 69.2% | 78.2% |
| SNO-698 | SEQ ID NO: 478, SEQ ID NO: 89 | hsa-miR-30e, hsa-miR-663 | 66.1% | 70.3% | 61.8% |
| SNO-699 | SEQ ID NO: 89, SEQ ID NO: 530 | hsa-miR-663, hsa-miR-23b* | 66.6% | 67.5% | 65.7% |
| SNO-700 | SEQ ID NO: 838, SEQ ID NO: 673, SEQ ID NO: 709 | hsa-miR-1228*, hsa-miR-181a, hsa-miR-146a | 73.3% | 75.2% | 71.3% |
| SNO-701 | SEQ ID NO: 673, SEQ ID NO: 709, | hsa-miR-181a, hsa-miR-146a, hsa- | 75.2% | 70.8% | 79.5% |

FIG 15 (continued)

| | | | | | |
|---|---|---|---|---|---|
| | SEQ ID NO: 395 | miR-383 | | | |
| SNO-702 | SEQ ID NO: 645, SEQ ID NO: 710, SEQ ID NO: 441 | hsa-miR-1908, hsa-miR-1469, hsa-miR-342-5p | 65.8% | 75.2% | 56.5% |
| SNO-703 | SEQ ID NO: 710, SEQ ID NO: 441, SEQ ID NO: 684 | hsa-miR-1469, hsa-miR-342-5p, hsa-miR-155 | 65.3% | 64.8% | 65.7% |
| SNO-704 | SEQ ID NO: 441, SEQ ID NO: 684, SEQ ID NO: 92 | hsa-miR-342-5p, hsa-miR-155, hsa-miR-660 | 68.6% | 70.7% | 66.5% |
| SNO-705 | SEQ ID NO: 684, SEQ ID NO: 92, SEQ ID NO: 442 | hsa-miR-155, hsa-miR-660, hsa-miR-342-3p | 75.3% | 73.5% | 77.2% |
| SNO-706 | SEQ ID NO: 92, SEQ ID NO: 442, SEQ ID NO: 542 | hsa-miR-660, hsa-miR-342-3p, hsa-miR-222 | 73.7% | 71.7% | 75.7% |
| SNO-707 | SEQ ID NO: 542, SEQ ID NO: 632, SEQ ID NO: 770 | hsa-miR-222, hsa-miR-1915, hsa-miR-1289 | 66.5% | 71.3% | 61.7% |
| SNO-708 | SEQ ID NO: 632, SEQ ID NO: 770, SEQ ID NO: 573 | hsa-miR-1915, hsa-miR-1289, hsa-miR-210 | 74.0% | 72.2% | 75.8% |
| SNO-709 | SEQ ID NO: 573, SEQ ID NO: 762, SEQ ID NO: 478 | hsa-miR-210, hsa-miR-1295, hsa-miR-30e | 70.6% | 70.2% | 71.0% |
| SNO-710 | SEQ ID NO: 762, SEQ ID NO: 478, SEQ ID NO: 378 | hsa-miR-1295, hsa-miR-30e, hsa-miR-431 | 63.5% | 67.5% | 59.5% |
| SNO-711 | SEQ ID NO: 897, SEQ ID NO: 669, SEQ ID NO: 530 | hsa-let-7d, hsa-miR-181c, hsa-miR-23b* | 77.7% | 74.2% | 81.2% |
| SNO-712 | SEQ ID NO: 673, SEQ ID NO: 709, SEQ ID NO: 189 | hsa-miR-181a, hsa-miR-146a, hsa-miR-574-5p | 71.8% | 66.3% | 77.2% |
| SNO-713 | SEQ ID NO: 874, SEQ ID NO: 645, SEQ ID NO: 441 | hsa-miR-106b, hsa-miR-1908, hsa-miR-342-5p | 65.8% | 72.3% | 59.2% |
| SNO-714 | SEQ ID NO: 710, SEQ ID NO: 441, SEQ ID NO: 92 | hsa-miR-1469, hsa-miR-342-5p, hsa-miR-660 | 64.5% | 66.0% | 63.0% |

FIG 15 (continued)

| | | | | | |
|---|---|---|---|---|---|
| SNO-715 | SEQ ID NO: 92, SEQ ID NO: 442, SEQ ID NO: 632 | hsa-miR-660, hsa-miR-342-3p, hsa-miR-1915 | 75.2% | 65.5% | 84.8% |
| SNO-716 | SEQ ID NO: 632, SEQ ID NO: 770, SEQ ID NO: 762 | hsa-miR-1915, hsa-miR-1289, hsa-miR-1295 | 68.3% | 60.8% | 75.7% |
| SNO-717 | SEQ ID NO: 762, SEQ ID NO: 478, SEQ ID NO: 253 | hsa-miR-1295, hsa-miR-30e, hsa-miR-526a | 65.1% | 67.7% | 62.5% |
| SNO-718 | SEQ ID NO: 89, SEQ ID NO: 897, SEQ ID NO: 530 | hsa-miR-663, hsa-let-7d, hsa-miR-23b* | 72.7% | 66.7% | 78.7% |
| SNO-719 | SEQ ID NO: 714, SEQ ID NO: 673, SEQ ID NO: 709 | hsa-miR-144*, hsa-miR-181a, hsa-miR-146a | 76.3% | 76.5% | 76.2% |
| SNO-720 | SEQ ID NO: 874, SEQ ID NO: 710, SEQ ID NO: 441 | hsa-miR-106b, hsa-miR-1469, hsa-miR-342-5p | 66.8% | 67.5% | 66.2% |
| SNO-721 | SEQ ID NO: 645, SEQ ID NO: 441, SEQ ID NO: 684 | hsa-miR-1908, hsa-miR-342-5p, hsa-miR-155 | 63.4% | 69.0% | 57.8% |
| SNO-722 | SEQ ID NO: 441, SEQ ID NO: 92, SEQ ID NO: 442 | hsa-miR-342-5p, hsa-miR-660, hsa-miR-342-3p | 76.8% | 73.3% | 80.2% |
| SNO-723 | SEQ ID NO: 442, SEQ ID NO: 632, SEQ ID NO: 770 | hsa-miR-342-3p, hsa-miR-1915, hsa-miR-1289 | 71.4% | 61.3% | 81.5% |
| SNO-724 | SEQ ID NO: 770, SEQ ID NO: 762, SEQ ID NO: 478 | hsa-miR-1289, hsa-miR-1295, hsa-miR-30e | 66.4% | 63.0% | 69.8% |
| SNO-725 | SEQ ID NO: 89, SEQ ID NO: 669, SEQ ID NO: 530 | hsa-miR-663, hsa-miR-181c, hsa-miR-23b* | 71.8% | 71.5% | 72.2% |
| SNO-726 | SEQ ID NO: 709, SEQ ID NO: 189, SEQ ID NO: 199 | hsa-miR-146a, hsa-miR-574-5p, hsa-miR-564 | 70.8% | 72.0% | 69.7% |
| SNO-727 | SEQ ID NO: 883, SEQ ID NO: 779, SEQ ID NO: 645 | hsa-miR-101, hsa-miR-1280, hsa-miR-1908 | 69.8% | 71.7% | 67.8% |
| SNO-728 | SEQ ID NO: 779, SEQ ID NO: 645, | hsa-miR-1280, hsa-miR-1908, hsa- | 69.9% | 78.7% | 61.2% |

FIG 15 (continued)

| | | | | | |
|---|---|---|---|---|---|
| | SEQ ID NO: 441 | miR-342-5p | | | |
| SNO-729 | SEQ ID NO: 645, SEQ ID NO: 441, SEQ ID NO: 92 | hsa-miR-1908, hsa-miR-342-5p, hsa-miR-660 | 63.1% | 72.2% | 54.0% |
| SNO-730 | SEQ ID NO: 441, SEQ ID NO: 92, SEQ ID NO: 542 | hsa-miR-342-5p, hsa-miR-660, hsa-miR-222 | 64.1% | 66.8% | 61.3% |
| SNO-731 | SEQ ID NO: 684, SEQ ID NO: 442, SEQ ID NO: 632 | hsa-miR-155, hsa-miR-342-3p, hsa-miR-1915 | 77.5% | 68.5% | 86.5% |
| SNO-732 | SEQ ID NO: 770, SEQ ID NO: 762, SEQ ID NO: 378 | hsa-miR-1289, hsa-miR-1295, hsa-miR-431 | 67.1% | 63.0% | 71.2% |
| SNO-733 | SEQ ID NO: 478, SEQ ID NO: 253, SEQ ID NO: 897 | hsa-miR-30e, hsa-miR-526a, hsa-let-7d | 68.3% | 70.2% | 66.3% |
| SNO-734 | SEQ ID NO: 253, SEQ ID NO: 897, SEQ ID NO: 530 | hsa-miR-526a, hsa-let-7d, hsa-miR-23b* | 71.4% | 61.3% | 81.5% |
| SNO-735 | SEQ ID NO: 673, SEQ ID NO: 709, SEQ ID NO: 883 | hsa-miR-181a, hsa-miR-146a, hsa-miR-101 | 73.9% | 70.0% | 77.8% |
| SNO-736 | SEQ ID NO: 709, SEQ ID NO: 395, SEQ ID NO: 199 | hsa-miR-146a, hsa-miR-383, hsa-miR-564 | 72.8% | 74.0% | 71.5% |
| SNO-737 | SEQ ID NO: 199, SEQ ID NO: 779, SEQ ID NO: 710 | hsa-miR-564, hsa-miR-1280, hsa-miR-1469 | 74.9% | 76.7% | 73.2% |
| SNO-738 | SEQ ID NO: 710, SEQ ID NO: 441, SEQ ID NO: 442 | hsa-miR-1469, hsa-miR-342-5p, hsa-miR-342-3p | 73.3% | 67.5% | 79.2% |
| SNO-739 | SEQ ID NO: 441, SEQ ID NO: 684, SEQ ID NO: 542 | hsa-miR-342-5p, hsa-miR-155, hsa-miR-222 | 66.4% | 69.5% | 63.3% |
| SNO-740 | SEQ ID NO: 684, SEQ ID NO: 92, SEQ ID NO: 632 | hsa-miR-155, hsa-miR-660, hsa-miR-1915 | 67.8% | 59.3% | 76.3% |
| SNO-741 | SEQ ID NO: 92, SEQ ID NO: 442, SEQ ID NO: 770 | hsa-miR-660, hsa-miR-342-3p, hsa-miR-1289 | 77.2% | 72.0% | 82.3% |

FIG 15 (continued)

| | | | | | |
|---|---|---|---|---|---|
| SNO-742 | SEQ ID NO: 632, SEQ ID NO: 770, SEQ ID NO: 478 | hsa-miR-1915, hsa-miR-1289, hsa-miR-30e | 61.5% | 60.8% | 62.2% |
| SNO-743 | SEQ ID NO: 770, SEQ ID NO: 573, SEQ ID NO: 378 | hsa-miR-1289, hsa-miR-210, hsa-miR-431 | 68.9% | 73.0% | 64.8% |
| SNO-744 | SEQ ID NO: 762, SEQ ID NO: 478, SEQ ID NO: 89 | hsa-miR-1295, hsa-miR-30e, hsa-miR-663 | 66.4% | 71.0% | 61.8% |
| SNO-745 | SEQ ID NO: 478, SEQ ID NO: 378, SEQ ID NO: 897 | hsa-miR-30e, hsa-miR-431, hsa-let-7d | 70.4% | 69.3% | 71.5% |
| SNO-746 | SEQ ID NO: 253, SEQ ID NO: 89, SEQ ID NO: 530 | hsa-miR-526a, hsa-miR-663, hsa-miR-23b* | 66.8% | 70.0% | 63.5% |
| SNO-747 | SEQ ID NO: 709, SEQ ID NO: 883, SEQ ID NO: 199 | hsa-miR-146a, hsa-miR-101, hsa-miR-564 | 73.0% | 68.8% | 77.2% |
| SNO-748 | SEQ ID NO: 779, SEQ ID NO: 710, SEQ ID NO: 441 | hsa-miR-1280, hsa-miR-1469, hsa-miR-342-5p | 71.1% | 76.8% | 65.3% |
| SNO-749 | SEQ ID NO: 710, SEQ ID NO: 92, SEQ ID NO: 442 | hsa-miR-1469, hsa-miR-660, hsa-miR-342-3p | 74.4% | 69.7% | 79.2% |
| SNO-750 | SEQ ID NO: 441, SEQ ID NO: 442, SEQ ID NO: 542 | hsa-miR-342-5p, hsa-miR-342-3p, hsa-miR-222 | 74.3% | 70.3% | 78.3% |
| SNO-751 | SEQ ID NO: 684, SEQ ID NO: 542, SEQ ID NO: 632 | hsa-miR-155, hsa-miR-222, hsa-miR-1915 | 68.0% | 69.2% | 66.8% |
| SNO-752 | SEQ ID NO: 92, SEQ ID NO: 632, SEQ ID NO: 770 | hsa-miR-660, hsa-miR-1915, hsa-miR-1289 | 67.8% | 64.5% | 71.2% |
| SNO-753 | SEQ ID NO: 632, SEQ ID NO: 762, SEQ ID NO: 478 | hsa-miR-1915, hsa-miR-1295, hsa-miR-30e | 64.5% | 63.5% | 65.5% |
| SNO-754 | SEQ ID NO: 770, SEQ ID NO: 478, SEQ ID NO: 378 | hsa-miR-1289, hsa-miR-30e, hsa-miR-431 | 62.1% | 67.2% | 57.0% |
| SNO-755 | SEQ ID NO: 478, SEQ ID NO: 89, SEQ | hsa-miR-30e, hsa-miR-663, hsa-let-7d | 67.8% | 69.3% | 66.2% |

FIG 15 (continued)

| | | | | | |
|---|---|---|---|---|---|
| | ID NO: 897 | | | | |
| SNO-756 | SEQ ID NO: 253, SEQ ID NO: 669, SEQ ID NO: 530 | hsa-miR-526a, hsa-miR-181c, h | 65.8% | 71.0% | 60.5% |

SEQUENCE LISTING

```
<160> NUMBER OF SEQ ID NOS: 962

<210> SEQ ID NO 1
<211> LENGTH: 22
<212> TYPE: RNA
<213> ORGANISM: Homo sapiens

<400> SEQUENCE: 1

caagcucgug ucugugggguc cg                                              22

<210> SEQ ID NO 2
<211> LENGTH: 22
<212> TYPE: RNA
<213> ORGANISM: Homo sapiens

<400> SEQUENCE: 2

cacccguaga accgaccuug cg                                               22

<210> SEQ ID NO 3
<211> LENGTH: 22
<212> TYPE: RNA
<213> ORGANISM: Homo sapiens

<400> SEQUENCE: 3

caagcucgcu ucuauggguc ug                                               22

<210> SEQ ID NO 4
<211> LENGTH: 22
<212> TYPE: RNA
<213> ORGANISM: Homo sapiens

<400> SEQUENCE: 4

aacccguaga uccgaucuug ug                                               22

<210> SEQ ID NO 5
<211> LENGTH: 22
<212> TYPE: RNA
<213> ORGANISM: Homo sapiens

<400> SEQUENCE: 5

ugagguagua aguuguauug uu                                               22

<210> SEQ ID NO 6
<211> LENGTH: 22
```

<212> TYPE: RNA
<213> ORGANISM: Homo sapiens

<400> SEQUENCE: 6
aaucaugugc agugccaaua ug 22

<210> SEQ ID NO 7
<211> LENGTH: 23
<212> TYPE: RNA
<213> ORGANISM: Homo sapiens

<400> SEQUENCE: 7
uuuggcacua gcacauuuuu gcu 23

<210> SEQ ID NO 8
<211> LENGTH: 22
<212> TYPE: RNA
<213> ORGANISM: Homo sapiens

<400> SEQUENCE: 8
uucaacgggu auuuauugag ca 22

<210> SEQ ID NO 9
<211> LENGTH: 22
<212> TYPE: RNA
<213> ORGANISM: Homo sapiens

<400> SEQUENCE: 9
aaauuauugu acaucggaug ag 22

<210> SEQ ID NO 10
<211> LENGTH: 21
<212> TYPE: RNA
<213> ORGANISM: Homo sapiens

<400> SEQUENCE: 10
cugacuguug ccguccucca g 21

<210> SEQ ID NO 11
<211> LENGTH: 22
<212> TYPE: RNA
<213> ORGANISM: Homo sapiens

<400> SEQUENCE: 11
ucuucucugu uuuggccaug ug 22

<210> SEQ ID NO 12
<211> LENGTH: 23
<212> TYPE: RNA
<213> ORGANISM: Homo sapiens

<400> SEQUENCE: 12
cacccggcug ugugcacaug ugc 23

<210> SEQ ID NO 13
<211> LENGTH: 21
<212> TYPE: RNA
<213> ORGANISM: Homo sapiens

<400> SEQUENCE: 13
aaggcagggc ccccgcuccc c 21

<210> SEQ ID NO 14

<211> LENGTH: 24
<212> TYPE: RNA
<213> ORGANISM: Homo sapiens

<400> SEQUENCE: 14
uggggagcug aggcucuggg ggug 24

<210> SEQ ID NO 15
<211> LENGTH: 22
<212> TYPE: RNA
<213> ORGANISM: Homo sapiens

<400> SEQUENCE: 15
ugcccuuaaa ggugaaccca gu 22

<210> SEQ ID NO 16
<211> LENGTH: 22
<212> TYPE: RNA
<213> ORGANISM: Homo sapiens

<400> SEQUENCE: 16
auccgcgcuc ugacucucug cc 22

<210> SEQ ID NO 17
<211> LENGTH: 22
<212> TYPE: RNA
<213> ORGANISM: Homo sapiens

<400> SEQUENCE: 17
acaguagagg gaggaaucgc ag 22

<210> SEQ ID NO 18
<211> LENGTH: 23
<212> TYPE: RNA
<213> ORGANISM: Homo sapiens

<400> SEQUENCE: 18
ccaguuaccg cuuccgcuac cgc 23

<210> SEQ ID NO 19
<211> LENGTH: 22
<212> TYPE: RNA
<213> ORGANISM: Homo sapiens

<400> SEQUENCE: 19
ugucuacuac uggagacacu gg 22

<210> SEQ ID NO 20
<211> LENGTH: 22
<212> TYPE: RNA
<213> ORGANISM: Homo sapiens

<400> SEQUENCE: 20
ugugcgcagg gagaccucuc cc 22

<210> SEQ ID NO 21
<211> LENGTH: 22
<212> TYPE: RNA
<213> ORGANISM: Homo sapiens

<400> SEQUENCE: 21
acugcugagc uagcacuucc cg 22

<210> SEQ ID NO 22
<211> LENGTH: 23
<212> TYPE: RNA
<213> ORGANISM: Homo sapiens

<400> SEQUENCE: 22
caaagugcug uucgugcagg uag 23

<210> SEQ ID NO 23
<211> LENGTH: 22
<212> TYPE: RNA
<213> ORGANISM: Homo sapiens

<400> SEQUENCE: 23
agggacggga cgcggugcag ug 22

<210> SEQ ID NO 24
<211> LENGTH: 22
<212> TYPE: RNA
<213> ORGANISM: Homo sapiens

<400> SEQUENCE: 24
uauugcacuc gucccggccu cc 22

<210> SEQ ID NO 25
<211> LENGTH: 22
<212> TYPE: RNA
<213> ORGANISM: Homo sapiens

<400> SEQUENCE: 25
ggguggggau uuguugcauu ac 22

<210> SEQ ID NO 26
<211> LENGTH: 23
<212> TYPE: RNA
<213> ORGANISM: Homo sapiens

<400> SEQUENCE: 26
agguugggau cgguugcaau gcu 23

<210> SEQ ID NO 27
<211> LENGTH: 22
<212> TYPE: RNA
<213> ORGANISM: Homo sapiens

<400> SEQUENCE: 27
uauugcacuu gucccggccu gu 22

<210> SEQ ID NO 28
<211> LENGTH: 20
<212> TYPE: RNA
<213> ORGANISM: Homo sapiens

<400> SEQUENCE: 28
agagucuugu gaugucuugc 20

<210> SEQ ID NO 29
<211> LENGTH: 23
<212> TYPE: RNA
<213> ORGANISM: Homo sapiens

<400> SEQUENCE: 29
gcagcagaga auaggacuac guc 23

<210> SEQ ID NO 30
<211> LENGTH: 25
<212> TYPE: RNA
<213> ORGANISM: Homo sapiens

<400> SEQUENCE: 30
cuagugaggg acagaaccag gauuc 25

<210> SEQ ID NO 31
<211> LENGTH: 20
<212> TYPE: RNA
<213> ORGANISM: Homo sapiens

<400> SEQUENCE: 31
ggggagcugu ggaagcagua 20

<210> SEQ ID NO 32
<211> LENGTH: 22
<212> TYPE: RNA
<213> ORGANISM: Homo sapiens

<400> SEQUENCE: 32
auaaagcuag auaaccgaaa gu 22

<210> SEQ ID NO 33
<211> LENGTH: 23
<212> TYPE: RNA
<213> ORGANISM: Homo sapiens

<400> SEQUENCE: 33
ucuuugguua ucuagcugua uga 23

<210> SEQ ID NO 34
<211> LENGTH: 22
<212> TYPE: RNA
<213> ORGANISM: Homo sapiens

<400> SEQUENCE: 34
cacuggcucc uuucugggua ga 22

<210> SEQ ID NO 35
<211> LENGTH: 21
<212> TYPE: RNA
<213> ORGANISM: Homo sapiens

<400> SEQUENCE: 35
cacugugucc uuucugcgua g 21

<210> SEQ ID NO 36
<211> LENGTH: 22
<212> TYPE: RNA
<213> ORGANISM: Homo sapiens

<400> SEQUENCE: 36
ugcaacuuac cugagucauu ga 22

<210> SEQ ID NO 37
<211> LENGTH: 22
<212> TYPE: RNA
<213> ORGANISM: Homo sapiens

<400> SEQUENCE: 37
ugcaacgaac cugagccacu ga 22

<210> SEQ ID NO 38
<211> LENGTH: 21
<212> TYPE: RNA
<213> ORGANISM: Homo sapiens

<400> SEQUENCE: 38
uacuuggaaa ggcaucaguu g 21

<210> SEQ ID NO 39
<211> LENGTH: 21
<212> TYPE: RNA
<213> ORGANISM: Homo sapiens

<400> SEQUENCE: 39
uuaauaucgg acaaccauug u 21

<210> SEQ ID NO 40
<211> LENGTH: 22
<212> TYPE: RNA
<213> ORGANISM: Homo sapiens

<400> SEQUENCE: 40
gacugacacc ucuuugggug aa 22

<210> SEQ ID NO 41
<211> LENGTH: 21
<212> TYPE: RNA
<213> ORGANISM: Homo sapiens

<400> SEQUENCE: 41
uacucaaaaa gcugucaguc a 21

<210> SEQ ID NO 42
<211> LENGTH: 22
<212> TYPE: RNA
<213> ORGANISM: Homo sapiens

<400> SEQUENCE: 42
gugaacgggc gccaucccga gg 22

<210> SEQ ID NO 43
<211> LENGTH: 23
<212> TYPE: RNA
<213> ORGANISM: Homo sapiens

<400> SEQUENCE: 43
cgggucggag uuagcucaag cgg 23

<210> SEQ ID NO 44
<211> LENGTH: 21
<212> TYPE: RNA
<213> ORGANISM: Homo sapiens

<400> SEQUENCE: 44
cgcgggugcu uacugacccu u 21

<210> SEQ ID NO 45
<211> LENGTH: 22
<212> TYPE: RNA
<213> ORGANISM: Homo sapiens

<400> SEQUENCE: 45
uccauuacac uacccugccu cu 22

<210> SEQ ID NO 46
<211> LENGTH: 22
<212> TYPE: RNA
<213> ORGANISM: Homo sapiens

<400> SEQUENCE: 46
aggcagcggg guguagugga ua 22

<210> SEQ ID NO 47
<211> LENGTH: 21
<212> TYPE: RNA
<213> ORGANISM: Homo sapiens

<400> SEQUENCE: 47
uccucuucuc ccuccuccca g 21

<210> SEQ ID NO 48
<211> LENGTH: 20
<212> TYPE: RNA
<213> ORGANISM: Homo sapiens

<400> SEQUENCE: 48
guagaggaga uggcgcaggg 20

<210> SEQ ID NO 49
<211> LENGTH: 22
<212> TYPE: RNA
<213> ORGANISM: Homo sapiens

<400> SEQUENCE: 49
uggauuucuu ugugaaucac ca 22

<210> SEQ ID NO 50
<211> LENGTH: 22
<212> TYPE: RNA
<213> ORGANISM: Homo sapiens

<400> SEQUENCE: 50
uggugguuua caaaguaauu ca 22

<210> SEQ ID NO 51
<211> LENGTH: 22
<212> TYPE: RNA
<213> ORGANISM: Homo sapiens

<400> SEQUENCE: 51
uauaccucag uuuuaucagg ug 22

<210> SEQ ID NO 52
<211> LENGTH: 21
<212> TYPE: RNA
<213> ORGANISM: Homo sapiens

<400> SEQUENCE: 52
ccuggaaaca cugagguugu g 21

<210> SEQ ID NO 53
<211> LENGTH: 22
<212> TYPE: RNA
<213> ORGANISM: Homo sapiens

<400> SEQUENCE: 53
cugcccuggc ccgagggacc ga 22

<210> SEQ ID NO 54
<211> LENGTH: 21
<212> TYPE: RNA
<213> ORGANISM: Homo sapiens

<400> SEQUENCE: 54
gcaggaacuu gugagucucc u 21

<210> SEQ ID NO 55
<211> LENGTH: 23
<212> TYPE: RNA
<213> ORGANISM: Homo sapiens

<400> SEQUENCE: 55
caguaacaaa gauucauccu ugu 23

<210> SEQ ID NO 56
<211> LENGTH: 23
<212> TYPE: RNA
<213> ORGANISM: Homo sapiens

<400> SEQUENCE: 56
uccaguacca cgugucaggg cca 23

<210> SEQ ID NO 57
<211> LENGTH: 22
<212> TYPE: RNA
<213> ORGANISM: Homo sapiens

<400> SEQUENCE: 57
ugagaccucu ggguucugag cu 22

<210> SEQ ID NO 58
<211> LENGTH: 23
<212> TYPE: RNA
<213> ORGANISM: Homo sapiens

<400> SEQUENCE: 58
cugggaucuc cggggucuug guu 23

<210> SEQ ID NO 59
<211> LENGTH: 23
<212> TYPE: RNA
<213> ORGANISM: Homo sapiens

<400> SEQUENCE: 59
ugcaccaugg uugucugagc aug 23

<210> SEQ ID NO 60
<211> LENGTH: 23
<212> TYPE: RNA
<213> ORGANISM: Homo sapiens

<400> SEQUENCE: 60
ucugcucaua ccccaugguu ucu 23

<210> SEQ ID NO 61
<211> LENGTH: 22
<212> TYPE: RNA
<213> ORGANISM: Homo sapiens

<400> SEQUENCE: 61
acuccagccc cacagccuca gc 22

<210> SEQ ID NO 62
<211> LENGTH: 21
<212> TYPE: RNA
<213> ORGANISM: Homo sapiens

<400> SEQUENCE: 62
uggaggagaa ggaaggugau g 21

<210> SEQ ID NO 63
<211> LENGTH: 22
<212> TYPE: RNA
<213> ORGANISM: Homo sapiens

<400> SEQUENCE: 63
gcaggugcuc acuuguccuc cu 22

<210> SEQ ID NO 64
<211> LENGTH: 22
<212> TYPE: RNA
<213> ORGANISM: Homo sapiens

<400> SEQUENCE: 64
ggggcugggg ccggggccga gc 22

<210> SEQ ID NO 65
<211> LENGTH: 22
<212> TYPE: RNA
<213> ORGANISM: Homo sapiens

<400> SEQUENCE: 65
gcagcagggu gaaacugaca ca 22

<210> SEQ ID NO 66
<211> LENGTH: 20
<212> TYPE: RNA
<213> ORGANISM: Homo sapiens

<400> SEQUENCE: 66
cggcucuggg ucugugggga 20

<210> SEQ ID NO 67
<211> LENGTH: 22
<212> TYPE: RNA
<213> ORGANISM: Homo sapiens

<400> SEQUENCE: 67
gcagagugca aacaauuuug ac 22

<210> SEQ ID NO 68
<211> LENGTH: 22
<212> TYPE: RNA
<213> ORGANISM: Homo sapiens

<400> SEQUENCE: 68
uuugugaccu gguccacuaa cc 22

<210> SEQ ID NO 69
<211> LENGTH: 22
<212> TYPE: RNA
<213> ORGANISM: Homo sapiens

<400> SEQUENCE: 69
cuguugccac uaaccucaac cu 22

<210> SEQ ID NO 70
<211> LENGTH: 22
<212> TYPE: RNA
<213> ORGANISM: Homo sapiens

<400> SEQUENCE: 70
ugcggggcua gggcuaacag ca 22

<210> SEQ ID NO 71
<211> LENGTH: 17
<212> TYPE: RNA
<213> ORGANISM: Homo sapiens

<400> SEQUENCE: 71
ucucgcuggg gccucca 17

<210> SEQ ID NO 72
<211> LENGTH: 22
<212> TYPE: RNA
<213> ORGANISM: Homo sapiens

<400> SEQUENCE: 72
caacaaaucc cagucuaccu aa 22

<210> SEQ ID NO 73
<211> LENGTH: 21
<212> TYPE: RNA
<213> ORGANISM: Homo sapiens

<400> SEQUENCE: 73
cuuccgcccc gccgggcguc g 21

<210> SEQ ID NO 74
<211> LENGTH: 22
<212> TYPE: RNA
<213> ORGANISM: Homo sapiens

<400> SEQUENCE: 74
gggacccagg gagagacgua ag 22

<210> SEQ ID NO 75
<211> LENGTH: 22
<212> TYPE: RNA
<213> ORGANISM: Homo sapiens

<400> SEQUENCE: 75
caacaaauca cagucugcca ua 22

<210> SEQ ID NO 76
<211> LENGTH: 22
<212> TYPE: RNA
<213> ORGANISM: Homo sapiens

<400> SEQUENCE: 76
caacuagacu gugagcuucu ag 22

<210> SEQ ID NO 77
<211> LENGTH: 23
<212> TYPE: RNA

<213> ORGANISM: Homo sapiens

<400> SEQUENCE: 77
aaggagcuua caaucuagcu ggg 23

<210> SEQ ID NO 78
<211> LENGTH: 23
<212> TYPE: RNA
<213> ORGANISM: Homo sapiens

<400> SEQUENCE: 78
uggaagacua gugauuuugu ugu 23

<210> SEQ ID NO 79
<211> LENGTH: 20
<212> TYPE: RNA
<213> ORGANISM: Homo sapiens

<400> SEQUENCE: 79
cuguaugccc ucaccgcuca 20

<210> SEQ ID NO 80
<211> LENGTH: 23
<212> TYPE: RNA
<213> ORGANISM: Homo sapiens

<400> SEQUENCE: 80
uggugcggag agggcccaca gug 23

<210> SEQ ID NO 81
<211> LENGTH: 23
<212> TYPE: RNA
<213> ORGANISM: Homo sapiens

<400> SEQUENCE: 81
aggaagcccu ggaggggcug gag 23

<210> SEQ ID NO 82
<211> LENGTH: 21
<212> TYPE: RNA
<213> ORGANISM: Homo sapiens

<400> SEQUENCE: 82
uccgguucuc agggcuccac c 21

<210> SEQ ID NO 83
<211> LENGTH: 20
<212> TYPE: RNA
<213> ORGANISM: Homo sapiens

<400> SEQUENCE: 83
gucccugagu guauguggug 20

<210> SEQ ID NO 84
<211> LENGTH: 23
<212> TYPE: RNA
<213> ORGANISM: Homo sapiens

<400> SEQUENCE: 84
ugucacucgg cucggcccac uac 23

<210> SEQ ID NO 85
<211> LENGTH: 20

<212> TYPE: RNA
<213> ORGANISM: Homo sapiens

<400> SEQUENCE: 85
accaggaggc ugaggccccu 20

<210> SEQ ID NO 86
<211> LENGTH: 24
<212> TYPE: RNA
<213> ORGANISM: Homo sapiens

<400> SEQUENCE: 86
acuggcuagg gaaaaugauu ggau 24

<210> SEQ ID NO 87
<211> LENGTH: 23
<212> TYPE: RNA
<213> ORGANISM: Homo sapiens

<400> SEQUENCE: 87
uauucauuua uccccagccu aca 23

<210> SEQ ID NO 88
<211> LENGTH: 22
<212> TYPE: RNA
<213> ORGANISM: Homo sapiens

<400> SEQUENCE: 88
gguggcccgg ccgugccuga gg 22

<210> SEQ ID NO 89
<211> LENGTH: 22
<212> TYPE: RNA
<213> ORGANISM: Homo sapiens

<400> SEQUENCE: 89
aggcggggcg ccgcgggacc gc 22

<210> SEQ ID NO 90
<211> LENGTH: 21
<212> TYPE: RNA
<213> ORGANISM: Homo sapiens

<400> SEQUENCE: 90
ucccacguug uggcccagca g 21

<210> SEQ ID NO 91
<211> LENGTH: 24
<212> TYPE: RNA
<213> ORGANISM: Homo sapiens

<400> SEQUENCE: 91
ugccuggguc ucuggccugc gcgu 24

<210> SEQ ID NO 92
<211> LENGTH: 22
<212> TYPE: RNA
<213> ORGANISM: Homo sapiens

<400> SEQUENCE: 92
uacccauugc auaucggagu ug 22

<210> SEQ ID NO 93

-continued

<211> LENGTH: 22
<212> TYPE: RNA
<213> ORGANISM: Homo sapiens

<400> SEQUENCE: 93
cuugguucag ggaggguccc ca 22

<210> SEQ ID NO 94
<211> LENGTH: 25
<212> TYPE: RNA
<213> ORGANISM: Homo sapiens

<400> SEQUENCE: 94
ggcggaggga aguagguccg uuggu 25

<210> SEQ ID NO 95
<211> LENGTH: 23
<212> TYPE: RNA
<213> ORGANISM: Homo sapiens

<400> SEQUENCE: 95
ggcagguucu cacccucucu agg 23

<210> SEQ ID NO 96
<211> LENGTH: 21
<212> TYPE: RNA
<213> ORGANISM: Homo sapiens

<400> SEQUENCE: 96
aauauuauac agucaaccuc u 21

<210> SEQ ID NO 97
<211> LENGTH: 22
<212> TYPE: RNA
<213> ORGANISM: Homo sapiens

<400> SEQUENCE: 97
auaauacaug guuaaccucu uu 22

<210> SEQ ID NO 98
<211> LENGTH: 22
<212> TYPE: RNA
<213> ORGANISM: Homo sapiens

<400> SEQUENCE: 98
uggugggccg cagaacaugu gc 22

<210> SEQ ID NO 99
<211> LENGTH: 22
<212> TYPE: RNA
<213> ORGANISM: Homo sapiens

<400> SEQUENCE: 99
uaugucugcu gaccaucacc uu 22

<210> SEQ ID NO 100
<211> LENGTH: 21
<212> TYPE: RNA
<213> ORGANISM: Homo sapiens

<400> SEQUENCE: 100
guguugaaac aaucucuacu g 21

<210> SEQ ID NO 101
<211> LENGTH: 21
<212> TYPE: RNA
<213> ORGANISM: Homo sapiens

<400> SEQUENCE: 101
aauggcgcca cuaggguugu g 21

<210> SEQ ID NO 102
<211> LENGTH: 22
<212> TYPE: RNA
<213> ORGANISM: Homo sapiens

<400> SEQUENCE: 102
uuuaggauaa gcuugacuuu ug 22

<210> SEQ ID NO 103
<211> LENGTH: 21
<212> TYPE: RNA
<213> ORGANISM: Homo sapiens

<400> SEQUENCE: 103
aggaggcagc gcucucagga c 21

<210> SEQ ID NO 104
<211> LENGTH: 22
<212> TYPE: RNA
<213> ORGANISM: Homo sapiens

<400> SEQUENCE: 104
aaaccugugu uguucaagag uc 22

<210> SEQ ID NO 105
<211> LENGTH: 19
<212> TYPE: RNA
<213> ORGANISM: Homo sapiens

<400> SEQUENCE: 105
aagugugcag ggcacuggu 19

<210> SEQ ID NO 106
<211> LENGTH: 21
<212> TYPE: RNA
<213> ORGANISM: Homo sapiens

<400> SEQUENCE: 106
guggcugcac ucacuuccuu c 21

<210> SEQ ID NO 107
<211> LENGTH: 19
<212> TYPE: RNA
<213> ORGANISM: Homo sapiens

<400> SEQUENCE: 107
aagcagcugc cucugaggc 19

<210> SEQ ID NO 108
<211> LENGTH: 19
<212> TYPE: RNA
<213> ORGANISM: Homo sapiens

<400> SEQUENCE: 108
ucuaggcugg uacugcuga 19

<210> SEQ ID NO 109
<211> LENGTH: 19
<212> TYPE: RNA
<213> ORGANISM: Homo sapiens

<400> SEQUENCE: 109
aguguggcuu ucuuagagc 19

<210> SEQ ID NO 110
<211> LENGTH: 22
<212> TYPE: RNA
<213> ORGANISM: Homo sapiens

<400> SEQUENCE: 110
acuuguaugc uagcucaggu ag 22

<210> SEQ ID NO 111
<211> LENGTH: 22
<212> TYPE: RNA
<213> ORGANISM: Homo sapiens

<400> SEQUENCE: 111
gucccucucc aaaugugucu ug 22

<210> SEQ ID NO 112
<211> LENGTH: 24
<212> TYPE: RNA
<213> ORGANISM: Homo sapiens

<400> SEQUENCE: 112
aaagacauag gauagaguca ccuc 24

<210> SEQ ID NO 113
<211> LENGTH: 21
<212> TYPE: RNA
<213> ORGANISM: Homo sapiens

<400> SEQUENCE: 113
augauccagg aaccugccuc u 21

<210> SEQ ID NO 114
<211> LENGTH: 23
<212> TYPE: RNA
<213> ORGANISM: Homo sapiens

<400> SEQUENCE: 114
aucgcugcgg uugcgagcgc ugu 23

<210> SEQ ID NO 115
<211> LENGTH: 25
<212> TYPE: RNA
<213> ORGANISM: Homo sapiens

<400> SEQUENCE: 115
agggaucgcg ggcggguggc ggccu 25

<210> SEQ ID NO 116
<211> LENGTH: 24
<212> TYPE: RNA
<213> ORGANISM: Homo sapiens

<400> SEQUENCE: 116
acugggggcu uucgggcucu gcgu 24

<210> SEQ ID NO 117
<211> LENGTH: 23
<212> TYPE: RNA
<213> ORGANISM: Homo sapiens

<400> SEQUENCE: 117
ugugcuugcu cgucccgccc gca 23

<210> SEQ ID NO 118
<211> LENGTH: 23
<212> TYPE: RNA
<213> ORGANISM: Homo sapiens

<400> SEQUENCE: 118
acuugggcac ugaaacaaug ucc 23

<210> SEQ ID NO 119
<211> LENGTH: 22
<212> TYPE: RNA
<213> ORGANISM: Homo sapiens

<400> SEQUENCE: 119
aaccagcacc ccaacuuugg ac 22

<210> SEQ ID NO 120
<211> LENGTH: 23
<212> TYPE: RNA
<213> ORGANISM: Homo sapiens

<400> SEQUENCE: 120
cuaauaguau cuaccacaau aaa 23

<210> SEQ ID NO 121
<211> LENGTH: 19
<212> TYPE: RNA
<213> ORGANISM: Homo sapiens

<400> SEQUENCE: 121
gugucugcuu ccuguggga 19

<210> SEQ ID NO 122
<211> LENGTH: 21
<212> TYPE: RNA
<213> ORGANISM: Homo sapiens

<400> SEQUENCE: 122
agaccuggcc cagaccucag c 21

<210> SEQ ID NO 123
<211> LENGTH: 22
<212> TYPE: RNA
<213> ORGANISM: Homo sapiens

<400> SEQUENCE: 123
aguauucugu accagggaag gu 22

<210> SEQ ID NO 124
<211> LENGTH: 22
<212> TYPE: RNA
<213> ORGANISM: Homo sapiens

<400> SEQUENCE: 124

-continued guucucccaa cguaagccca gc 22

<210> SEQ ID NO 125
<211> LENGTH: 21
<212> TYPE: RNA
<213> ORGANISM: Homo sapiens

<400> SEQUENCE: 125
uggguuuacg uugggagaac u 21

<210> SEQ ID NO 126
<211> LENGTH: 22
<212> TYPE: RNA
<213> ORGANISM: Homo sapiens

<400> SEQUENCE: 126
augcugacau auuuacuaga gg 22

<210> SEQ ID NO 127
<211> LENGTH: 21
<212> TYPE: RNA
<213> ORGANISM: Homo sapiens

<400> SEQUENCE: 127
ucuaguaaga guggcagucg a 21

<210> SEQ ID NO 128
<211> LENGTH: 22
<212> TYPE: RNA
<213> ORGANISM: Homo sapiens

<400> SEQUENCE: 128
gugagucucu aagaaaagag ga 22

<210> SEQ ID NO 129
<211> LENGTH: 19
<212> TYPE: RNA
<213> ORGANISM: Homo sapiens

<400> SEQUENCE: 129
agcugucuga aaaugucuu 19

<210> SEQ ID NO 130
<211> LENGTH: 22
<212> TYPE: RNA
<213> ORGANISM: Homo sapiens

<400> SEQUENCE: 130
gacuauagaa cuuucccccu ca 22

<210> SEQ ID NO 131
<211> LENGTH: 21
<212> TYPE: RNA
<213> ORGANISM: Homo sapiens

<400> SEQUENCE: 131
agggggaaag uucuauaguc c 21

<210> SEQ ID NO 132
<211> LENGTH: 22
<212> TYPE: RNA
<213> ORGANISM: Homo sapiens

<400> SEQUENCE: 132

-continued uaguaccagu accuuguguu ca                                                22

<210> SEQ ID NO 133
<211> LENGTH: 21
<212> TYPE: RNA
<213> ORGANISM: Homo sapiens

<400> SEQUENCE: 133
cacaagguau ugguauuacc u                                                 21

<210> SEQ ID NO 134
<211> LENGTH: 23
<212> TYPE: RNA
<213> ORGANISM: Homo sapiens

<400> SEQUENCE: 134
aucccuugca ggggcuguug ggu                                               23

<210> SEQ ID NO 135
<211> LENGTH: 21
<212> TYPE: RNA
<213> ORGANISM: Homo sapiens

<400> SEQUENCE: 135
acagucugcu gagguuggag c                                                 21

<210> SEQ ID NO 136
<211> LENGTH: 21
<212> TYPE: RNA
<213> ORGANISM: Homo sapiens

<400> SEQUENCE: 136
ggcuagcaac agcgcuuacc u                                                 21

<210> SEQ ID NO 137
<211> LENGTH: 20
<212> TYPE: RNA
<213> ORGANISM: Homo sapiens

<400> SEQUENCE: 137
auggagauag auauagaaau                                                   20

<210> SEQ ID NO 138
<211> LENGTH: 24
<212> TYPE: RNA
<213> ORGANISM: Homo sapiens

<400> SEQUENCE: 138
gaccuggaca uguuugugcc cagu                                              24

<210> SEQ ID NO 139
<211> LENGTH: 23
<212> TYPE: RNA
<213> ORGANISM: Homo sapiens

<400> SEQUENCE: 139
aaacucuacu uguccuucug agu                                               23

<210> SEQ ID NO 140
<211> LENGTH: 22
<212> TYPE: RNA
<213> ORGANISM: Homo sapiens

<400> SEQUENCE: 140
agacuuccca uuugaaggug gc 22

<210> SEQ ID NO 141
<211> LENGTH: 22
<212> TYPE: RNA
<213> ORGANISM: Homo sapiens

<400> SEQUENCE: 141
acucaaaacc cuucagugac uu 22

<210> SEQ ID NO 142
<211> LENGTH: 22
<212> TYPE: RNA
<213> ORGANISM: Homo sapiens

<400> SEQUENCE: 142
agucauugga ggguuugagc ag 22

<210> SEQ ID NO 143
<211> LENGTH: 22
<212> TYPE: RNA
<213> ORGANISM: Homo sapiens

<400> SEQUENCE: 143
gggggucccc ggugcucgga uc 22

<210> SEQ ID NO 144
<211> LENGTH: 22
<212> TYPE: RNA
<213> ORGANISM: Homo sapiens

<400> SEQUENCE: 144
uccgagccug ggucucccuc uu 22

<210> SEQ ID NO 145
<211> LENGTH: 23
<212> TYPE: RNA
<213> ORGANISM: Homo sapiens

<400> SEQUENCE: 145
gaacgccugu ucuugccagg ugg 23

<210> SEQ ID NO 146
<211> LENGTH: 20
<212> TYPE: RNA
<213> ORGANISM: Homo sapiens

<400> SEQUENCE: 146
aggaauguuc cuucuuugcc 20

<210> SEQ ID NO 147
<211> LENGTH: 25
<212> TYPE: RNA
<213> ORGANISM: Homo sapiens

<400> SEQUENCE: 147
gcugggcagg gcuucugagc uccuu 25

<210> SEQ ID NO 148
<211> LENGTH: 23
<212> TYPE: RNA
<213> ORGANISM: Homo sapiens

<400> SEQUENCE: 148
gcgaggaccc cucggggucu gac 23

<210> SEQ ID NO 149
<211> LENGTH: 21
<212> TYPE: RNA
<213> ORGANISM: Homo sapiens

<400> SEQUENCE: 149
ugagcuaaau gugugcuggg a 21

<210> SEQ ID NO 150
<211> LENGTH: 20
<212> TYPE: RNA
<213> ORGANISM: Homo sapiens

<400> SEQUENCE: 150
aggguguuuc ucucaucucu 20

<210> SEQ ID NO 151
<211> LENGTH: 25
<212> TYPE: RNA
<213> ORGANISM: Homo sapiens

<400> SEQUENCE: 151 aggggugggug uugggacagc uccgu 25

<210> SEQ ID NO 152
<211> LENGTH: 21
<212> TYPE: RNA
<213> ORGANISM: Homo sapiens

<400> SEQUENCE: 152
guucaaaucc agaucuauaa c 21

<210> SEQ ID NO 153
<211> LENGTH: 21
<212> TYPE: RNA
<213> ORGANISM: Homo sapiens

<400> SEQUENCE: 153
aaacuacuga aaaucaaaga u 21

<210> SEQ ID NO 154
<211> LENGTH: 23
<212> TYPE: RNA
<213> ORGANISM: Homo sapiens

<400> SEQUENCE: 154
uaaaucccau ggugccuucu ccu 23

<210> SEQ ID NO 155
<211> LENGTH: 19
<212> TYPE: RNA
<213> ORGANISM: Homo sapiens

<400> SEQUENCE: 155
aggcugcgga auucaggac 19

<210> SEQ ID NO 156
<211> LENGTH: 22
<212> TYPE: RNA

<213> ORGANISM: Homo sapiens

<400> SEQUENCE: 156
cacacacugc aauuacuuuu gc 22

<210> SEQ ID NO 157
<211> LENGTH: 23
<212> TYPE: RNA
<213> ORGANISM: Homo sapiens

<400> SEQUENCE: 157
gacacgggcg acagcugcgg ccc 23

<210> SEQ ID NO 158
<211> LENGTH: 22
<212> TYPE: RNA
<213> ORGANISM: Homo sapiens

<400> SEQUENCE: 158
uggucuagga uuguuggagg ag 22

<210> SEQ ID NO 159
<211> LENGTH: 23
<212> TYPE: RNA
<213> ORGANISM: Homo sapiens

<400> SEQUENCE: 159
acuuacagac aagagccuug cuc 23

<210> SEQ ID NO 160
<211> LENGTH: 20
<212> TYPE: RNA
<213> ORGANISM: Homo sapiens

<400> SEQUENCE: 160
guugugucag uuuaucaaac 20

<210> SEQ ID NO 161
<211> LENGTH: 22
<212> TYPE: RNA
<213> ORGANISM: Homo sapiens

<400> SEQUENCE: 161
uacgucaucg uugucaucgu ca 22

<210> SEQ ID NO 162
<211> LENGTH: 22
<212> TYPE: RNA
<213> ORGANISM: Homo sapiens

<400> SEQUENCE: 162
ugugucacuc gaugaccacu gu 22

<210> SEQ ID NO 163
<211> LENGTH: 21
<212> TYPE: RNA
<213> ORGANISM: Homo sapiens

<400> SEQUENCE: 163
aagccugccc ggcuccucgg g 21

<210> SEQ ID NO 164
<211> LENGTH: 21

-continued

<212> TYPE: RNA
<213> ORGANISM: Homo sapiens

<400> SEQUENCE: 164
gaagugugcc gugguguguc u 21

<210> SEQ ID NO 165
<211> LENGTH: 25
<212> TYPE: RNA
<213> ORGANISM: Homo sapiens

<400> SEQUENCE: 165
aggcaccagc caggcauugc ucagc 25

<210> SEQ ID NO 166
<211> LENGTH: 19
<212> TYPE: RNA
<213> ORGANISM: Homo sapiens

<400> SEQUENCE: 166
ugucucugcu gggguuucu 19

<210> SEQ ID NO 167
<211> LENGTH: 22
<212> TYPE: RNA
<213> ORGANISM: Homo sapiens

<400> SEQUENCE: 167
uugugucaau augcgaugau gu 22

<210> SEQ ID NO 168
<211> LENGTH: 20
<212> TYPE: RNA
<213> ORGANISM: Homo sapiens

<400> SEQUENCE: 168
agaccauggg uucucauugu 20

<210> SEQ ID NO 169
<211> LENGTH: 22
<212> TYPE: RNA
<213> ORGANISM: Homo sapiens

<400> SEQUENCE: 169
gagcuuauuc auaaaagugc ag 22

<210> SEQ ID NO 170
<211> LENGTH: 21
<212> TYPE: RNA
<213> ORGANISM: Homo sapiens

<400> SEQUENCE: 170
uaauuuuaug uauaagcuag u 21

<210> SEQ ID NO 171
<211> LENGTH: 24
<212> TYPE: RNA
<213> ORGANISM: Homo sapiens

<400> SEQUENCE: 171
ucagaacaaa ugccgguucc caga 24

<210> SEQ ID NO 172

<211> LENGTH: 22
<212> TYPE: RNA
<213> ORGANISM: Homo sapiens

<400> SEQUENCE: 172
ugagaaccac gucugcucug ag 22

<210> SEQ ID NO 173
<211> LENGTH: 21
<212> TYPE: RNA
<213> ORGANISM: Homo sapiens

<400> SEQUENCE: 173
uuggccacaa uggguuagaa c 21

<210> SEQ ID NO 174
<211> LENGTH: 21
<212> TYPE: RNA
<213> ORGANISM: Homo sapiens

<400> SEQUENCE: 174
uuuccauagg ugaugaguca c 21

<210> SEQ ID NO 175
<211> LENGTH: 22
<212> TYPE: RNA
<213> ORGANISM: Homo sapiens

<400> SEQUENCE: 175
uaugcauugu auuuuuaggu cc 22

<210> SEQ ID NO 176
<211> LENGTH: 19
<212> TYPE: RNA
<213> ORGANISM: Homo sapiens

<400> SEQUENCE: 176
ugggcguauc uguaugcua 19

<210> SEQ ID NO 177
<211> LENGTH: 22
<212> TYPE: RNA
<213> ORGANISM: Homo sapiens

<400> SEQUENCE: 177
uuaugguuug ccugggacug ag 22

<210> SEQ ID NO 178
<211> LENGTH: 21
<212> TYPE: RNA
<213> ORGANISM: Homo sapiens

<400> SEQUENCE: 178
caaagaggaa ggucccauua c 21

<210> SEQ ID NO 179
<211> LENGTH: 23
<212> TYPE: RNA
<213> ORGANISM: Homo sapiens

<400> SEQUENCE: 179
uuacaguugu ucaaccaguu acu 23

<210> SEQ ID NO 180
<211> LENGTH: 22
<212> TYPE: RNA
<213> ORGANISM: Homo sapiens

<400> SEQUENCE: 180
uaacugguug aacaacugaa cc 22

<210> SEQ ID NO 181
<211> LENGTH: 21
<212> TYPE: RNA
<213> ORGANISM: Homo sapiens

<400> SEQUENCE: 181
ucuuguguuc ucuagaucag u 21

<210> SEQ ID NO 182
<211> LENGTH: 22
<212> TYPE: RNA
<213> ORGANISM: Homo sapiens

<400> SEQUENCE: 182
uugagaauga ugaaucauua gg 22

<210> SEQ ID NO 183
<211> LENGTH: 23
<212> TYPE: RNA
<213> ORGANISM: Homo sapiens

<400> SEQUENCE: 183
uucauuuggu auaaaccgcg auu 23

<210> SEQ ID NO 184
<211> LENGTH: 21
<212> TYPE: RNA
<213> ORGANISM: Homo sapiens

<400> SEQUENCE: 184
cuucuugugc ucuaggauug u 21

<210> SEQ ID NO 185
<211> LENGTH: 21
<212> TYPE: RNA
<213> ORGANISM: Homo sapiens

<400> SEQUENCE: 185
uagauaaaau auugguaccu g 21

<210> SEQ ID NO 186
<211> LENGTH: 22
<212> TYPE: RNA
<213> ORGANISM: Homo sapiens

<400> SEQUENCE: 186
auucuaauuu cuccacgucu uu 22

<210> SEQ ID NO 187
<211> LENGTH: 22
<212> TYPE: RNA
<213> ORGANISM: Homo sapiens

<400> SEQUENCE: 187
aagaugugga aaaauuggaa uc 22

<210> SEQ ID NO 188
<211> LENGTH: 19
<212> TYPE: RNA
<213> ORGANISM: Homo sapiens

<400> SEQUENCE: 188
gagccaguug gacaggagc 19

<210> SEQ ID NO 189
<211> LENGTH: 23
<212> TYPE: RNA
<213> ORGANISM: Homo sapiens

<400> SEQUENCE: 189
ugagugugug ugugugagug ugu 23

<210> SEQ ID NO 190
<211> LENGTH: 22
<212> TYPE: RNA
<213> ORGANISM: Homo sapiens

<400> SEQUENCE: 190
cacgcucaug cacacaccca ca 22

<210> SEQ ID NO 191
<211> LENGTH: 24
<212> TYPE: RNA
<213> ORGANISM: Homo sapiens

<400> SEQUENCE: 191
cugaagugau guguaacuga ucag 24

<210> SEQ ID NO 192
<211> LENGTH: 20
<212> TYPE: RNA
<213> ORGANISM: Homo sapiens

<400> SEQUENCE: 192
guccgcucgg cgguggccca 20

<210> SEQ ID NO 193
<211> LENGTH: 21
<212> TYPE: RNA
<213> ORGANISM: Homo sapiens

<400> SEQUENCE: 193
ugaguuggcc aucugaguga g 21

<210> SEQ ID NO 194
<211> LENGTH: 22
<212> TYPE: RNA
<213> ORGANISM: Homo sapiens

<400> SEQUENCE: 194
cgaaaacagc aauuaccuuu gc 22

<210> SEQ ID NO 195
<211> LENGTH: 21
<212> TYPE: RNA
<213> ORGANISM: Homo sapiens

<400> SEQUENCE: 195
aguuaaugaa uccuggaaag u 21

<210> SEQ ID NO 196
<211> LENGTH: 20
<212> TYPE: RNA
<213> ORGANISM: Homo sapiens

<400> SEQUENCE: 196
auguauaaau guauacacac 20

<210> SEQ ID NO 197
<211> LENGTH: 23
<212> TYPE: RNA
<213> ORGANISM: Homo sapiens

<400> SEQUENCE: 197
aguauguucu uccaggacag aac 23

<210> SEQ ID NO 198
<211> LENGTH: 19
<212> TYPE: RNA
<213> ORGANISM: Homo sapiens

<400> SEQUENCE: 198
gggcgccugu gaucccaac 19

<210> SEQ ID NO 199
<211> LENGTH: 19
<212> TYPE: RNA
<213> ORGANISM: Homo sapiens

<400> SEQUENCE: 199
aggcacggug ucagcaggc 19

<210> SEQ ID NO 200
<211> LENGTH: 19
<212> TYPE: RNA
<213> ORGANISM: Homo sapiens

<400> SEQUENCE: 200
agguugacau acguuuccc 19

<210> SEQ ID NO 201
<211> LENGTH: 20
<212> TYPE: RNA
<213> ORGANISM: Homo sapiens

<400> SEQUENCE: 201
aaaguagcug uaccauuugc 20

<210> SEQ ID NO 202
<211> LENGTH: 22
<212> TYPE: RNA
<213> ORGANISM: Homo sapiens

<400> SEQUENCE: 202
caaaguuuaa gauccuugaa gu 22

<210> SEQ ID NO 203
<211> LENGTH: 21
<212> TYPE: RNA
<213> ORGANISM: Homo sapiens

<400> SEQUENCE: 203
uaaaguaaau augcaccaaa a 21

<210> SEQ ID NO 204
<211> LENGTH: 19
<212> TYPE: RNA
<213> ORGANISM: Homo sapiens

<400> SEQUENCE: 204
ugagcugcug uaccaaaau 19

<210> SEQ ID NO 205
<211> LENGTH: 23
<212> TYPE: RNA
<213> ORGANISM: Homo sapiens

<400> SEQUENCE: 205
guuugcacgg gugggccuug ucu 23

<210> SEQ ID NO 206
<211> LENGTH: 22
<212> TYPE: RNA
<213> ORGANISM: Homo sapiens

<400> SEQUENCE: 206
gaugagcuca uuguaauaug ag 22

<210> SEQ ID NO 207
<211> LENGTH: 22
<212> TYPE: RNA
<213> ORGANISM: Homo sapiens

<400> SEQUENCE: 207
auauuaccau uagcucaucu uu 22

<210> SEQ ID NO 208
<211> LENGTH: 21
<212> TYPE: RNA
<213> ORGANISM: Homo sapiens

<400> SEQUENCE: 208
aggguaagcu gaaccucuga u 21

<210> SEQ ID NO 209
<211> LENGTH: 21
<212> TYPE: RNA
<213> ORGANISM: Homo sapiens

<400> SEQUENCE: 209
gcuaguccug acucagccag u 21

<210> SEQ ID NO 210
<211> LENGTH: 21
<212> TYPE: RNA
<213> ORGANISM: Homo sapiens

<400> SEQUENCE: 210
aaaacgguga gauuuuguuu u 21

<210> SEQ ID NO 211
<211> LENGTH: 21
<212> TYPE: RNA
<213> ORGANISM: Homo sapiens

<400> SEQUENCE: 211
aacaggugac ugguuagaca a 21

<210> SEQ ID NO 212
<211> LENGTH: 22
<212> TYPE: RNA
<213> ORGANISM: Homo sapiens

<400> SEQUENCE: 212
gaaaucaagc gugggugaga cc 22

<210> SEQ ID NO 213
<211> LENGTH: 21
<212> TYPE: RNA
<213> ORGANISM: Homo sapiens

<400> SEQUENCE: 213
gcgacccaua cuugguuuca g 21

<210> SEQ ID NO 214
<211> LENGTH: 21
<212> TYPE: RNA
<213> ORGANISM: Homo sapiens

<400> SEQUENCE: 214
gcgacccacu cuugguuucc a 21

<210> SEQ ID NO 215
<211> LENGTH: 22
<212> TYPE: RNA
<213> ORGANISM: Homo sapiens

<400> SEQUENCE: 215
ugucuuacuc ccucaggcac au 22

<210> SEQ ID NO 216
<211> LENGTH: 23
<212> TYPE: RNA
<213> ORGANISM: Homo sapiens

<400> SEQUENCE: 216
agugccugag ggaguaagag ccc 23

<210> SEQ ID NO 217
<211> LENGTH: 21
<212> TYPE: RNA
<213> ORGANISM: Homo sapiens

<400> SEQUENCE: 217
ugacaacuau ggaugagcuc u 21

<210> SEQ ID NO 218
<211> LENGTH: 22
<212> TYPE: RNA
<213> ORGANISM: Homo sapiens

<400> SEQUENCE: 218
gcuggugcaa aaguaauggc gg 22

<210> SEQ ID NO 219
<211> LENGTH: 22
<212> TYPE: RNA
<213> ORGANISM: Homo sapiens

<400> SEQUENCE: 219
uagcaaaaac ugcaguuacu uu 22

<210> SEQ ID NO 220
<211> LENGTH: 22
<212> TYPE: RNA
<213> ORGANISM: Homo sapiens

<400> SEQUENCE: 220
ccaaaacugc aguuacuuuu gc 22

<210> SEQ ID NO 221
<211> LENGTH: 22
<212> TYPE: RNA
<213> ORGANISM: Homo sapiens

<400> SEQUENCE: 221
caaaaguaau uguggauuuu gu 22

<210> SEQ ID NO 222
<211> LENGTH: 21
<212> TYPE: RNA
<213> ORGANISM: Homo sapiens

<400> SEQUENCE: 222
caaagguauu ugugguuuuu g 21

<210> SEQ ID NO 223
<211> LENGTH: 22
<212> TYPE: RNA
<213> ORGANISM: Homo sapiens

<400> SEQUENCE: 223
aaaaguauuu gcggguuuug uc 22

<210> SEQ ID NO 224
<211> LENGTH: 22
<212> TYPE: RNA
<213> ORGANISM: Homo sapiens

<400> SEQUENCE: 224
aaaaguacuu gcggauuuug cu 22

<210> SEQ ID NO 225
<211> LENGTH: 22
<212> TYPE: RNA
<213> ORGANISM: Homo sapiens

<400> SEQUENCE: 225
aaaaguaauu gcggucuuug gu 22

<210> SEQ ID NO 226
<211> LENGTH: 22
<212> TYPE: RNA
<213> ORGANISM: Homo sapiens

<400> SEQUENCE: 226
aaaaguaauu gcggauuuug cc 22

<210> SEQ ID NO 227
<211> LENGTH: 22
<212> TYPE: RNA
<213> ORGANISM: Homo sapiens

<400> SEQUENCE: 227
aaaaguaauc gcgguuuuug uc 22

<210> SEQ ID NO 228
<211> LENGTH: 22
<212> TYPE: RNA
<213> ORGANISM: Homo sapiens

<400> SEQUENCE: 228
aaaacuguaa uuacuuuugu ac 22

<210> SEQ ID NO 229
<211> LENGTH: 19
<212> TYPE: RNA
<213> ORGANISM: Homo sapiens

<400> SEQUENCE: 229
aaaaacugua auuacuuuu 19

<210> SEQ ID NO 230
<211> LENGTH: 22
<212> TYPE: RNA
<213> ORGANISM: Homo sapiens

<400> SEQUENCE: 230
aaaaacugag acuacuuuug ca 22

<210> SEQ ID NO 231
<211> LENGTH: 22
<212> TYPE: RNA
<213> ORGANISM: Homo sapiens

<400> SEQUENCE: 231
aaaaguaauu gugguuuuug cc 22

<210> SEQ ID NO 232
<211> LENGTH: 22
<212> TYPE: RNA
<213> ORGANISM: Homo sapiens

<400> SEQUENCE: 232
caaaaaccac aguuucuuuu gc 22

<210> SEQ ID NO 233
<211> LENGTH: 22
<212> TYPE: RNA
<213> ORGANISM: Homo sapiens

<400> SEQUENCE: 233
aaaaguaauu gcgguuuuug cc 22

<210> SEQ ID NO 234
<211> LENGTH: 22
<212> TYPE: RNA
<213> ORGANISM: Homo sapiens

<400> SEQUENCE: 234
caaaaaucuc aauuacuuuu gc 22

<210> SEQ ID NO 235
<211> LENGTH: 22
<212> TYPE: RNA

<213> ORGANISM: Homo sapiens

<400> SEQUENCE: 235
aaaaguaauu gugguuuugg cc 22

<210> SEQ ID NO 236
<211> LENGTH: 22
<212> TYPE: RNA
<213> ORGANISM: Homo sapiens

<400> SEQUENCE: 236
caagaaccuc aguugcuuuu gu 22

<210> SEQ ID NO 237
<211> LENGTH: 22
<212> TYPE: RNA
<213> ORGANISM: Homo sapiens

<400> SEQUENCE: 237
aaaaguaauu gcgaguuuua cc 22

<210> SEQ ID NO 238
<211> LENGTH: 22
<212> TYPE: RNA
<213> ORGANISM: Homo sapiens

<400> SEQUENCE: 238
caaaacuggc aauuacuuuu gc 22

<210> SEQ ID NO 239
<211> LENGTH: 22
<212> TYPE: RNA
<213> ORGANISM: Homo sapiens

<400> SEQUENCE: 239
ucaguaaaug uuuauuagau ga 22

<210> SEQ ID NO 240
<211> LENGTH: 22
<212> TYPE: RNA
<213> ORGANISM: Homo sapiens

<400> SEQUENCE: 240
ucagcaaaca uuuauugugu gc 22

<210> SEQ ID NO 241
<211> LENGTH: 22
<212> TYPE: RNA
<213> ORGANISM: Homo sapiens

<400> SEQUENCE: 241
auucugcauu uuuagcaagu uc 22

<210> SEQ ID NO 242
<211> LENGTH: 22
<212> TYPE: RNA
<213> ORGANISM: Homo sapiens

<400> SEQUENCE: 242
aaacauucgc ggugcacuuc uu 22

<210> SEQ ID NO 243
<211> LENGTH: 23

<212> TYPE: RNA
<213> ORGANISM: Homo sapiens

<400> SEQUENCE: 243
ucggggauca ucaugucacg aga 23

<210> SEQ ID NO 244
<211> LENGTH: 22
<212> TYPE: RNA
<213> ORGANISM: Homo sapiens

<400> SEQUENCE: 244
ugugacagau ugauaacuga aa 22

<210> SEQ ID NO 245
<211> LENGTH: 25
<212> TYPE: RNA
<213> ORGANISM: Homo sapiens

<400> SEQUENCE: 245
aaaggauucu gcugucgguc ccacu 25

<210> SEQ ID NO 246
<211> LENGTH: 22
<212> TYPE: RNA
<213> ORGANISM: Homo sapiens

<400> SEQUENCE: 246
uggugggcac agaaucugga cu 22

<210> SEQ ID NO 247
<211> LENGTH: 22
<212> TYPE: RNA
<213> ORGANISM: Homo sapiens

<400> SEQUENCE: 247
ggagaaauua uccuuggugu gu 22

<210> SEQ ID NO 248
<211> LENGTH: 22
<212> TYPE: RNA
<213> ORGANISM: Homo sapiens

<400> SEQUENCE: 248
caugccuuga guguaggacc gu 22

<210> SEQ ID NO 249
<211> LENGTH: 22
<212> TYPE: RNA
<213> ORGANISM: Homo sapiens

<400> SEQUENCE: 249
ccucccacac ccaaggcuug ca 22

<210> SEQ ID NO 250
<211> LENGTH: 20
<212> TYPE: RNA
<213> ORGANISM: Homo sapiens

<400> SEQUENCE: 250
cugcaaaggg aagcccuuuc 20

<210> SEQ ID NO 251

<211> LENGTH: 22
<212> TYPE: RNA
<213> ORGANISM: Homo sapiens

<400> SEQUENCE: 251
gaaagugcuu ccuuuuagag gc 22

<210> SEQ ID NO 252
<211> LENGTH: 23
<212> TYPE: RNA
<213> ORGANISM: Homo sapiens

<400> SEQUENCE: 252
cucuugaggg aagcacuuuc ugu 23

<210> SEQ ID NO 253
<211> LENGTH: 22
<212> TYPE: RNA
<213> ORGANISM: Homo sapiens

<400> SEQUENCE: 253
cucuagaggg aagcacuuuc ug 22

<210> SEQ ID NO 254
<211> LENGTH: 21
<212> TYPE: RNA
<213> ORGANISM: Homo sapiens

<400> SEQUENCE: 254
cuccagaggg augcacuuuc u 21

<210> SEQ ID NO 255
<211> LENGTH: 22
<212> TYPE: RNA
<213> ORGANISM: Homo sapiens

<400> SEQUENCE: 255
gaaggcgcuu cccuuuagag cg 22

<210> SEQ ID NO 256
<211> LENGTH: 22
<212> TYPE: RNA
<213> ORGANISM: Homo sapiens

<400> SEQUENCE: 256
cuacaaaggg aagcacuuuc uc 22

<210> SEQ ID NO 257
<211> LENGTH: 21
<212> TYPE: RNA
<213> ORGANISM: Homo sapiens

<400> SEQUENCE: 257
gaaggcgcuu cccuuuggag u 21

<210> SEQ ID NO 258
<211> LENGTH: 22
<212> TYPE: RNA
<213> ORGANISM: Homo sapiens

<400> SEQUENCE: 258
cucuagaggg aagcgcuuuc ug 22

<210> SEQ ID NO 259
<211> LENGTH: 23
<212> TYPE: RNA
<213> ORGANISM: Homo sapiens

<400> SEQUENCE: 259
gaacgcgcuu cccuauagag ggu 23

<210> SEQ ID NO 260
<211> LENGTH: 22
<212> TYPE: RNA
<213> ORGANISM: Homo sapiens

<400> SEQUENCE: 260
cucuagaggg aagcgcuuuc ug 22

<210> SEQ ID NO 261
<211> LENGTH: 22
<212> TYPE: RNA
<213> ORGANISM: Homo sapiens

<400> SEQUENCE: 261
aaaaugguuc ccuuuagagu gu 22

<210> SEQ ID NO 262
<211> LENGTH: 22
<212> TYPE: RNA
<213> ORGANISM: Homo sapiens

<400> SEQUENCE: 262
aacgcacuuc ccuuuagagu gu 22

<210> SEQ ID NO 263
<211> LENGTH: 22
<212> TYPE: RNA
<213> ORGANISM: Homo sapiens

<400> SEQUENCE: 263
acaaagugcu ucccuuuaga gu 22

<210> SEQ ID NO 264
<211> LENGTH: 24
<212> TYPE: RNA
<213> ORGANISM: Homo sapiens

<400> SEQUENCE: 264
acaaagugcu ucccuuuaga gugu 24

<210> SEQ ID NO 265
<211> LENGTH: 22
<212> TYPE: RNA
<213> ORGANISM: Homo sapiens

<400> SEQUENCE: 265
aagugcuucc uuuuagaggg uu 22

<210> SEQ ID NO 266
<211> LENGTH: 21
<212> TYPE: RNA
<213> ORGANISM: Homo sapiens

<400> SEQUENCE: 266
aaagugcuuc cuuuuugagg g 21

<210> SEQ ID NO 267
<211> LENGTH: 20
<212> TYPE: RNA
<213> ORGANISM: Homo sapiens

<400> SEQUENCE: 267
cuacaaaggg aagcccuuuc 20

<210> SEQ ID NO 268
<211> LENGTH: 22
<212> TYPE: RNA
<213> ORGANISM: Homo sapiens

<400> SEQUENCE: 268
aaagugcuuc ucuuuggugg gu 22

<210> SEQ ID NO 269
<211> LENGTH: 22
<212> TYPE: RNA
<213> ORGANISM: Homo sapiens

<400> SEQUENCE: 269
cucuagaggg aagcacuuuc ug 22

<210> SEQ ID NO 270
<211> LENGTH: 22
<212> TYPE: RNA
<213> ORGANISM: Homo sapiens

<400> SEQUENCE: 270
aaagugcuuc cuuuuagagg gu 22

<210> SEQ ID NO 271
<211> LENGTH: 21
<212> TYPE: RNA
<213> ORGANISM: Homo sapiens

<400> SEQUENCE: 271
aaagugcuuc cuuuuagagg g 21

<210> SEQ ID NO 272
<211> LENGTH: 21
<212> TYPE: RNA
<213> ORGANISM: Homo sapiens

<400> SEQUENCE: 272
cuccagaggg aaguacuuuc u 21

<210> SEQ ID NO 273
<211> LENGTH: 22
<212> TYPE: RNA
<213> ORGANISM: Homo sapiens

<400> SEQUENCE: 273
aaagugcuuc ccuuuggacu gu 22

<210> SEQ ID NO 274
<211> LENGTH: 22
<212> TYPE: RNA
<213> ORGANISM: Homo sapiens

<400> SEQUENCE: 274
uucuccaaaa gggagcacuu uc 22

<210> SEQ ID NO 275
<211> LENGTH: 22
<212> TYPE: RNA
<213> ORGANISM: Homo sapiens

<400> SEQUENCE: 275
aagugccucc uuuuagagug uu 22

<210> SEQ ID NO 276
<211> LENGTH: 22
<212> TYPE: RNA
<213> ORGANISM: Homo sapiens

<400> SEQUENCE: 276
caaagugccu cccuuuagag ug 22

<210> SEQ ID NO 277
<211> LENGTH: 22
<212> TYPE: RNA
<213> ORGANISM: Homo sapiens

<400> SEQUENCE: 277
cucuagaggg aagcgcuuuc ug 22

<210> SEQ ID NO 278
<211> LENGTH: 22
<212> TYPE: RNA
<213> ORGANISM: Homo sapiens

<400> SEQUENCE: 278
aaagugcauc uuuuuagagg au 22

<210> SEQ ID NO 279
<211> LENGTH: 22
<212> TYPE: RNA
<213> ORGANISM: Homo sapiens

<400> SEQUENCE: 279
cucuagaggg aagcgcuuuc ug 22

<210> SEQ ID NO 280
<211> LENGTH: 22
<212> TYPE: RNA
<213> ORGANISM: Homo sapiens

<400> SEQUENCE: 280
aaagugcauc cuuuuagagg uu 22

<210> SEQ ID NO 281
<211> LENGTH: 22
<212> TYPE: RNA
<213> ORGANISM: Homo sapiens

<400> SEQUENCE: 281
cucuagaggg aagcgcuuuc ug 22

<210> SEQ ID NO 282
<211> LENGTH: 22
<212> TYPE: RNA
<213> ORGANISM: Homo sapiens

<400> SEQUENCE: 282
aaagugcauc cuuuuagagu gu 22

<210> SEQ ID NO 283
<211> LENGTH: 22
<212> TYPE: RNA
<213> ORGANISM: Homo sapiens

<400> SEQUENCE: 283
cucuagaggg aagcacuuuc uc 22

<210> SEQ ID NO 284
<211> LENGTH: 21
<212> TYPE: RNA
<213> ORGANISM: Homo sapiens

<400> SEQUENCE: 284
gaaagcgcuu cucuuuagag g 21

<210> SEQ ID NO 285
<211> LENGTH: 22
<212> TYPE: RNA
<213> ORGANISM: Homo sapiens

<400> SEQUENCE: 285
cucuagaggg aagcgcuuuc ug 22

<210> SEQ ID NO 286
<211> LENGTH: 21
<212> TYPE: RNA
<213> ORGANISM: Homo sapiens

<400> SEQUENCE: 286
aaagcgcuuc ccuucagagu g 21

<210> SEQ ID NO 287
<211> LENGTH: 22
<212> TYPE: RNA
<213> ORGANISM: Homo sapiens

<400> SEQUENCE: 287
cucuagaggg aagcacuuuc ug 22

<210> SEQ ID NO 288
<211> LENGTH: 21
<212> TYPE: RNA
<213> ORGANISM: Homo sapiens

<400> SEQUENCE: 288
caaagcgcuu cccuuuggag c 21

<210> SEQ ID NO 289
<211> LENGTH: 23
<212> TYPE: RNA
<213> ORGANISM: Homo sapiens

<400> SEQUENCE: 289
ucucuggagg gaagcacuuu cug 23

<210> SEQ ID NO 290
<211> LENGTH: 23
<212> TYPE: RNA
<213> ORGANISM: Homo sapiens

<400> SEQUENCE: 290
caaagcgcuu cucuuuagag ugu 23

<210> SEQ ID NO 291
<211> LENGTH: 22
<212> TYPE: RNA
<213> ORGANISM: Homo sapiens

<400> SEQUENCE: 291
caaagcgcuc cccuuuagag gu 22

<210> SEQ ID NO 292
<211> LENGTH: 20
<212> TYPE: RNA
<213> ORGANISM: Homo sapiens

<400> SEQUENCE: 292
cugcaaaggg aagcccuuuc 20

<210> SEQ ID NO 293
<211> LENGTH: 22
<212> TYPE: RNA
<213> ORGANISM: Homo sapiens

<400> SEQUENCE: 293
gaaagcgcuu cccuuugcug ga 22

<210> SEQ ID NO 294
<211> LENGTH: 22
<212> TYPE: RNA
<213> ORGANISM: Homo sapiens

<400> SEQUENCE: 294
aucgugcauc cuuuuagagu gu 22

<210> SEQ ID NO 295
<211> LENGTH: 22
<212> TYPE: RNA
<213> ORGANISM: Homo sapiens

<400> SEQUENCE: 295
ucgugcaucc cuuuagagug uu 22

<210> SEQ ID NO 296
<211> LENGTH: 22
<212> TYPE: RNA
<213> ORGANISM: Homo sapiens

<400> SEQUENCE: 296
aucgugcauc ccuuuagagu gu 22

<210> SEQ ID NO 297
<211> LENGTH: 22
<212> TYPE: RNA
<213> ORGANISM: Homo sapiens

<400> SEQUENCE: 297
ccucuagaug gaagcacugu cu 22

<210> SEQ ID NO 298
<211> LENGTH: 18
<212> TYPE: RNA
<213> ORGANISM: Homo sapiens

<400> SEQUENCE: 298
ugcuuccuuu cagagggu 18

<210> SEQ ID NO 299
<211> LENGTH: 22
<212> TYPE: RNA
<213> ORGANISM: Homo sapiens

<400> SEQUENCE: 299
aucuggaggu aagaagcacu uu 22

<210> SEQ ID NO 300
<211> LENGTH: 23
<212> TYPE: RNA
<213> ORGANISM: Homo sapiens

<400> SEQUENCE: 300
uucucgagga aagaagcacu uuc 23

<210> SEQ ID NO 301
<211> LENGTH: 18
<212> TYPE: RNA
<213> ORGANISM: Homo sapiens

<400> SEQUENCE: 301
ugcuuccuuu cagagggu 18

<210> SEQ ID NO 302
<211> LENGTH: 24
<212> TYPE: RNA
<213> ORGANISM: Homo sapiens

<400> SEQUENCE: 302
uucuccaaaa gaaagcacuu ucug 24

<210> SEQ ID NO 303
<211> LENGTH: 22
<212> TYPE: RNA
<213> ORGANISM: Homo sapiens

<400> SEQUENCE: 303
gagugccuuc uuuuggagcg uu 22

<210> SEQ ID NO 304
<211> LENGTH: 21
<212> TYPE: RNA
<213> ORGANISM: Homo sapiens

<400> SEQUENCE: 304
auugacacuu cugugaguag a 21

<210> SEQ ID NO 305
<211> LENGTH: 22
<212> TYPE: RNA
<213> ORGANISM: Homo sapiens

<400> SEQUENCE: 305
uucucaagga ggugucguuu au 22

<210> SEQ ID NO 306
<211> LENGTH: 22
<212> TYPE: RNA
<213> ORGANISM: Homo sapiens

<400> SEQUENCE: 306
uucacaagga ggugucauuu au 22

<210> SEQ ID NO 307
<211> LENGTH: 18
<212> TYPE: RNA
<213> ORGANISM: Homo sapiens

<400> SEQUENCE: 307
uucacaggga ggugucau 18

<210> SEQ ID NO 308
<211> LENGTH: 23
<212> TYPE: RNA
<213> ORGANISM: Homo sapiens

<400> SEQUENCE: 308
uaaauuucac cuuucugaga agg 23

<210> SEQ ID NO 309
<211> LENGTH: 23
<212> TYPE: RNA
<213> ORGANISM: Homo sapiens

<400> SEQUENCE: 309
cacucagccu ugagggcacu uuc 23

<210> SEQ ID NO 310
<211> LENGTH: 22
<212> TYPE: RNA
<213> ORGANISM: Homo sapiens

<400> SEQUENCE: 310
aagugcuguc auagcugagg uc 22

<210> SEQ ID NO 311
<211> LENGTH: 21
<212> TYPE: RNA
<213> ORGANISM: Homo sapiens

<400> SEQUENCE: 311
gugucuuuug cucugcaguc a 21

<210> SEQ ID NO 312
<211> LENGTH: 22
<212> TYPE: RNA
<213> ORGANISM: Homo sapiens

<400> SEQUENCE: 312
uacucaggag aguggcaauc ac 22

<210> SEQ ID NO 313
<211> LENGTH: 21
<212> TYPE: RNA
<213> ORGANISM: Homo sapiens

<400> SEQUENCE: 313
uacugcagac aguggcaauc a 21

<210> SEQ ID NO 314
<211> LENGTH: 22
<212> TYPE: RNA

<213> ORGANISM: Homo sapiens

<400> SEQUENCE: 314
ugauugguac gucugugggu ag 22

<210> SEQ ID NO 315
<211> LENGTH: 22
<212> TYPE: RNA
<213> ORGANISM: Homo sapiens

<400> SEQUENCE: 315
uacugcagac guggcaauca ug 22

<210> SEQ ID NO 316
<211> LENGTH: 23
<212> TYPE: RNA
<213> ORGANISM: Homo sapiens

<400> SEQUENCE: 316
uacuccagag ggcgucacuc aug 23

<210> SEQ ID NO 317
<211> LENGTH: 23
<212> TYPE: RNA
<213> ORGANISM: Homo sapiens

<400> SEQUENCE: 317
ugauuguagc cuuuuggagu aga 23

<210> SEQ ID NO 318
<211> LENGTH: 21
<212> TYPE: RNA
<213> ORGANISM: Homo sapiens

<400> SEQUENCE: 318
uuuugcaccu uuuggaguga a 21

<210> SEQ ID NO 319
<211> LENGTH: 21
<212> TYPE: RNA
<213> ORGANISM: Homo sapiens

<400> SEQUENCE: 319
uaaggcaccc uucugaguag a 21

<210> SEQ ID NO 320
<211> LENGTH: 22
<212> TYPE: RNA
<213> ORGANISM: Homo sapiens

<400> SEQUENCE: 320
gggagccagg aaguauugau gu 22

<210> SEQ ID NO 321
<211> LENGTH: 22
<212> TYPE: RNA
<213> ORGANISM: Homo sapiens

<400> SEQUENCE: 321
cgucaacacu ugcugguuuc cu 22

<210> SEQ ID NO 322
<211> LENGTH: 22

<212> TYPE: RNA
<213> ORGANISM: Homo sapiens

<400> SEQUENCE: 322
agacccuggu cugcacucua uc 22

<210> SEQ ID NO 323
<211> LENGTH: 23
<212> TYPE: RNA
<213> ORGANISM: Homo sapiens

<400> SEQUENCE: 323
uagcagcggg aacaguucug cag 23

<210> SEQ ID NO 324
<211> LENGTH: 21
<212> TYPE: RNA
<213> ORGANISM: Homo sapiens

<400> SEQUENCE: 324
auccuugcua ucugggugcu a 21

<210> SEQ ID NO 325
<211> LENGTH: 22
<212> TYPE: RNA
<213> ORGANISM: Homo sapiens

<400> SEQUENCE: 325
aaugcaccug ggcaaggauu ca 22

<210> SEQ ID NO 326
<211> LENGTH: 22
<212> TYPE: RNA
<213> ORGANISM: Homo sapiens

<400> SEQUENCE: 326
aauccuuugu cccugggguga ga 22

<210> SEQ ID NO 327
<211> LENGTH: 22
<212> TYPE: RNA
<213> ORGANISM: Homo sapiens

<400> SEQUENCE: 327
aaugcacccg ggcaaggauu cu 22

<210> SEQ ID NO 328
<211> LENGTH: 22
<212> TYPE: RNA
<213> ORGANISM: Homo sapiens

<400> SEQUENCE: 328
augcaccugg gcaaggauuc ug 22

<210> SEQ ID NO 329
<211> LENGTH: 23
<212> TYPE: RNA
<213> ORGANISM: Homo sapiens

<400> SEQUENCE: 329
uaauccuugc uaccugggug aga 23

<210> SEQ ID NO 330

<211> LENGTH: 21
<212> TYPE: RNA
<213> ORGANISM: Homo sapiens

<400> SEQUENCE: 330
uuaagacuug cagugauguu u 21

<210> SEQ ID NO 331
<211> LENGTH: 22
<212> TYPE: RNA
<213> ORGANISM: Homo sapiens

<400> SEQUENCE: 331
aacaucacag caagucugug cu 22

<210> SEQ ID NO 332
<211> LENGTH: 23
<212> TYPE: RNA
<213> ORGANISM: Homo sapiens

<400> SEQUENCE: 332
uuucaagcca gggggcguuu uuc 23

<210> SEQ ID NO 333
<211> LENGTH: 22
<212> TYPE: RNA
<213> ORGANISM: Homo sapiens

<400> SEQUENCE: 333
caaaccacac ugugguguua ga 22

<210> SEQ ID NO 334
<211> LENGTH: 21
<212> TYPE: RNA
<213> ORGANISM: Homo sapiens

<400> SEQUENCE: 334
cagcagcaca cugugguuug u 21

<210> SEQ ID NO 335
<211> LENGTH: 22
<212> TYPE: RNA
<213> ORGANISM: Homo sapiens

<400> SEQUENCE: 335
ugaguauuac auggccaauc uc 22

<210> SEQ ID NO 336
<211> LENGTH: 22
<212> TYPE: RNA
<213> ORGANISM: Homo sapiens

<400> SEQUENCE: 336
aaacaaacau ggugcacuuc uu 22

<210> SEQ ID NO 337
<211> LENGTH: 22
<212> TYPE: RNA
<213> ORGANISM: Homo sapiens

<400> SEQUENCE: 337
ugaaacauac acgggaaacc uc 22

<210> SEQ ID NO 338
<211> LENGTH: 22
<212> TYPE: RNA
<213> ORGANISM: Homo sapiens

<400> SEQUENCE: 338
uuguacaugg uaggcuuuca uu 22

<210> SEQ ID NO 339
<211> LENGTH: 22
<212> TYPE: RNA
<213> ORGANISM: Homo sapiens

<400> SEQUENCE: 339
ugaaggucua cugugugcca gg 22

<210> SEQ ID NO 340
<211> LENGTH: 23
<212> TYPE: RNA
<213> ORGANISM: Homo sapiens

<400> SEQUENCE: 340
aggaccugcg ggacaagauu cuu 23

<210> SEQ ID NO 341
<211> LENGTH: 22
<212> TYPE: RNA
<213> ORGANISM: Homo sapiens

<400> SEQUENCE: 341
aguggggaac ccuuccauga gg 22

<210> SEQ ID NO 342
<211> LENGTH: 22
<212> TYPE: RNA
<213> ORGANISM: Homo sapiens

<400> SEQUENCE: 342
cuuaugcaag auucccuucu ac 22

<210> SEQ ID NO 343
<211> LENGTH: 20
<212> TYPE: RNA
<213> ORGANISM: Homo sapiens

<400> SEQUENCE: 343
ccauggaucu ccaggugggu 20

<210> SEQ ID NO 344
<211> LENGTH: 22
<212> TYPE: RNA
<213> ORGANISM: Homo sapiens

<400> SEQUENCE: 344
caaccuggag gacuccaugc ug 22

<210> SEQ ID NO 345
<211> LENGTH: 22
<212> TYPE: RNA
<213> ORGANISM: Homo sapiens

<400> SEQUENCE: 345
gugacaucac auauacggca gc 22

<210> SEQ ID NO 346
<211> LENGTH: 21
<212> TYPE: RNA
<213> ORGANISM: Homo sapiens

<400> SEQUENCE: 346
cccagauaau ggcacucuca a 21

<210> SEQ ID NO 347
<211> LENGTH: 21
<212> TYPE: RNA
<213> ORGANISM: Homo sapiens

<400> SEQUENCE: 347
uugaaaggcu auuucuuggu c 21

<210> SEQ ID NO 348
<211> LENGTH: 22
<212> TYPE: RNA
<213> ORGANISM: Homo sapiens

<400> SEQUENCE: 348
aaucguacag ggucauccac uu 22

<210> SEQ ID NO 349
<211> LENGTH: 22
<212> TYPE: RNA
<213> ORGANISM: Homo sapiens

<400> SEQUENCE: 349
aaucauacag ggacauccag uu 22

<210> SEQ ID NO 350
<211> LENGTH: 22
<212> TYPE: RNA
<213> ORGANISM: Homo sapiens

<400> SEQUENCE: 350
uccuguacug agcugccccg ag 22

<210> SEQ ID NO 351
<211> LENGTH: 21
<212> TYPE: RNA
<213> ORGANISM: Homo sapiens

<400> SEQUENCE: 351
cggggcagcu caguacagga u 21

<210> SEQ ID NO 352
<211> LENGTH: 22
<212> TYPE: RNA
<213> ORGANISM: Homo sapiens

<400> SEQUENCE: 352
agaggcuggc cgugaugaau uc 22

<210> SEQ ID NO 353
<211> LENGTH: 22
<212> TYPE: RNA
<213> ORGANISM: Homo sapiens

<400> SEQUENCE: 353
gucauacacg gcucuccucu cu 22

<210> SEQ ID NO 354
<211> LENGTH: 22
<212> TYPE: RNA
<213> ORGANISM: Homo sapiens

<400> SEQUENCE: 354
ucaggcucag uccccucccg au 22

<210> SEQ ID NO 355
<211> LENGTH: 22
<212> TYPE: RNA
<213> ORGANISM: Homo sapiens

<400> SEQUENCE: 355
aagacgggag gaaagaaggg ag 22

<210> SEQ ID NO 356
<211> LENGTH: 21
<212> TYPE: RNA
<213> ORGANISM: Homo sapiens

<400> SEQUENCE: 356
ucacuccucu ccucccgucu u 21

<210> SEQ ID NO 357
<211> LENGTH: 22
<212> TYPE: RNA
<213> ORGANISM: Homo sapiens

<400> SEQUENCE: 357
uaugugccuu uggacuacau cg 22

<210> SEQ ID NO 358
<211> LENGTH: 21
<212> TYPE: RNA
<213> ORGANISM: Homo sapiens

<400> SEQUENCE: 358
gcaguccaug ggcauauaca c 21

<210> SEQ ID NO 359
<211> LENGTH: 22
<212> TYPE: RNA
<213> ORGANISM: Homo sapiens

<400> SEQUENCE: 359
acccuaucaa uauugucucu gc 22

<210> SEQ ID NO 360
<211> LENGTH: 23
<212> TYPE: RNA
<213> ORGANISM: Homo sapiens

<400> SEQUENCE: 360
uagugcaaua uugcuuauag ggu 23

<210> SEQ ID NO 361
<211> LENGTH: 23
<212> TYPE: RNA
<213> ORGANISM: Homo sapiens

<400> SEQUENCE: 361

-continued agguuguccg uggugaguuc gca 23

<210> SEQ ID NO 362
<211> LENGTH: 22
<212> TYPE: RNA
<213> ORGANISM: Homo sapiens

<400> SEQUENCE: 362
cucaucugca aagaaguaag ug 22

<210> SEQ ID NO 363
<211> LENGTH: 22
<212> TYPE: RNA
<213> ORGANISM: Homo sapiens

<400> SEQUENCE: 363
aacuguuugc agaggaaacu ga 22

<210> SEQ ID NO 364
<211> LENGTH: 22
<212> TYPE: RNA
<213> ORGANISM: Homo sapiens

<400> SEQUENCE: 364
aaaccguuac cauuacugag uu 22

<210> SEQ ID NO 365
<211> LENGTH: 22
<212> TYPE: RNA
<213> ORGANISM: Homo sapiens

<400> SEQUENCE: 365
uuuugcaaua uguuccugaa ua 22

<210> SEQ ID NO 366
<211> LENGTH: 22
<212> TYPE: RNA
<213> ORGANISM: Homo sapiens

<400> SEQUENCE: 366
uugggaucau uuugcaucca ua 22

<210> SEQ ID NO 367
<211> LENGTH: 22
<212> TYPE: RNA
<213> ORGANISM: Homo sapiens

<400> SEQUENCE: 367
uuuugcgaug uguuccuaau au 22

<210> SEQ ID NO 368
<211> LENGTH: 23
<212> TYPE: RNA
<213> ORGANISM: Homo sapiens

<400> SEQUENCE: 368
uugcuaguug cacuccucuc ugu 23

<210> SEQ ID NO 369
<211> LENGTH: 25
<212> TYPE: RNA
<213> ORGANISM: Homo sapiens

<400> SEQUENCE: 369

-continued uaggcagugu auugcuagcg gcugu                                          25

<210> SEQ ID NO 370
<211> LENGTH: 22
<212> TYPE: RNA
<213> ORGANISM: Homo sapiens

<400> SEQUENCE: 370
cagccacaac uacccugcca cu                                             22

<210> SEQ ID NO 371
<211> LENGTH: 22
<212> TYPE: RNA
<213> ORGANISM: Homo sapiens

<400> SEQUENCE: 371
aggcagugua uuguuagcug gc                                             22

<210> SEQ ID NO 372
<211> LENGTH: 22
<212> TYPE: RNA
<213> ORGANISM: Homo sapiens

<400> SEQUENCE: 372
uggcagugua uuguuagcug gu                                             22

<210> SEQ ID NO 373
<211> LENGTH: 22
<212> TYPE: RNA
<213> ORGANISM: Homo sapiens

<400> SEQUENCE: 373
uugcauaugu aggauguccc au                                             22

<210> SEQ ID NO 374
<211> LENGTH: 22
<212> TYPE: RNA
<213> ORGANISM: Homo sapiens

<400> SEQUENCE: 374
aucaugaugg gcuccucggu gu                                             22

<210> SEQ ID NO 375
<211> LENGTH: 21
<212> TYPE: RNA
<213> ORGANISM: Homo sapiens

<400> SEQUENCE: 375
cuggauggcu ccuccauguc u                                              21

<210> SEQ ID NO 376
<211> LENGTH: 23
<212> TYPE: RNA
<213> ORGANISM: Homo sapiens

<400> SEQUENCE: 376
ucuuggagua ggucauuggg ugg                                            23

<210> SEQ ID NO 377
<211> LENGTH: 22
<212> TYPE: RNA
<213> ORGANISM: Homo sapiens

<400> SEQUENCE: 377
caggucgucu ugcagggcuu cu 22

<210> SEQ ID NO 378
<211> LENGTH: 21
<212> TYPE: RNA
<213> ORGANISM: Homo sapiens

<400> SEQUENCE: 378
ugucuugcag gccgucaugc a 21

<210> SEQ ID NO 379
<211> LENGTH: 22
<212> TYPE: RNA
<213> ORGANISM: Homo sapiens

<400> SEQUENCE: 379
uaauacuguc ugguaaaacc gu 22

<210> SEQ ID NO 380
<211> LENGTH: 22
<212> TYPE: RNA
<213> ORGANISM: Homo sapiens

<400> SEQUENCE: 380
aucgggaaug ucguguccgc cc 22

<210> SEQ ID NO 381
<211> LENGTH: 23
<212> TYPE: RNA
<213> ORGANISM: Homo sapiens

<400> SEQUENCE: 381
aaugacacga ucacucccgu uga 23

<210> SEQ ID NO 382
<211> LENGTH: 21
<212> TYPE: RNA
<213> ORGANISM: Homo sapiens

<400> SEQUENCE: 382
caaaacguga ggcgcugcua u 21

<210> SEQ ID NO 383
<211> LENGTH: 22
<212> TYPE: RNA
<213> ORGANISM: Homo sapiens

<400> SEQUENCE: 383
cagcagcaau ucauguuuug aa 22

<210> SEQ ID NO 384
<211> LENGTH: 23
<212> TYPE: RNA
<213> ORGANISM: Homo sapiens

<400> SEQUENCE: 384
ugaggggcag agagcgagac uuu 23

<210> SEQ ID NO 385
<211> LENGTH: 23
<212> TYPE: RNA
<213> ORGANISM: Homo sapiens

<400> SEQUENCE: 385
agcucggucu gaggccccuc agu 23

<210> SEQ ID NO 386
<211> LENGTH: 22
<212> TYPE: RNA
<213> ORGANISM: Homo sapiens

<400> SEQUENCE: 386
acuggacuua gggucagaag gc 22

<210> SEQ ID NO 387
<211> LENGTH: 23
<212> TYPE: RNA
<213> ORGANISM: Homo sapiens

<400> SEQUENCE: 387
aucaacagac auuaauuggg cgc 23

<210> SEQ ID NO 388
<211> LENGTH: 23
<212> TYPE: RNA
<213> ORGANISM: Homo sapiens

<400> SEQUENCE: 388
acuucaccug guccacuagc cgu 23

<210> SEQ ID NO 389
<211> LENGTH: 22
<212> TYPE: RNA
<213> ORGANISM: Homo sapiens

<400> SEQUENCE: 389
uauguaacac gguccacuaa cc 22

<210> SEQ ID NO 390
<211> LENGTH: 21
<212> TYPE: RNA
<213> ORGANISM: Homo sapiens

<400> SEQUENCE: 390
uaguagaccg uauagcguac g 21

<210> SEQ ID NO 391
<211> LENGTH: 21
<212> TYPE: RNA
<213> ORGANISM: Homo sapiens

<400> SEQUENCE: 391
aauauaacac agauggccug u 21

<210> SEQ ID NO 392
<211> LENGTH: 23
<212> TYPE: RNA
<213> ORGANISM: Homo sapiens

<400> SEQUENCE: 392
agguuacccg agcaacuuug cau 23

<210> SEQ ID NO 393
<211> LENGTH: 22
<212> TYPE: RNA

<213> ORGANISM: Homo sapiens

<400> SEQUENCE: 393
gaauguugcu cggugaaccc cu 22

<210> SEQ ID NO 394
<211> LENGTH: 20
<212> TYPE: RNA
<213> ORGANISM: Homo sapiens

<400> SEQUENCE: 394
auuccuagaa auuguucaua 20

<210> SEQ ID NO 395
<211> LENGTH: 22
<212> TYPE: RNA
<213> ORGANISM: Homo sapiens

<400> SEQUENCE: 395
agaucagaag gugauugugg cu 22

<210> SEQ ID NO 396
<211> LENGTH: 22
<212> TYPE: RNA
<213> ORGANISM: Homo sapiens

<400> SEQUENCE: 396
gaaguuguuc gugguggauu cg 22

<210> SEQ ID NO 397
<211> LENGTH: 22
<212> TYPE: RNA
<213> ORGANISM: Homo sapiens

<400> SEQUENCE: 397
uauacaaggg caagcucucu gu 22

<210> SEQ ID NO 398
<211> LENGTH: 22
<212> TYPE: RNA
<213> ORGANISM: Homo sapiens

<400> SEQUENCE: 398
ugguugacca uagaacaugc gc 22

<210> SEQ ID NO 399
<211> LENGTH: 22
<212> TYPE: RNA
<213> ORGANISM: Homo sapiens

<400> SEQUENCE: 399
uauguaauau gguccacauc uu 22

<210> SEQ ID NO 400
<211> LENGTH: 22
<212> TYPE: RNA
<213> ORGANISM: Homo sapiens

<400> SEQUENCE: 400
uauguaacau gguccacuaa cu 22

<210> SEQ ID NO 401
<211> LENGTH: 21

<212> TYPE: RNA
<213> ORGANISM: Homo sapiens

<400> SEQUENCE: 401
ugguagacua uggaacguag g 21

<210> SEQ ID NO 402
<211> LENGTH: 22
<212> TYPE: RNA
<213> ORGANISM: Homo sapiens

<400> SEQUENCE: 402
cuccugacuc cagguccugu gu 22

<210> SEQ ID NO 403
<211> LENGTH: 21
<212> TYPE: RNA
<213> ORGANISM: Homo sapiens

<400> SEQUENCE: 403
acuggacuug gagucagaag g 21

<210> SEQ ID NO 404
<211> LENGTH: 22
<212> TYPE: RNA
<213> ORGANISM: Homo sapiens

<400> SEQUENCE: 404
agagguugcc cuuggugaau uc 22

<210> SEQ ID NO 405
<211> LENGTH: 22
<212> TYPE: RNA
<213> ORGANISM: Homo sapiens

<400> SEQUENCE: 405
aucacacaaa ggcaacuuuu gu 22

<210> SEQ ID NO 406
<211> LENGTH: 21
<212> TYPE: RNA
<213> ORGANISM: Homo sapiens

<400> SEQUENCE: 406
aacauagagg aaauuccacg u 21

<210> SEQ ID NO 407
<211> LENGTH: 22
<212> TYPE: RNA
<213> ORGANISM: Homo sapiens

<400> SEQUENCE: 407
aucauagagg aaaauccaug uu 22

<210> SEQ ID NO 408
<211> LENGTH: 22
<212> TYPE: RNA
<213> ORGANISM: Homo sapiens

<400> SEQUENCE: 408
guagauucuc cuucuaugag ua 22

<210> SEQ ID NO 409

<211> LENGTH: 21
<212> TYPE: RNA
<213> ORGANISM: Homo sapiens

<400> SEQUENCE: 409
aucauagagg aaaauccacg u 21

<210> SEQ ID NO 410
<211> LENGTH: 22
<212> TYPE: RNA
<213> ORGANISM: Homo sapiens

<400> SEQUENCE: 410
uuuguucguu cggcucgcgu ga 22

<210> SEQ ID NO 411
<211> LENGTH: 22
<212> TYPE: RNA
<213> ORGANISM: Homo sapiens

<400> SEQUENCE: 411
cuuagcaggu uguauuauca uu 22

<210> SEQ ID NO 412
<211> LENGTH: 22
<212> TYPE: RNA
<213> ORGANISM: Homo sapiens

<400> SEQUENCE: 412
auauaauaca accugcuaag ug 22

<210> SEQ ID NO 413
<211> LENGTH: 22
<212> TYPE: RNA
<213> ORGANISM: Homo sapiens

<400> SEQUENCE: 413
cuuaucagau uguauuguaa uu 22

<210> SEQ ID NO 414
<211> LENGTH: 22
<212> TYPE: RNA
<213> ORGANISM: Homo sapiens

<400> SEQUENCE: 414
uuauaauaca accugauaag ug 22

<210> SEQ ID NO 415
<211> LENGTH: 22
<212> TYPE: RNA
<213> ORGANISM: Homo sapiens

<400> SEQUENCE: 415
acucaaaaug ggggcgcuuu cc 22

<210> SEQ ID NO 416
<211> LENGTH: 23
<212> TYPE: RNA
<213> ORGANISM: Homo sapiens

<400> SEQUENCE: 416
gaagugcuuc gauuuugggg ugu 23

<210> SEQ ID NO 417
<211> LENGTH: 23
<212> TYPE: RNA
<213> ORGANISM: Homo sapiens

<400> SEQUENCE: 417
aaagugcugc gacauuugag cgu 23

<210> SEQ ID NO 418
<211> LENGTH: 20
<212> TYPE: RNA
<213> ORGANISM: Homo sapiens

<400> SEQUENCE: 418
acucaaacug ugggggcacu 20

<210> SEQ ID NO 419
<211> LENGTH: 23
<212> TYPE: RNA
<213> ORGANISM: Homo sapiens

<400> SEQUENCE: 419
aagugccgcc aucuuuugag ugu 23

<210> SEQ ID NO 420
<211> LENGTH: 22
<212> TYPE: RNA
<213> ORGANISM: Homo sapiens

<400> SEQUENCE: 420
gccugcuggg guggaaccug gu 22

<210> SEQ ID NO 421
<211> LENGTH: 22
<212> TYPE: RNA
<213> ORGANISM: Homo sapiens

<400> SEQUENCE: 421
agaucgaccg uguuauauuc gc 22

<210> SEQ ID NO 422
<211> LENGTH: 21
<212> TYPE: RNA
<213> ORGANISM: Homo sapiens

<400> SEQUENCE: 422
aauaauacau gguugaucuu u 21

<210> SEQ ID NO 423
<211> LENGTH: 22
<212> TYPE: RNA
<213> ORGANISM: Homo sapiens

<400> SEQUENCE: 423
acuguugcua auaugcaacu cu 22

<210> SEQ ID NO 424
<211> LENGTH: 22
<212> TYPE: RNA
<213> ORGANISM: Homo sapiens

<400> SEQUENCE: 424
aauugcacuu uagcaauggu ga 22

<210> SEQ ID NO 425
<211> LENGTH: 22
<212> TYPE: RNA
<213> ORGANISM: Homo sapiens

<400> SEQUENCE: 425
agggacuuuc aggggcagcu gu 22

<210> SEQ ID NO 426
<211> LENGTH: 22
<212> TYPE: RNA
<213> ORGANISM: Homo sapiens

<400> SEQUENCE: 426
uaaugccccu aaaaauccuu au 22

<210> SEQ ID NO 427
<211> LENGTH: 22
<212> TYPE: RNA
<213> ORGANISM: Homo sapiens

<400> SEQUENCE: 427
cggguggauc acgaugcaau uu 22

<210> SEQ ID NO 428
<211> LENGTH: 22
<212> TYPE: RNA
<213> ORGANISM: Homo sapiens

<400> SEQUENCE: 428
aauugcacgg uauccaucug ua 22

<210> SEQ ID NO 429
<211> LENGTH: 24
<212> TYPE: RNA
<213> ORGANISM: Homo sapiens

<400> SEQUENCE: 429
aauccuugga accuaggugu gagu 24

<210> SEQ ID NO 430
<211> LENGTH: 22
<212> TYPE: RNA
<213> ORGANISM: Homo sapiens

<400> SEQUENCE: 430
aacacaccua uucaaggauu ca 22

<210> SEQ ID NO 431
<211> LENGTH: 22
<212> TYPE: RNA
<213> ORGANISM: Homo sapiens

<400> SEQUENCE: 431
uuaucagaau cuccaggggu ac 22

<210> SEQ ID NO 432
<211> LENGTH: 23
<212> TYPE: RNA
<213> ORGANISM: Homo sapiens

<400> SEQUENCE: 432
ucccccaggu gugauucuga uuu 23

<210> SEQ ID NO 433
<211> LENGTH: 23
<212> TYPE: RNA
<213> ORGANISM: Homo sapiens

<400> SEQUENCE: 433
aggcagugua guuagcugau ugc 23

<210> SEQ ID NO 434
<211> LENGTH: 22
<212> TYPE: RNA
<213> ORGANISM: Homo sapiens

<400> SEQUENCE: 434
aaucacuaac cacacggcca gg 22

<210> SEQ ID NO 435
<211> LENGTH: 23
<212> TYPE: RNA
<213> ORGANISM: Homo sapiens

<400> SEQUENCE: 435
uaggcagugu cauuagcuga uug 23

<210> SEQ ID NO 436
<211> LENGTH: 22
<212> TYPE: RNA
<213> ORGANISM: Homo sapiens

<400> SEQUENCE: 436
caaucacuaa cuccacugcc au 22

<210> SEQ ID NO 437
<211> LENGTH: 22
<212> TYPE: RNA
<213> ORGANISM: Homo sapiens

<400> SEQUENCE: 437
caaucagcaa guauacugcc cu 22

<210> SEQ ID NO 438
<211> LENGTH: 22
<212> TYPE: RNA
<213> ORGANISM: Homo sapiens

<400> SEQUENCE: 438
uggcaguguc uuagcugguu gu 22

<210> SEQ ID NO 439
<211> LENGTH: 23
<212> TYPE: RNA
<213> ORGANISM: Homo sapiens

<400> SEQUENCE: 439
ugucugcccg caugccugcc ucu 23

<210> SEQ ID NO 440
<211> LENGTH: 22
<212> TYPE: RNA
<213> ORGANISM: Homo sapiens

<400> SEQUENCE: 440
gcugacuccu aguccagggc uc 22

<210> SEQ ID NO 441
<211> LENGTH: 21
<212> TYPE: RNA
<213> ORGANISM: Homo sapiens

<400> SEQUENCE: 441
aggggugcua ucugugauug a 21

<210> SEQ ID NO 442
<211> LENGTH: 23
<212> TYPE: RNA
<213> ORGANISM: Homo sapiens

<400> SEQUENCE: 442
ucucacacag aaaucgcacc cgu 23

<210> SEQ ID NO 443
<211> LENGTH: 22
<212> TYPE: RNA
<213> ORGANISM: Homo sapiens

<400> SEQUENCE: 443
uccgucucag uuacuuuaua gc 22

<210> SEQ ID NO 444
<211> LENGTH: 22
<212> TYPE: RNA
<213> ORGANISM: Homo sapiens

<400> SEQUENCE: 444
uuauaaagca augagacuga uu 22

<210> SEQ ID NO 445
<211> LENGTH: 22
<212> TYPE: RNA
<213> ORGANISM: Homo sapiens

<400> SEQUENCE: 445
cagugccucg gcagugcagc cc 22

<210> SEQ ID NO 446
<211> LENGTH: 20
<212> TYPE: RNA
<213> ORGANISM: Homo sapiens

<400> SEQUENCE: 446
gugcauugcu guugcauugc 20

<210> SEQ ID NO 447
<211> LENGTH: 22
<212> TYPE: RNA
<213> ORGANISM: Homo sapiens

<400> SEQUENCE: 447
caauguuucc acagugcauc ac 22

<210> SEQ ID NO 448
<211> LENGTH: 21
<212> TYPE: RNA
<213> ORGANISM: Homo sapiens

<400> SEQUENCE: 448
gugcauugua guugcauugc a 21

<210> SEQ ID NO 449
<211> LENGTH: 23
<212> TYPE: RNA
<213> ORGANISM: Homo sapiens

<400> SEQUENCE: 449
ucccuguccu ccaggagcuc acg 23

<210> SEQ ID NO 450
<211> LENGTH: 23
<212> TYPE: RNA
<213> ORGANISM: Homo sapiens

<400> SEQUENCE: 450
ugagcgccuc gacgacagag ccg 23

<210> SEQ ID NO 451
<211> LENGTH: 22
<212> TYPE: RNA
<213> ORGANISM: Homo sapiens

<400> SEQUENCE: 451
aacaauaucc uggugcugag ug 22

<210> SEQ ID NO 452
<211> LENGTH: 22
<212> TYPE: RNA
<213> ORGANISM: Homo sapiens

<400> SEQUENCE: 452
uccagcauca gugauuuugu ug 22

<210> SEQ ID NO 453
<211> LENGTH: 21
<212> TYPE: RNA
<213> ORGANISM: Homo sapiens

<400> SEQUENCE: 453
gaacggcuuc auacaggagu u 21

<210> SEQ ID NO 454
<211> LENGTH: 22
<212> TYPE: RNA
<213> ORGANISM: Homo sapiens

<400> SEQUENCE: 454
cuccuauaug augccuuucu uc 22

<210> SEQ ID NO 455
<211> LENGTH: 22
<212> TYPE: RNA
<213> ORGANISM: Homo sapiens

<400> SEQUENCE: 455
uuuuucauua uugcuccuga cc 22

<210> SEQ ID NO 456
<211> LENGTH: 23
<212> TYPE: RNA
<213> ORGANISM: Homo sapiens

<400> SEQUENCE: 456
ucaagagcaa uaacgaaaaa ugu 23

<210> SEQ ID NO 457
<211> LENGTH: 22
<212> TYPE: RNA
<213> ORGANISM: Homo sapiens

<400> SEQUENCE: 457
cuagguaugg ucccagggau cc 22

<210> SEQ ID NO 458
<211> LENGTH: 21
<212> TYPE: RNA
<213> ORGANISM: Homo sapiens

<400> SEQUENCE: 458
gccccugggc cuauccuaga a 21

<210> SEQ ID NO 459
<211> LENGTH: 22
<212> TYPE: RNA
<213> ORGANISM: Homo sapiens

<400> SEQUENCE: 459
ucucugggcc ugugucuuag gc 22

<210> SEQ ID NO 460
<211> LENGTH: 23
<212> TYPE: RNA
<213> ORGANISM: Homo sapiens

<400> SEQUENCE: 460
gcaaagcaca cggccugcag aga 23

<210> SEQ ID NO 461
<211> LENGTH: 22
<212> TYPE: RNA
<213> ORGANISM: Homo sapiens

<400> SEQUENCE: 461
aacacaccug guuaaccucu uu 22

<210> SEQ ID NO 462
<211> LENGTH: 22
<212> TYPE: RNA
<213> ORGANISM: Homo sapiens

<400> SEQUENCE: 462
cuggcccucu cugcccuucc gu 22

<210> SEQ ID NO 463
<211> LENGTH: 20
<212> TYPE: RNA
<213> ORGANISM: Homo sapiens

<400> SEQUENCE: 463
ccucugggcc cuuccuccag 20

<210> SEQ ID NO 464
<211> LENGTH: 23
<212> TYPE: RNA
<213> ORGANISM: Homo sapiens

<400> SEQUENCE: 464
ccuaguaggu guccaguaag ugu 23

<210> SEQ ID NO 465
<211> LENGTH: 23
<212> TYPE: RNA
<213> ORGANISM: Homo sapiens

<400> SEQUENCE: 465 cgcaucccu agggcauugg ugu 23

<210> SEQ ID NO 466
<211> LENGTH: 20
<212> TYPE: RNA
<213> ORGANISM: Homo sapiens

<400> SEQUENCE: 466
acugccccag gugcugcugg 20

<210> SEQ ID NO 467
<211> LENGTH: 22
<212> TYPE: RNA
<213> ORGANISM: Homo sapiens

<400> SEQUENCE: 467
aggugguccg uggcgcguuc gc 22

<210> SEQ ID NO 468
<211> LENGTH: 21
<212> TYPE: RNA
<213> ORGANISM: Homo sapiens

<400> SEQUENCE: 468
cacauuacac ggucgaccuc u 21

<210> SEQ ID NO 469
<211> LENGTH: 19
<212> TYPE: RNA
<213> ORGANISM: Homo sapiens

<400> SEQUENCE: 469
aaaagcuggg uugagagga 19

<210> SEQ ID NO 470
<211> LENGTH: 20
<212> TYPE: RNA
<213> ORGANISM: Homo sapiens

<400> SEQUENCE: 470
aaaagcuggg uugagagggu 20

<210> SEQ ID NO 471
<211> LENGTH: 22
<212> TYPE: RNA
<213> ORGANISM: Homo sapiens

<400> SEQUENCE: 471
aaaagcuggg uugagagggc aa 22

<210> SEQ ID NO 472
<211> LENGTH: 22
<212> TYPE: RNA

<213> ORGANISM: Homo sapiens

<400> SEQUENCE: 472
aaaagcuggg uugagagggc ga 22

<210> SEQ ID NO 473
<211> LENGTH: 22
<212> TYPE: RNA
<213> ORGANISM: Homo sapiens

<400> SEQUENCE: 473
caauuuagug ugugugauau uu 22

<210> SEQ ID NO 474
<211> LENGTH: 22
<212> TYPE: RNA
<213> ORGANISM: Homo sapiens

<400> SEQUENCE: 474
uauugcacau uacuaaguug ca 22

<210> SEQ ID NO 475
<211> LENGTH: 22
<212> TYPE: RNA
<213> ORGANISM: Homo sapiens

<400> SEQUENCE: 475
ugcuaugcca acauauugcc au 22

<210> SEQ ID NO 476
<211> LENGTH: 21
<212> TYPE: RNA
<213> ORGANISM: Homo sapiens

<400> SEQUENCE: 476
aggcaagaug cuggcauagc u 21

<210> SEQ ID NO 477
<211> LENGTH: 22
<212> TYPE: RNA
<213> ORGANISM: Homo sapiens

<400> SEQUENCE: 477
cuuucagucg gauguuuaca gc 22

<210> SEQ ID NO 478
<211> LENGTH: 22
<212> TYPE: RNA
<213> ORGANISM: Homo sapiens

<400> SEQUENCE: 478
uguaaacauc cuugacugga ag 22

<210> SEQ ID NO 479
<211> LENGTH: 22
<212> TYPE: RNA
<213> ORGANISM: Homo sapiens

<400> SEQUENCE: 479
cuuucaguca gauguuugcu gc 22

<210> SEQ ID NO 480
<211> LENGTH: 22

<212> TYPE: RNA
<213> ORGANISM: Homo sapiens

<400> SEQUENCE: 480
uguaaacauc cccgacugga ag 22

<210> SEQ ID NO 481
<211> LENGTH: 22
<212> TYPE: RNA
<213> ORGANISM: Homo sapiens

<400> SEQUENCE: 481
cugggagaag gcuguuuacu cu 22

<210> SEQ ID NO 482
<211> LENGTH: 22
<212> TYPE: RNA
<213> ORGANISM: Homo sapiens

<400> SEQUENCE: 482
cugggagagg guuguuuacu cc 22

<210> SEQ ID NO 483
<211> LENGTH: 23
<212> TYPE: RNA
<213> ORGANISM: Homo sapiens

<400> SEQUENCE: 483
uguaaacauc cuacacucuc agc 23

<210> SEQ ID NO 484
<211> LENGTH: 22
<212> TYPE: RNA
<213> ORGANISM: Homo sapiens

<400> SEQUENCE: 484
cugggaggug gauguuuacu uc 22

<210> SEQ ID NO 485
<211> LENGTH: 22
<212> TYPE: RNA
<213> ORGANISM: Homo sapiens

<400> SEQUENCE: 485
uguaaacauc cuacacucag cu 22

<210> SEQ ID NO 486
<211> LENGTH: 22
<212> TYPE: RNA
<213> ORGANISM: Homo sapiens

<400> SEQUENCE: 486
cuuucagucg gauguuugca gc 22

<210> SEQ ID NO 487
<211> LENGTH: 22
<212> TYPE: RNA
<213> ORGANISM: Homo sapiens

<400> SEQUENCE: 487
uguaaacauc cucgacugga ag 22

<210> SEQ ID NO 488

<211> LENGTH: 17
<212> TYPE: RNA
<213> ORGANISM: Homo sapiens

<400> SEQUENCE: 488
uaauugcuuc cauguuu 17

<210> SEQ ID NO 489
<211> LENGTH: 17
<212> TYPE: RNA
<213> ORGANISM: Homo sapiens

<400> SEQUENCE: 489
uaagugcuuc caugcuu 17

<210> SEQ ID NO 490
<211> LENGTH: 22
<212> TYPE: RNA
<213> ORGANISM: Homo sapiens

<400> SEQUENCE: 490
acuuuaacau ggaggcacuu gc 22

<210> SEQ ID NO 491
<211> LENGTH: 23
<212> TYPE: RNA
<213> ORGANISM: Homo sapiens

<400> SEQUENCE: 491
uaagugcuuc cauguuugag ugu 23

<210> SEQ ID NO 492
<211> LENGTH: 22
<212> TYPE: RNA
<213> ORGANISM: Homo sapiens

<400> SEQUENCE: 492
uuuaacaugg ggguaccugc ug 22

<210> SEQ ID NO 493
<211> LENGTH: 23
<212> TYPE: RNA
<213> ORGANISM: Homo sapiens

<400> SEQUENCE: 493
uaagugcuuc cauguuucag ugg 23

<210> SEQ ID NO 494
<211> LENGTH: 22
<212> TYPE: RNA
<213> ORGANISM: Homo sapiens

<400> SEQUENCE: 494
acuuuaacau ggaagugcuu uc 22

<210> SEQ ID NO 495
<211> LENGTH: 23
<212> TYPE: RNA
<213> ORGANISM: Homo sapiens

<400> SEQUENCE: 495
uaagugcuuc cauguuuuag uag 23

<210> SEQ ID NO 496
<211> LENGTH: 23
<212> TYPE: RNA
<213> ORGANISM: Homo sapiens

<400> SEQUENCE: 496
acuuaaacgu ggauguacuu gcu 23

<210> SEQ ID NO 497
<211> LENGTH: 23
<212> TYPE: RNA
<213> ORGANISM: Homo sapiens

<400> SEQUENCE: 497
uaagugcuuc cauguuuugg uga 23

<210> SEQ ID NO 498
<211> LENGTH: 23
<212> TYPE: RNA
<213> ORGANISM: Homo sapiens

<400> SEQUENCE: 498
cagugcaaug auauugucaa agc 23

<210> SEQ ID NO 499
<211> LENGTH: 23
<212> TYPE: RNA
<213> ORGANISM: Homo sapiens

<400> SEQUENCE: 499
cagugcaaua guauugucaa agc 23

<210> SEQ ID NO 500
<211> LENGTH: 22
<212> TYPE: RNA
<213> ORGANISM: Homo sapiens

<400> SEQUENCE: 500
uauacaaggg cagacucucu cu 22

<210> SEQ ID NO 501
<211> LENGTH: 22
<212> TYPE: RNA
<213> ORGANISM: Homo sapiens

<400> SEQUENCE: 501
ugaccgauuu cuccuggugu uc 22

<210> SEQ ID NO 502
<211> LENGTH: 22
<212> TYPE: RNA
<213> ORGANISM: Homo sapiens

<400> SEQUENCE: 502
uagcaccauu ugaaaucggu ua 22

<210> SEQ ID NO 503
<211> LENGTH: 22
<212> TYPE: RNA
<213> ORGANISM: Homo sapiens

<400> SEQUENCE: 503
cugguuucac augguggcuu ag 22

<210> SEQ ID NO 504
<211> LENGTH: 24
<212> TYPE: RNA
<213> ORGANISM: Homo sapiens

<400> SEQUENCE: 504
gcugguuuca uauggugguu uaga 24

<210> SEQ ID NO 505
<211> LENGTH: 23
<212> TYPE: RNA
<213> ORGANISM: Homo sapiens

<400> SEQUENCE: 505
uagcaccauu ugaaaucagu guu 23

<210> SEQ ID NO 506
<211> LENGTH: 22
<212> TYPE: RNA
<213> ORGANISM: Homo sapiens

<400> SEQUENCE: 506
acugauuucu uuugguguuc ag 22

<210> SEQ ID NO 507
<211> LENGTH: 22
<212> TYPE: RNA
<213> ORGANISM: Homo sapiens

<400> SEQUENCE: 507
uagcaccauc ugaaaucggu ua 22

<210> SEQ ID NO 508
<211> LENGTH: 22
<212> TYPE: RNA
<213> ORGANISM: Homo sapiens

<400> SEQUENCE: 508
ugguuuaccg ucccacauac au 22

<210> SEQ ID NO 509
<211> LENGTH: 22
<212> TYPE: RNA
<213> ORGANISM: Homo sapiens

<400> SEQUENCE: 509
uaugugggau gguaaaccgc uu 22

<210> SEQ ID NO 510
<211> LENGTH: 24
<212> TYPE: RNA
<213> ORGANISM: Homo sapiens

<400> SEQUENCE: 510
agcagaagca gggagguucu ccca 24

<210> SEQ ID NO 511
<211> LENGTH: 21
<212> TYPE: RNA
<213> ORGANISM: Homo sapiens

<400> SEQUENCE: 511
auguaugugu gcaugugcau g 21

<210> SEQ ID NO 512
<211> LENGTH: 21
<212> TYPE: RNA
<213> ORGANISM: Homo sapiens

<400> SEQUENCE: 512
agggcccccc cucaauccug u 21

<210> SEQ ID NO 513
<211> LENGTH: 22
<212> TYPE: RNA
<213> ORGANISM: Homo sapiens

<400> SEQUENCE: 513
gaggguuggg uggaggcucu cc 22

<210> SEQ ID NO 514
<211> LENGTH: 22
<212> TYPE: RNA
<213> ORGANISM: Homo sapiens

<400> SEQUENCE: 514
aaggagcuca cagucuauug ag 22

<210> SEQ ID NO 515
<211> LENGTH: 22
<212> TYPE: RNA
<213> ORGANISM: Homo sapiens

<400> SEQUENCE: 515
cacuagauug ugagcuccug ga 22

<210> SEQ ID NO 516
<211> LENGTH: 22
<212> TYPE: RNA
<213> ORGANISM: Homo sapiens

<400> SEQUENCE: 516
agagcuuagc ugauugguga ac 22

<210> SEQ ID NO 517
<211> LENGTH: 21
<212> TYPE: RNA
<213> ORGANISM: Homo sapiens

<400> SEQUENCE: 517
uucacagugg cuaaguucug c 21

<210> SEQ ID NO 518
<211> LENGTH: 22
<212> TYPE: RNA
<213> ORGANISM: Homo sapiens

<400> SEQUENCE: 518
agggcuuagc ugcuugugag ca 22

<210> SEQ ID NO 519
<211> LENGTH: 21
<212> TYPE: RNA
<213> ORGANISM: Homo sapiens

<400> SEQUENCE: 519
uucacagugg cuaaguuccg c 21

<210> SEQ ID NO 520
<211> LENGTH: 22
<212> TYPE: RNA
<213> ORGANISM: Homo sapiens

<400> SEQUENCE: 520
ccuguucucc auuacuuggc uc 22

<210> SEQ ID NO 521
<211> LENGTH: 21
<212> TYPE: RNA
<213> ORGANISM: Homo sapiens

<400> SEQUENCE: 521
uucaaguaau ucaggauagg u 21

<210> SEQ ID NO 522
<211> LENGTH: 22
<212> TYPE: RNA
<213> ORGANISM: Homo sapiens

<400> SEQUENCE: 522
ccuauucuug auuacuuguu uc 22

<210> SEQ ID NO 523
<211> LENGTH: 22
<212> TYPE: RNA
<213> ORGANISM: Homo sapiens

<400> SEQUENCE: 523
ccuauucuug guuacuugca cg 22

<210> SEQ ID NO 524
<211> LENGTH: 22
<212> TYPE: RNA
<213> ORGANISM: Homo sapiens

<400> SEQUENCE: 524
uucaaguaau ccaggauagg cu 22

<210> SEQ ID NO 525
<211> LENGTH: 21
<212> TYPE: RNA
<213> ORGANISM: Homo sapiens

<400> SEQUENCE: 525
aggcggagac uugggcaauu g 21

<210> SEQ ID NO 526
<211> LENGTH: 22
<212> TYPE: RNA
<213> ORGANISM: Homo sapiens

<400> SEQUENCE: 526
cauugcacuu gucucggucu ga 22

<210> SEQ ID NO 527
<211> LENGTH: 22
<212> TYPE: RNA
<213> ORGANISM: Homo sapiens

<400> SEQUENCE: 527
ugccuacuga gcugaaacac ag 22

<210> SEQ ID NO 528
<211> LENGTH: 22
<212> TYPE: RNA
<213> ORGANISM: Homo sapiens

<400> SEQUENCE: 528
ugccuacuga gcugauauca gu 22

<210> SEQ ID NO 529
<211> LENGTH: 22
<212> TYPE: RNA
<213> ORGANISM: Homo sapiens

<400> SEQUENCE: 529
uggcucaguu cagcaggaac ag 22

<210> SEQ ID NO 530
<211> LENGTH: 22
<212> TYPE: RNA
<213> ORGANISM: Homo sapiens

<400> SEQUENCE: 530
uggguuccug gcaugcugau uu 22

<210> SEQ ID NO 531
<211> LENGTH: 21
<212> TYPE: RNA
<213> ORGANISM: Homo sapiens

<400> SEQUENCE: 531
aucacauugc cagggauuac c 21

<210> SEQ ID NO 532
<211> LENGTH: 22
<212> TYPE: RNA
<213> ORGANISM: Homo sapiens

<400> SEQUENCE: 532
gggguuccug gggaugggau uu 22

<210> SEQ ID NO 533
<211> LENGTH: 21
<212> TYPE: RNA
<213> ORGANISM: Homo sapiens

<400> SEQUENCE: 533
aucacauugc cagggauuuc c 21

<210> SEQ ID NO 534
<211> LENGTH: 22
<212> TYPE: RNA
<213> ORGANISM: Homo sapiens

<400> SEQUENCE: 534
gagagcagug uguguugccu gg 22

<210> SEQ ID NO 535
<211> LENGTH: 21
<212> TYPE: RNA
<213> ORGANISM: Homo sapiens

<400> SEQUENCE: 535
ugacagcgcc cugccuggcu c 21

<210> SEQ ID NO 536
<211> LENGTH: 22
<212> TYPE: RNA
<213> ORGANISM: Homo sapiens

<400> SEQUENCE: 536
ucugcaagug ucagaggcga gg 22

<210> SEQ ID NO 537
<211> LENGTH: 23
<212> TYPE: RNA
<213> ORGANISM: Homo sapiens

<400> SEQUENCE: 537
aaaauggugc ccuagugacu aca 23

<210> SEQ ID NO 538
<211> LENGTH: 21
<212> TYPE: RNA
<213> ORGANISM: Homo sapiens

<400> SEQUENCE: 538
caagucacua gugguuccgu u 21

<210> SEQ ID NO 539
<211> LENGTH: 22
<212> TYPE: RNA
<213> ORGANISM: Homo sapiens

<400> SEQUENCE: 539
cguguauuug acaagcugag uu 22

<210> SEQ ID NO 540
<211> LENGTH: 22
<212> TYPE: RNA
<213> ORGANISM: Homo sapiens

<400> SEQUENCE: 540
ugucaguuug ucaaauaccc ca 22

<210> SEQ ID NO 541
<211> LENGTH: 22
<212> TYPE: RNA
<213> ORGANISM: Homo sapiens

<400> SEQUENCE: 541
cucaguagcc aguguagauc cu 22

<210> SEQ ID NO 542
<211> LENGTH: 21
<212> TYPE: RNA
<213> ORGANISM: Homo sapiens

<400> SEQUENCE: 542
agcuacaucu ggcuacuggg u 21

<210> SEQ ID NO 543
<211> LENGTH: 22
<212> TYPE: RNA
<213> ORGANISM: Homo sapiens

<400> SEQUENCE: 543
accuggcaua caauguagau uu 22

<210> SEQ ID NO 544
<211> LENGTH: 23
<212> TYPE: RNA
<213> ORGANISM: Homo sapiens

<400> SEQUENCE: 544
agcuacauug ucugcugggu uuc 23

<210> SEQ ID NO 545
<211> LENGTH: 22
<212> TYPE: RNA
<213> ORGANISM: Homo sapiens

<400> SEQUENCE: 545
acacagggcu guugugaaga cu 22

<210> SEQ ID NO 546
<211> LENGTH: 21
<212> TYPE: RNA
<213> ORGANISM: Homo sapiens

<400> SEQUENCE: 546
ccaccaccgu gucugacacu u 21

<210> SEQ ID NO 547
<211> LENGTH: 21
<212> TYPE: RNA
<213> ORGANISM: Homo sapiens

<400> SEQUENCE: 547
ccacaccgua ucugacacuu u 21

<210> SEQ ID NO 548
<211> LENGTH: 22
<212> TYPE: RNA
<213> ORGANISM: Homo sapiens

<400> SEQUENCE: 548
aguucuucag uggcaagcuu ua 22

<210> SEQ ID NO 549
<211> LENGTH: 22
<212> TYPE: RNA
<213> ORGANISM: Homo sapiens

<400> SEQUENCE: 549
aagcugccag uugaagaacu gu 22

<210> SEQ ID NO 550
<211> LENGTH: 21
<212> TYPE: RNA
<213> ORGANISM: Homo sapiens

<400> SEQUENCE: 550
ugauugucca aacgcaauuc u 21

<210> SEQ ID NO 551
<211> LENGTH: 22
<212> TYPE: RNA

<213> ORGANISM: Homo sapiens

<400> SEQUENCE: 551
agaauugugg cuggacaucu gu 22

<210> SEQ ID NO 552
<211> LENGTH: 22
<212> TYPE: RNA
<213> ORGANISM: Homo sapiens

<400> SEQUENCE: 552
agaguugagu cuggacgucc cg 22

<210> SEQ ID NO 553
<211> LENGTH: 22
<212> TYPE: RNA
<213> ORGANISM: Homo sapiens

<400> SEQUENCE: 553
caugguucug ucaagcaccg cg 22

<210> SEQ ID NO 554
<211> LENGTH: 22
<212> TYPE: RNA
<213> ORGANISM: Homo sapiens

<400> SEQUENCE: 554
augguuccgu caagcaccau gg 22

<210> SEQ ID NO 555
<211> LENGTH: 21
<212> TYPE: RNA
<213> ORGANISM: Homo sapiens

<400> SEQUENCE: 555
uugugcuuga ucuaaccaug u 21

<210> SEQ ID NO 556
<211> LENGTH: 23
<212> TYPE: RNA
<213> ORGANISM: Homo sapiens

<400> SEQUENCE: 556
uacugcauca ggaacugauu gga 23

<210> SEQ ID NO 557
<211> LENGTH: 22
<212> TYPE: RNA
<213> ORGANISM: Homo sapiens

<400> SEQUENCE: 557
aaaucucugc aggcaaaugu ga 22

<210> SEQ ID NO 558
<211> LENGTH: 22
<212> TYPE: RNA
<213> ORGANISM: Homo sapiens

<400> SEQUENCE: 558
uaaucucagc uggcaacugu ga 22

<210> SEQ ID NO 559
<211> LENGTH: 21

<212> TYPE: RNA
<213> ORGANISM: Homo sapiens

<400> SEQUENCE: 559
augaccuaug aauugacaga c 21

<210> SEQ ID NO 560
<211> LENGTH: 22
<212> TYPE: RNA
<213> ORGANISM: Homo sapiens

<400> SEQUENCE: 560
ugccugucua cacuugcugu gc 22

<210> SEQ ID NO 561
<211> LENGTH: 22
<212> TYPE: RNA
<213> ORGANISM: Homo sapiens

<400> SEQUENCE: 561
acagcaggca cagacaggca gu 22

<210> SEQ ID NO 562
<211> LENGTH: 21
<212> TYPE: RNA
<213> ORGANISM: Homo sapiens

<400> SEQUENCE: 562
uaacagucuc cagucacggc c 21

<210> SEQ ID NO 563
<211> LENGTH: 21
<212> TYPE: RNA
<213> ORGANISM: Homo sapiens

<400> SEQUENCE: 563
uguucucuuu gccaaggaca g 21

<210> SEQ ID NO 564
<211> LENGTH: 21
<212> TYPE: RNA
<213> ORGANISM: Homo sapiens

<400> SEQUENCE: 564
ccucccaugc caagaacucc c 21

<210> SEQ ID NO 565
<211> LENGTH: 21
<212> TYPE: RNA
<213> ORGANISM: Homo sapiens

<400> SEQUENCE: 565
gguucuuagc auaggagguc u 21

<210> SEQ ID NO 566
<211> LENGTH: 22
<212> TYPE: RNA
<213> ORGANISM: Homo sapiens

<400> SEQUENCE: 566
caucagaauu cauggaggcu ag 22

<210> SEQ ID NO 567

<211> LENGTH: 22
<212> TYPE: RNA
<213> ORGANISM: Homo sapiens

<400> SEQUENCE: 567
agcuuccaug acuccugaug ga 22

<210> SEQ ID NO 568
<211> LENGTH: 21
<212> TYPE: RNA
<213> ORGANISM: Homo sapiens

<400> SEQUENCE: 568
cgagccucaa gcaagggacu u 21

<210> SEQ ID NO 569
<211> LENGTH: 22
<212> TYPE: RNA
<213> ORGANISM: Homo sapiens

<400> SEQUENCE: 569
uagucccuuc cuugaagcgg uc 22

<210> SEQ ID NO 570
<211> LENGTH: 21
<212> TYPE: RNA
<213> ORGANISM: Homo sapiens

<400> SEQUENCE: 570
auuugugcuu ggcucuguca c 21

<210> SEQ ID NO 571
<211> LENGTH: 22
<212> TYPE: RNA
<213> ORGANISM: Homo sapiens

<400> SEQUENCE: 571
uuggggaaac ggccgcugag ug 22

<210> SEQ ID NO 572
<211> LENGTH: 22
<212> TYPE: RNA
<213> ORGANISM: Homo sapiens

<400> SEQUENCE: 572
uucccuuugu cauccuucgc cu 22

<210> SEQ ID NO 573
<211> LENGTH: 22
<212> TYPE: RNA
<213> ORGANISM: Homo sapiens

<400> SEQUENCE: 573
cugugcgugu gacagcggcu ga 22

<210> SEQ ID NO 574
<211> LENGTH: 21
<212> TYPE: RNA
<213> ORGANISM: Homo sapiens

<400> SEQUENCE: 574
caacaccagu cgaugggcug u 21

<210> SEQ ID NO 575
<211> LENGTH: 22
<212> TYPE: RNA
<213> ORGANISM: Homo sapiens

<400> SEQUENCE: 575
uagcuuauca gacugauguu ga 22

<210> SEQ ID NO 576
<211> LENGTH: 22
<212> TYPE: RNA
<213> ORGANISM: Homo sapiens

<400> SEQUENCE: 576
acuguaguau gggcacuucc ag 22

<210> SEQ ID NO 577
<211> LENGTH: 23
<212> TYPE: RNA
<213> ORGANISM: Homo sapiens

<400> SEQUENCE: 577
caaagugcuc auagugcagg uag 23

<210> SEQ ID NO 578
<211> LENGTH: 22
<212> TYPE: RNA
<213> ORGANISM: Homo sapiens

<400> SEQUENCE: 578
acugcauuau gagcacuuaa ag 22

<210> SEQ ID NO 579
<211> LENGTH: 23
<212> TYPE: RNA
<213> ORGANISM: Homo sapiens

<400> SEQUENCE: 579
uaaagugcuu auagugcagg uag 23

<210> SEQ ID NO 580
<211> LENGTH: 22
<212> TYPE: RNA
<213> ORGANISM: Homo sapiens

<400> SEQUENCE: 580
auaagacgaa caaaagguuu gu 22

<210> SEQ ID NO 581
<211> LENGTH: 22
<212> TYPE: RNA
<213> ORGANISM: Homo sapiens

<400> SEQUENCE: 581
auaagacgag caaaaagcuu gu 22

<210> SEQ ID NO 582
<211> LENGTH: 22
<212> TYPE: RNA
<213> ORGANISM: Homo sapiens

<400> SEQUENCE: 582
uggaauguaa ggaagugugu gg 22

<210> SEQ ID NO 583
<211> LENGTH: 23
<212> TYPE: RNA
<213> ORGANISM: Homo sapiens

<400> SEQUENCE: 583
cuguaauaua aauuuaauuu auu 23

<210> SEQ ID NO 584
<211> LENGTH: 23
<212> TYPE: RNA
<213> ORGANISM: Homo sapiens

<400> SEQUENCE: 584
guguuaauua aaccucuauu uac 23

<210> SEQ ID NO 585
<211> LENGTH: 20
<212> TYPE: RNA
<213> ORGANISM: Homo sapiens

<400> SEQUENCE: 585
uguuuugaua acaguaaugu 20

<210> SEQ ID NO 586
<211> LENGTH: 21
<212> TYPE: RNA
<213> ORGANISM: Homo sapiens

<400> SEQUENCE: 586
gauuucagug gagugaaguu c 21

<210> SEQ ID NO 587
<211> LENGTH: 22
<212> TYPE: RNA
<213> ORGANISM: Homo sapiens

<400> SEQUENCE: 587
uccuucauuc caccggaguc ug 22

<210> SEQ ID NO 588
<211> LENGTH: 22
<212> TYPE: RNA
<213> ORGANISM: Homo sapiens

<400> SEQUENCE: 588
uucccuuugu cauccuaugc cu 22

<210> SEQ ID NO 589
<211> LENGTH: 22
<212> TYPE: RNA
<213> ORGANISM: Homo sapiens

<400> SEQUENCE: 589
gugaaauguu uaggaccacu ag 22

<210> SEQ ID NO 590
<211> LENGTH: 22
<212> TYPE: RNA
<213> ORGANISM: Homo sapiens

<400> SEQUENCE: 590
uuccuaugca uauacuucuu ug 22

<210> SEQ ID NO 591
<211> LENGTH: 20
<212> TYPE: RNA
<213> ORGANISM: Homo sapiens

<400> SEQUENCE: 591
agagguauag ggcaugggaa 20

<210> SEQ ID NO 592
<211> LENGTH: 22
<212> TYPE: RNA
<213> ORGANISM: Homo sapiens

<400> SEQUENCE: 592
cgucuuaccc agcaguguuu gg 22

<210> SEQ ID NO 593
<211> LENGTH: 23
<212> TYPE: RNA
<213> ORGANISM: Homo sapiens

<400> SEQUENCE: 593
uaauacugcc ggguaaugau gga 23

<210> SEQ ID NO 594
<211> LENGTH: 22
<212> TYPE: RNA
<213> ORGANISM: Homo sapiens

<400> SEQUENCE: 594
caucuuacug ggcagcauug ga 22

<210> SEQ ID NO 595
<211> LENGTH: 22
<212> TYPE: RNA
<213> ORGANISM: Homo sapiens

<400> SEQUENCE: 595
uaauacugcc ugguaaugau ga 22

<210> SEQ ID NO 596
<211> LENGTH: 22
<212> TYPE: RNA
<213> ORGANISM: Homo sapiens

<400> SEQUENCE: 596
caucuuaccg gacagugcug ga 22

<210> SEQ ID NO 597
<211> LENGTH: 22
<212> TYPE: RNA
<213> ORGANISM: Homo sapiens

<400> SEQUENCE: 597
uaacacuguc ugguaacgau gu 22

<210> SEQ ID NO 598
<211> LENGTH: 22
<212> TYPE: RNA
<213> ORGANISM: Homo sapiens

<400> SEQUENCE: 598
aguuuugcag guuugcauuu ca 22

<210> SEQ ID NO 599
<211> LENGTH: 23
<212> TYPE: RNA
<213> ORGANISM: Homo sapiens

<400> SEQUENCE: 599
aguuuugcag guuugcaucc agc 23

<210> SEQ ID NO 600
<211> LENGTH: 23
<212> TYPE: RNA
<213> ORGANISM: Homo sapiens

<400> SEQUENCE: 600
ugugcaaauc caugcaaaac uga 23

<210> SEQ ID NO 601
<211> LENGTH: 22
<212> TYPE: RNA
<213> ORGANISM: Homo sapiens

<400> SEQUENCE: 601
aguuuugcau aguugcacua ca 22

<210> SEQ ID NO 602
<211> LENGTH: 23
<212> TYPE: RNA
<213> ORGANISM: Homo sapiens

<400> SEQUENCE: 602
ugugcaaauc uaugcaaaac uga 23

<210> SEQ ID NO 603
<211> LENGTH: 23
<212> TYPE: RNA
<213> ORGANISM: Homo sapiens

<400> SEQUENCE: 603
cccaguguuu agacuaucug uuc 23

<210> SEQ ID NO 604
<211> LENGTH: 22
<212> TYPE: RNA
<213> ORGANISM: Homo sapiens

<400> SEQUENCE: 604
acaguagucu gcacauuggu ua 22

<210> SEQ ID NO 605
<211> LENGTH: 23
<212> TYPE: RNA
<213> ORGANISM: Homo sapiens

<400> SEQUENCE: 605
cccaguguuc agacuaccug uuc 23

<210> SEQ ID NO 606
<211> LENGTH: 22
<212> TYPE: RNA
<213> ORGANISM: Homo sapiens

<400> SEQUENCE: 606

-continued acaguagucu gcacauuggu ua 22

<210> SEQ ID NO 607
<211> LENGTH: 22
<212> TYPE: RNA
<213> ORGANISM: Homo sapiens

<400> SEQUENCE: 607
gguccagagg ggagauaggu uc 22

<210> SEQ ID NO 608
<211> LENGTH: 22
<212> TYPE: RNA
<213> ORGANISM: Homo sapiens

<400> SEQUENCE: 608
cucccacugc uucacuugac ua 22

<210> SEQ ID NO 609
<211> LENGTH: 21
<212> TYPE: RNA
<213> ORGANISM: Homo sapiens

<400> SEQUENCE: 609
gguuuggucc uagccuuucu a 21

<210> SEQ ID NO 610
<211> LENGTH: 22
<212> TYPE: RNA
<213> ORGANISM: Homo sapiens

<400> SEQUENCE: 610
gauuagggug cuuagcuguu aa 22

<210> SEQ ID NO 611
<211> LENGTH: 20
<212> TYPE: RNA
<213> ORGANISM: Homo sapiens

<400> SEQUENCE: 611
ccuccugccc uccuugcugu 20

<210> SEQ ID NO 612
<211> LENGTH: 25
<212> TYPE: RNA
<213> ORGANISM: Homo sapiens

<400> SEQUENCE: 612
cccccacaac cgcgcuugac uagcu 25

<210> SEQ ID NO 613
<211> LENGTH: 23
<212> TYPE: RNA
<213> ORGANISM: Homo sapiens

<400> SEQUENCE: 613
ugguuguagu ccgugcgaga aua 23

<210> SEQ ID NO 614
<211> LENGTH: 19
<212> TYPE: RNA
<213> ORGANISM: Homo sapiens

<400> SEQUENCE: 614
accgugcaaa gguagcaua 19

<210> SEQ ID NO 615
<211> LENGTH: 22
<212> TYPE: RNA
<213> ORGANISM: Homo sapiens

<400> SEQUENCE: 615
ucaggccagg cacaguggcu ca 22

<210> SEQ ID NO 616
<211> LENGTH: 22
<212> TYPE: RNA
<213> ORGANISM: Homo sapiens

<400> SEQUENCE: 616
uucaccaccu ucuccaccca gc 22

<210> SEQ ID NO 617
<211> LENGTH: 22
<212> TYPE: RNA
<213> ORGANISM: Homo sapiens

<400> SEQUENCE: 617
ucgacagcac gacacugccu uc 22

<210> SEQ ID NO 618
<211> LENGTH: 22
<212> TYPE: RNA
<213> ORGANISM: Homo sapiens

<400> SEQUENCE: 618
uagguaguuu ccuguuguug gg 22

<210> SEQ ID NO 619
<211> LENGTH: 22
<212> TYPE: RNA
<213> ORGANISM: Homo sapiens

<400> SEQUENCE: 619
cggcaacaag aaacugccug ag 22

<210> SEQ ID NO 620
<211> LENGTH: 22
<212> TYPE: RNA
<213> ORGANISM: Homo sapiens

<400> SEQUENCE: 620
uagguaguuu cauguuguug gg 22

<210> SEQ ID NO 621
<211> LENGTH: 22
<212> TYPE: RNA
<213> ORGANISM: Homo sapiens

<400> SEQUENCE: 621
ccaauauugg cugugcugcu cc 22

<210> SEQ ID NO 622
<211> LENGTH: 21
<212> TYPE: RNA
<213> ORGANISM: Homo sapiens

<400> SEQUENCE: 622
uagcagcaca gaaauauugg c 21

<210> SEQ ID NO 623
<211> LENGTH: 22
<212> TYPE: RNA
<213> ORGANISM: Homo sapiens

<400> SEQUENCE: 623
ccaguggggc ugcuguuauc ug 22

<210> SEQ ID NO 624
<211> LENGTH: 22
<212> TYPE: RNA
<213> ORGANISM: Homo sapiens

<400> SEQUENCE: 624
uguaacagca acuccaugug ga 22

<210> SEQ ID NO 625
<211> LENGTH: 22
<212> TYPE: RNA
<213> ORGANISM: Homo sapiens

<400> SEQUENCE: 625 cggguuuug agggcgagau ga 22

<210> SEQ ID NO 626
<211> LENGTH: 22
<212> TYPE: RNA
<213> ORGANISM: Homo sapiens

<400> SEQUENCE: 626
aacuggcccu caaagucccg cu 22

<210> SEQ ID NO 627
<211> LENGTH: 22
<212> TYPE: RNA
<213> ORGANISM: Homo sapiens

<400> SEQUENCE: 627
ugggucuuug cgggcgagau ga 22

<210> SEQ ID NO 628
<211> LENGTH: 22
<212> TYPE: RNA
<213> ORGANISM: Homo sapiens

<400> SEQUENCE: 628
aacuggccua caaaguccca gu 22

<210> SEQ ID NO 629
<211> LENGTH: 22
<212> TYPE: RNA
<213> ORGANISM: Homo sapiens

<400> SEQUENCE: 629
cugccaauuc cauaggucac ag 22

<210> SEQ ID NO 630
<211> LENGTH: 21
<212> TYPE: RNA

<213> ORGANISM: Homo sapiens

<400> SEQUENCE: 630
cugaccuaug aauugacagc c 21

<210> SEQ ID NO 631
<211> LENGTH: 22
<212> TYPE: RNA
<213> ORGANISM: Homo sapiens

<400> SEQUENCE: 631
accuugccuu gcugcccggg cc 22

<210> SEQ ID NO 632
<211> LENGTH: 20
<212> TYPE: RNA
<213> ORGANISM: Homo sapiens

<400> SEQUENCE: 632
ccccagggcg acgcggcggg 20

<210> SEQ ID NO 633
<211> LENGTH: 22
<212> TYPE: RNA
<213> ORGANISM: Homo sapiens

<400> SEQUENCE: 633
ggaggggucc cgcacuggga gg 22

<210> SEQ ID NO 634
<211> LENGTH: 22
<212> TYPE: RNA
<213> ORGANISM: Homo sapiens

<400> SEQUENCE: 634
cccugugccc ggcccacuuc ug 22

<210> SEQ ID NO 635
<211> LENGTH: 22
<212> TYPE: RNA
<213> ORGANISM: Homo sapiens

<400> SEQUENCE: 635
ucugcccccu ccgcugcugc ca 22

<210> SEQ ID NO 636
<211> LENGTH: 22
<212> TYPE: RNA
<213> ORGANISM: Homo sapiens

<400> SEQUENCE: 636
uacccagagc augcagugug aa 22

<210> SEQ ID NO 637
<211> LENGTH: 20
<212> TYPE: RNA
<213> ORGANISM: Homo sapiens

<400> SEQUENCE: 637
caccaggcau uguggucucc 20

<210> SEQ ID NO 638
<211> LENGTH: 23

<212> TYPE: RNA
<213> ORGANISM: Homo sapiens

<400> SEQUENCE: 638
ugaguaccgc caugucuguu ggg 23

<210> SEQ ID NO 639
<211> LENGTH: 21
<212> TYPE: RNA
<213> ORGANISM: Homo sapiens

<400> SEQUENCE: 639
ccaguccugu gccugccgcc u 21

<210> SEQ ID NO 640
<211> LENGTH: 22
<212> TYPE: RNA
<213> ORGANISM: Homo sapiens

<400> SEQUENCE: 640
gcugcgcuug gauuucgucc cc 22

<210> SEQ ID NO 641
<211> LENGTH: 23
<212> TYPE: RNA
<213> ORGANISM: Homo sapiens

<400> SEQUENCE: 641
caacggaauc ccaaaagcag cug 23

<210> SEQ ID NO 642
<211> LENGTH: 21
<212> TYPE: RNA
<213> ORGANISM: Homo sapiens

<400> SEQUENCE: 642
ugauauguuu gauauugggu u 21

<210> SEQ ID NO 643
<211> LENGTH: 21
<212> TYPE: RNA
<213> ORGANISM: Homo sapiens

<400> SEQUENCE: 643
ugagugccgg ugccugcccu g 21

<210> SEQ ID NO 644
<211> LENGTH: 22
<212> TYPE: RNA
<213> ORGANISM: Homo sapiens

<400> SEQUENCE: 644
cgcaggggcc gggugcucac cg 22

<210> SEQ ID NO 645
<211> LENGTH: 21
<212> TYPE: RNA
<213> ORGANISM: Homo sapiens

<400> SEQUENCE: 645
cggcggggac ggcgauuggu c 21

<210> SEQ ID NO 646

<211> LENGTH: 22
<212> TYPE: RNA
<213> ORGANISM: Homo sapiens

<400> SEQUENCE: 646
ugauauguuu gauauauuag gu 22

<210> SEQ ID NO 647
<211> LENGTH: 22
<212> TYPE: RNA
<213> ORGANISM: Homo sapiens

<400> SEQUENCE: 647
ugcccuaaau gccccuucug gc 22

<210> SEQ ID NO 648
<211> LENGTH: 23
<212> TYPE: RNA
<213> ORGANISM: Homo sapiens

<400> SEQUENCE: 648
uaaggugcau cuagugcagu uag 23

<210> SEQ ID NO 649
<211> LENGTH: 23
<212> TYPE: RNA
<213> ORGANISM: Homo sapiens

<400> SEQUENCE: 649
acugcccuaa gugcuccuuc ugg 23

<210> SEQ ID NO 650
<211> LENGTH: 23
<212> TYPE: RNA
<213> ORGANISM: Homo sapiens

<400> SEQUENCE: 650
uaaggugcau cuagugcaga uag 23

<210> SEQ ID NO 651
<211> LENGTH: 21
<212> TYPE: RNA
<213> ORGANISM: Homo sapiens

<400> SEQUENCE: 651
caucccuugc augguggagg g 21

<210> SEQ ID NO 652
<211> LENGTH: 21
<212> TYPE: RNA
<213> ORGANISM: Homo sapiens

<400> SEQUENCE: 652
cucccacaug caggguuugc a 21

<210> SEQ ID NO 653
<211> LENGTH: 22
<212> TYPE: RNA
<213> ORGANISM: Homo sapiens

<400> SEQUENCE: 653
ggcuacaaca caggacccgg gc 22

<210> SEQ ID NO 654
<211> LENGTH: 22
<212> TYPE: RNA
<213> ORGANISM: Homo sapiens

<400> SEQUENCE: 654
ucgugucuug uguugcagcc gg 22

<210> SEQ ID NO 655
<211> LENGTH: 22
<212> TYPE: RNA
<213> ORGANISM: Homo sapiens

<400> SEQUENCE: 655
gcccaaaggu gaauuuuuug gg 22

<210> SEQ ID NO 656
<211> LENGTH: 22
<212> TYPE: RNA
<213> ORGANISM: Homo sapiens

<400> SEQUENCE: 656
caaagaauuc uccuuuuggg cu 22

<210> SEQ ID NO 657
<211> LENGTH: 22
<212> TYPE: RNA
<213> ORGANISM: Homo sapiens

<400> SEQUENCE: 657
aggggcuggc uuuccucugg uc 22

<210> SEQ ID NO 658
<211> LENGTH: 22
<212> TYPE: RNA
<213> ORGANISM: Homo sapiens

<400> SEQUENCE: 658
uggagagaaa ggcaguuccu ga 22

<210> SEQ ID NO 659
<211> LENGTH: 22
<212> TYPE: RNA
<213> ORGANISM: Homo sapiens

<400> SEQUENCE: 659
uggacggaga acugauaagg gu 22

<210> SEQ ID NO 660
<211> LENGTH: 22
<212> TYPE: RNA
<213> ORGANISM: Homo sapiens

<400> SEQUENCE: 660
gugaauuacc gaagggccau aa 22

<210> SEQ ID NO 661
<211> LENGTH: 22
<212> TYPE: RNA
<213> ORGANISM: Homo sapiens

<400> SEQUENCE: 661
uauggcacug guagaauuca cu 22

<210> SEQ ID NO 662
<211> LENGTH: 18
<212> TYPE: RNA
<213> ORGANISM: Homo sapiens

<400> SEQUENCE: 662
ugaggcagua gauugaau 18

<210> SEQ ID NO 663
<211> LENGTH: 27
<212> TYPE: RNA
<213> ORGANISM: Homo sapiens

<400> SEQUENCE: 663
auugaucauc gacacuucga acgcaau 27

<210> SEQ ID NO 664
<211> LENGTH: 18
<212> TYPE: RNA
<213> ORGANISM: Homo sapiens

<400> SEQUENCE: 664
uccagugccc uccucucc 18

<210> SEQ ID NO 665
<211> LENGTH: 21
<212> TYPE: RNA
<213> ORGANISM: Homo sapiens

<400> SEQUENCE: 665
ugguucuaga cuugccaacu a 21

<210> SEQ ID NO 666
<211> LENGTH: 24
<212> TYPE: RNA
<213> ORGANISM: Homo sapiens

<400> SEQUENCE: 666
uuuggcaaug guagaacuca cacu 24

<210> SEQ ID NO 667
<211> LENGTH: 23
<212> TYPE: RNA
<213> ORGANISM: Homo sapiens

<400> SEQUENCE: 667
aacauucauu guugucggug ggu 23

<210> SEQ ID NO 668
<211> LENGTH: 22
<212> TYPE: RNA
<213> ORGANISM: Homo sapiens

<400> SEQUENCE: 668
aaccaucgac cguugagugg ac 22

<210> SEQ ID NO 669
<211> LENGTH: 22
<212> TYPE: RNA
<213> ORGANISM: Homo sapiens

<400> SEQUENCE: 669
aacauucaac cugucgguga gu 22

<210> SEQ ID NO 670
<211> LENGTH: 23
<212> TYPE: RNA
<213> ORGANISM: Homo sapiens

<400> SEQUENCE: 670
aacauucauu gcugucggug ggu 23

<210> SEQ ID NO 671
<211> LENGTH: 22
<212> TYPE: RNA
<213> ORGANISM: Homo sapiens

<400> SEQUENCE: 671
accacugacc guugacugua cc 22

<210> SEQ ID NO 672
<211> LENGTH: 22
<212> TYPE: RNA
<213> ORGANISM: Homo sapiens

<400> SEQUENCE: 672
accaucgacc guugauugua cc 22

<210> SEQ ID NO 673
<211> LENGTH: 23
<212> TYPE: RNA
<213> ORGANISM: Homo sapiens

<400> SEQUENCE: 673
aacauucaac gcugucggug agu 23

<210> SEQ ID NO 674
<211> LENGTH: 22
<212> TYPE: RNA
<213> ORGANISM: Homo sapiens

<400> SEQUENCE: 674
acugcaguga aggcacuugu ag 22

<210> SEQ ID NO 675
<211> LENGTH: 23
<212> TYPE: RNA
<213> ORGANISM: Homo sapiens

<400> SEQUENCE: 675
caaagugcuu acagugcagg uag 23

<210> SEQ ID NO 676
<211> LENGTH: 22
<212> TYPE: RNA
<213> ORGANISM: Homo sapiens

<400> SEQUENCE: 676
ccaauauuac ugugcugcuu ua 22

<210> SEQ ID NO 677
<211> LENGTH: 22
<212> TYPE: RNA
<213> ORGANISM: Homo sapiens

<400> SEQUENCE: 677
ccaguauuaa cugugcugcu ga 22

<210> SEQ ID NO 678
<211> LENGTH: 22
<212> TYPE: RNA
<213> ORGANISM: Homo sapiens

<400> SEQUENCE: 678
uagcagcacg uaaauauugg cg 22

<210> SEQ ID NO 679
<211> LENGTH: 22
<212> TYPE: RNA
<213> ORGANISM: Homo sapiens

<400> SEQUENCE: 679
cgaaucauua uuugcugcuc ua 22

<210> SEQ ID NO 680
<211> LENGTH: 22
<212> TYPE: RNA
<213> ORGANISM: Homo sapiens

<400> SEQUENCE: 680
uagcagcaca ucaugguuua ca 22

<210> SEQ ID NO 681
<211> LENGTH: 22
<212> TYPE: RNA
<213> ORGANISM: Homo sapiens

<400> SEQUENCE: 681
caggccauau ugugcugccu ca 22

<210> SEQ ID NO 682
<211> LENGTH: 22
<212> TYPE: RNA
<213> ORGANISM: Homo sapiens

<400> SEQUENCE: 682
uagcagcaca uaaugguuug ug 22

<210> SEQ ID NO 683
<211> LENGTH: 22
<212> TYPE: RNA
<213> ORGANISM: Homo sapiens

<400> SEQUENCE: 683
cuccuacaua uuagcauuaa ca 22

<210> SEQ ID NO 684
<211> LENGTH: 23
<212> TYPE: RNA
<213> ORGANISM: Homo sapiens

<400> SEQUENCE: 684
uuaaugcuaa ucgugauagg ggu 23

<210> SEQ ID NO 685
<211> LENGTH: 22
<212> TYPE: RNA
<213> ORGANISM: Homo sapiens

<400> SEQUENCE: 685
aaucauacac gguugaccua uu 22

<210> SEQ ID NO 686
<211> LENGTH: 22
<212> TYPE: RNA
<213> ORGANISM: Homo sapiens

<400> SEQUENCE: 686
uagguuaucc guguugccuu cg 22

<210> SEQ ID NO 687
<211> LENGTH: 21
<212> TYPE: RNA
<213> ORGANISM: Homo sapiens

<400> SEQUENCE: 687
uccugcgcgu cccagaugcc c 21

<210> SEQ ID NO 688
<211> LENGTH: 23
<212> TYPE: RNA
<213> ORGANISM: Homo sapiens

<400> SEQUENCE: 688
cggcccgggc ugcugcuguu ccu 23

<210> SEQ ID NO 689
<211> LENGTH: 22
<212> TYPE: RNA
<213> ORGANISM: Homo sapiens

<400> SEQUENCE: 689
aaaaccgucu aguuacaguu gu 22

<210> SEQ ID NO 690
<211> LENGTH: 22
<212> TYPE: RNA
<213> ORGANISM: Homo sapiens

<400> SEQUENCE: 690
uugcauaguc acaaaaguga uc 22

<210> SEQ ID NO 691
<211> LENGTH: 21
<212> TYPE: RNA
<213> ORGANISM: Homo sapiens

<400> SEQUENCE: 691
ucagugcaug acagaacuug g 21

<210> SEQ ID NO 692
<211> LENGTH: 21
<212> TYPE: RNA
<213> ORGANISM: Homo sapiens

<400> SEQUENCE: 692
ucgaggagcu cacagucuag u 21

<210> SEQ ID NO 693
<211> LENGTH: 21
<212> TYPE: RNA
<213> ORGANISM: Homo sapiens

<400> SEQUENCE: 693
cuagacugaa gcuccuugag g 21

<210> SEQ ID NO 694
<211> LENGTH: 22
<212> TYPE: RNA
<213> ORGANISM: Homo sapiens

<400> SEQUENCE: 694
cugguacagg ccugggggac ag 22

<210> SEQ ID NO 695
<211> LENGTH: 22
<212> TYPE: RNA
<213> ORGANISM: Homo sapiens

<400> SEQUENCE: 695
ucucccaacc cuuguaccag ug 22

<210> SEQ ID NO 696
<211> LENGTH: 21
<212> TYPE: RNA
<213> ORGANISM: Homo sapiens

<400> SEQUENCE: 696
agggagggac gggggcugug c 21

<210> SEQ ID NO 697
<211> LENGTH: 23
<212> TYPE: RNA
<213> ORGANISM: Homo sapiens

<400> SEQUENCE: 697
ucuggcuccg ugucuucacu ccc 23

<210> SEQ ID NO 698
<211> LENGTH: 22
<212> TYPE: RNA
<213> ORGANISM: Homo sapiens

<400> SEQUENCE: 698
aaguucuguu auacacucag gc 22

<210> SEQ ID NO 699
<211> LENGTH: 22
<212> TYPE: RNA
<213> ORGANISM: Homo sapiens

<400> SEQUENCE: 699
ucagugcauc acagaacuuu gu 22

<210> SEQ ID NO 700
<211> LENGTH: 22
<212> TYPE: RNA
<213> ORGANISM: Homo sapiens

<400> SEQUENCE: 700
aaaguucuga gacacuccga cu 22

<210> SEQ ID NO 701
<211> LENGTH: 22
<212> TYPE: RNA
<213> ORGANISM: Homo sapiens

<400> SEQUENCE: 701
ucagugcacu acagaacuuu gu 22

<210> SEQ ID NO 702
<211> LENGTH: 22
<212> TYPE: RNA
<213> ORGANISM: Homo sapiens

<400> SEQUENCE: 702
gugugcggaa augcuucugc ua 22

<210> SEQ ID NO 703
<211> LENGTH: 22
<212> TYPE: RNA
<213> ORGANISM: Homo sapiens

<400> SEQUENCE: 703
gcccgcgugu ggagccaggu gu 22

<210> SEQ ID NO 704
<211> LENGTH: 21
<212> TYPE: RNA
<213> ORGANISM: Homo sapiens

<400> SEQUENCE: 704
gcccuccgcc cgugcacccc g 21

<210> SEQ ID NO 705
<211> LENGTH: 20
<212> TYPE: RNA
<213> ORGANISM: Homo sapiens

<400> SEQUENCE: 705
guguguggaa augcuucugc 20

<210> SEQ ID NO 706
<211> LENGTH: 22
<212> TYPE: RNA
<213> ORGANISM: Homo sapiens

<400> SEQUENCE: 706
ugagaacuga auuccauagg cu 22

<210> SEQ ID NO 707
<211> LENGTH: 22
<212> TYPE: RNA
<213> ORGANISM: Homo sapiens

<400> SEQUENCE: 707
ugcccugugg acucaguucu gg 22

<210> SEQ ID NO 708
<211> LENGTH: 22
<212> TYPE: RNA
<213> ORGANISM: Homo sapiens

<400> SEQUENCE: 708
ccucugaaau ucaguucuuc ag 22

<210> SEQ ID NO 709
<211> LENGTH: 22
<212> TYPE: RNA

<213> ORGANISM: Homo sapiens

<400> SEQUENCE: 709
ugagaacuga auuccauggg uu 22

<210> SEQ ID NO 710
<211> LENGTH: 22
<212> TYPE: RNA
<213> ORGANISM: Homo sapiens

<400> SEQUENCE: 710
cucggcgcgg ggcgcgggcu cc 22

<210> SEQ ID NO 711
<211> LENGTH: 21
<212> TYPE: RNA
<213> ORGANISM: Homo sapiens

<400> SEQUENCE: 711
cuccguuugc cuguuucgcu g 21

<210> SEQ ID NO 712
<211> LENGTH: 22
<212> TYPE: RNA
<213> ORGANISM: Homo sapiens

<400> SEQUENCE: 712
ggauuccugg aaauacuguu cu 22

<210> SEQ ID NO 713
<211> LENGTH: 23
<212> TYPE: RNA
<213> ORGANISM: Homo sapiens

<400> SEQUENCE: 713
guccaguuuu cccaggaauc ccu 23

<210> SEQ ID NO 714
<211> LENGTH: 22
<212> TYPE: RNA
<213> ORGANISM: Homo sapiens

<400> SEQUENCE: 714
ggauaucauc auauacugua ag 22

<210> SEQ ID NO 715
<211> LENGTH: 20
<212> TYPE: RNA
<213> ORGANISM: Homo sapiens

<400> SEQUENCE: 715
uacaguauag augauguacu 20

<210> SEQ ID NO 716
<211> LENGTH: 22
<212> TYPE: RNA
<213> ORGANISM: Homo sapiens

<400> SEQUENCE: 716
ggugcagugc ugcaucucug gu 22

<210> SEQ ID NO 717
<211> LENGTH: 21

<212> TYPE: RNA
<213> ORGANISM: Homo sapiens

<400> SEQUENCE: 717
ugagaugaag cacuguagcu c 21

<210> SEQ ID NO 718
<211> LENGTH: 21
<212> TYPE: RNA
<213> ORGANISM: Homo sapiens

<400> SEQUENCE: 718
cauaaaguag aaagcacuac u 21

<210> SEQ ID NO 719
<211> LENGTH: 23
<212> TYPE: RNA
<213> ORGANISM: Homo sapiens

<400> SEQUENCE: 719
uguaguguuu ccuacuuuau gga 23

<210> SEQ ID NO 720
<211> LENGTH: 22
<212> TYPE: RNA
<213> ORGANISM: Homo sapiens

<400> SEQUENCE: 720
caucuuccag uacaguguug ga 22

<210> SEQ ID NO 721
<211> LENGTH: 22
<212> TYPE: RNA
<213> ORGANISM: Homo sapiens

<400> SEQUENCE: 721
uaacacuguc ugguaaagau gg 22

<210> SEQ ID NO 722
<211> LENGTH: 22
<212> TYPE: RNA
<213> ORGANISM: Homo sapiens

<400> SEQUENCE: 722
cagugguuuu acccuauggu ag 22

<210> SEQ ID NO 723
<211> LENGTH: 21
<212> TYPE: RNA
<213> ORGANISM: Homo sapiens

<400> SEQUENCE: 723
uaccacaggg uagaaccacg g 21

<210> SEQ ID NO 724
<211> LENGTH: 22
<212> TYPE: RNA
<213> ORGANISM: Homo sapiens

<400> SEQUENCE: 724
ucuacagugc acgugucucc ag 22

<210> SEQ ID NO 725

<211> LENGTH: 22
<212> TYPE: RNA
<213> ORGANISM: Homo sapiens

<400> SEQUENCE: 725
ggagacgcgg cccuguugga gu 22

<210> SEQ ID NO 726
<211> LENGTH: 22
<212> TYPE: RNA
<213> ORGANISM: Homo sapiens

<400> SEQUENCE: 726
gcuauuucac gacaccaggg uu 22

<210> SEQ ID NO 727
<211> LENGTH: 22
<212> TYPE: RNA
<213> ORGANISM: Homo sapiens

<400> SEQUENCE: 727
gcuacuucac aacaccaggg cc 22

<210> SEQ ID NO 728
<211> LENGTH: 23
<212> TYPE: RNA
<213> ORGANISM: Homo sapiens

<400> SEQUENCE: 728
agcugguguu gugaaucagg ccg 23

<210> SEQ ID NO 729
<211> LENGTH: 23
<212> TYPE: RNA
<213> ORGANISM: Homo sapiens

<400> SEQUENCE: 729
uuauugcuua agaauacgcg uag 23

<210> SEQ ID NO 730
<211> LENGTH: 22
<212> TYPE: RNA
<213> ORGANISM: Homo sapiens

<400> SEQUENCE: 730
caucaucguc ucaaaugagu cu 22

<210> SEQ ID NO 731
<211> LENGTH: 23
<212> TYPE: RNA
<213> ORGANISM: Homo sapiens

<400> SEQUENCE: 731
acuccauuug uuuugaugau gga 23

<210> SEQ ID NO 732
<211> LENGTH: 22
<212> TYPE: RNA
<213> ORGANISM: Homo sapiens

<400> SEQUENCE: 732
auguagggcu aaaagccaug gg 22

<210> SEQ ID NO 733
<211> LENGTH: 23
<212> TYPE: RNA
<213> ORGANISM: Homo sapiens

<400> SEQUENCE: 733
uauggcuuuu cauuccuaug uga 23

<210> SEQ ID NO 734
<211> LENGTH: 22
<212> TYPE: RNA
<213> ORGANISM: Homo sapiens

<400> SEQUENCE: 734
uauagggauu ggagccgugg cg 22

<210> SEQ ID NO 735
<211> LENGTH: 23
<212> TYPE: RNA
<213> ORGANISM: Homo sapiens

<400> SEQUENCE: 735
uauggcuuuu uauuccuaug uga 23

<210> SEQ ID NO 736
<211> LENGTH: 22
<212> TYPE: RNA
<213> ORGANISM: Homo sapiens

<400> SEQUENCE: 736
ugugacuggu ugaccagagg gg 22

<210> SEQ ID NO 737
<211> LENGTH: 22
<212> TYPE: RNA
<213> ORGANISM: Homo sapiens

<400> SEQUENCE: 737
uuuggucccc uucaaccagc ua 22

<210> SEQ ID NO 738
<211> LENGTH: 22
<212> TYPE: RNA
<213> ORGANISM: Homo sapiens

<400> SEQUENCE: 738
uuuggucccc uucaaccagc ug 22

<210> SEQ ID NO 739
<211> LENGTH: 24
<212> TYPE: RNA
<213> ORGANISM: Homo sapiens

<400> SEQUENCE: 739
ccagacagaa uucuaugcac uuuc 24

<210> SEQ ID NO 740
<211> LENGTH: 22
<212> TYPE: RNA
<213> ORGANISM: Homo sapiens

<400> SEQUENCE: 740
ucaaaacuga ggggcauuuu cu 22

<210> SEQ ID NO 741
<211> LENGTH: 19
<212> TYPE: RNA
<213> ORGANISM: Homo sapiens

<400> SEQUENCE: 741
gaugaugcug cugaugcug 19

<210> SEQ ID NO 742
<211> LENGTH: 18
<212> TYPE: RNA
<213> ORGANISM: Homo sapiens

<400> SEQUENCE: 742
cagggaggug aaugugau 18

<210> SEQ ID NO 743
<211> LENGTH: 22
<212> TYPE: RNA
<213> ORGANISM: Homo sapiens

<400> SEQUENCE: 743
accguggcuu ucgauuguua cu 22

<210> SEQ ID NO 744
<211> LENGTH: 22
<212> TYPE: RNA
<213> ORGANISM: Homo sapiens

<400> SEQUENCE: 744
uaacagucua cagccauggu cg 22

<210> SEQ ID NO 745
<211> LENGTH: 21
<212> TYPE: RNA
<213> ORGANISM: Homo sapiens

<400> SEQUENCE: 745
acucuuuccc uguugcacua c 21

<210> SEQ ID NO 746
<211> LENGTH: 22
<212> TYPE: RNA
<213> ORGANISM: Homo sapiens

<400> SEQUENCE: 746
cagugcaaug augaaagggc au 22

<210> SEQ ID NO 747
<211> LENGTH: 22
<212> TYPE: RNA
<213> ORGANISM: Homo sapiens

<400> SEQUENCE: 747
uucacauugu gcuacugucu gc 22

<210> SEQ ID NO 748
<211> LENGTH: 22
<212> TYPE: RNA
<213> ORGANISM: Homo sapiens

<400> SEQUENCE: 748
cagugcaaug uuaaaagggc au 22

<210> SEQ ID NO 749
<211> LENGTH: 18
<212> TYPE: RNA
<213> ORGANISM: Homo sapiens

<400> SEQUENCE: 749
gcaugggugg uucagugg 18

<210> SEQ ID NO 750
<211> LENGTH: 22
<212> TYPE: RNA
<213> ORGANISM: Homo sapiens

<400> SEQUENCE: 750
acucggcgug gcgucggucg ug 22

<210> SEQ ID NO 751
<211> LENGTH: 18
<212> TYPE: RNA
<213> ORGANISM: Homo sapiens

<400> SEQUENCE: 751
acguuggcuc ugguggug 18

<210> SEQ ID NO 752
<211> LENGTH: 22
<212> TYPE: RNA
<213> ORGANISM: Homo sapiens

<400> SEQUENCE: 752
uuuucaacuc uaaugggaga ga 22

<210> SEQ ID NO 753
<211> LENGTH: 22
<212> TYPE: RNA
<213> ORGANISM: Homo sapiens

<400> SEQUENCE: 753
uuugaggcua cagugagaug ug 22

<210> SEQ ID NO 754
<211> LENGTH: 22
<212> TYPE: RNA
<213> ORGANISM: Homo sapiens

<400> SEQUENCE: 754
uuuagagacg gggucuugcu cu 22

<210> SEQ ID NO 755
<211> LENGTH: 21
<212> TYPE: RNA
<213> ORGANISM: Homo sapiens

<400> SEQUENCE: 755
uugggacaua cuuaugcuaa a 21

<210> SEQ ID NO 756
<211> LENGTH: 24
<212> TYPE: RNA
<213> ORGANISM: Homo sapiens

<400> SEQUENCE: 756
uugcagcugc cugggaguga cuuc 24

<210> SEQ ID NO 757
<211> LENGTH: 22
<212> TYPE: RNA
<213> ORGANISM: Homo sapiens

<400> SEQUENCE: 757
uucuggaauu cugugugagg ga 22

<210> SEQ ID NO 758
<211> LENGTH: 22
<212> TYPE: RNA
<213> ORGANISM: Homo sapiens

<400> SEQUENCE: 758
uucauucggc uguccagaug ua 22

<210> SEQ ID NO 759
<211> LENGTH: 17
<212> TYPE: RNA
<213> ORGANISM: Homo sapiens

<400> SEQUENCE: 759
uucaaguaau ucaggug 17

<210> SEQ ID NO 760
<211> LENGTH: 22
<212> TYPE: RNA
<213> ORGANISM: Homo sapiens

<400> SEQUENCE: 760
uuagggcccu ggcuccaucu cc 22

<210> SEQ ID NO 761
<211> LENGTH: 21
<212> TYPE: RNA
<213> ORGANISM: Homo sapiens

<400> SEQUENCE: 761
cuuuuugcgg ucugggcuug c 21

<210> SEQ ID NO 762
<211> LENGTH: 21
<212> TYPE: RNA
<213> ORGANISM: Homo sapiens

<400> SEQUENCE: 762
uuaggccgca gaucugggug a 21

<210> SEQ ID NO 763
<211> LENGTH: 22
<212> TYPE: RNA
<213> ORGANISM: Homo sapiens

<400> SEQUENCE: 763
ugugagguug gcauuguugu cu 22

<210> SEQ ID NO 764
<211> LENGTH: 22
<212> TYPE: RNA
<213> ORGANISM: Homo sapiens

<400> SEQUENCE: 764
aagcccuuac cccaaaaagc au 22

<210> SEQ ID NO 765
<211> LENGTH: 22
<212> TYPE: RNA
<213> ORGANISM: Homo sapiens

<400> SEQUENCE: 765
uggguggucu ggagauuugu gc 22

<210> SEQ ID NO 766
<211> LENGTH: 25
<212> TYPE: RNA
<213> ORGANISM: Homo sapiens

<400> SEQUENCE: 766
ugggaacggg uuccggcaga cgcug 25

<210> SEQ ID NO 767
<211> LENGTH: 24
<212> TYPE: RNA
<213> ORGANISM: Homo sapiens

<400> SEQUENCE: 767
uggcccugac ugaagaccag cagu 24

<210> SEQ ID NO 768
<211> LENGTH: 19
<212> TYPE: RNA
<213> ORGANISM: Homo sapiens

<400> SEQUENCE: 768
uggauuuuug gaucaggga 19

<210> SEQ ID NO 769
<211> LENGTH: 22
<212> TYPE: RNA
<213> ORGANISM: Homo sapiens

<400> SEQUENCE: 769
aagcccuuac cccaaaaagu au 22

<210> SEQ ID NO 770
<211> LENGTH: 23
<212> TYPE: RNA
<213> ORGANISM: Homo sapiens

<400> SEQUENCE: 770
uggaguccag gaaucugcau uuu 23

<210> SEQ ID NO 771
<211> LENGTH: 21
<212> TYPE: RNA
<213> ORGANISM: Homo sapiens

<400> SEQUENCE: 771
uggacugccc ugaucuggag a 21

<210> SEQ ID NO 772
<211> LENGTH: 22
<212> TYPE: RNA
<213> ORGANISM: Homo sapiens

<400> SEQUENCE: 772
ugcuggauca gugguucgag uc 22

<210> SEQ ID NO 773
<211> LENGTH: 21
<212> TYPE: RNA
<213> ORGANISM: Homo sapiens

<400> SEQUENCE: 773
ugcaggacca agaugagccc u 21

<210> SEQ ID NO 774
<211> LENGTH: 22
<212> TYPE: RNA
<213> ORGANISM: Homo sapiens

<400> SEQUENCE: 774
ucugggcaac aaagugagac cu 22

<210> SEQ ID NO 775
<211> LENGTH: 22
<212> TYPE: RNA
<213> ORGANISM: Homo sapiens

<400> SEQUENCE: 775
ucuauacaga cccuggcuuu uc 22

<210> SEQ ID NO 776
<211> LENGTH: 22
<212> TYPE: RNA
<213> ORGANISM: Homo sapiens

<400> SEQUENCE: 776
ucuacaaagg aaagcgcuuu cu 22

<210> SEQ ID NO 777
<211> LENGTH: 20
<212> TYPE: RNA
<213> ORGANISM: Homo sapiens

<400> SEQUENCE: 777
ucguuugccu uuuucugcuu 20

<210> SEQ ID NO 778
<211> LENGTH: 17
<212> TYPE: RNA
<213> ORGANISM: Homo sapiens

<400> SEQUENCE: 778
ucgccuccuc cucuccc 17

<210> SEQ ID NO 779
<211> LENGTH: 17
<212> TYPE: RNA
<213> ORGANISM: Homo sapiens

<400> SEQUENCE: 779
ucccaccgcu gccaccc 17

<210> SEQ ID NO 780
<211> LENGTH: 21
<212> TYPE: RNA
<213> ORGANISM: Homo sapiens

<400> SEQUENCE: 780
ucacagugaa ccggucucuu u 21

<210> SEQ ID NO 781
<211> LENGTH: 17
<212> TYPE: RNA
<213> ORGANISM: Homo sapiens

<400> SEQUENCE: 781
ucauauugcu ucuuucu 17

<210> SEQ ID NO 782
<211> LENGTH: 22
<212> TYPE: RNA
<213> ORGANISM: Homo sapiens

<400> SEQUENCE: 782
uaguacugug cauaucaucu au 22

<210> SEQ ID NO 783
<211> LENGTH: 22
<212> TYPE: RNA
<213> ORGANISM: Homo sapiens

<400> SEQUENCE: 783
uacguagaua uauauguauu uu 22

<210> SEQ ID NO 784
<211> LENGTH: 20
<212> TYPE: RNA
<213> ORGANISM: Homo sapiens

<400> SEQUENCE: 784
uaaagagccc uguggagaca 20

<210> SEQ ID NO 785
<211> LENGTH: 22
<212> TYPE: RNA
<213> ORGANISM: Homo sapiens

<400> SEQUENCE: 785
cugaagcuca gagggcucug au 22

<210> SEQ ID NO 786
<211> LENGTH: 17
<212> TYPE: RNA
<213> ORGANISM: Homo sapiens

<400> SEQUENCE: 786
gugggggaga ggcuguc 17

<210> SEQ ID NO 787
<211> LENGTH: 17
<212> TYPE: RNA
<213> ORGANISM: Homo sapiens

<400> SEQUENCE: 787
ucccuguucg ggcgcca 17

<210> SEQ ID NO 788
<211> LENGTH: 18
<212> TYPE: RNA

```
<213> ORGANISM: Homo sapiens

<400> SEQUENCE: 788

gucccuguuc aggcgcca                                                 18

<210> SEQ ID NO 789
<211> LENGTH: 22
<212> TYPE: RNA
<213> ORGANISM: Homo sapiens

<400> SEQUENCE: 789

ucggauccgu cugagcuugg cu                                            22

<210> SEQ ID NO 790
<211> LENGTH: 25
<212> TYPE: RNA
<213> ORGANISM: Homo sapiens

<400> SEQUENCE: 790

gggcgacaaa gcaagacucu uucuu                                         25

<210> SEQ ID NO 791
<211> LENGTH: 26
<212> TYPE: RNA
<213> ORGANISM: Homo sapiens

<400> SEQUENCE: 791

gaugaugaug gcagcaaauu cugaaa                                        26

<210> SEQ ID NO 792
<211> LENGTH: 22
<212> TYPE: RNA
<213> ORGANISM: Homo sapiens

<400> SEQUENCE: 792

cuuggcaccu agcaagcacu ca                                            22

<210> SEQ ID NO 793
<211> LENGTH: 23
<212> TYPE: RNA
<213> ORGANISM: Homo sapiens

<400> SEQUENCE: 793

cuggagauau ggaagagcug ugu                                           23

<210> SEQ ID NO 794
<211> LENGTH: 22
<212> TYPE: RNA
<213> ORGANISM: Homo sapiens

<400> SEQUENCE: 794

cuggacugag ccgugcuacu gg                                            22

<210> SEQ ID NO 795
<211> LENGTH: 18
<212> TYPE: RNA
<213> ORGANISM: Homo sapiens

<400> SEQUENCE: 795

cgggcguggu gguggggg                                                 18

<210> SEQ ID NO 796
<211> LENGTH: 21
```

<212> TYPE: RNA
<213> ORGANISM: Homo sapiens

<400> SEQUENCE: 796
ccuguugaag uguaaucccc a 21

<210> SEQ ID NO 797
<211> LENGTH: 23
<212> TYPE: RNA
<213> ORGANISM: Homo sapiens

<400> SEQUENCE: 797
ccucagggcu guagaacagg gcu 23

<210> SEQ ID NO 798
<211> LENGTH: 22
<212> TYPE: RNA
<213> ORGANISM: Homo sapiens

<400> SEQUENCE: 798
caggaugugg ucaaguguug uu 22

<210> SEQ ID NO 799
<211> LENGTH: 23
<212> TYPE: RNA
<213> ORGANISM: Homo sapiens

<400> SEQUENCE: 799
caagucuuau uugagcaccu guu 23

<210> SEQ ID NO 800
<211> LENGTH: 22
<212> TYPE: RNA
<213> ORGANISM: Homo sapiens

<400> SEQUENCE: 800
augguacccu ggcauacuga gu 22

<210> SEQ ID NO 801
<211> LENGTH: 22
<212> TYPE: RNA
<213> ORGANISM: Homo sapiens

<400> SEQUENCE: 801
augggugaau uuguagaagg au 22

<210> SEQ ID NO 802
<211> LENGTH: 19
<212> TYPE: RNA
<213> ORGANISM: Homo sapiens

<400> SEQUENCE: 802
auggauaagg cuuuggcuu 19

<210> SEQ ID NO 803
<211> LENGTH: 18
<212> TYPE: RNA
<213> ORGANISM: Homo sapiens

<400> SEQUENCE: 803
aucccaccuc ugccacca 18

<210> SEQ ID NO 804

<211> LENGTH: 21
<212> TYPE: RNA
<213> ORGANISM: Homo sapiens

<400> SEQUENCE: 804
cauuauuacu uuugguacgc g 21

<210> SEQ ID NO 805
<211> LENGTH: 22
<212> TYPE: RNA
<213> ORGANISM: Homo sapiens

<400> SEQUENCE: 805
ucguaccgug aguaauaaug cg 22

<210> SEQ ID NO 806
<211> LENGTH: 22
<212> TYPE: RNA
<213> ORGANISM: Homo sapiens

<400> SEQUENCE: 806
ucacaaguca ggcucuuggg ac 22

<210> SEQ ID NO 807
<211> LENGTH: 22
<212> TYPE: RNA
<213> ORGANISM: Homo sapiens

<400> SEQUENCE: 807
acggguuagg cucuugggag cu 22

<210> SEQ ID NO 808
<211> LENGTH: 22
<212> TYPE: RNA
<213> ORGANISM: Homo sapiens

<400> SEQUENCE: 808
ucccugagac ccuaacuugu ga 22

<210> SEQ ID NO 809
<211> LENGTH: 24
<212> TYPE: RNA
<213> ORGANISM: Homo sapiens

<400> SEQUENCE: 809
ucccugagac ccuuuaaccu guga 24

<210> SEQ ID NO 810
<211> LENGTH: 22
<212> TYPE: RNA
<213> ORGANISM: Homo sapiens

<400> SEQUENCE: 810
acaggugagg uucuugggag cc 22

<210> SEQ ID NO 811
<211> LENGTH: 21
<212> TYPE: RNA
<213> ORGANISM: Homo sapiens

<400> SEQUENCE: 811
auauaugaug acuuagcuuu u 21

<210> SEQ ID NO 812
<211> LENGTH: 21
<212> TYPE: RNA
<213> ORGANISM: Homo sapiens

<400> SEQUENCE: 812
aguuaggauu aggucgugga a 21

<210> SEQ ID NO 813
<211> LENGTH: 21
<212> TYPE: RNA
<213> ORGANISM: Homo sapiens

<400> SEQUENCE: 813
agugaaugau ggguucugac c 21

<210> SEQ ID NO 814
<211> LENGTH: 22
<212> TYPE: RNA
<213> ORGANISM: Homo sapiens

<400> SEQUENCE: 814
aggcauugac uucucacuag cu 22

<210> SEQ ID NO 815
<211> LENGTH: 22
<212> TYPE: RNA
<213> ORGANISM: Homo sapiens

<400> SEQUENCE: 815
cggaugagca aagaaagugg uu 22

<210> SEQ ID NO 816
<211> LENGTH: 23
<212> TYPE: RNA
<213> ORGANISM: Homo sapiens

<400> SEQUENCE: 816
aggaugagca aagaaaguag auu 23

<210> SEQ ID NO 817
<211> LENGTH: 24
<212> TYPE: RNA
<213> ORGANISM: Homo sapiens

<400> SEQUENCE: 817
agccuggaag cuggagccug cagu 24

<210> SEQ ID NO 818
<211> LENGTH: 21
<212> TYPE: RNA
<213> ORGANISM: Homo sapiens

<400> SEQUENCE: 818
agagaagaag aucagccugc a 21

<210> SEQ ID NO 819
<211> LENGTH: 22
<212> TYPE: RNA
<213> ORGANISM: Homo sapiens

<400> SEQUENCE: 819
agaaggaaau ugaauucauu ua 22

<210> SEQ ID NO 820
<211> LENGTH: 21
<212> TYPE: RNA
<213> ORGANISM: Homo sapiens

<400> SEQUENCE: 820
acucuagcug ccaaaggcgc u 21

<210> SEQ ID NO 821
<211> LENGTH: 21
<212> TYPE: RNA
<213> ORGANISM: Homo sapiens

<400> SEQUENCE: 821
acggugcugg auguggccuu u 21

<210> SEQ ID NO 822
<211> LENGTH: 22
<212> TYPE: RNA
<213> ORGANISM: Homo sapiens

<400> SEQUENCE: 822
acgcccuucc cccccuucuu ca 22

<210> SEQ ID NO 823
<211> LENGTH: 27
<212> TYPE: RNA
<213> ORGANISM: Homo sapiens

<400> SEQUENCE: 823
accuucuugu auaagcacug ugcuaaa 27

<210> SEQ ID NO 824
<211> LENGTH: 22
<212> TYPE: RNA
<213> ORGANISM: Homo sapiens

<400> SEQUENCE: 824
acccgucccg uucguccccg ga 22

<210> SEQ ID NO 825
<211> LENGTH: 19
<212> TYPE: RNA
<213> ORGANISM: Homo sapiens

<400> SEQUENCE: 825
aauggauuuu uggagcagg 19

<210> SEQ ID NO 826
<211> LENGTH: 21
<212> TYPE: RNA
<213> ORGANISM: Homo sapiens

<400> SEQUENCE: 826
aagugaucua aaggccuaca u 21

<210> SEQ ID NO 827
<211> LENGTH: 26
<212> TYPE: RNA
<213> ORGANISM: Homo sapiens

<400> SEQUENCE: 827
aaguaguugg uuuguaugag augguu 26

<210> SEQ ID NO 828
<211> LENGTH: 22
<212> TYPE: RNA
<213> ORGANISM: Homo sapiens

<400> SEQUENCE: 828
aacuggauca auuauaggag ug 22

<210> SEQ ID NO 829
<211> LENGTH: 22
<212> TYPE: RNA
<213> ORGANISM: Homo sapiens

<400> SEQUENCE: 829
cguguucaca gcggaccuug au 22

<210> SEQ ID NO 830
<211> LENGTH: 20
<212> TYPE: RNA
<213> ORGANISM: Homo sapiens

<400> SEQUENCE: 830
uaaggcacgc ggugaaugcc 20

<210> SEQ ID NO 831
<211> LENGTH: 20
<212> TYPE: RNA
<213> ORGANISM: Homo sapiens

<400> SEQUENCE: 831
cuuccucguc ugucugcccc 20

<210> SEQ ID NO 832
<211> LENGTH: 21
<212> TYPE: RNA
<213> ORGANISM: Homo sapiens

<400> SEQUENCE: 832
uccuucugcu ccguccccca g 21

<210> SEQ ID NO 833
<211> LENGTH: 22
<212> TYPE: RNA
<213> ORGANISM: Homo sapiens

<400> SEQUENCE: 833
ccucuucccc uugucucucc ag 22

<210> SEQ ID NO 834
<211> LENGTH: 22
<212> TYPE: RNA
<213> ORGANISM: Homo sapiens

<400> SEQUENCE: 834
ucggccugac cacccacccc ac 22

<210> SEQ ID NO 835
<211> LENGTH: 20
<212> TYPE: RNA
<213> ORGANISM: Homo sapiens

<400> SEQUENCE: 835
ugagcccugu ccucccgcag 20

<210> SEQ ID NO 836
<211> LENGTH: 20
<212> TYPE: RNA
<213> ORGANISM: Homo sapiens

<400> SEQUENCE: 836
gugucugggc ggacagcugc 20

<210> SEQ ID NO 837
<211> LENGTH: 23
<212> TYPE: RNA
<213> ORGANISM: Homo sapiens

<400> SEQUENCE: 837
cucucaccac ugcccuccca cag 23

<210> SEQ ID NO 838
<211> LENGTH: 21
<212> TYPE: RNA
<213> ORGANISM: Homo sapiens

<400> SEQUENCE: 838
gugggcgggg gcaggugugu g 21

<210> SEQ ID NO 839
<211> LENGTH: 20
<212> TYPE: RNA
<213> ORGANISM: Homo sapiens

<400> SEQUENCE: 839
ucacaccugc cucgcccccc 20

<210> SEQ ID NO 840
<211> LENGTH: 20
<212> TYPE: RNA
<213> ORGANISM: Homo sapiens

<400> SEQUENCE: 840
cgugccaccc uuuuccccag 20

<210> SEQ ID NO 841
<211> LENGTH: 26
<212> TYPE: RNA
<213> ORGANISM: Homo sapiens

<400> SEQUENCE: 841
gugagggcau gcaggccugg augggg 26

<210> SEQ ID NO 842
<211> LENGTH: 22
<212> TYPE: RNA
<213> ORGANISM: Homo sapiens

<400> SEQUENCE: 842
ucaccagccc uguguucccu ag 22

<210> SEQ ID NO 843
<211> LENGTH: 22
<212> TYPE: RNA
<213> ORGANISM: Homo sapiens

<400> SEQUENCE: 843 gugggguacgg cccagugggg gg 22

<210> SEQ ID NO 844
<211> LENGTH: 22
<212> TYPE: RNA
<213> ORGANISM: Homo sapiens

<400> SEQUENCE: 844
ugagccccug ugccgccccc ag 22

<210> SEQ ID NO 845
<211> LENGTH: 19
<212> TYPE: RNA
<213> ORGANISM: Homo sapiens

<400> SEQUENCE: 845
gugaggacuc gggaggugg 19

<210> SEQ ID NO 846
<211> LENGTH: 21
<212> TYPE: RNA
<213> ORGANISM: Homo sapiens

<400> SEQUENCE: 846
ccccaccucc ucucuccuca g 21

<210> SEQ ID NO 847
<211> LENGTH: 22
<212> TYPE: RNA
<213> ORGANISM: Homo sapiens

<400> SEQUENCE: 847
aacgccauua ucacacuaaa ua 22

<210> SEQ ID NO 848
<211> LENGTH: 22
<212> TYPE: RNA
<213> ORGANISM: Homo sapiens

<400> SEQUENCE: 848
uggaguguga caaugguguu ug 22

<210> SEQ ID NO 849
<211> LENGTH: 20
<212> TYPE: RNA
<213> ORGANISM: Homo sapiens

<400> SEQUENCE: 849
ucacuguuca gacaggcgga 20

<210> SEQ ID NO 850
<211> LENGTH: 21
<212> TYPE: RNA
<213> ORGANISM: Homo sapiens

<400> SEQUENCE: 850
uggcagggag gcugggaggg g 21

<210> SEQ ID NO 851
<211> LENGTH: 18
<212> TYPE: RNA
<213> ORGANISM: Homo sapiens

<400> SEQUENCE: 851
ucagcuggcc cucauuuc 18

<210> SEQ ID NO 852
<211> LENGTH: 21
<212> TYPE: RNA
<213> ORGANISM: Homo sapiens

<400> SEQUENCE: 852
uguucaugua gauguuuaag c 21

<210> SEQ ID NO 853
<211> LENGTH: 20
<212> TYPE: RNA
<213> ORGANISM: Homo sapiens

<400> SEQUENCE: 853
ucugcagggu uugcuuugag 20

<210> SEQ ID NO 854
<211> LENGTH: 21
<212> TYPE: RNA
<213> ORGANISM: Homo sapiens

<400> SEQUENCE: 854
ucguggccug gucuccauua u 21

<210> SEQ ID NO 855
<211> LENGTH: 21
<212> TYPE: RNA
<213> ORGANISM: Homo sapiens

<400> SEQUENCE: 855
cccggagcca ggaugcagcu c 21

<210> SEQ ID NO 856
<211> LENGTH: 21
<212> TYPE: RNA
<213> ORGANISM: Homo sapiens

<400> SEQUENCE: 856
gugccagcug caguggggga g 21

<210> SEQ ID NO 857
<211> LENGTH: 24
<212> TYPE: RNA
<213> ORGANISM: Homo sapiens

<400> SEQUENCE: 857
agccugauua aacacaugcu cuga 24

<210> SEQ ID NO 858
<211> LENGTH: 22
<212> TYPE: RNA
<213> ORGANISM: Homo sapiens

<400> SEQUENCE: 858
cuccugagcc auucugagcc uc 22

<210> SEQ ID NO 859
<211> LENGTH: 21
<212> TYPE: RNA
<213> ORGANISM: Homo sapiens

<400> SEQUENCE: 859
uaggacacau ggucuacuuc u 21

<210> SEQ ID NO 860
<211> LENGTH: 21
<212> TYPE: RNA
<213> ORGANISM: Homo sapiens

<400> SEQUENCE: 860
agaggauacc cuuuguaugu u 21

<210> SEQ ID NO 861
<211> LENGTH: 23
<212> TYPE: RNA
<213> ORGANISM: Homo sapiens

<400> SEQUENCE: 861
ccugcagcga cuugauggcu ucc 23

<210> SEQ ID NO 862
<211> LENGTH: 27
<212> TYPE: RNA
<213> ORGANISM: Homo sapiens

<400> SEQUENCE: 862
cacuguaggu gauggugaga gugggca 27

<210> SEQ ID NO 863
<211> LENGTH: 23
<212> TYPE: RNA
<213> ORGANISM: Homo sapiens

<400> SEQUENCE: 863
gagggucuug ggagggaugu gac 23

<210> SEQ ID NO 864
<211> LENGTH: 21
<212> TYPE: RNA
<213> ORGANISM: Homo sapiens

<400> SEQUENCE: 864
ccgucgccgc cacccgagcc g 21

<210> SEQ ID NO 865
<211> LENGTH: 22
<212> TYPE: RNA
<213> ORGANISM: Homo sapiens

<400> SEQUENCE: 865
uuuccggcuc gcgugggugu gu 22

<210> SEQ ID NO 866
<211> LENGTH: 21
<212> TYPE: RNA
<213> ORGANISM: Homo sapiens

<400> SEQUENCE: 866
aagcauucuu ucauugguug g 21

<210> SEQ ID NO 867
<211> LENGTH: 21
<212> TYPE: RNA

<213> ORGANISM: Homo sapiens

<400> SEQUENCE: 867
uugcucacug uucuucccua g 21

<210> SEQ ID NO 868
<211> LENGTH: 22
<212> TYPE: RNA
<213> ORGANISM: Homo sapiens

<400> SEQUENCE: 868
acagauucga uucuagggga au 22

<210> SEQ ID NO 869
<211> LENGTH: 23
<212> TYPE: RNA
<213> ORGANISM: Homo sapiens

<400> SEQUENCE: 869
uacccuguag aaccgaauuu gug 23

<210> SEQ ID NO 870
<211> LENGTH: 22
<212> TYPE: RNA
<213> ORGANISM: Homo sapiens

<400> SEQUENCE: 870
caaauucgua ucuaggggaa ua 22

<210> SEQ ID NO 871
<211> LENGTH: 23
<212> TYPE: RNA
<213> ORGANISM: Homo sapiens

<400> SEQUENCE: 871
uacccuguag auccgaauuu gug 23

<210> SEQ ID NO 872
<211> LENGTH: 23
<212> TYPE: RNA
<213> ORGANISM: Homo sapiens

<400> SEQUENCE: 872
agcagcauug uacagggcua uca 23

<210> SEQ ID NO 873
<211> LENGTH: 22
<212> TYPE: RNA
<213> ORGANISM: Homo sapiens

<400> SEQUENCE: 873
ccgcacugug gguacuugcu gc 22

<210> SEQ ID NO 874
<211> LENGTH: 21
<212> TYPE: RNA
<213> ORGANISM: Homo sapiens

<400> SEQUENCE: 874
uaaagugcug acagugcaga u 21

<210> SEQ ID NO 875
<211> LENGTH: 22

<212> TYPE: RNA
<213> ORGANISM: Homo sapiens

<400> SEQUENCE: 875
cugcaaugua agcacuucuu ac 22

<210> SEQ ID NO 876
<211> LENGTH: 23
<212> TYPE: RNA
<213> ORGANISM: Homo sapiens

<400> SEQUENCE: 876
aaaagugcuu acagugcagg uag 23

<210> SEQ ID NO 877
<211> LENGTH: 22
<212> TYPE: RNA
<213> ORGANISM: Homo sapiens

<400> SEQUENCE: 877
acggauguuu gagcaugugc ua 22

<210> SEQ ID NO 878
<211> LENGTH: 23
<212> TYPE: RNA
<213> ORGANISM: Homo sapiens

<400> SEQUENCE: 878
ucaaaugcuc agacuccugu ggu 23

<210> SEQ ID NO 879
<211> LENGTH: 23
<212> TYPE: RNA
<213> ORGANISM: Homo sapiens

<400> SEQUENCE: 879
ucauagcccu guacaaugcu gcu 23

<210> SEQ ID NO 880
<211> LENGTH: 23
<212> TYPE: RNA
<213> ORGANISM: Homo sapiens

<400> SEQUENCE: 880
agcuucuuua cagugcugcc uug 23

<210> SEQ ID NO 881
<211> LENGTH: 23
<212> TYPE: RNA
<213> ORGANISM: Homo sapiens

<400> SEQUENCE: 881
agcagcauug uacagggcua uga 23

<210> SEQ ID NO 882
<211> LENGTH: 22
<212> TYPE: RNA
<213> ORGANISM: Homo sapiens

<400> SEQUENCE: 882
caguuaucac agugcugaug cu 22

<210> SEQ ID NO 883

<211> LENGTH: 21
<212> TYPE: RNA
<213> ORGANISM: Homo sapiens

<400> SEQUENCE: 883
uacaguacug ugauaacuga a 21

<210> SEQ ID NO 884
<211> LENGTH: 22
<212> TYPE: RNA
<213> ORGANISM: Homo sapiens

<400> SEQUENCE: 884
caagcuugua ucuauaggua ug 22

<210> SEQ ID NO 885
<211> LENGTH: 22
<212> TYPE: RNA
<213> ORGANISM: Homo sapiens

<400> SEQUENCE: 885
aacccguaga uccgaacuug ug 22

<210> SEQ ID NO 886
<211> LENGTH: 22
<212> TYPE: RNA
<213> ORGANISM: Homo sapiens

<400> SEQUENCE: 886
uggaauguaa agaaguaugu au 22

<210> SEQ ID NO 887
<211> LENGTH: 22
<212> TYPE: RNA
<213> ORGANISM: Homo sapiens

<400> SEQUENCE: 887
cugcgcaagc uacugccuug cu 22

<210> SEQ ID NO 888
<211> LENGTH: 22
<212> TYPE: RNA
<213> ORGANISM: Homo sapiens

<400> SEQUENCE: 888
ugagguagua guuugugcug uu 22

<210> SEQ ID NO 889
<211> LENGTH: 21
<212> TYPE: RNA
<213> ORGANISM: Homo sapiens

<400> SEQUENCE: 889
cuguacaggc cacugccuug c 21

<210> SEQ ID NO 890
<211> LENGTH: 22
<212> TYPE: RNA
<213> ORGANISM: Homo sapiens

<400> SEQUENCE: 890
ugagguagua guuuguacag uu 22

<210> SEQ ID NO 891
<211> LENGTH: 22
<212> TYPE: RNA
<213> ORGANISM: Homo sapiens

<400> SEQUENCE: 891
cuauacaguc uacugucuuu cc 22

<210> SEQ ID NO 892
<211> LENGTH: 22
<212> TYPE: RNA
<213> ORGANISM: Homo sapiens

<400> SEQUENCE: 892
cuauacaauc uauugccuuc cc 22

<210> SEQ ID NO 893
<211> LENGTH: 22
<212> TYPE: RNA
<213> ORGANISM: Homo sapiens

<400> SEQUENCE: 893
ugagguagua gauuguauag uu 22

<210> SEQ ID NO 894
<211> LENGTH: 22
<212> TYPE: RNA
<213> ORGANISM: Homo sapiens

<400> SEQUENCE: 894
cuauacggcc uccuagcuuu cc 22

<210> SEQ ID NO 895
<211> LENGTH: 22
<212> TYPE: RNA
<213> ORGANISM: Homo sapiens

<400> SEQUENCE: 895
ugagguagga gguuguauag uu 22

<210> SEQ ID NO 896
<211> LENGTH: 22
<212> TYPE: RNA
<213> ORGANISM: Homo sapiens

<400> SEQUENCE: 896
cuauacgacc ugcugccuuu cu 22

<210> SEQ ID NO 897
<211> LENGTH: 22
<212> TYPE: RNA
<213> ORGANISM: Homo sapiens

<400> SEQUENCE: 897
agagguagua gguugcauag uu 22

<210> SEQ ID NO 898
<211> LENGTH: 22
<212> TYPE: RNA
<213> ORGANISM: Homo sapiens

<400> SEQUENCE: 898
uagaguuaca cccugggagu ua 22

<210> SEQ ID NO 899
<211> LENGTH: 22
<212> TYPE: RNA
<213> ORGANISM: Homo sapiens

<400> SEQUENCE: 899
ugagguagua gguuguaugg uu 22

<210> SEQ ID NO 900
<211> LENGTH: 22
<212> TYPE: RNA
<213> ORGANISM: Homo sapiens

<400> SEQUENCE: 900
cuauacaacc uacugccuuc cc 22

<210> SEQ ID NO 901
<211> LENGTH: 22
<212> TYPE: RNA
<213> ORGANISM: Homo sapiens

<400> SEQUENCE: 901
ugagguagua gguugugugg uu 22

<210> SEQ ID NO 902
<211> LENGTH: 22
<212> TYPE: RNA
<213> ORGANISM: Homo sapiens

<400> SEQUENCE: 902
cuguacagcc uccuagcuuu cc 22

<210> SEQ ID NO 903
<211> LENGTH: 21
<212> TYPE: RNA
<213> ORGANISM: Homo sapiens

<400> SEQUENCE: 903
cuauacaauc uacugucuuu c 21

<210> SEQ ID NO 904
<211> LENGTH: 22
<212> TYPE: RNA
<213> ORGANISM: Homo sapiens

<400> SEQUENCE: 904
ugagguagua gguuguauag uu 22

<210> SEQ ID NO 905
<211> LENGTH: 22
<212> TYPE: RNA
<213> ORGANISM: Homo sapiens

<400> SEQUENCE: 905
uaauacugcc ugguaaugau ga 22

<210> SEQ ID NO 906
<211> LENGTH: 21
<212> TYPE: RNA
<213> ORGANISM: Homo sapiens

<400> SEQUENCE: 906
cucuccucuc cuaaccucgc u 21

<210> SEQ ID NO 907
<211> LENGTH: 23
<212> TYPE: RNA
<213> ORGANISM: Homo sapiens

<400> SEQUENCE: 907
agucgagagu gggagaagag cgg 23

<210> SEQ ID NO 908
<211> LENGTH: 19
<212> TYPE: RNA
<213> ORGANISM: Homo sapiens

<400> SEQUENCE: 908
aaaaccgucu aguuacagu 19

<210> SEQ ID NO 909
<211> LENGTH: 23
<212> TYPE: RNA
<213> ORGANISM: Homo sapiens

<400> SEQUENCE: 909
cucagugaug aaaacuuugu cca 23

<210> SEQ ID NO 910
<211> LENGTH: 21
<212> TYPE: RNA
<213> ORGANISM: Homo sapiens

<400> SEQUENCE: 910
guugccuuuu uguucccaug c 21

<210> SEQ ID NO 911
<211> LENGTH: 21
<212> TYPE: RNA
<213> ORGANISM: Homo sapiens

<400> SEQUENCE: 911
uaggcaccaa aaagcaacaa c 21

<210> SEQ ID NO 912
<211> LENGTH: 21
<212> TYPE: RNA
<213> ORGANISM: Homo sapiens

<400> SEQUENCE: 912
gcugcaccgg agacugggua a 21

<210> SEQ ID NO 913
<211> LENGTH: 21
<212> TYPE: RNA
<213> ORGANISM: Homo sapiens

<400> SEQUENCE: 913
uacccagucu ccggugcagc c 21

<210> SEQ ID NO 914
<211> LENGTH: 24
<212> TYPE: RNA
<213> ORGANISM: Homo sapiens

<400> SEQUENCE: 914
uuccucugau gacuuccugu uagu 24

<210> SEQ ID NO 915
<211> LENGTH: 21
<212> TYPE: RNA
<213> ORGANISM: Homo sapiens

<400> SEQUENCE: 915
uggaacugag gaucugagga a 21

<210> SEQ ID NO 916
<211> LENGTH: 21
<212> TYPE: RNA
<213> ORGANISM: Homo sapiens

<400> SEQUENCE: 916
aguggcaaag ucuuuccaua u 21

<210> SEQ ID NO 917
<211> LENGTH: 22
<212> TYPE: RNA
<213> ORGANISM: Homo sapiens

<400> SEQUENCE: 917
uuagcucagc gguuacuucg ac 22

<210> SEQ ID NO 918
<211> LENGTH: 21
<212> TYPE: RNA
<213> ORGANISM: Homo sapiens

<400> SEQUENCE: 918
caagcaaccu gucuggguug u 21

<210> SEQ ID NO 919
<211> LENGTH: 19
<212> TYPE: RNA
<213> ORGANISM: Homo sapiens

<400> SEQUENCE: 919
uaacgcauaa uauggacau 19

<210> SEQ ID NO 920
<211> LENGTH: 21
<212> TYPE: RNA
<213> ORGANISM: Homo sapiens

<400> SEQUENCE: 920
auguccauau uaugggguuag u 21

<210> SEQ ID NO 921
<211> LENGTH: 21
<212> TYPE: RNA
<213> ORGANISM: Homo sapiens

<400> SEQUENCE: 921
caguugcuag uugcacuccu c 21

<210> SEQ ID NO 922
<211> LENGTH: 21
<212> TYPE: RNA
<213> ORGANISM: Homo sapiens

<400> SEQUENCE: 922
aggcagugua uugcuagcgg c 21

<210> SEQ ID NO 923
<211> LENGTH: 21
<212> TYPE: RNA
<213> ORGANISM: Homo sapiens

<400> SEQUENCE: 923
aguucuugcc ugguuucucu a 21

<210> SEQ ID NO 924
<211> LENGTH: 18
<212> TYPE: RNA
<213> ORGANISM: Homo sapiens

<400> SEQUENCE: 924
ucugcauugc cagggauu 18

<210> SEQ ID NO 925
<211> LENGTH: 19
<212> TYPE: RNA
<213> ORGANISM: Homo sapiens

<400> SEQUENCE: 925
uagcuuuaga gacugagag 19

<210> SEQ ID NO 926
<211> LENGTH: 23
<212> TYPE: RNA
<213> ORGANISM: Homo sapiens

<400> SEQUENCE: 926
ugagacaggc uuaugcugcu auc 23

<210> SEQ ID NO 927
<211> LENGTH: 21
<212> TYPE: RNA
<213> ORGANISM: Homo sapiens

<400> SEQUENCE: 927
agcagcauga accugucuca c 21

<210> SEQ ID NO 928
<211> LENGTH: 21
<212> TYPE: RNA
<213> ORGANISM: Homo sapiens

<400> SEQUENCE: 928
ccggcggcag ggguggcacc g 21

<210> SEQ ID NO 929
<211> LENGTH: 20
<212> TYPE: RNA
<213> ORGANISM: Homo sapiens

<400> SEQUENCE: 929
gccuuaggag aaaguuucug 20

<210> SEQ ID NO 930
<211> LENGTH: 19
<212> TYPE: RNA
<213> ORGANISM: Homo sapiens

<400> SEQUENCE: 930
uccuaaggca gucccugga 19

<210> SEQ ID NO 931
<211> LENGTH: 21
<212> TYPE: RNA
<213> ORGANISM: Homo sapiens

<400> SEQUENCE: 931
aaggucgccc ucaaggugac c 21

<210> SEQ ID NO 932
<211> LENGTH: 21
<212> TYPE: RNA
<213> ORGANISM: Homo sapiens

<400> SEQUENCE: 932
augccuggga guugcgaucu g 21

<210> SEQ ID NO 933
<211> LENGTH: 21
<212> TYPE: RNA
<213> ORGANISM: Homo sapiens

<400> SEQUENCE: 933
uggaguuaaa gacuuuuucu c 21

<210> SEQ ID NO 934
<211> LENGTH: 24
<212> TYPE: RNA
<213> ORGANISM: Homo sapiens

<400> SEQUENCE: 934
cagagaauag uuuaaauuag aauc 24

<210> SEQ ID NO 935
<211> LENGTH: 23
<212> TYPE: RNA
<213> ORGANISM: Homo sapiens

<400> SEQUENCE: 935
ugcaacuuac ugagggcuuu gaa 23

<210> SEQ ID NO 936
<211> LENGTH: 21
<212> TYPE: RNA
<213> ORGANISM: Homo sapiens

<400> SEQUENCE: 936 uggggguuuug caguccuuag c 21

<210> SEQ ID NO 937
<211> LENGTH: 21
<212> TYPE: RNA
<213> ORGANISM: Homo sapiens

<400> SEQUENCE: 937
agacacuaua cgagucauau a 21

<210> SEQ ID NO 938
<211> LENGTH: 21
<212> TYPE: RNA
<213> ORGANISM: Homo sapiens

<400> SEQUENCE: 938
auaggacuca uauagugcca g 21

<210> SEQ ID NO 939
<211> LENGTH: 22
<212> TYPE: RNA
<213> ORGANISM: Homo sapiens

<400> SEQUENCE: 939
auccccagau acaauggaca au 22

<210> SEQ ID NO 940
<211> LENGTH: 23
<212> TYPE: RNA
<213> ORGANISM: Homo sapiens

<400> SEQUENCE: 940
uucaccuguu agccugucca gag 23

<210> SEQ ID NO 941
<211> LENGTH: 23
<212> TYPE: RNA
<213> ORGANISM: Homo sapiens

<400> SEQUENCE: 941
ugacagcgcc cugccuggcu cgg 23

<210> SEQ ID NO 942
<211> LENGTH: 23
<212> TYPE: RNA
<213> ORGANISM: Homo sapiens

<400> SEQUENCE: 942
agcgcgggcu gagcgcugcc agu 23

<210> SEQ ID NO 943
<211> LENGTH: 22
<212> TYPE: RNA
<213> ORGANISM: Homo sapiens

<400> SEQUENCE: 943
uauacuacau auaauauaug ua 22

<210> SEQ ID NO 944
<211> LENGTH: 22
<212> TYPE: RNA
<213> ORGANISM: Homo sapiens

<400> SEQUENCE: 944
uauacuacau auaauauaug ua 22

<210> SEQ ID NO 945
<211> LENGTH: 23
<212> TYPE: RNA
<213> ORGANISM: Homo sapiens

<400> SEQUENCE: 945
uagcaccauc ugaaaucggu uau 23

<210> SEQ ID NO 946
<211> LENGTH: 22
<212> TYPE: RNA

<213> ORGANISM: Homo sapiens

<400> SEQUENCE: 946
gugcaaaagu caucacgguu uu 22

<210> SEQ ID NO 947
<211> LENGTH: 21
<212> TYPE: RNA
<213> ORGANISM: Homo sapiens

<400> SEQUENCE: 947
accgcgauga cuuuugcauc a 21

<210> SEQ ID NO 948
<211> LENGTH: 23
<212> TYPE: RNA
<213> ORGANISM: Homo sapiens

<400> SEQUENCE: 948
ucaccgcggu cuuuuccucc cac 23

<210> SEQ ID NO 949
<211> LENGTH: 21
<212> TYPE: RNA
<213> ORGANISM: Homo sapiens

<400> SEQUENCE: 949
uuggggaaac ggccgcugag u 21

<210> SEQ ID NO 950
<211> LENGTH: 21
<212> TYPE: RNA
<213> ORGANISM: Homo sapiens

<400> SEQUENCE: 950
uccucccaug ccaagaacuc c 21

<210> SEQ ID NO 951
<211> LENGTH: 21
<212> TYPE: RNA
<213> ORGANISM: Homo sapiens

<400> SEQUENCE: 951
gguucuuagc auaggagguc u 21

<210> SEQ ID NO 952
<211> LENGTH: 22
<212> TYPE: RNA
<213> ORGANISM: Homo sapiens

<400> SEQUENCE: 952
cugcgugucc cuaggugagg gg 22

<210> SEQ ID NO 953
<211> LENGTH: 22
<212> TYPE: RNA
<213> ORGANISM: Homo sapiens

<400> SEQUENCE: 953
ggcacagggc gaguggaaag aa 22

<210> SEQ ID NO 954
<211> LENGTH: 22

<212> TYPE: RNA
<213> ORGANISM: Homo sapiens

<400> SEQUENCE: 954
ucacuaccug acaauacagu au 22

<210> SEQ ID NO 955
<211> LENGTH: 22
<212> TYPE: RNA
<213> ORGANISM: Homo sapiens

<400> SEQUENCE: 955
ugcuguauug ucagguagug au 22

<210> SEQ ID NO 956
<211> LENGTH: 24
<212> TYPE: RNA
<213> ORGANISM: Homo sapiens

<400> SEQUENCE: 956
uggaggugau gaacugucug agcc 24

<210> SEQ ID NO 957
<211> LENGTH: 21
<212> TYPE: RNA
<213> ORGANISM: Homo sapiens

<400> SEQUENCE: 957
ugcguguccc gccuguuccc u 21

<210> SEQ ID NO 958
<211> LENGTH: 24
<212> TYPE: RNA
<213> ORGANISM: Homo sapiens

<400> SEQUENCE: 958
ugugcugauu gucacguucu gauu 24

<210> SEQ ID NO 959
<211> LENGTH: 24
<212> TYPE: RNA
<213> ORGANISM: Homo sapiens

<400> SEQUENCE: 959
acagaugaug aacuuauuga cggg 24

<210> SEQ ID NO 960
<211> LENGTH: 23
<212> TYPE: RNA
<213> ORGANISM: Homo sapiens

<400> SEQUENCE: 960
accuuccucu ccaugggucu uuc 23

<210> SEQ ID NO 961
<211> LENGTH: 22
<212> TYPE: RNA
<213> ORGANISM: Homo sapiens

<400> SEQUENCE: 961
agacccauug aggagaaggu uc 22

<210> SEQ ID NO 962

-continued

```
<211> LENGTH: 21
<212> TYPE: RNA
<213> ORGANISM: Homo sapiens

<400> SEQUENCE: 962

uucucaagag ggaggcaauc a                                           21
```

MIRNA IN THE DIAGNOSIS OF OVARIAN CANCER

CROSS REFERENCE TO RELATED APPLICATION

This application is a 35 U.S.C. 371 National Phase Entry Application from PCT/EP2011/051734, filed Feb. 7, 2011, which claims the benefit of European Patent Application No. 10152809.9 filed on Feb. 5, 2010, the disclosures of which are incorporated herein in their entirety by reference.

BACKGROUND OF THE INVENTION

MicroRNAs (miRNA) are a recently discovered class of small non-coding RNAs (17-14 nucleotides). Due to their function as regulators of gene expression they play a critical role both in physiological and in pathological processes, such as cancer (Calin and Croce 2006; Esquela-Kerscher and Slack 2006; Zhang, Pan et al. 2007; Sassen, Miska et al. 2008).

There is increasing evidence that miRNAs are not only found in tissues but also in human blood both as free circulating nucleic acids and in mononuclear cells. A recent proof-of-principle study demonstrated miRNA expression pattern in pooled blood sera and pooled blood cells, both in healthy individuals and in cancer patients including patients with lung cancer (Chen, Ba et al. 2008). In addition, a remarkable stability of miRNAs in human sera was recently demonstrated (Chen, Ba et al. 2008; Gilad, Meiri et al. 2008). These findings make miRNA a potential tool for diagnostics for various types of diseases based on blood analysis.

Thus, although various markers have been proposed to indicate specific types of disorders such as Ovarian cancer there is still a need for more efficient and effective methods and compositions for the diagnosis of diseases.

Ovarian Cancer

Ovarian cancer is a cancerous growth arising from different parts of the ovary.

The most common form of ovarian cancer (≥80%) arises from the outer lining (epithelium) of the ovary. However, recent evidence shows cells that line the Fallopian tube (epithelium) also to be prone to develop into the same kind of cancer as seen in the ovaries. Since the ovaries and tubes are closely related to each other, it is hypothesized that these cells can mimic ovarian cancer. Other forms arise from the egg cells (germ cell tumor).

In 2004, in the United States, 25,580 new cases were diagnosed and 16,090 women died of ovarian cancer. The risk increases with age and decreases with pregnancy. Lifetime risk is about 1.6%, but women with affected first-relatives have a 5% risk. Women with a mutated BRCA1 or BRCA2 gene carry a risk between 25% and 60% depending on the specific mutation. Ovarian cancer is the fifth leading cause of death from cancer in women and the leading cause of death from gynecological cancer.

In early stages ovarian cancer is associated with abdominal distension 10-year relative survival ranges from 84.1% in stage 1A to 10.4% in stage IIIC Ovarian cancer causes non-specific symptoms. Early diagnosis would result in better survival, on the assumption that stage I and II cancers progress to stage III and IV cancers (but this has not been proven). Most women with ovarian cancer report one or more symptoms such as abdominal pain or discomfort, an abdominal mass, bloating, back pain, urinary urgency, constipation, tiredness and a range of other non-specific symptoms, as well as more specific symptoms such as pelvic pain, abnormal vaginal bleeding or involuntary weight loss. There can be a build-up of fluid (ascites) in the abdominal cavity.

Diagnosis of ovarian cancer starts with a physical examination (including a pelvic examination), a blood test (for CA-125 and sometimes other markers), and transvaginal ultrasound. The diagnosis must be confirmed with surgery to inspect the abdominal cavity, take biopsies (tissue samples for microscopic analysis) and look for cancer cells in the abdominal fluid.

Treatment usually involves chemotherapy and surgery, and sometimes radiotherapy.

In most cases, the cause of ovarian cancer remains unknown. Older women, and in those who have a first or second degree relative with the disease, have an increased risk. Hereditary forms of ovarian cancer can be caused by mutations in specific genes (most notably BRCA1 and BRCA2, but also in genes for hereditary nonpolyposis colorectal cancer). Infertile women and those with a condition called endometriosis, those who have never been pregnant and those who use postmenopausal estrogen replacement therapy are at increased risk. Use of combined oral contraceptive pills is a protective factor. The risk is also lower in women who have had their uterine tubes blocked surgically (tubal ligation).

Ovarian cancer can also be a secondary cancer, the result of metastasis from a primary cancer elsewhere in the body. 7% of ovarian cancers are due to metastases while the rest are primary cancers. Common primary cancers are breast cancer and gastrointestinal cancer (A common mistake is to name all peritoneal metastases from any gastrointestinal cancer as Krukenberg cancer, but this is only the case if it originates from primary gastric cancer). Surface epithelial-stromal tumor can originate in the peritoneum (the lining of the abdominal cavity), in which case the ovarian cancer is secondary to primary peritoneal cancer, but treatment is basically the same as for primary surface epithelial-stromal tumor involving the peritoneum.

Staging

Ovarian cancer is staging is by the FIGO staging system and uses information obtained after surgery, which can include a total abdominal hysterectomy, removal of (usually) both ovaries and fallopian tubes, (usually) the omentum, and pelvic (peritomeal) washings for cytopathology. The AJCC stage is the same as the FIGO stage.

Stage I—limited to one or both ovaries
- IA—involves one ovary; capsule intact; no tumor on ovarian surface; no malignant cells in ascites or peritoneal washings
- IB—involves both ovaries; capsule intact; no tumor on ovarian surface; negative washings
- IC—tumor limited to ovaries with any of the following: capsule ruptured, tumor on ovarian surface, positive washings Stage II—pelvic extension or implants
- IIA—extension or implants onto uterus or fallopian tube; negative washings
- IIB—extension or implants onto other pelvic structures; negative washings
- IIC—pelvic extension or implants with positive peritoneal washings Stage III—microscopic peritoneal implants outside of the pelvis; or limited to the pelvis with extension to the small bowel or omentum IIIA—microscopic peritoneal metastases beyond pelvis IIIB—macroscopic peritoneal metastases beyond pelvis less than 2 cm in size IIIC—peritoneal metastases beyond pelvis >2 cm or lymph node metastases Stage IV—distant metastases to the liver or outside the peritoneal cavity Para-aortic lymph node metastases are considered regional lymph nodes (Stage IIIC).

Screening

Routine screening of the general population is not recommended by any professional society. This includes the U.S. Preventative Services Task Force, the American Cancer Society, the American College of Obstetricians and Gynecologists, and the National Comprehensive Cancer Network.

No trial has shown improved survival for women undergoing screening.

Screening tests include the CA-125 marker, transvaginal ultrasound, and combinations of markers such as OvaSure (LabCorp). A definitive diagnosis requires surgical excision of the ovaries and fallopian tubes, so a positive screening test must be followed up by surgery.

The purpose of screening is to discover ovarian cancer in early stages, when it is more curable, on the hypothesis that early-stage cancer develops into later-stage cancer. However, it is not known whether early stage ovarian cancer evolves to later stage cancer, or whether stage III (peritoneal cavity involvement) arises as a diffuse process.

The goal of ovarian cancer screening is to detect ovarian cancer at stage Several large studies are ongoing, but none have recommended screening In 2009, however, Menon et al. reported from the UKCTOCS that utilizing mutimodal screening, in essence first performing annual CA 125 testing, followed by ultrasound imaging on the secondary level, the positive predictive value was 35.1% for primary invasive epithelial ovarian and tubal carcinoma, making such screening feasible. However, it remains to be seen if such screening is effective to reduce mortality.

SUMMARY OF THE INVENTION

The present invention provides novel methods for diagnosing diseases based on the determination of specific miRNAs that have altered expression levels in disease states compared to healthy controls or altered expression levels in a condition 1 (biological state or health state 1) compared to a condition 2 (biological state or health state 2).

The present invention further provides novel methods for the diagnosis and prognosis of ovarian cancer based on miRNA-biomarkers.

Definitions miRNA microRNAs (miRNA or µRNA) are single-stranded RNA molecules of ~21-23 nucleotides in length, which regulate gene expression. miRNAs are encoded by genes from whose DNA they are transcribed but miRNAs are not translated into protein (i.e. they are non-coding RNAs). The genes encoding miRNAs are much longer than the processed mature miRNA molecule; miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide or passenger strand, is degraded as a RISC substrate. Therefore the miRNA*s are derived from the same hairpin structure like the "normal" miRNAs. So if the "normal" miRNA is then later called the "mature miRNA" or "guided strand", the miRNA* is the passenger strand.

miRNA* (See Also See "miRNA")

The miRNA*s, also known as the anti-guide or passenger strand, are mostly complementary to the guide strand, but there are usually single-stranded overhangs on each end, there is usually one or a few mispairs and there are sometimes extra or missing bases causing single-stranded "bubbles. The miRNA*s are likely to act in a regulatory fashion as the miRNAs.

It is understood that according to the present invention the term "miRNA" also includes the term "miRNA*".

miRBase

The miRBase is a searchable database of published miRNA sequences and annotation. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download.

miRNA-(Expression) Profile or miRNA Fingerprint

A miRNA-Profile represents the collection of expression levels of a plurality of miRNAs, therefore it is a quantitative measure of individual miRNA expression levels. Hereby, each miRNA is represented by a numerical value. The higher the value of an individual miRNA the higher is the expression level of this miRNA. A miRNA-profile is obtained from the RNA of a biological sample. There are various technologies to determine a miRNA-Profile, e.g. microarrays, RT-PCR, Next Generation Sequencing. As a starting material for analysis, RNA or total-RNA or any fraction thereof can be used. The plurality of miRNAs that are determined by a miRNA-profile can range from a selection of one up to all known miRNAs.

Pre-Determined Set of miRNAs or miRNA Signature

The pre-determined set of miRNAs or miRNA signature is understood in the present invention as a fixed defined set of miRNAs which is able to differentiate between a condition 1 and another condition 2. e.g. when condition 1 is lung cancer and condition 2 is normal control, the corresponding pre-determined set of miRNAs is able to differentiate between a samples derived from a lung cancer patient or a normal control patient. Alternatively, condition 1 is lung cancer and condition 2 is multiple sclerosis, the corresponding pre-determined set of miRNAs is able to differentiate between a lung cancer patient and a multiple sclerosis patient. In order to be able to perform the sample analysis it is required that, e.g. on the matrix that will be used to determine a miRNA profile, these fixed defined set of miRNAs have to be represented by capture probes that are defined by the pre-determined set of miRNAs. For example, when the predetermined set of miRNAs for diagnosing lung cancer from healthy controls consists of 25 miRNAs, probes capable for detecting these 25 miRNAs have to be implemented for performing the diagnostic analysis.

Common miRNA Signature Profile

A common miRNA signature profile is understood in the present invention as a non-fixed defined set of miRNAs or non-coding RNAs which is able to differentiate between a condition 1 and another condition 2. The common miRNA or non-coding RNA signature profile is calculated "on-the-fly" from a plurality of miRNA-profiles that are stored, e.g. in database. The common miRNA signature profile which is able to differentiate between a condition and another condition 2 is changing as soon as an new profile is added to the database which is relevant to either to state of health 1 or another condition 2. In this respect it is different from a predetermined set of miRNAs (see above). Furthermore, the basis for generating the common miRNA signature profile—hence the miRNA profiles stored in the database—is generated from capture probes, e.g. on a matrix that is representing as much as possible different capture probes for detecting as much as possible, ideally all known, miRNAs.

Non-Coding RNA

A non-coding RNA (ncRNA) is a functional RNA molecule that is not translated into a protein. Less-frequently used synonyms are non-protein-coding RNA (npcRNA), non-messenger RNA (nmRNA), small non-messenger RNA (snmRNA), functional RNA (fRNA). The term small RNA (sRNA) is often used for bacterial ncRNAs. The DNA sequence from which a non-coding RNA is transcribed as the end product is often called an RNA gene or non-coding RNA gene.

Non-coding RNA genes include highly abundant and functionally important RNAs such as transfer RNA (tRNA) and ribosomal RNA (rRNA), as well as RNAs such as snoRNAs, microRNAs, siRNAs and piRNAs and the long ncRNAs that include examples such as Xist and HOTAIR (see here for a more complete list of ncRNAs). The number of ncRNAs encoded within the human genome is unknown, however recent transcriptomic and bioinformatic studies suggest the existence of thousands of ncRNAs. Since most of the newly identified ncRNAs have not been validated for their function, it is possible that many are non-functional.

Condition

A condition (biological state or health state or state of health) is understood in the present invention as status of a subject that can be described by physical, mental or social criteria. It includes as well so-called "healthy" and"diseased" conditions, therefore it is not limited to the WHO definition of health as "a state of complete physical, mental, and social well-being and not merely the absence of disease or infirmity." but includes disease and infirmity. For the definition of diseases comprised, e.g. by the conditions of the present invention, it is referred to the international classification of diseases (ICD) of the WHO. When 2 or more conditions are compared according to the present invention, it is understood that this is possible for all conditions that can be defined and is not limited to a comparison of a disease versus healthy and extends to multi-way comparisons. Examples for comparison are, but not limited to:

Pairwise Comparisons:

- lung cancer vs. healthy control, pancreatic cancer vs. healthy control
- lung cancer vs. pancreatic cancer, lung cancer vs. multiple sclerosis
- lung cancer WHO grade 1 vs. lung cancer WHO grade 2
- lung cancer WHO grade 1 metastasing vs. lung cancer WHO grade 1 non-metastasing
- Morbus Crohn vs. Collitis
- Pancreatic cancer vs. Pancreatitis Multi-Way Comparisons:

- Lung cancer vs. pancreatic cancer vs. multiple sclerosis
- Pancreas cancer vs. pancreatitis vs. lung cancer WHO grade 1 non-metastasing Biological Sample A "biological sample" in terms of the invention means a sample of biological tissue or fluid. Examples of biological samples are sections of tissues, blood, blood fractions, plasma, serum, urine or samples from other peripheral sources. or cell cultures, cell colonies of even single cells, or a collection of single cells. Furthermore, also pools or mixture of the above mentioned samples may be employed. A biological sample may be provided by removing a sample of cells from a subject, but can also be provided by using a previously isolated sample. For example, a tissue sample can be removed from a subject suspected of having a disease by conventional biopsy techniques. In a preferred embodiment, a blood sample is taken from the subject. In one embodiment, the blood or tissue sample is obtained from the subject prior to initiation of radiotherapy, chemotherapy or other therapeutic treatment. According to the invention, the biological sample preferably is a blood or a serum sample. Further, it is also preferred to use blood cells, e.g. erythrocytes, leukocytes or thrombocytes.

A biological sample from a patient means a sample from a subject suspected to be affected by a disease. As used herein, the term "subject" refers to any mammal, including both human and other mammals. Preferably, the methods of the present invention are applied to human subjects.

Subject-matter of the invention is a method for diagnosing a disease, comprising the steps (a) determining an expression profile of a predetermined set of miRNAs in a biological sample from a patient (or subject); and (b) comparing said expression profile to a reference expression profile, wherein the comparison of said determined expression profile to said reference expression profile allows for the diagnosis of the disease, wherein the disease is ovarian cancer.

In step (a) of the above method of the invention, an expression profile of a predetermined set of miRNAs is determined. The determination may be carried out by any convenient means for determining nucleic acids. For expression profiling, qualitative, semi-quantitative and preferably quantitative detection methods can be used. A variety of techniques are well known to those of skill in the art. In particular, the determination may comprise nucleic acid hybridization and/or nucleic acid amplification steps.

Nucleic acid hybridization may for example be performed using a solid phase nucleic acid biochip array, in particular a microarray, or in situ hybridization. The miRNA microarray technology affords the analysis of a complex biological sample for all expressed miRNAs. Nucleotides with complementarity to the corresponding miRNAs are spotted on coated carriers or are fabricated by in-situ synthesis methods on a carrier. Preferably, miRNAs isolated from the sample of interest are not labelled, e.g. before hybridization of the miRNAs to the complementary sequences on the carrier and the resulting signal indicating the occurrence of a distinct miRNA is generated by incorporation of a detectable label (e.g. biotin, fluorescent dye) by means of an enzyme reaction.

According to another embodiment of the invention, miRNAs isolated from the sample of interest are labelled, e.g. fluorescently labelled, so that upon hybridization of the miRNAs to the complementary sequences on the carrier the resulting signal indicates the occurrence of a distinct miRNA.

On one miRNA microarray, preferably at least the whole predetermined set of miRNAs can be analyzed.

Further, quantitative real-time polymerase chain reaction (RT-PCR) can be used to detect miRNAs even at very low abundance.

Alternative methods for obtaining expression profiles may also contain sequencing, next generation sequencing or mass spectroscopy.

The predetermined set of miRNAs in step (a) of the above method of the invention depends on the disease to be diagnosed. The inventors found out that single miRNA biomarkers lack sufficient accuracy, specificity and sensitivity, and therefore it is preferred to analyze more complex miRNA expression patterns, so-called miRNA signatures. The predetermined set of miRNAs comprises one or more, preferably a larger number of miRNAs (miRNA signatures) that are differentially regulated in samples of a patient affected by a particular disease compared to healthy controls. Alternatively, the disease can also be compared to any other defined condition (e.g. another disease).

The expression profile determined in the above step (a) is subsequently compared to a reference expression profile or to a plurality of reference profiles in the above step (b). The reference expression profile is the expression profile of the same set of miRNAs in a biological sample originating from the same source as the biological sample from a patient but obtained from a healthy subject. Preferably, both the reference expression profile and the expression profile of the above step (a) are determined in a blood or serum sample or in a sample of erythrocytes, leukocytes and/or thrombocytes. It is understood that the reference expression profile is not necessarily obtained from a single healthy subject but may be an average expression profile of a plurality of healthy subjects. It is preferred to use a reference expression profile obtained from a person of the same gender, and a similar age as the patient.

The above method of the invention is suitable for diagnosing any diseases for which a differential expression of miRNAs compared to healthy controls or other diseases exists. In particular, the method may be used for diagnosing ovarian cancer. The method of the invention also allows a differential diagnosis of ovarian cancer compared to other diseases including other cancers such as bladder cancer, brain cancer, breast cancer, colon cancer, endometrium cancer, gastrointestinal stromal cancer, glioma, head- and neck cancer, kidney cancer, leukemia, liver cancer, lung cancer, lymph node cancer, melanoma, meninges cancer, pancreas cancer, e.g. pancreas cancer ductal or non-ductal, prostate cancer, sarcoma, stomach cancer, testicular cancer, thyroid cancer, thymus cancer and Wilm's tumor or COPD. The diagnosis may comprise determining type, rate and/or stage of cancer. The course of the disease and the success of therapy such as chemotherapy may be monitored. The method of the invention provides a prognosis on the survivor rate and enables to determine a patient's response to drugs.

The inventors succeeded in developing an approach to arrive at miRNA signatures that are correlated with ovarian cancer. In more detail, the following steps are accomplished:

1. miRNAs are extracted from a biological sample of a patient (subject), preferably a blood or serum or urine sample or a sample comprising erythrocytes, leukocytes or thrombocytes, using suitable kits/purification methods. From these samples preferably the RNA-fraction is used for analysis.
2. The respective samples are measured using experimental techniques. These techniques include but are not restricted to:
   - Array based approaches
   - Real time quantitative polymerase chain reaction
   - Sequencing
   - Next Generation Sequencing
   - Mass Spectroscopy
3. Mathematical approaches are applied to gather information on the value and the redundancy of single biomarkers. These methods include, but are not restricted to:
   - basic mathematic approaches (e.g. Fold Quotients, Signal to Noise ratios, Correlation)
   - statistical methods as hypothesis tests (e.g. t-test, Wilcoxon-Mann-Whitney test), the Area under the Receiver operator Characteristics Curve
   - Information Theory approaches, (e.g. the Mutual Information, Cross-entropy)
   - Probability theory (e.g. joint and conditional probabilities)
   - Combinations and modifications of the previously mentioned examples
4. The information collected in 3) are used to estimate for each biomarker the diagnostic content or value. Usually, however, this diagnostic value of only one biomarker is too small to get a highly accurate diagnosis with accuracy rates, specificities and sensitivities beyond the 90% barrier. Please note that the diagnostic content for our miRNAs can be found in the tables in FIGS. 2, and 7-13. These tables includes the miRNAs and the corresponding significance value as computed by a t-test (column: ttest_adjp=adjusted t-test values) for the comparison of ovarian cancer to healthy controls (FIG. 2) and ovarian cancer to other diseases (FIG. 7-13).
5. Thus statistical learning/machine learning/bioinformatics/computational approaches are applied to define subsets of biomarkers that are tailored for the detection of diseases. These techniques includes but are not restricted to
   - Wrapper subset selection techniques (e.g. forward step-wise, backward step-wise, combinatorial approaches, optimization approaches)
   - Filter subset selection methods (e.g. the methods mentioned in 3)
   - Principal Component Analysis
   - Combinations and modifications of such methods (e.g. hybrid approaches)
6. The diagnostic content of each detected set can be estimated by mathematical and/or computational techniques to define the diagnostic information content of subsets.
7. The subsets, detected in step 5, which may range from only a small number (at least two) to all measured biomarkers is then used to carry out a diagnosis. To this end, statistical learning/machine learning/bioinformatics/computational approaches are applied that include but are not restricted to any type of supervised or unsupervised analysis:
   - Classification techniques (e.g. naïve Bayes, Linear Discriminant Analysis, Quadratic Discriminant Analysis Neural Nets, Tree based approaches, Support Vector Machines, Nearest Neighbour Approaches)
   - Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression)

Clustering techniques (e.g. k-means clustering, hierarchical clustering, PCA)

Adaptations, extensions, and combinations of the previously mentioned approaches The inventors surprisingly found out that the described approach yields in miRNA signatures that provide high diagnostic accuracy, specificity and sensitivity in the determination of ovarian cancer.

The inventors succeeded in determining miRNAs that are differentially regulated in samples from ovarian cancer patients as compared to healthy controls. A complete overview of all miRNAs that are found to be differentially regulated in blood samples of ovarian cancer patients compared to healthy controls is provided in the tables shown in FIG. 2.

FIGS. 7-13 include a list of miRNAs found to be differentially regulated between:

Ovarian cancer vs Lung cancer (FIG. 7)
Ovarian cancer vs Melanoma (FIG. 8)
Ovarian cancer vs Pancreatic cancer (FIG. 9)
Ovarian cancer vs Prostate cancer (FIG. 10)
Ovarian cancer vs Wilms tumor (FIG. 11)
Ovarian cancer vs Pancreatic cancer non ductal (FIG. 12)
Ovarian cancer vs Pancreatic cancer ductal (FIG. 13)

In the tables shown in FIGS. 2 and 7-13 the miRNAs that are found to be differentially regulated are sorted in the order of their t-test significance (see column: ttest_adjp=adjusted t-test values).

Another method for assessing the significance is to compute the Mutual information (MI) (Shannon, 1984) which is an adequate measure to estimate the overall diagnostic information content of single biomarkers (Keller, Ludwig et al., 2006). According to the invention mutual information is considered as the reduction in uncertainty about the class labels "0" for controls and "1" for tumor samples due to the knowledge of the miRNA expression. The higher the value of the MI of a miRNA, the higher is the diagnostic content of the respective miRNA.

Surprisingly, the inventors found out that miRNAs are differentially regulated in samples from ovarian cancer patients as compared to health controls. A complete overview of all miRNAs that are found to be differentially regulated in blood samples of ovarian cancer patients is provided in the table shown in FIG. 2. In total, 75 miRNAs were found to be significantly deregulated (t-test significance <0.05) in blood cells of ovarian cancer patients as compared to the healthy controls.

Preferably, the predetermined set of miRNAs for the diagnosis of ovarian cancer comprises one or more nucleic acids selected from the deregulated miRNAs presented in the table in FIG. 2.

The predetermined set of miRNAs should preferably comprise at least 1, preferably at least 7, 10, 15, 20, 25, 30, 35, 40, 50, 60, 70, or 75 of the indicated nucleic acids. It is particularly preferred to include the 75, 70, 60, 50, 40, 35, 30, 25, 20, 15, 10, 7 or at least 1 of the first mentioned miRNAs according to their order in the table in FIG. 2.

Thus, preferably the predetermined set of miRNAs for the diagnosis of ovarian cancer comprises one or more nucleic acids selected from the 75 most deregulated miRNAs.

Thus, preferably the predetermined set of miRNAs for the diagnosis of ovarian cancer comprises one or more nucleic acids selected from the 75 most deregulated miRNAs.

Preferably, the predetermined set of miRNAs comprises at least 1, preferably at least 7, 10, 15, 20, 25, 30, 35, 40, 50, 60, 70 or 75 or all of the above-indicated nucleic acids (listed in FIG. 2).

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454*.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR-518f, hsa-miR-488, hsa-miR-182, hsa-miR-10a*, hsa-miR-19b.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR-518f, hsa-miR-488, hsa-miR-182, hsa-miR-10a*, hsa-miR-19b, hsa-miR-15a, hsa-miR-1289, hsa-miR-500, hsa-miR-1281, hsa-miR-942.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR-518f, hsa-miR-488, hsa-miR-182, hsa-miR-10a*, hsa-miR-19b, hsa-miR-15a, hsa-miR-1289, hsa-miR-500, hsa-miR-1281, hsa-miR-942, hsa-miR-877*, hsa-let-7f-1*, hsa-miR-651, hsa-miR-610, hsa-miR-664, hsa-miR-613, hsa-miR-483-3p, hsa-miR-320c, hsa-miR-720, hsa-miR-299-5p.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR-518f, hsa-miR-488, hsa-miR-182, hsa-miR-10a*, hsa-miR-19b, hsa-miR-15a, hsa-miR-1289, hsa-miR-500, hsa-miR-1281, hsa-miR-942, hsa-miR-877*, hsa-let-7f-1*, hsa-miR-651, hsa-miR-610, hsa-miR-664, hsa-miR-613, hsa-miR-483-3p, hsa-miR-320c, hsa-miR-720, hsa-miR-299-5p, hsa-miR-579, hsa-miR-636, hsa-miR-197, hsa-miR-668, hsa-miR-494, hsa-miR-1262, hsa-miR-578, hsa-miR-708*, hsa-miR-329.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR-518f, hsa-miR-488, hsa-miR-182, hsa-miR-10a*, hsa-miR-19b, hsa-miR-15a, hsa-miR-1289, hsa-miR-500, hsa-miR-1281, hsa-miR-942, hsa-miR-877*, hsa-let-7f-1*, hsa-miR-651, hsa-miR-610, hsa-miR-664, hsa-miR-613, hsa-miR-483-3p, hsa-miR-320c, hsa-miR-720, hsa-miR-299-5p, hsa-miR-579, hsa-miR-636, hsa-miR-197, hsa-miR-668, hsa-miR-494, hsa-miR-1262, hsa-miR-578, hsa-miR-708*, hsa-miR-329, hsa-miR-941, hsa-miR-155, hsa-miR-26a-1*, hsa-miR-1246, hsa-miR-892b, hsa-miR-146a, hsa-miR-337-3p, hsa-miR-130a*, hsa-let-7b, hsa-miR-744*.

In a further embodiment the predetermined set of miRNAs for the diagnosis of Ovarian cancer comprises one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR-518f, hsa-miR-488, hsa-miR-182, hsa-miR-10a*, hsa-miR-19b, hsa-miR-15a, hsa-miR-1289, hsa-miR-500, hsa-miR-1281, hsa-miR-942, hsa-miR-877*, hsa-let-7f-1*, hsa-miR-651, hsa-miR-610, hsa-miR-664, hsa-miR-613, hsa-miR-483-3p, hsa-miR-320c, hsa-miR-720, hsa-miR-299-5p, hsa-miR-579, hsa-miR-636, hsa-miR-197, hsa-miR-668, hsa-miR-494, hsa-miR-1262, hsa-miR-578, hsa-miR-708*, hsa-miR-329, hsa-miR-941, hsa-miR-155, hsa-miR-26a-1*, hsa-miR-1246, hsa-miR-892b, hsa-miR-146a, hsa-miR-337-3p, hsa-miR-130a*, hsa-let-7b, hsa-miR-744*, hsa-miR-140-3p, hsa-miR-573, hsa-miR-378, hsa-miR-1237, hsa-miR-363*.

In a further embodiment, the measured miRNA profiles were classified using statistical learning approaches in order to compute accuracy, specificity, and sensitivity for the diagnosis of ovarian cancer (see FIG. 3). The miRNAs that performed best for the diagnosis of ovarian cancer according to their accuracy, specificity, and sensitivity are the 440 miRNAs listed in the table in FIG. 2 (entries No. 1-440) leading to an accuracy 82.8%, a specificity of 87.5% and a sensitivity of 71.9%

The predetermined set of miRNAs for the diagnosis of ovarian cancer should preferably comprise at least 1, preferably at least 7.10, 15, 20, 25, 30, 35, 40, 50, 60, 70, 75, 440 or preferably all of the known miRNAs, preferably all of the 962 (see FIG. 1, representing the current status of all known miRNAs in the version 12, 13, and 14 of the miRBase repository.

Another embodiment of the present invention is a kit for diagnosing a disease, comprising means for determining an expression profile of a predetermined set of miRNAs in a biological sample, in particular in a blood and/or serum or urine sample. Preferably, one or more reference expression profiles are also provided which show the expression profile of the same set of miRNAs in the same type of biological sample, in particular in a blood and/or serum or urine sample, obtained from one or more healthy subjects. A comparison to said reference expression profile(s) allows for the diagnosis of the disease.

Another preferred embodiment of the present invention is a kit for diagnosing ovarian cancer, comprising means for determining the expression profile of one or more miRNAs presented in the table in FIG. 2, preferably one or more miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-150, hsa-miR-412, hsa-miR-548i, hsa-let-7e*, hsa-miR-324-3p (20), hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR- 518f, hsa-miR-488, hsa-miR-182, hsa-miR-10a*, hsa-miR-19b, hsa-miR-15a, hsa-miR-1289, hsa-miR-500, hsa-miR-1281, hsa-miR-942, hsa-miR-877*, hsa-let-7f-1*, hsa-miR-651, hsa-miR-610, hsa-miR-664, hsa-miR-613, hsa-miR-483-3p, hsa-miR-320c, hsa-miR-720, hsa-miR-299-5p, hsa-miR-579, hsa-miR-636, hsa-miR-197, hsa-miR-668, hsa-miR-494, hsa-miR-1262, hsa-miR-578, hsa-miR-708*, hsa-miR-329, hsa-miR-941, hsa-miR-155, hsa-miR-26a-1*, hsa-miR-1246, hsa-miR-892b, hsa-miR-146a, hsa-miR-337-3p, hsa-miR-130a*, hsa-let-7b, hsa-miR-744*, hsa-miR-140-3p, hsa-miR-573, hsa-miR-378, hsa-miR-1237, hsa-miR-363*.

In a preferred embodiment the kit comprises means for determining at least 1, preferably at least 7, 10, 15, 20, 25, 30, 35, 40, 50, 60, 70, 75, 440 or all of the indicated miRNAs. It is particularly preferred to include means for determining the 440, 75, 70, 60, 50, 40, 35, 30, 25, 20, 15, 10 or 7 at least 1 first mentioned miRNAs in the order of their diagnostic significance as represented by their order in the table in FIG. 2. The kit for diagnosing ovarian cancer is particularly suitable for diagnosing ovarian cancer in a blood and/or serum or urine sample or in a sample comprising erythrocytes, leukocytes and/or thrombocytes.

The means for determining a predetermined set of miRNAs may for example comprise a microarray comprising miRNA-specific oligonucleotide probes. In a preferred embodiment, the microarray comprises miRNA-specific oligonucleotide probes for the detection of miRNAs. Depending on the intended use of the microarray in the diagnosis or prognosis of a particular disease (e.g ovarian cancer), probes for detecting different miRNAs may be included.

A microarray intended for use in the diagnosis of ovarian cancer preferably comprises miRNA specific oligonucleotide probes for one or more miRNAs presented in the table in FIG. 2, preferably for one or more miRNAs selected from the group consisting hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454* hsa-miR-150, hsa-miR-412, hsa-miR-548i, hsa-let-7e*, hsa-miR-324-3p (20), hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR-518f, hsa-miR-488, hsa-miR-182, hsa-miR-10a*, hsa-miR-19b, hsa-miR-15a, hsa-miR-1289, hsa-miR-500, hsa-miR-1281, hsa-miR-942, hsa-miR-877*, hsa-let-7f-1*, hsa-miR-651, hsa-miR-610, hsa-miR-664, hsa-miR-613, hsa-miR-483-3p, hsa-miR-320c, hsa-miR-720, hsa-miR-299-5p, hsa-miR-579, hsa-miR-636, hsa-miR-197, hsa-miR-668, hsa-miR-494, hsa-miR-1262, hsa-miR-578, hsa-miR-708*, hsa-miR-329, hsa-miR-941, hsa-miR-155, hsa-miR-26a-1*, hsa-miR-1246, hsa-miR-892b, hsa-miR-146a, hsa-miR-337-3p, hsa-miR-130a*, hsa-let-7b, hsa-miR-744*, hsa-miR-140-3p, hsa-miR-573, hsa-miR-378, hsa-miR-1237, hsa-miR-363*.

In a preferred embodiment the microarray comprises oligonucleotide probes for determining at least 1, preferably at least 7, 10, 15, 20, 25, 30, 35, 40, 50, 60, 70, 75, 440 or all of the indicated miRNAs. It is particularly preferred to include oligonucleotide probes for determining the most significant miRNAs, which is represented by their order in the table depicted in FIG. 2.

The microarray can comprise oligonucleotide probes obtained from known or predicted miRNA sequences. The array may contain different oligonucleotide probes for each miRNA, for example one containing the active mature sequence and another being specific for the precursor of the miRNA. The array may also contain controls such as one or more sequences differing from the human orthologs by only a few bases, which can serve as controls for hybridization stringency conditions. It is also possible to include viral miRNAs or putative miRNAs as predicted from bioinformatic tools. Further, it is possible to include appropriate controls for non-specific hybridization on the microarray.

Differential Diagnosis: Ovarian Cancer Vs. Lung Cancer

Surprisingly, the inventors found out that miRNAs are differentially regulated in samples from ovarian cancer patients as compared to lung cancer patients. In total, 154 miRNAs were found to be significantly deregulated (t-test significance <0.05) in blood cells of ovarian cancer patients as compared to the lung cancer patients. In FIG. 7 the 70 miRNAs with the highest diagnostic content or value for discrimination of ovarian cancer from lung cancer patients are listed.

These miRNAs include hsa-miR-1224-3p, hsa-miR-610, hsa-miR-668, hsa-miR-328, hsa-miR-942, hsa-miR-500, hsa-miR-423-5p, hsa-miR-1248, hsa-miR-324-3p, hsa-miR-1281, hsa-miR-193a-5p, hsa-miR-1825, hsa-miR-605, hsa-miR-383, hsa-miR-485-3p, hsa-miR-148a*, hsa-miR-877*, hsa-miR-130a*, hsa-let-7d*, hsa-miR-337-3p, hsa-miR-1226, hsa-miR-148a, hsa-miR-219-1-3p, hsa-miR-29c*, hsa-miR-483-3p, hsa-miR-133a, hsa-miR-323-3p, hsa-miR-125a-5p, hsa-miR-130b*, hsa-miR-133b, hsa-miR-186*, hsa-miR-576-3p, hsa-miR-150, hsa-miR-26b*, hsa-miR-302c, hsa-miR-299-5p, hsa-miR-361-5p, hsa-miR-770-5p, hsa-miR-1303, hsa-miR-576-5p, hsa-miR-636, hsa-miR-1237, hsa-miR-15a, hsa-miR-15b, hsa-miR-720, hsa-miR-409-3p, hsa-miR-659, hsa-miR-664, hsa-miR-21*, hsa-miR-199a-5p, hsa-miR-518f*, hsa-miR-146b-3p, hsa-miR-23b*, hsa-miR-331-3p, hsa-miR-708*, hsa-miR-329, hsa-miR-564, hsa-miR-744*, hsa-miR-1282, hsa-miR-454*, hsa-miR-302d*, hsa-miR-197, hsa-miR-1538, hsa-miR-877, hsa-miR-652, hsa-miR-573, hsa-miR-18b*, hsa-miR-494, hsa-miR-220b, hsa-miR-1274a.

In a further embodiment the predetermined set of miRNAs for the differential diagnosis of ovarian cancer and lung cancer comprises one or more miRNAs, at least 1, preferably at least 7, 10, 15, 20, 25, 30, 35, 40, 50, 60, 70 or all of the above indicated miRNAs.

In a preferred embodiment the kit for diagnosis of ovarian cancer from lung cancer comprises means for determining one or more, at least 1, preferably at least 7, 10, 15, 20, 25, 30, 35, 40, 50, 60, 70 or all of the above indicated miRNAs.

A microarray intended for use in the differential diagnosis of ovarian cancer and lung cancer preferably comprises miRNA specific oligonucleotide probes for one or more miRNAs, at least 1, preferably at least 7, 10, 15, 20, 25, 30, 35, 40, 50, 60, 70 or all of the above indicated miRNAs.

Differential Diagnosis: Ovarian Cancer vs Melanoma

Surprisingly, the inventors found out that miRNAs are differentially regulated in samples from ovarian cancer patients as compared to melanoma patients. In total, 352 miRNAs were found to be significantly deregulated (t-test significance <0.05) in blood cells of ovarian cancer patients as compared to the melanoma patients. In FIG. 8 the 70 miRNAs with the highest diagnostic content or value for discrimination of ovarian cancer from melanoma patients are listed.

These miRNAs include hsa-miR-328, hsa-miR-500, hsa-miR-424*, hsa-miR-1281, hsa-miR-186, hsa-miR-1224-3p, hsa-miR-1248, hsa-miR-483-3p, hsa-miR-1295, hsa-miR-130a*, hsa-miR-409-3p, hsa-miR-664, hsa-miR-146a, hsa-miR-155, hsa-miR-1249, hsa-miR-629*, hsa-miR-148a*, hsa-miR-193a-5p, hsa-miR-1226, hsa-miR-29c*, hsa-let-7d*, hsa-miR-99a, hsa-miR-1237, hsa-miR-361-5p, hsamiR-30a, hsa-miR-634, hsa-miR-877*, hsa-miR-133a, hsa-miR-454*, hsa-miR-133b, hsa-miR-30e*, hsa-miR-501-5p, hsa-miR-150, hsa-miR-181a-2*, hsa-miR-1825, hsa-miR-135b, hsa-miR-337-3p, hsa-miR-383, hsa-miR-26b*, hsa-miR-365, hsa-miR-942, hsa-miR-342-5p, hsa-miR-146b-3p, hsa-miR-363*, hsa-miR-636, hsa-miR-605, hsa-miR-610, hsa-miR-1289, hsa-miR-519c-5p, hsa-miR-220a, hsa-miR-1324, hsa-miR-125a-5p, hsa-miR-1274a, hsa-miR-1259, hsa-miR-378, hsa-let-7d, hsa-miR-421, hsa-miR-148a, hsa-miR-224, hsa-miR-541, hsa-miR-15b, hsa-miR-490-3p, hsa-miR-485-3p, hsa-miR-299-5p, hsa-miR-1288, hsa-miR-494, hsa-miR-1228, hsa-miR-744*, hsa-miR-668, hsa-miR-92a.

In a further embodiment the predetermined set of miRNAs for the differential diagnosis of ovarian cancer and melanoma comprises one or more miRNAs, at least 1, preferably at least 7, 10, 15, 20, 25, 30, 35, 40, 50, 60, 70 or all of the above indicated miRNAs.

In a preferred embodiment the kit for diagnosis of ovarian cancer from melanoma comprises means for determining one or more, at least 1, preferably at least 7, 10, 15, 20, 25, 30, 35, 40, 50, 60, 70 or all of the above indicated miRNAs.

A microarray intended for use in the differential diagnosis of ovarian cancer and melanoma preferably comprises miRNA specific oligonucleotide probes for one or more miRNAs, at least 1, preferably at least 7, 10, 15, 20, 25, 30, 35, 40, 50, 60, 70 or all of the above indicated miRNAs.

Differential Diagnosis: Ovarian Cancer Vs. Pancreatic Cancer

Surprisingly, the inventors found out that miRNAs are differentially regulated in samples from ovarian cancer patients as compared to pancreatic cancer patients. In total, 96 miRNAs were found to be significantly deregulated (t-test significance <0.05) in blood cells of ovarian cancer patients as compared to the pancreatic cancer patients. In FIG. 9 the 70 miRNAs with the highest diagnostic content or value for discrimination of ovarian cancer from pancreatic cancer patients are listed.

These miRNAs include hsa-let-7d, hsa-miR-146b-3p, hsa-miR-150, hsa-miR-454*, hsa-miR-1248, hsa-miR-133b, hsa-miR-610, hsa-miR-148a, hsa-miR-888, hsa-miR-519e*, hsa-miR-1288, hsa-miR-655, hsa-miR-302d*, hsa-miR-942, hsa-miR-374b*, hsa-miR-605, hsa-miR-10a*, hsa-miR-182, hsa-miR-148a*, hsa-miR-656, hsa-miR-374a, hsa-miR-744*, hsa-miR-429, hsa-miR-144*, hsa-miR-144, hsa-miR-668, hsa-miR-888*, hsa-miR-1259, hsa-miR-29a, hsa-miR-194, hsa-miR-1205, hsa-miR-149*, hsa-miR-221*, hsa-miR-302d, hsa-miR-299-5p, hsa-miR-1908, hsa-miR-573, hsa-miR-877, hsa-miR-212, hsa-miR-130a*, hsa-miR-551a, hsa-miR-936, hsa-miR-1226, hsa-miR-892b, hsa-miR-200a*, hsa-miR-519a*, hsa-miR-891a, hsa-miR-1287, hsa-miR-770-5p, hsa-miR-363*, hsa-miR-302c, hsa-miR-218-1*, hsa-miR-541, hsa-miR-500*, hsa-miR-485-3p, hsa-miR-21*, hsa-miR-662, hsa-miR-506, hsa-miR-1200, hsa-miR-22, hsa-miR-101, hsa-miR-129*, hsa-miR-224, hsa-miR-371-5p, hsa-miR-106a, hsa-miR-647, hsa-miR-219-1-3p, hsa-miR-519c-5p, hsa-miR-330-5p, hsa-miR-450a.

In a further embodiment the predetermined set of miRNAs for the differential diagnosis of ovarian cancer and pancreatic cancer comprises one or more miRNAs, at least 1, preferably at least 7, 10, 15, 20, 25, 30, 35, 40, 50, 60, 70 or all of the above indicated miRNAs.

In a preferred embodiment the kit for diagnosis of ovarian cancer from pancreatic cancer comprises means for determining one or more, at least 1, preferably at least 7, 10, 15, 20, 25, 30, 35, 40, 50, 60, 70 or all of the above indicated miRNAs.

A microarray intended for use in the differential diagnosis of ovarian cancer and pancreatic cancer preferably comprises miRNA specific oligonucleotide probes for one or more miRNAs, at least 1, preferably at least 7, 10, 15, 20, 25, 30, 35, 40, 50, 60, 70 or all of the above indicated miRNAs.

Differential Diagnosis: Ovarian Cancer Vs. Prostate Cancer

Surprisingly, the inventors found out that miRNAs are differentially regulated in samples from ovarian cancer patients as compared to prostate cancer patients. In total, 302 miRNAs were found to be significantly deregulated (t-test significance <0.05) in blood cells of ovarian cancer patients as compared to the prostate cancer patients. In FIG. 10 the 70 miRNAs with the highest diagnostic content or value for discrimination of ovarian cancer from prostate cancer patients are listed.

These miRNAs include hsa-miR-500, hsa-miR-342-3p, hsa-miR-744*, hsa-miR-363*, hsa-miR-1295, hsa-miR-361-5p, hsa-miR-519b-5p, hsa-miR-1324, hsa-miR-519c-5p, hsa-miR-942, hsa-miR-15b, hsa-miR-148a, hsa-miR-335*, hsa-miR-20a*, hsa-miR-1289, hsa-miR-133b, hsa-miR-423-5p, hsa-miR-708*, hsa-miR-490-3p, hsa-miR-383, hsa-miR-877*, hsa-miR-1226, hsa-miR-629*, hsa-miR-1281, hsa-miR-664, hsa-miR-338-3p, hsa-miR-378, hsa-miR-137, hsa-miR-328, hsa-miR-1225-5p, hsa-miR-668, hsa-miR-320a, hsa-miR-27a*, hsa-miR-135a*, hsa-miR-1825, hsa-miR-483-3p, hsa-miR-522*, hsa-miR-15a, hsa-miR-193a-5p, hsa-miR-424*, hsa-miR-21*, hsa-miR-494, hsa-miR-1237, hsa-miR-578, hsa-miR-635, hsa-miR-33b, hsa-miR-541, hsa-miR-526a, hsa-miR-519a*, hsa-miR-573, hsa-miR-888, hsa-miR-33a, hsa-miR-1229, hsa-miR-103-as, hsa-miR-197, hsa-miR-324-3p, hsa-miR-433, hsa-miR-671-3p, hsa-miR-211, hsa-miR-150, hsa-miR-885-5p, hsa-miR-34b, hsa-miR-551b*, hsa-miR-362-5p, hsa-miR-409-3p, hsa-miR-186*, hsa-miR-216a, hsa-miR-516b*, hsa-miR-1205, hsa-miR-1224-3p.

In a further embodiment the predetermined set of miRNAs for the differential diagnosis of ovarian cancer and prostate cancer comprises one or more miRNAs, at least 1, preferably at least 7, 10, 15, 20, 25, 30, 35, 40, 50, 60, 70 or all of the above indicated miRNAs.

In a preferred embodiment the kit for diagnosis of ovarian cancer from prostate cancer comprises means for determining one or more, at least 1, preferably at least 7, 10, 15, 20, 25, 30, 35, 40, 50, 60, 70 or all of the above indicated miRNAs.

A microarray intended for use in the differential diagnosis of ovarian cancer and prostate cancer preferably comprises miRNA specific oligonucleotide probes for one or more miRNAs, at least 1, preferably at least 7, 10, 15, 20, 25, 30, 35, 40, 50, 60, 70 or all of the above indicated miRNAs.

Differential Diagnosis: Ovarian Cancer vs. Wilm's Tumor

Surprisingly, the inventors found out that miRNAs are differentially regulated in samples from ovarian cancer patients as compared to Wilm's tumor patients. In total, 4 miRNAs were found to be significantly deregulated (t-test significance <0.05) in blood cells of ovarian cancer patients as compared to the melanoma patients. In FIG. 11 the 70 miRNAs with the highest diagnostic content or value for discrimination of ovarian cancer from Wilm's tumor patients are listed.

These miRNAs include hsa-miR-363, hsa-miR-144, hsa-miR-139-5p, hsa-miR-639, hsa-miR-662, hsa-miR-886-3p, hsa-miR-342-3p, hsa-miR-218, hsa-miR-22, hsa-miR-140-5p, hsa-miR-590-5p, hsa-miR-20b, hsa-miR-206, hsa-miR-614, hsa-miR-103, hsa-miR-720, hsa-miR-181d, hsa-miR-17, hsa-miR-20a, hsa-miR-580, hsa-miR-96, hsa-miR-425, hsa-miR-144*, hsa-miR-875-5p, hsa-miR-92a-1*, hsa-miR- 15a, hsa-miR-16, hsa-miR-21, hsa-miR-323-5p, hsa-miR-105*, hsa-miR-30b*, hsa-miR-324-3p, hsa-miR-665, hsa-miR-384, hsa-miR-1276, hsa-miR-19a, hsa-miR-106a, hsa-miR-182, hsa-miR-632, hsa-miR-141*, hsa-miR-1288, hsa-miR-16-1*, hsa-miR-1268, hsa-miR-550, hsa-miR-517b, hsa-miR-545, hsa-miR-668, hsa-miR-374b, hsa-miR-10b*, hsa-miR-320a, hsa-miR-30b, hsa-miR-526b, hsa-miR-302d*, hsa-miR-187, hsa-miR-382, hsa-miR-453, hsa-miR-1250, hsa-miR-30c, hsa-miR-943, hsa-miR-636, hsa-miR-107, hsa-miR-744*, hsa-miR-1294, hsa-miR-802, hsa-miR-181a-2*, hsa-miR-572, hsa-miR-93, hsa-miR-595, hsa-miR-195*, hsa-miR-126.

In a further embodiment the predetermined set of miRNAs for the differential diagnosis of ovarian cancer and Wilm's tumor comprises one or more miRNAs, at least 1, preferably at least 7, 10, 15, 20, 25, 30, 35, 40, 50, 60, 70 or all of the above indicated miRNAs.

In a preferred embodiment the kit for diagnosis of ovarian cancer from Wilm's tumor comprises means for determining one or more, at least 1, preferably at least 7, 10, 15, 20, 25, 30, 35, 40, 50, 60, 70 or all of the above indicated miRNAs.

A microarray intended for use in the differential diagnosis of ovarian cancer and Wilm's tumor preferably comprises miRNA specific oligonucleotide probes for one or more miRNAs, at least 1, preferably at least 7, 10, 15, 20, 25, 30, 35, 40, 50, 60, 70 or all of the above indicated miRNAs.

Differential Diagnosis: Ovarian Cancer vs. Pancreatic Cancer Ductal

Surprisingly, the inventors found out that miRNAs are differentially regulated in samples from ovarian cancer patients as compared to pancreatic cancer ductal patients. In total, 217 miRNAs were found to be significantly deregulated (t-test significance <0.05) in blood cells of ovarian cancer patients as compared to the pancreatic cancer ductal patients. In FIG. 12 the 70 miRNAs with the highest diagnostic content or value for discrimination of ovarian cancer from pancreatic cancer ductal patients.

These miRNAs include hsa-miR-1248, hsa-miR-1295, hsa-miR-454*, hsa-miR-942, hsa-miR-1228, hsa-miR-337-3p, hsa-miR-605, hsa-miR-363*, hsa-let-7d, hsa-miR-135b, hsa-miR-133b, hsa-miR-130a*, hsa-miR-589, hsa-miR-610, hsa-miR-150, hsa-miR-655, hsa-miR-409-3p, hsa-miR-1259, hsa-miR-573, hsa-miR-539, hsa-miR-578, hsa-miR-668, hsa-miR-576-5p, hsa-miR-651, hsa-miR-335*, hsa-miR-744*, hsa-miR-148a, hsa-miR-516b*, hsa-miR-302c, hsa-miR-892b, hsa-miR-26b*, hsa-miR-520a-3p, hsa-miR-146b-3p, hsa-miR-877*, hsa-miR-522*, hsa-miR-582-5p, hsa-miR-9, hsa-miR-133a, hsa-miR-599, hsa-miR-299-5p, hsa-miR-302d, hsa-miR-374a, hsa-miR-576-3p, hsa-miR-383, hsa-miR-374b*, hsa-miR-1911, hsa-miR-182, hsa-miR-564, hsa-miR-223*, hsa-miR-1226, hsa-miR-302d*, hsa-miR-92a, hsa-miR-548b-5p, hsa-miR-551a, hsa-miR-205, hsa-miR-1249, hsa-miR-496, hsa-miR-130b*, hsa-miR-618, hsa-miR-23b*, hsa-miR-211, hsa-miR-500*, hsa-miR-204, hsa-miR-1288, hsa-miR-19b-1*, hsa-miR-126*, hsa-miR-888, hsa-miR-526a, hsa-miR-26a-1*, hsa-miR-26a-2*.

In a further embodiment the predetermined set of miRNAs for the differential diagnosis of ovarian cancer and pancreatic cancer ductal comprises one or more miRNAs, at least 1, preferably at least 7, 10, 15, 20, 25, 30, 35, 40, 50, 60, 70 or all of the above indicated miRNAs.

In a preferred embodiment the kit for diagnosis of ovarian cancer from pancreatic cancer ductal comprises means for determining one or more, at least 1, preferably at least 7, 10, 15, 20, 25, 30, 35, 40, 50, 60, 70 or all of the above indicated miRNAs.

A microarray intended for use in the differential diagnosis of ovarian cancer and pancreatic cancer ductal preferably comprises miRNA specific oligonucleotide probes for one or more miRNAs, at least 1, preferably at least 7, 10, 15, 20, 25, 30, 35, 40, 50, 60, 70 or all of the above indicated miRNAs.

Differential Diagnosis: Ovarian Cancer vs. Pancreatic Cancer Non-Ductal

Surprisingly, the inventors found out that miRNAs are differentially regulated in samples from ovarian cancer patients as compared to pancreatic cancer non-ductal patients. In total, 96 miRNAs were found to be significantly deregulated (t-test significance <0.05) in blood cells of ovarian cancer patients as compared to the pancreatic cancer non-ductal patients. In FIG. 13 the 70 miRNAs with the highest diagnostic content or value for discrimination of ovarian cancer from pancreatic cancer non-ductal patients.

These miRNAs include hsa-let-7d, hsa-miR-146b-3p, hsa-miR-150, hsa-miR-454*, hsa-miR-1248, hsa-miR-133b, hsa-miR-610, hsa-miR-148a, hsa-miR-888, hsa-miR-519e*, hsa-miR-1288, hsa-miR-655, hsa-miR-302d*, hsa-miR-942, hsa-miR-374b*, hsa-miR-605, hsa-miR-10a*, hsa-miR-182, hsa-miR-148a*, hsa-miR-656, hsa-miR-374a, hsa-miR-744*, hsa-miR-429, hsa-miR-144*, hsa-miR-144, hsa-miR-668, hsa-miR-888*, hsa-miR-1259, hsa-miR-29a, hsa-miR-194, hsa-miR-1205, hsa-miR-149*, hsa-miR-221*, hsa-miR-302d, hsa-miR-299-5p, hsa-miR-1908, hsa-miR-573, hsa-miR-877, hsa-miR-212, hsa-miR-130a*, hsa-miR-551a, hsa-miR-936, hsa-miR-1226, hsa-miR-892b, hsa-miR-200a*, hsa-miR-519a*, hsa-miR-891a, hsa-miR-1287, hsa-miR-770-5p, hsa-miR-363*, hsa-miR-302c, hsa-miR-218-1*, hsa-miR-541, hsa-miR-500*, hsa-miR-485-3p, hsa-miR-21*, hsa-miR-662, hsa-miR-506, hsa-miR-1200, hsa-miR-22, hsa-miR-101, hsa-miR-129*, hsa-miR-224, hsa-miR-371-5p, hsa-miR-106a, hsa-miR-647, hsa-miR-219-1-3p, hsa-miR-519c-5p, hsa-miR-330-5p, hsa-miR-450a.

In a further embodiment the predetermined set of miRNAs for the differential diagnosis of ovarian cancer and pancreatic cancer non-ductal comprises one or more miRNAs, at least 1, preferably at least 7, 10, 15, 20, 25, 30, 35, 40, 50, 60, 70 or all of the above indicated miRNAs.

In a preferred embodiment the kit for diagnosis of ovarian cancer from pancreatic cancer non-ductal comprises means for determining one or more, at least 1, preferably at least 7, 10, 15, 20, 25, 30, 35, 40, 50, 60, 70 or all of the above indicated miRNAs.

A microarray intended for use in the differential diagnosis of ovarian cancer and pancreatic cancer non-ductal preferably comprises miRNA specific oligonucleotide probes for one or more miRNAs, at least 1, preferably at least 7, 10, 15, 20, 25, 30, 35, 40, 50, 60, 70 or all of the above indicated miRNAs.

The differential diagnosis is not limited to the example of differentiating ovarian cancer from the above mentioned diseases. According to the present invention the differential diagnosis is possible for each and every disease as soon as a set of biomarkers are available that exhibit a high diagnostic value to differentiate between the 2 diseases—or more general to differentiate between 2 clinical conditions.

The invention will now be illustrated by the following figures and the non-limiting experimental examples.

FIGURES

FIG. 1:

Overview of miRNA sequences published in the miRNA database 14.0 plus additional miRNA sequences.

FIG. 2:

Overview of all miRNAs that are found to be differentially regulated in blood samples of ovarian cancer patients compared to healthy controls, grouped accordingly to their results in t-tests (see column "ttest_adjp").

FIG. 3:

This classification plot which is based on 440 miRNAs was computed using a radial basis function Support Vector Machine as described in [17-18]. The blue boxes showing the accuracy ("acc"), specificity ("spec") and sensitivity ("sens") for classification of all ovarian cancer and control samples (n=15 for each group) and were calculated via 100 repetitions of 10-fold cross validation. The red boxes show the results obtained when the same mathematical operation is performed in permutation tests ("random") in which the class labels (ovarian cancer vs. control) have been assigned randomly before the values are computed. This is used to validate the classification procedure. The ordinate shows the percentage of samples that were classified correctly to their group

FIG. 4:

Shown is the logarithmic intensity of expression for miR-383 (left) and miR-889 (right) in ovarian cancer samples (red, OV1 to OV15) and healthy controls (blue, neg1 to neg15). Median values are indicated for both groups (** indicates p<0.01 for ovarian cancer patients vs. healthy controls by unadjusted, two-tailed t-test).

FIG. 5:

This classification plot which is based on 140 miRNAs: serous ovarian cancer (n=12) were compared with an extended group of healthy controls (n=37) as in FIG. 3, using 20 repetitions and 140 miRNAs.

FIG. 6:

Ovarian cancer patients characteristics

FIG. 7:

Differential diagnosis: ovarian cancer vs. lung cancer; listed are the 70 miRNAs with the highest diagnostic content for differentiating between ovarian cancer and lung cancer.

FIG. 8:

Differential diagnosis: ovarian cancer vs. melanoma; listed are the 70 miRNAs with the highest diagnostic content for differentiating between ovarian cancer and melanoma.

FIG. 9:

Differential diagnosis: ovarian cancer vs. pancreatic cancer; listed are the 70 miRNAs with the highest diagnostic content for differentiating between ovarian cancer and pancreatic cancer.

FIG. 10:

Differential diagnosis: ovarian cancer vs. prostate cancer; listed are the 70 miRNAs with the highest diagnostic content for differentiating between ovarian cancer and prostate cancer.

FIG. 11:

Differential diagnosis: ovarian cancer vs. Wilm's tumor; listed are the 70 miRNAs with the highest diagnostic content for differentiating between ovarian cancer and Wilm's tumor.

FIG. 12:

Differential diagnosis: ovarian cancer vs. pancreatic cancer ductal; listed are the 70 miRNAs with the highest diagnostic content for differentiating between ovarian cancer and pancreatic cancer ductal.

FIG. 13:

Differential diagnosis: ovarian cancer vs. pancreatic cancer non-ductal; listed are the 70 miRNAs with the highest diagnostic content for differentiating between ovarian cancer and pancreatic cancer non-ductal.

FIG. 14:

Overview of miRNAs that are found to be differentially regulated between healthy controls and subjects suffering from ovarian cancer. Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with ovarian cancer, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, wmw_rawp: p-value obtained when applying wmw-test (Wilcoxon Mann Whitney test), wmw_adjp: adjusted p-value in order to reduce false discovery rate by Benjamini-Hochberg adjustment.

FIG. 15:

Predetermined sets of miRNAs (miRNA signatures SNO-1 to 756) that allow for effective diagnosis and/or prognosis of subjects suffering or subjects suspected to suffering from ovarian cancer. Experimental details: SEQ ID NO: sequence identification number, miRNA: identifier of the miRNA according to miRBase, Acc=accuracy, Spec=specificity, Sens=sensitivity

EXAMPLES

Screening is still an unsolved problem for ovarian cancer which is mostly discovered when already incurable. Recent findings suggest that patients suffering from various malignancies may be identified via characteristic miRNA profiles in blood cells. Thus, we investigated whether ovarian cancer patients display characteristically deregulated miRNAs that could form the basis of a blood-based test for disease progression or even for preventive screening of wider collectives.

Results:

Comparing blood-borne miRNA profiles from 15 patients with ovarian cancer (OvCA) and 15 age- and sex-matched healthy controls, 51 out of >900 tested miRNAs were found to be significantly deregulated by unadjusted Student's t-test. The 30 most significantly deregulated miRNAs comprised candidates known to be associated with cancer (e.g. miR-155) but also 25 miRNAs which had never been connected to a specific disease. A radial basis function Support Vector Machine and filter subset selection allowed for discrimination between blood samples of OvCA patients and healthy controls with an accuracy of 73.9%, a specificity of 76.6%, and a sensitivity of 67.1% by using a subset of 440 miRNAs. When an extended control group (n=37) and just carcinomas of the serous subtype were analyzed, accuracy became 79.2%, specificity 70.8% and sensitivity 91.7%, based on 140 miRNAs.

CONCLUSION

This study strengthens the hypothesis that neoplastic diseases generate characteristic miRNA fingerprints in blood cells. While combining our approach with other markers may lead to further increased specificity and sensitivity, the present proof-of-principle study already demonstrates that microarray-based miRNA-profiling from peripheral blood may help to establish a biomarker profile that could improve the notoriously difficult screening for ovarian cancer.

Methods

Samples

Blood sampling from OvCA patients and healthy controls has been approved by the local ethics committee. All donors gave written informed consent. All 15 patients (median age: 64 years, range 29-80 years) had been diagnosed with relapsed ovarian cancer. The time elapsed since the last application of chemotherapy was sufficient to allow for a complete clearance of the drugs. Control samples were obtained from 15 age- and sex-matched volunteers without known disease (median age: 58 years, range 36-83 years). More detailed information on patients is given in Table 1. miRNA profiles from 22 additional healthy controls were generously provided by Eckart Meese (University of Homburg, Germany).

miRNA Extraction and Microarray Screening

Blood samples (5 ml per patient) were collected in PAXgene Blood RNA tubes (BD Biosciences, Heidelberg, Germany) and frozen at −86° C. After thawing, cellular fractions were obtained by centrifugation (5000 g, 10 min), resuspended in 10 ml RNAse free water and subjected to total RNA isolation using the miRNeasy kit (Qiagen GmbH, Hilden, Germany). RNA was eluted in water and shipped on dry ice to be analyzed on febit's Geniom real-time analyzer (GRTA, febit gmbh, Heidelberg, Germany) using the Geniom Biochip miRNA homo sapiens. Each array contains 7 replicates of 904 miRNAs and miRNA star sequences as annotated in the Sanger miRBase 14.0. Samples were biotinylated using either the miRVANA™ miRNA Labeling Kit (Applied Biosystems Inc, Foster City, Calif. USA) or by microfluidic-based enzymatic on-chip labeling of miRNAs (MPEA).

After hybridization for 16 hours at 42° C., the biochip was washed automatically and a program for signal enhancement was processed with the GRTA. Results were analyzed using the Geniom Wizard Software. For each array, the median signal intensity was extracted from the raw data file such that for each miRNA seven intensity values have been calculated corresponding to each replicate copy of miRBase on the array.

Following background correction, median values were calculated from the seven replicate intensity values of each miRNA. To normalize arrays, Variance Stabilizing Normalization (VSN) as implemented in the R package vsn has been applied and all further analyses were carried out using the normalized and background-subtracted intensity values. All microarray data were stored in the freely accessible miRDBXP database which is designed to store any type of microRNA expression pattern (manuscript in preparation). In addition, the data have also been deposited in GEO (GSE).

Statistical Analysis

The approximate normal distribution of the measured data was verified by Shapiro-Wilk test. Next, miRNAs showing a different behavior in the two groups were identified by unpaired two-tailed parametric t-test. p-values obtained for each individual miRNA were adjusted for multiple testing by Benjamini-Hochberg adjustment. In addition to the single biomarker analysis, samples were also classified according to miRNA patterns as calculated using Support Vector Machines (SVM) implemented in the R e1071 package. In detail, different kernel (linear, polynomial, sigmoid, radial basis function) Support Vector Machines were evaluated with the cost parameter being sampled from 0.01 to 10 in decimal powers. The measured miRNA profiles were classified using either 20 or 100 repetitions of standard 10-fold cross-validation and subsets were selected according to a t-test based filter approach. This means that in each repeat of the cross validation the s miRNAs with lowest p-values were computed on the training set, with s being sampled from 1 to 904. The respective subset was then used to train the SVM for the prediction of the test samples which enabled a calculation of the mean accuracy, specificity, and sensitivity for each subset size.

Permutation tests were applied to check for overtraining. Here, the class labels were sampled at random and classifications were carried out using the permuted class labels. All statistical analyses were performed using R.

In summary the present invention is composed of the following items:

1. A method of diagnosing a disease, comprising the steps
   (a) determining an expression profile of a predetermined set of non-coding RNAs, including miRNAs, in a biological sample from a patient; and
   (b) comparing said expression profile to a reference expression profile, wherein the comparison of said determined expression profile to said reference expression profile allows for the diagnosis of the disease, wherein the disease is ovarian cancer.

2. The method according to item 1, wherein the reference expression profile is derived from a plurality of expression profiles obtained from a plurality of reference subjects.
3. The method according to item 1 or 2, wherein the reference expression profile is derived from healthy controls.
4. The method according to item 1 or 2, wherein the reference expression profile is derived from diseased subjects.
5. The method according to any one of items 1 to 4, wherein the expression profile is determined of non-coding RNAs, including miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454*, hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR-518f, hsa-miR-488, hsa-miR-182, hsa-miR-10a*, hsa-miR-19b, hsa-miR-15a, hsa-miR-1289, hsa-miR-500, hsa-miR-1281, hsa-miR-942, hsa-miR-877*, hsa-let-7f-1*, hsa-miR-651, hsa-miR-610, hsa-miR-664, hsa-miR-613, hsa-miR-483-3p, hsa-miR-320c, hsa-miR-720, hsa-miR-299-5p, hsa-miR-579, hsa-miR-636, hsa-miR-197, hsa-miR-668, hsa-miR-494, hsa-miR-1262, hsa-miR-578, hsa-miR-708*, hsa-miR-369-3p, hsa-miR-329, hsa-miR-941, hsa-miR-155, hsa-miR-26a-1*, hsa-miR-1246, hsa-miR-892b, hsa-miR-146a, hsa-miR-337-3p, hsa-miR-130a*, hsa-let-7b, hsa-miR-744*, hsa-miR-140-3p, hsa-miR-573, hsa-miR-378, hsa-miR-1237, hsa-miR-363*, hsa-miR-888, hsa-miR-607, hsa-miR-1236, hsa-miR-34b, hsa-miR-532-3p, hsa-miR-1229, hsa-miR-520g, hsa-miR-581, hsa-miR-323-3p, hsa-miR-155*, hsa-miR-15b, hsa-miR-548d-3p, hsa-miR-302d*, hsa-miR-496, hsa-miR-186*, hsa-miR-599, hsa-miR-589, hsa-miR-519c-5p, hsa-miR-1249, hsa-miR-22, hsa-miR-614, hsa-miR-634, hsa-miR-486-5p, hsa-miR-548h, hsa-miR-19a, hsamiR-32*, hsa-miR-367*, hsa-miR-218-1*, hsa-let-7a*, hsa-miR-328, hsa-miR-571, hsa-miR-424*, hsa-miR-374b*, hsa-let-7d, hsa-miR-16, hsa-miR-490-3p, hsa-miR-1914*, hsa-miR-543, hsa-miR-526a, hsa-miR-875-5p, hsa-miR-1252, hsa-miR-495, hsa-miR-210, hsa-miR-514, hsa-miR-572, hsa-miR-1228, hsa-miR-589*, hsa-miR-1538, hsa-miR-300, hsa-miR-320b, hsa-miR-190b, hsa-miR-330-5p, hsa-miR-506, hsa-miR-1295, hsa-miR-485-3p, hsa-miR-629*, hsa-miR-130b*, hsa-miR-297, hsa-miR-1915*, hsa-miR-623, hsa-miR-133a, hsa-miR-433, hsa-miR-148b*, hsa-miR-372, hsa-miR-1288, hsa-miR-520e, hsa-miR-429, hsa-miR-30a, hsa-miR-556-3p, hsa-miR-576-3p, hsa-miR-200a*, hsa-miR-450b-5p, hsa-miR-219-2-3p, hsa-miR-633, hsa-miR-182*, hsa-miR-582-5p, hsa-miR-520c-5p, hsa-miR-934, hsa-miR-526b*, hsa-miR-770-5p, hsa-miR-660, hsa-miR-411*, hsa-miR-576-5p, hsa-miR-606, hsa-miR-205, hsa-miR-1302, hsa-miR-301b, hsa-miR-891a, hsa-miR-516b*, hsa-miR-376a*, hsa-miR-936, hsa-miR-26a-2*, hsa-miR-544, hsa-miR-134, hsa-miR-542-3p, hsa-miR-518d-5p, hsa-miR-513a-3p, hsa-miR-548a-3p, hsa-miR-559, hsa-miR-1308, hsa-miR-1825, hsa-miR-585, hsa-miR-181a, hsa-miR-1470, hsa-miR-513c, hsa-miR-885-3p, hsa-miR-1205, hsa-miR-518f*, hsa-miR-1305, hsa-miR-190, hsa-miR-363, hsa-miR-519d, hsa-miR-181a-2*, hsa-miR-220b, hsa-miR-29c*, hsa-miR-1265, hsa-miR-1468, hsa-miR-96*, hsa-miR-562, hsa-miR-580, hsa-miR-92b, hsa-miR-523*, hsa-miR-548c-3p, hsa-miR-618, hsa-miR-662, hsa-miR-539, hsa-miR-548n, hsa-miR-203, hsa-miR-152, hsa-miR-1279, hsa-miR-640, hsa-miR-520a-5p, hsa-miR-23b, hsa-miR-431, hsa-miR-376b, hsa-miR-92a, hsa-miR-548k, hsa-miR-380, hsa-miR-202, hsa-miR-19b-2*, hsa-miR-128, hsa-miR-520d-3p, hsa-miR-1282, hsa-miR-564, hsa-miR-1226, hsa-miR-224, hsa-miR-574-5p, hsa-miR-548b-5p, hsa-miR-512-3p, hsa-miR-296-5p, hsa-miR-302a, hsa-miR-501-5p, hsa-miR-382, hsa-miR-18b*, hsa-miR-24-2*, hsa-miR-944, hsa-miR-520f, hsa-miR-1290, hsa-miR-595, hsa-miR-144*, hsa-miR-644, hsa-miR-650, hsa-miR-518a-5p, hsa-miR-129*, hsa-miR-1238, hsa-miR-154, hsa-miR-106b, hsa-miR-431*, hsa-miR-1202, hsa-miR-587, hsa-miR-708, hsa-miR-451, hsa-miR-519a*, hsa-miR-105*, hsa-miR-625*, hsa-miR-127-3p, hsa-miR-1911, hsa-let-7c, hsa-miR-1269, hsa-miR-370, hsa-miR-298, hsa-miR-1, hsa-miR-28-3p, hsa-miR-635, hsa-miR-26a, hsa-miR-1261, hsa-miR-211, hsa-miR-99b*, hsa-miR-183, hsa-miR-1184, hsa-let-7g*, hsa-miR-519e, hsa-miR-453, hsa-miR-30a*, hsa-miR-1324, hsa-miR-611, hsa-miR-1322, hsa-miR-1250, hsa-miR-574-3p, hsa-miR-518e, hsa-miR-410, hsa-miR-125b-2*, hsa-miR-146b-3p, hsa-miR-1537, hsa-miR-34c-3p, hsa-miR-1264, hsa-miR-302d, hsa-miR-221*, hsa-miR-1471, hsa-miR-1183, hsa-miR-338-3p, hsa-miR-519e*, hsa-miR-1298, hsa-miR-376a, hsa-miR-517c, hsa-miR-1286, hsa-miR-30b*, hsa-miR-361-5p, hsa-miR-509-3-5p, hsa-miR-194, hsa-miR-135b, hsa-miR-153, hsa-miR-522*, hsa-miR-1301, hsa-miR-147b, hsa-miR-548d-5p, hsa-miR-29a, hsa-miR-943, hsa-miR-1306, hsa-miR-521, hsa-miR-124, hsa-miR-485-5p, hsa-miR-212, hsa-miR-886-3p, hsa-miR-652, hsa-miR-135a, hsa-miR-608, hsa-miR-887, hsa-miR-106b*, hsa-miR-34b*, hsa-miR-1257, hsa-miR-1263, hsa-miR-588, hsa-miR-30d*, hsa-miR-423-3p, hsa-miR-766, hsa-miR-122, hsa-miR-29a*, hsa-miR-107, hsa-miR-493, hsa-miR-1323, hsa-miR-486-3p, hsa-miR-583, hsa-miR-19a*, hsa-miR-497, hsa-miR-504, hsa-miR-508-3p, hsa-miR-93*, hsa-miR-659, hsa-miR-524-3p, hsa-miR-503, hsa-miR-517b, hsa-miR-617, hsa-miR-590-5p, hsa-miR-138-1*, hsa-miR-135a*, hsa-miR-577, hsa-miR-549, hsa-miR-194*, hsa-miR-199b-3p, hsa-miR-541*, hsa-miR-1299, hsa-miR-374a*, hsa-miR-7-2*, hsa-miR-621, hsa-miR-1203, hsa-miR-27a*, hsa-miR-548f, hsa-miR-151-3p, hsa-miR-409-5p, hsa-miR-129-3p, hsa-miR-922, hsa-miR-890, hsa-miR-7-1*, hsa-miR-548j, hsa-miR-498, hsa-miR-195*, hsa-miR-507, hsa-miR-593*, hsa-miR-501-3p, hsa-miR-302e, hsa-miR-204, hsa-miR-767-3p, hsa-miR-483-5p, hsa-miR-193a-5p, hsa-miR-1270, hsa-miR-658, hsa-miR-656, hsa-miR-1197, hsa-miR-342-5p, hsa-miR-612, hsa-miR-876-5p, hsa-miR-136, hsa-miR-1253, hsa-miR-641, hsa-miR-671-3p, hsa-miR-548g, hsa-miR-548c-5p, hsa-miR-603, hsa-miR-520b, hsa-miR-1283, hsa-miR-1255a, hsa-miR-296-3p, hsa-miR-202*, hsa-miR-1200, hsa-miR-630, hsa-miR-609, hsa-miR-149, hsa-miR-767-5p, hsa-miR-548m, hsa-miR-381, hsa-miR-200c*, hsa-miR-425*, hsa-miR-30c, hsa-miR-1201, hsa-miR-548a-5p, hsa-miR-33a*, hsa-miR-450a, hsa-miR-331-3p, hsa-miR-32, hsa-miR-223*, hsa-miR-200b, hsa-miR-509-3p, hsa-miR-129-5p, hsa-miR-10b*, hsa-miR-195, hsa-miR-92a-2*, hsa-miR-5481, hsa-miR-345, hsa-miR-377*, hsa-miR-181c, hsa-miR-33b*, hsa-miR-455-5p, hsa-miR-181c*, hsa-miR-616, hsa-miR-208b, hsa-miR-891b, hsa-miR-138, hsa-miR-135b*, hsa-miR-1266, hsa-let-7i*, hsa-miR-877, hsa-miR-132*, hsa-miR-192, hsa-miR-940, hsa-miR-24-1*, hsa-miR-302b*, hsa-miR-602, hsa-miR-33b, hsa-miR-323-5p, hsa-miR-1908, hsa-miR-339-5p, hsa-miR-657, hsa-miR-553, hsa-miR-183*, hsa-miR-516a-3p, hsa-miR-125b, hsa-miR-1909*, hsa-miR-505, hsa-miR-616*, hsa-miR-875-3p, hsa-miR-527, hsa-miR-365, hsa-miR-147, hsa-miR-516a-5p, hsa-miR-493*, hsa-miR-933, hsa-miR-20a*, hsa-miR-671-5p, hsa-miR-490-5p, hsa-miR-302c*, hsa-let-7c*, hsa-miR-484, hsa-miR-187, hsa-miR-1251, hsa-miR-1307, hsa-miR-17*, hsa-miR-648, hsa-miR-1274b, hsa-miR-96, hsa-miR-302f, hsa-miR-331-5p, hsa-miR-149*, hsa-miR-99a, hsa-miR-1228*, hsa-miR-30d, hsa-miR-21*, hsa-miR-545, hsa-miR-600, hsa-miR-424, hsa-miR-21, hsa-miR-18b, hsa-miR-448, hsa-miR-126*, hsa-miR-98, hsa-miR-148a, hsa-miR-1280, hsa-miR-380*, hsa-miR-136*, hsa-miR-411, hsa-miR-523, hsa-miR-187*, hsa-miR-196b, hsa-miR-34c-5p, hsa-miR-627, hsa-miR-1296, hsa-miR-637, hsa-miR-1268, hsa-miR-379, hsa-miR-362-5p, hsa-miR-557, hsa-miR-326, hsa-miR-34a*, hsa-miR-548p, hsa-miR-1271, hsa-miR-876-3p, hsa-miR-30c-1*, hsa-miR-489, hsa-miR-500*, hsa-miR-100*, hsa-miR-892a, hsa-miR-556-5p, hsa-miR-140-5p, hsa-miR-20b*, hsa-miR-760, hsa-miR-101*, hsa-miR-1224-5p, hsa-miR-19b-1*, hsa-miR-92a-1*, hsa-miR-16-2*, hsa-miR-373*, hsa-let-7i, hsa-miR-555, hsa-miR-218, hsa-miR-25*, hsa-miR-449a, hsa-miR-582-3p, hsa-miR-502-5p, hsa-miR-515-3p, hsa-miR-654-5p, hsa-miR-214*, hsa-miR-455-3p, hsa-miR-199b-5p, hsa-miR-509-5p, hsa-miR-421, hsa-miR-1909, hsa-miR-425, hsa-miR-1273, hsa-miR-1293, hsa-miR-566, hsa-miR-7, hsa-miR-638, hsa-miR-1284, hsa-miR-1913, hsa-miR-1178, hsa-miR-1304, hsa-miR-1911*, hsa-miR-518a-3p, hsa-miR-330-3p, hsa-miR-518c*, hsa-miR-491-3p, hsa-miR-649, hsa-miR-558, hsa-miR-10b, hsa-miR-335, hsa-miR-103-as, hsa-miR-106a*, hsa-miR-27b, hsa-miR-1278, hsa-miR-505*, hsa-miR-628-3p, hsa-miR-542-5p, hsa-miR-1233, hsa-miR-185, hsa-miR-132, hsa-miR-139-3p, hsa-miR-1226*, hsa-miR-1272, hsa-miR-512-5p, hsa-miR-299-3p, hsa-miR-937, hsa-miR-499-3p, hsa-miR-216b, hsa-miR-568, hsa-miR-596, hsa-miR-619, hsa-miR-1225-5p, hsa-miR-1181, hsa-miR-188-5p, hsa-let-7d*, hsa-miR-218-2*, hsa-miR-647, hsa-miR-139-5p, hsa-miR-654-3p, hsamiR-138-2*, hsa-miR-675, hsa-miR-377, hsa-miR-374a, hsa-miR-215, hsa-miR-15a*, hsa-miR-769-5p, hsa-miR-362-3p, hsa-miR-192*, hsa-miR-125a-5p, hsa-miR-491-5p, hsa-miR-802, hsa-miR-33a, hsa-miR-142-5p, hsa-miR-663b, hsa-miR-1539, hsa-miR-95, hsa-miR-1275, hsa-miR-191*, hsa-miR-502-3p, hsa-miR-563, hsa-miR-1321, hsa-miR-1914, hsa-miR-185*, hsa-miR-639, hsa-miR-122*, hsa-miR-643, hsa-miR-1469, hsa-miR-1234, hsa-miR-622, hsa-miR-222*, hsa-miR-499-5p, hsa-miR-1260, hsa-miR-517a, hsa-miR-34a, hsa-miR-624*, hsa-miR-28-5p, hsa-miR-100, hsa-miR-625, hsa-miR-148b, hsa-miR-584, hsa-miR-769-3p, hsa-miR-1182, hsa-miR-198, hsa-miR-18a*, hsa-miR-206, hsa-miR-645, hsa-miR-508-5p, hsa-miR-518b, hsa-miR-873, hsa-miR-371-5p, hsa-miR-1910, hsa-miR-646, hsa-miR-452, hsa-miR-106a, hsa-miR-1287, hsa-miR-217, hsa-miR-1258, hsa-miR-620, hsa-miR-511, hsa-miR-301a, hsa-miR-1247, hsa-miR-325, hsa-miR-552, hsa-miR-642, hsa-miR-92b*, hsa-miR-193b*, hsa-miR-340, hsa-miR-520h, hsa-miR-9*, hsa-miR-758, hsa-miR-101, hsa-miR-591, hsa-miR-1297, hsa-miR-548e, hsa-miR-524-5p, hsa-miR-935, hsa-miR-575, hsa-miR-145*, hsa-miR-29b-1*, hsa-miR-27a, hsa-miR-615-3p, hsa-miR-1243, hsa-miR-525-3p, hsa-miR-551b*, hsa-miR-1292, hsa-miR-302a*, hsa-miR-30e, hsa-miR-541, hsa-miR-124*, hsa-miR-196a*, hsa-miR-222, hsa-miR-519c-3p, hsa-miR-146a*, hsa-miR-432, hsa-miR-601, hsa-miR-663, hsa-let-7b*, hsa-miR-452*, hsa-miR-220c, hsa-miR-519b-3p, hsa-miR-1227, hsa-miR-200b*, hsa-miR-143, hsa-miR-1274a, hsa-miR-25, hsa-miR-938, hsa-miR-519b-5p, hsa-miR-924, hsa-miR-127-5p, hsa-miR-920, hsa-miR-525-5p, hsa-miR-17, hsa-miR-324-5p, hsa-miR-188-3p, hsa-miR-31, hsa-miR-661, hsa-miR-379*, hsa-miR-1245, hsa-miR-142-3p, hsa-miR-513a-5p, hsa-let-7f-2*, hsa-miR-150*, hsa-miR-367, hsa-miR-548b-3p, hsa-miR-518c, hsa-miR-99b, hsa-miR-27b*, hsa-miR-214, hsa-miR-145, hsa-miR-653, hsa-miR-765, hsa-miR-570, hsa-miR-604, hsa-miR-93, hsa-miR-146b-5p, hsa-miR-29b, hsa-miR-181a*, hsa-miR-422a, hsa-miR-1206, hsa-miR-23a, hsa-miR-487b, hsa-miR-339-3p, hsa-miR-191, hsa-miR-340*, hsa-miR-1291, hsa-miR-208a, hsa-miR-23a*, hsa-miR-1826, hsa-miR-1208, hsa-miR-1207-5p, hsa-miR-31*, hsa-miR-143*, hsa-let-7f, hsa-miR-105, hsa-miR-569, hsa-miR-30c-2*, hsa-miR-921, hsa-miR-628-5p, hsa-miR-1225-3p, hsa-miR-597, hsa-miR-10a, hsa-miR-302b, hsa-miR-1277, hsa-miR-1207-3p, hsa-miR-186, hsa-miR-626, hsa-miR-554, hsa-miR-99a*, hsa-miR-497*, hsa-miR-487a, hsa-miR-199a-5p, hsa-miR-454, hsa-miR-492, hsa-miR-338-5p, hsa-miR-125a-3p, hsa-miR-20a, hsa-miR-518d-3p, hsa-miR-664*, hsa-miR-520c-3p, hsa-miR-1303, hsa-miR-26b, hsa-miR-1256, hsa-miR-361-3p, hsa-miR-22*, hsa-miR-103, hsa-miR-888*, hsa-miR-1180, hsa-miR-432*, hsa-miR-126, hsa-miR-200a, hsa-miR-1285, hsa-miR-154*, hsa-miR-371-3p, hsa-miR-193a-3p, hsa-miR-1244, hsa-miR-200c, hsa-miR-125b-1*, hsa-miR-517*, hsa-miR-216a, hsa-miR-586, hsa-miR-375, hsa-let-7a, hsa-miR-1827, hsa-miR-518e*, hsa-miR-513b, hsa-miR-196a, hsa-miR-1915, hsa-miR-1204, hsa-miR-15b*, hsa-miR-516b, hsa-miR-1912, hsa-miR-550*, hsa-miR-632, hsa-miR-24, hsa-miR-561, hsa-miR-219-5p, hsa-miR-20b, hsa-miR-220a, hsa-miR-199a-3p, hsa-miR-665, hsa-miR-519a, hsa-miR-488*, hsa-miR-449b, hsa-miR-151-5p, hsa-miR-567, hsa-miR-522, hsa-miR-1267, hsa-miR-874, hsa-miR-376c, hsa-miR-510, hsa-miR-374b, hsa-miR-29c, hsa-miR-137, hsa-miR-337-5p, hsa-miR-1254, hsa-miR-193b, hsa-miR-520d-5p, hsa-miR-1179, hsa-miR-181b, hsa-miR-30b, hsa-miR-532-5p, hsa-miR-369-5p, hsa-miR-631, hsa-miR-130b, hsa-miR-551a, hsa-miR-551b, hsa-miR-593, hsa-miR-886-5p, hsa-miR-184, hsa-miR-624, hsa-miR-548o, hsa-miR-223, hsa-miR-1231, hsa-miR-1276, hsa-miR-29b-2*, hsa-miR-346, hsa-miR-141*, hsa-miR-181d, hsa-miR-615-5p, hsa-miR-1185, hsa-miR-141, hsa-miR-885-5p, hsa-miR-18a, hsa-let-7g, hsa-miR-130a, hsa-miR-744, hsa-miR-221, hsa-miR-1255b, hsa-miR-378*, hsa-miR-629, hsa-miR-526b, hsa-miR-373, hsa-miR-515-5p, hsa-miR-592, hsa-miR-16-1*, hsa-miR-30e*, hsa-let-7e, hsa-miR-550, hsa-miR-1294, hsa-miR-144, hsa-miR-939, hsa-miR-384, hsa-miR-598.

6. The method according to item 5, wherein the predetermined set of non-coding RNAs, including miRNAs representative for diagnosis of ovarian cancer comprises all of said miRNAs.
7. The method according to item 5, wherein the predetermined set of non-coding RNAs, including miRNAs representative for diagnosis of ovarian cancer comprises at least 1, 7, 10, 15, 20, 25, 30, 35, 40, 50, 75, 100 or 440 of said miRNAs.
8. The method according to item 5, wherein the predetermined set of miRNAs representative for diagnosis of ovarian cancer comprises at least 1, 7, 10, 15, 20, 25, 30, 35, 40, 50, 60, 70 or 75 of the miRNAs selected from the group consisting of hsa-miR-1248, hsa-miR-342-3p, hsa-miR-133b, hsa-miR-605, hsa-miR-450b-3p, hsa-miR-520a-3p, hsa-miR-23b*, hsa-miR-423-5p, hsa-miR-219-1-3p, hsa-miR-454*, hsa-miR-26b*, hsa-miR-1259, hsa-miR-655, hsa-miR-302c, hsa-miR-383, hsa-miR-150, hsa-miR-412, hsa-miR-548i, hsa-let-7e*, hsa-miR-324-3p, hsa-miR-335*, hsa-miR-320a, hsa-miR-320d, hsa-miR-409-3p, hsa-miR-590-3p, hsa-miR-545*, hsa-miR-889, hsa-miR-1224-3p, hsa-miR-148a*, hsa-miR-9, hsa-miR-518f, hsa-miR-488, hsa-miR-182, hsa-miR-10a*, hsa-miR-19b, hsa-miR-15a, hsa-miR-1289, hsa-miR-500, hsa-miR-1281, hsa-miR-942, hsa-miR-877*, hsa-let-7f-1*, hsa-miR-651, hsa-miR-610, hsa-miR-664, hsa-miR-613, hsa-miR-483-3p, hsa-miR-320c, hsa-miR-720, hsa-miR-299-5p, hsa-miR-579, hsa-miR-636, hsa-miR-197, hsa-miR-668, hsa-miR-494, hsa-miR-1262, hsa-miR-578, hsa-miR-708*, hsa-miR-369-3p, hsa-miR-329, hsa-miR-941, hsa-miR-155, hsa-miR-26a-1*, hsa-miR-1246, hsa-miR-892b, hsa-miR-146a, hsa-miR-337-3p, hsa-miR-130a*, hsa-let-7b, hsa-miR-744*, hsa-miR-140-3p, hsa-miR-573, hsa-miR-378, hsa-miR-1237, hsa-miR-363*.
9. The method according to any one of items 1-8 wherein said biological sample is selected from blood and/or serum or urine samples.
10. The method according to any one of items 1-9 wherein miRNA the expression profile is determined by nucleic acid hybridization, nucleic acid amplification, polymerase extension, sequencing, mass spectroscopy or any combinations thereof.
11. The method according to any one of items 1-10, wherein the miRNA expression profile of said subject and the reference expression profiles and optionally the predetermined set of miRNAs are stored in a database.
12. The method according to any one of items 1-11, wherein the biological sample is not labeled prior to determination of the expression profile.
13. The method according to any one of items 1-12 wherein the diagnosis comprises determining survival rate, responsiveness to drugs, and/or monitoring the course of the disease or the therapy, e.g. chemotherapy.
14. A kit for diagnosing and/or predicting ovarian cancer of a subject, comprising:

(a) means for determining the miRNA expression profile of a RNA sample of a subject, and (b) at least one reference miRNA expression profile characteristic for ovarian cancer, and (c) means for comparing the miRNA-profile of the said subject to the reference expression profile 15. A microarray for diagnosing and/or predicting ovarian cancer of a subject, comprising probes that are specific for the analysis of miRNAs selected from the group of miRNAs listed in any of the items 5, 6, 7 or 8.

So far, miRNAs have been extensively studied in tissue material. It has been found that miRNAs are expressed in a highly tissue-specific manner. Disease-specific expression of miRNAs has been reported in many human cancers employing primarily tissue material as the miRNA source. In this context miRNAs expression profiles were found to be useful in identifying the tissue of origin for cancers of unknown primary origin. Since recently it is known that miRNAs are not only present in tissues but also in other body fluid samples, including human blood. Nevertheless, the mechanism why miRNAs are found in body fluids, especially in blood, or their function in these body fluids is not understood yet.

Various miRNA biomarkers found in tissue material have been proposed to be correlated with certain diseases, e.g. cancer. However, there is still a need for novel miRNAs as biomarkers for the detection and/or prediction of these and other types of diseases. Especially desirable are non-invasive biomarkers, that allow for quick, easy and cost-effective diagnosis/prognosis which cause only minimal stress for the patient eliminating the need for surgical intervention.

Particularly, the potential role of miRNAs as non-invasive biomarkers for the diagnosis and/or prognosis of Ovarian cancer has not been systematically evaluated yet. In addition, many of the miRNA biomarkers presently available for diagnosing and/or prognosing of diseases have shortcomings such as reduced sensitivity, not sufficient specificity or do not allow timely diagnosis or represent invasive biomarkers. Accordingly, there is still a need for novel and efficient miRNAs or sets of miRNAs as markers, effective methods and kits for the non-invasive diagnosis and/or prognosis of diseases such as Ovarian cancer.

The inventors of the present invention assessed for the first time the expression of miRNAs on a whole-genome level in subjects with Ovarian cancer as non-invasive biomarkers from body fluids, preferably in blood. They surprisingly found that miRNAs are significantly dysregulated in blood of Ovarian cancer subjects in comparison to healthy controls and thus, miRNAs are appropriated non-invasive biomarkers for diagnosing and/or prognosing of Ovarian cancer. This finding is surprising, since there is nearly no overlap of the miRNA biomarkers found in blood and the miRNA biomarkers found in tissue material representing the origin of the disease.

The inventors of the present invention surprisingly found miRNA biomarkers in body fluids, especially in blood, that were not yet known to be correlated to Ovarian cancer when tissue material was used for this kind of analysis. Therefore, the inventors of the invention identified for the first time miRNAs as non-invasive surrogate biomarkers for diagnosis and/or prognosis of Ovarian cancer. The inventors of the present invention identified single miRNAs which predict Ovarian cancer with high specificity, sensitivity and accuracy. The inventors of the present invention also pursued a multiple biomarker strategy, thus implementing sets of miRNA biomarkers for diagnosing and/or prognosing of Ovarian cancer leading to added specificity, sensitivity, accuracy and predictive power, thereby circumventing the limitations of single biomarkers. They identified unique sets of miRNAs (miRNA signatures) that allow for non-invasive diagnosis of Ovarian cancer with even higher power, indicating that sets of miRNAs (miRNA signatures) is derived from a body fluid sample, such as blood from a subject (e.g. human) can be used as novel non-invasive biomarkers.

The inventors of the present invention surprisingly found that miRNAs are significantly dysregulated in body fluid samples such as blood of Ovarian cancer subjects in comparison to a cohort of controls (healthy subjects) and thus, miRNAs are appropriate biomarkers for diagnosing and/or prognosing of Ovarian cancer in a non-invasive fashion. Furthermore, the predetermined sets of miRNAs of the present invention led to high performance in diagnosing and/or prognosing of Ovarian cancer providing very high specificity, sensitivity and accuracy. They succeeded in determining the miRNAs that are differentially regulated in body fluid samples from patients having Ovarian cancer compared to a cohort of controls (healthy subjects) (see experimental section for experimental details). Additionally, the inventors of the present invention performed hypothesis tests (e.g. t-test, limma-test) or other measurements (e.g. AUC, mutual information) on the expression level of the found miRNAs, in all controls (healthy subjects) and subjects suffering from Ovarian cancer. These tests resulted in a significance value (p-value) for each miRNA. This p-value is a measure for the diagnostic power of each of these single miRNAs to discriminate, for example, between the two clinical conditions: controls (healthy subjects), i.e. not suffering from Ovarian cancer, or diseased, i.e. suffering from Ovarian cancer. Since a manifold of tests are carried out, one for each miRNA, the p-values were corrected for multiple testing by the Benjamini Hochberg approach.

The term "body fluid sample", as used in the context of the present invention, refers to liquids originating from the body of a subject. Said body fluid samples include, but are not limited to, blood, urine, sputum, breast milk, cerebrospinal fluid, cerumen (earwax), endolymph, perilymph, gastric juice, mucus, peritoneal fluid, pleural fluid, saliva, sebum (skin oil), semen, sweat, tears, vaginal secretion, vomit including components or fractions thereof. Said body fluid samples may be mixed or pooled, e.g. a body fluid sample may be a mixture of blood and urine samples or blood and tissue material. A "body fluid sample" may be provided by removing a body liquid from a subject, but may also be provided by using previously isolated sample material.

The term "blood sample", as used in the context of the present invention, refers to a blood sample originating from a subject. The "blood sample" may be derived by removing blood from a subject by conventional blood collecting techniques, but may also be provided by using previously isolated and/or stored blood samples. For example a blood sample may be whole blood, plasma, serum, PBMC (peripheral blood mononuclear cells), blood cellular fractions including red blood cells (erythrocytes), white blood cells (leukocytes), platelets (thrombocytes), or blood collected in blood collection tubes (e.g. EDTA-, heparin-, citrate-, PAX-gene-, Tempus-tubes) including components or fractions thereof. For example, a blood sample may be taken from a subject suspected to be affected or to be suspected to be affected by Ovarian cancer, prior to initiation of a therapeutic treatment, during the therapeutic treatment and/or after the therapeutic treatment.

Preferably, the body fluid, e.g. blood sample from a subject (e.g. human or animal) has a volume of between 0.1 and 20 ml, more preferably of between 0.5 and 10 ml, more preferably between 1 and 8 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml. In the context of the present invention said "body fluid sample" or "blood sample" allows for a non-invasive diagnosis and/or prognosis of a subject.

Preferably, the collected blood sample, particularly the RNA-fraction, especially the miRNA fraction thereof, is protected against degradation. For this purpose special collection tubes (e.g. PAXgene RNA tubes from Preanalytix, Tempus Blood RNA tubes from Applied Biosystems) and/or additives (e.g. RNAlater from Ambion, RNAsin from Promega) that stabilize the RNA fraction and/or the miRNA fraction may be employed.

The biological sample, preferably the body fluid sample may originate from a subject (e.g. human or mammal) who is therapeutically treated, has been therapeutically treated or has not yet been therapeutically treated. In one embodiment, the therapeutical treatment may be monitored on the basis of the detection of an miRNA or a set of miRNAs by the polynucleotide or set of polynucleotides of the invention. The detection may involve the use of miRNAs or sets of miRNAs isolated (e.g. extracted) from a biological sample of a subject (e.g. human or animal), and/or the use of polynucleotides or sets of polynucleotides or primer pairs of the invention.

The term "non-invasive", as used in the context of the present invention, refers to methods for obtaining a biological sample, particularly a body fluid sample, without the need for an invasive surgical intervention or invasive medical procedure. In the context of the present invention, drawing blood represents a non-invasive procedure. Therefore a blood-based test (utilizing blood or fractions thereof) is a non-invasive test. Other body fluid samples for non-invasive tests are e.g. urine, sputum, tears, mothers mild, cerumen, sweat, saliva, vaginal secretion, vomit, etc.

The term "diagnosis" as used in the context of the present invention refers to the process of determining a possible disease or disorder and therefore is a process attempting to define the (clinical) condition of a subject. The determination of the expression level of a set of miRNAs according to the present invention correlates with the (clinical) condition of a subject. Preferably, the diagnosis comprises (i) determining the occurrence/presence of Ovarian cancer, (ii) monitoring the course of Ovarian cancer, (iii) staging of Ovarian cancer, (iv) measuring the response of a patient with Ovarian cancer to therapeutic intervention, and/or (v) segmentation of a subject suffering from Ovarian cancer.

The term "prognosis" as used in the context of the present invention refers to describing the likelihood of the outcome or course of a disease or a disorder. Preferably, the prognosis comprises (i) identifying of a subject who has a risk to develop Ovarian cancer, (ii) predicting/estimating the occurrence, preferably the severity of occurrence of Ovarian cancer, and/or (iii) predicting the response of a subject with Ovarian cancer to therapeutic intervention.

The term "suffering or suspected to be suffering from Ovarian cancer" as used in the context of the present invention comprises the diagnosis and/or prognosis of Ovarian cancer in a suspect as defined above.

The present invention particularly comprises nine aspects as follows:

In a first aspect, the present invention relates to a method for diagnosing and/or prognosing of Ovarian cancer comprising the steps of:

(i) determining an expression profile of a predetermined set comprising at least two miRNAs representative for Ovarian cancer in a body fluid sample from a subject, and
(ii) comparing said expression profile to a reference expression profile, wherein the comparison of said expression profile to said reference expression profile allows for the diagnosis and/or prognosis of Ovarian cancer.

In this aspect (and in the following aspects), it is preferred that the body fluid sample is a blood sample, particularly preferred it is a whole blood, PBMC, serum or plasma sample, more particularly preferred it is a whole blood sample. The preferred subject may be a mammal including both a human and a non-human mammal, e.g. an animal such as a mouse, a rat, a rabbit, or a monkey. It is particularly preferred that the subject is a human.

In this aspect (and in the following aspects), the predetermined set comprising at least two miRNAs is preferably selected from the set of miRNAs listed in FIG. 2 or 14, and/or from the sets of miRNAs listed in FIG. 15 (SNO-1 to SNO-756). The predetermined set comprising at least two miRNAs may comprise at least one set of miRNAs listed in FIG. 15, e.g. one set or a plurality of sets of miRNAs listed in FIG. 15.

For example, a set comprising 30 miRNAs representative for Ovarian cancer in a body fluid sample from a subject comprises at least the miRNAs from one predetermined set or several sets of miRNAs listed in FIG. 15. Alternatively, a set comprising 29, 28, 27, 26, 25, 24, 23, 22, 21, 20, 19, 18, 17, 16, 15, 14, 13, 12, 11, 10, 9, 8, 7, 6, 5, 4 or 3 miRNAs representative for Ovarian cancer comprises at least the miRNAs from one set or several sets of miRNAs listed in FIG. 15.

Further, in another preferred embodiment, the invention comprises determining an expression profile of combinations of sets of miRNAs listed in FIG. 15.

For example, said predetermined set comprising 30 miRNAs representative for Ovarian cancer in a body fluid sample from a subject comprises at least 2, e.g. 2, 3, 4, 5 or 6 of the sets of miRNAs listed in FIG. 15. Alternatively, said predetermined set comprising 29, 28, 27, 26, 25, 24, 23, 22, 21, 20, 19, 18, 17, 16, 15, 14, 13, 12, 11, 10, 9, 8, 7, 6, 5 or 4 miRNAs comprises at least 2, e.g. 2, 3, 4, 5 or 6 of the sets of miRNAs listed in FIG. 15.

The reference expression profile may be obtained from at least two subjects (e.g. human or animal). Preferably the reference expression profile is an average expression profile (data) of at least 2 to 400 subjects, more preferably at least 20 to 200 subjects, and most preferably at least 40 to 150 subjects, with a specific clinical condition which is Ovarian cancer or a specific form of Ovarian cancer.

It is particularly preferred that the reference expression profile is an algorithm or mathematical function. Preferably the algorithm or mathematical function is obtained from a reference expression profile (data) of at least two subjects, preferably the algorithm or mathematical function is obtained from an average reference expression profile (data) of at least 2 to 400 subjects, more preferably of at least 20 to 200 subjects, and most preferably of at least 40 to 150 subjects. It is preferred that the algorithm or mathematical function is obtained using a machine learning approach. The algorithm or mathematical function may be saved on a data carrier comprised in the kit (according to the seventh aspect of the invention) or the computer program, wherein the algorithm or mathematical function is comprised, may be saved on a data carrier comprised in the kit.

It is preferred that the miRNA expression profile may be generated by any convenient means, e.g. nucleic acid hybridization (e.g. to a microarray), nucleic acid amplification (PCR, RT-PCR, qRT-PCR, high-throughput RT-PCR), ELISA for quantitation, next generation sequencing (e.g. ABI SOLID, Illumina Genome Analyzer, Roche/454 GS FLX), flow cytometry (e.g. LUMINEX) and the like, that allow the analysis of differential miRNA expression levels between samples of a subject (e.g. diseased) and a control subject (e.g. healthy, reference sample).

Nucleic acid hybridization may be performed using a microarray/biochip or in situ hybridization. In situ hybridization is preferred for the analysis of a single miRNA or a set comprising a low number of miRNAs (e.g. a set of at least 2 to 50 miRNAs such as a set of 2, 5, 10, 20, 30, or 40 miRNAs). The microarray/biochip, however, allows the analysis of a single miRNA as well as a complex set of miRNAs (e.g. a all known miRNAs or subsets thereof).

Nucleic acid amplification may be performed using real time polymerase chain reaction (RT-PCR) such as real time quantitative polymerase chain reaction (RT qPCR). The standard real time polymerase chain reaction (RT-PCR) is preferred for the analysis of a single miRNA or a set comprising a low number of miRNAs (e.g. a set of at least 2 to 50 miRNAs such as a set of 2, 5, 10, 20, 30, or 40 miRNAs), whereas high-throughput RT-PCR technologies (e.g. OpenArray from Applied Biosystems, SmartPCR from Wafergen, Biomark System from Fluidigm) are also able to measure large sets of miRNAS (e.g a set of 10, 20, 30, 50, 80, 100, 200 or more) or all known miRNAs in a high parallel fashion. RT-PCR is particularly suitable for detecting low abandoned miRNAs.

In a second aspect, the invention relates to a set comprising polynucleotides for detecting a predetermined set comprising at least two miRNAs for diagnosing and/or prognosing of Ovarian cancer in a body fluid sample from a subject.

It is preferred that the polynucleotides comprised in the set of the present invention are complementary to the miRNAs comprised in the predetermined set, wherein the nucleotide sequences of said miRNAs are preferably selected from the group consisting of miRNAs listed in FIG. 2 or 14 or sets of miRNAs listed in FIG. 15, fragments thereof, and sequences having at least 80%, 85%, 90% or 95% sequence identity thereto.

For example, the polynucleotides of the present invention are for detecting a predetermined set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 miRNAs wherein the predetermined set of miRNAs comprises at least one, e.g. 1, 2, 3, 4, 5 or 6, of the sets of miRNAs listed in FIG. 15.

In a third aspect, the invention relates to the use of a set of polynucleotides according to the second aspect of the invention for diagnosing and/or prognosing Ovarian cancer in a subject.

In a fourth aspect, the invention relates to a set of at least two primer pairs for determining the expression level of a predetermined set of miRNAs in a body fluid sample of a subject suffering or suspected of suffering from Ovarian cancer.

It is preferred that the set of at least two primer pairs for determining the expression level of a predetermined set of miRNAs in a body fluid sample of a subject suffering or suspected of suffering from Ovarian cancer are primer pairs that are specific for at least one miRNA listed in FIG. 2 or 14.

It is further preferred that the set of at least two primer pairs for determining the expression level of a predetermined set of miRNAs in a body fluid sample of a subject suffering or suspected of suffering from Ovarian cancer are primer pairs that are specific for at least one set of miRNAs listed in FIG. 15.

It is preferred that the set of at least two primer pairs of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or more miRNAs, and wherein the predetermined set of miRNAs comprises at least one of the sets listed in FIG. 15.

For example, the set of at least two primer pairs of the present invention are for detecting a predetermined set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 or 2 miRNAs wherein the predetermined set of miRNAs comprises at least one of the sets of miRNAs listed in FIG. 15.

Preferably, the primer pairs are used for amplifying cDNA transcripts of the predetermined set of miRNAs selected from the miRNAs listed in FIG. 2 or FIG. 14. Furthermore, the primer pairs may be used for amplifying cDNA transcripts of the set of miRNAs listed in FIG. 15.

It is understood that the primer pairs for detecting a predetermined set of miRNAs may consist of specific primers, of a specific and a non-specific primer and/or of non-specific primers. Additionally, the set of primer pairs may be complemented by other substances or reagents (e.g. buffers, enzymes, dyes, labelled probes) known to the skilled in the art for conducting amplification reactions, e.g. real time polymerase chain reaction (RT-PCR).

In a fifth aspect, the invention relates to the use of a set of primer pairs according to the fourth aspect of the invention for diagnosing and/or prognosing Ovarian cancer in a subject.

In a sixth aspect, the invention relates to means for diagnosing and/or prognosing of Ovarian cancer in a body fluid sample of a subject.

Preferably, the invention relates to means for diagnosing and/or prognosing of Ovarian cancer in a body fluid sample of a subject comprising

- a set of at least two polynucleotides according to the second aspect of the invention and/or
- a set of at least two primer pairs according the fourth aspect of the invention.

It is preferred that the set of at least two polynucleotides or the set of at least 2 primer pairs are for detecting a predetermined set comprising at least two miRNAs for diagnosing and/or prognosing of Ovarian cancer in a body fluid sample, e.g. blood sample, from a subject, e.g. patient, human or animal, wherein the set of miRNAs is selected from the sets of miRNAs listed in FIG. 15 (SNO-1 to SNO-756).

It is preferred that the set of at least two primer pairs for determining the expression level of a predetermined set of miRNAs in a body fluid sample of a subject suffering or suspected of suffering from Ovarian cancer are primer pairs that are specific for at least two miRNAs selected from the miRNAs listed in FIG. 2 or FIG. 14.

It is preferred that the set of at least two primer pairs for determining the expression level of a set of miRNAs in a body fluid sample of a subject suffering or suspected of suffering from Ovarian cancer are primer pairs that are specific for at least one set of miRNAs listed in FIG. 15.

It is also preferred that said means for diagnosing and/or prognosing of Ovarian cancer comprise, of a set of beads comprising a at least two polynucleotides according to the second aspect of the present invention. It is especially preferred that the beads are employed within a flow cytometer setup for diagnosing and/or prognosing of Ovarian cancer, e.g. in a LUMINEX system.

In a seventh aspect, the invention relates to a kit for diagnosing and/or prognosing of Ovarian cancer in a subject.

Preferably, the invention relates to a kit for diagnosing and/or prognosing of Ovarian cancer comprising
(i) means for determining an expression profile of a predetermined set comprising at least two miRNAs representative for Ovarian cancer in a body fluid sample from a subject, and
(ii) at least one reference.

Said means may comprise of at least two polynucleotides according to the second aspect of the present invention, a set of at least 2 primer pairs according to the fourth aspect of the invention; means according to the sixth aspect of the present invention; primers suitable to perform reverse transcriptase reaction and/or real time polymerase chain reaction such as quantitative polymerase chain reaction; and/or means for conducting next generation sequencing.

In an eighth aspect, the invention relates to a predetermined set of miRNAs in a body fluid sample isolated from a subject for diagnosing and/or prognosing of Ovarian cancer.

In a ninth aspect, the invention relates to the use of a set of miRNAs according to the eighth aspect of the invention for diagnosing and/or prognosing of Ovarian cancer in a subject.

The invention claimed is:

1. A method of detecting a miRNA expression profile in a human subject, the method comprising:

(a) providing a blood cell sample comprising erythrocytes, leukocytes, and thrombocytes from a human subject;

(b) detecting the expression level of an miRNA set consisting of hsa-miR-342-3p (SEQ ID NO: 442) and hsa-miR-146a (SEQ ID NO: 709) in the blood cell sample using an RT-PCR assay.

2. The method of claim 1, wherein step (b) comprises:

(i) isolating RNA from the blood cell sample;

(ii) amplifying the isolated RNA to produce an amplified nucleic acid sample;

(iii) contacting the amplified nucleic acid sample with a first probe complementary to hsa-miR-342-3p (SEQ ID NO: 442) and a second probe complementary to hsa-miR-146a (SEQ ID NO: 709); and (iv) detecting binding of the first and second probes.

3. The method of claim 1, wherein step (a) comprises obtaining a blood sample from the human subject and isolating a cellular fraction from the blood sample, thereby producing blood cell sample.

4. The method of claim 1, wherein the human subject is a subject suspected of having ovarian cancer.

* * * * *